(12) United States Patent
Lee et al.

(10) Patent No.: US 8,338,565 B2
(45) Date of Patent: Dec. 25, 2012

(54) MACROCYCLIC COMPOUNDS FOR INHIBITION OF TUMOR NECROSIS FACTOR ALPHA

(75) Inventors: Jinbo Lee, Andover, MA (US); Julian F. Bond, Weymouth, MA (US); Nicholas Terrett, Sherborn, MA (US); Frank G. Favaloro, Jr., North Attleboro, MA (US); Daniel Wang, Duxbury, MA (US); Timothy F. Briggs, Cambridge, MA (US); Benjamin Adam Seigal, Watertown, MA (US); Wei-Chuan Sun, Menlo Park, CA (US); Stephen P. Hale, Belmont, MA (US)

(73) Assignee: Ensemble Therapeutics Corporation, Cambridge, MA (US)

( * ) Notice: Subject to any disclaimer, the term of this patent is extended or adjusted under 35 U.S.C. 154(b) by 463 days.

(21) Appl. No.: 12/544,604

(22) Filed: Aug. 20, 2009

(65) Prior Publication Data

US 2010/0152099 A1    Jun. 17, 2010

Related U.S. Application Data

(60) Provisional application No. 61/090,410, filed on Aug. 20, 2008, provisional application No. 61/098,865, filed on Sep. 22, 2008, provisional application No. 61/151,245, filed on Feb. 10, 2009.

(51) Int. Cl.
*C07K 11/02* (2006.01)
*A61K 38/12* (2006.01)

(52) U.S. Cl. ........................ 530/317; 514/21.1

(58) Field of Classification Search .................... None
See application file for complete search history.

(56) References Cited

U.S. PATENT DOCUMENTS

| | | |
|---|---|---|
| 4,485,039 A | 11/1984 | Hruby et al. |
| 4,649,191 A | 3/1987 | Hruby |
| 4,703,034 A | 10/1987 | Freidinger et al. |
| 5,326,751 A | 7/1994 | Haaseth et al. |
| 5,631,230 A | 5/1997 | Fang et al. |
| 5,683,981 A | 11/1997 | Hadley et al. |
| 5,731,408 A | 3/1998 | Hadley et al. |
| 5,952,320 A | 9/1999 | Davidsen et al. |
| 5,977,159 A | 11/1999 | Fandriks et al. |
| 6,608,027 B1 | 8/2003 | Tsantrizos et al. |
| 7,070,928 B2 | 7/2006 | Liu et al. |
| 7,223,545 B2 | 5/2007 | Liu et al. |
| 7,442,160 B2 | 10/2008 | Liu et al. |
| 7,491,494 B2 | 2/2009 | Liu et al. |
| 7,521,420 B2 | 4/2009 | Fraser et al. |
| 7,557,068 B2 | 7/2009 | Liu et al. |
| 7,771,935 B2 | 8/2010 | Liu et al. |
| 7,998,904 B2 | 8/2011 | Liu et al. |
| 8,017,323 B2 | 9/2011 | Liu et al. |
| 8,129,561 B2 | 3/2012 | Marsault et al. |
| 2002/0198165 A1 | 12/2002 | Bratzler et al. |
| 2005/0042669 A1 | 2/2005 | Liu et al. |
| 2005/0054562 A1 | 3/2005 | Fraser et al. |
| 2005/0119169 A1 | 6/2005 | Deslongchamps et al. |
| 2005/0153877 A1 | 7/2005 | Miao et al. |
| 2006/0229236 A1* | 10/2006 | Satoh et al. ........................ 514/9 |
| 2007/0021331 A1 | 1/2007 | Fraser et al. |
| 2008/0125472 A1 | 5/2008 | Scholkens et al. |
| 2008/0318807 A1 | 12/2008 | Liu et al. |
| 2009/0035824 A1 | 2/2009 | Liu et al. |
| 2009/0149347 A1 | 6/2009 | Liu et al. |
| 2009/0163371 A1 | 6/2009 | Stern et al. |
| 2009/0170757 A1 | 7/2009 | Fraser et al. |
| 2009/0198050 A1 | 8/2009 | Marsault et al. |
| 2009/0203530 A1 | 8/2009 | Liu et al. |
| 2009/0240027 A1 | 9/2009 | Marsault et al. |
| 2010/0152099 A1 | 6/2010 | Lee et al. |
| 2011/0059458 A1 | 3/2011 | Huang et al. |
| 2011/0190141 A1 | 8/2011 | Liu et al. |

FOREIGN PATENT DOCUMENTS

| | | |
|---|---|---|
| CA | 1340107 C | 10/1998 |
| EP | 125469 A1 | 11/1984 |
| EP | 292291 A2 | 11/1988 |
| JP | 03081293 A | 4/1991 |
| WO | WO-86/01516 A1 | 3/1986 |
| WO | WO-87/02676 A1 | 5/1987 |
| WO | WO-87/04623 A1 | 8/1987 |
| WO | WO-90/00564 A1 | 1/1990 |
| WO | WO-91/00736 A1 | 1/1991 |
| WO | WO-92/00091 A1 | 1/1992 |
| WO | WO-97/26014 A1 | 7/1997 |
| WO | WO-01/15673 A2 | 3/2001 |
| WO | WO-03/057722 A2 | 7/2003 |
| WO | WO-2005/020971 A1 | 3/2005 |
| WO | WO-2008/113095 A1 | 9/2008 |
| WO | WO-2009/047523 A1 | 4/2009 |

OTHER PUBLICATIONS

Bednarek et al. (2001) "Selective, high affinity peptide antagonists of alpha-melanotropin action at human melanocortin receptor 4: Their synthesis and biological evaluation in vitro," *Journal of Medicinal Chemistry* 44(22):3665-3672.
Giolitti et al. (2002) "Monocyclic human tachykinin NK-2 receptor antagonists as evolution of a potent bicyclic antagonist: QSAR and site-directed mutagenesis studies," *Journal of Medicinal Chemistry* 45(16):3418-3429.
International Search Report of the Patent Cooperation Treaty for PCT/US2009/054487, dated Feb. 15, 2010, 8 pages.
Miyazaki et al. (2004) "Design and synthesis of novel type somatostatin analogs with antiproliferative activities on A431 tumor cells," *Tetrahedron Letters* 45(33):6323-6327.
Rothe et al. (1976) "Makrocyclische Peptide in Anionischen Polymerisaten von Aminosaeure-N-Carbonsaeureanhydriden," *Angewandte Chemie* 88(10)338-339.

(Continued)

*Primary Examiner* — Julie Ha
(74) *Attorney, Agent, or Firm* — Goodwin Procter LLP

(57) ABSTRACT

Disclosed herein are macrocyclic compounds and methods for their synthesis and use. In particular, macrocyclic compounds are disclosed that modulate the activity of tumor necrosis factor alpha and/or are useful in the treatment of medical conditions, such as, rheumatoid arthritis, psoriasis, and asthma.

4 Claims, 1 Drawing Sheet

OTHER PUBLICATIONS

Schwyzer et al. (1956) "Synthesen zyklischer Polypeptide. c-Tetraglycyl and c-Hexaglycyl. Über aktivierte Ester VII," *Helvetica Chimica Acta* 39(3):872-883.

Sheh et al. (1985) "Cyclization studies of tetrapeptide homologs," *Tetrahedron Letters* 26(47):5755-5758.

Written Opinion of the International Searching Authority for PCT/US2009/054487, dated Feb. 15, 2010, 10 pages.

Bodmer et al. (2002) "The molecular architecture of the TNF superfamily," *Trends in Biochemical Sciences* 27(1):19-26.

Grieco et al. (2008) "Design and Microwave-Assisted Synthesis of Novel Macrocyclic Peptides Active at Melanocortin Receptors: Discovery of Potent and Selective hMC5R Receptor Antagonists," *Journal of Medicinal Chemistry* 5(19); 2701-2707.

Han et al. (2008) "Synthesis of Heterocyclic Residue Containing and Backbone Atypically Cyclized RGD Related Peptides," *Huaxue Xuebao* 66(2): 257-265, abstract only.

Mayorov et al. (2006) "Effects of Macrocycle Size and Rigidity on Melanocortin Receptor-1 and -5 Selectivity in Cyclic Lactam α-Melanocyte-Stimulating Hormone Analogs," *Chemical Biology& Drug Design* 67(5): 329-335.

Mayorov et al. (2008) "Structure-Activity Relationships of Cyclic Lactam Analogues of α-Melanocyte-Stimulating Hormone (α-MSH) Targeting the Human Melanocortin-3 Receptor," *Journal of Medicinal Chemistry* 51(2): 187-195.

Morita et al. (1996) "Cyclic Peptides From Higher Plants. 27. Configurational and Conformtional Analyses of a Cyclic Octapeptide, Lyciumin A, From Lycium Chinense Mill," *Tetrahedron* 52(8): 2795-2802, abstract only.

Morita et al. (2004) "Celogenamide A, A New Cyclic Peptide From the Seeds of Celosia Argentea," *Journal of Natural Products* 67(9): 1628-1630, abstract only.

Schmidt et al. (1992) "The Total Synthesis of Lyciumins A and B," *Journal of the Chemical Society, Chemical Communications* 18:1353-1354, abstract only.

Yahara et al.(1989) "Structures of Anti-ACE and -Renin Peptides From Lycii Radicis Cortex," *Tennen Yuki Kagobutsu Toronkai Koen Yoshishu* 31$^{st}$ : 633-640, abstract only.

Yahara et al.(1989) "Structures of Anti-ACE and -Renin Peptides From Lycii Radicis Cortex," *Tetrahedron Letters* 30(44): 6041-6042, abstract only.

Yahara et al. (1993) "Studies on the Solanaceous Plants. XXVI. Cyclic Peptides, Acyclic Diterpene Glycosides and Other Compounds from Lycium Chinense Mill," *Chemical & Pharmaceutical Bulletin* 41(4): 703-709, abstract only.

Ying et al. (2006) "Design, Synthesis, and Biological Evaluation of New Cyclic Melanotropin Peptide Analogues Selective for the Human Melanocortin-4 Receptor," *Journal of Medicinal Chemistry* 49(23): 6888-6896.

\* cited by examiner

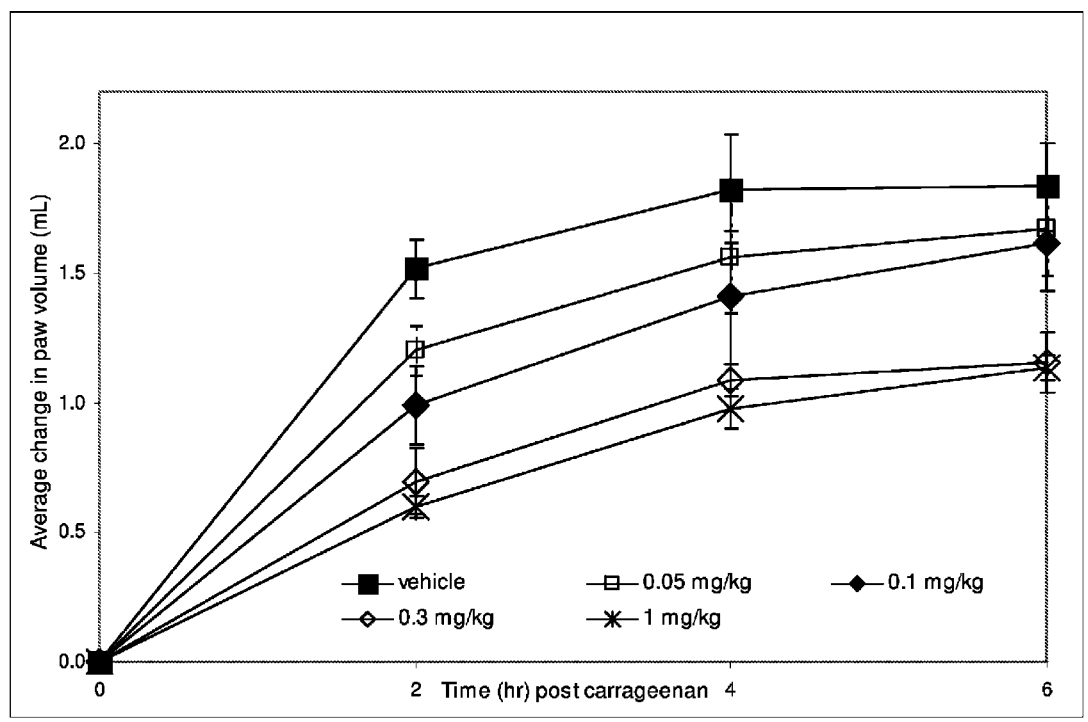

MACROCYCLIC COMPOUNDS FOR INHIBITION OF TUMOR NECROSIS FACTOR ALPHA

RELATED APPLICATIONS

This application claims the benefit of priority to U.S. Provisional Patent Application Ser. No. 61/090,410, filed Aug. 20, 2008; U.S. Provisional Patent Application Sero. 61/098,865, filed Sep. 22, 2008; and U.S. Provisional Patent Application Ser. No. 61/151,245, filed Feb. 10, 2009; the contents of each of which are hereby incorporated by reference.

FIELD OF THE INVENTION

The invention relates generally to macrocyclic compounds and their therapeutic use. More particularly, the invention relates to macrocyclic compounds that modulate the activity of tumor necrosis factor alpha and/or are useful in the treatment of medical conditions, such as rheumatoid arthritis, psoriasis, and asthma.

BACKGROUND OF THE INVENTION

Tumor necrosis factor alpha (TNF-alpha) is a pleiotropic inflammatory cytokine having a molecular weight of 17-26 kDa. This cytokine exists in a soluble form and a membrane-bound form, the active form usually being a homotrimer. TNF-alpha is produced in vivo by a variety of cell types. The primary producers of TNF-alpha are stimulated monocytes, fibroblasts, and endothelial cells. However, macrophages, T-cells, B-lymphocytes, granulocytes, smooth muscle cells, eosinophils, chondrocytes, osteoblasts, mast cells, glial cells, and keratinocytes also produce TNF-alpha after stimulation. Physiological stimuli for the synthesis of TNF-alpha include interleukin-1, bacterial endotoxins, platelet-derived growth factor (PDGF), and Oncostatin M. In fibroblasts, the synthesis of TNF-alpha is stimulated by beta-interferon, PDGF, and viral infections. In thymic stromal cells, the synthesis of TNF-alpha can be induced by nerve growth factor. TNF-alpha can also stimulate or inhibits its own synthesis, depending upon the cell type.

TNF-alpha affects many organs in the body and serves a variety of biological functions. For example, this cytokine possesses both growth stimulating properties and growth inhibiting properties. It also appears to have self regulatory properties. The varied biological impact of this cytokine makes it an attractive target for the development of compounds capable of modulating the activity of this physiologically important protein.

Thus, the need exists for new compounds that can modulate the activity of tumor necrosis factor alpha. The present invention fulfills this need and has other related advantages.

SUMMARY

The present invention provides macrocyclic compounds, methods of modulating the activity of tumor necrosis factor alpha, and methods for treating various medical conditions using such compounds. In one aspect, the invention provides a compound represented by formula I:

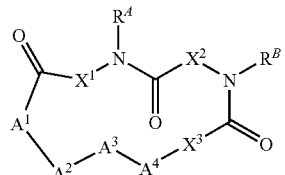

(I)

including pharmaceutically acceptable salts thereof, wherein the variables are as defined in the detailed description.

In another aspect, the invention provides a method of treating a patient suffering from or susceptible to a medical condition. The method comprises administering to the patient a therapeutically effective amount of a composition comprising a macrocyclic compound described herein. A number of medical conditions can be treated using the macrocyclic compounds described herein. For example, the compounds described herein may be used to treat rheumatoid arthritis, juvenile rheumatoid arthritis, ankylosing spondylitis, psoriatic arthritis, psoriasis, Crohn's disease, Behcet's disease, ulcerative colitis, Wegener's granulomatosis, sarcoidosis, systemic lupus erythematosus, systemic sclerosis, insulin-dependent diabetes mellitus, cancer, multiple sclerosis, septic shock syndrome, asthma, Alzheimer's disease, an inflammatory eye disease, uveitis, and inflammation. The therapeutic methods embrace combination therapies, such as co-administration of a macrocyclic compound together with a therapeutically effective amount of an anti-inflammatory agent or a therapeutic agent for the treatment of any of the aforementioned diseases, including multiple sclerosis.

In another aspect, the invention provides a method of modulating the activity of tumor necrosis factor alpha on a cell comprising a receptor for tumor necrosis factor alpha on its surface. The method comprises exposing the cell to a compound described herein. In an embodiment, the receptor is on the surface of a mammalian cell.

The foregoing and other aspects and embodiments of the invention may be more fully understood by reference to the following detailed description and claims.

BRIEF DESCRIPTION OF THE DRAWINGS

FIG. 1 depicts the effect of various doses of a compound of this invention on paw volume in a rat paw edema model.

DETAILED DESCRIPTION OF THE INVENTION

The present invention provides macrocyclic compounds, methods of modulating the activity of tumor necrosis factor alpha, and methods for treating various medical conditions using such compounds. The practice of the present invention employs, unless otherwise indicated, conventional techniques of organic chemistry, pharmacology, and biochemistry. For example, procedures for synthesizing organic compounds are described in the literature, such as "Comprehensive Organic Synthesis" (B. M. Trost & I. Fleming, eds., 1991-1992). Various aspects of the invention are set forth below in sections; however, aspects of the invention described in one particular section are not to be limited to any particular section. Further, when a variable is not accompanied by a definition, the previous definition of the variable controls.

I. Macrocyclic Compounds

In one aspect, the invention provides a compound represented by formula I:

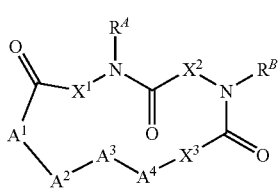

(I)

including pharmaceutically acceptable salts thereof, wherein $X^1$, $X^2$, and $X^3$ are each independently —C($R^1$)($R^2$)— or —C($R^1$)($R^2$)—C($R^3$)($R^4$)—;

$R^1$, $R^2$, $R^3$, and $R^4$ each represent independently for each occurrence hydrogen, deuterium, —($C_1$-$C_6$)-alkyl, —($C_2$-$C_6$)-alkenyl, —($C_2$-$C_6$)-alkynyl, —($C_1$-$C_6$)-alkyl-heterocyclyl, —($C_2$-$C_6$)-alkenyl-heterocyclyl, —($C_2$-$C_6$)-alkynyl-heterocyclyl, —($C_1$-$C_6$)-alkyl-biphenyl, —($C_1$-$C_6$)-alkyl-carbocyclyl, —($C_2$-$C_6$)-alkenyl-carbocyclyl, —($C_2$-$C_6$)-alkynyl-carbocyclyl, —O—($C_1$-$C_6$)-alkyl, —O—($C_2$-$C_6$)-alkenyl, —O—($C_2$-$C_6$)-alkynyl, —O—($C_1$-$C_6$)-alkyl-heterocyclyl, —O—($C_2$-$C_6$)-alkenyl-heterocyclyl, —O—($C_1$-$C_6$)-alkynyl-heterocyclyl, —O—($C_1$-$C_6$)-alkyl-carbocyclyl, —O—($C_2$-$C_6$)-alkenyl-carbocyclyl, —O—($C_2$-$C_6$)-alkynyl-carbocyclyl, -heterocyclyl, or -carbocyclyl, and, when $R^1$ is bound to the same carbon atom as $R^{10}$, $R^1$ is additionally selected from —$CO_2$—($C_1$-$C_6$)-alkyl, wherein $R^1$, $R^2$, $R^3$, and $R^4$ are optionally substituted with up to three substituents independently selected from the group consisting of halogen, —$NO_2$, —NHC(=NH)$NH_2$, $R^5$, halo-substituted $R^5$, —C(O)—$R^5$, —C(O)O$R^5$, —CN, —O$R^5$, —C(O)N($R^5$)($R^6$), —N($R^5$)($R^6$), —S$R^5$, —NHC(O)O$R^5$, —NHC(O)$R^5$, —NHC(O)N($R^5$)($R^6$), —NHS(O)$_2$$R^5$, —OC(O)$R^5$, —OC(O)N($R^5$)($R^6$), —S(O)$_2$N($R^5$)($R^6$), and —$SO_2$—($C_1$-$C_6$)-alkyl;

$R^5$ and $R^6$ each represent independently for each occurrence deuterium, hydrogen, heterocyclyl, carbocyclyl, —($C_1$-$C_4$)-alkyl, —($C_2$-$C_4$)-alkenyl, —($C_2$-$C_4$)-alkynyl, —($C_1$-$C_4$)-alkyl-heterocyclyl, —($C_2$-$C_4$)-alkynyl-heterocyclyl, —($C_2$-$C_4$)-alkynyl-heterocyclyl, —($C_2$-$C_4$)-alkenyl-carbocyclyl, —($C_2$-$C_4$)-alkynyl-carbocyclyl, or —($C_1$-$C_4$)-alkyl-carbocyclyl; or $R^5$ and $R^6$, are taken together with the nitrogen atom to which they are both attached to form a heterocyclic ring; and any ring in $R^5$ or $R^6$, or formed by $R^5$ and $R^6$, is optionally substituted with up to two substituents independently selected from the group consisting of halogen, —($C_1$-$C_4$)-alkyl, —O—($C_1$-$C_4$)-alkyl, —C(O)aryl, —C(O)($C_1$-$C_4$)alkyl, —S(O)$_2$aryl, —S(O)$_2$($C_1$-$C_4$)alkyl, —$CO_2$H, —C(O)N(H)aryl, —C(O)N(H)($C_1$-$C_4$)alkyl, —OH, =O, —$N_3$, —$NH_2$, —N(H)(($C_1$-$C_4$)-alkyl), and —N(($C_1$-$C_4$)-alkyl)$_2$;

$R^A$ and $R^B$ each represent independently hydrogen, deuterium, —($C_1$-$C_4$)-alkyl, —($C_1$-$C_4$)-alkyl-heterocyclyl, —($C_1$-$C_4$)-alkyl-carbocyclyl, -heterocyclyl, or -carbocyclyl, wherein $R^A$ and $R^B$ are optionally substituted with up to three substituents independently selected from the group consisting of deuterium, halogen, —$NO_2$, —N(H)C(=NH)$NH_2$, $R^5$, halo-substituted $R^5$, —C(O)—$R^5$, —C(O)O$R^5$, —O$R^5$, —C(O)N($R^5$)($R^6$), —OC(O)($R^5$), —OC(O)N($R^5$)($R^6$), —N($R^5$)($R^6$), —S$R^5$, —N(H)C(O)O$R^5$, —N(H)C(O)$R^5$, —N(H)C(O)N($R^5$)($R^6$), —N(H)S(O)$_2$$R^5$, and —S(O)$_2$N($R^5$)($R^6$); or $R^A$ or $R^B$ and an occurrence of $R^1$, $R^2$, $R^3$, or $R^4$; when said $R^1$, $R^2$, $R^3$, or $R^4$ is attached to a carbon atom adjacent a nitrogen atom to which said $R^A$ or $R^B$ is attached; are taken together with the carbon atom and the nitrogen atom to form a heterocyclic ring optionally substituted with up to three substituents independently selected from group consisting of deuterium, halogen, —$NO_2$, —NHC(=NH)$NH_2$, $R^5$, halo-substituted $R^5$, —C(O)—$R^5$, —C(O)O$R^5$, —O$R^5$, —C(O)N($R^5$)($R^6$), —OC(O)($R^5$), —OC(O)N($R^5$)($R^6$), —N($R^5$)($R^6$), —S$R^5$, —N(H)C(O)O$R^5$, —N(H)C(O)$R^5$, —N(H)C(O)N($R^5$)($R^6$), —N(H)S(O)$_2$$R^5$ and —S(O)$_2$N($R^5$)($R^6$);

$A^1$ is —(N$R^7$)—($CH_2$)$_n$-† or —(N$R^7$)—($CH_2$)$_n$—(Y)$_p$—($CH_2$)$_n$†, wherein $R^7$ is hydrogen, deuterium, —($C_1$-$C_4$)-alkyl, —($C_1$-$C_4$)-alkyl-heterocyclyl, —($C_1$-$C_4$)-alkyl-carbocyclyl, -heterocyclyl, or -carbocyclyl, wherein $R^7$ is optionally substituted with up to three substituents independently selected from the group consisting of deuterium, halogen, —$NO_2$, —N(H)C(=NH)$NH_2$, $R^5$, halo-substituted $R^5$, —C(O)—$R^5$, —C(O)O$R^5$, —O$R^5$, —C(O)N($R^5$)($R^6$), —OC(O)($R^5$), —OC(O)N($R^5$)($R^6$), —N($R^5$)($R^6$), —S$R^5$, —N(H)C(O)O$R^5$, —N(H)C(O)$R^5$, —N(H)C(O)N($R^5$)($R^6$), —N(H)S(O)$_2$$R^5$, and —S(O)$_2$N($R^5$)($R^6$);

Y represents independently for each occurrence carbocyclyl or heterocyclyl;

n represents independently for each occurrence 0, 1, 2, 3, 4, or 5;

p is 1 or 2;

"†" represents the portion of $A^1$ attached to $A^2$; and one —$CH_2$— unit in $A^1$ is replaced with

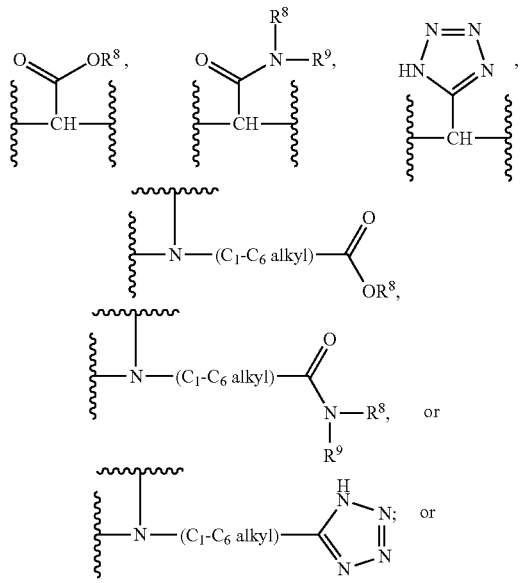

the —N$R^7$ unit in $A^1$ is replaced with

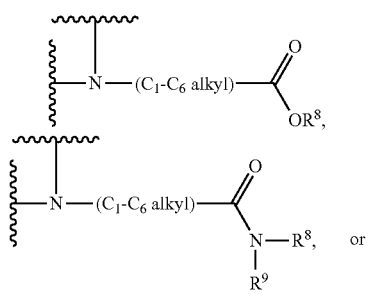

-continued

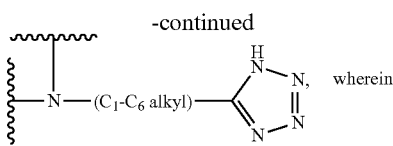 wherein

R$^8$ is hydrogen, deuterium, —(C$_1$-C$_6$)-alkyl, —(C$_1$-C$_6$)-alkyl-carbocyclyl or —(C$_1$-C$_6$)-alkyl-heterocyclyl, wherein the alkyl, carbocyclyl, or heterocyclyl portion of R$^8$ is optionally substituted;

R$^9$ is hydrogen, deuterium, —(C$_1$-C$_6$)-alkyl, —(C$_1$-C$_6$)-alkyl-O—(C$_1$-C$_6$)-alkyl, —(C$_1$-C$_6$)-alkyl-OH, —(CH$_2$)$_t$—C(R$^1$)(R$^{10}$)—(CH$_2$)$_t$—COOH, —(CH$_2$)$_t$—C(R$^1$)(R$^{10}$)—(CH$_2$)$_t$—SO$_3$H, —(CH$_2$)$_t$—C(R$^1$)(R$^{10}$)—(CH$_2$)$_t$—C(O)—NH—(CH$_2$)$_t$—C(R$^1$)(R$^{10}$)—SO$_3$H, —(CH$_2$)$_t$—C(R$^1$)(R$^{10}$)—(CH$_2$)$_t$—C(O)—NH—(CH$_2$)$_t$—C(R$^1$)(R$^{10}$)—COOH, —S(O)$_2$R$^5$, —(C$_1$-C$_6$)-alkyl-N(H)S(O)$_2$-carbocyclyl, a carbocyclyl or a heterocyclyl, wherein the —(C$_1$-C$_6$)-alkyl-N(H)S(O)$_2$-carbocyclyl, carbocyclyl or heterocyclyl is optionally substituted with up to three substituents independently selected from the group consisting of deuterium, halogen, —(C$_1$-C$_4$)-alkyl, —O—(C$_1$-C$_4$)-alkyl, —OH, =O, —CO$_2$H, —NH$_2$, —NH((C$_1$-C$_4$)-alkyl), and —N((C$_1$-C$_4$)-alkyl)$_2$; or R$^8$ and R$^9$, taken together with the nitrogen atom to which they are attached to form a heterocyclic ring optionally substituted with up to three substituents independently selected from the group consisting of halogen, —NO$_2$, —NHC(=NH)NH$_2$, R$^5$, halo-substituted R$^5$, —C(O)—R$^5$, —C(O)OR$^5$, —OR$^5$, —C(O)N(R$^5$)(R$^6$), —N(R$^5$)(R$^6$), —SR$^5$, —N(H)C(O)OR$^5$, —N(H)C(O)R$^5$, —N(H)C(O)N(R$^5$)(R$^6$), —N(H)S(O)$_2$R$^5$ and —S(O)$_2$N(R$^5$)(R$^6$);

t represents independently for each occurrence 0, 1, or 2;

each R$^{10}$ represents independently for each occurrence hydrogen, deuterium, —(C$_1$-C$_6$)-alkyl, —(C$_1$-C$_6$)-alkyl-heterocyclyl, —(C$_1$-C$_6$)-alkyl-carbocyclyl, —CO$_2$—(C$_1$-C$_6$)-alkyl, -heterocyclyl, or -carbocyclyl; wherein R$^{10}$ is optionally substituted with —(C$_1$-C$_4$)-alkyl, fluorine-substituted-(C$_1$-C$_4$)-alkyl, —C(O)—(C$_1$-C$_4$)-alkyl, —CN, —C(O)OH, —C(O)—O—(C$_1$-C$_4$)-alkyl, —C(O)(C$_1$-C$_4$)alkyl, —OH, —C(O)NH$_2$, —NO$_2$, —NH$_2$, —N(H)((C$_1$-C$_4$)-alkyl), —N((C$_1$-C$_4$)-alkyl)$_2$, —N(H)C(=NH)NH$_2$, —SCH$_3$, —SH, —N(H)C(O)—(C$_1$-C$_4$)-alkyl, —N(H)C(O)—(C$_1$-C$_4$)-alkyl-C(O)NH$_2$, or —N(H)C(O)O—(C$_1$-C$_4$)-alkyl; or R$^1$ and R$^{10}$ bound to a common carbon atom are taken together with the carbon atom to form a 3-7 membered cycloalkane ring;

A$^2$ is a bond, —O—, —NH—, —C(O)—, —NHC(O)-‡, —NHC(O)(CH$_2$)—O-‡, —C(O)NH-‡, —C(O)O-‡, or —OC(O)-‡, wherein "‡" represents the portion of A$^2$ attached to A$^3$;

A$^3$ is —(CR$^{11}$R$^{12}$)$_m$— or —(CR$^{11}$R$^{12}$)$_m$—C(O)-*, wherein

"*" represents the portion of A$^3$ attached to A$^4$;

m is 1, 2, 3, 4, 5, or 6; and

R$^{11}$ and R$^{12}$ each represent independently for each occurrence hydrogen, deuterium, R$^{13}$, —OH, —OR$^{13}$, —OC(O)R$^{13}$, —NH$_2$, —(C$_1$-C$_6$)-alkyl-NH$_2$, —NH(C$_1$-C$_6$)-alkyl, —N((C$_1$-C$_6$)-alkyl)$_2$, —N(H)S(O)$_2$—R$^{13}$, —N(H)C(O)—R$^{13}$, —N(H)C(O)—OR$^{13}$, or —N(H)C(O)—N(H)R$^{13}$; or R$^{11}$ and R$^{12}$ are taken together with the carbon atom or carbon atoms to which they are attached to form a carbocyclyl or a heterocyclyl;

R$^{13}$ is —(C$_1$-C$_6$)-alkyl, —(C$_1$-C$_6$)-alkyl-CO$_2$H, aryl, or —(C$_1$-C$_6$)-alkyl-aryl; and A$^4$ is a bond, —O—, —S—, or —N(R$^{14}$)—, wherein R$^{14}$ is hydrogen, deuterium, —(C$_1$-C$_4$)-alkyl, —(C$_1$-C$_4$)-alkyl-heterocyclyl, —(C$_1$-C$_4$)-alkyl-carbocyclyl, -heterocyclyl, or -carbocyclyl, wherein R$^{14}$ is optionally substituted with up to three substituents independently selected from the group consisting of deuterium, halogen, —NO$_2$, —N(H)C(=NH)NH$_2$, R$^5$, halo-substituted R$^5$, —C(O)—R$^5$, —C(O)OR$^5$, —OR$^5$, —C(O)N(R$^5$)(R$^6$), —OC(O)(R$^5$), —OC(O)N(R$^5$)(R$^6$), —N(R$^5$)(R$^6$), —SR$^5$, —N(H)C(O)OR$^5$, —N(H)C(O)R$^5$, —N(H)C(O)N(R$^5$)(R$^6$), —N(H)S(O)$_2$R$^5$, and —S(O)$_2$N(R$^5$)(R$^6$); and R$^{15}$ and R$^{16}$ each represent independently hydrogen, C$_1$-C$_4$ alkyl, or —C(O)—O—C$_1$-C$_4$ alkyl.

In certain embodiments, the compound is not

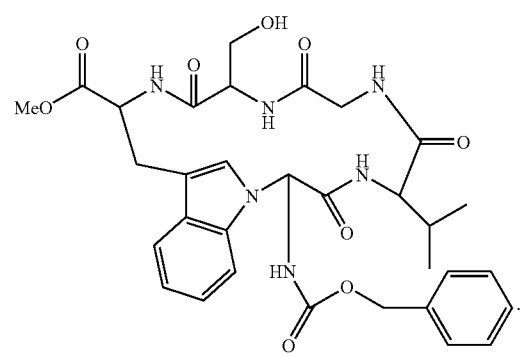

In certain other embodiments, Y is carbocyclyl. In certain other embodiments, A$^2$ is —O—, —NH—, —C(O)—, —NHC(O)-‡, —NHC(O)(CH$_2$)—O-‡, —C(O)NH-‡, —C(O)O-‡, or —OC(O)-‡. In certain other embodiments, Y is aryl, and A$^2$ is —O—, —NH—, —C(O)—, —NHC(O)-‡, —NHC(O)(CH$_2$)—O-‡, —C(O)NH-‡, —C(O)O-‡, or —OC(O)-‡.

In another aspect, the invention provides a compound represented by formula Ia:

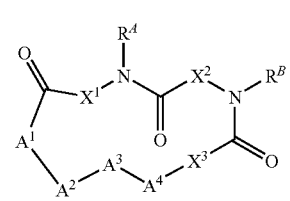

including pharmaceutically acceptable salts thereof, wherein X$^1$, X$^2$, and X$^3$ are each independently —C(R$^1$)(R$^2$)— or —C(R$^1$)(R$^2$)—C(R$^3$)(R$^4$)—;

R$^1$, R$^2$, R$^3$, and R$^4$ each represent independently for each occurrence hydrogen, —(C$_1$-C$_6$)-alkyl, —(C$_1$-C$_6$)-alkyl-heterocyclyl, —(C$_2$-C$_6$)-alkenyl-heterocyclyl, —(C$_1$-C$_6$)-alkyl-biphenyl, —(C$_1$-C$_6$)-alkyl-carbocyclyl, —(C$_2$-C$_6$)-alkenyl-carbocyclyl, -heterocyclyl, or -carbocyclyl, and, when R$^1$ is bound to the same carbon atom as R$^{10}$, R$^1$ is additionally selected from —CO$_2$—(C$_1$-C$_6$)-alkyl, wherein R$^1$, R$^2$, R$^3$, and R$^4$ are optionally substituted with up to three substituents independently selected from the group consisting of halogen, —NO$_2$, —CN, —N(H)C (=NH)NH$_2$, R$^5$, halo-substituted R$^5$, —C(O)—R$^5$, —C(O)OR$^5$, —OR$^5$, —C(O)N(R$^5$)(R$^6$), —N(R$^5$)(R$^6$), —SR$^5$, —N(H)C(O)OR$^5$, —N(H)C(O)R$^5$, —N(H)C(O)N(R$^5$)(R$^6$), —N(H)S(O)$_2$R$^5$, —OC(O)R$^5$, —OC(O)N(R$^5$)(R$^6$) and —S(O)$_2$N(R$^5$)(R$^6$);

R$^5$ and R$^6$ each represent independently for each occurrence hydrogen, heterocyclyl, carbocyclyl, —(C$_1$-C$_4$)-alkyl, —(C$_1$-C$_4$)-alkyl-heterocyclyl, or —(C$_1$-C$_4$)-alkyl-carbocyclyl, or R$^5$ and R$^6$ are taken together with the nitrogen atom to which they are both attached to form a heterocyclic ring; and any ring in R$^5$ or R$^6$, or formed by R$^5$ and R$^6$, is optionally substituted with up to two substituents independently selected from the group consisting of halogen, —(C$_1$-C$_4$)-alkyl, —O—(C$_1$-C$_4$)-alkyl, —C(O)aryl, —C(O)(C$_1$-C$_4$)alkyl, —S(O)$_2$aryl, —S(O)$_2$(C$_1$-C$_4$)alkyl, —CO$_2$H, —C(O)N(H)aryl, —C(O)N(H)(C$_1$-C$_4$)alkyl, —OH, =O, —N$_3$, —NH$_2$, —N(H)((C$_1$-C$_4$)-alkyl), and —N((C$_1$-C$_4$)-alkyl)$_2$;

R$^A$ and R$^B$ each represent independently hydrogen, —(C$_1$-C$_4$)-alkyl, —(C$_1$-C$_4$)-alkyl-heterocyclyl, —(C$_1$-C$_4$)-alkyl-carbocyclyl, -heterocyclyl, or -carbocyclyl; wherein R$^A$ and R$^B$ are optionally substituted with up to three substituents independently selected from the group consisting of halogen, R$^5$, halo-substituted R$^5$, —OR$^5$, —C(O)N(R$^5$)(R$^6$), —OC(O)(R$^5$), —OC(O)N(R$^5$)(R$^6$), —N(R$^5$)(R$^6$), —N(H)C(O)OR$^5$, —N(H)C(O)R$^5$, —N(H)C(O)N(R$^5$)(R$^6$), —N(H)S(O)$_2$R$^5$ and —S(O)$_2$N(R$^5$)(R$^6$); or R$^A$ or R$^B$ and an occurrence of R$^1$, R$^2$, R$^3$, or R$^4$; when said R$^1$, R$^2$, R$^3$, or R$^4$ is attached to a carbon atom adjacent a nitrogen atom to which said R$^A$ or R$^B$ is attached; are taken together with the carbon atom and the nitrogen atom to form a heterocyclic ring optionally substituted with up to three substituents independently selected from the group consisting of halogen, R$^5$, halo-substituted R$^5$, —C(O)—R$^5$, —C(O)OR$^5$, —OR$^5$, —C(O)N(R$^5$)(R$^6$), —OC(O)(R$^5$), —OC(O)N(R$^5$)(R$^6$), —SR$^5$, —N(H)C(O)OR$^5$, —N(H)C(O)R$^5$, —N(H)C(O)N(R$^5$)(R$^6$), —N(H)S(O)$_2$R$^5$ and —S(O)$_2$N(R$^5$)(R$^6$);

A$^1$ is —(NR$^7$)—(CH$_2$)$_n$-† or —(NR$^7$)—(CH$_2$)$_n$—(Y)$_p$—(CH$_2$)$_n$-†, wherein Y represents independently for each occurrence carbocyclyl or heterocyclyl;

n represents independently for each occurrence 0, 1, 2, 3, or 4;

p is 1 or 2;

"†" represents the portion of A$^1$ attached to A$^2$; and one —CH$_2$— unit in A$^1$ is replaced with

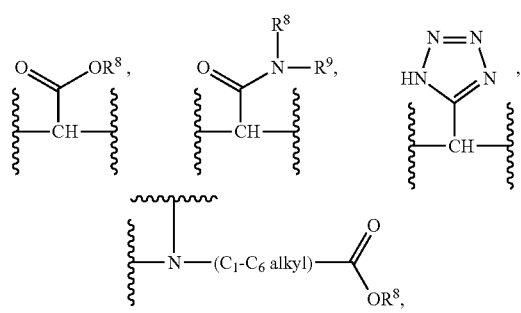

-continued

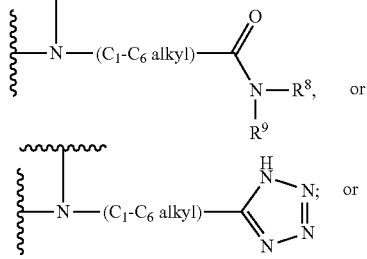

the —NR$^7$ unit in A$^1$ is replaced with

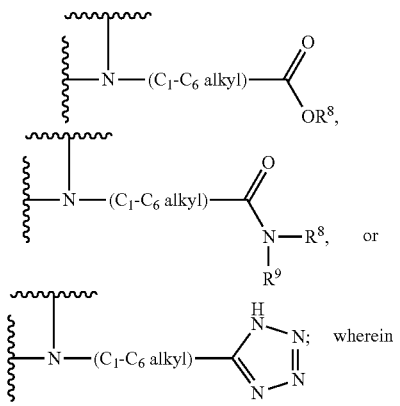

R$^8$ is hydrogen, —(C$_1$-C$_6$)-alkyl, —(C$_1$-C$_6$)-alkyl-carbocyclyl or —(C$_1$-C$_6$)-alkyl-heterocyclyl, wherein the alkyl, carbocyclyl, or heterocyclyl portion of R$^8$ is optionally substituted;

R$^9$ is hydrogen, —(C$_1$-C$_6$)-alkyl, —(C$_1$-C$_6$)-alkyl-O—(C$_1$-C$_6$)-alkyl, —(C$_1$-C$_6$)-alkyl-OH, —(CH$_2$)$_t$—C(R$^1$)(R$^{10}$)—(CH$_2$)$_t$—COOH, —(CH$_2$)$_t$—C(R$^1$)(R$^{10}$)—(CH$_2$)$_t$—SO$_3$H, —(CH$_2$)$_t$—C(R$^1$)(R$^{10}$)—(CH$_2$)$_t$—C(O)—NH—(CH$_2$)$_t$—C(R$^1$)(R$^{10}$)—SO$_3$H, —S(O)$_2$R$^5$, a carbocyclyl or a heterocyclyl, wherein the carbocyclyl or heterocyclyl is optionally substituted with up to three substituents independently selected from the group consisting of halogen, —(C$_1$-C$_4$)-alkyl, —O—(C$_1$-C$_4$)-alkyl, —C(O)OH, —C(O)(C$_1$-C$_4$)alkyl, —OH, =O, —NH$_2$, —NH((C$_1$-C$_4$)-alkyl), and —N((C$_1$-C$_4$)-alkyl)$_2$; or R$^8$ and R$^9$, when taken together with the nitrogen atom to which they are attached, form a heterocyclic ring optionally substituted with up to three substituents independently selected from the group consisting of halogen, R$^5$, halo-substituted R$^5$, —C(O)—R$^5$, —C(O)OR$^5$, —OR$^5$, —C(O)N(R$^5$)(R$^6$), —N(R$^5$)(R$^6$), —SR$^5$, —NHC(O)R$^5$, and —NHC(O)N(R$^5$)(R$^6$);

t represents independently for each occurrence 0, 1, or 2; and

R$^{10}$ represents independently for each occurrence hydrogen, —(C$_1$-C$_6$)-alkyl, —(C$_1$-C$_6$)-alkyl-heterocyclyl, —(C$_1$-C$_6$)-alkyl-carbocyclyl, —CO$_2$—(C$_1$-C$_6$)-alkyl, -heterocyclyl, or -carbocyclyl, wherein R$^{10}$ is optionally substituted with —(C$_1$-C$_4$)-alkyl, fluorine-substituted-(C$_1$-C$_4$)-alkyl, —C(O)—(C$_1$-C$_4$)-alkyl, —CN, —C(O)OH, —OH, —C(O)NH$_2$, —NH$_2$, —NH((C$_1$-C$_4$)-alkyl), —N((C$_1$-C$_4$)-alkyl)$_2$, or —NH—C(O)—(C$_1$-C$_4$)-alkyl, or $R^1$ and $R^{10}$ bound to a common carbon atom are taken together with the carbon atom to form a 3-7 membered cycloalkane ring;

$A^2$ is a bond, —O—, —NH—, —C(O)—, —NHC(O)-‡, —C(O)NH-‡, —C(O)O-‡, or —OC(O)-‡, wherein "‡" represents the portion of $A^2$ bound to $A^3$;

$A^3$ is —$(CR^{11}R^{12})_m$—C(O)-*, wherein
"*" represents the portion of $A^3$ bound to $A^4$;

m is 1, 2, 3, 4, 5, or 6; and $R^{11}$ and $R^{12}$ each represent independently for each occurrence hydrogen, deuterium, $R^{13}$, —OH, —$OR^{13}$, —OC(O)$R^{13}$, —$NH_2$, —$(C_1-C_6)$-alkyl-$NH_2$, —NH$(C_1-C_6)$-alkyl, —N$((C_1-C_6)$-alkyl$)_2$, —N(H)S(O)$_2$—$R^{13}$, —N(H)C(O)—$R^{13}$, —N(H)C(O)—$OR^{13}$, and —N(H)C(O)—N(H)$R^{13}$; or $R^{11}$ and $R^{12}$, when taken together with the carbon atom or carbon atoms to which they are attached, form a carbocyclyl or a heterocyclyl;

$R^{13}$ is —$(C_1-C_6)$-alkyl, aryl or —$(C_1-C_6)$-alkyl-aryl; and $A^4$ is a bond, —O—, —S—, or —N($R^{14}$)—, wherein $R^{14}$ is hydrogen, deuterium, —$(C_1-C_4)$-alkyl, —$(C_1-C_4)$-alkyl-heterocyclyl, —$(C_1-C_4)$-alkyl-carbocyclyl, -heterocyclyl, or -carbocyclyl, wherein $R^{14}$ is optionally substituted with up to three substituents independently selected from the group consisting of deuterium, halogen, —$NO_2$, —N(H)C(=NH)$NH_2$, $R^5$, halo-substituted $R^5$, —C(O)—$R^5$, —C(O)O$R^5$, —$OR^5$, —C(O)N($R^5$)($R^6$), —OC(O)($R^5$), —OC(O)N($R^5$)($R^6$), —N($R^5$)($R^6$), —S$R^5$, —N(H)C(O)O$R^5$, —N(H)C(O)$R^5$, —N(H)C(O)N($R^5$)($R^6$), —N(H)S(O)$_2$$R^5$, and —S(O)$_2$N($R^5$)($R^6$).

In certain embodiments, the compound is not

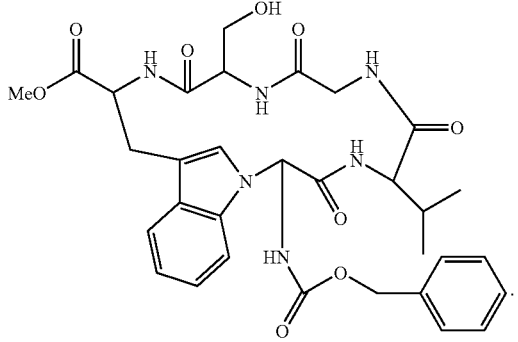

In certain other embodiments, Y is carbocyclyl. In certain other embodiments, $A^2$ is —O—, —NH—, —C(O)—, —NHC(O)-‡, —NHC(O)(CH$_2$)—O-‡, —C(O)NH-‡, —C(O)O-‡, or —OC(O)-‡. In certain other embodiments, Y is aryl, and $A^2$ is —O—, —NH—, —C(O)—, —NHC(O)-‡, —NHC(O)(CH$_2$)—O-‡, —C(O)NH-‡, —C(O)O-‡, or —OC(O)-‡.

In certain instances, $R^1$, $R^2$, $R^3$, and $R^4$ each represent independently for each occurrence hydrogen, —$(C_1-C_4)$-alkyl, —$(C_1-C_2)$-alkyl-heterocyclyl, —$(C_1-C_3)$-alkyl-biphenyl, —$(C_1-C_3)$-alkyl-carbocyclyl, or -carbocyclyl, and, when $R^1$ is bound to the same carbon atom as $R^{10}$, $R^1$ is additionally selected from —$CO_2$—$(C_1-C_6)$-alkyl, wherein each of $R^1$, $R^2$, $R^3$, and $R^4$ are independently substituted with up to three substituents selected from the group consisting of halogen, —$NO_2$, —NHC(=NH)$NH_2$, $R^5$, halo-substituted $R^5$, —C(O)—$R^5$, —C(O)O$R^5$, —$OR^5$, —N($R^5$)($R^6$), —N(H)C(O)$R^5$, —N(H)C(O)O$R^5$, —N(H)C(O)N($R^5$)($R^6$), and —N(H)S(O)$_2$$R^5$; wherein $R^5$ and $R^6$ each represent independently for each occurrence hydrogen, heterocyclyl, carbocyclyl, —$(C_1-C_4)$-alkyl, —$(C_1-C_4)$-alkyl-heterocyclyl, carbocyclyl, or —$(C_1-C_4)$-alkyl-carbocyclyl;

$R^A$ and $R^B$ each represent independently hydrogen, $(C_1-C_4)$-alkyl, —$(C_1-C_4)$-alkyl-heterocyclyl, —$(C_1-C_4)$-alkyl-carbocyclyl, -heterocyclyl, or -carbocyclyl, wherein $R^A$ and $R^B$ are optionally substituted with up to three substituents independently selected from the group consisting of halogen, $R^5$, halo-substituted $R^5$, and —$OR^5$; or $R^A$ or $R^B$ and an occurrence of $R^1$, $R^2$, $R^3$, or $R^4$; when said $R^1$, $R^2$, $R^3$, or $R^4$ is attached to a carbon atom adjacent a nitrogen atom to which said $R^A$ or $R^B$ is attached; are taken together with the carbon atom and the nitrogen atom to form a heterocyclic ring optionally substituted with up to three substituents independently selected from the group consisting of halogen, $R^5$, and halo-substituted $R^5$;

$A^1$ is —(N$R^7$)—(CH$_2$)$_n$—(Y)$_p$—(CH$_2$)$_n$-†, wherein

Y represents independently for each occurrence carbocyclyl or heterocyclyl;

n represents independently for each occurrence 0, 1, 2, 3, or 4;

p is 1 or 2;

"†" represents the portion of $A^1$ attached to $A^2$; and one —CH$_2$— unit in $A^1$ is replaced with

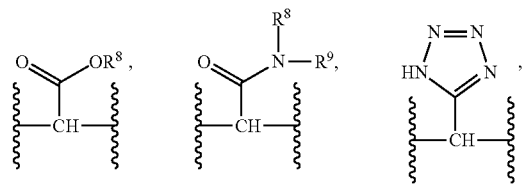

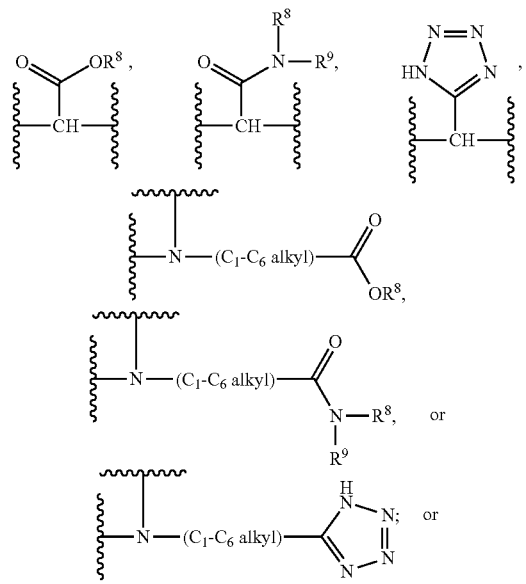

the —N$R^7$ unit in $A^1$ is replaced with

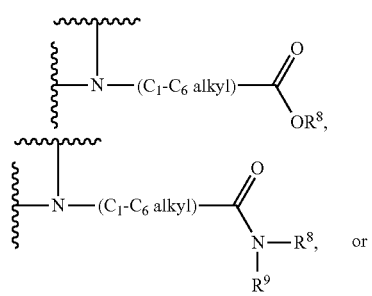

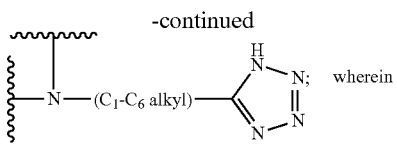

R⁸ is hydrogen, —(C₁-C₆)-alkyl, or —(C₁-C₆)-alkyl-carbocyclyl;

R⁹ is hydrogen, —(C₁-C₆)-alkyl, —(C₁-C₆)-alkyl-OH, —(CH₂)ₜ—C(R¹)(R¹⁰)—(CH₂)ₜ—COOH, —(CH₂)ₜ—C(R¹)(R¹⁰)—(CH₂)ₜ—SO₃H, —(CH₂)ₜ—C(R¹)(R¹⁰)—(CH₂)ₜ—C(O)—NH—(CH₂)ₜ—C(R¹)(R¹⁰)—SO₃H, —S(O)₂R⁵, a carbocyclyl or a heterocyclyl; wherein the carbocyclyl or heterocyclyl is optionally substituted with up to three substituents independently selected from the group consisting of halogen, —(C₁-C₄)-alkyl, —O—(C₁-C₄)-alkyl, —C(O)OH, —C(O)(C₁-C₄)alkyl, —OH, =O, —NH₂, —NH((C₁-C₄)-alkyl), or —N((C₁-C₄)-alkyl)₂; or R⁸ and R⁹, when taken together with the nitrogen atom to which they are attached, form an optionally substituted heterocyclic ring;

t represents independently for each occurrence 0, 1, or 2; and

R¹⁰ represents independently for each occurrence hydrogen, —(C₁-C₆)-alkyl, —(C₁-C₆)-alkyl-carbocyclyl, —(C₁-C₆)-alkyl-heterocyclyl, or —CO₂—(C₁-C₆)-alkyl, or R¹ and R¹⁰ bound to a common carbon atom are taken together with the carbon atom to form a 3-7 membered cycloalkane ring;

A² is a bond, —O—, —NH—, —C(O)—, —NHC(O)-‡, —C(O)NH-‡, —C(O)O-‡, or —OC(O)-‡, wherein "‡" represents the portion of A² bound to A³;

A³ is —(CR¹¹R¹²)ₘ— or —(CR¹¹R¹²)ₘ—C(O)-*, wherein

"*" represents the portion of A³ bound to A⁴;

m is 1, 2, 3, 4, 5, or 6;

R¹¹ and R¹² each represent independently for each occurrence hydrogen, —OH, —OC(O)R¹³, —NH₂, —(C₁-C₆)-alkyl-NH₂, —N(H)(C₁-C₆)-alkyl, —N((C₁-C₆)-alkyl)₂, —N(H)S(O)₂—R¹³, —N(H)C(O)—R¹³, —N(H)C(O)—N(H)R¹³, or —N(H)C(O)—OR¹³, or R¹¹ and R¹², when taken together with the carbon atom or carbon atoms to which they are attached, form a carbocyclyl or a heterocyclyl;

R¹³ is —(C₁-C₆)-alkyl, aryl or —(C₁-C₆)-alkyl-aryl; and

A⁴ is a bond, —O—, —S—, or —N(R¹⁴)—, wherein

R¹⁴ is hydrogen, (C₁-C₄)-alkyl, —(C₁-C₄)-alkyl-heterocyclyl, —(C₁-C₄)-alkyl-carbocyclyl, -heterocyclyl, or -carbocyclyl, wherein Rᴬ and Rᴮ are optionally substituted with up to three substituents independently selected from the group consisting of halogen, R⁵, halo-substituted R⁵, and —OR⁵.

In certain instances, A³ is —(C₁-C₄)-alkyl-C(O)-*, —(C₃-C₇-cycloalkyl)-C(O)-*, —CH₂CH(NH₂)—C(O)-*, —CH(OH)—CH(OH)—C(O)-*, or —CH(OAc)—CH(OAc)—C(O)-*. In certain other instances, A³ is —CH₂—CH₂—C(O)-* or —CH(OH)—CH(OH)—C(O)-*.

In certain instances, A² is —NH—, —O—, —C(O)NH-‡, —NH—C(O)-‡, or a bond. In certain other instances, A² is —NH—C(O)-‡.

In certain instances, Rᴬ and Rᴮ each represent independently hydrogen, —CH₃ or benzyl. In certain other instances, X¹, X², and X³ are each independently —CHR¹— or —CHR¹—CH₂—, and each R¹ is independently aryl, heteroaryl, benzofused-cycloalkyl, —(C₁-C₃)-alkyl-biphenyl, —(C₁-C₃)-alkyl-aryl, —(C₁-C₃)-alkyl-heteroaryl, —(C₁-C₃)-alkyl-O-aryl, —(C₁-C₃)-alkyl-O—(C₁-C₃)-alkyl-aryl, —(C₁-C₃)-alkyl-O—(C₁-C₃)-alkyl-heteroaryl, or —CH(aryl)(aryl), wherein each aryl or heteroaryl is optionally substituted with an additional aryl or heteroaryl, and any aryl or heteroaryl in R¹ is optionally substituted with up to three substituents independently selected from the group consisting of halogen, —(C₁-C₄)-alkyl, —O—(C₁-C₄)-alkyl, —C(O)OH, —C(O)(C₁-C₄)alkyl, —OH, —NH₂, —NH((C₁-C₄)-alkyl), and —N((C₁-C₄)-alkyl)₂, —N(H)C(O)OR⁵, —N(H)C(O)N(R⁵)(R⁶), and —N(H)S(O)₂R⁵. In certain other instances, the R¹ substituent of X¹ is in an (R) orientation; the R¹ substituent of X² is in an (S) orientation; and the R¹ substituent of X³ is in an (R) orientation. In still other instances, the chiral center to which the R¹ substituent of X¹ is attached is in an (S) orientation; the chiral center to which the R¹ substituent of X² is attached is in an (R) orientation; and the chiral center to which the R¹ substituent of X³ is attached is in an (S) orientation.

In certain instances, A¹ is —NR⁷—(CH₂)ₙ—Y—(CH₂)ₙ-†; Y represents independently for each occurrence phenyl or triazolyl; n represents independently for each occurrence 0, 1, or 2; and one —CH₂— unit in A¹ is replaced with

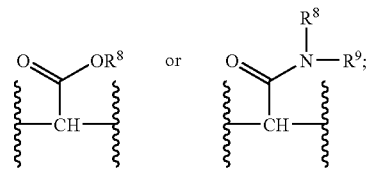

or the —NR⁷ unit in A¹ is replaced with

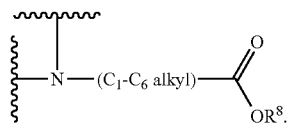

In certain other instances, A¹ is —NH—CH₂—CH₂—C₆H₅-†, —NH—CH₂—C₆H₅—CH₂-†, —NH—CH₂—CH₂-triazolyl-†, or —NH—C₆H₅—CH₂—CH₂-†, wherein one —CH₂— unit in A¹ is replaced with

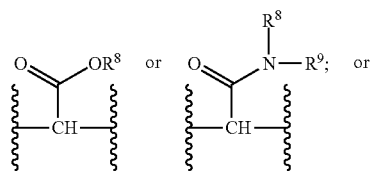

the —NH— unit in A¹ is replaced with

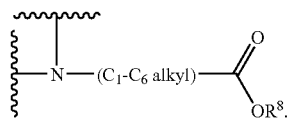

In certain other instances, $A^1$ is †-C$_6$H$_5$—CH$_2$—CH(COOR$^4$)—NH— or †-C$_6$H$_5$—CH$_2$—CH(C(O)NHR$^5$)—NH—. In certain instances, R$^4$ is OH; and R$^5$ is 1-carboxy-2-phenylethyl or 1-carboxycyclopropyl. In certain other instances, $A^4$ is NR$^{14}$. In certain other instances, $A^4$ is NH.

In another aspect, the invention provides a compound represented by formula II:

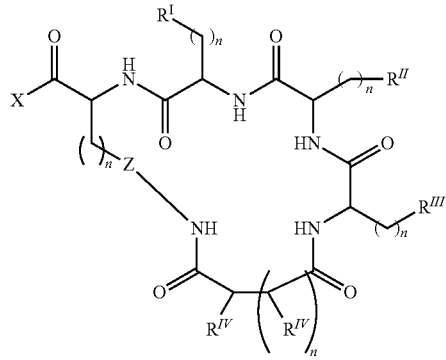

(II)

including pharmaceutically acceptable salts thereof, wherein

X is —OH, —O-alkyl, —NH$_2$, —N(H), —N(H)alkyl, —N(H)(substituted alkyl), —N(alkyl)$_2$, —N(substituted alkyl)$_2$, —N(H)—(C$_1$-C$_6$)-alkyl-O—(C$_1$-C$_6$)-alkyl, —N(H)—(CH$_2$)$_t$—C(R$^V$)$_2$—(CH$_2$)$_t$—COOH, —N(H)—(CH$_2$)$_t$—C(R$^V$)$_2$—(CH$_2$)$_t$—SO$_3$H, —NH—(CH$_2$)$_t$—C(R$^V$)$_2$—(CH$_2$)$_t$—C(O)—NH—(CH$_2$)$_t$—C(R$^V$)$_2$—(CH$_2$)$_t$—SO$_3$H, —N(alkyl)-(C$_1$-C$_6$)-alkyl-O—(C$_1$-C$_6$)-alkyl, —N(alkyl)-(CH$_2$)$_t$—C(R$^V$)$_2$—(CH$_2$)$_t$—COOH, —N(alkyl)-(CH$_2$)$_t$—C(R$^V$)$_2$—(CH$_2$)$_t$—SO$_3$H, —N(alkyl)-(CH$_2$)$_t$—C(R$^V$)$_2$—(CH$_2$)$_t$—C(O)—NH—(CH$_2$)$_t$—C(R$^V$)$_2$—SO$_3$H, carboxypiperidin-1-yl, carboxypyrrolidin-1-yl, or N-carboxymethyl-N-benzylamino;

Z is alkylene or arylene;

R$^I$ is (C$_1$-C$_4$)-alkyl or aryl;

R$^{II}$ is aryl optionally substituted with up to two substituents independently selected from the group consisting of alkyl, haloalkyl, and aryl;

R$^{III}$ is heteroaryl;

R$^{IV}$ represents independently for each occurrence H or OH;

R$^V$ represents independently for each occurrence hydrogen, —(C$_1$-C$_6$)-alkyl, —(C$_1$-C$_6$)-alkyl-heterocyclyl, —(C$_1$-C$_6$)-alkyl-carbocyclyl, or —CO$_2$—(C$_1$-C$_6$)-alkyl, wherein each R$^V$ is optionally substituted with a substituent selected independently from the group consisting of —NH$_2$, —NH—C(O)—(C$_1$-C$_4$)-alkyl and —OH;

or two R$^V$ are taken together with the carbon atom to which they are bound to form a 3-7 membered cycloalkane ring;

n represents independently for each occurrence 0, 1, 2, 3, or 4; and t represents independently for each occurrence 0, 1, or 2.

In certain instances, R$^I$ is phenyl, R$^{II}$ is biphenyl, and R$^{III}$ is thiophenyl. In certain instances, n is 1.

In another aspect, the invention provides a compound represented by formula III:

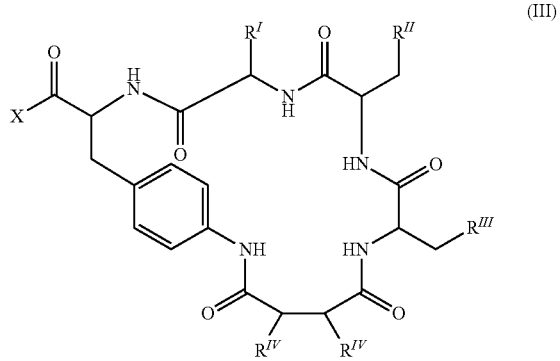

(III)

including pharmaceutically acceptable salts thereof, wherein

X is —OH, —N(H)—(CH$_2$)$_t$—C(R$^V$)$_2$—(CH$_2$)$_t$—SO$_3$H, —NH—(CH$_2$)$_t$—C(R$^V$)$_2$—(CH$_2$)$_t$—C(O)—NH—(CH$_2$)$_t$—C(R$^V$)$_2$—SO$_3$H, —N(H)—(CH$_2$)$_t$—C(R$^V$)$_2$—(CH$_2$)$_t$—COOH, carboxypiperidin-1-yl, carboxypyrrolidin-1-yl, or N-carboxymethyl-N-benzylamino;

R$^I$ is aryl, —CH$_2$-aryl, or —CH$_2$-heteroaryl;

R$^{II}$ is aryl optionally substituted with up to two substituents independently selected from the group consisting of alkyl, halogen, haloalkyl, aryl and heteroaryl;

R$^{III}$ is aryl or heteroaryl;

R$^{IV}$ represents independently for each occurrence H or OH;

R$^V$ represents independently for each occurrence hydrogen, —(C$_1$-C$_6$)-alkyl, —(C$_1$-C$_6$)-alkyl-heterocyclyl, —(C$_1$-C$_6$)-alkyl-carbocyclyl, or —CO$_2$—(C$_1$-C$_6$)-alkyl, wherein each R$^V$ is optionally and independently substituted with a substituent selected independently from the group consisting of —NH$_2$, —NH—C(O)—(C$_1$-C$_4$)-alkyl and —OH; or two R$^V$ are taken together with the carbon atom to which they are bound to form a 3-7 membered cycloalkane ring; and t represents independently for each occurrence 0, 1, or 2.

In certain instances, R$^I$ is benzyl, R$^{II}$ is biphenyl, R$^{III}$ is thiophenyl. In certain instances, the compound is represented by formula III-A:

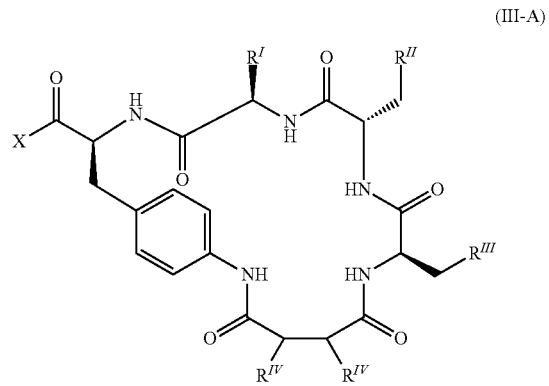

(III-A)

including pharmaceutically acceptable salts thereof, wherein

X is —OH, —N(H)—(CH$_2$)$_t$—C(R$^V$)$_2$—(CH$_2$)$_t$—SO$_3$H, —NH—(CH$_2$)$_t$—C(R$^V$)$_2$—(CH$_2$)$_t$—C(O)—NH—(CH$_2$)$_t$—C(R$^V$)$_2$—SO$_3$H, —N(H)—(CH$_2$)$_t$—C(R$^V$)$_2$—(CH$_2$)$_t$—COOH, carboxypiperidin-1-yl, carboxypyrrolidin-1-yl, or N-carboxymethyl-N-benzylamino;

R$^I$ is aryl, —CH$_2$-aryl, or —CH$_2$-heteroaryl;

R$^{II}$ is aryl optionally substituted with up to two substituents independently selected from the group consisting of alkyl, halogen, haloalkyl, aryl and heteroaryl;

$R^{III}$ is aryl or heteroaryl;

$R^{IV}$ represents independently for each occurrence H or OH;

$R^V$ represents independently for each occurrence hydrogen, —($C_1$-$C_6$)-alkyl, —($C_1$-$C_6$)-alkyl-heterocyclyl, —($C_1$-$C_6$)-alkyl-carbocyclyl, or —$CO_2$—($C_1$-$C_6$)-alkyl, wherein each $R^V$ is optionally and independently substituted with a substituent selected independently from the group consisting of —$NH_2$, —NH—C(O)—($C_1$-$C_4$)-alkyl and —OH; or two $R^V$ are taken together with the carbon atom to which they are bound to form a 3-7 membered cycloalkane ring; and t represents independently for each occurrence 0, 1, or 2.

In another aspect, the invention provides a compound represented by formula IV:

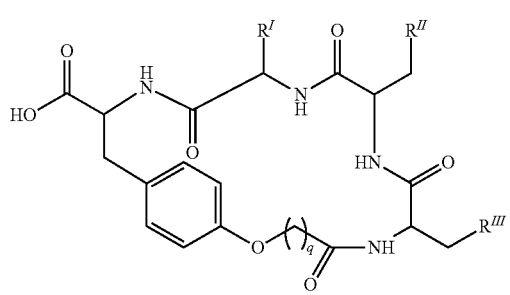

(IV)

including pharmaceutically acceptable salts thereof, wherein $R^I$ is —$CH_2$-aryl, —$CH_2CH_2$-aryl, —$CH_2$-heteroaryl, or —$CH_2CH_2$-heteroaryl;

$R^{II}$ is aryl optionally substituted with up to two substituents independently selected from the group consisting of alkyl, halogen, haloalkyl, aryl, and heteroaryl;

$R^{III}$ is aryl or heteroaryl; and q is 1, 2, or 3.

In certain instances, $R^I$ is —$CH_2CH_2$-aryl or —$CH_2CH_2$-heteroaryl.

In another aspect, the invention provides a compound represented by formula V:

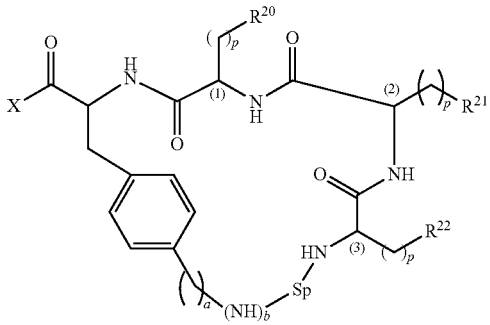

(V)

including pharmaceutically acceptable salts thereof, wherein $R^{20}$ is phenyl, monocyclic heteroaryl, —$C_1$-$C_3$-alkyl-NH—C(O)—$C_1$-$C_4$-alkyl, or —$C_1$-$C_3$-alkyl-C(O)O—$C_1$-$C_4$-alkyl, wherein the phenyl is optionally substituted at the 2-position and the 4-position with a substituent independently selected from the group consisting of chloro, —CN, —OH and —O—$C_1$-$C_4$-alkyl;

$R^{21}$ is naphthyl, 2,4-dichlorophenyl,

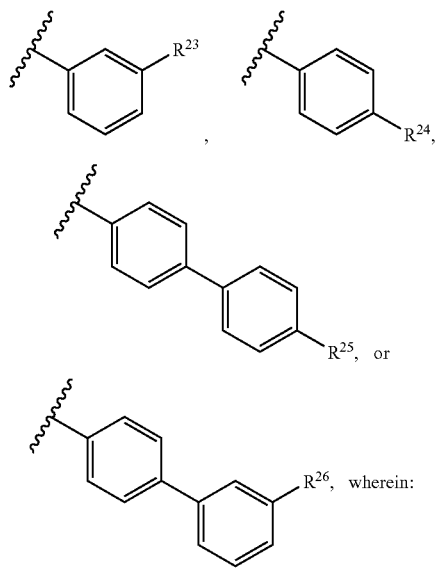

$R^{23}$ is hydrogen, $CF_3$, or phenyl;

$R^{24}$ is hydrogen, chloro, fluoro, bromo, $CF_3$, methoxy, phenoxy, benzyloxy, or 4-pyridyl; and $R^{25}$ is hydrogen, chloro, fluoro, methoxy, —C(O)O—$CH_2$—$R^{27}$, —NH—C(O)O—$CH_2$—$R^{27}$, or —O—$CH_2$—$R^{27}$, wherein $R^{27}$ is selected from hydrogen, $C_1$-$C_3$-alkyl, or phenyl; and $R^{26}$ is hydrogen, fluoro, or methoxy;

$R^{22}$ is phenyl, monocyclic heteroaryl, or —$C_1$-$C_3$-alkyl-NH—C(O)—$C_1$-$C_4$-alkyl, wherein the phenyl is (i) optionally monosubstituted at 2-, 3- or 4-position with a substituent selected from the group consisting of bromo, chloro, fluoro, —CN, $NO_2$, $CF_3$, —O—$C_1$-$C_4$-alkyl, and t-butyl; (ii) additionally optionally substituted at the 4-position with 4-pyridyl, phenylethyl, benzyl, or phenyl; and (iii) optionally disubstituted at the 3- and 4-positions with fluoro:

Sp is

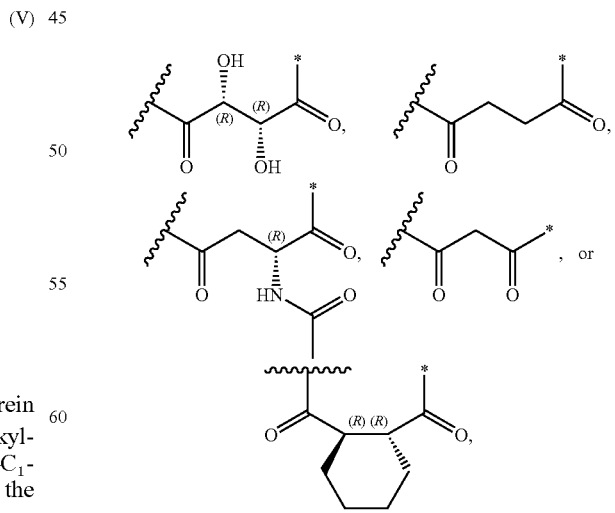

and when a and b are simultaneously 0, Sp is additionally selected from

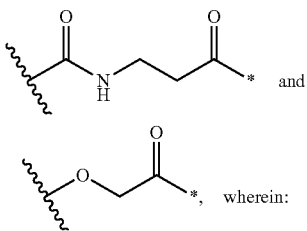 and

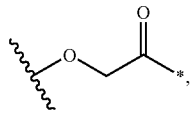, wherein:

wherein:
"∿" represents the portion of Sp bound to the $(NH)_b$ portion of the compound; and
"*" represents the portion of Sp bound to the NH—CH$((CH_2)_p$—$R^{22})$ portion of the compound;
X is —OH, —NH—$(CH_2)_t$—$C(R^V)_2$—$(CH_2)_t$—COOH, —NH—$(CH_2)_t$—$C(R^V)_2$—$SO_3H$, —NH—$(CH_2)_t$—$C(R^V)_2$—$(CH_2)_t$—C(O)—NH—$(CH_2)_t$—$C(R^V)_2$—$SO_3H$, carboxypiperidin-1-yl, carboxypyrrolidin-1-yl, or N-carboxymethyl-N-benzylamino, and when Sp is

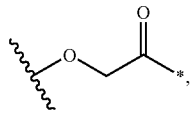,

X is additionally selected from —NH—$(C_1$-$C_6)$-alkyl-OH, wherein:
  each t independently represents 0, 1 or 2; and
  each $R^V$ independently represents hydrogen, —$(C_1$-$C_6)$-alkyl, —$(C_1$-$C_6)$-alkyl-heterocyclyl, —$(C_1$-$C_6)$-alkyl-carbocyclyl, or —$CO_2$—$(C_1$-$C_6)$-alkyl, wherein each $R^V$ is optionally and independently substituted with a substituent selected independently from the group consisting of —$NH_2$, —NH—C(O)—$(C_1$-$C_4)$-alkyl and —OH; or
  two $R^V$ are taken together with the carbon atom to which they are bound to form a 3-7 membered cycloalkane ring,
a is 0 or 1;
b is 0 or 1;
each p is independently selected from 1 or 2;
the stereochemistry at (1) and (3) are the same; and
the stereochemistry at (1) and (2) are different.

In another aspect, the invention provides a compound represented by formula VI:

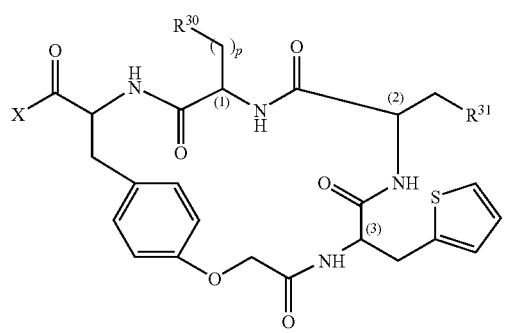

(VI)

including pharmaceutically acceptable salts thereof, wherein:
$R^{30}$ is an unsubstituted aryl, 4-t-butoxyphenyl, 4-hydroxyphenyl, or an unsubstituted heteroaryl;

$R^{31}$ is

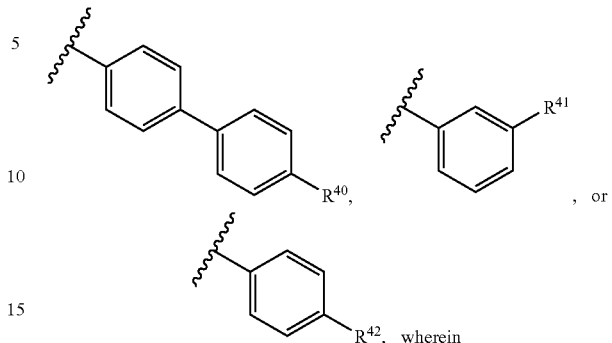, or $R^{40}$ is hydrogen, halogen, —$CF_3$, methoxy, —NH—C(O)O—$CH_2$-phenyl, or —O—$CH_2$-phenyl;
$R^{41}$ is hydrogen or —$CF_3$;
$R^{42}$ is hydrogen, 4-pyridyl, or halogen; and
X is —OH, —NH—$(CH_2)_t$—$C(R^V)_2$—$(CH_2)_t$—COOH, —NH—$(CH_2)_t$—$C(R^V)_2$—$SO_3H$, —NH—$(CH_2)_t$—$C(R^V)_2$—$(CH_2)_t$—C(O)—NH—$(CH_2)_t$—$C(R^V)_2$—$SO_3H$, carboxypiperidin-1-yl, carboxypyrrolidin-1-yl, N-carboxymethyl-N-benzylamino, or —NH—$(C_1$-$C_6)$-alkyl-OH, wherein:
  each t independently represents 0, 1 or 2; and
  each $R^V$ independently represents hydrogen, —$(C_1$-$C_6)$-alkyl, —$(C_1$-$C_6)$-alkyl-heterocyclyl, —$(C_1$-$C_6)$-alkyl-carbocyclyl, or —$CO_2$-alkyl, wherein each $R^V$ is optionally substituted with a substituent selected independently from the group consisting of —$NH_2$, —NH—C(O)—$(C_1$-$C_4)$-alkyl and —OH; or
  two $R^V$ are taken together with the carbon atom to which they are bound to form a 3-7 membered cycloalkane ring,
p is 1 or 2;
the stereochemistry at (1) is (S);
the stereochemistry at (2) is (S); and
the stereochemistry at (3) is (S).

In yet another aspect, the invention provides a compound represented by formula VII:

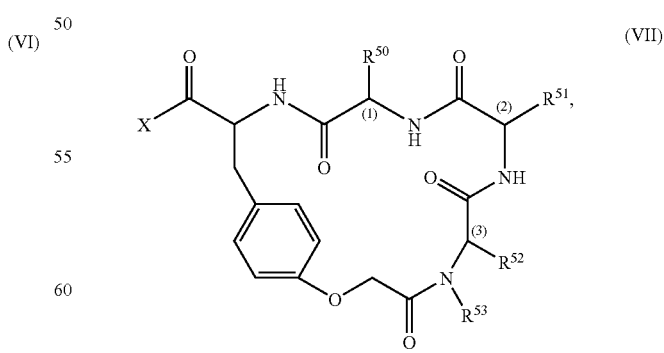

(VII)

including pharmaceutically acceptable salts thereof, wherein:
$R^{50}$ is benzyl, phenylethyl, indol-3-ylmethyl, thien-2-ylmethyl, biphenyl-4-ylmethyl, 4-(pyridin-4-yl)benzyl, 4-(pyridin-3-yl)benzyl, or 4-(pyridin-2-yl)benzyl, wherein the benzyl, biphenyl-4-yl or phenylethyl group in $R^{50}$ is optionally substituted on a terminal phenyl ring with a single substituent selected from the group consisting of halo, methoxy, $CF_3$, hydroxy, cyano, and $C_1$-$C_4$ alkyl; or is optionally substituted with chloro at each of the 2 and 4 positions of the terminal phenyl ring;

$R^{51}$ is biphenyl-4-ylmethyl, 4-(pyridin-4-yl)benzyl, or 4-(pyridin-3-yl)benzyl, wherein the biphenyl group in $R^{51}$ is optionally monosubstituted at the 4-position of the terminal phenyl ring with amino, halo or hydroxy;

$R^{52}$ is phenyl, naphthyl, benzyl, naphthylmethyl, phenylethyl, heteroarylmethyl, 4-(heteroaryl)benzyl, or biphenyl-4-ylmethyl, wherein the phenyl, naphthyl, benzyl, naphthylmethyl, phenylethyl or biphenyl-4-ylmethyl group in $R^{52}$ is optionally on a terminal phenyl ring with 1 to 2 substituents independently selected from the group consisting of halo, methoxy, hydroxy, $C_1$-$C_4$ alkyl, and $C_1$-$C_4$ haloalkyl;

$R^{53}$ is hydrogen or methyl;

X is —OH, —N($R^W$)—[C($R^V$)$_2$]$_{1-4}$—COOH, —N($R^W$)—[C($R^V$)$_2$]$_{1-3}$—SO$_3$H, —N($R^W$)—[C($R^V$)$_2$]$_{0-4}$—S(O)$_2$CH$_3$, or —N($R^W$)—[C($R^V$)$_2$]$_{1-3}$-1H-tetrazol-5-yl, wherein:

$R^W$ represents hydrogen, methyl or benzyl; and each $R^V$ independently represents hydrogen, —(C$_1$-C$_6$)-alkyl, —(C$_1$-C$_6$)-alkyl-heterocyclyl, —(C$_1$-C$_6$)-alkyl-carbocyclyl, or —CO$_2$-alkyl, wherein each $R^V$ is optionally substituted with a substituent selected independently from the group consisting of —NH$_2$, —NH—C(O)—(C$_1$-C$_4$)-alkyl and —OH; or two $R^V$ are taken together with the carbon atom to which they are bound to form a 3-7 membered cycloalkane ring, the stereochemistry at (1) is the same as the stereochemistry at (3); and the stereochemistry at (1) is opposite the stereochemistry at (2).

In a more specific aspect of a compound of Formula VII, $R^{50}$ is selected from benzyl, 2-fluorobenzyl, 4-fluorobenzyl, 2-trifluoromethylbenzyl, 4-trifluoromethylbenzyl, 2,4-dichlorobenzyl, 3-methoxybenzyl, 4-hydroxybenzyl, 4-cyanobenzyl, 4-methoxybenzyl, 4-t-butylbenzyl, phenylethyl, 2-fluorophenylethyl, indol-3-ylmethyl, thien-2-ylmethyl, biphenyl-4-ylmethyl, 4-(pyridin-4-yl)benzyl, 4-(pyridin-3-yl)benzyl, or 4-(pyridin-2-yl)benzyl;

$R^{51}$ is biphenyl-4-ylmethyl, 4-(pyridin-4-yl)benzyl, 4-(pyridin-3-yl)benzyl, 4-(4-aminophenyl)benzyl, 4-(4-bromophenyl)benzyl, 4-(4-fluorophenyl)benzyl, or 4-(4-hydroxyphenyl)benzyl;

$R^{52}$ is 2,4-dichlorobenzyl, 2-fluorobenzyl, 3-fluorobenzyl, 3-methoxybenzyl, 3-trifluoromethylbenzyl, 4-trifluoromethylbenzyl, 4-hydroxybenzyl, 4-chlorobenzyl, 4-fluorobenzyl, 4-methylbenzyl, biphenyl-4-ylmethyl, indol-3-ylmethyl, thien-2-ylmethyl, 4-(pyridin-4-yl)benzyl, 4-(pyridin-3-yl)benzyl, 4-(pyridin-2-yl)benzyl, pyridin-2-ylmethyl, pyridin-3-ylmethyl, pyridin-4-ylmethyl, naphthyl, naphthylmethyl, phenylethyl, thiazol-3ylmethyl, 4-(thien-2-yl)benzyl, furan-2ylmethyl, N-phenyl-1H-triazol-4ylmethyl, 4-(4-fluorophenyl)benzyl, or 4-(4-chlorophenyl)benzyl; and X is —N(CH$_3$)CH$_2$SO$_3$H, —N(CH$_3$)CH(benzyl)COOH, —N(CH$_3$)CH(CH$_3$)COOH, —NHCH$_2$COOH, —NHCH$_2$SO$_3$H, —NHCH$_2$-1H-tetrazol-5-yl, —NH(CH$_2$)$_2$COOH, —NH(CH$_2$)$_2$SO$_3$H, —NH(CH$_2$)$_3$COOH, —NH(CH$_2$)$_3$SO$_3$H, —NH(CH$_2$)$_2$-1H-tetrazol-5-yl, —NHCH(4-hydroxybenzyl)COOH, —NHCH(benzyl)COOH, —NHCH(benzyl)-1H-tetrazol-5-yl, —NHCH(CH$_2$OH)COOH, —NHCH(phenylethyl)COOH, or —NHS(O)$_2$CH$_3$.

In another aspect, the invention provides the compounds listed in Table 1.

TABLE 1

| Compound No. | Structure | MS Calcd | MS Observed |
|---|---|---|---|
| 1 | 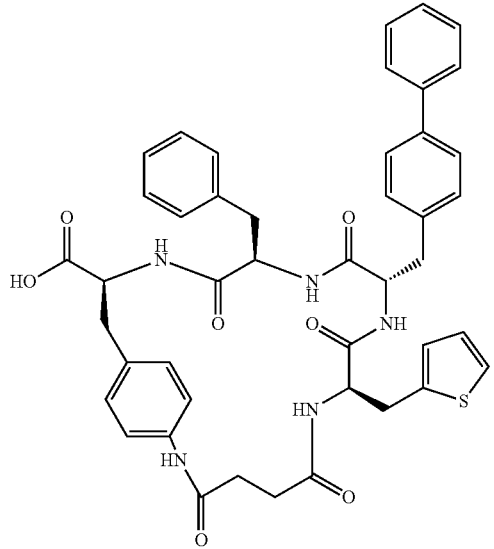 | 786.2961 | 786.2882 |

TABLE 1-continued

| Compound No. | Structure | MS Calcd | MS Observed |
|---|---|---|---|
| 2 | 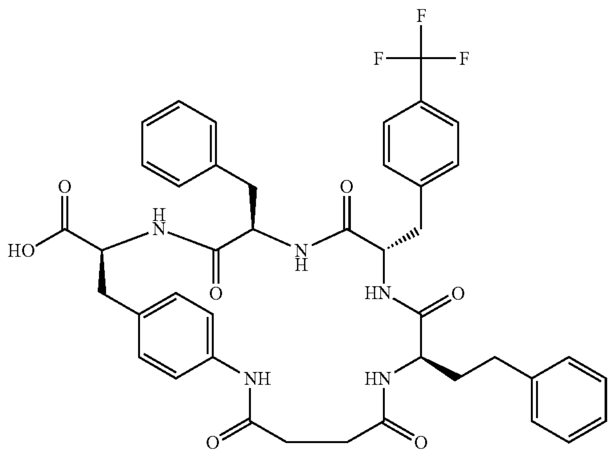 | 786.3109 | 786.3170 |
| 3 | 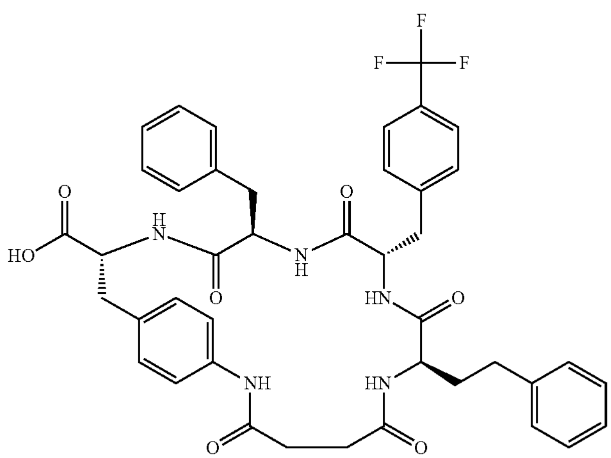 | 786.3109 | 786.3104 |
| 4 | 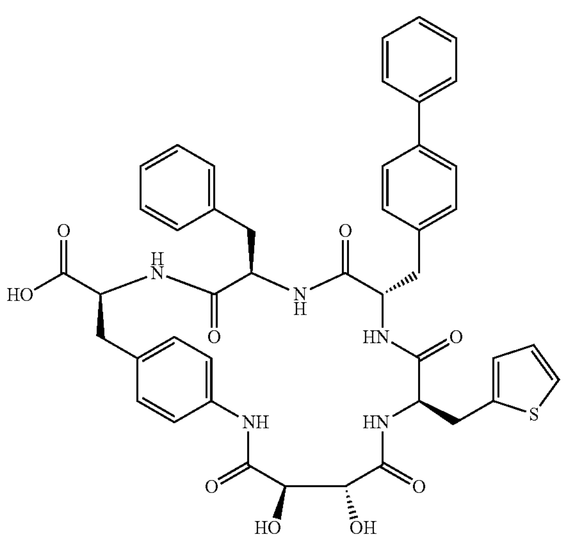 | 818.2855 | 818.2896 |

TABLE 1-continued

| Compound No. | Structure | MS Calcd | MS Observed |
|---|---|---|---|
| 5 | 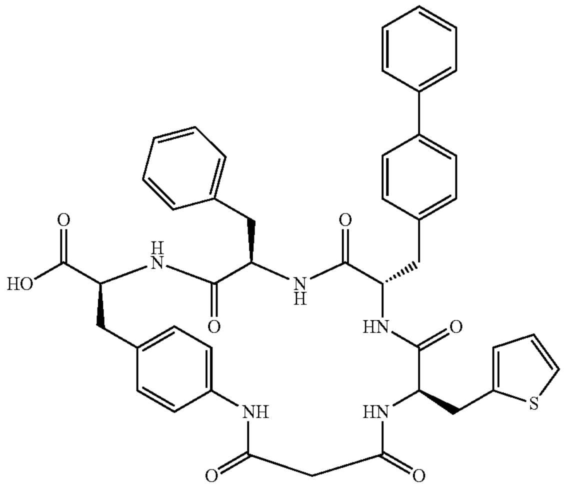 | 772.2800 | 772.2828 |
| 6 | 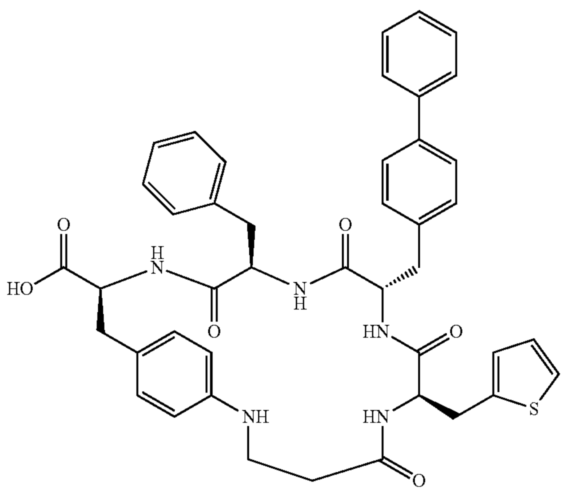 | 758.3007 | 758.2973 |
| 7 | 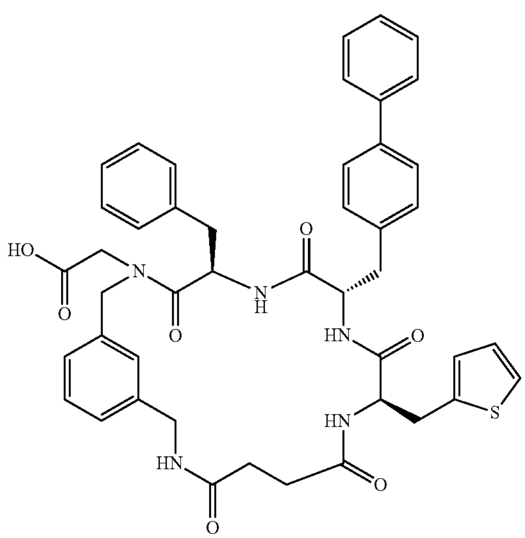 | 800.3113 | 800.3155 |

TABLE 1-continued

| Compound No. | Structure | MS Calcd | MS Observed |
|---|---|---|---|
| 8 | 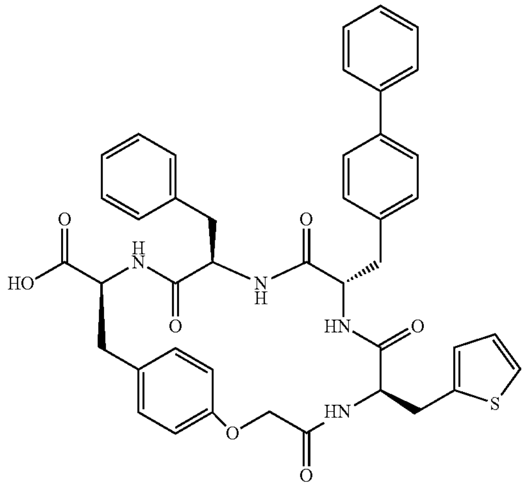 | 745.2691 | 745.2740 |
| 9 | 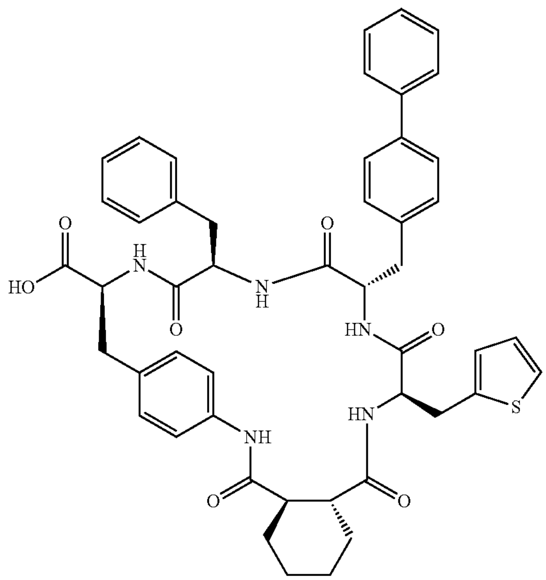 | 840.3426 | 840.3406 |
| 10 | 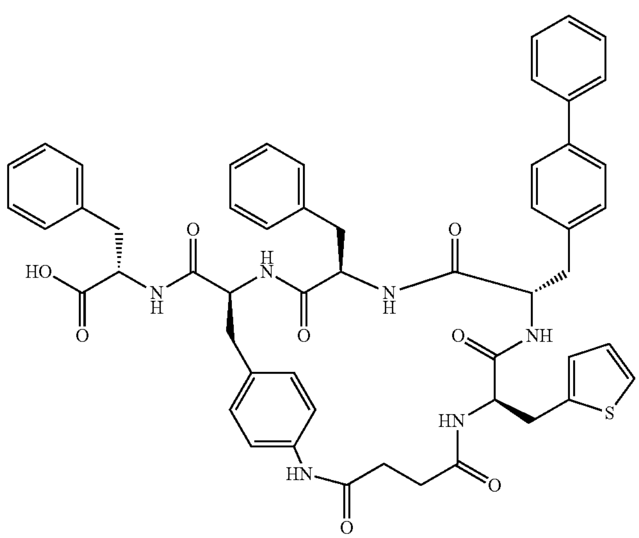 | 933.3640 | 933.3749 |

TABLE 1-continued

| Compound No. | Structure | MS Calcd | MS Observed |
|---|---|---|---|
| 11 | 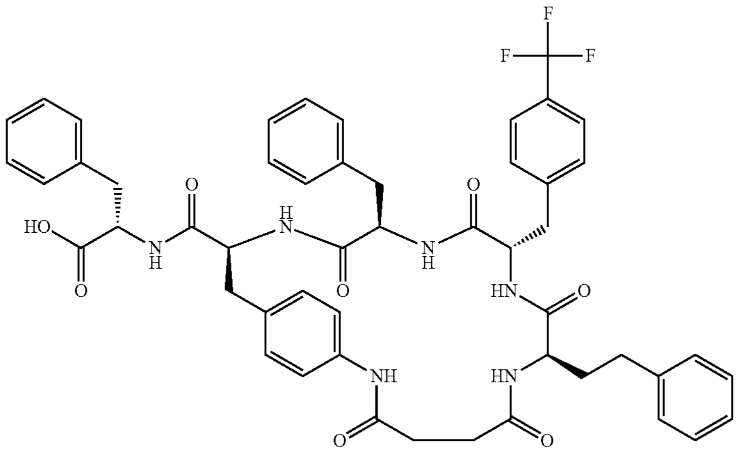 | 933.3794 | 933.3770 |
| 12 | 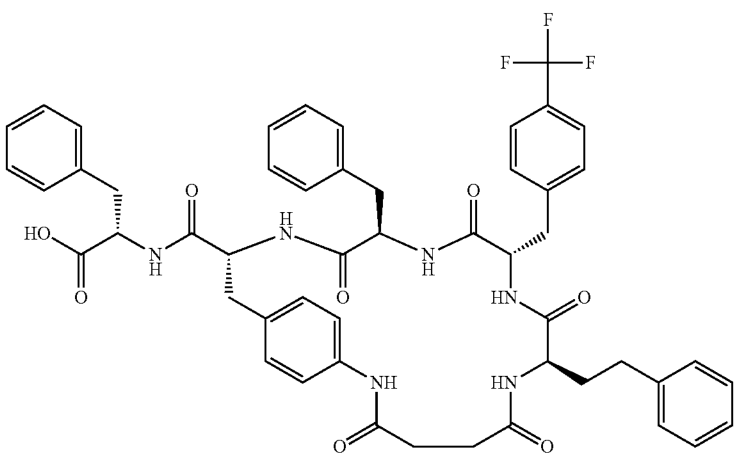 | 933.3794 | 933.3788 |
| 13 | 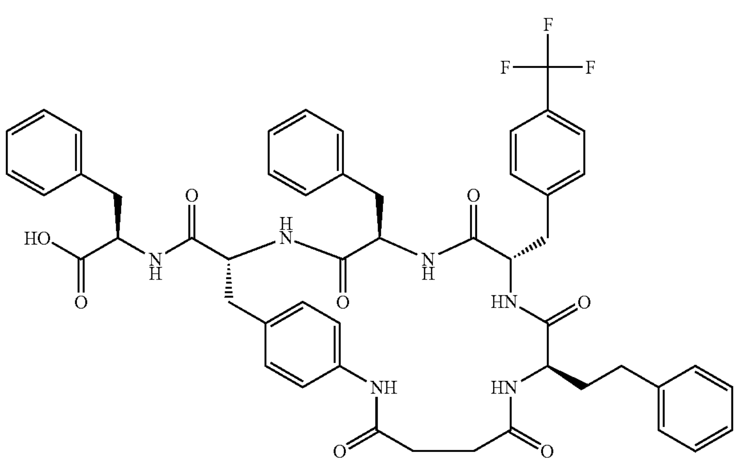 | 933.3794 | 933.3763 |

TABLE 1-continued

| Compound No. | Structure | MS Calcd | MS Observed |
|---|---|---|---|
| 14 | 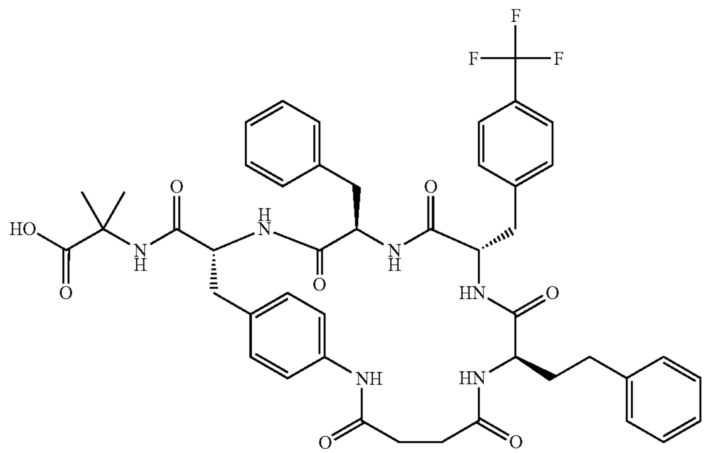 | 871.3637 | 871.3625 |
| 15 | 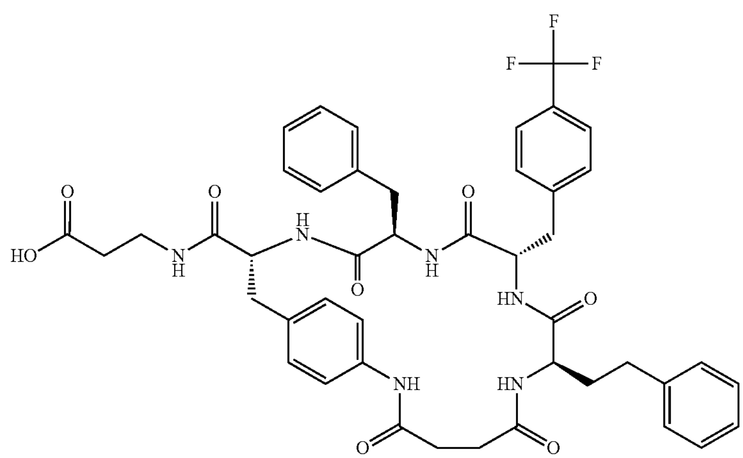 | 857.3481 | 857.3528 |
| 16 | 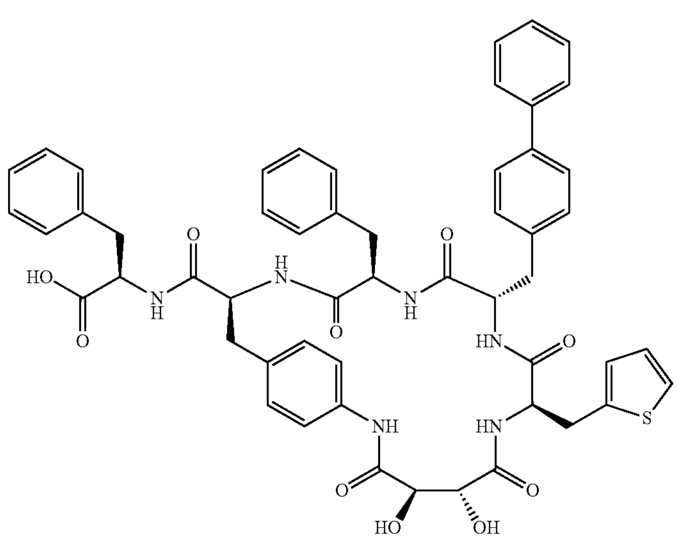 | 965.3539 | 965.3506 |

TABLE 1-continued
| Compound No. | Structure | MS Calcd | MS Observed |
|---|---|---|---|
| 17 | 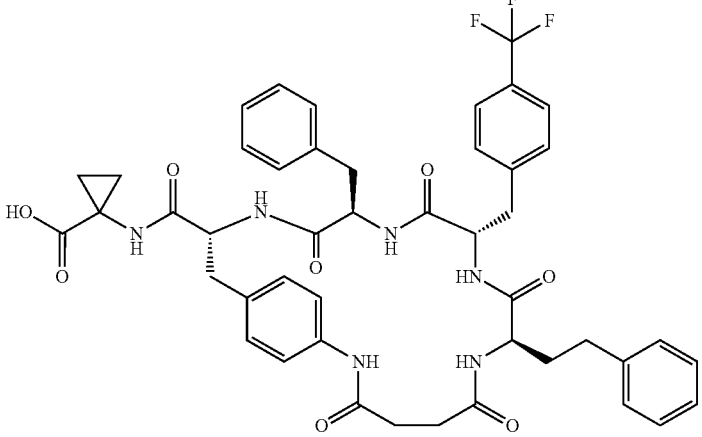 | 869.3481 | 869.3429 |
| 18 | 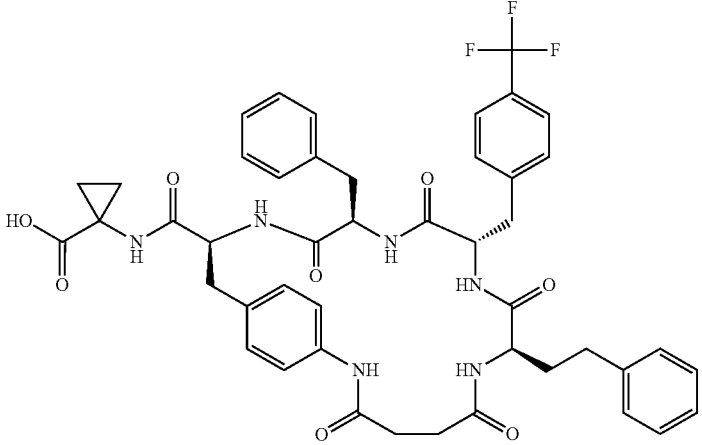 | 869.3481 | 869.3526 |
| 19 | 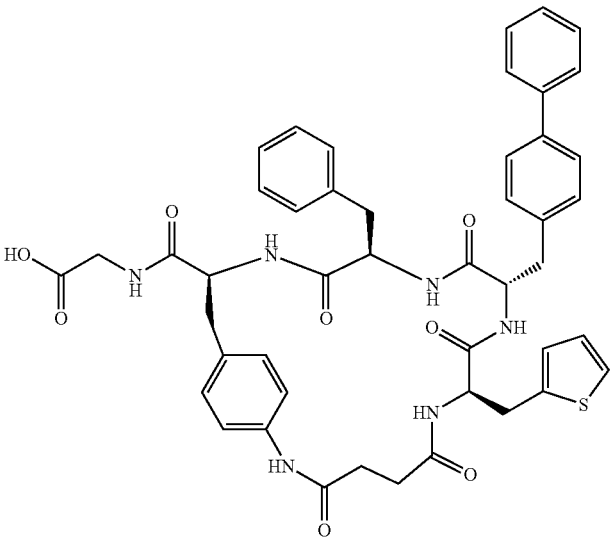 | 843.3171 | 843.3121 |

TABLE 1-continued

| Compound No. | Structure | MS Calcd | MS Observed |
|---|---|---|---|
| 20 | 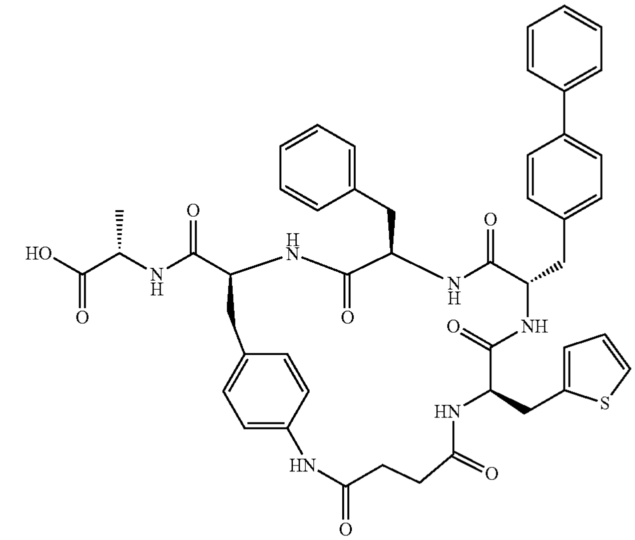 | 857.3327 | 857.3318 |
| 21 | 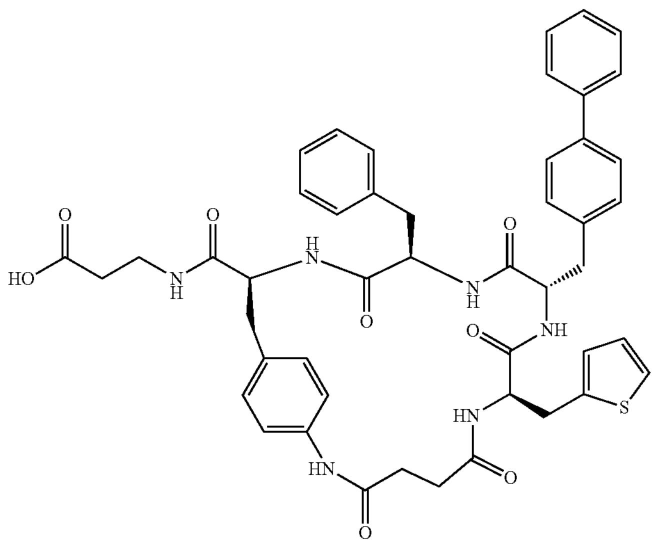 | 857.3327 | 857.3372 |
| 22 | 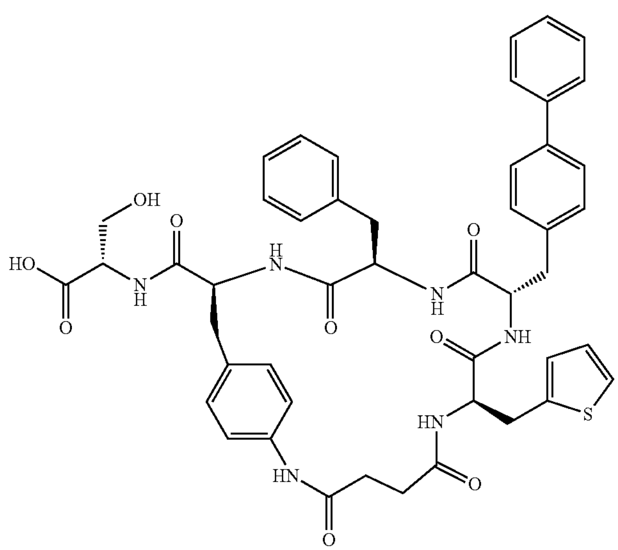 | 873.3276 | 873.3365 |

TABLE 1-continued

| Compound No. | Structure | MS Calcd | MS Observed |
|---|---|---|---|
| 23 | 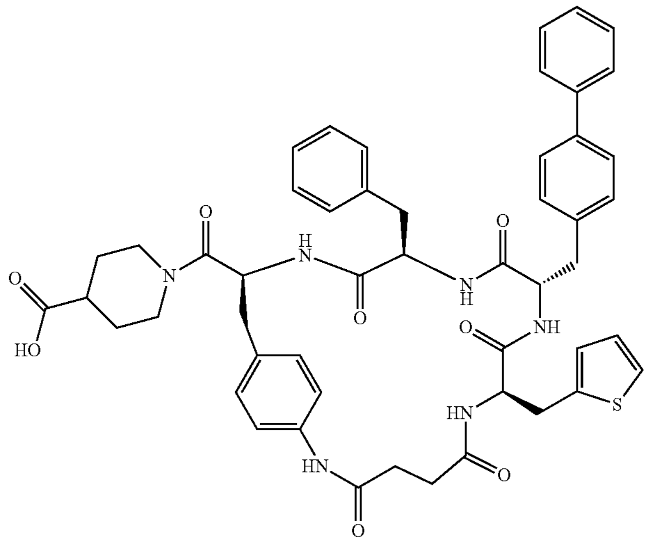 | 897.3640 | 897.3596 |
| 24 | 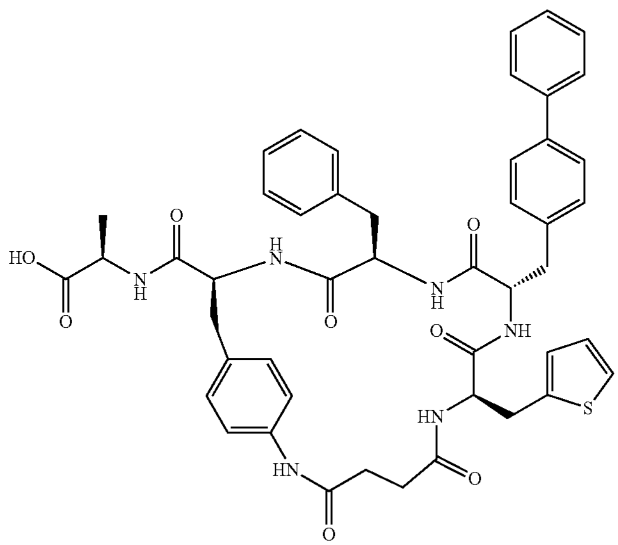 | 857.3327 | 857.3305 |
| 25 | 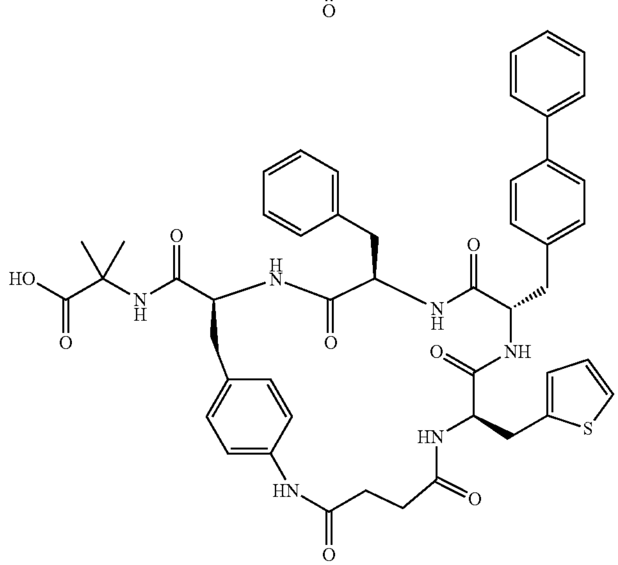 | 871.3484 | 871.3495 |

TABLE 1-continued

| Compound No. | Structure | MS Calcd | MS Observed |
|---|---|---|---|
| 26 | 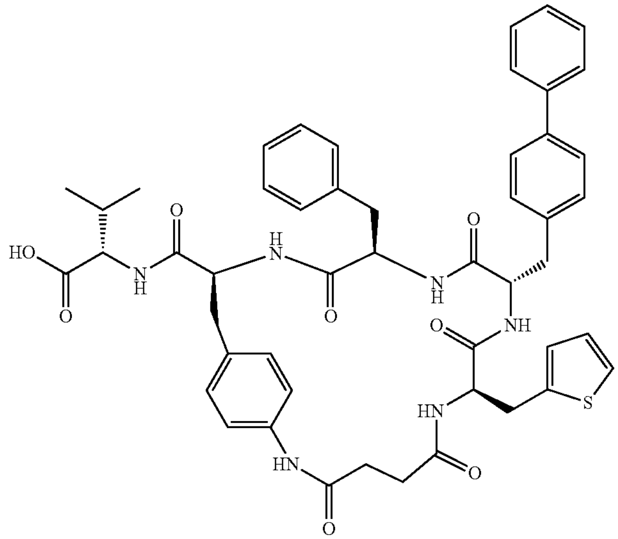 | 885.3640 | 885.3698 |
| 27 | 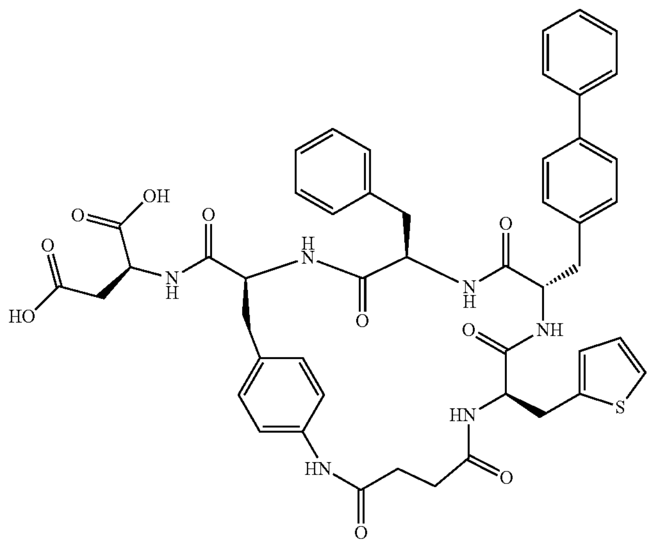 | 901.3231 | 901.3143 |
| 28 | 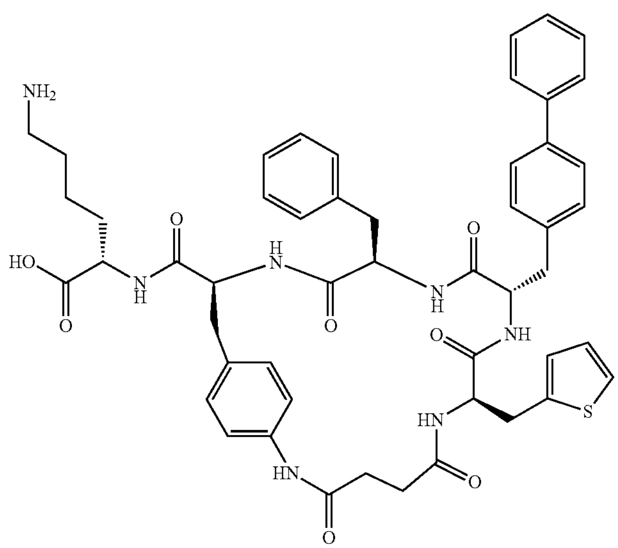 | 914.3911 | 914.3812 |

| Compound No. | Structure | MS Calcd | MS Observed |
|---|---|---|---|
| 29 | 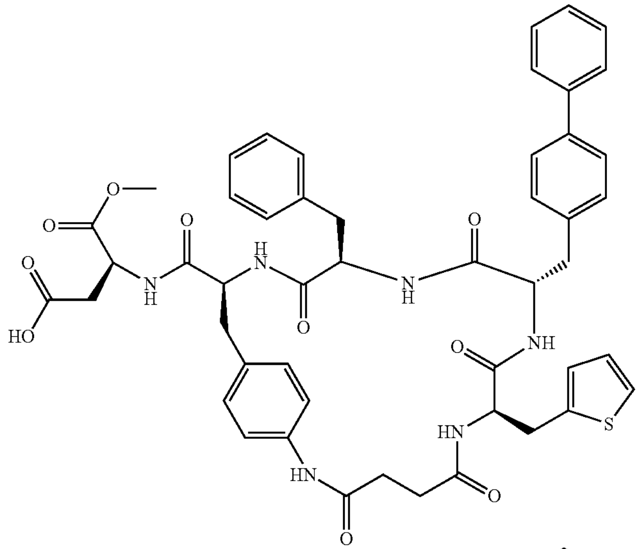 | 915.3387 | 915.3327 |
| 30 | 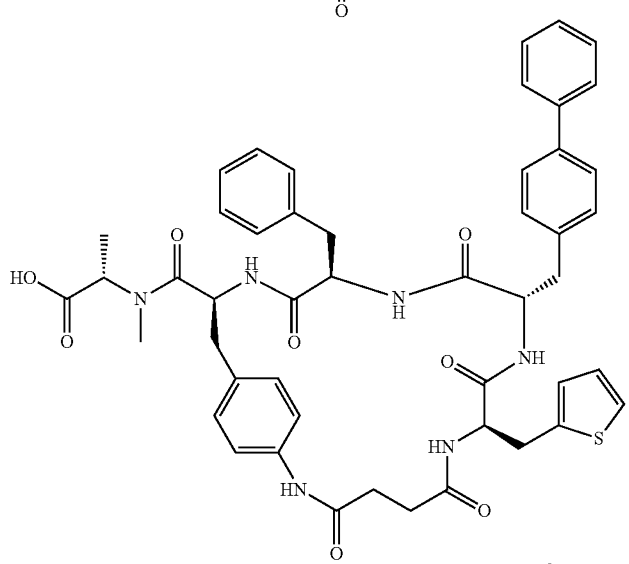 | 871.3484 | 871.3432 |
| 31 | 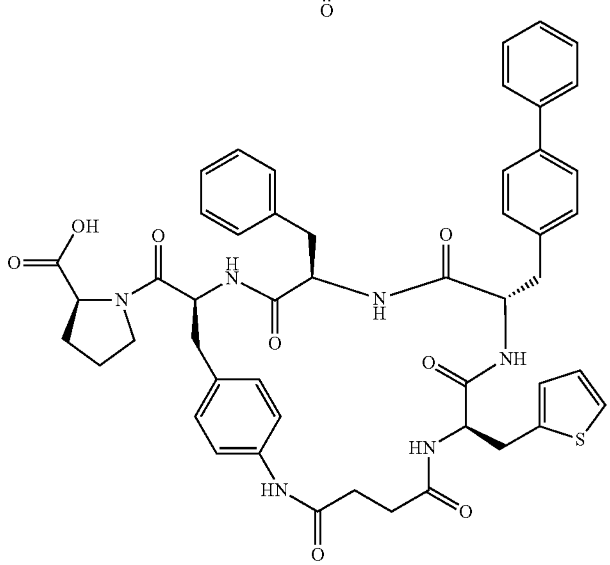 | 883.3484 | 883.3467 |

TABLE 1-continued

| Compound No. | Structure | MS Calcd | MS Observed |
|---|---|---|---|
| 32 | 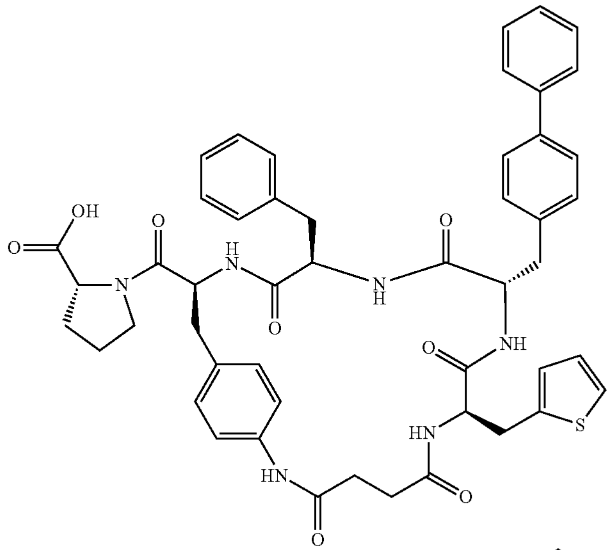 | 883.3484 | 883.3474 |
| 33 | 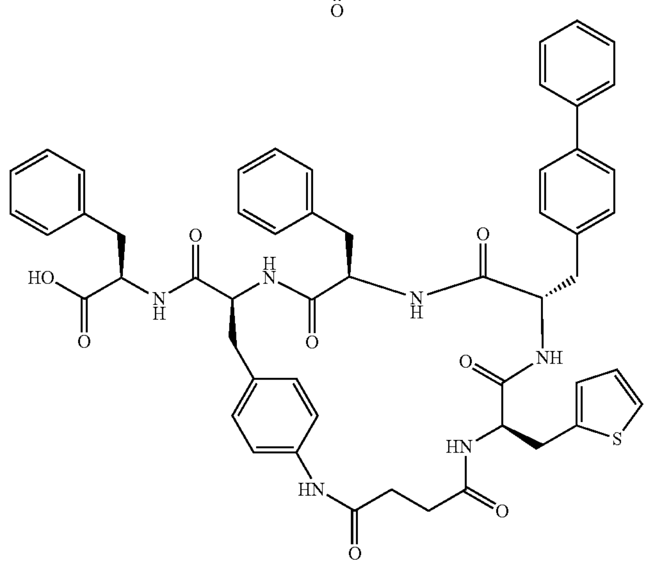 | 933.3640 | 933.3663 |
| 34 | 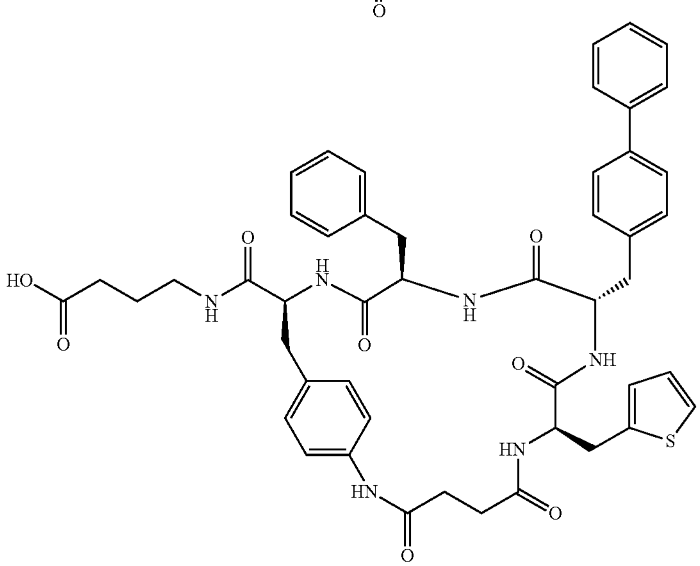 | 871.3406 | 871.3464 |

US 8,338,565 B2
43 44
TABLE 1-continued
| Compound No. | Structure | MS Calcd | MS Observed |
|---|---|---|---|
| 35 | 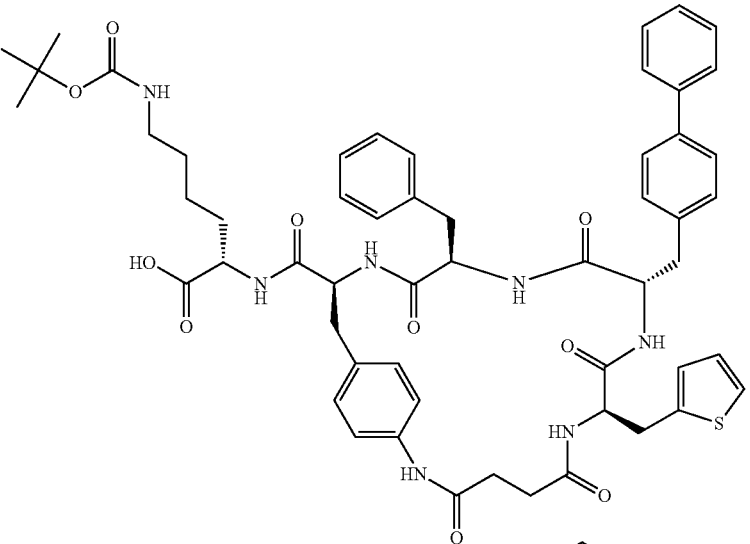 | 1014.4435 | 1014.4315 |
| 36 | 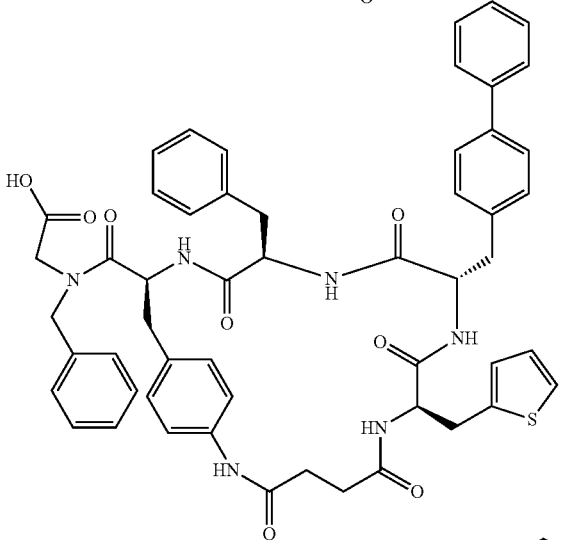 | 931.3489 | 931.3433 |
| 37 | 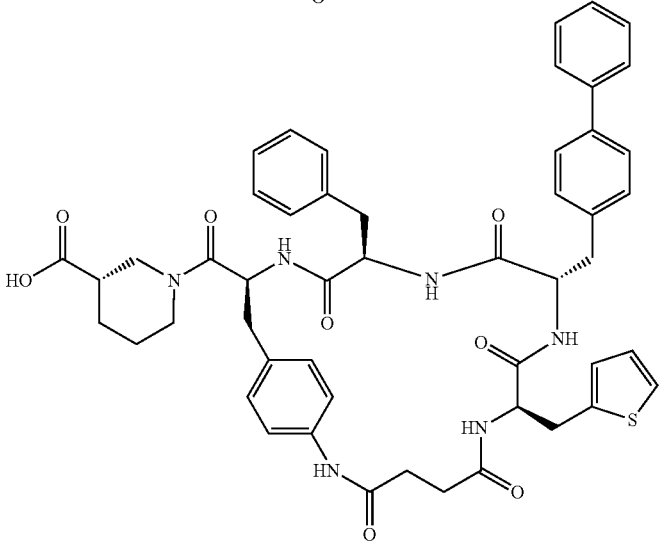 | 897.3640 | 897.3610 |

TABLE 1-continued
| Compound No. | Structure | MS Calcd | MS Observed |
|---|---|---|---|
| 38 | 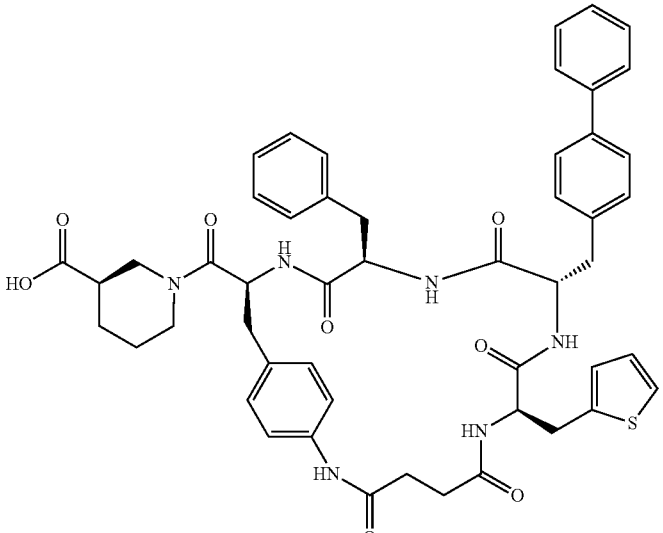 | 897.3640 | 897.3634 |
| 39 | 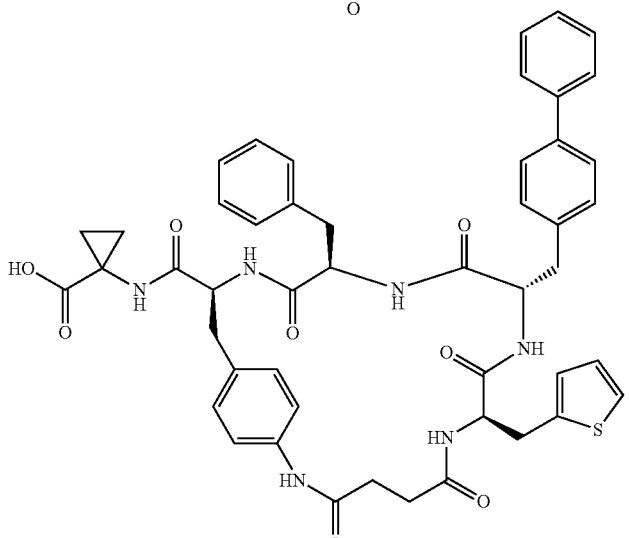 | 869.3327 | 869.3422 |
| 42 | 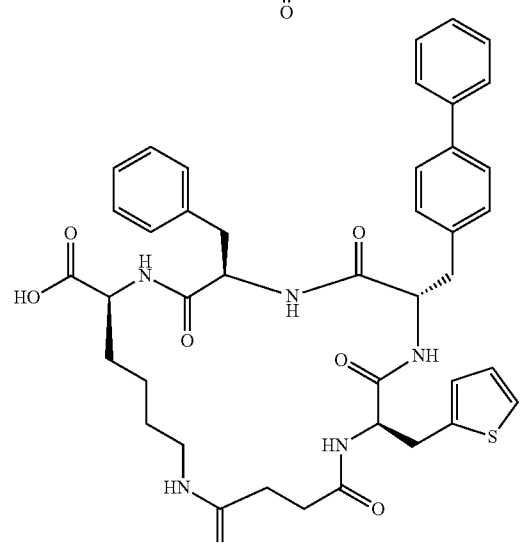 | 752.3113 | 752.3077 |

TABLE 1-continued

| Compound No. | Structure | MS Calcd | MS Observed |
|---|---|---|---|
| 43 | 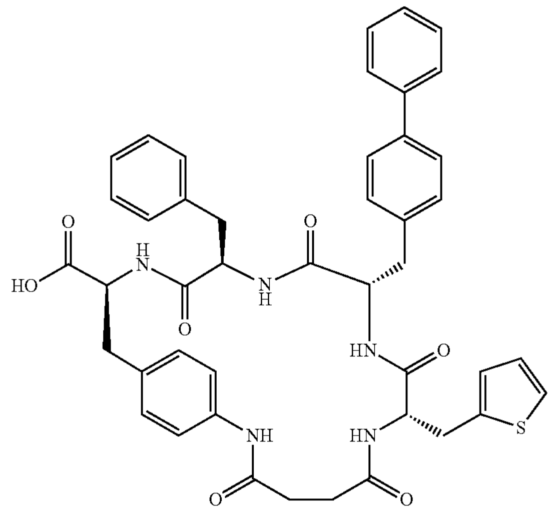 | 786.2956 | 786.2896 |
| 44 | 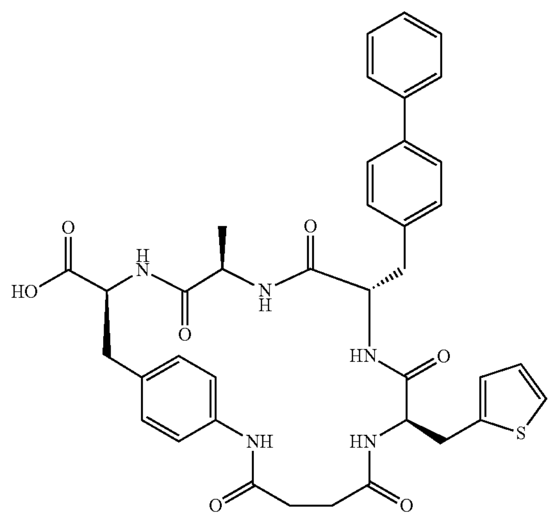 | 710.2643 | 710.2554 |
| 45 | 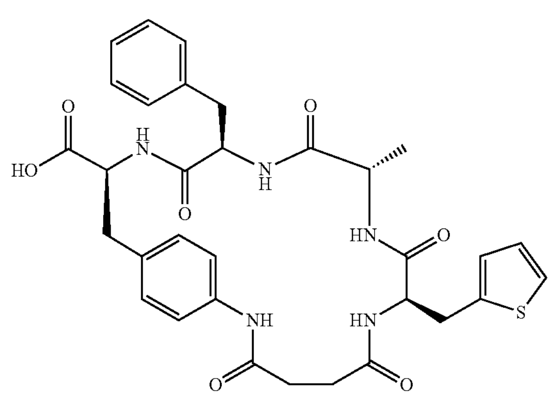 | 634.2330 | 634.2209 |

TABLE 1-continued

| Compound No. | Structure | MS Calcd | MS Observed |
|---|---|---|---|
| 46 | 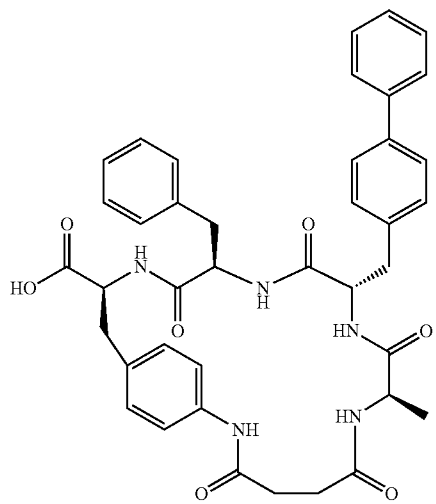 | 704.3079 | 704.2955 |
| 47 | 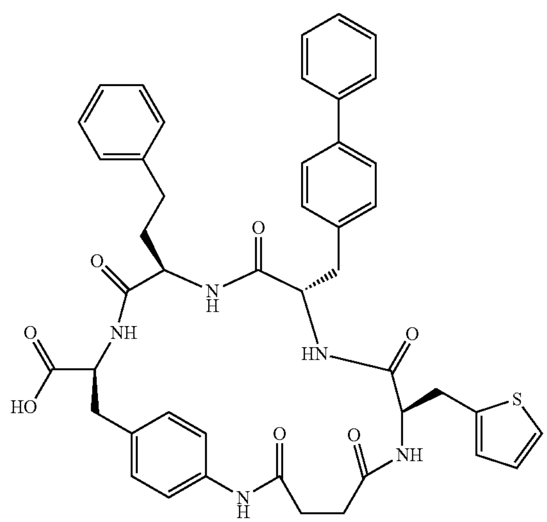 | 800.3113 | 800.3095 |
| 48 | 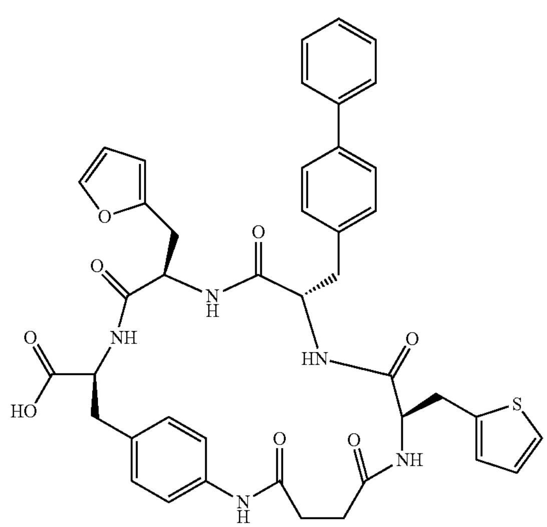 | 774.2603 | 774.2522 |

TABLE 1-continued

| Compound No. | Structure | MS Calcd | MS Observed |
|---|---|---|---|
| 49 | 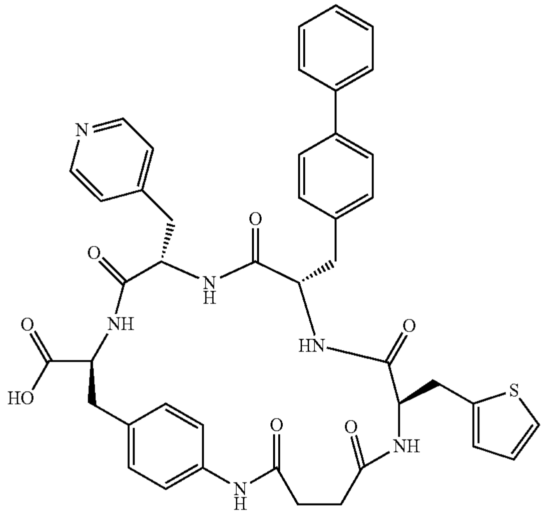 | 785.2763 | 785.2687 |
| 50 | 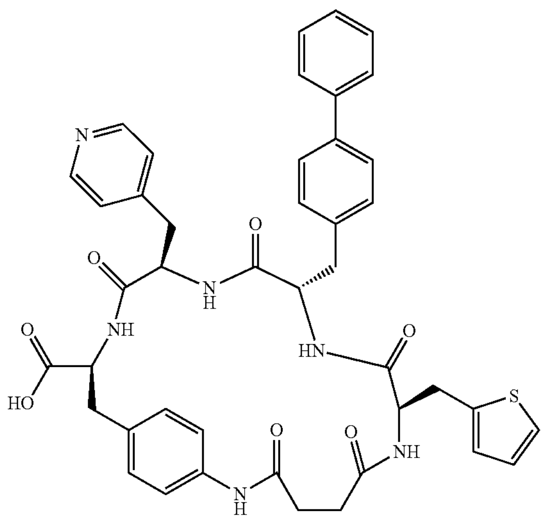 | 787.2909 | 787.2942 |
| 51 | 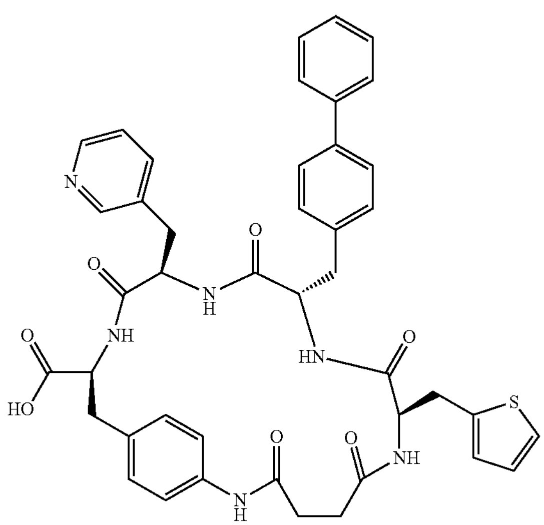 | 785.2763 | 785.2692 |

TABLE 1-continued

| Compound No. | Structure | MS Calcd | MS Observed |
| --- | --- | --- | --- |
| 52 | 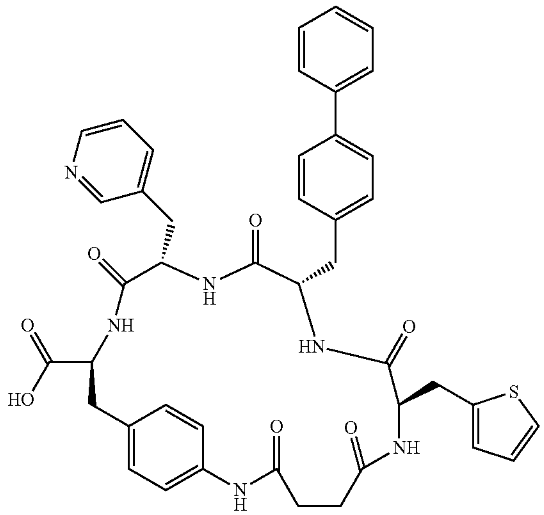 | 785.2763 | 785.2809 |
| 53 | 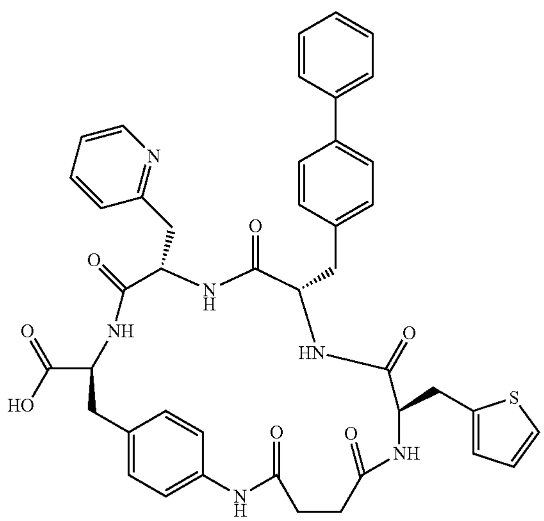 | 785.2763 | 785.2703 |
| 54 | 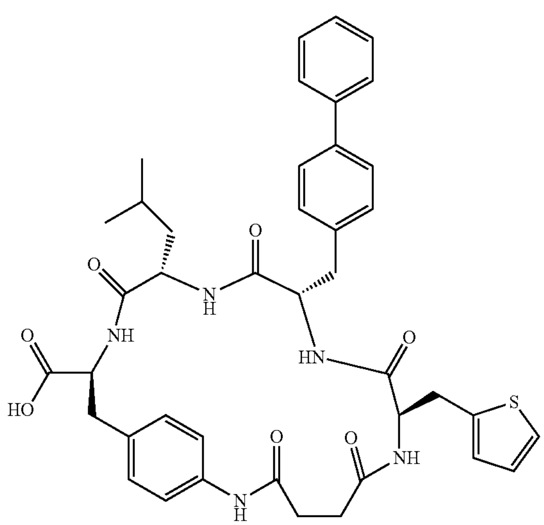 | 750.2967 | 750.2972 |

TABLE 1-continued

| Compound No. | Structure | MS Calcd | MS Observed |
|---|---|---|---|
| 55 | 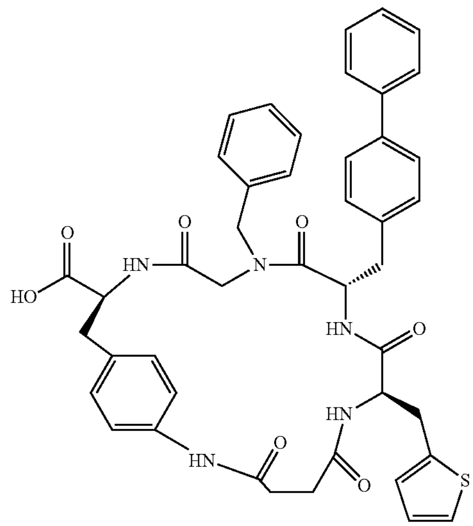 | 786.2956 | 786.3016 |
| 56 | 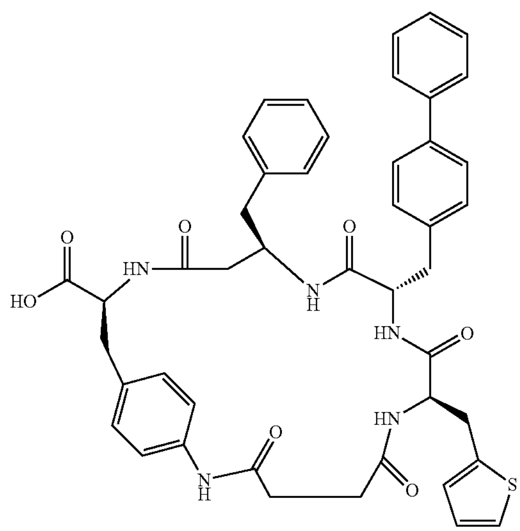 | 798.2967 | 798.2900 |
| 57 | 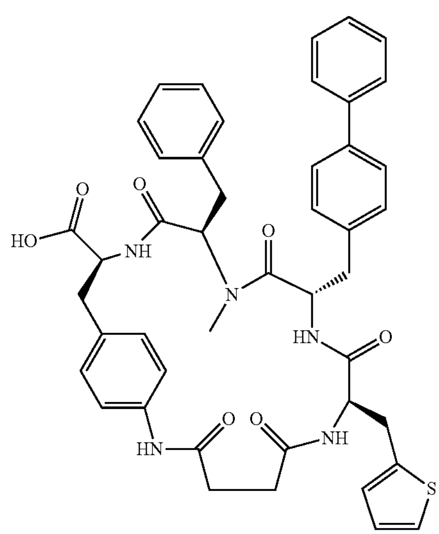 | 798.2967 | 798.2913 |

TABLE 1-continued

| Compound No. | Structure | MS Calcd | MS Observed |
|---|---|---|---|
| 58 | 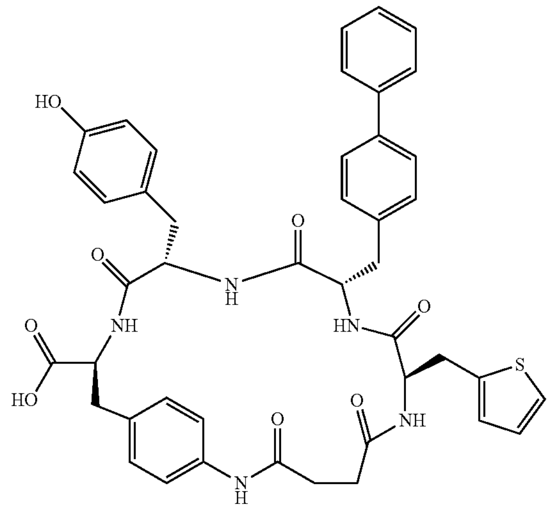 | 800.2759 | 800.2723 |
| 59 | 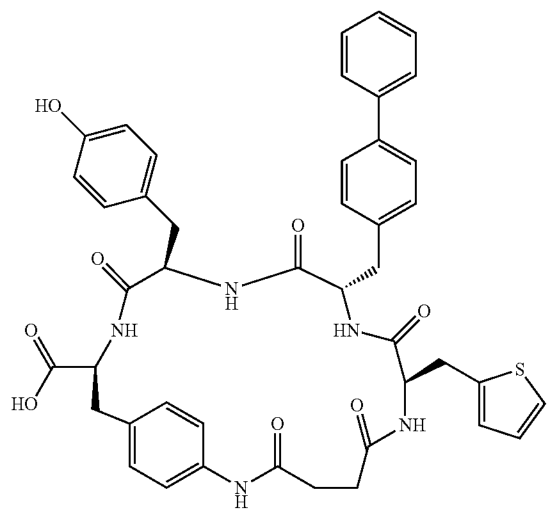 | 800.2759 | 800.2648 |
| 60 | 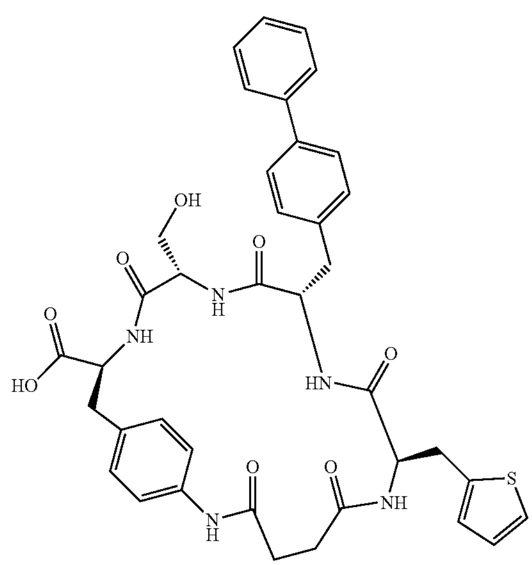 | 726.2592 | 726.2609 |

TABLE 1-continued

| Compound No. | Structure | MS Calcd | MS Observed |
|---|---|---|---|
| 61 | 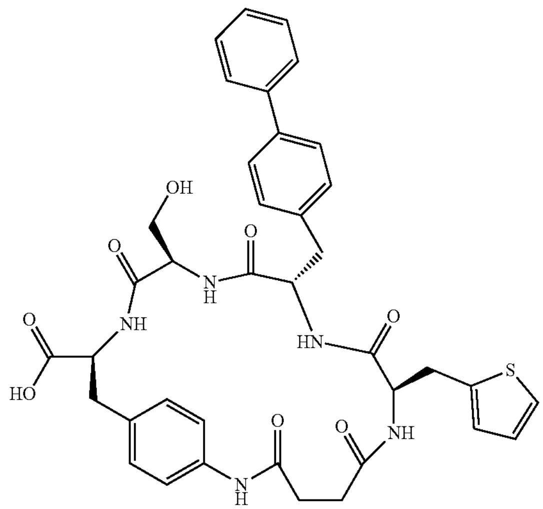 | 724.2446 | 724.2427 |
| 62 | 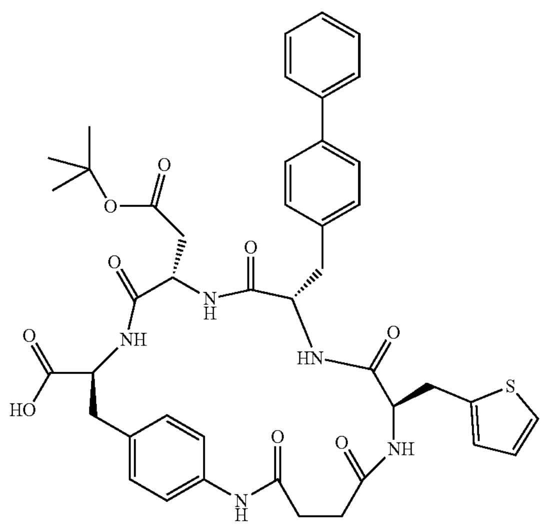 | 808.3022 | 808.2966 |
| 63 | 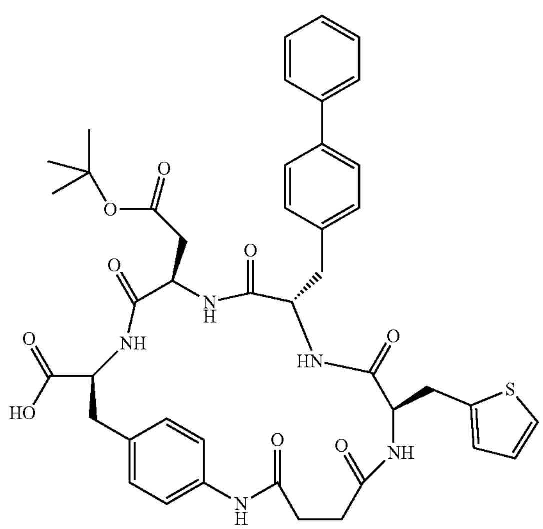 | 808.3022 | 808.2992 |

TABLE 1-continued

| Compound No. | Structure | MS Calcd | MS Observed |
|---|---|---|---|
| 64 | 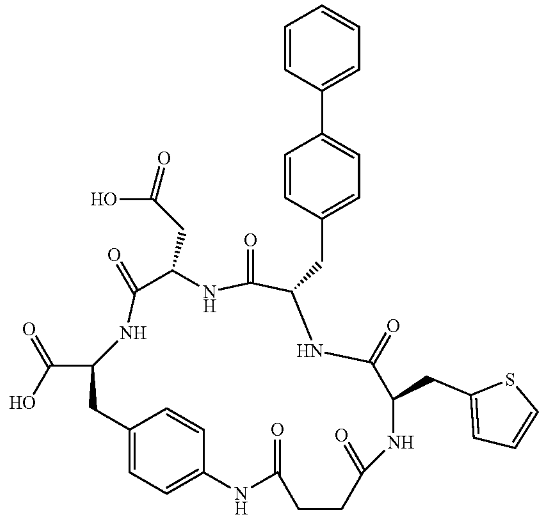 | 754.2542 | 754.2531 |
| 65 | 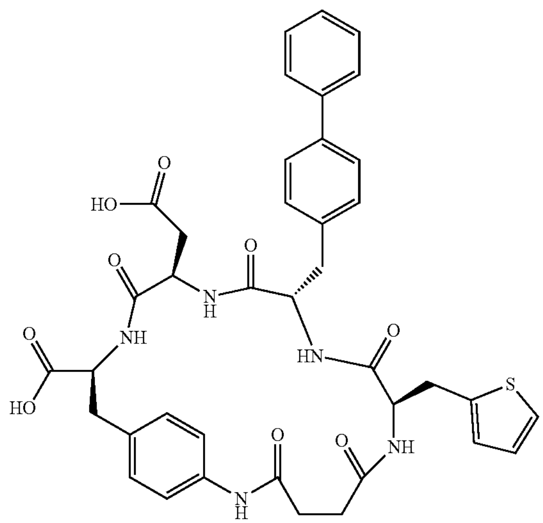 | 752.2396 | 752.2330 |
| 66 | 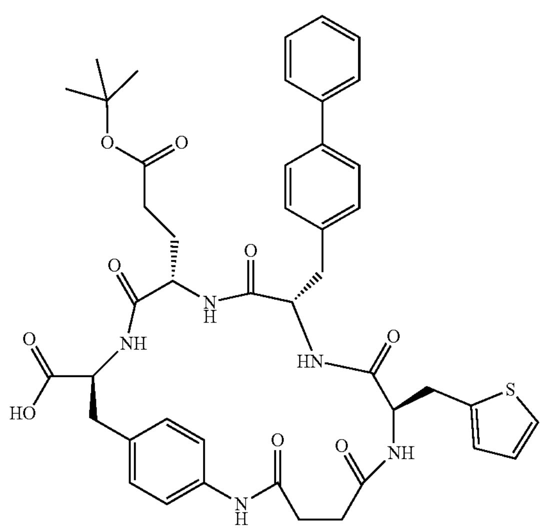 | 822.3178 | 822.3117 |

TABLE 1-continued
| Compound No. | Structure | MS Calcd | MS Observed |
|---|---|---|---|
| 67 | 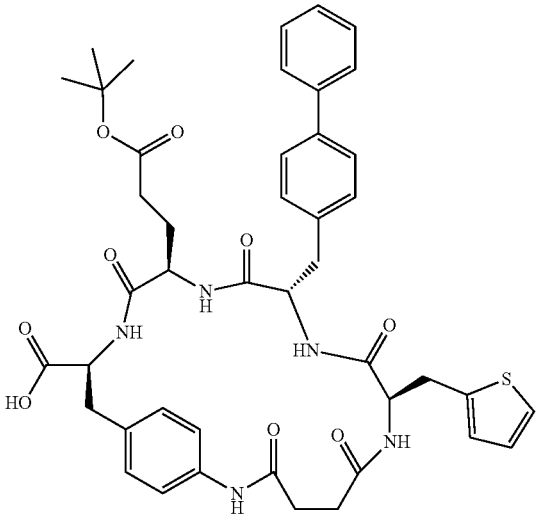 | 824.3324 | 824.3272 |
| 68 | 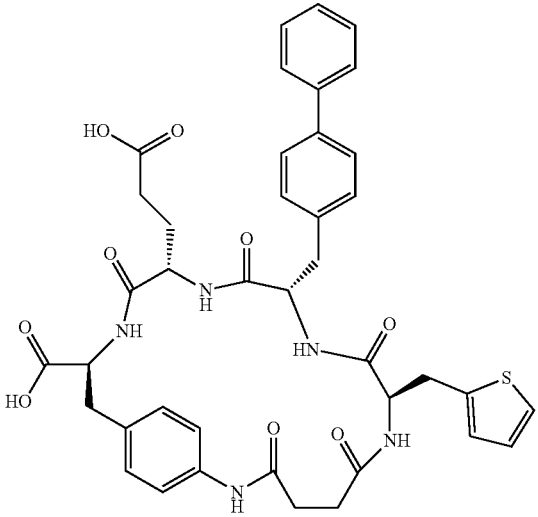 | 768.2698 | 768.2757 |
| 69 | 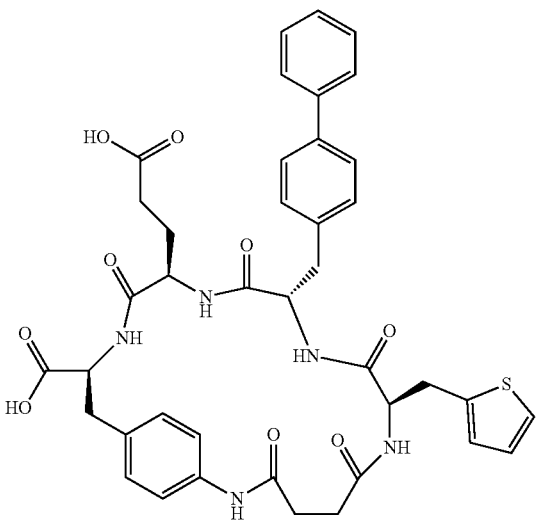 | 768.2698 | 768.2698 |

TABLE 1-continued
| Compound No. | Structure | MS Calcd | MS Observed |
|---|---|---|---|
| 72 | 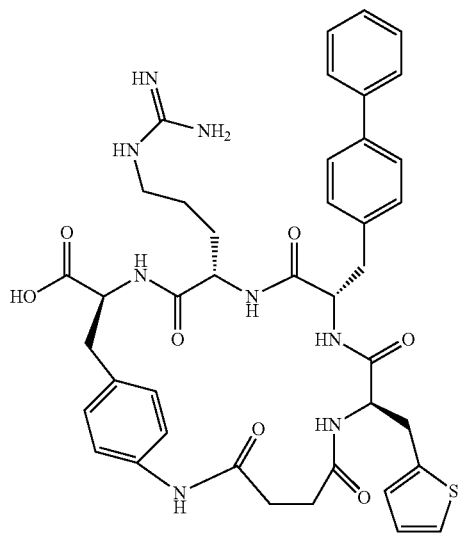 | 793.3137 | 793.3073 |
| 73 | 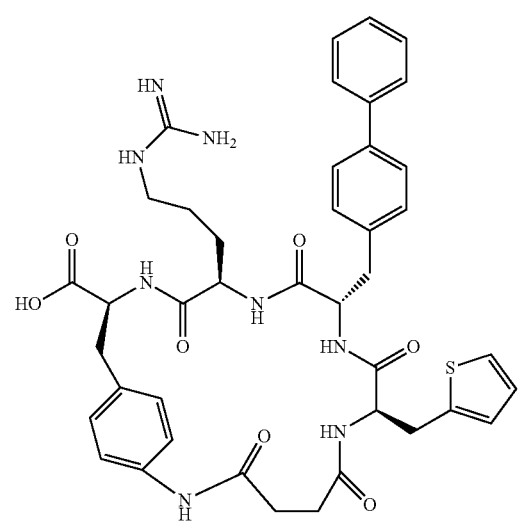 | 793.3137 | 793.3129 |
| 74 | 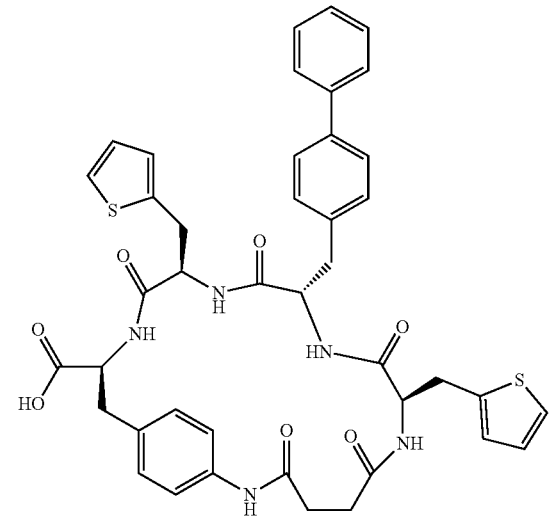 | 792.2520 | 792.2447 |

TABLE 1-continued

| Compound No. | Structure | MS Calcd | MS Observed |
|---|---|---|---|
| 75 | 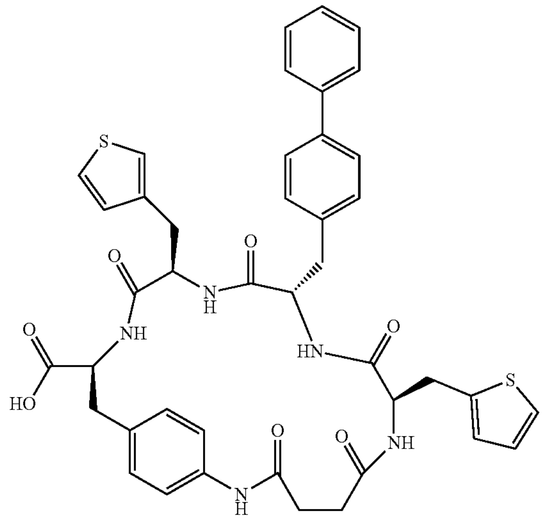 | 792.2520 | 792.2620 |
| 76 | 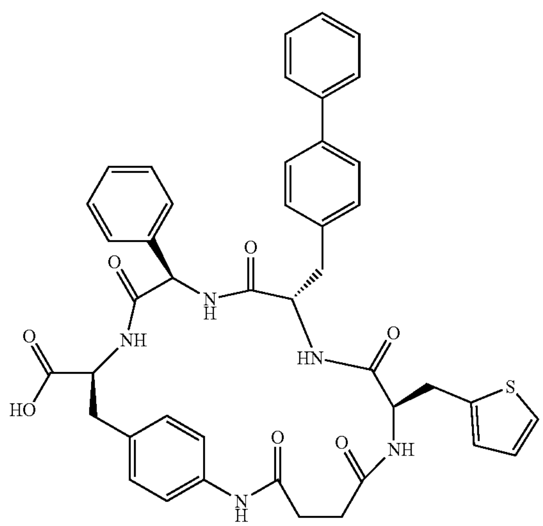 | 772.2800 | 772.2802 |
| 77 | 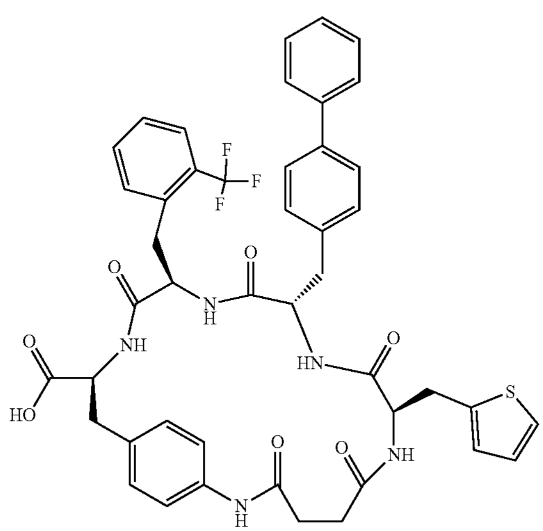 | 854.2830 | 854.2804 |

TABLE 1-continued

| Compound No. | Structure | MS Calcd | MS Observed |
|---|---|---|---|
| 78 | 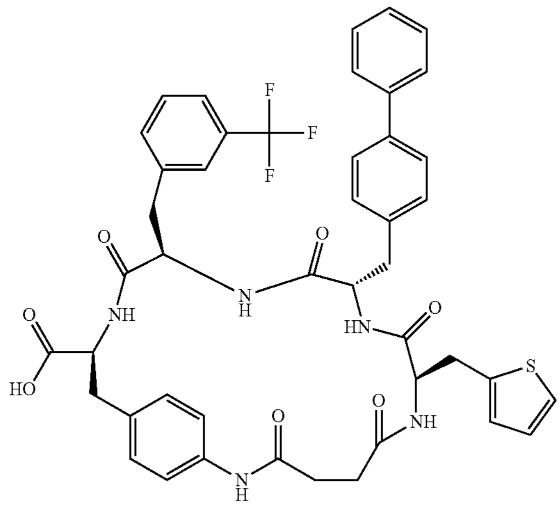 | 854.2830 | 854.2861 |
| 79 | 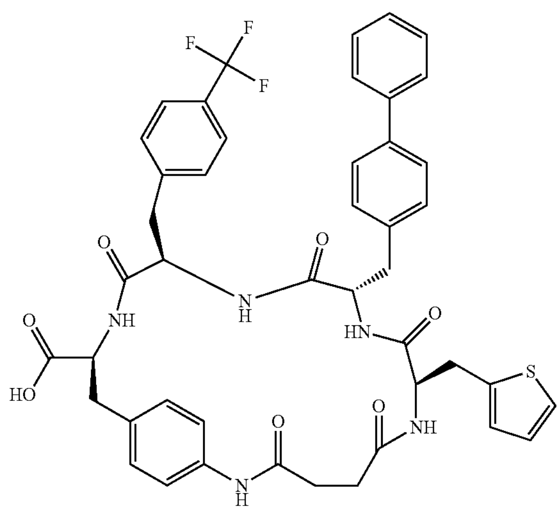 | 854.2830 | 854.2835 |
| 80 | 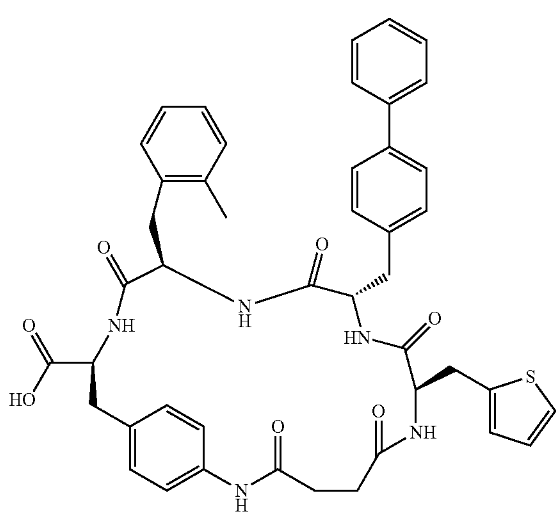 | 800.3113 | 800.3138 |

TABLE 1-continued
| Compound No. | Structure | MS Calcd | MS Observed |
|---|---|---|---|
| 81 | 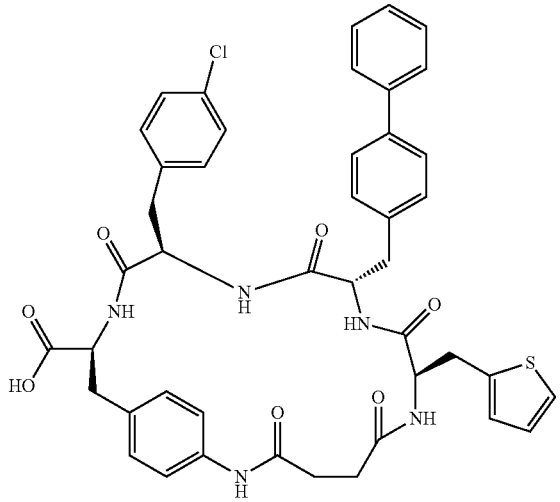 | 820.2567 | 820.2551 |
| 82 | 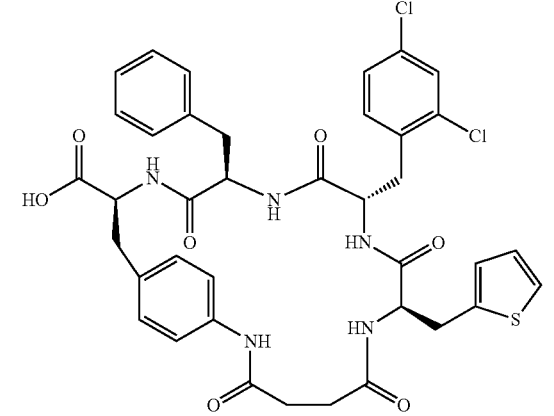 | 778.1869 | 778.1863 |
| 83 | 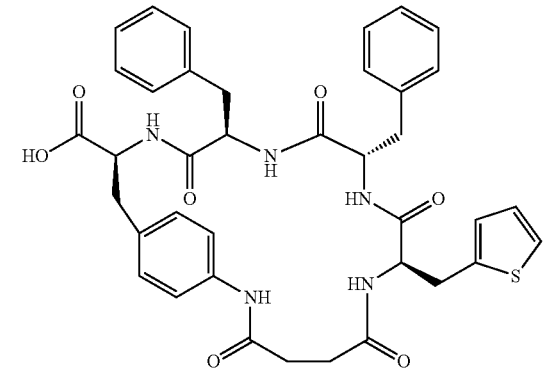 | 710.2643 | 710.2559 |

TABLE 1-continued

| Compound No. | Structure | MS Calcd | MS Observed |
|---|---|---|---|
| 84 | 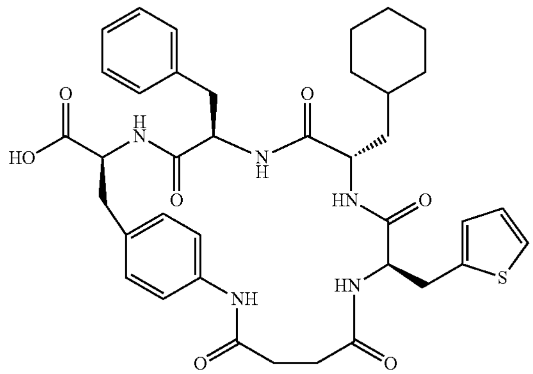 | 716.3113 | 716.3038 |
| 85 | 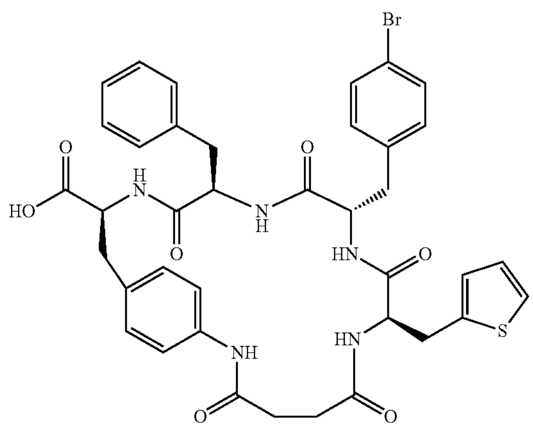 | 788.1748 | 788.1722 |
| 86 | 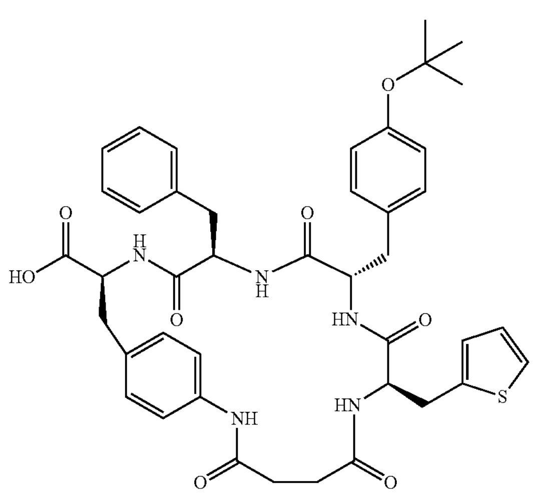 | 782.3218 | 782.3104 |

TABLE 1-continued

| Compound No. | Structure | MS Calcd | MS Observed |
| --- | --- | --- | --- |
| 87 | 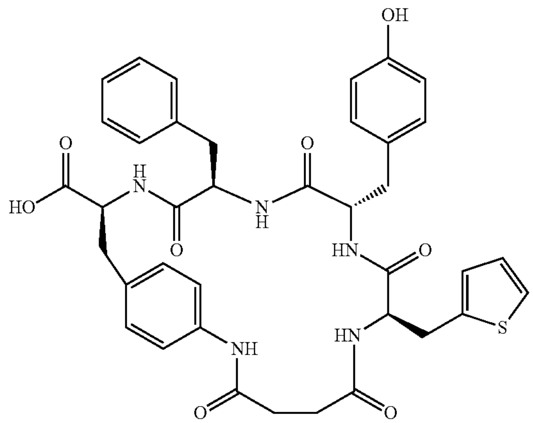 | 726.2592 | 726.2487 |
| 88 | 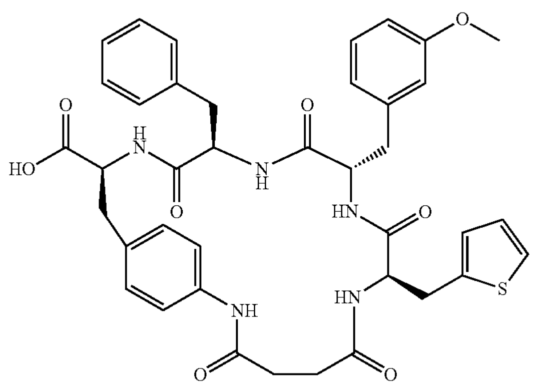 | 740.2749 | 740.2802 |
| 89 | 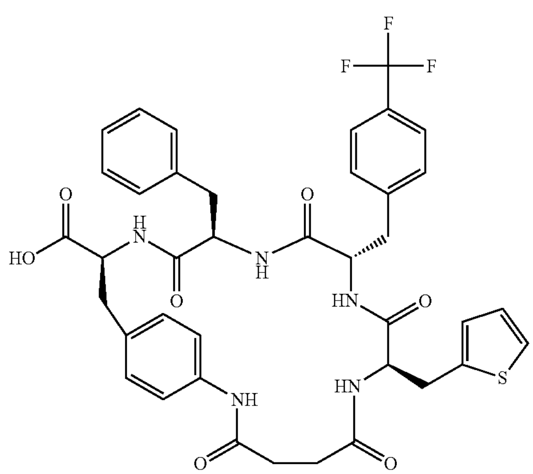 | 778.2517 | 778.2587 |

TABLE 1-continued

| Compound No. | Structure | MS Calcd | MS Observed |
|---|---|---|---|
| 90 | 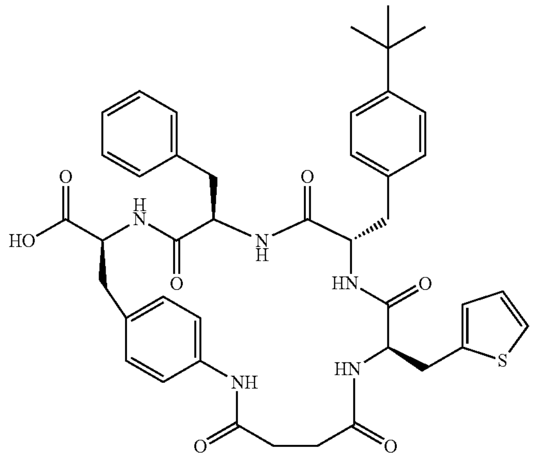 | 766.3269 | 766.3218 |
| 91 | 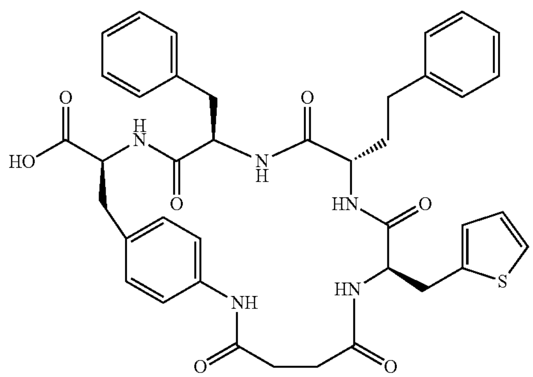 | 724.2800 | 724.2870 |
| 92 | 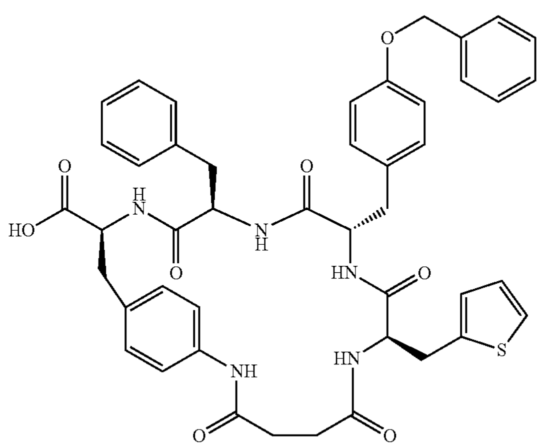 | 816.3062 | 816.3036 |

TABLE 1-continued

| Compound No. | Structure | MS Calcd | MS Observed |
|---|---|---|---|
| 93 | 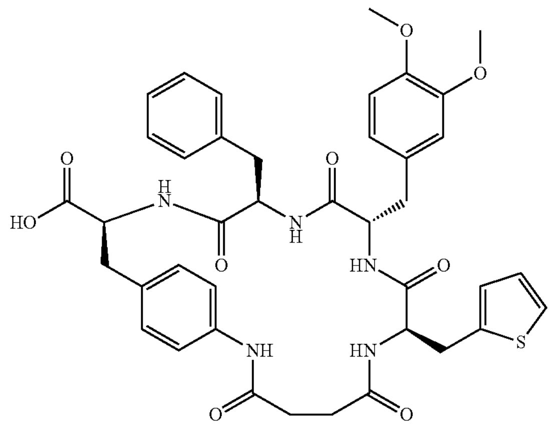 | 770.2854 | 770.2805 |
| 94 | 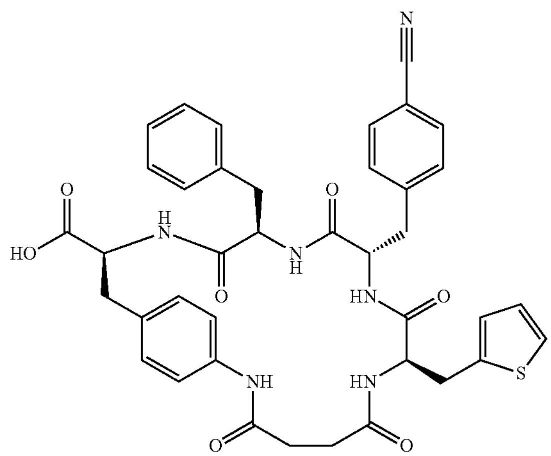 | 735.2596 | 735.2504 |
| 95 | 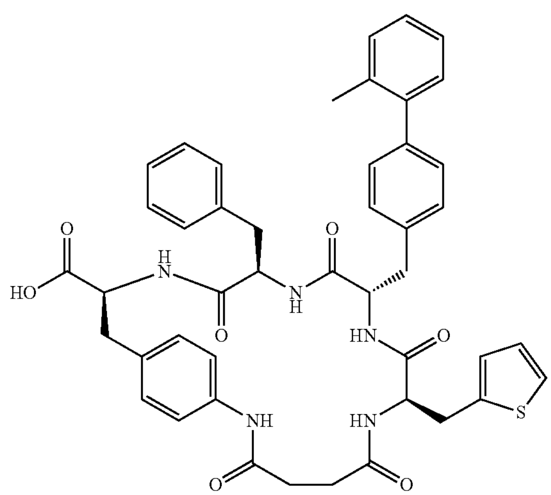 | 800.3113 | 800.3062 |

| Compound No. | Structure | MS Calcd | MS Observed |
|---|---|---|---|
| 96 | 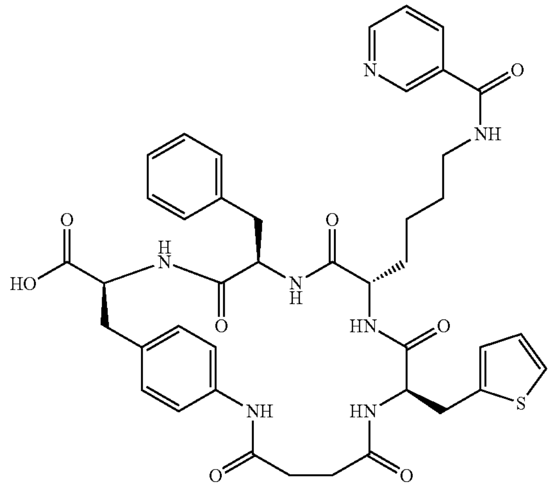 | 796.3123 | 796.3118 |
| 97 | 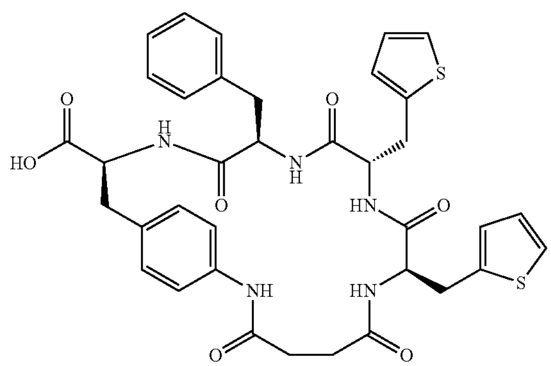 | 716.2207 | 716.2266 |
| 98 | 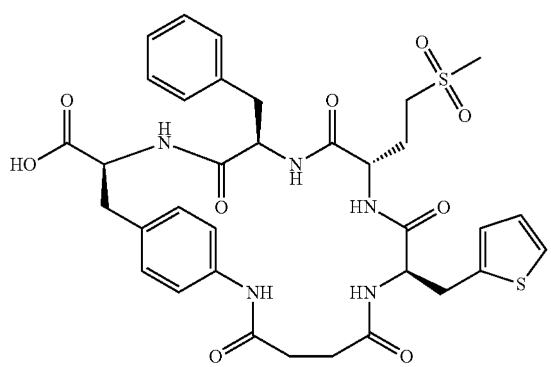 | 726.2262 | 726.2288 |
| 99 | 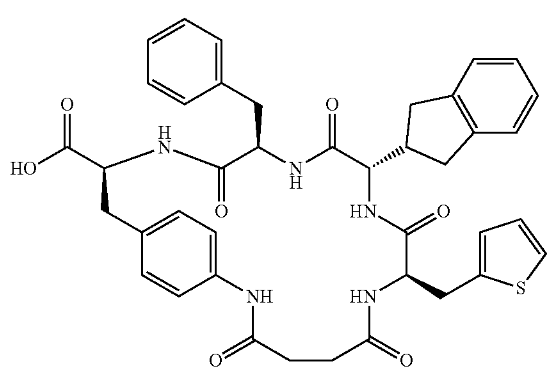 | 736.2800 | 736.2870 |

TABLE 1-continued
| Compound No. | Structure | MS Calcd | MS Observed |
|---|---|---|---|
| 100 | 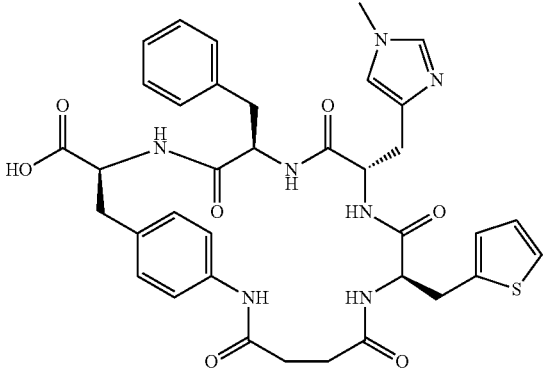 | 714.2705 | 714.2690 |
| 101 | 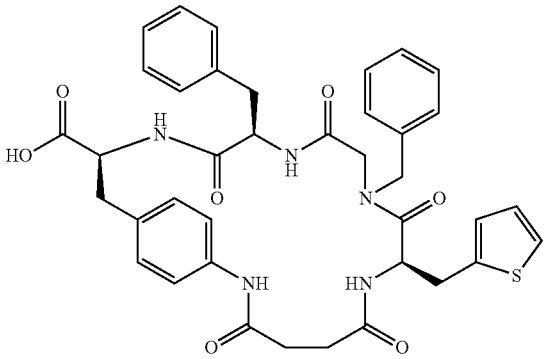 | 710.2643 | 710.2703 |
| 102 | 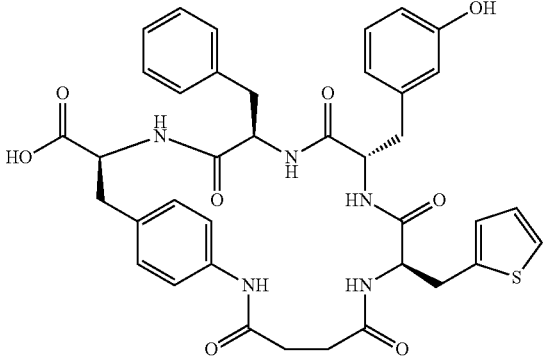 | 726.2597 | 726.2664 |
| 103 | 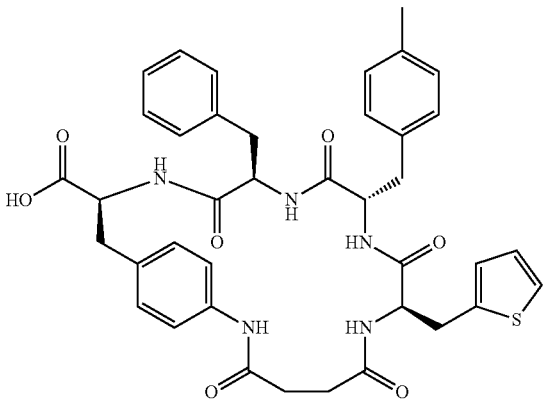 | 724.2805 | 724.2864 |

TABLE 1-continued

| Compound No. | Structure | MS Calcd | MS Observed |
|---|---|---|---|
| 104 | 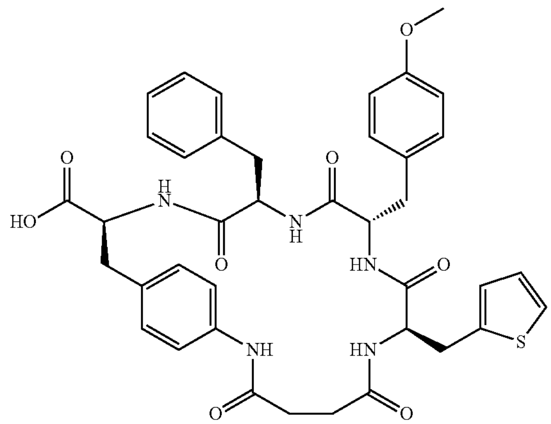 | 740.2754 | 740.2775 |
| 105 | 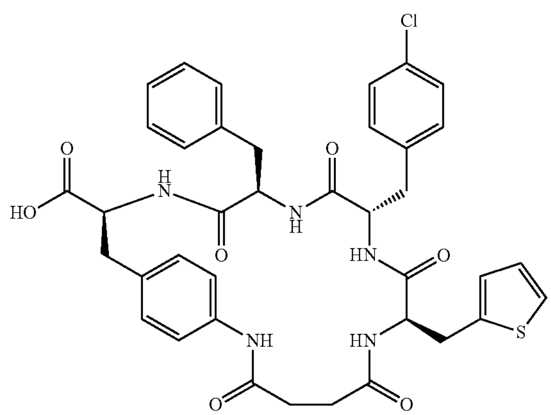 | 744.2258 | 744.2218 |
| 106 | 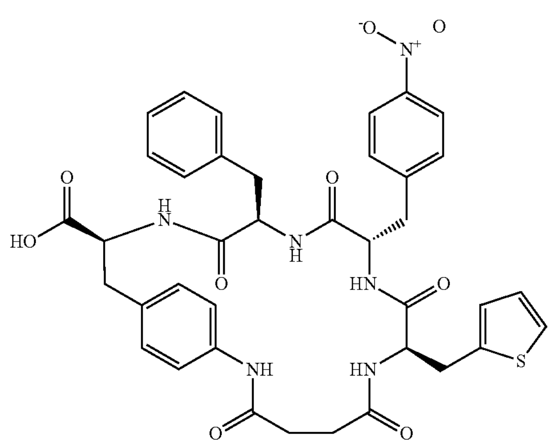 | 755.2499 | 755.2486 |

TABLE 1-continued

| Compound No. | Structure | MS Calcd | MS Observed |
|---|---|---|---|
| 107 | 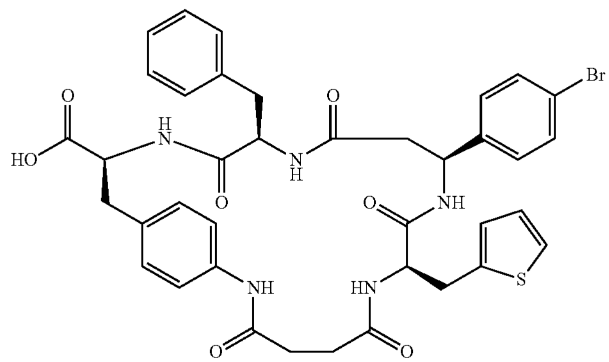 | 788.1753 | 788.1765 |
| 108 | 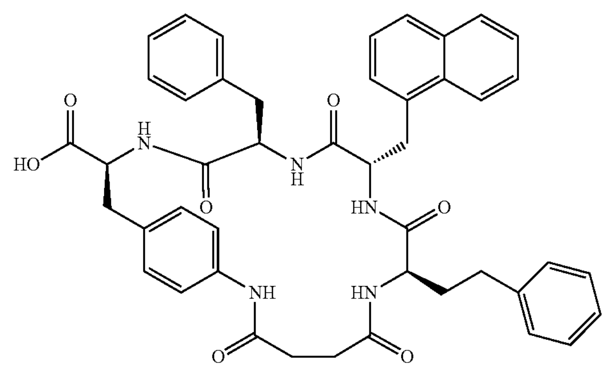 | 768.3397 | 768.3386 |
| 109 | 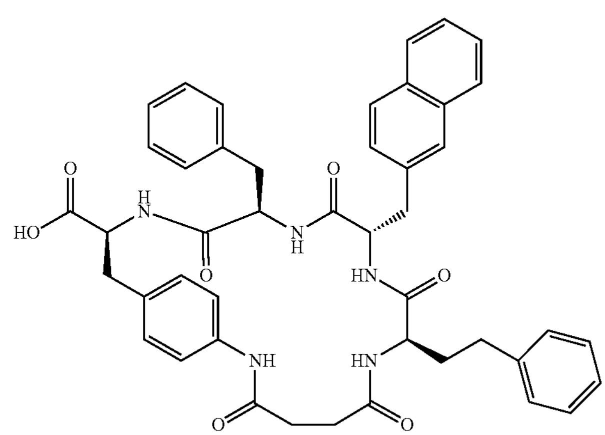 | 768.3397 | 768.3410 |

TABLE 1-continued

| Compound No. | Structure | MS Calcd | MS Observed |
|---|---|---|---|
| 110 | 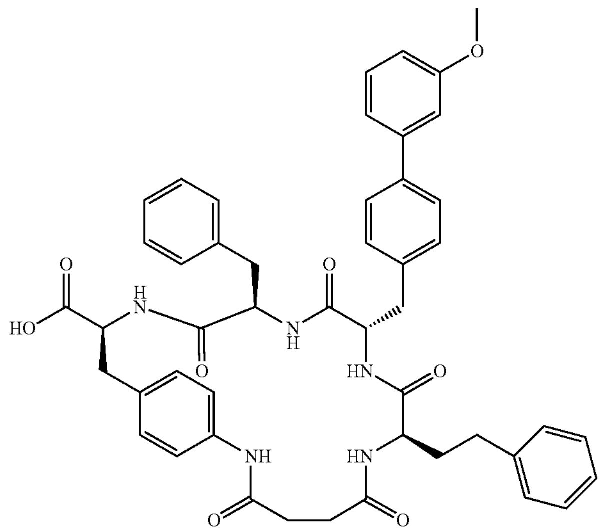 | 824.3659 | 824.3666 |
| 111 | 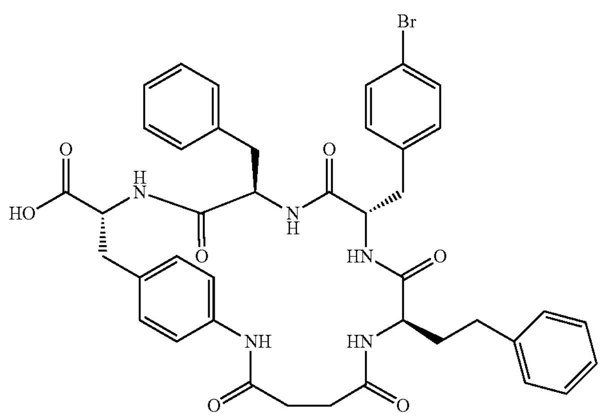 | 796.2346 | 796.2358 |
| 112 | 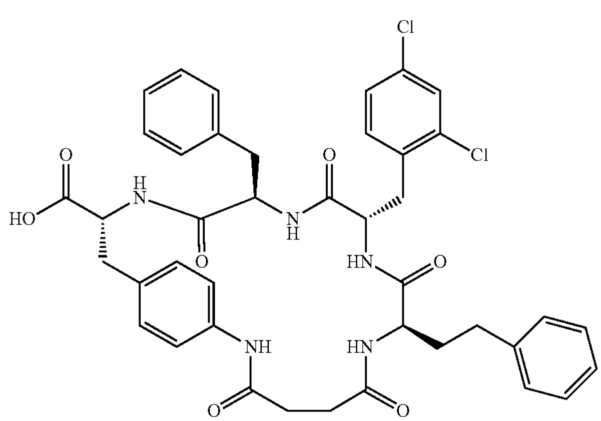 | 786.2461 | 786.2463 |

| Compound No. | Structure | MS Calcd | MS Observed |
|---|---|---|---|
| 113 | 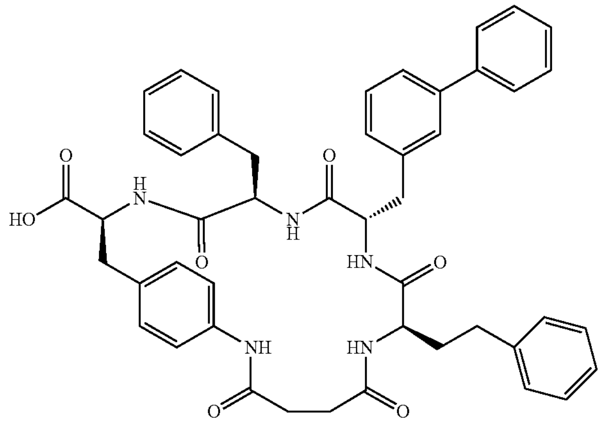 | 794.3553 | 794.3627 |
| 114 | 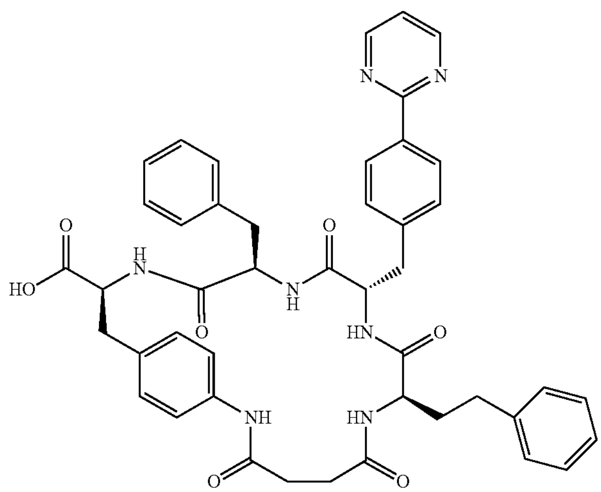 | 796.3458 | 796.3522 |
| 115 | 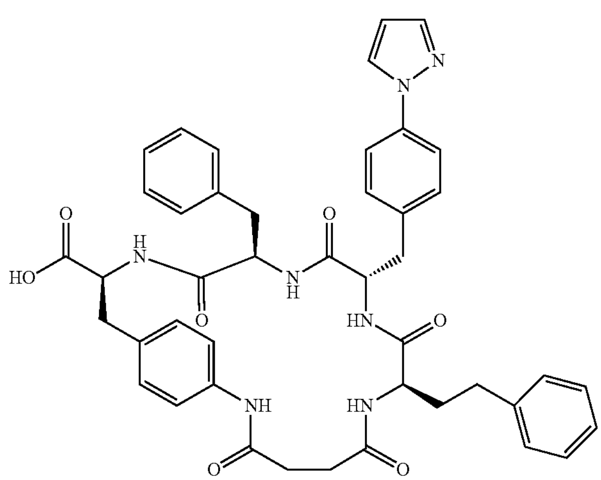 | 784.3458 | 784.3484 |

TABLE 1-continued

| Compound No. | Structure | MS Calcd | MS Observed |
|---|---|---|---|
| 116 | 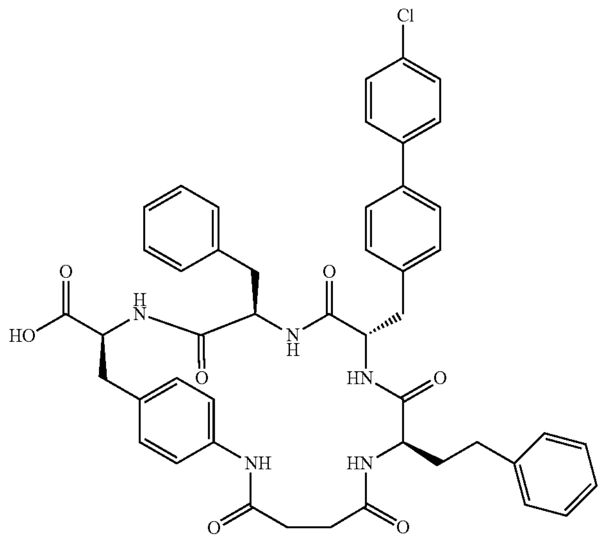 | 828.3159 | 828.3107 |
| 117 | 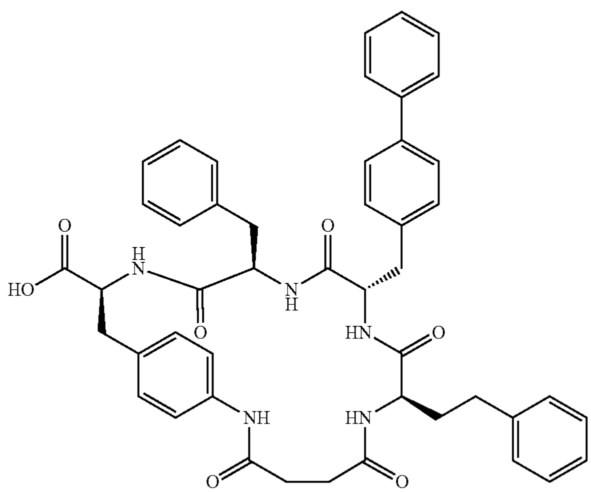 | 792.3397 | 792.341 |
| 118 | 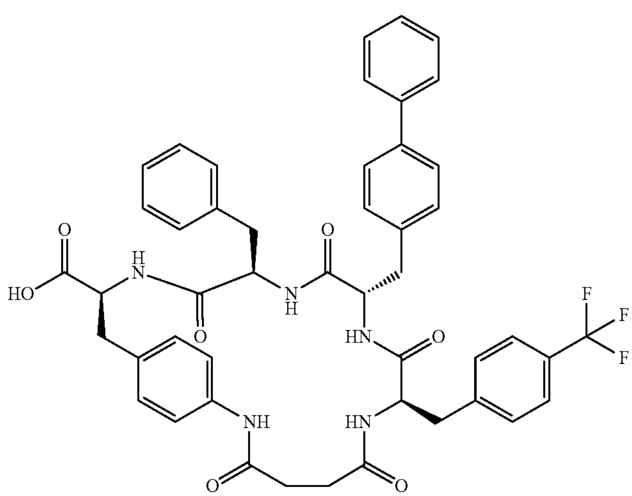 | 846.3115 | 846.3118 |

TABLE 1-continued

| Compound No. | Structure | MS Calcd | MS Observed |
|---|---|---|---|
| 119 | 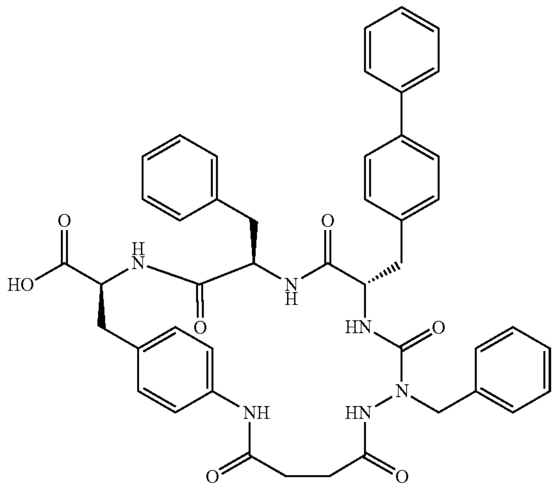 | 780.3397 | 780.3353 |
| 120 | 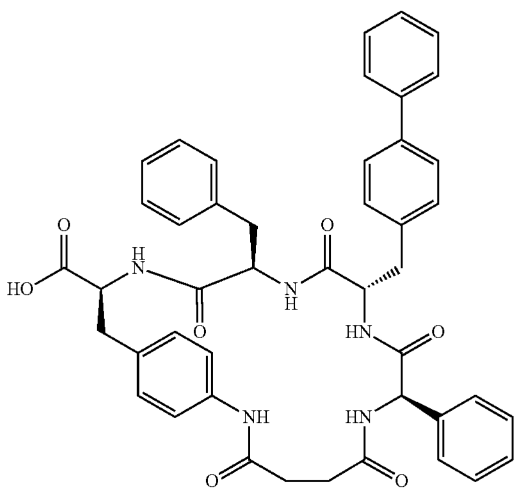 | 766.3241 | 766.3179 |
| 121 | 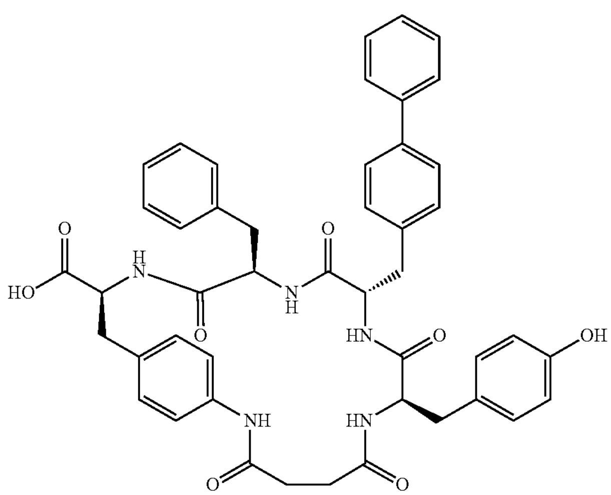 | 796.3346 | 796.3316 |

TABLE 1-continued

| Compound No. | Structure | MS Calcd | MS Observed |
|---|---|---|---|
| 122 | 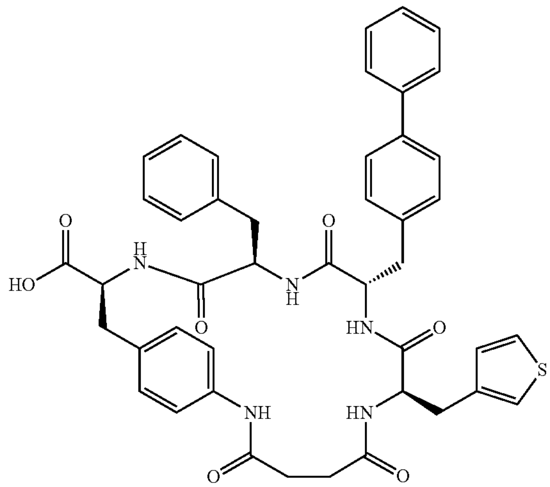 | 784.2805 | 784.2748 |
| 123 | 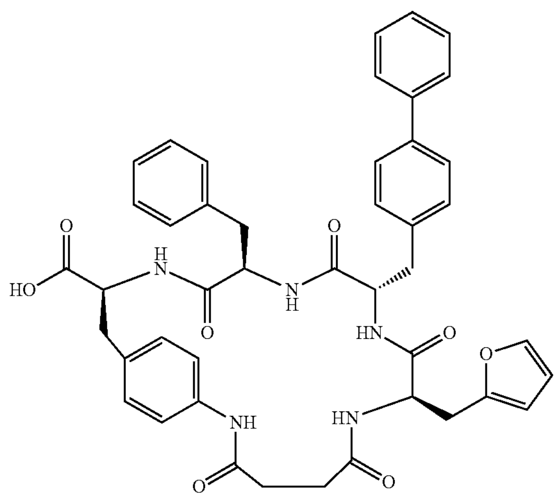 | 768.3033 | 768.3011 |
| 124 | 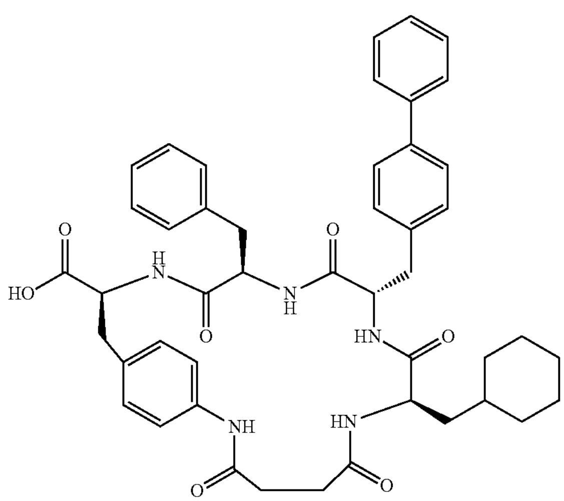 | 784.371 | 784.368 |

TABLE 1-continued

| Compound No. | Structure | MS Calcd | MS Observed |
|---|---|---|---|
| 125 | 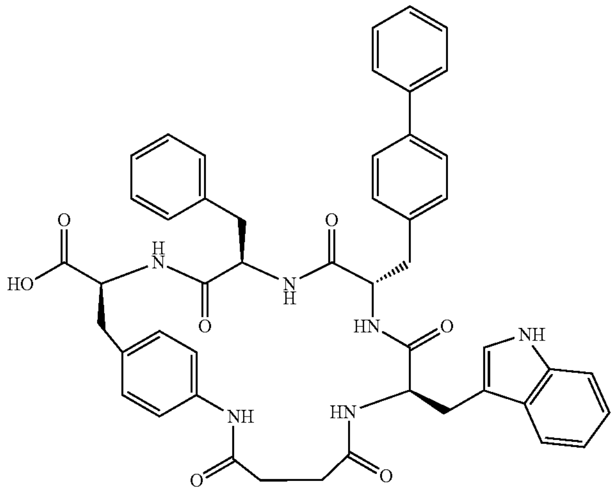 | 819.3506 | 819.3434 |
| 126 | 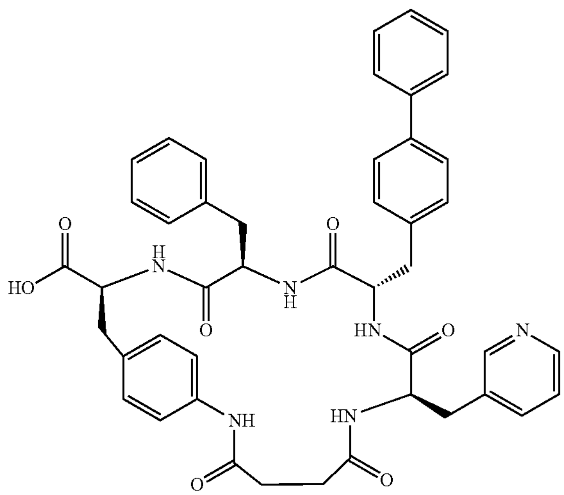 | 781.335 | 781.3309 |
| 127 | 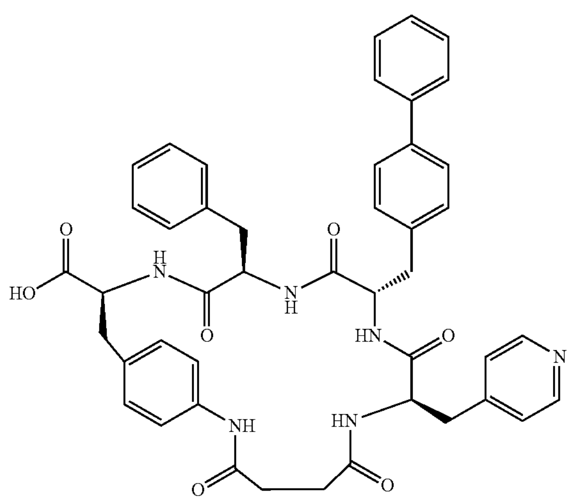 | 779.3193 | 779.3175 |

TABLE 1-continued

| Compound No. | Structure | MS Calcd | MS Observed |
|---|---|---|---|
| 128 | 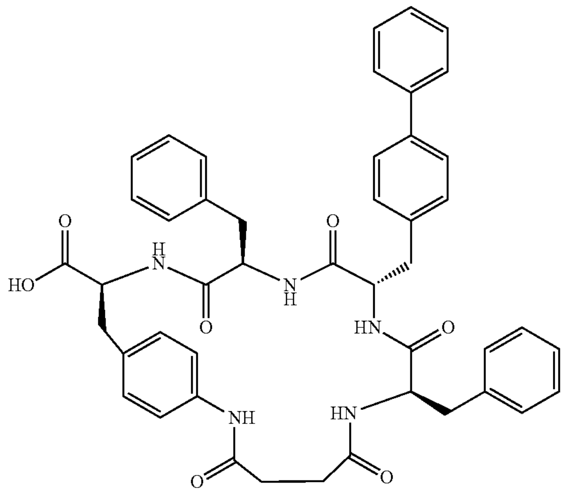 | 780.3397 | 780.3350 |
| 129 | 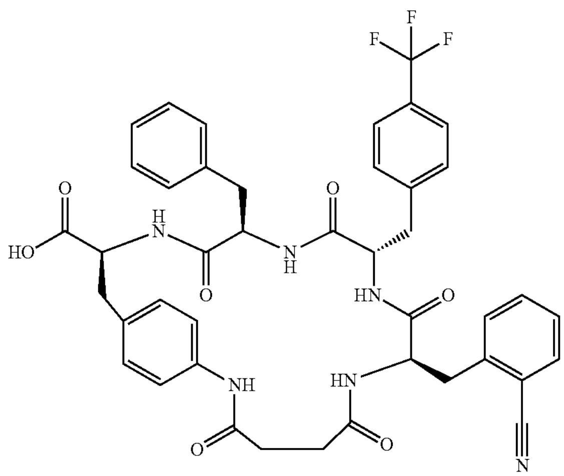 | 795.2754 | 795.2748 |
| 130 | 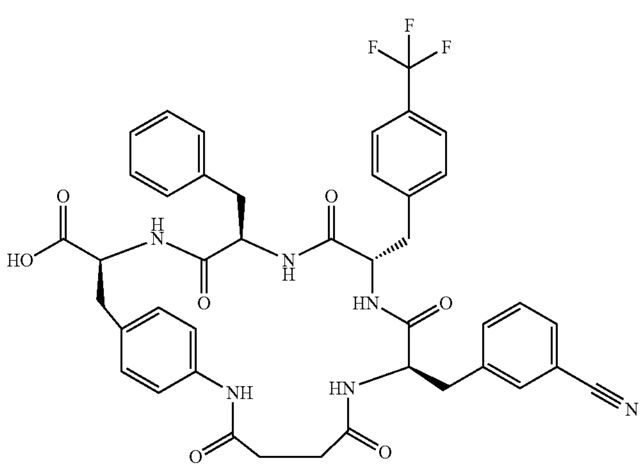 | 795.2754 | 795.2807 |

TABLE 1-continued

| Compound No. | Structure | MS Calcd | MS Observed |
|---|---|---|---|
| 131 | 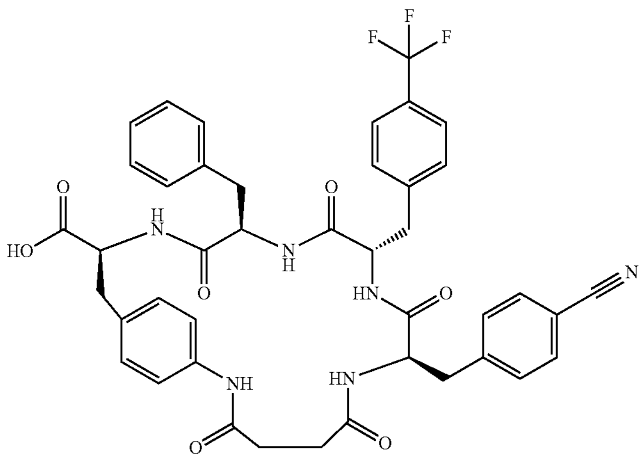 | 795.2754 | 795.265 |
| 132 | 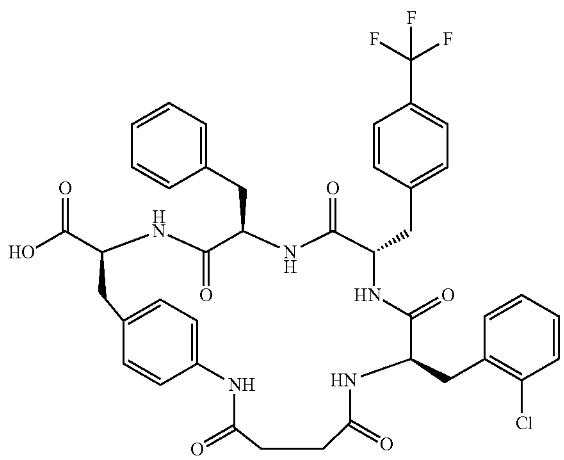 | 804.2412 | 804.2449 |
| 133 | 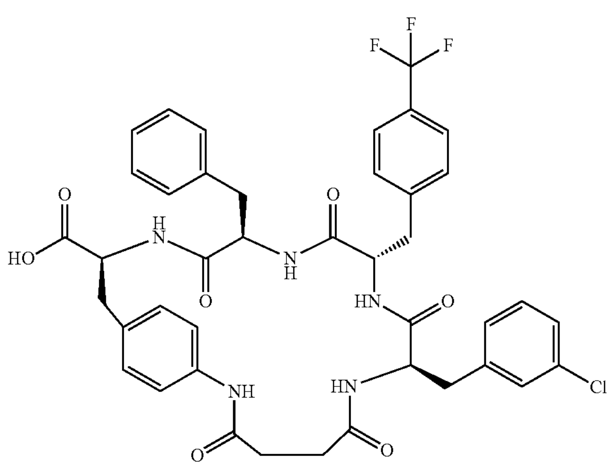 | 806.2568 | 806.2598 |

TABLE 1-continued

| Compound No. | Structure | MS Calcd | MS Observed |
|---|---|---|---|
| 134 | 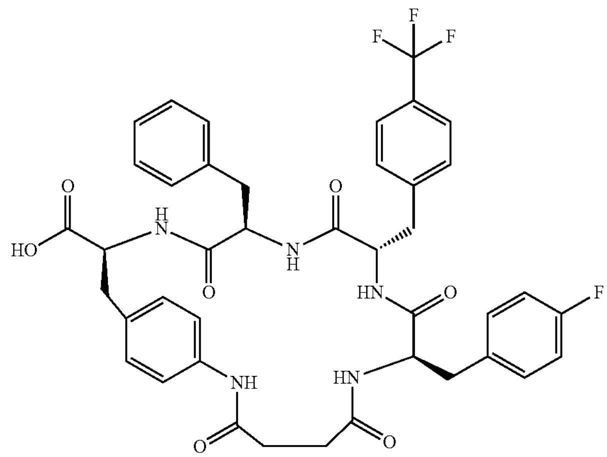 | 788.2716 | 788.2716 |
| 135 | 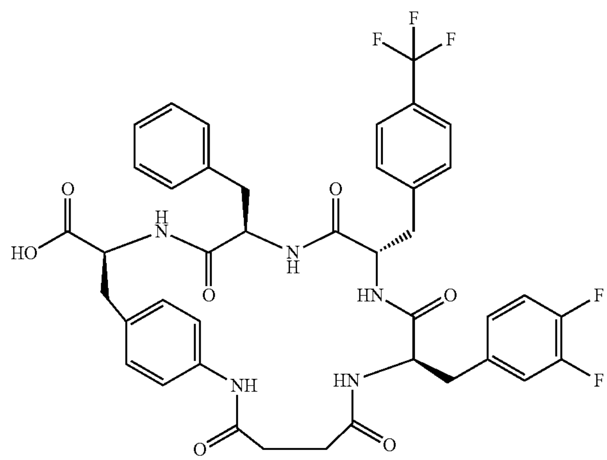 | 808.277 | 808.2766 |
| 136 | 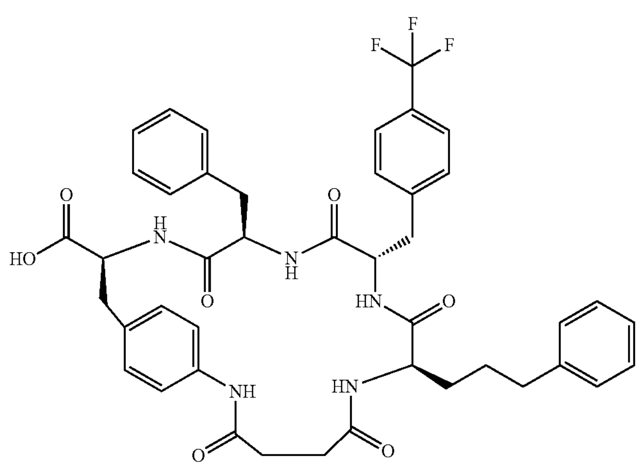 | 800.3271 | 800.3324 |

TABLE 1-continued

| Compound No. | Structure | MS Calcd | MS Observed |
|---|---|---|---|
| 137 | 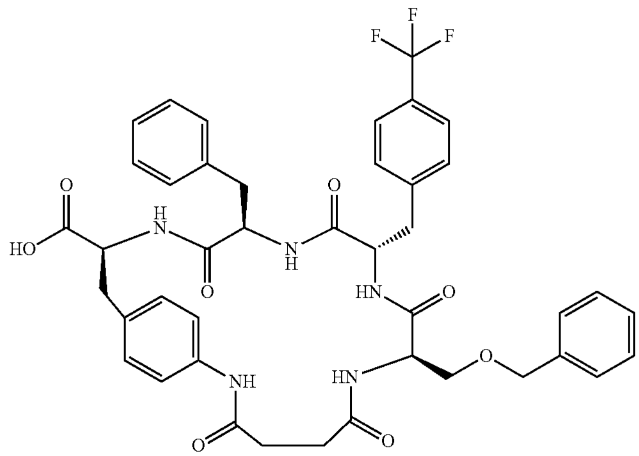 | 802.3064 | 802.3115 |
| 138 | 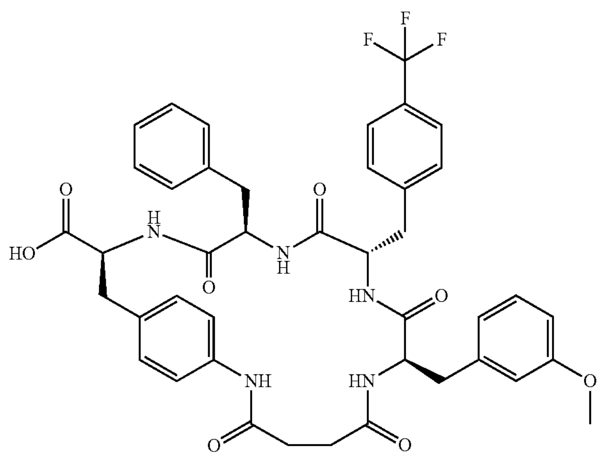 | 802.3064 | 802.3099 |
| 139 | 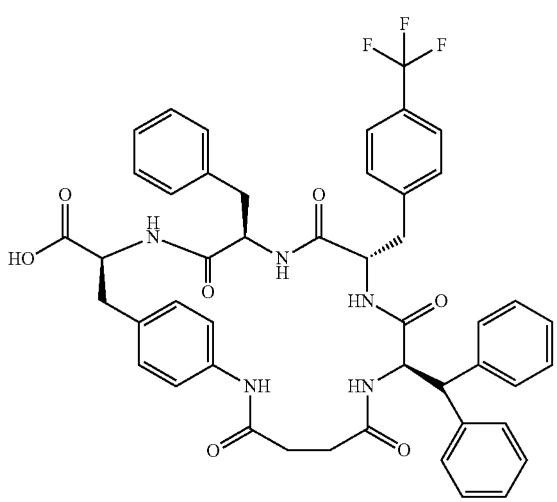 | 784.2958 | 784.2958 |

TABLE 1-continued

| Compound No. | Structure | MS Calcd | MS Observed |
|---|---|---|---|
| 140 | 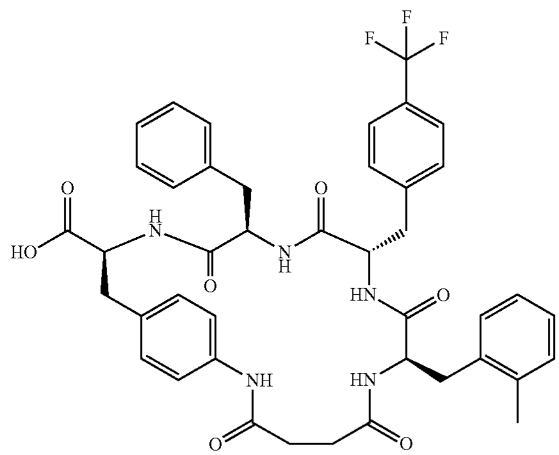 | 846.3115 | 846.3099 |
| 141 | 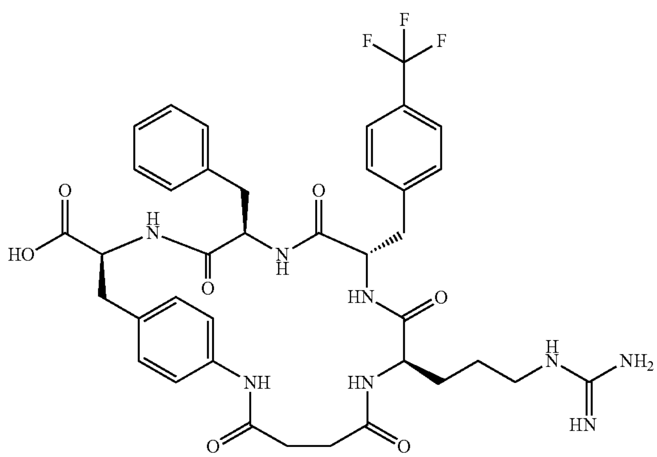 | 781.3285 | 781.3350 |
| 142 | 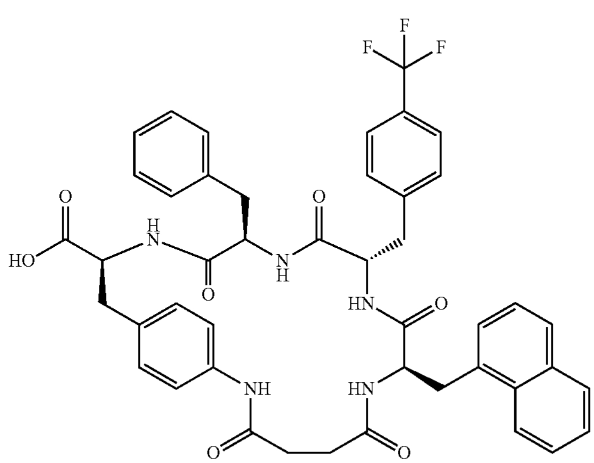 | 822.3115 | 822.3170 |

TABLE 1-continued

| Compound No. | Structure | MS Calcd | MS Observed |
|---|---|---|---|
| 143 | 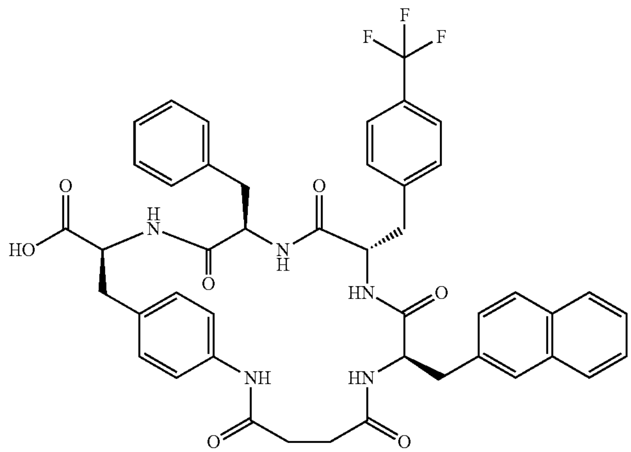 | 822.3115 | 822.3237 |
| 144 | 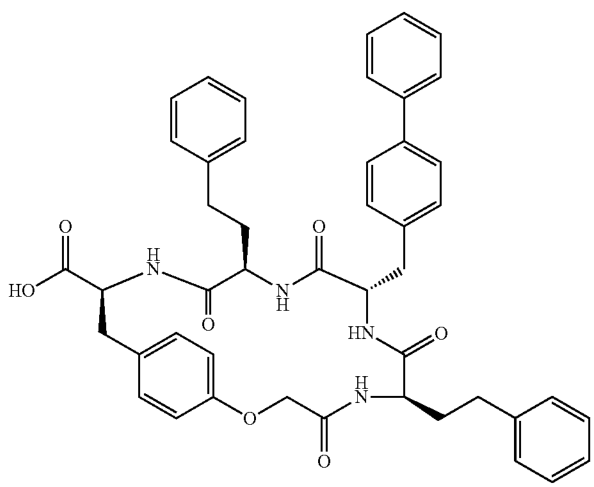 | 767.3445 | 767.3433 |
| 145 | 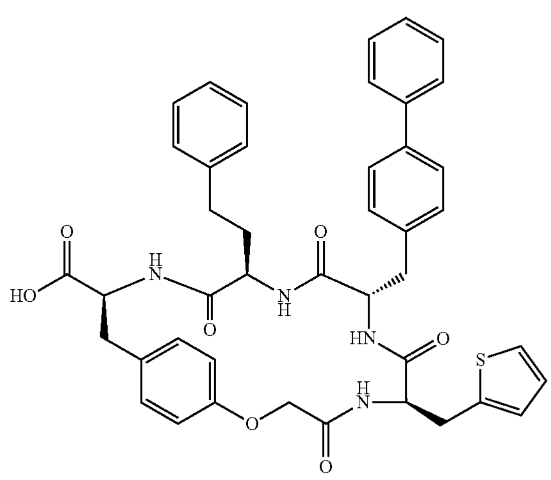 | 759.2852 | 759.2859 |

TABLE 1-continued

| Compound No. | Structure | MS Calcd | MS Observed |
|---|---|---|---|
| 146 | 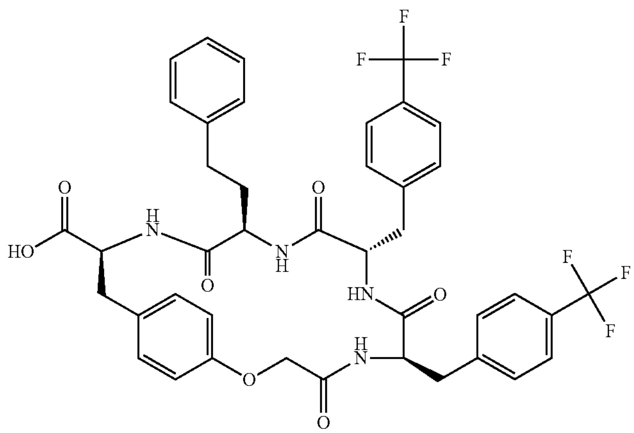 | 813.2723 | 813.2751 |
| 147 | 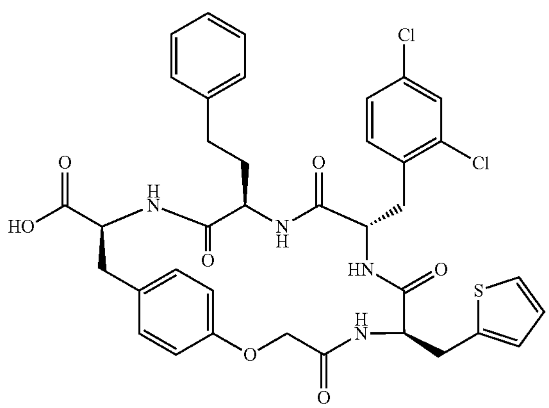 | 751.1760 | 751.1730 |
| 148 | 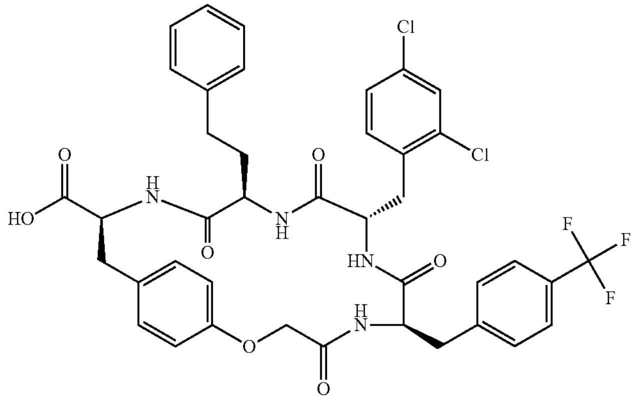 | 813.2070 | 813.2111 |

TABLE 1-continued

| Compound No. | Structure | MS Calcd | MS Observed |
|---|---|---|---|
| 149 | 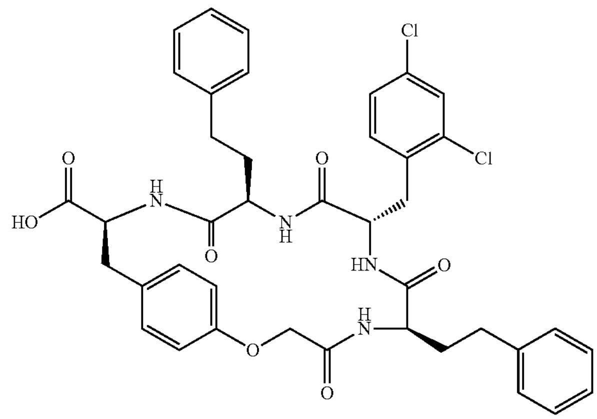 | 759.2352 | 759.2335 |
| 150 | 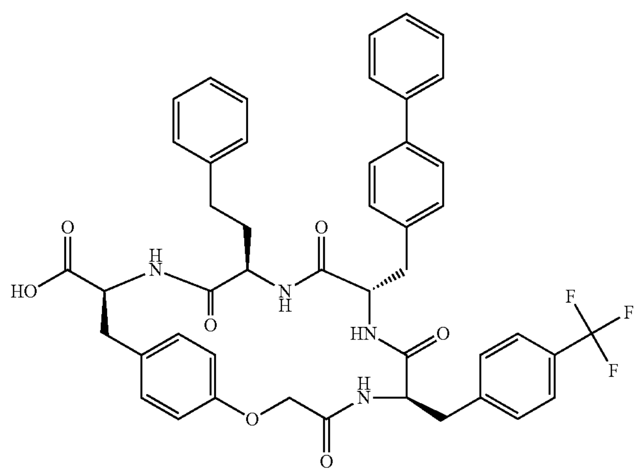 | 821.3162 | 821.3181 |
| 151 | 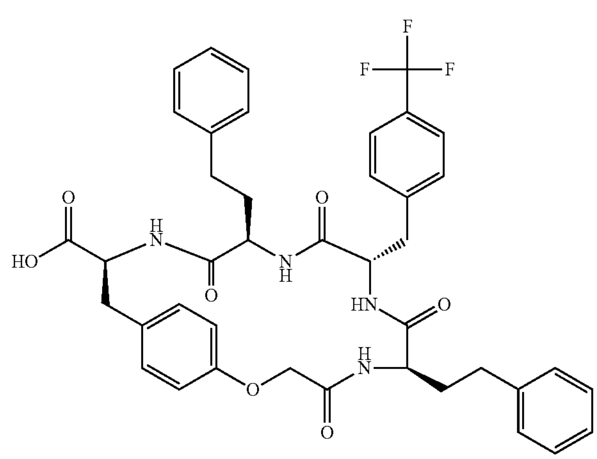 | 759.3006 | 759.2996 |

TABLE 1-continued

| Compound No. | Structure | MS Calcd | MS Observed |
|---|---|---|---|
| 152 | 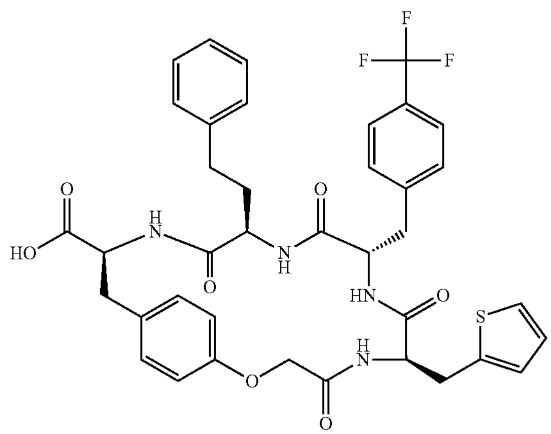 | 757.2849 | 757.2880 |
| 153 | 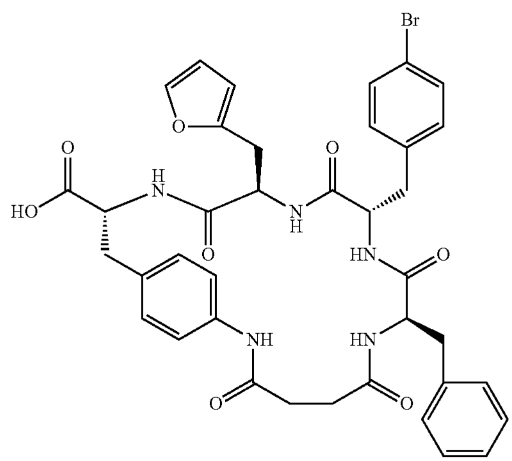 | 772.1982 | 772.1990 |
| 154 | 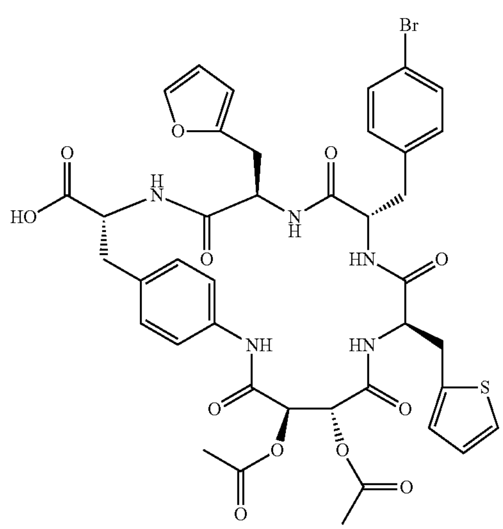 | 894.1656 | 894.1656 |

TABLE 1-continued
| Compound No. | Structure | MS Calcd | MS Observed |
|---|---|---|---|
| 155 | 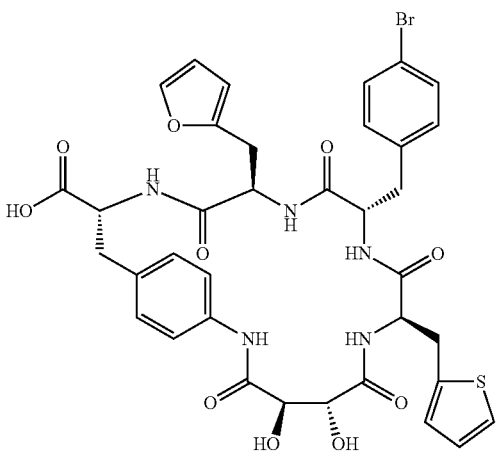 | 810.1444 | 810.1420 |
| 156 | 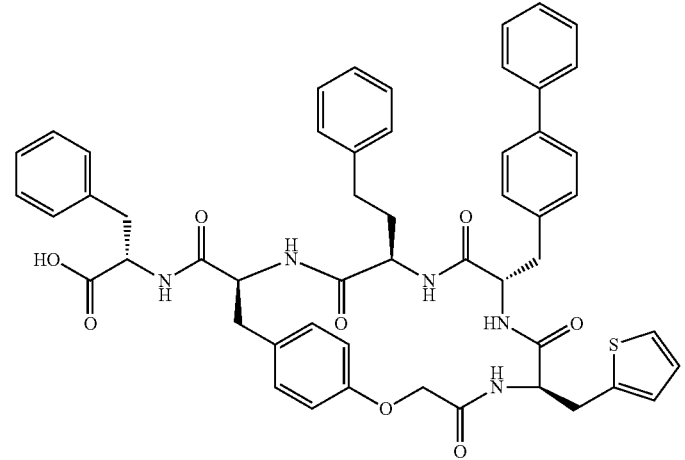 | 906.3536 | 906.3494 |
| 157 | 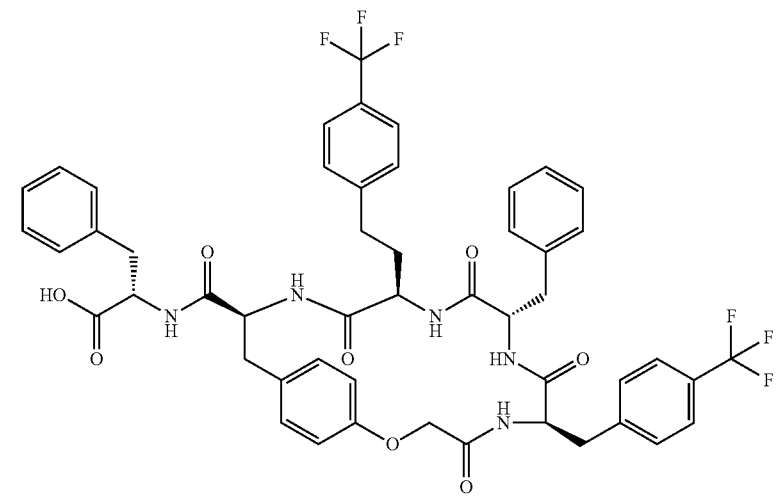 | 960.3407 | 960.3359 |

TABLE 1-continued
| Compound No. | Structure | MS Calcd | MS Observed |
|---|---|---|---|
| 158 | 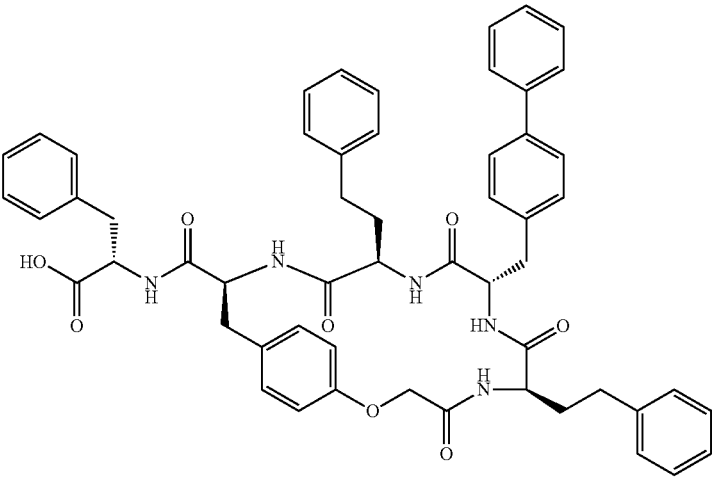 | 914.4129 | 914.4084 |
| 159 | 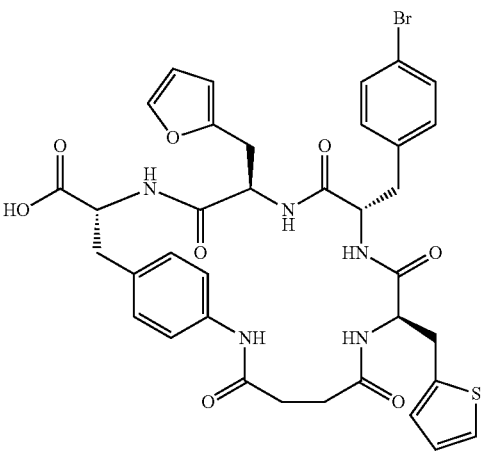 | 778.1546 | 778.1512 |
| 160 | 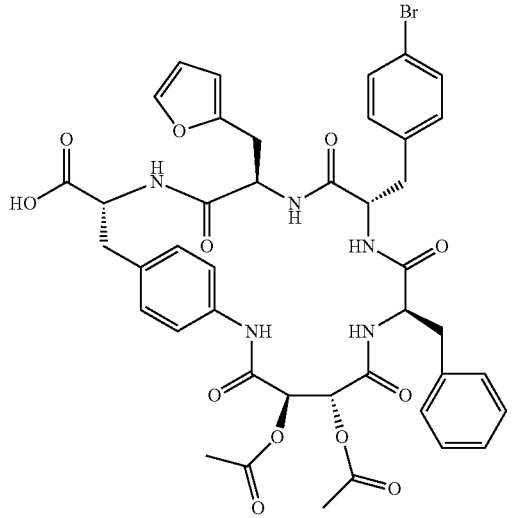 | 888.2091 | 888.2062 |

TABLE 1-continued
| Compound No. | Structure | MS Calcd | MS Observed |
|---|---|---|---|
| 161 | 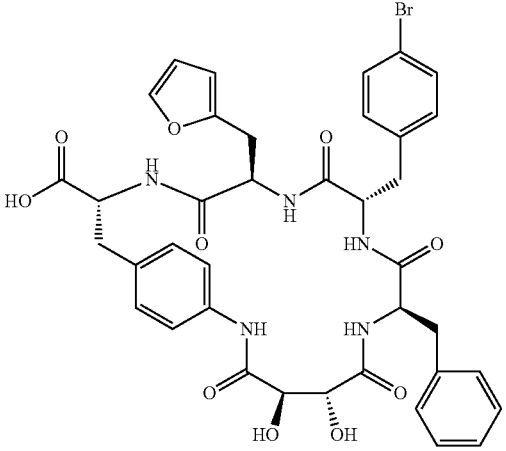 | 804.1880 | 804.1841 |
| 162 | 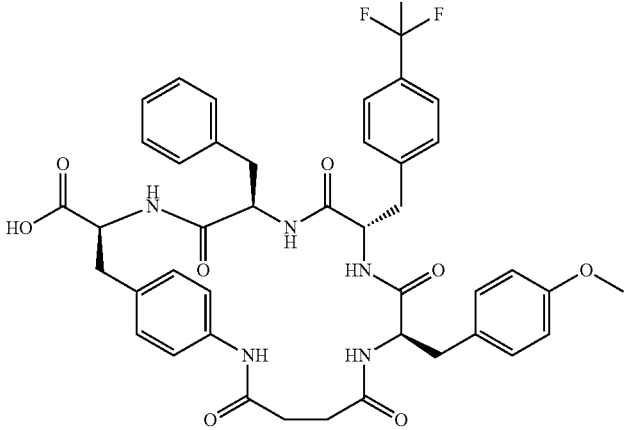 | 802.3064 | 802.3086 |
| 163 | 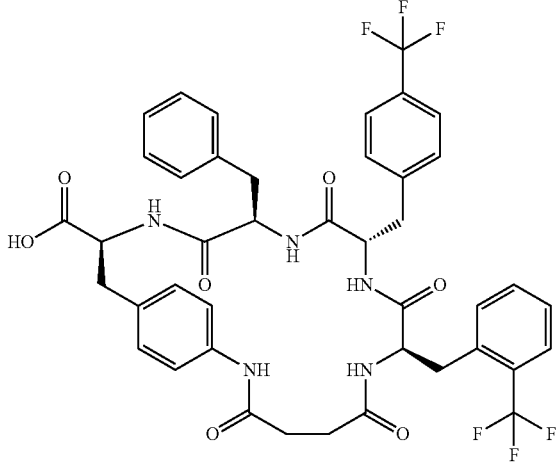 | 840.2832 | 840.2830 |

TABLE 1-continued

| Compound No. | Structure | MS Calcd | MS Observed |
|---|---|---|---|
| 164 | 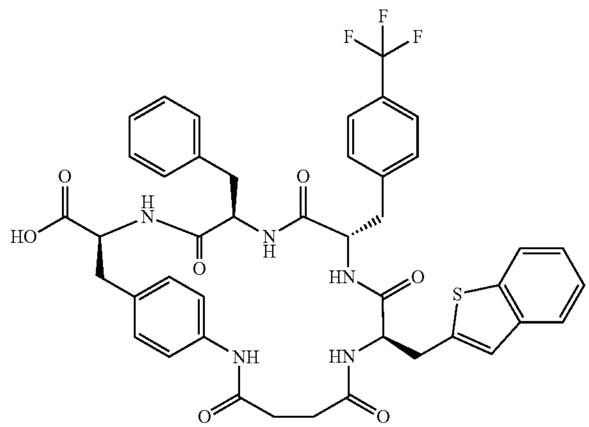 | 828.2679 | 828.2648 |
| 165 | 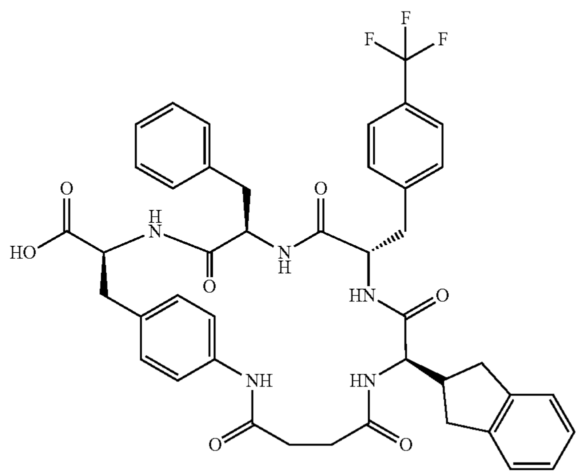 | 798.3115 | 798.3129 |
| 166 | 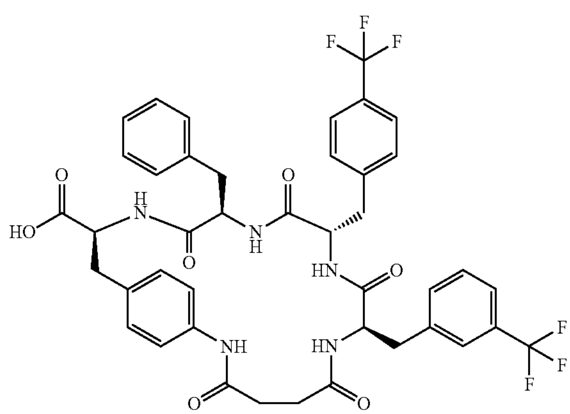 | 840.2832 | 840.2820 |

TABLE 1-continued

| Compound No. | Structure | MS Calcd | MS Observed |
|---|---|---|---|
| 167 | 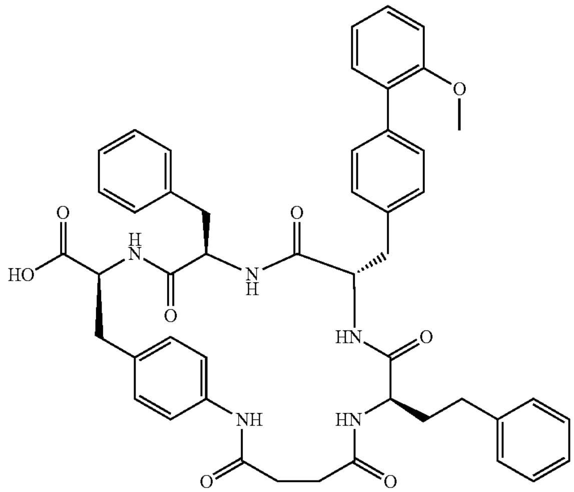 | 824.3659 | 824.3759 |
| 168 | 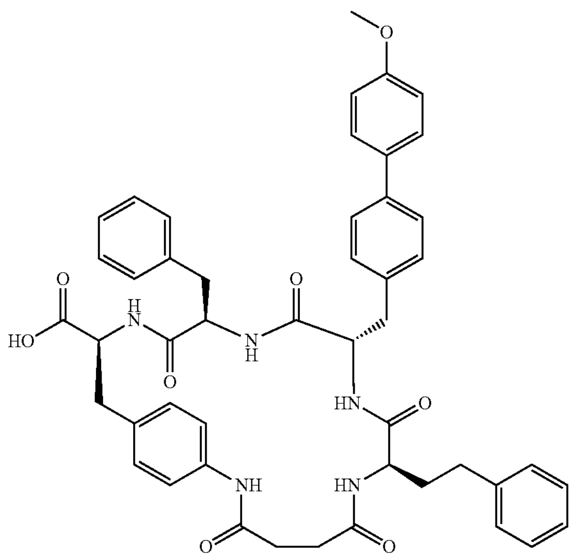 | 824.3659 | 824.3644 |
| 169 | 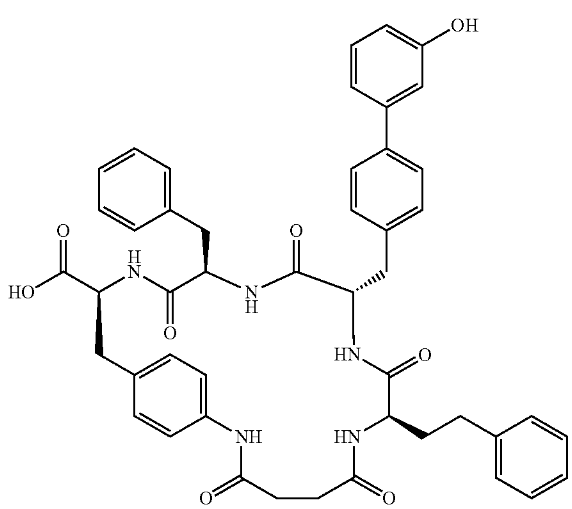 | 810.3503 | 810.3486 |

TABLE 1-continued

| Compound No. | Structure | MS Calcd | MS Observed |
|---|---|---|---|
| 170 | 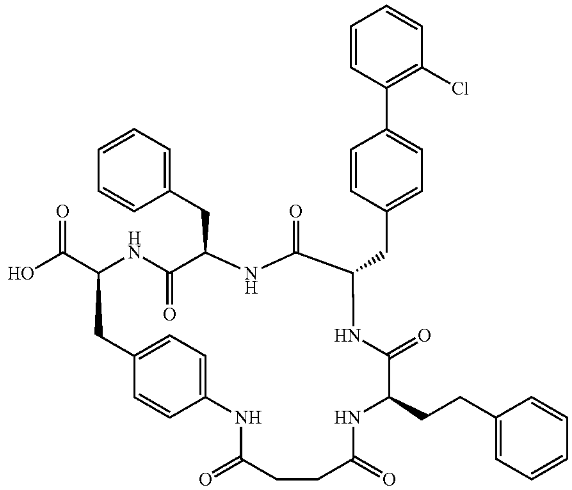 | 828.3164 | 828.3195 |
| 171 | 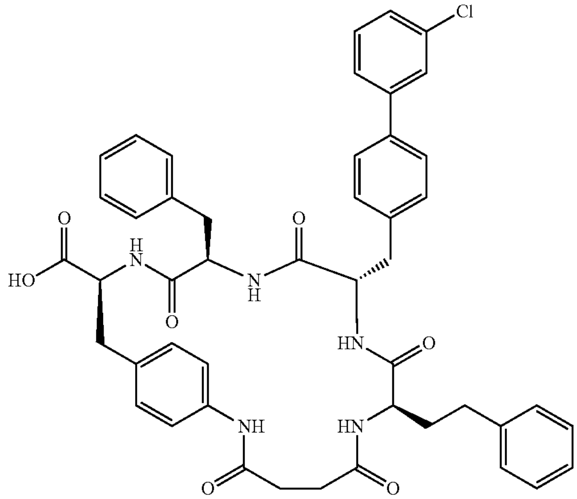 | 828.3164 | 828.3139 |
| 172 | 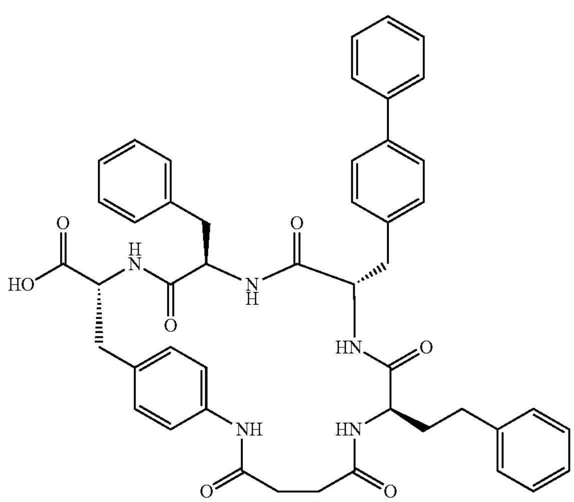 | 794.3553 | 794.3563 |

TABLE 1-continued
| Compound No. | Structure | MS Calcd | MS Observed |
|---|---|---|---|
| 173 | 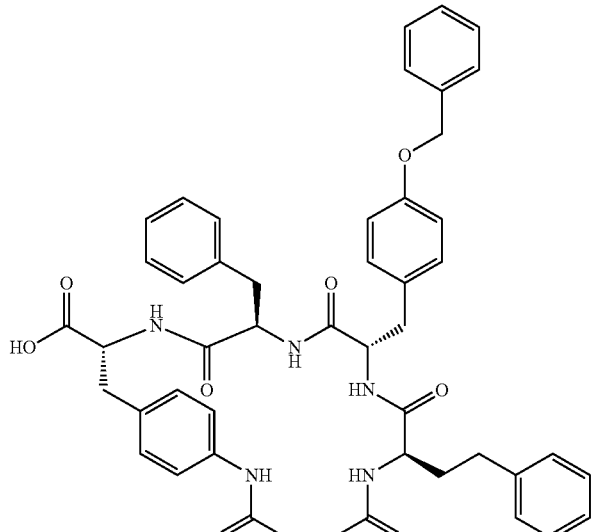 | 824.3659 | 824.3635 |
| 174 | 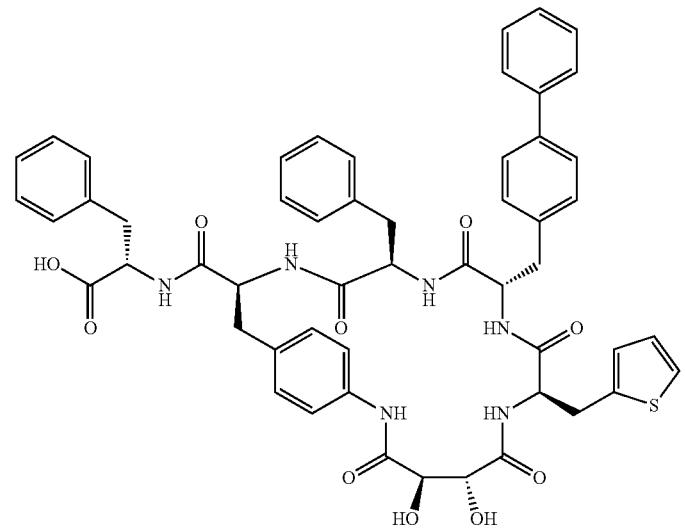 | 963.3393 | 963.3379 |
| 175 | 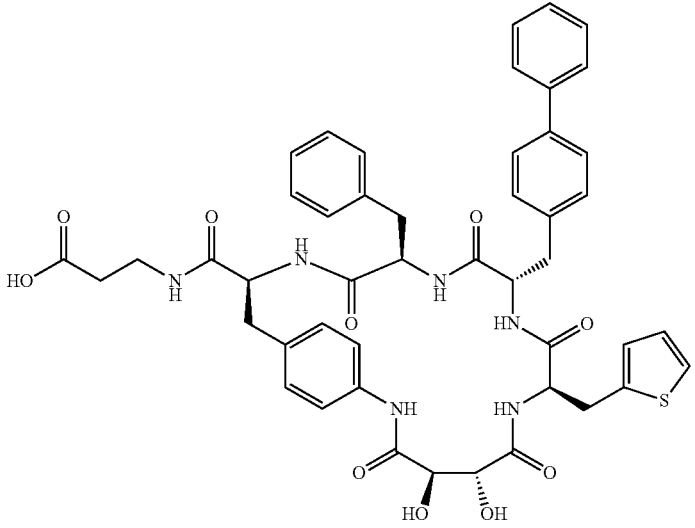 | 887.3080 | 887.3105 |

TABLE 1-continued

| Compound No. | Structure | MS Calcd | MS Observed |
|---|---|---|---|
| 176 | 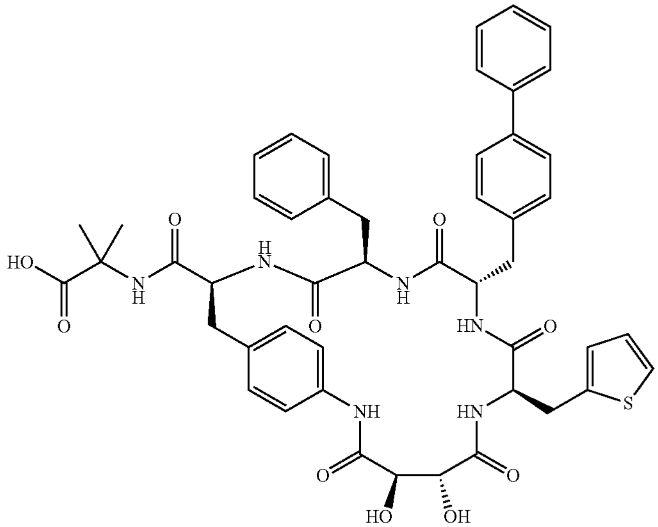 | 901.3236 | 901.3301 |
| 177 | 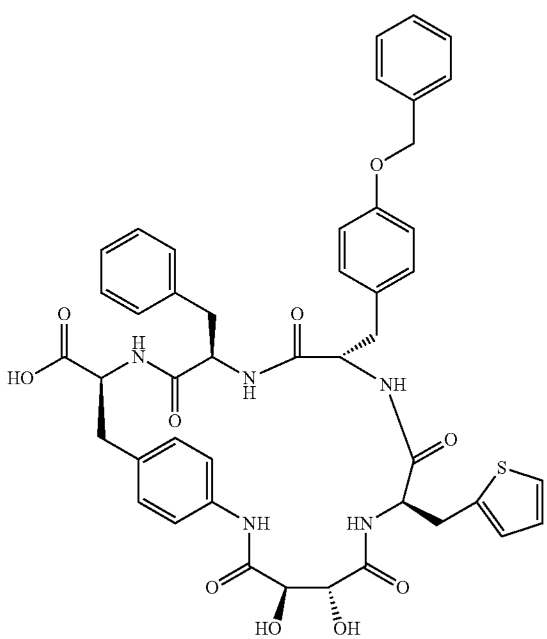 | 848.2965 | 848.2952 |

TABLE 1-continued
| Compound No. | Structure | MS Calcd | MS Observed |
|---|---|---|---|
| 178 | 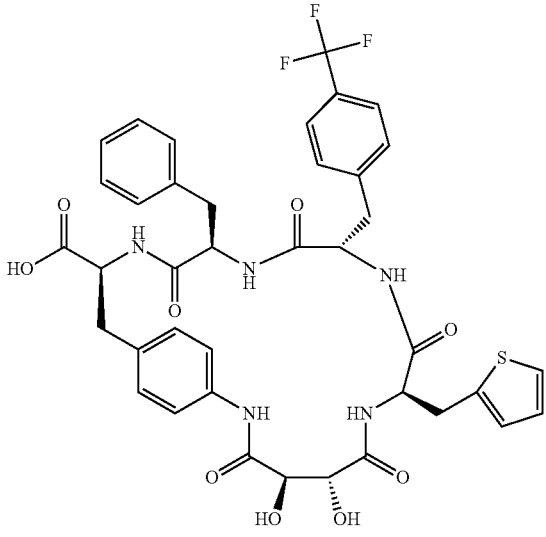 | 810.2421 | 810.2445 |
| 180 | 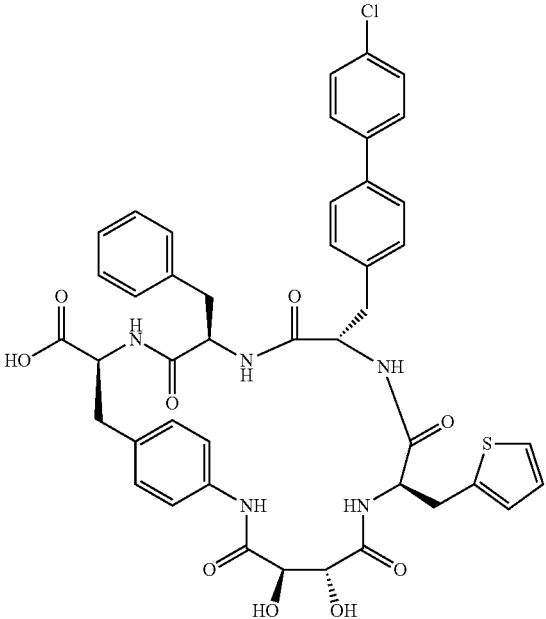 | 852.2470 | 852.2488 |

TABLE 1-continued
| Compound No. | Structure | MS Calcd | MS Observed |
|---|---|---|---|
| 181 | 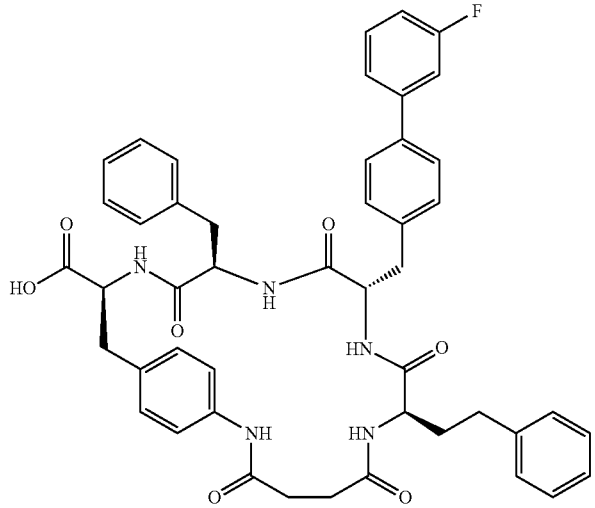 | 812.3459 | 812.3497 |
| 182 | 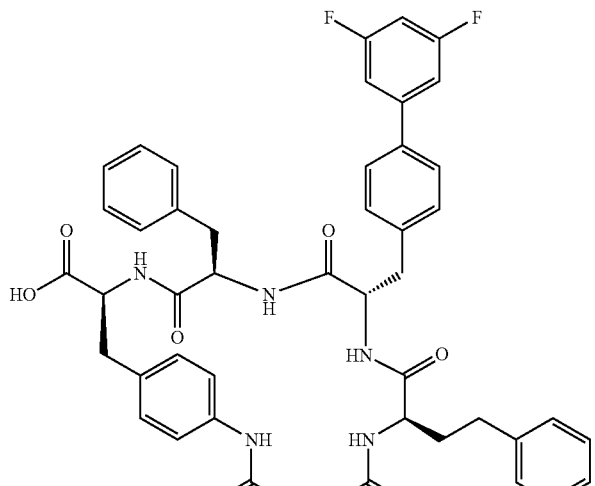 | 830.3365 | 830.3406 |
| 183 | 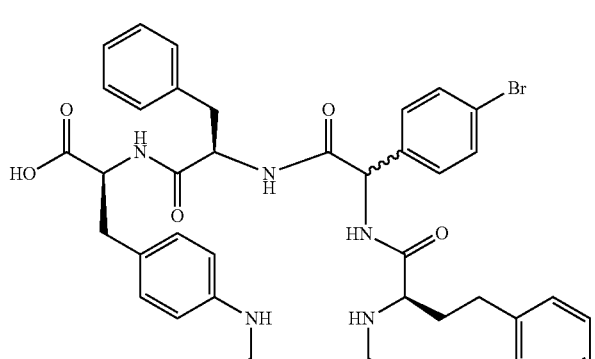 | 782.2189 | 782.2195 |

TABLE 1-continued

| Compound No. | Structure | MS Calcd | MS Observed |
|---|---|---|---|
| 184 | 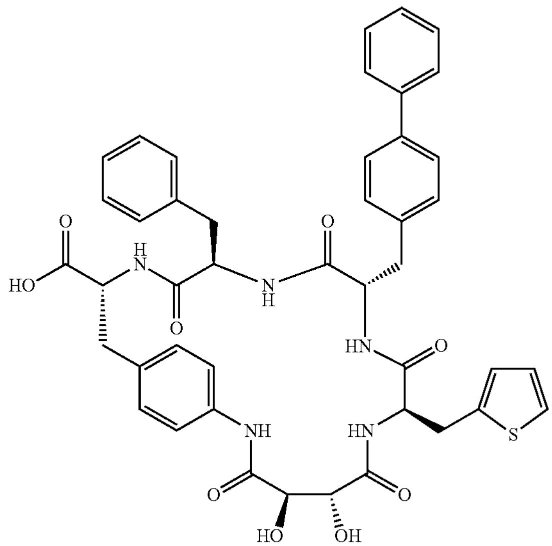 | 818.2854 | 818.2902 |
| 185 | 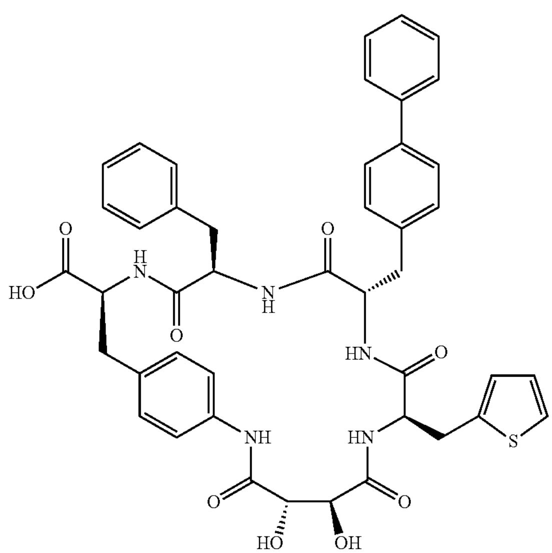 | 818.2854 | 818.2885 |

| Compound No. | Structure | MS Calcd | MS Observed |
|---|---|---|---|
| 186 | 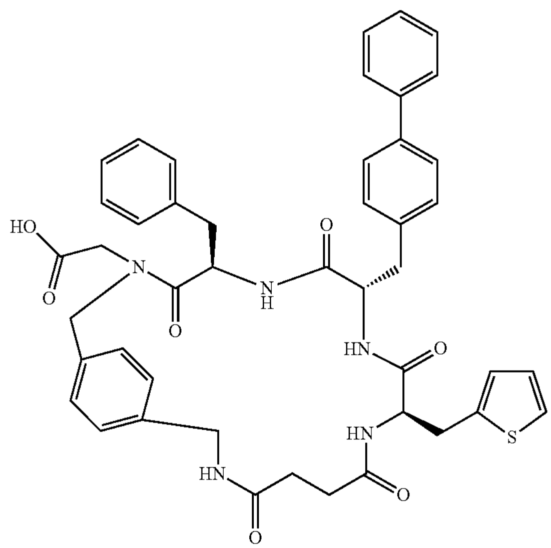 | 800.3113 | 800.3123 |
| 187 | 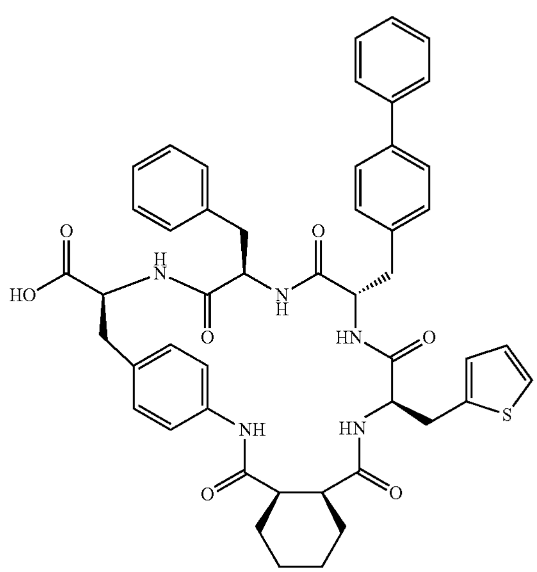 | 840.3426 | 840.3450 |

TABLE 1-continued

| Compound No. | Structure | MS Calcd | MS Observed |
|---|---|---|---|
| 188 | 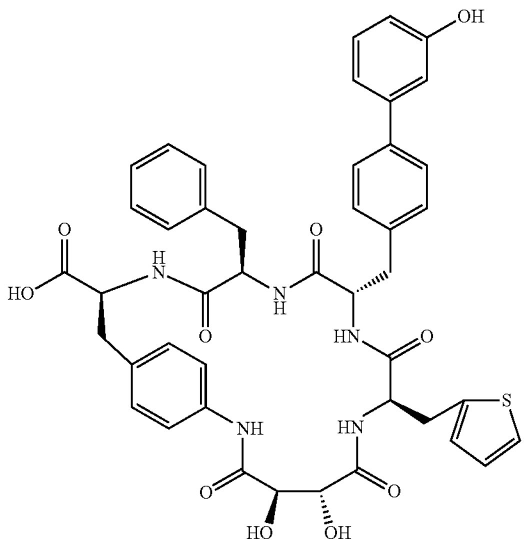 | 834.2809 | 834.2820 |
| 189 | 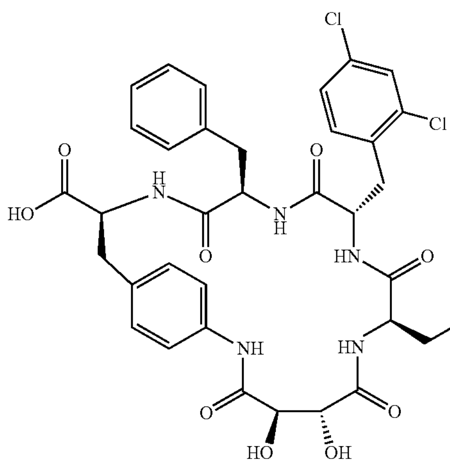 | 810.1767 | 810.1759 |
| 190 | 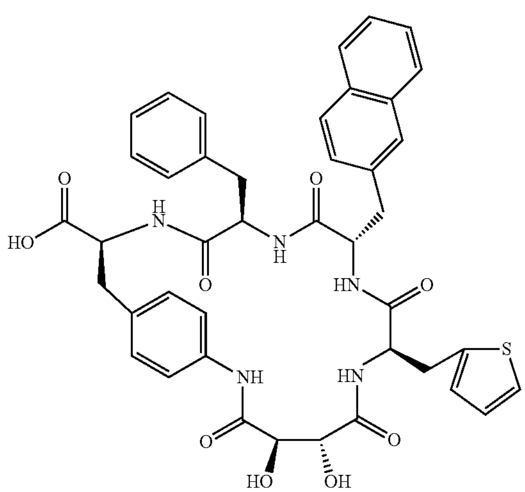 | 792.2703 | 792.2725 |

TABLE 1-continued

| Compound No. | Structure | MS Calcd | MS Observed |
|---|---|---|---|
| 191 | 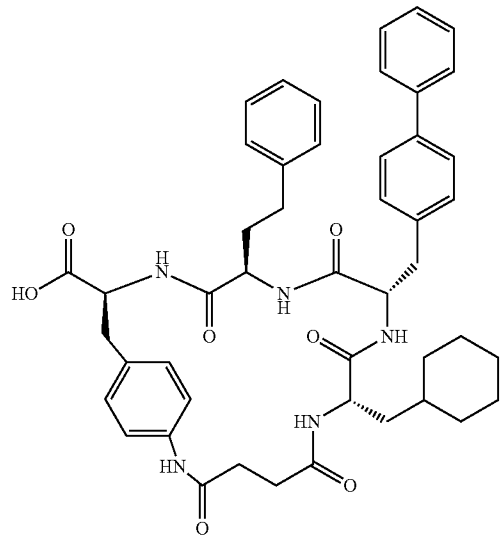 | 800.4018 | 800.4058 |
| 192 | 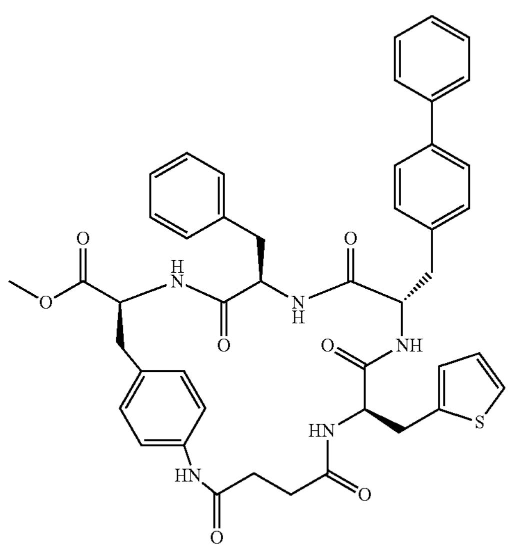 | 800.3113 | 800.3146 |

| Compound No. | Structure | MS Calcd | MS Observed |
|---|---|---|---|
| 193 | 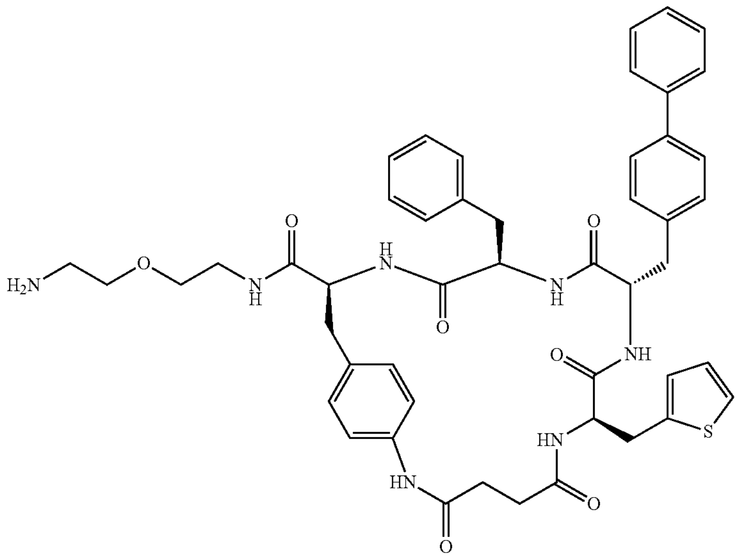 | 872.3805 | 872.3761 |
| 194 | 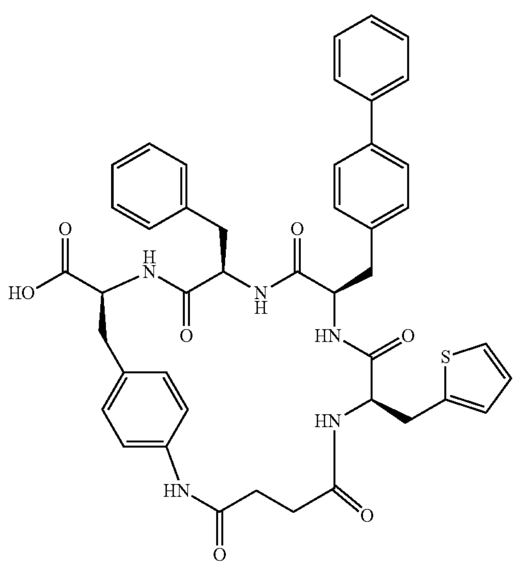 | 786.2961 | 786.3031 |

| Compound No. | Structure | MS Calcd | MS Observed |
|---|---|---|---|
| 195 | 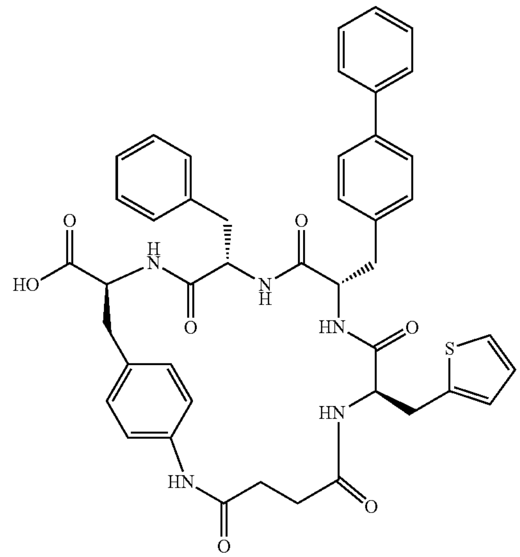 | 786.2961 | 786.3047 |
| 196 | 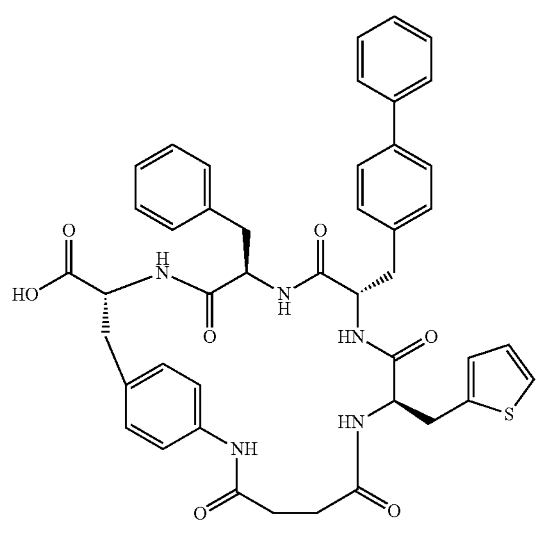 | 786.2961 | 786.2951 |

TABLE 1-continued

| Compound No. | Structure | MS Calcd | MS Observed |
|---|---|---|---|
| 197 | 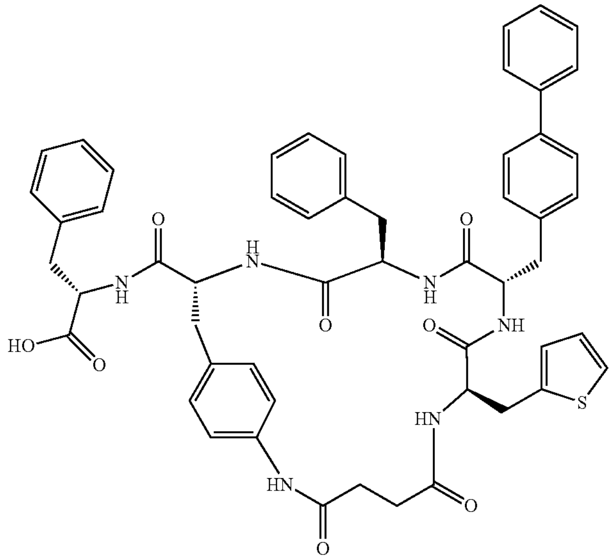 | 798.3861 | 798.3885 |
| 198 | 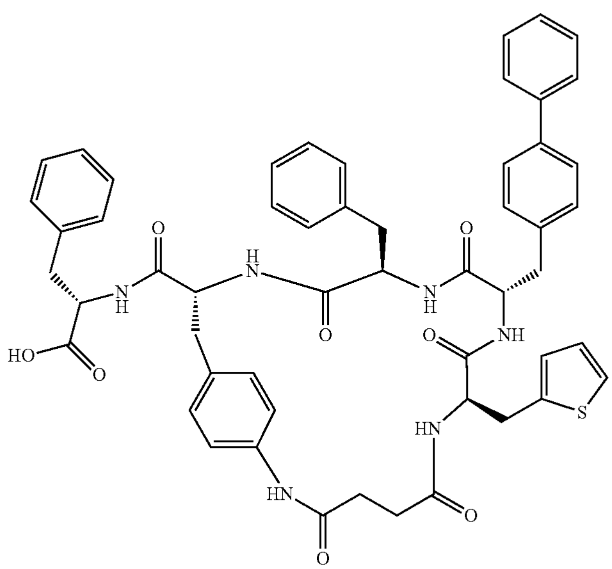 | 933.3645 | 933.3659 |

TABLE 1-continued
| Compound No. | Structure | MS Calcd | MS Observed |
|---|---|---|---|
| 199 | 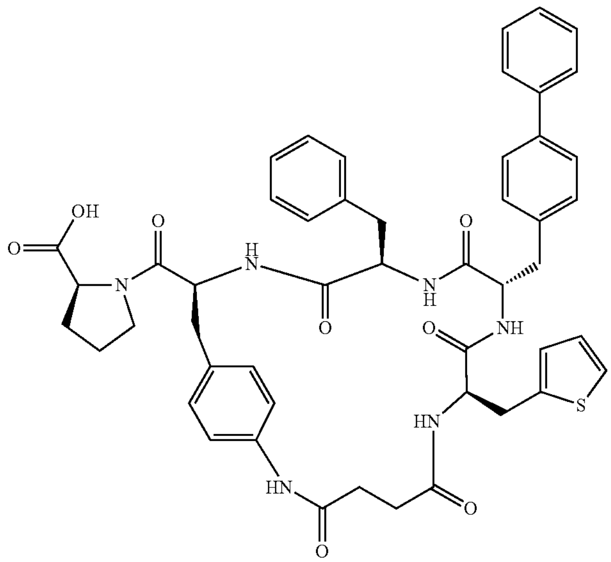 | 883.3489 | 883.3597 |
| 200 | 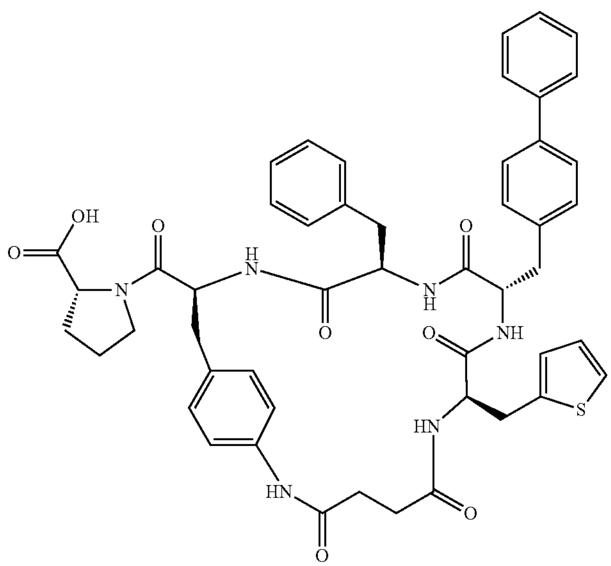 | 883.3489 | 883.3520 |
| 201 | 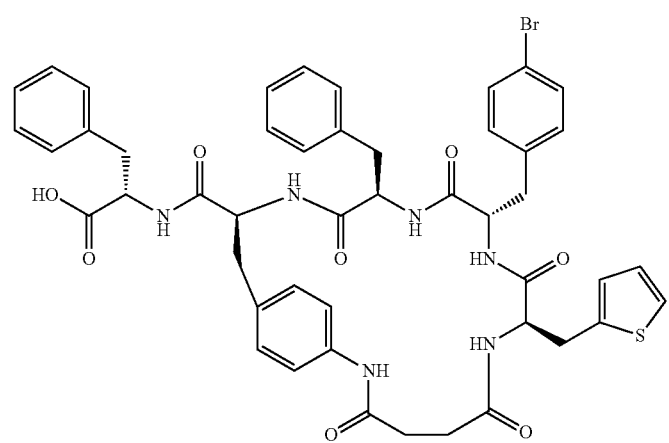 | 935.2438 | 935.236* |

TABLE 1-continued

| Compound No. | Structure | MS Calcd | MS Observed |
|---|---|---|---|
| 202 | 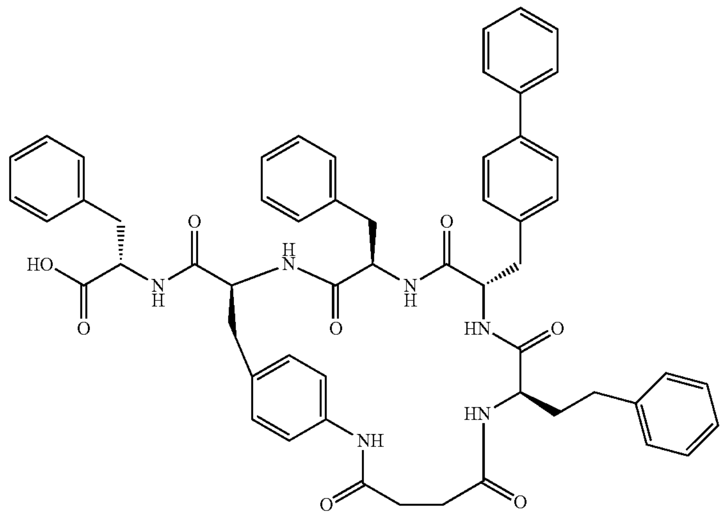 | 941.4238 | 941.4236 |
| 203 | 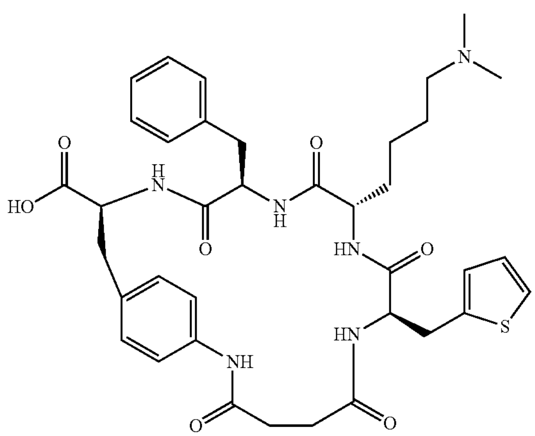 | 719.3227 | 719.3286 |
| 205 | 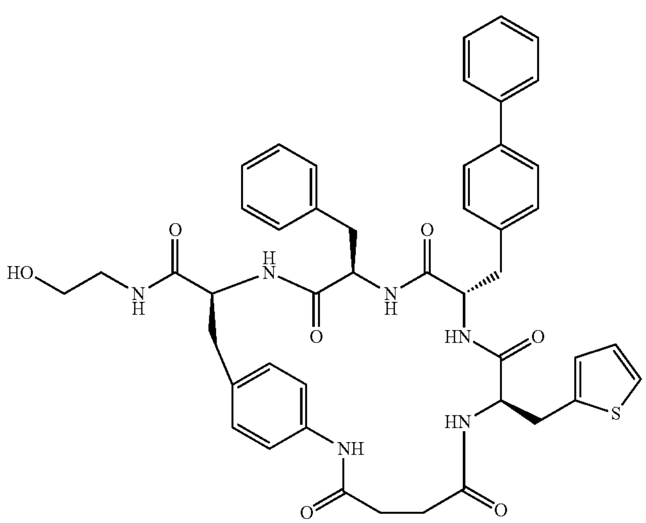 | 829.3383 | 829.3420 |

TABLE 1-continued

| Compound No. | Structure | MS Calcd | MS Observed |
|---|---|---|---|
| 206 | 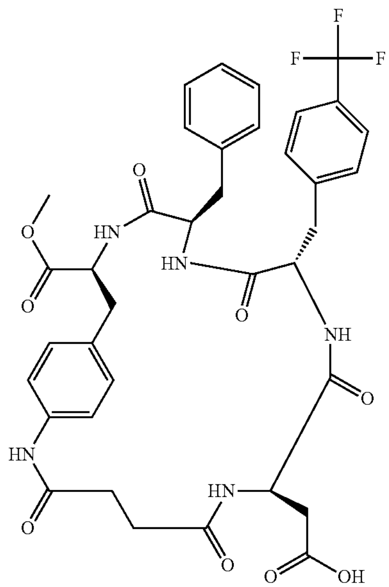 | 754.2700 | 754.2690 |
| 208 | 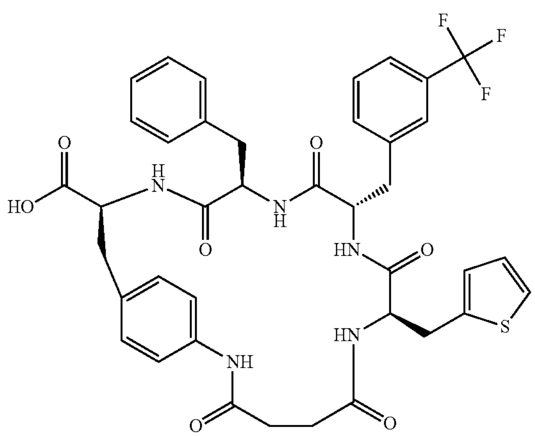 | 778.2522 | 778.2562 |
| 209 | 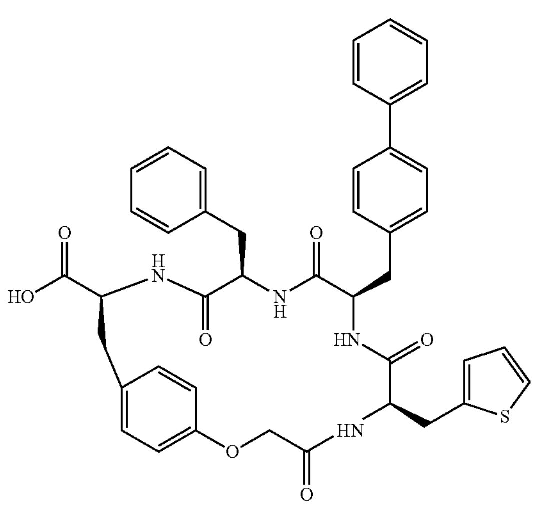 | 745.2696 | 745.2599 |

TABLE 1-continued

| Compound No. | Structure | MS Calcd | MS Observed |
|---|---|---|---|
| 210 | 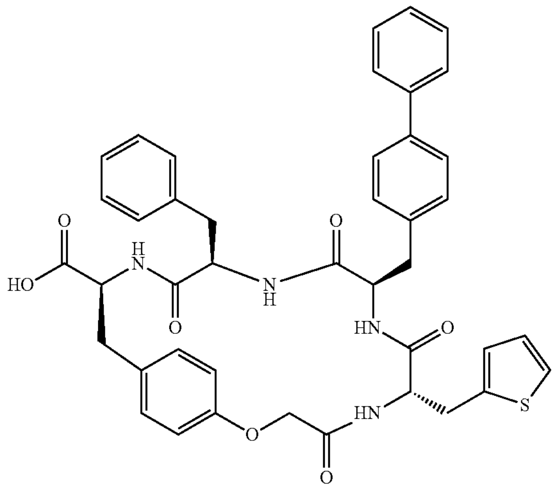 | 745.2696 | 745.2562 |
| 211 | 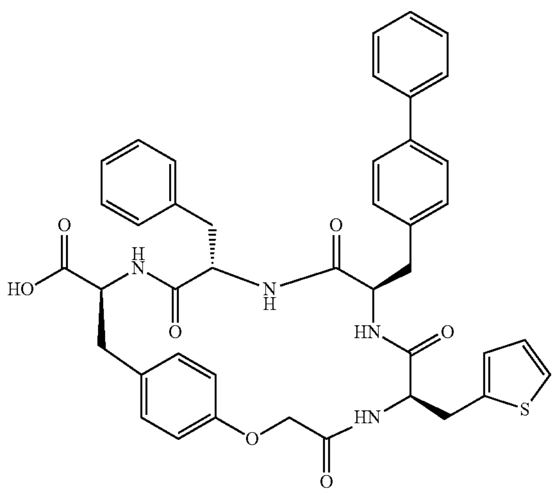 | 745.2696 | 745.2599 |
| 212 | 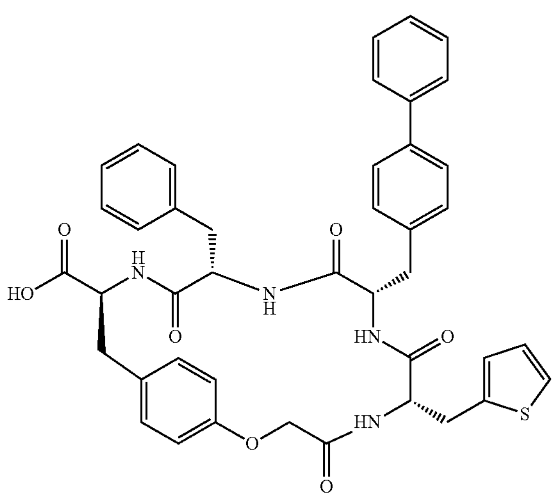 | 745.2696 | 745.2620 |

TABLE 1-continued

| Compound No. | Structure | MS Calcd | MS Observed |
|---|---|---|---|
| 213 | 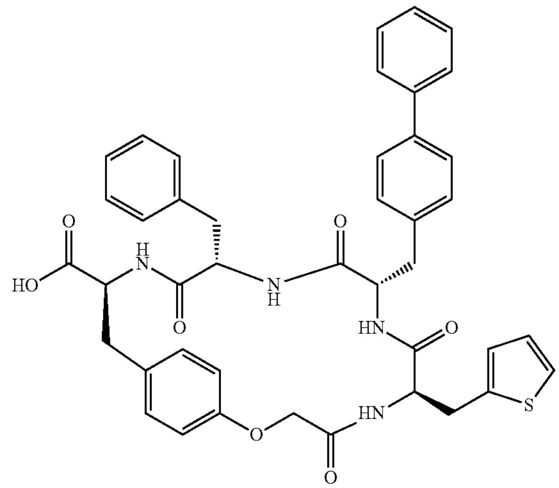 | 745.2696 | 745.2573 |
| 214 | 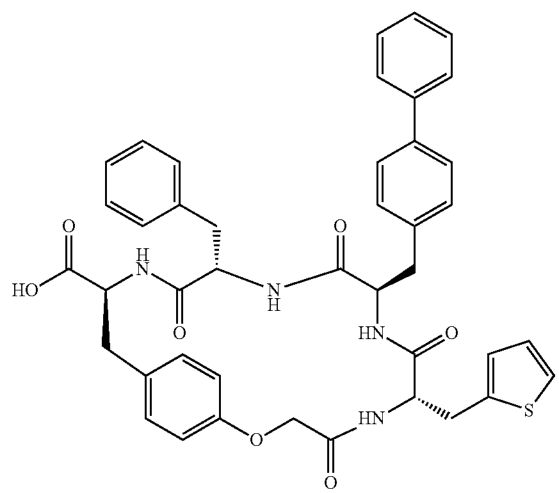 | 745.2696 | 745.2604 |
| 215 | 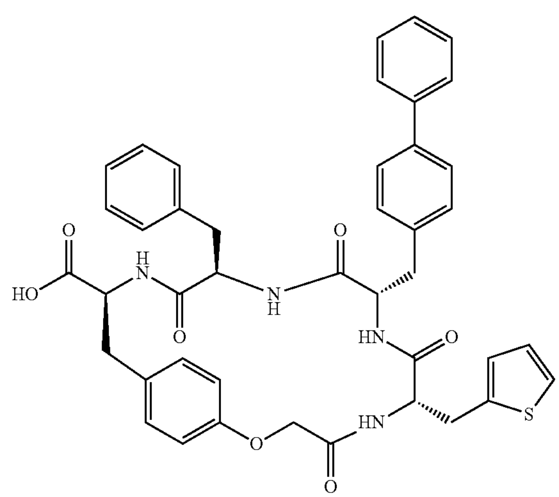 | 745.2696 | 745.2604 |

TABLE 1-continued
| Compound No. | Structure | MS Calcd | MS Observed |
|---|---|---|---|
| 216 | 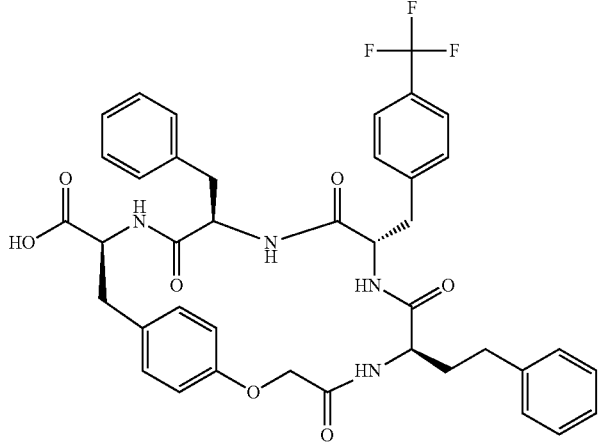 | 745.2844 | 745.2858 |
| 217 | 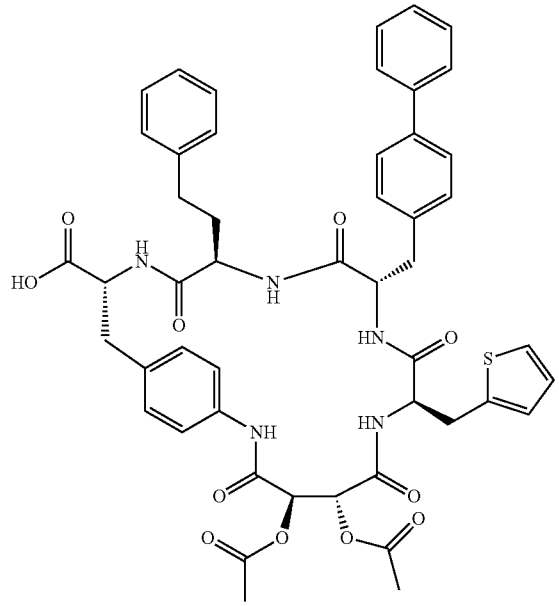 | 916.3227 | 916.3212 |

TABLE 1-continued
| Compound No. | Structure | MS Calcd | MS Observed |
|---|---|---|---|
| 218 | 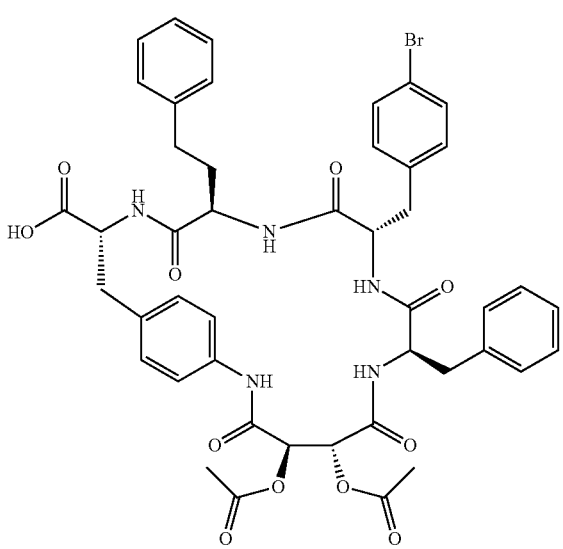 | 912.2455 | 912.2509 |
| 219 | 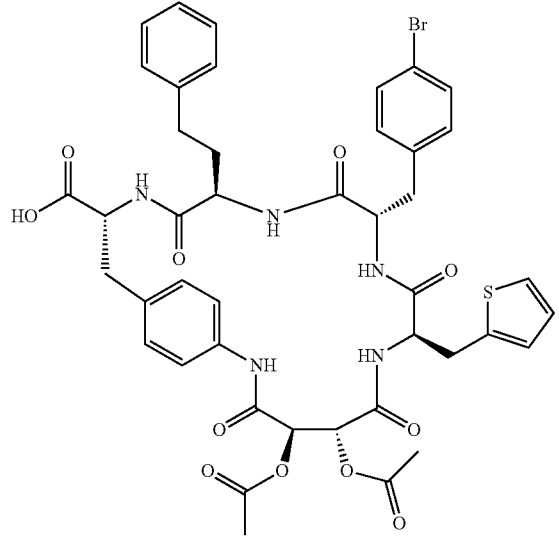 | 918.2019 | 918.2039 |

TABLE 1-continued

| Compound No. | Structure | MS Calcd | MS Observed |
|---|---|---|---|
| 220 | 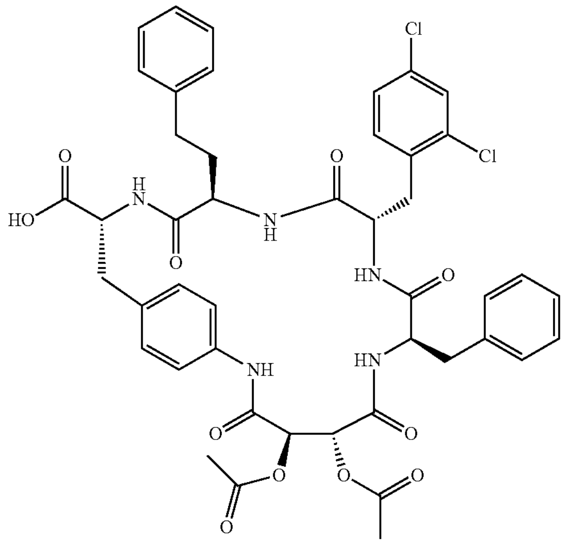 | 902.2571 | 902.2573 |
| 221 | 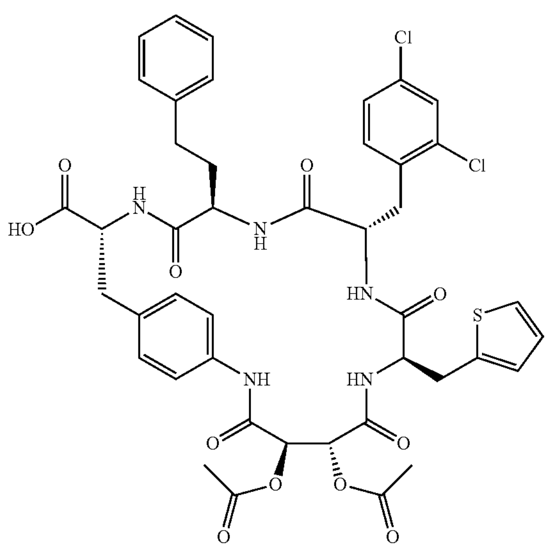 | 908.2135 | 908.2154 |

TABLE 1-continued

| Compound No. | Structure | MS Calcd | MS Observed |
|---|---|---|---|
| 222 | 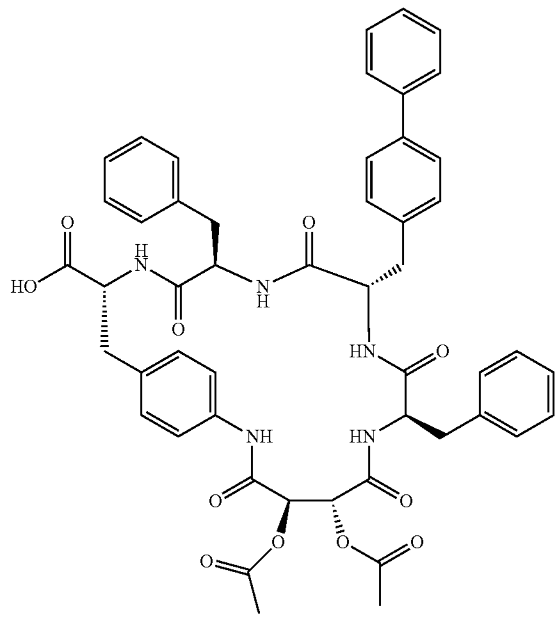 | 896.3507 | 896.3550 |
| 223 | 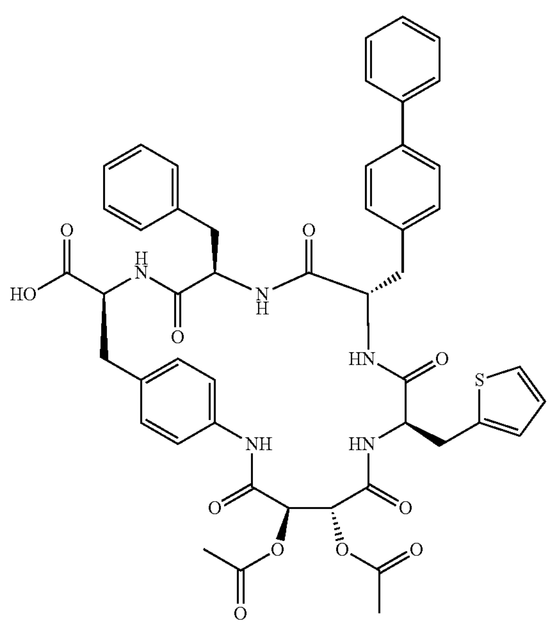 | 902.3071 | 902.3079 |

TABLE 1-continued

| Compound No. | Structure | MS Calcd | MS Observed |
|---|---|---|---|
| 224 | 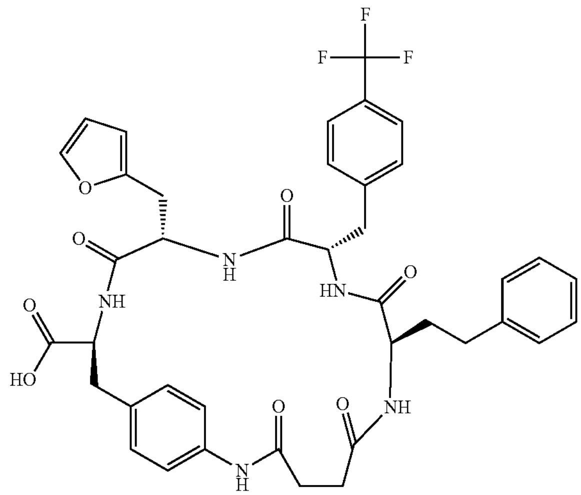 | 775.2829 | 776.2931 |
| 225 | 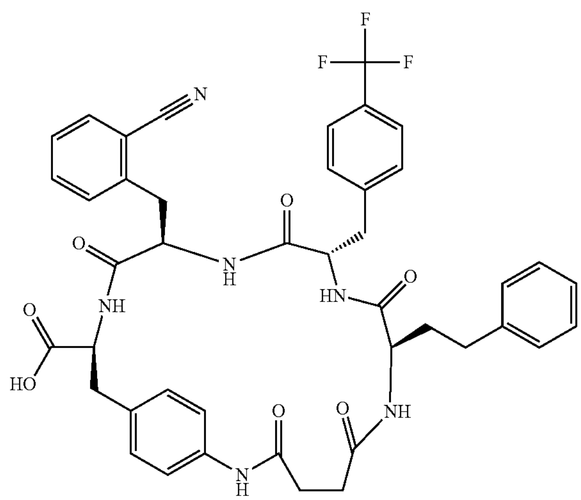 | 811.3067 | 811.3107 |
| 226 | 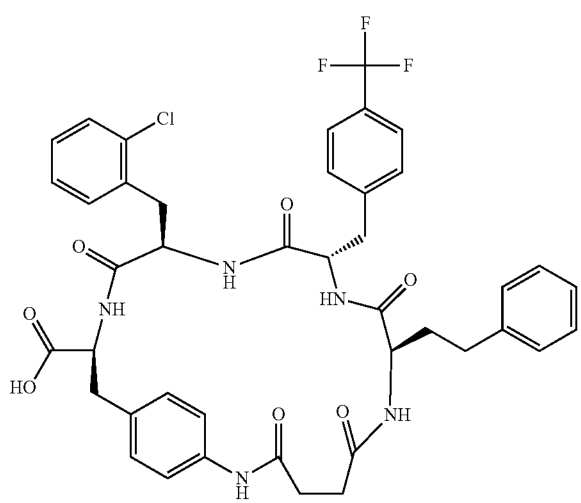 | 820.2725 | 820.2759 |

TABLE 1-continued

| Compound No. | Structure | MS Calcd | MS Observed |
|---|---|---|---|
| 227 | 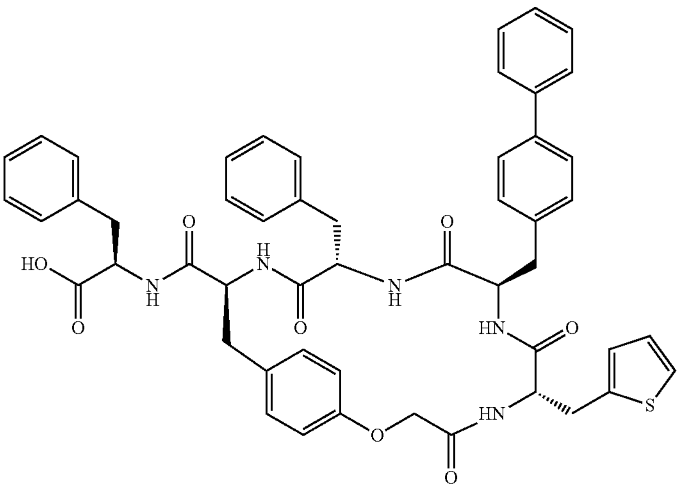 | 892.3380 | 892.3388 |
| 228 | 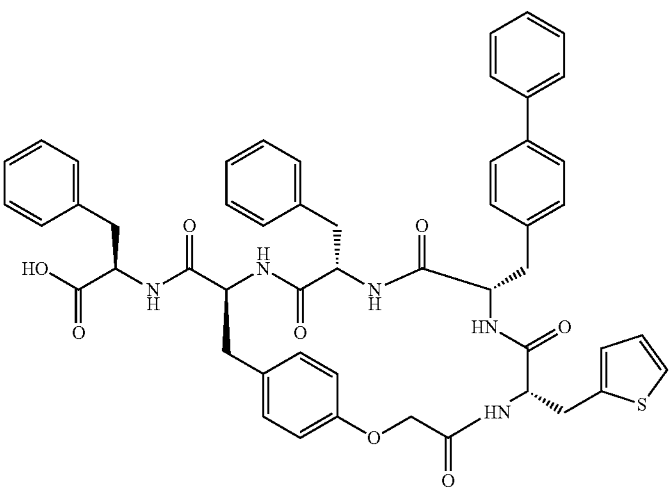 | 892.3380 | 892.3397 |
| 229 | 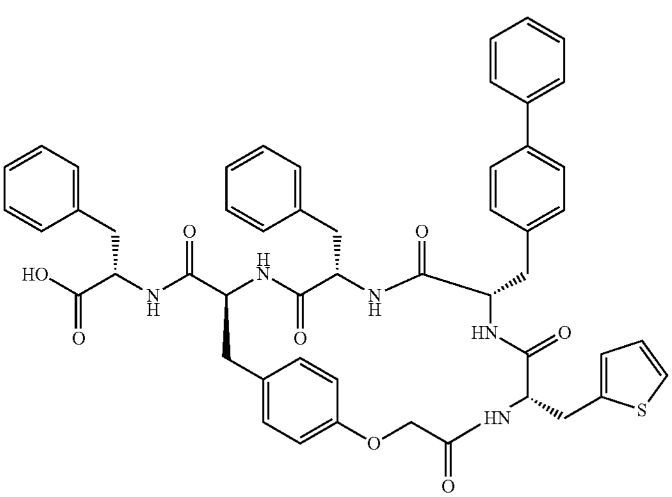 | 892.3380 | 892.3362 |

TABLE 1-continued
| Compound No. | Structure | MS Calcd | MS Observed |
|---|---|---|---|
| 230 | 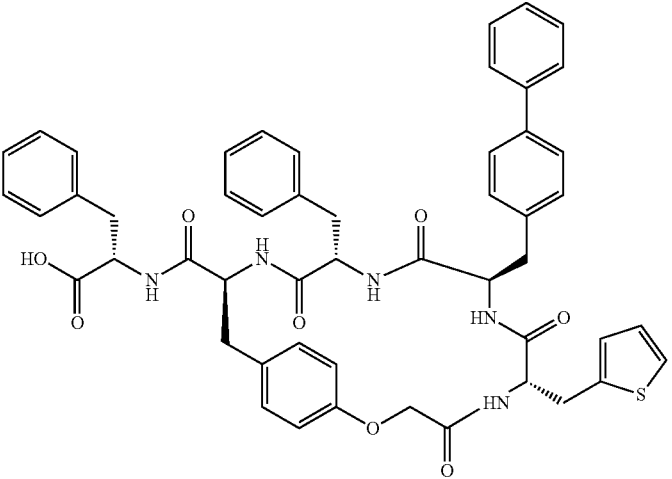 | 892.3380 | 892.3380 |
| 231 | 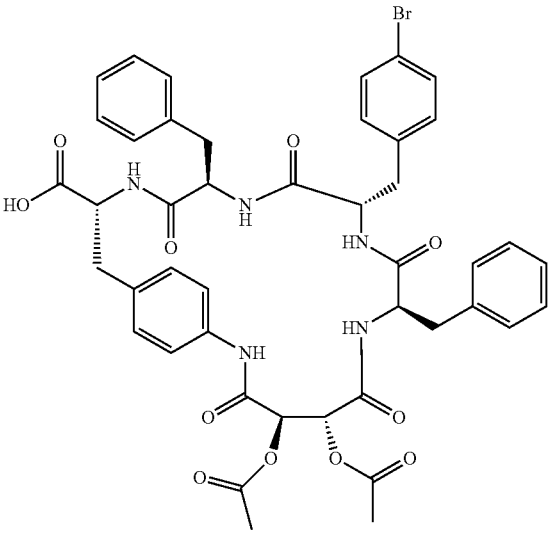 | 898.2299 | 898.2328 |
| 232 | 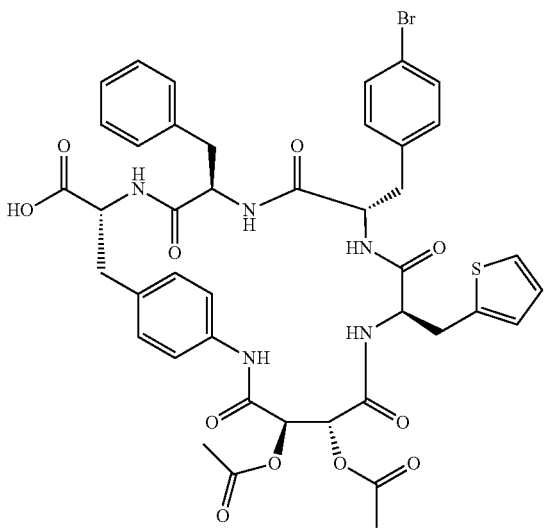 | 904.1863 | 904.1883 |

TABLE 1-continued

| Compound No. | Structure | MS Calcd | MS Observed |
|---|---|---|---|
| 233 | 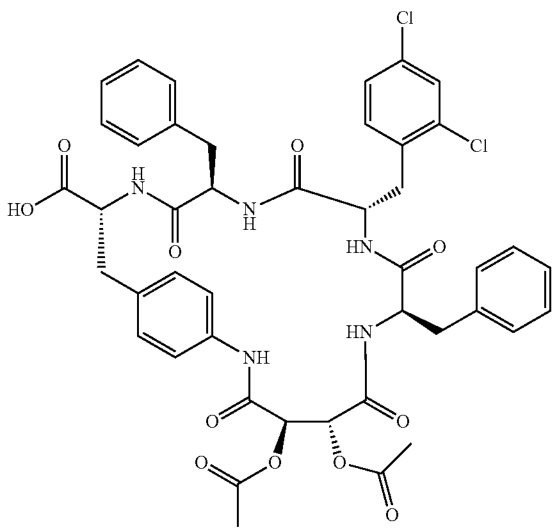 | 888.2414 | 888.2430 |
| 234 | 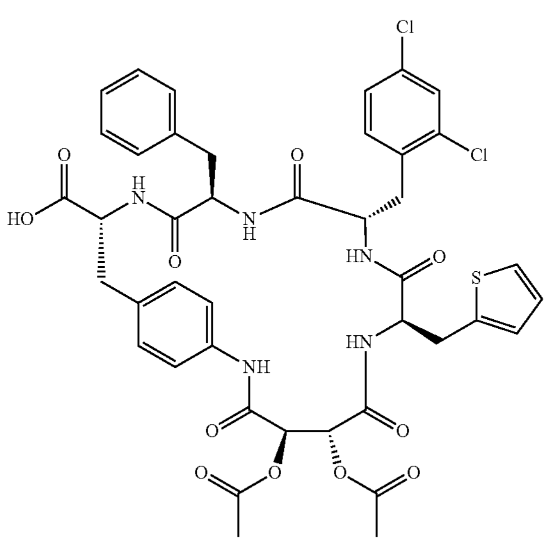 | 894.1978 | 894.1982 |

TABLE 1-continued
| Compound No. | Structure | MS Calcd | MS Observed |
|---|---|---|---|
| 235 | 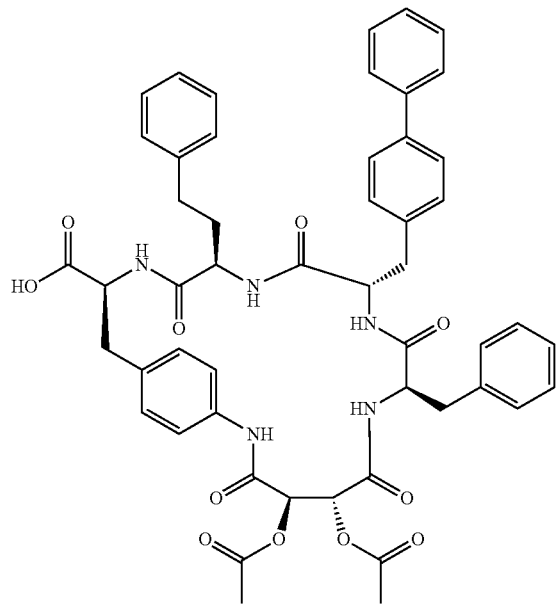 | 910.3663 | 910.3668 |
| 236 | 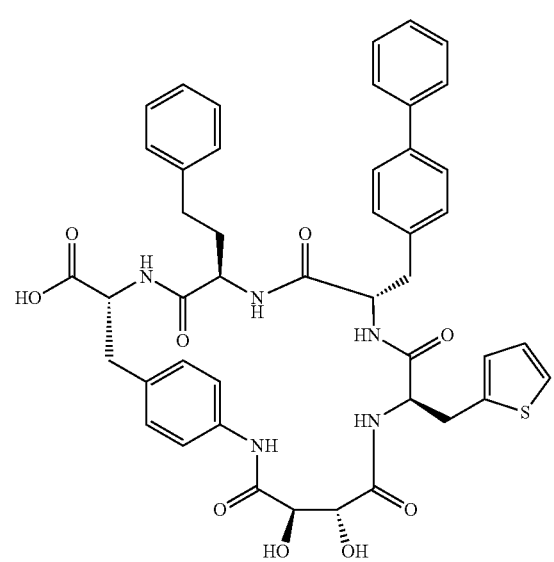 | 832.3016 | 832.3033 |

TABLE 1-continued

| Compound No. | Structure | MS Calcd | MS Observed |
|---|---|---|---|
| 237 | 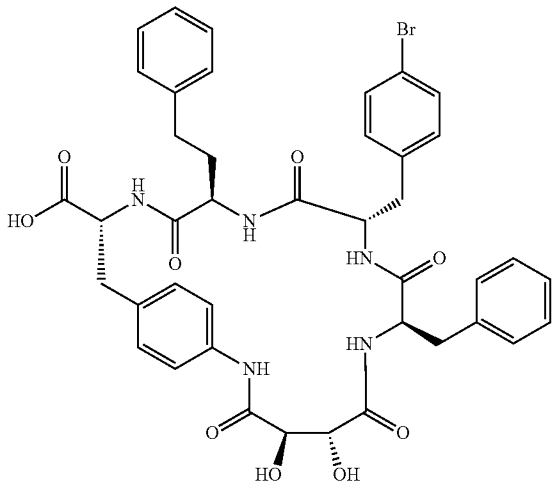 | 828.2244 | 828.2286 |
| 238 | 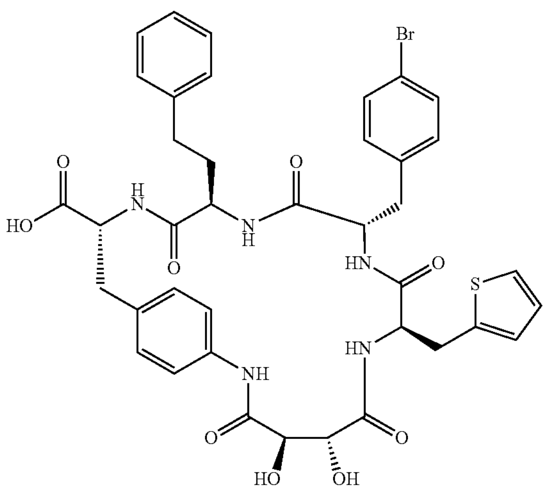 | 834.1808 | 834.1801 |
| 239 | 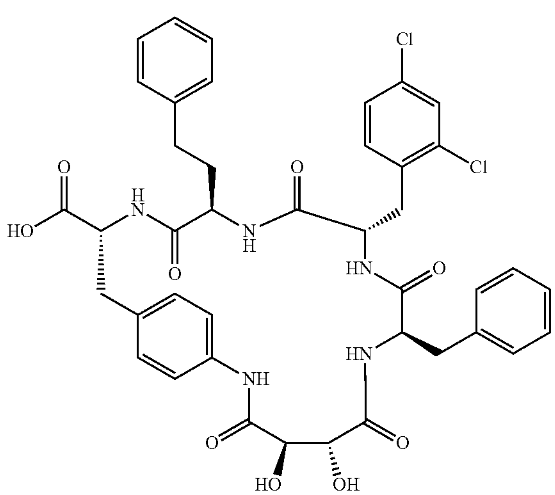 | 818.2359 | 818.2381 |

TABLE 1-continued

| Compound No. | Structure | MS Calcd | MS Observed |
|---|---|---|---|
| 240 | 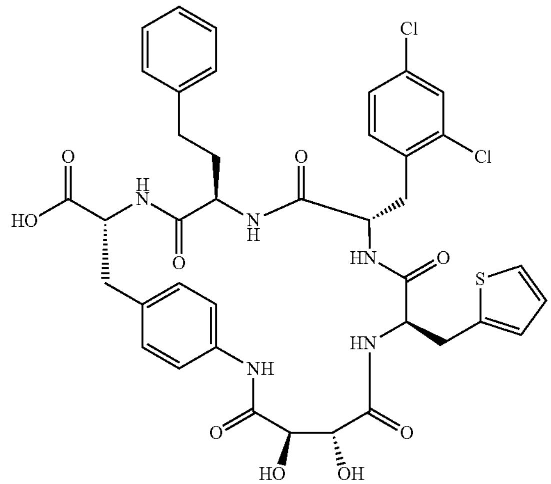 | 824.1924 | 824.1951 |
| 241 | 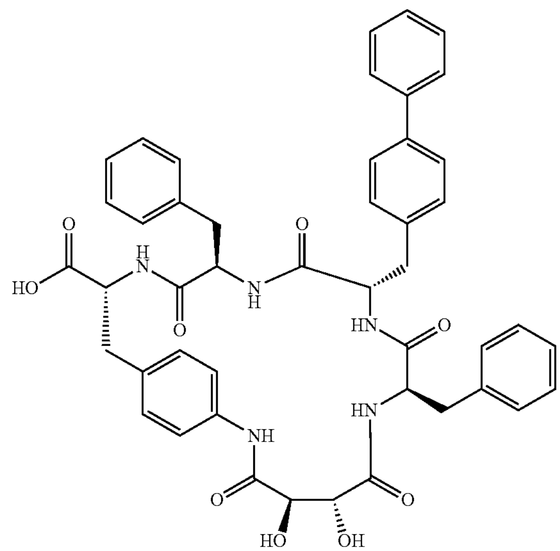 | 812.3295 | 812.3320 |
| 242 | 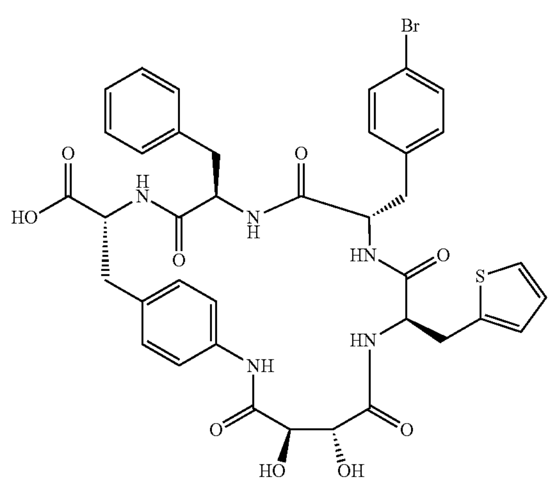 | 820.1652 | 820.1672 |

TABLE 1-continued

| Compound No. | Structure | MS Calcd | MS Observed |
|---|---|---|---|
| 243 | 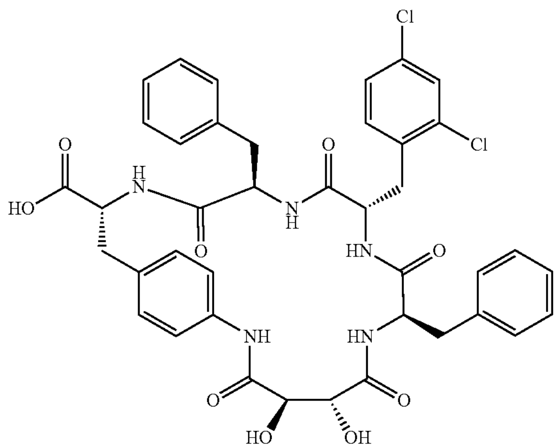 | 804.2203 | 804.2228 |
| 244 | 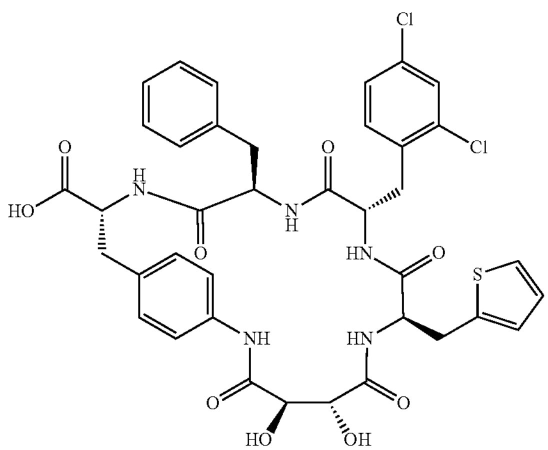 | 810.1767 | 810.1761 |
| 245 | 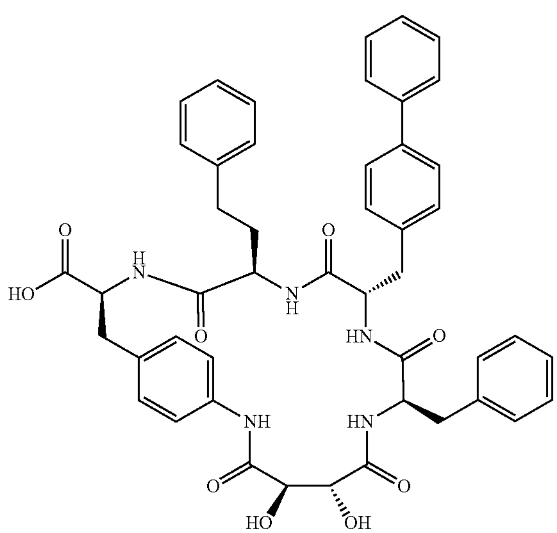 | 826.3452 | 826.3470 |

TABLE 1-continued

| Compound No. | Structure | MS Calcd | MS Observed |
|---|---|---|---|
| 246 | 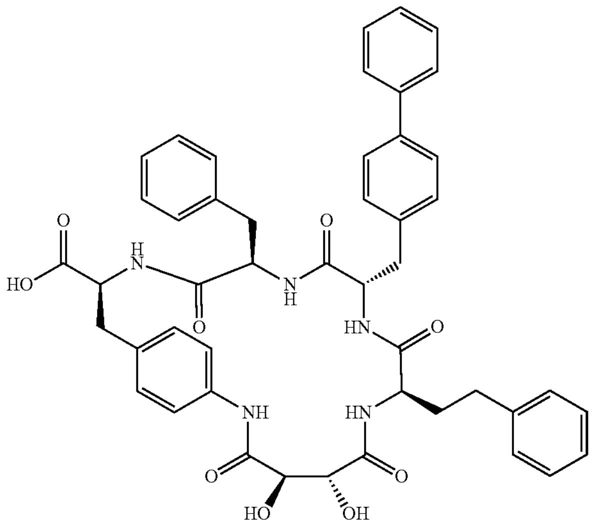 | 826.3452 | 826.3428 |
| 247 | 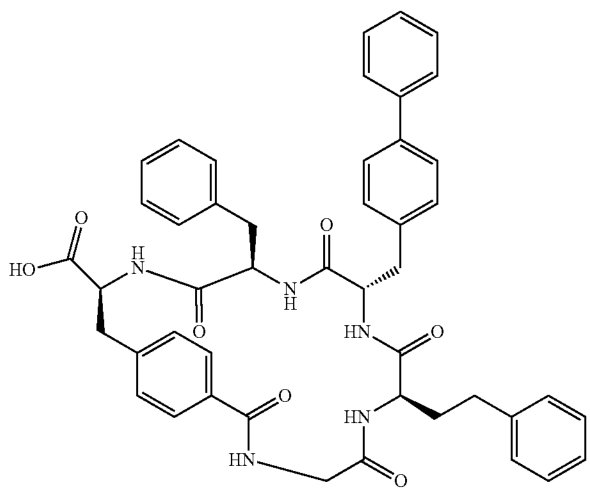 | 780.3392 | 780.3430 |
| 248 | 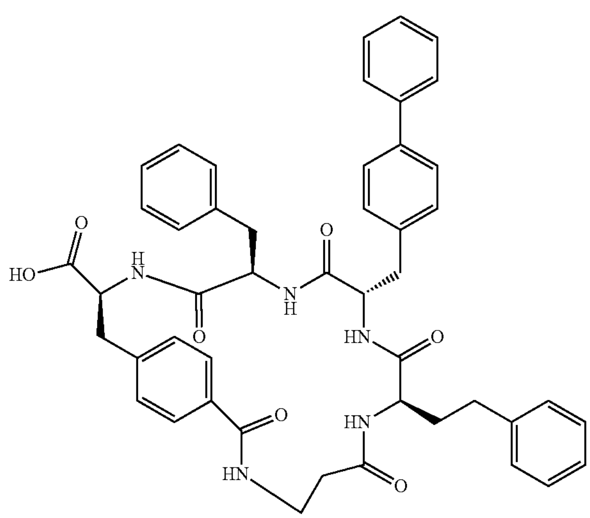 | 794.3548 | 794.3606 |

TABLE 1-continued

| Compound No. | Structure | MS Calcd | MS Observed |
| --- | --- | --- | --- |
| 249 | 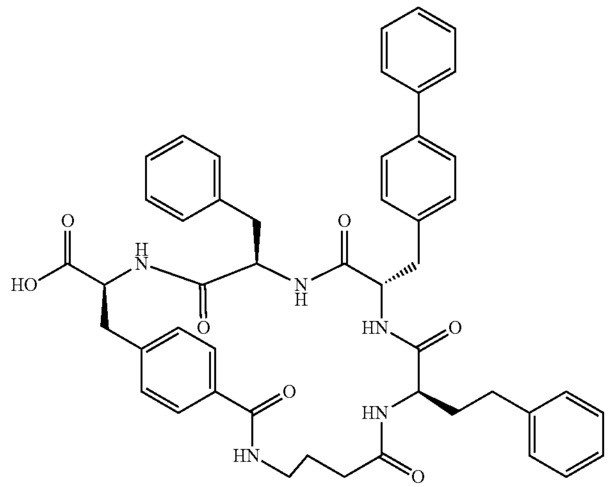 | 808.3705 | 808.3718 |
| 250 | 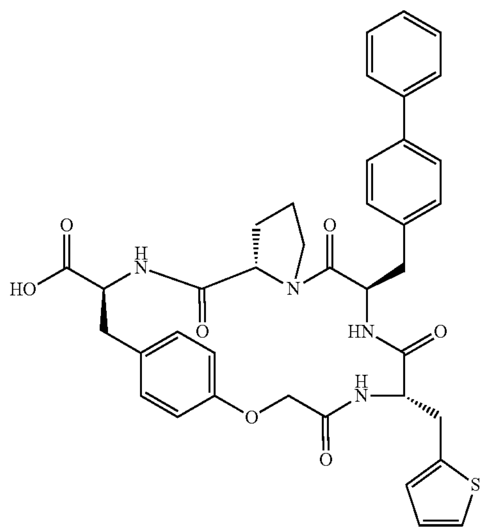 | 695.2539 | 695.2518 |
| 251 | 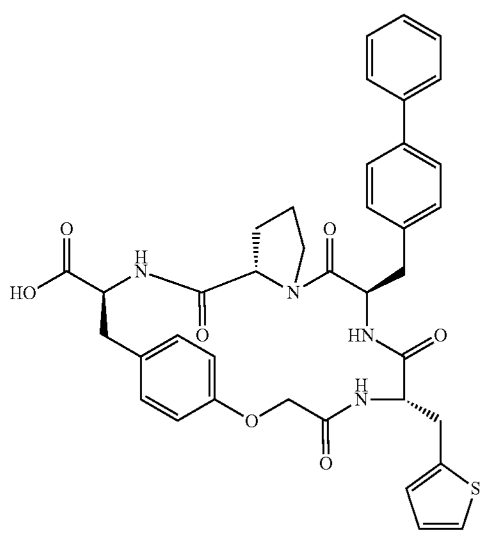 | 695.2539 | 695.2592 |

TABLE 1-continued

| Compound No. | Structure | MS Calcd | MS Observed |
|---|---|---|---|
| 252 | 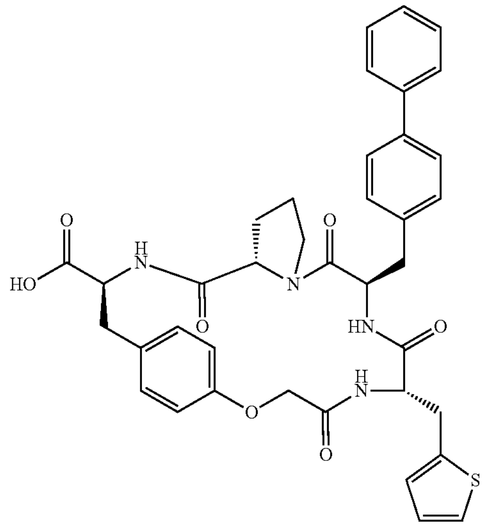 | 695.2539 | 695.2556 |
| 253 | 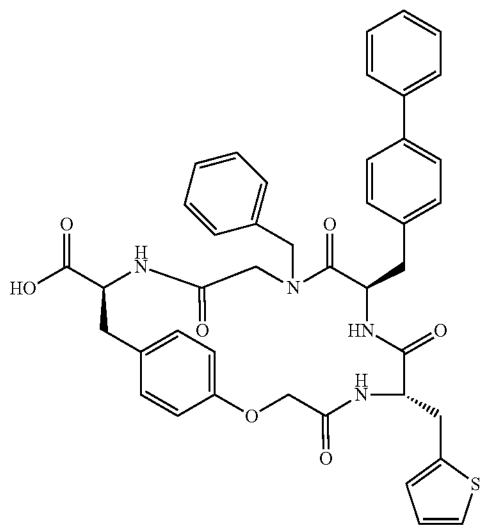 | 745.2696 | 745.2686 |
| 254 | 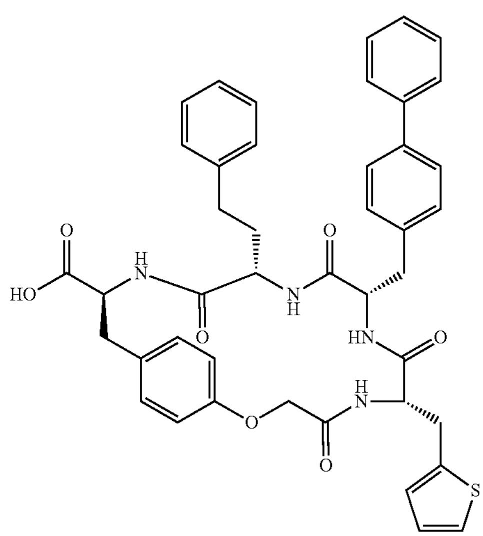 | 759.2852 | 759.2868 |

TABLE 1-continued

| Compound No. | Structure | MS Calcd | MS Observed |
|---|---|---|---|
| 255 | 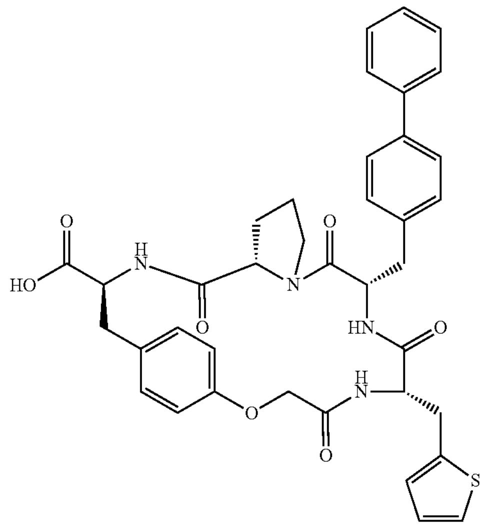 | 695.2539 | 695.2545 |
| 256 | 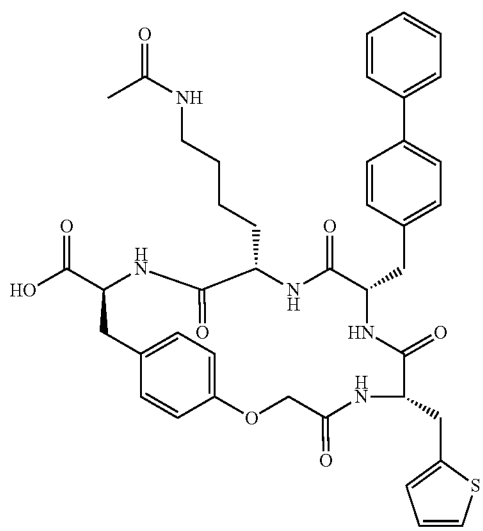 | 768.3067 | 768.3075 |
| 257 | 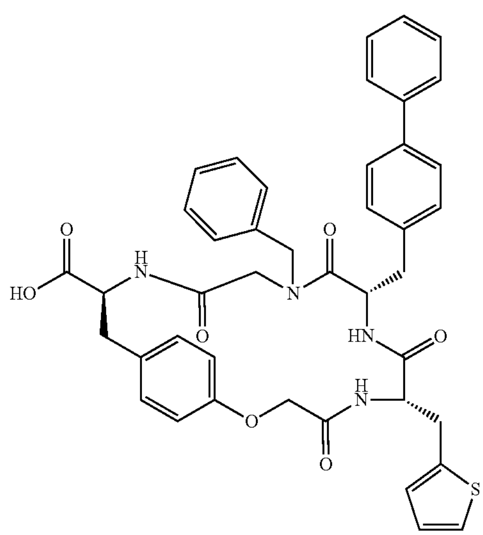 | 745.2696 | 745.2701 |

TABLE 1-continued

| Compound No. | Structure | MS Calcd | MS Observed |
| --- | --- | --- | --- |
| 258 | 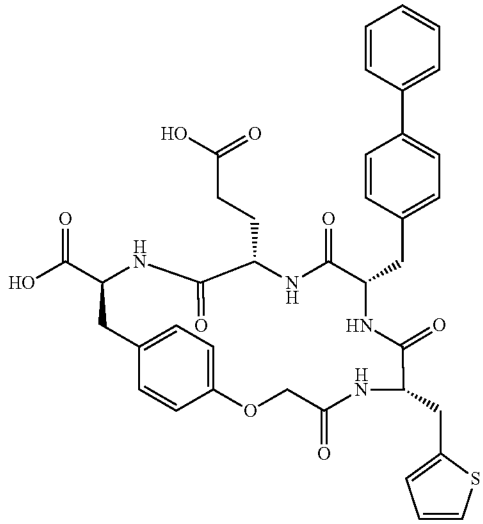 | 727.2438 | 727.2429 |
| 259 | 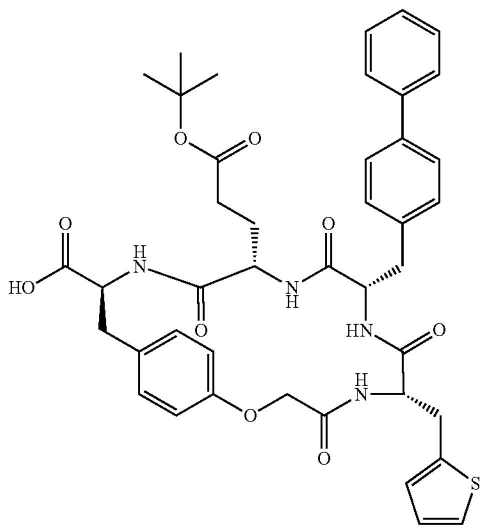 | 783.3064 | 783.3069 |
| 260 | 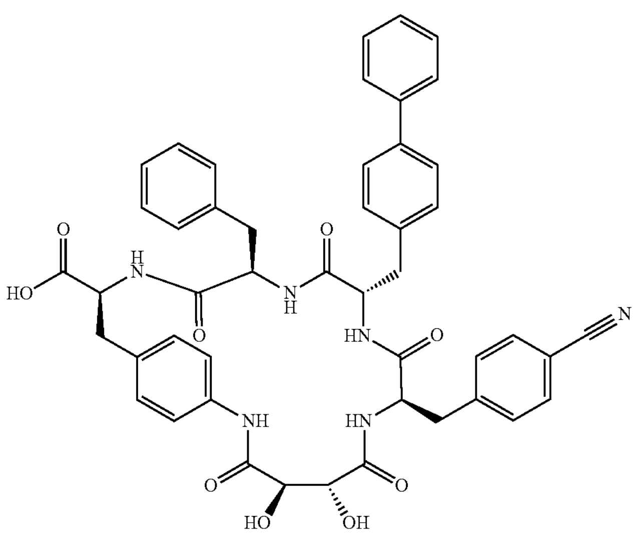 | 837.3248 | 837.3255 |

TABLE 1-continued

| Compound No. | Structure | MS Calcd | MS Observed |
|---|---|---|---|
| 261 | 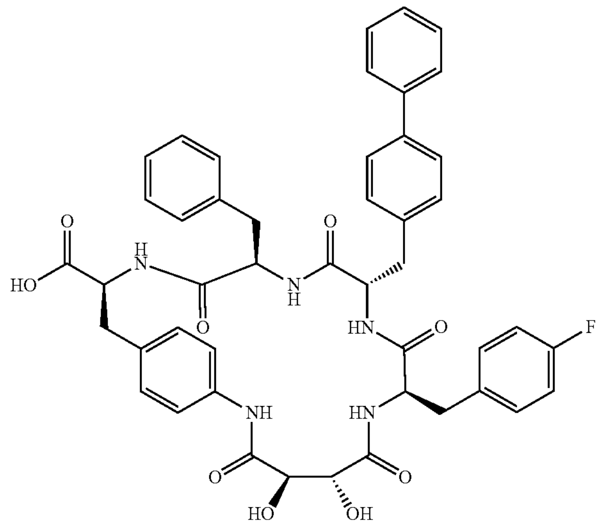 | 830.3201 | 830.3194 |
| 262 | 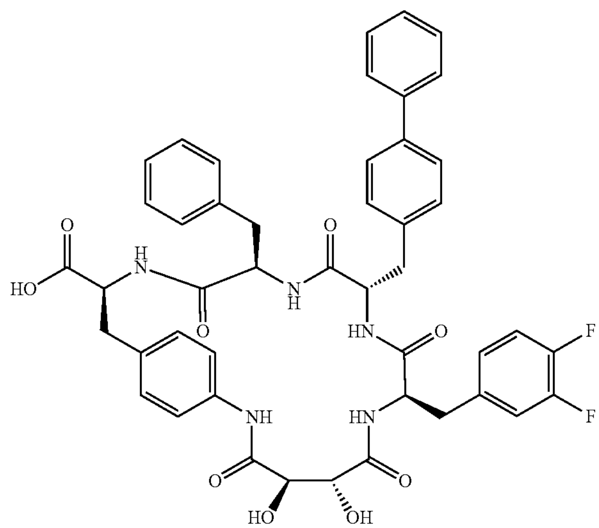 | 848.3107 | 848.3094 |
| 263 | 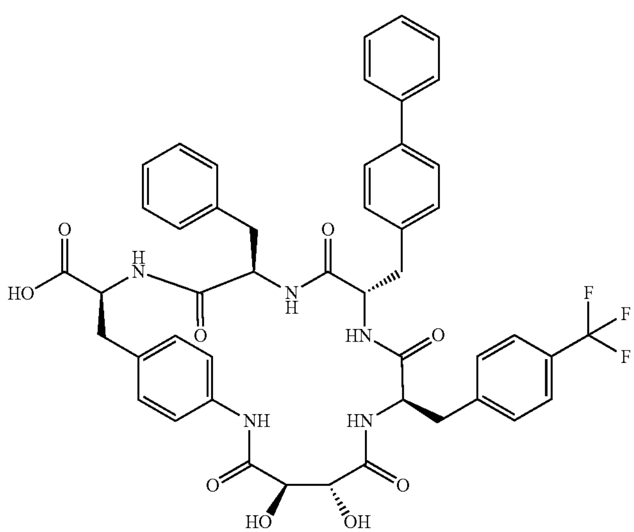 | 880.3169 | 880.3190 |

TABLE 1-continued
| Compound No. | Structure | MS Calcd | MS Observed |
|---|---|---|---|
| 264 | 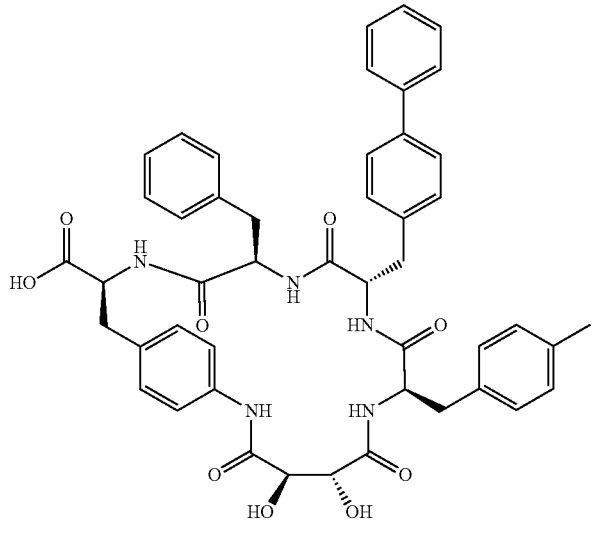 | 826.3452 | 826.3390 |
| 265 | 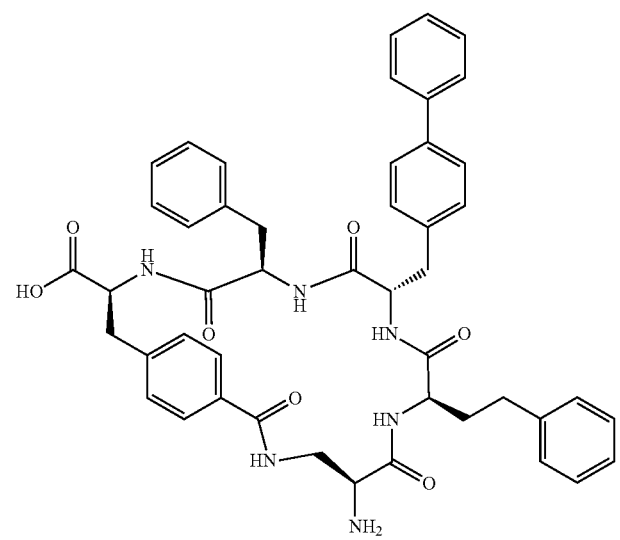 | 809.3657 | 809.3674 |

TABLE 1-continued

| Compound No. | Structure | MS Calcd | MS Observed |
|---|---|---|---|
| 266 | 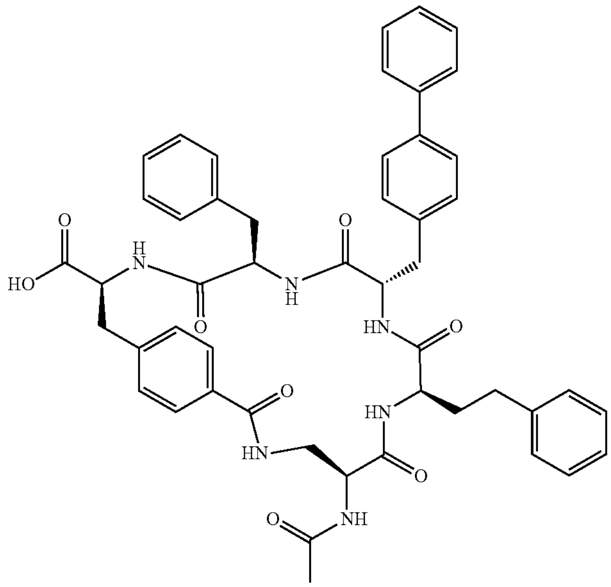 | 851.3763 | 851.3777 |
| 267 | 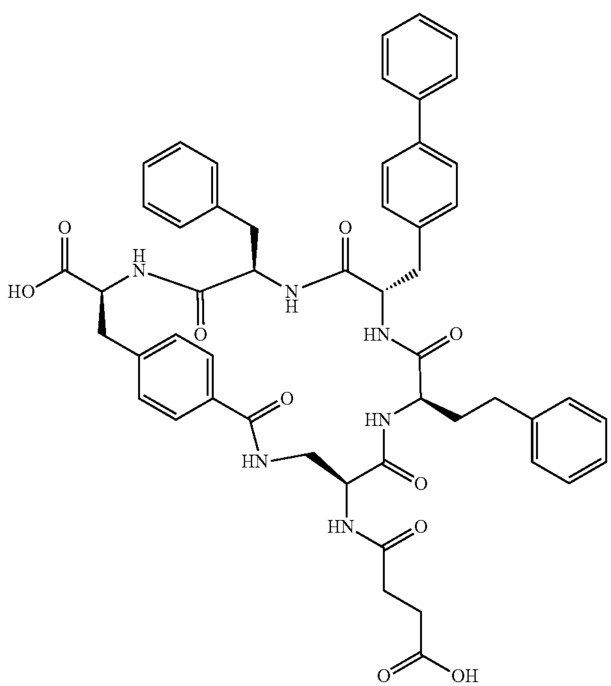 | 909.3818 | 909.3823 |

TABLE 1-continued
| Compound No. | Structure | MS Calcd | MS Observed |
|---|---|---|---|
| 268 | 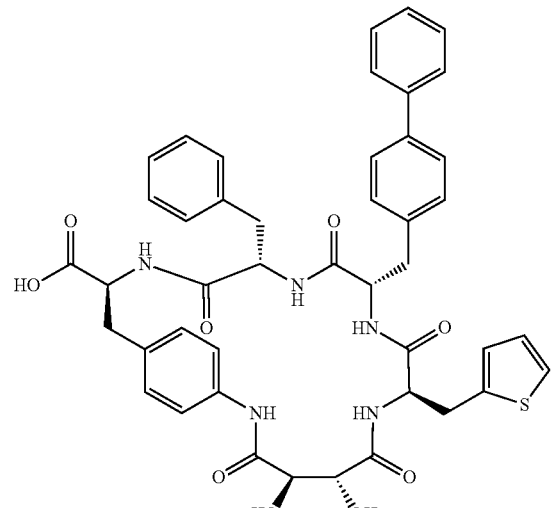 | 818.2855 | 818.2851 |
| 269 | 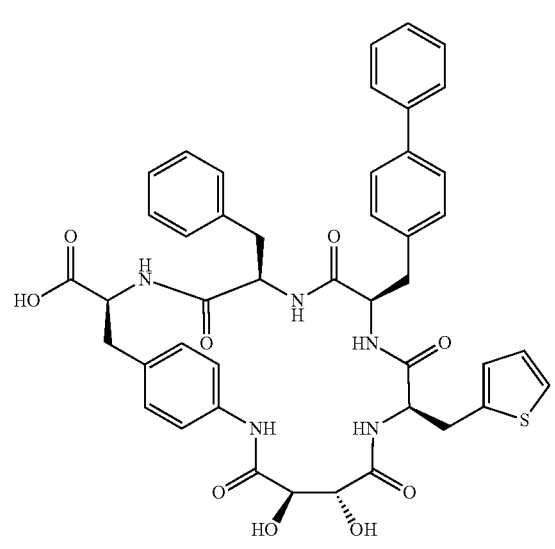 | 818.2855 | 818.2839 |
| 270 | 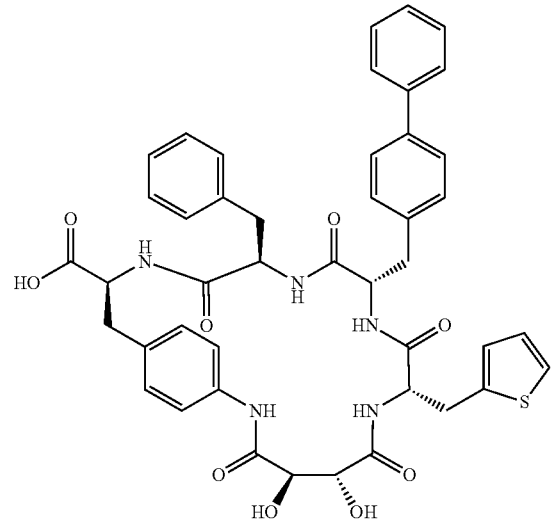 | 818.2855 | 818.2806 |

TABLE 1-continued
| Compound No. | Structure | MS Calcd | MS Observed |
|---|---|---|---|
| 271 | 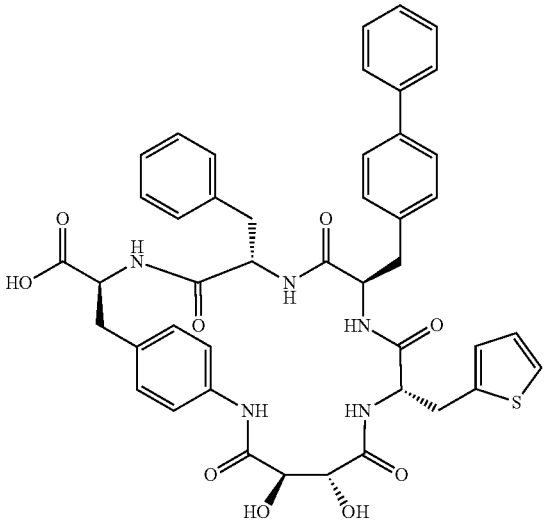 | 818.2855 | 818.2854 |
| 272 | 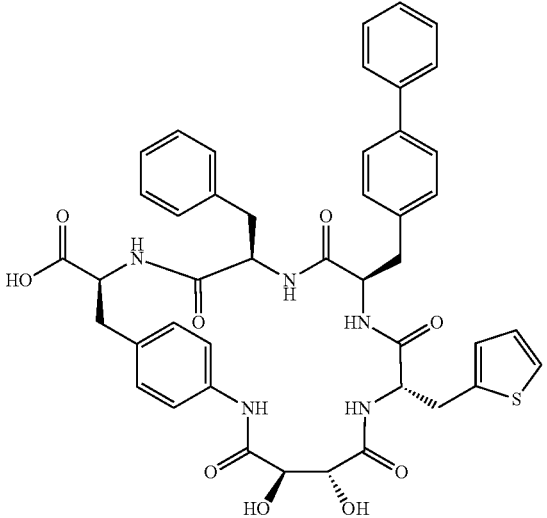 | 818.2855 | 818.2883 |

TABLE 1-continued
| Compound No. | Structure | MS Calcd | MS Observed |
|---|---|---|---|
| 273 | 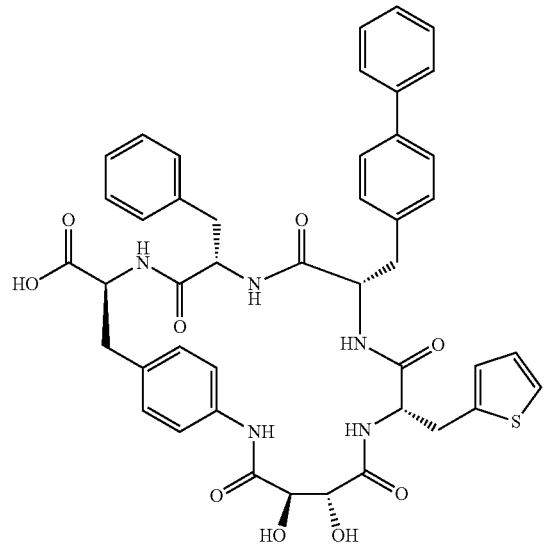 | 818.2855 | 818.2860 |
| 274 | 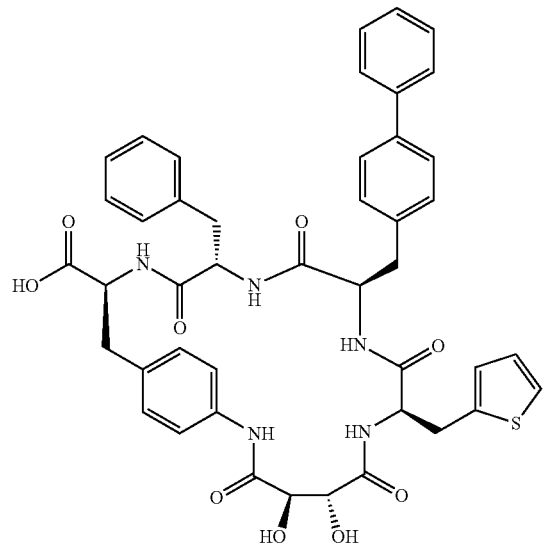 | 818.2855 | 818.2892 |

TABLE 1-continued
| Compound No. | Structure | MS Calcd | MS Observed |
|---|---|---|---|
| 275 | 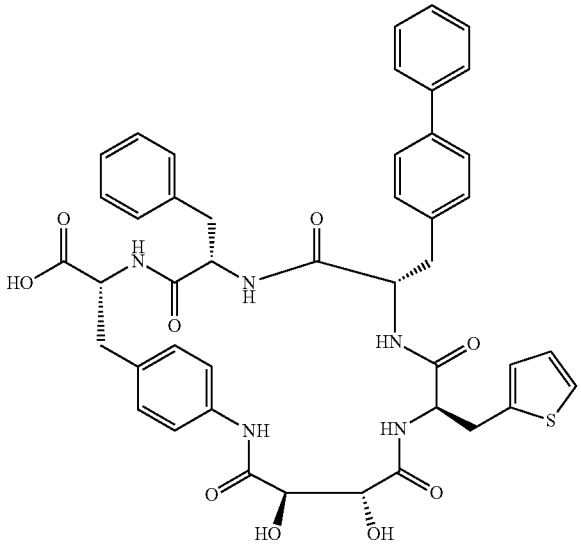 | 818.2855 | 818.2838 |
| 276 | 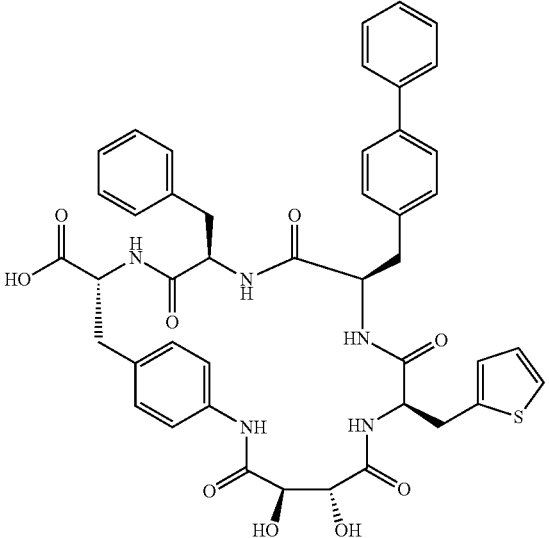 | 818.2855 | 818.2811 |

TABLE 1-continued

| Compound No. | Structure | MS Calcd | MS Observed |
|---|---|---|---|
| 277 | 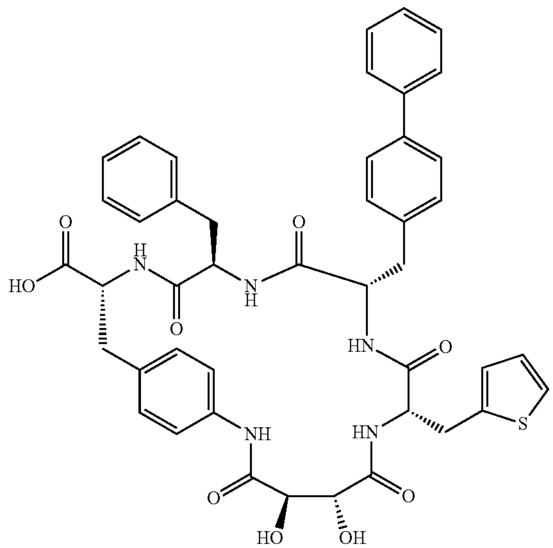 | 818.2855 | 818.2833 |
| 278 | 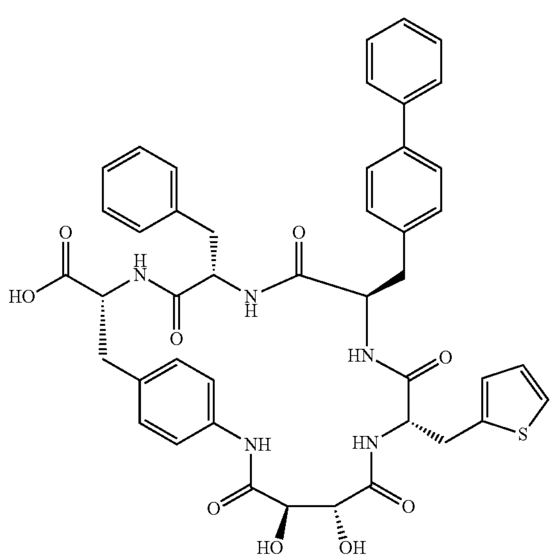 | 818.2855 | 818.2837 |

TABLE 1-continued
| Compound No. | Structure | MS Calcd | MS Observed |
|---|---|---|---|
| 279 | 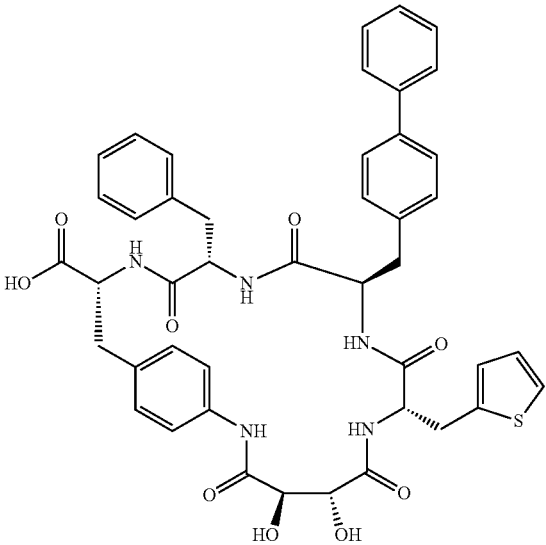 | 818.2855 | 818.2859 |
| 280 | 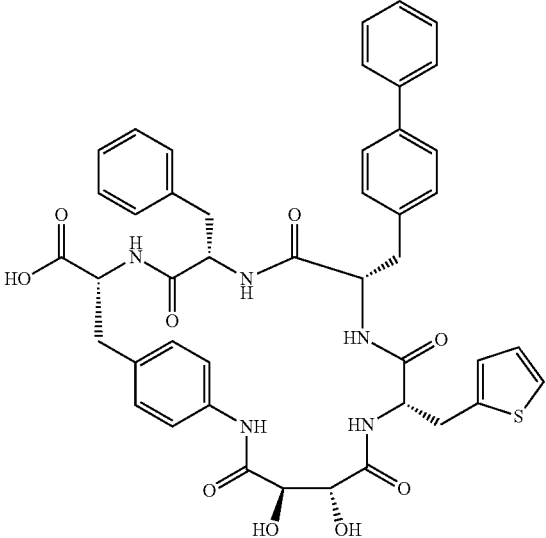 | 818.2855 | 818.2875 |

TABLE 1-continued
| Compound No. | Structure | MS Calcd | MS Observed |
|---|---|---|---|
| 281 | 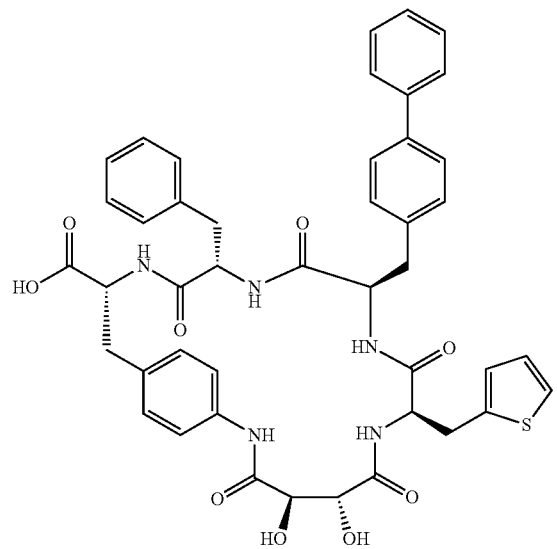 | 818.2855 | 818.2849 |
| 282 | 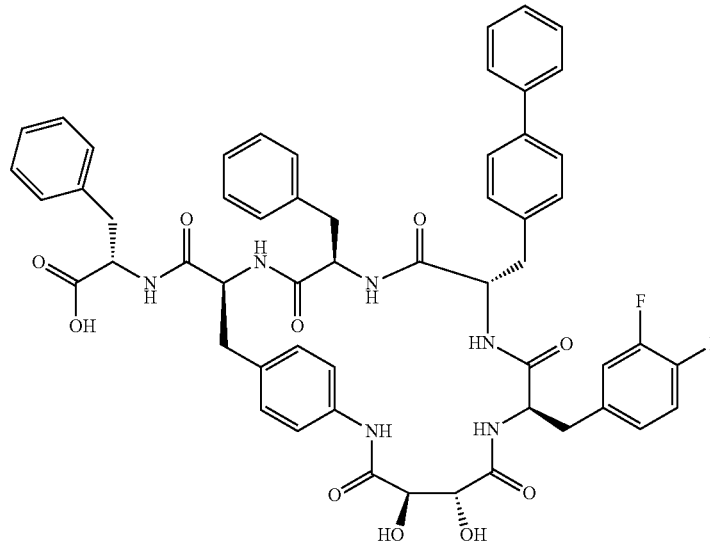 | 995.3791 | 995.3835 |

TABLE 1-continued
| Compound No. | Structure | MS Calcd | MS Observed |
|---|---|---|---|
| 283 | 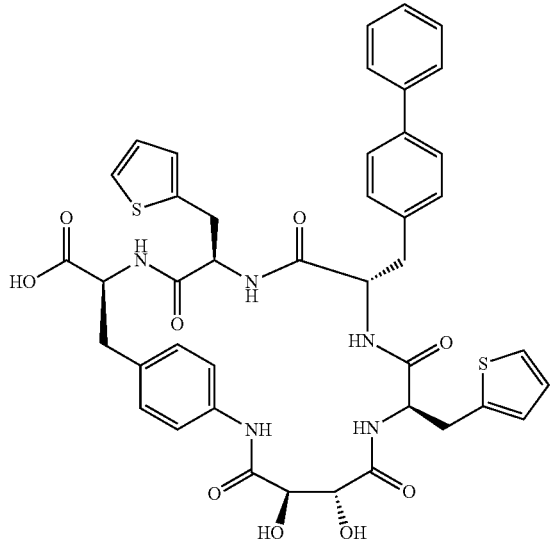 | 824.2424 | 824.2457 |
| 284 | 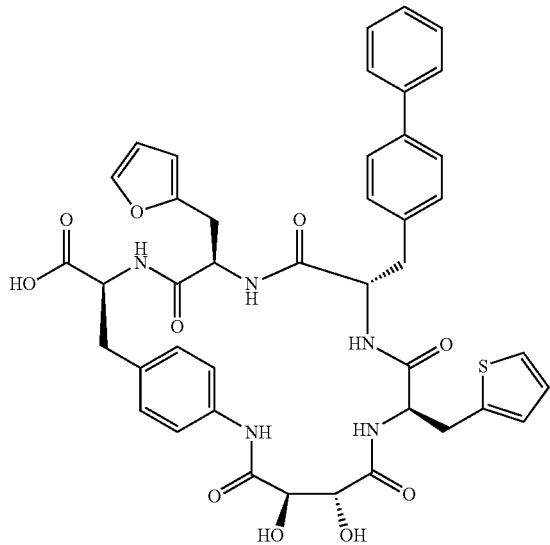 | 808.2652 | 808.2674 |

TABLE 1-continued

| Compound No. | Structure | MS Calcd | MS Observed |
|---|---|---|---|
| 285 | 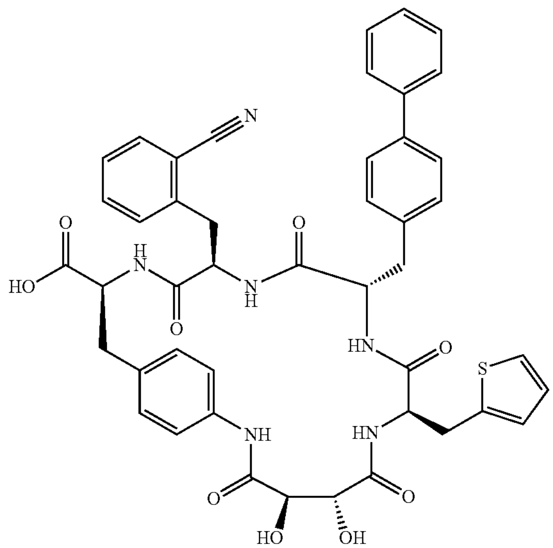 | 843.2812 | 843.2819 |
| 286 | 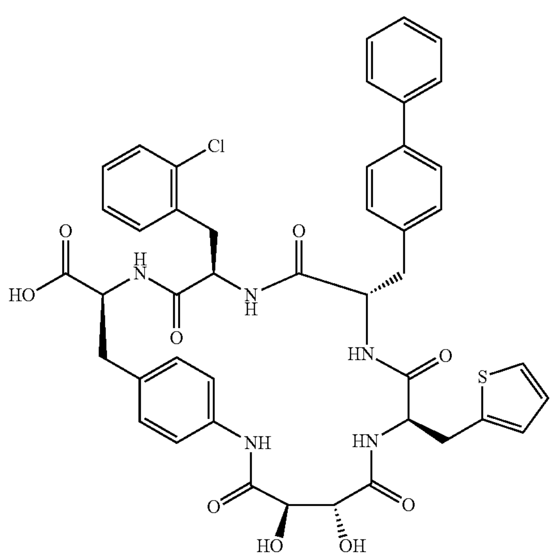 | 852.2470 | 852.2487 |

TABLE 1-continued

| Compound No. | Structure | MS Calcd | MS Observed |
|---|---|---|---|
| 287 | 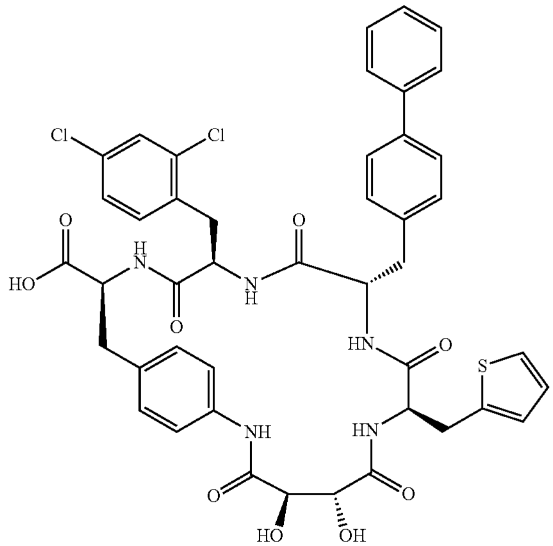 | 886.2080 | 886.2091 |
| 288 | 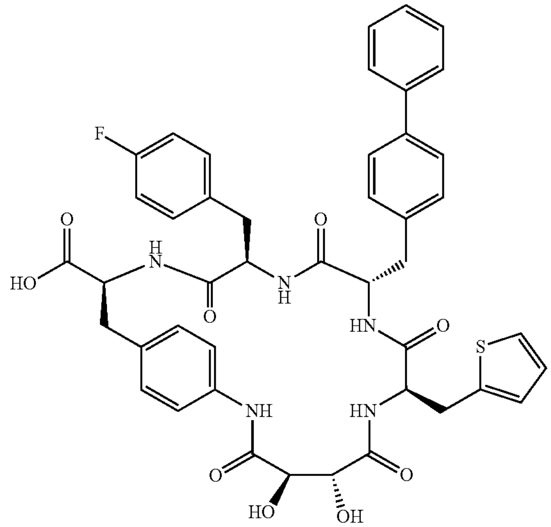 | 836.2765 | 836.2786 |

TABLE 1-continued

| Compound No. | Structure | MS Calcd | MS Observed |
|---|---|---|---|
| 289 | 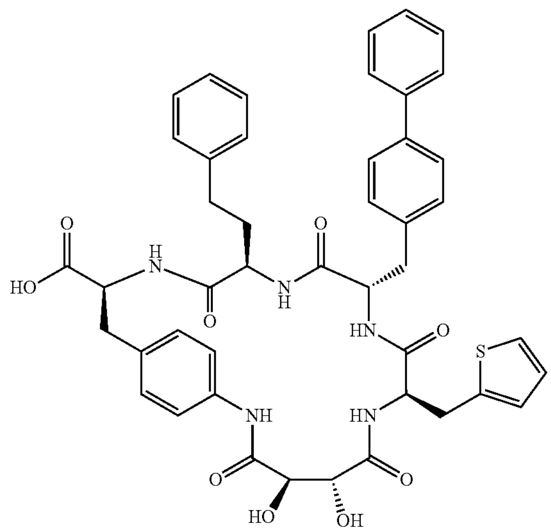 | 832.3016 | 832.3036 |
| 290 | 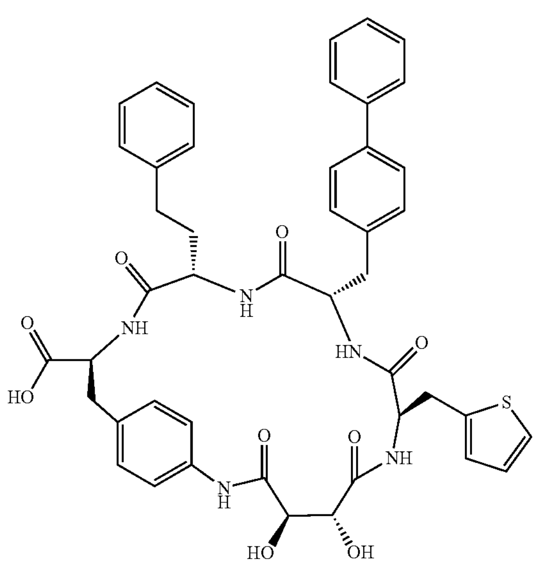 | 832.3016 | 832.3040 |

TABLE 1-continued

| Compound No. | Structure | MS Calcd | MS Observed |
|---|---|---|---|
| 291 | 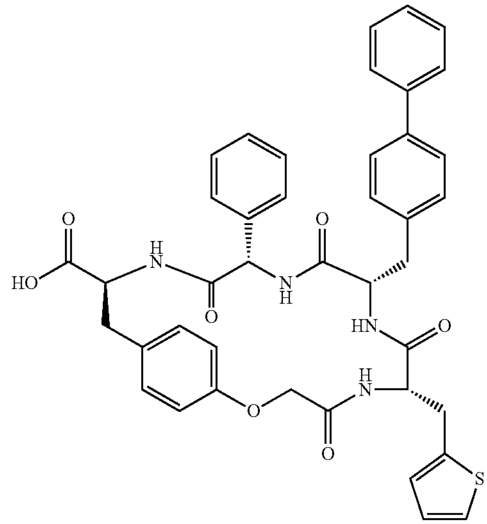 | 731.2539 | 731.2563 |
| 292 | 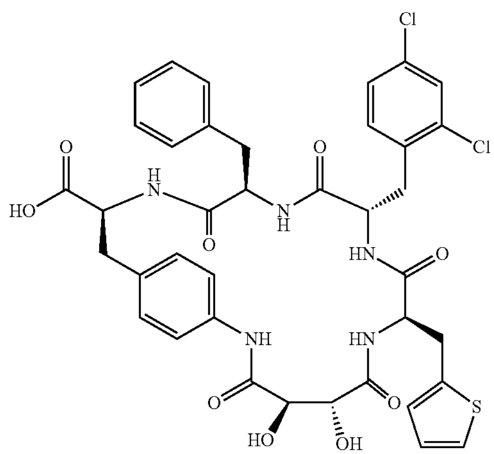 | 810.1767 | 810.1782 |
| 293 | 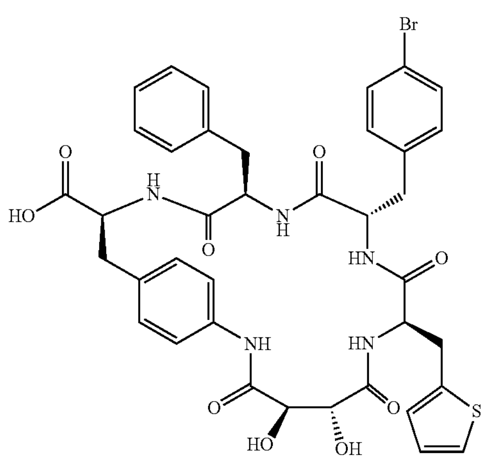 | 820.1652 | 820.1610 |

| Compound No. | Structure | MS Calcd | MS Observed |
|---|---|---|---|
| 294 | 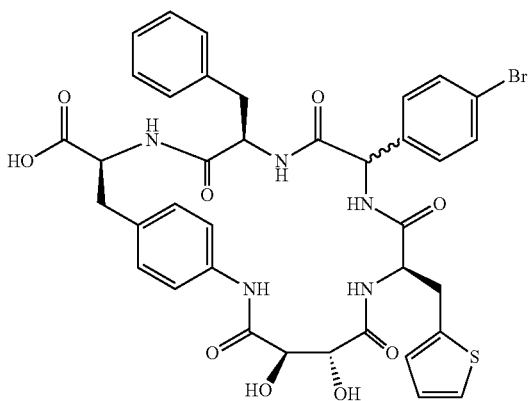 | 806.1495 | 806.1500 |
| 295 | 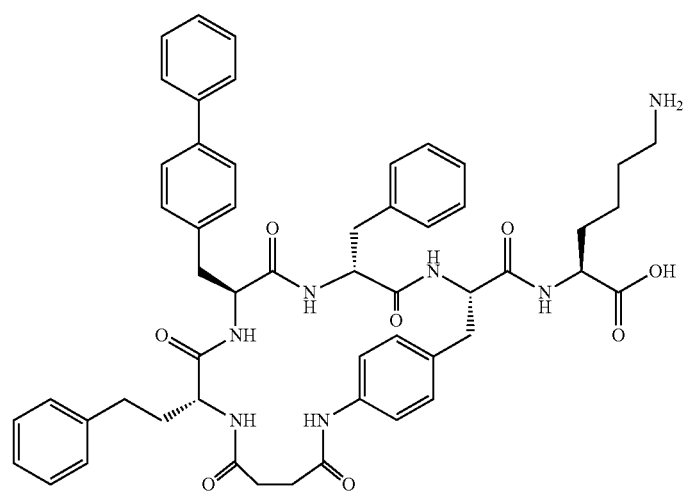 | 922.4498 | 922.4511 |
| 296 | 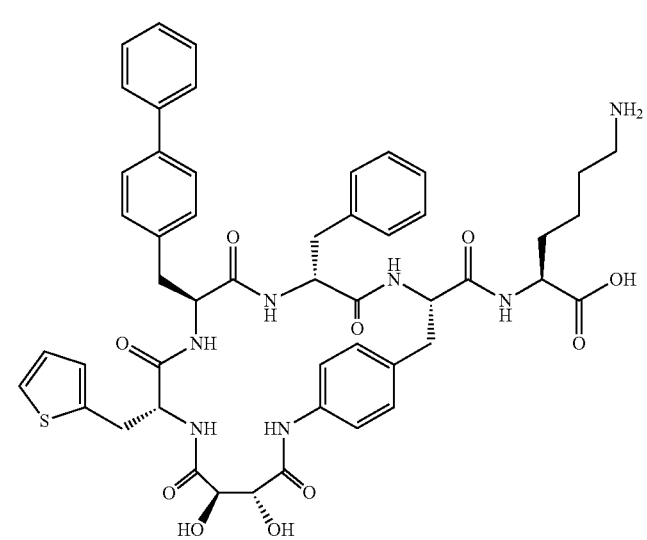 | 946.3809 | 946.3768 |

TABLE 1-continued

| Compound No. | Structure | MS Calcd | MS Observed |
|---|---|---|---|
| 297 | 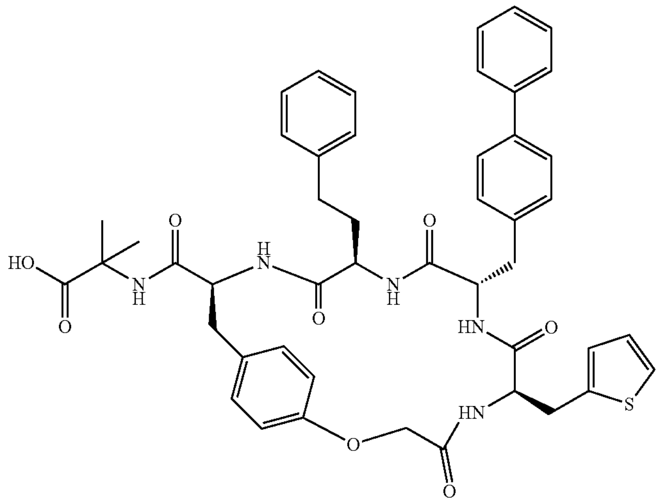 | 842.3224 | 842.3187 |
| 298 | 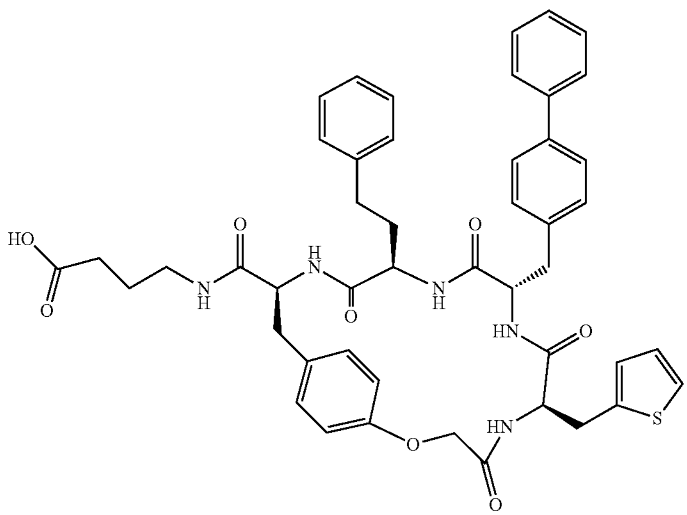 | 842.3224 | 842.3213 |
| 299 | 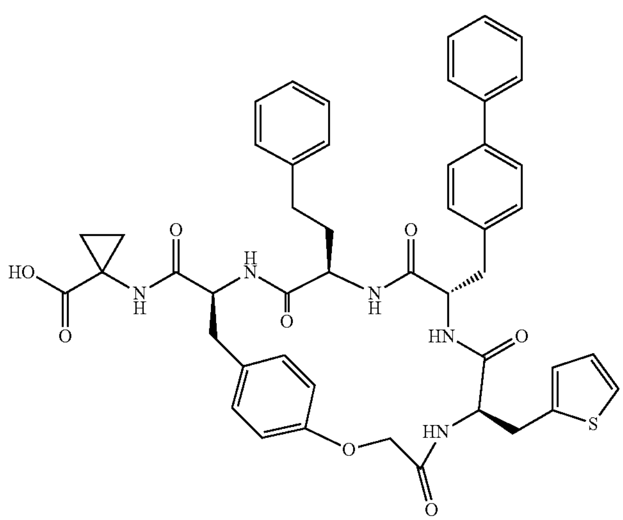 | 840.3067 | 840.3047 |

TABLE 1-continued

| Compound No. | Structure | MS Calcd | MS Observed |
|---|---|---|---|
| 300 | 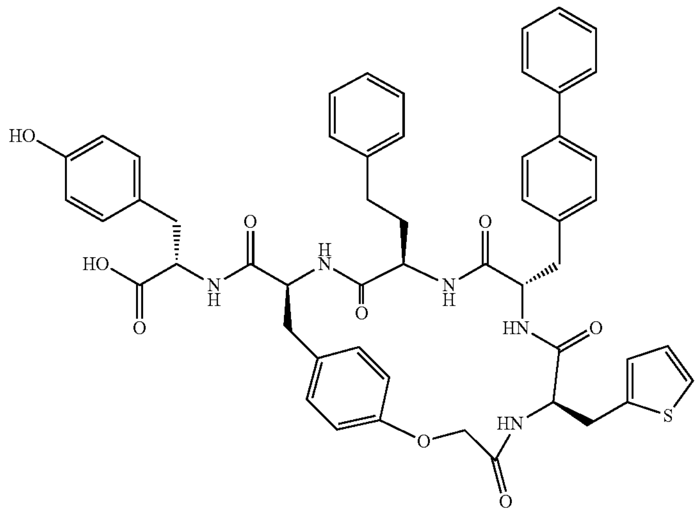 | 920.3329 | 920.3302 |
| 301 | 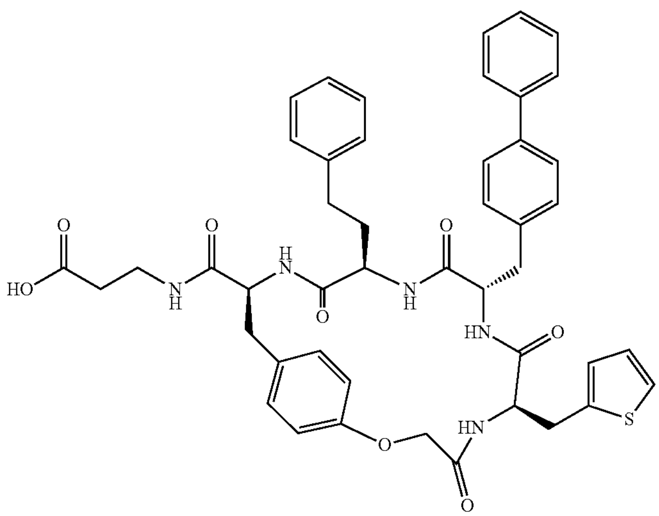 | 828.3067 | 830.430* |
| 302 | 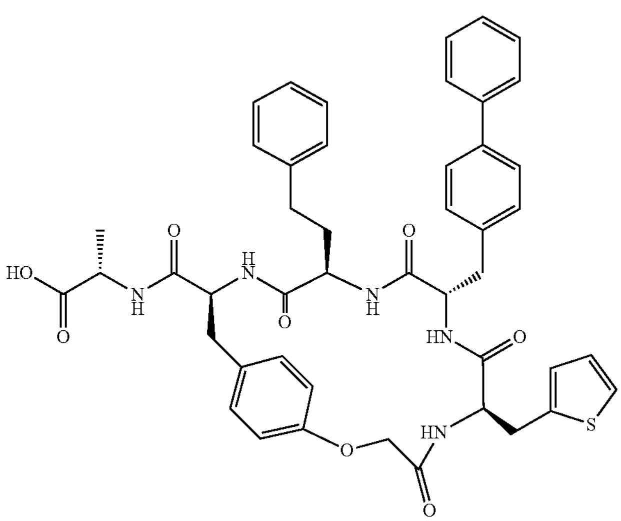 | 828.3067 | 828.3053 |

TABLE 1-continued

| Compound No. | Structure | MS Calcd | MS Observed |
|---|---|---|---|
| 303 | 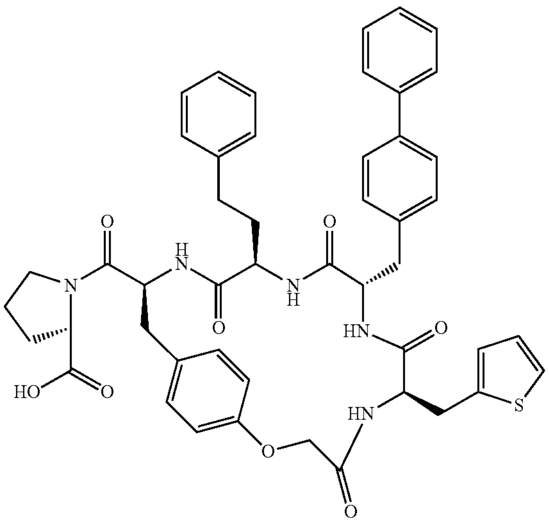 | 854.3224 | 854.3203 |
| 304 | 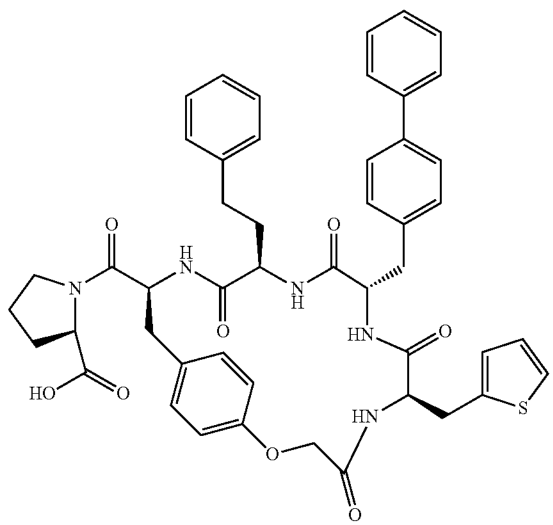 | 854.3224 | 854.3184 |
| 305 | 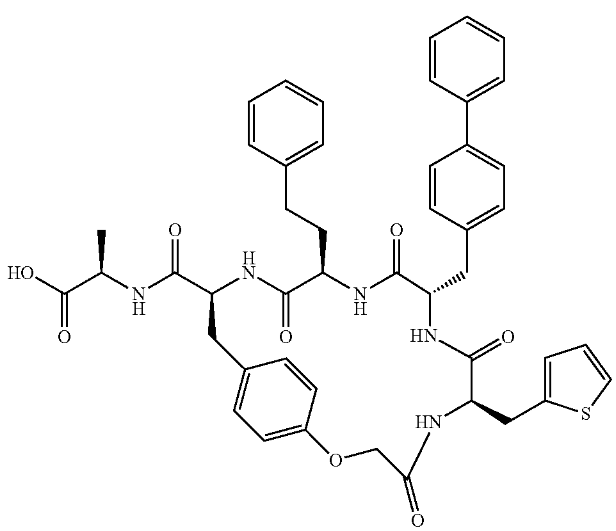 | 828.3067 | 828.3050 |

TABLE 1-continued
| Compound No. | Structure | MS Calcd | MS Observed |
|---|---|---|---|
| 306 | 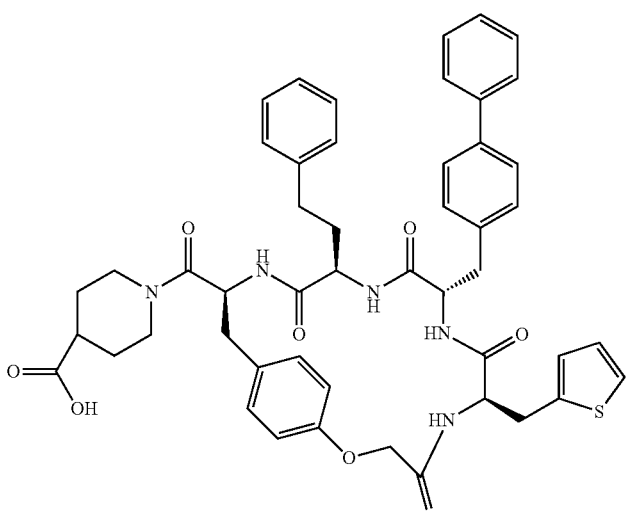 | 868.3380 | 868.3387 |
| 307 | 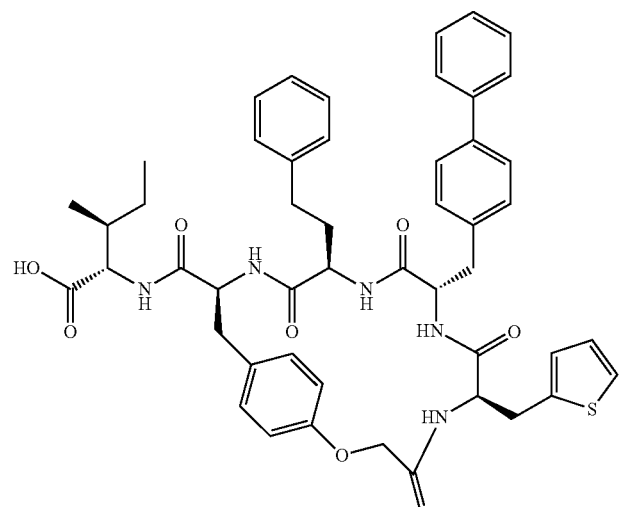 | 870.3537 | 870.3533 |
| 308 | 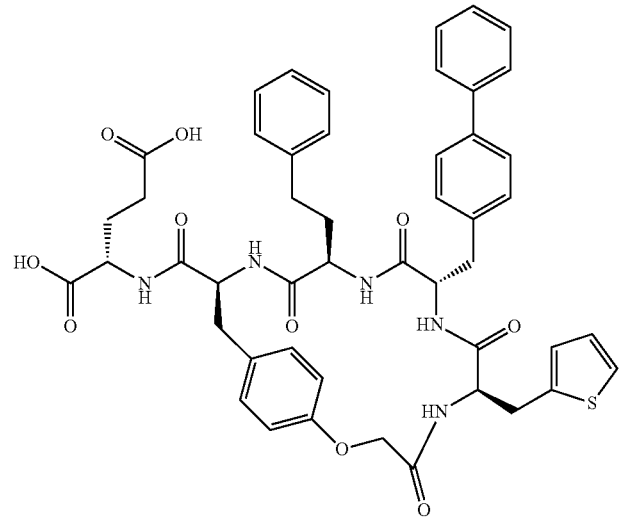 | 886.3122 | 886.3110 |

TABLE 1-continued

| Compound No. | Structure | MS Calcd | MS Observed |
| --- | --- | --- | --- |
| 309 | 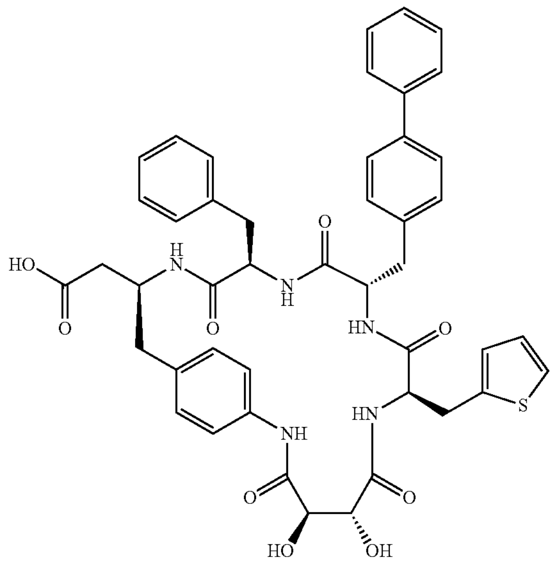 | 832.3011 | 832.3054 |
| 310 | 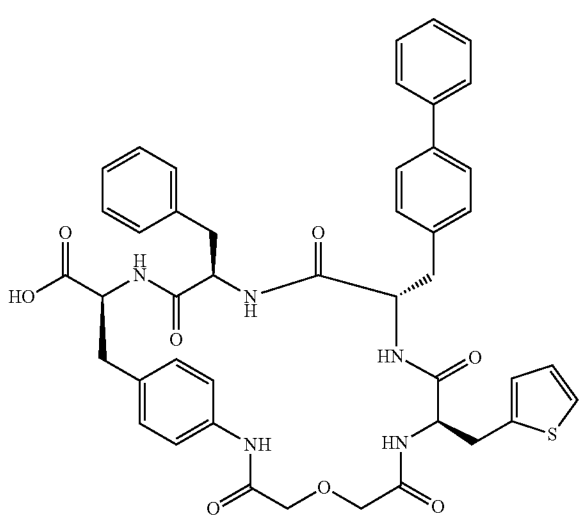 | 802.2905 | 802.2928 |

TABLE 1-continued
| Compound No. | Structure | MS Calcd | MS Observed |
|---|---|---|---|
| 311 | 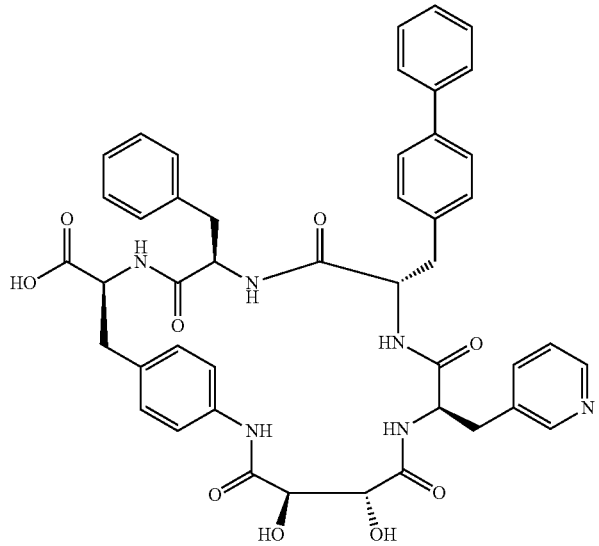 | 813.3248 | 813.3250 |
| 312 | 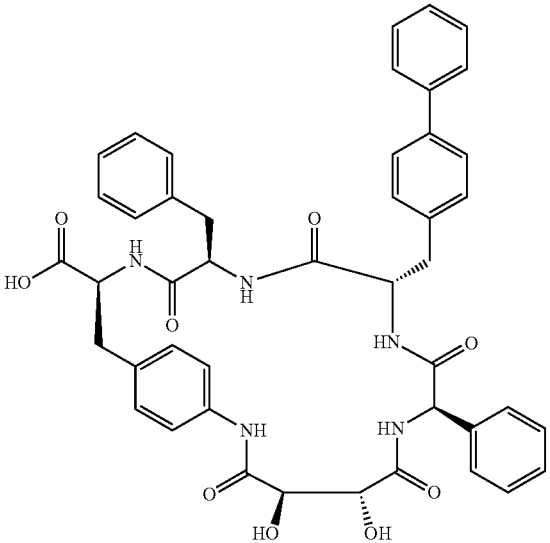 | 798.3139 | 798.3173 |

TABLE 1-continued

| Compound No. | Structure | MS Calcd | MS Observed |
|---|---|---|---|
| 313 | 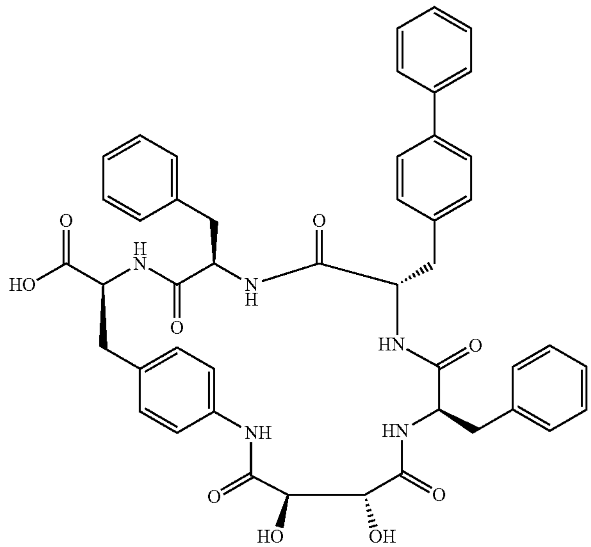 | 812.3296 | 812.3334 |
| 314 | 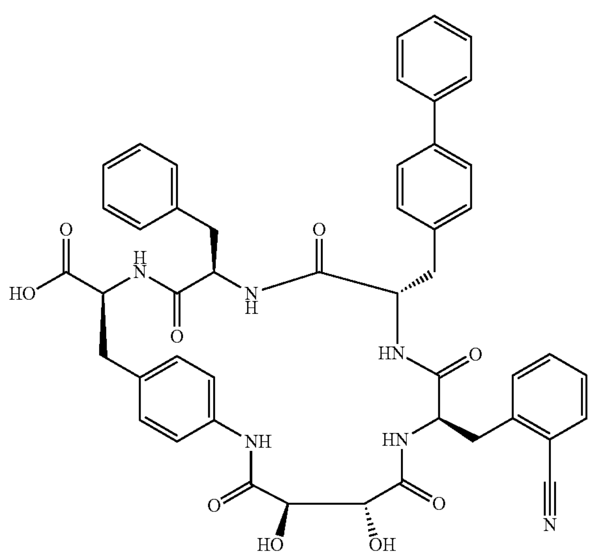 | 837.3248 | 837.3281 |

TABLE 1-continued

| Compound No. | Structure | MS Calcd | MS Observed |
|---|---|---|---|
| 315 | 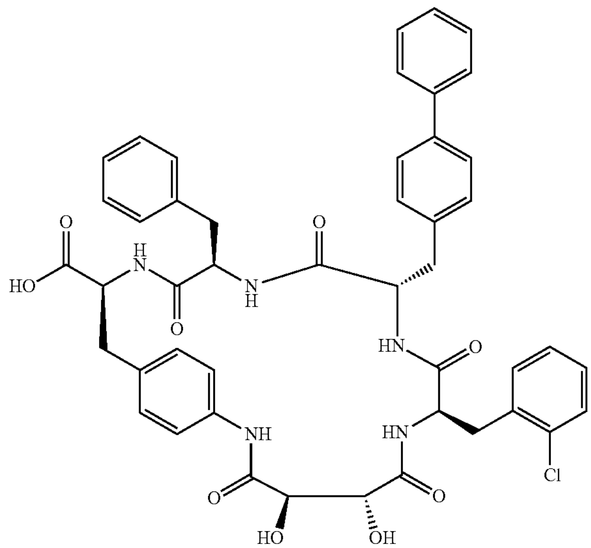 | 846.2906 | 846.3013 |
| 316 | 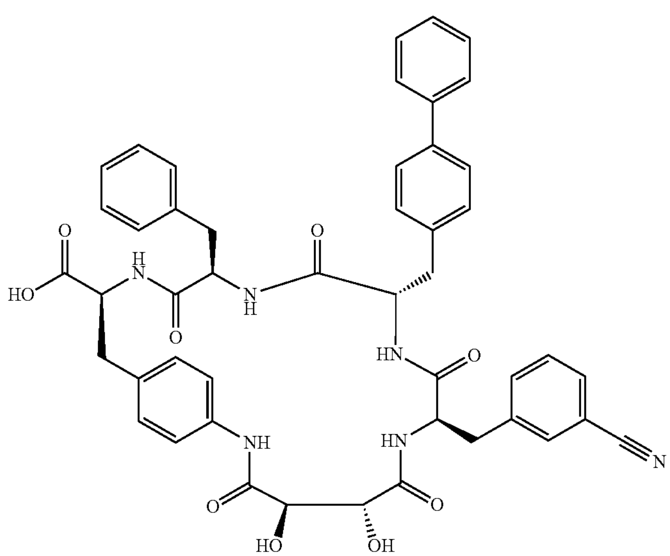 | 837.3248 | 837.3282 |

TABLE 1-continued

| Compound No. | Structure | MS Calcd | MS Observed |
|---|---|---|---|
| 317 | 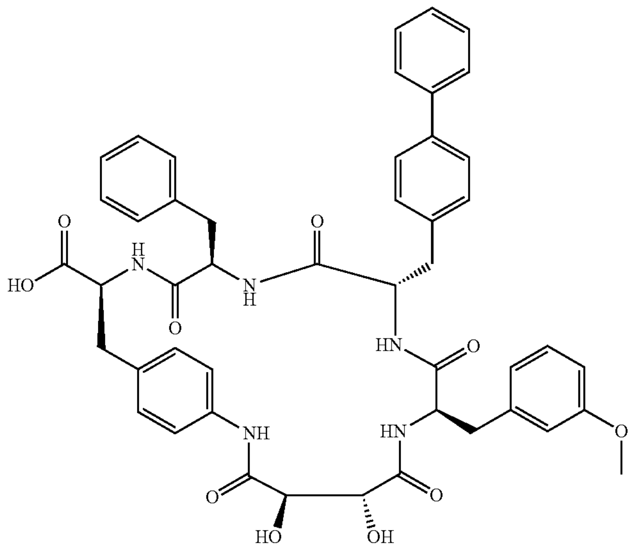 | 842.3401 | 842.3423 |
| 318 | 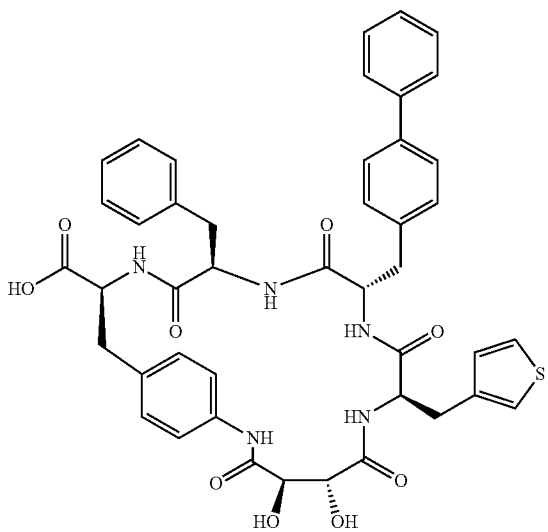 | 818.2860 | 818.2899 |
| 319 | 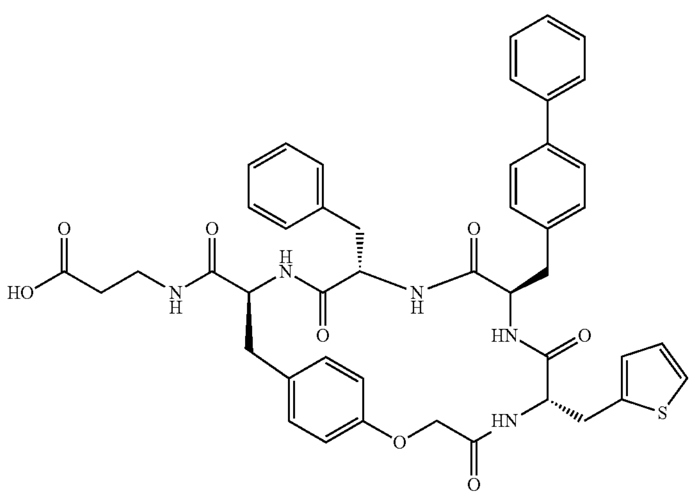 | 816.3067 | 816.3090 |

TABLE 1-continued

| Compound No. | Structure | MS Calcd | MS Observed |
|---|---|---|---|
| 320 | 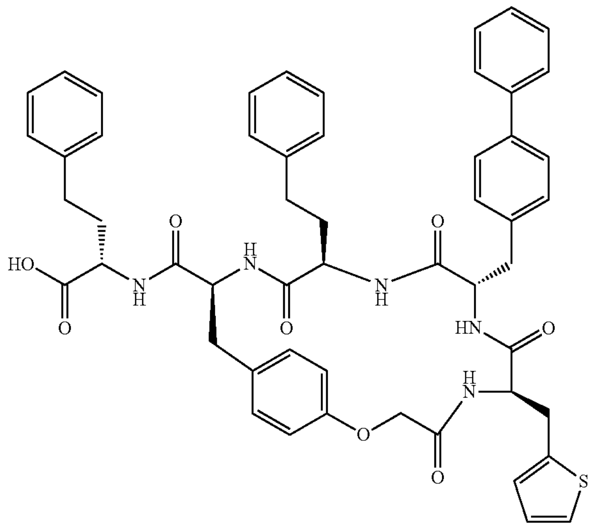 | 920.3693 | 920.3743 |
| 321 | 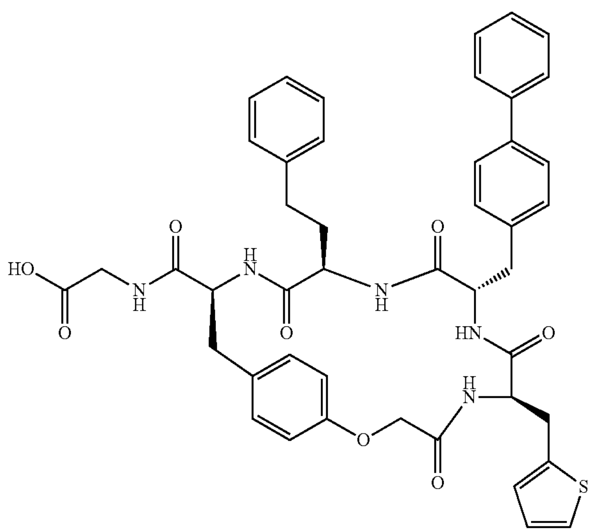 | 816.3067 | 816.3123 |
| 322 | 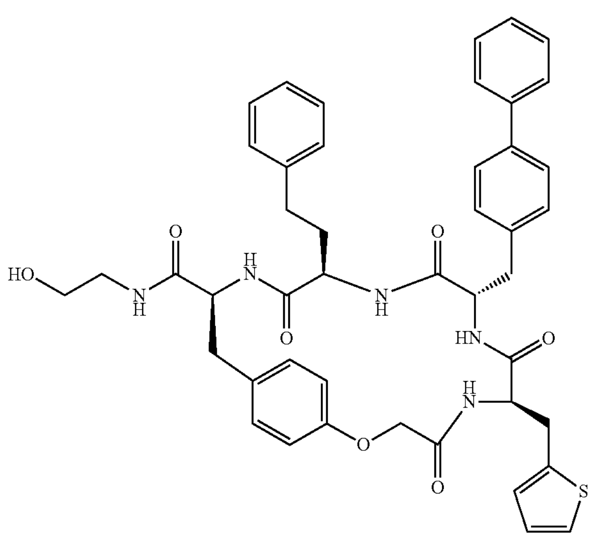 | 802.3274 | 802.3325 |

TABLE 1-continued
| Compound No. | Structure | MS Calcd | MS Observed |
|---|---|---|---|
| 323 | 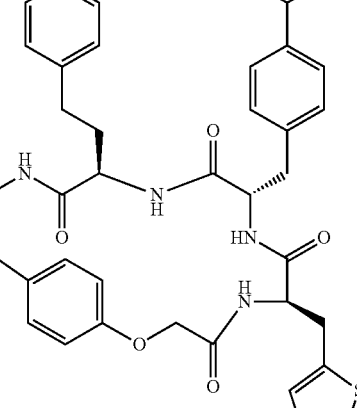 | 906.3537 | 906.3605 |
| 324 | 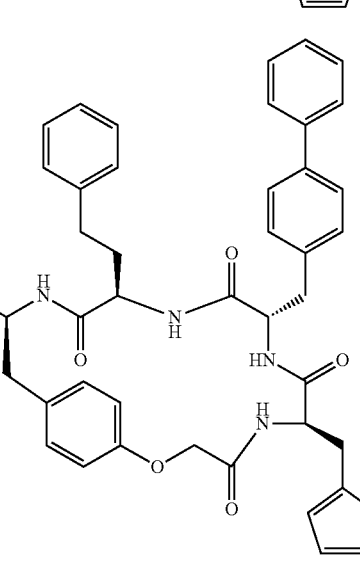 | 906.3537 | 906.3553 |
| 325 | 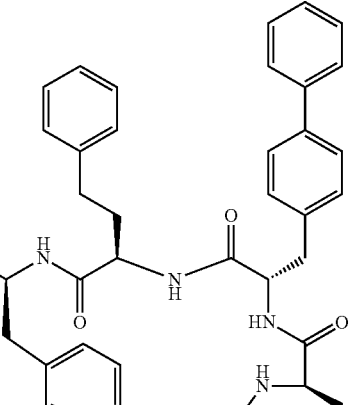 | 888.3278 | 888.3301 |

TABLE 1-continued

| Compound No. | Structure | MS Calcd | MS Observed |
|---|---|---|---|
| 326 | 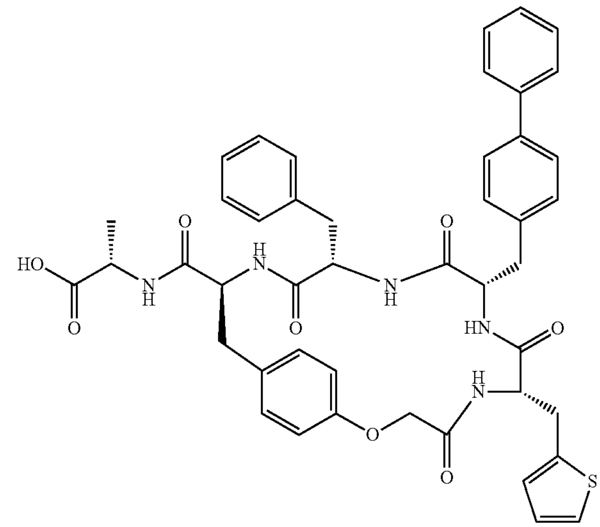 | 816.3067 | 816.3098 |
| 327 | 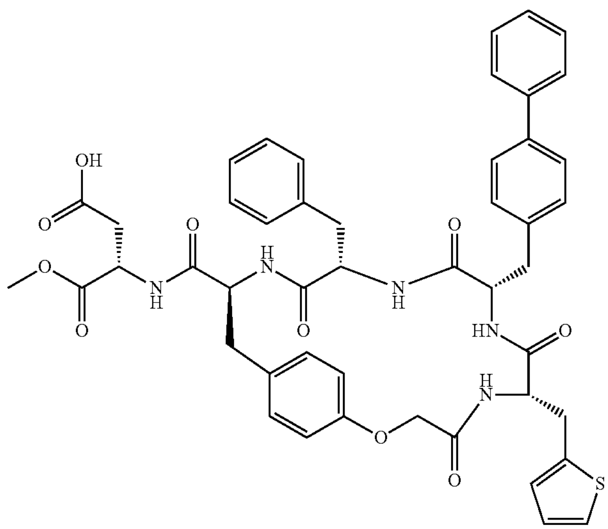 | 874.3122 | 874.3143 |
| 328 | 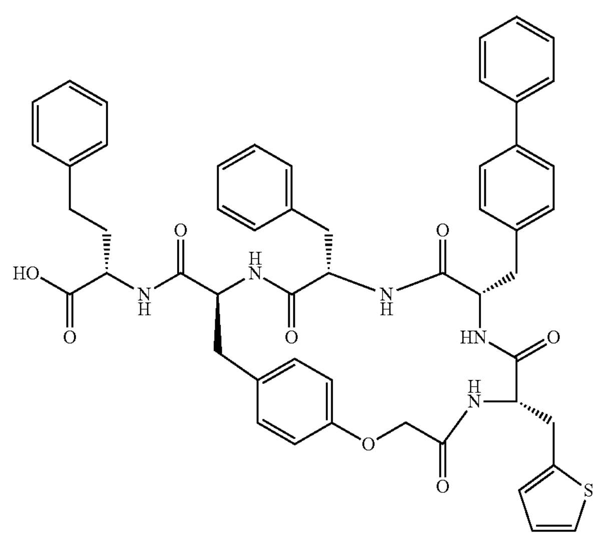 | 906.3537 | 906.3549 |

TABLE 1-continued

| Compound No. | Structure | MS Calcd | MS Observed |
|---|---|---|---|
| 329 | 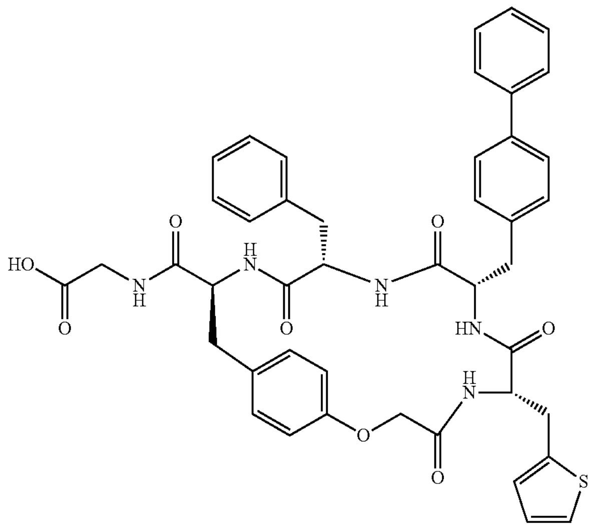 | 802.2911 | 802.2952 |
| 330 | 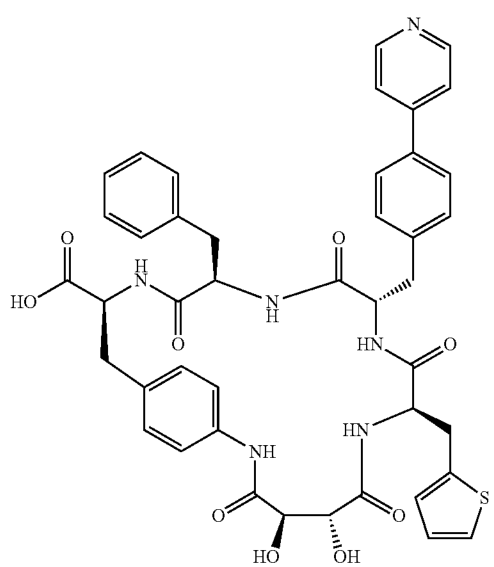 | 819.2812 | 819.2822 |

TABLE 1-continued
| Compound No. | Structure | MS Calcd | MS Observed |
|---|---|---|---|
| 332 | 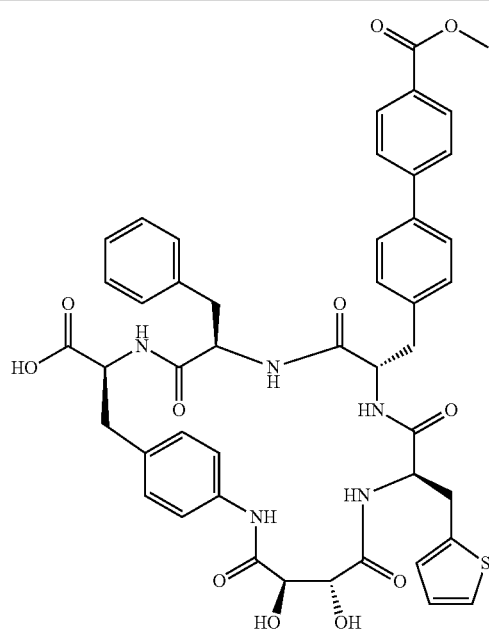 | 876.2914 | 876.2925 |
| 333 | 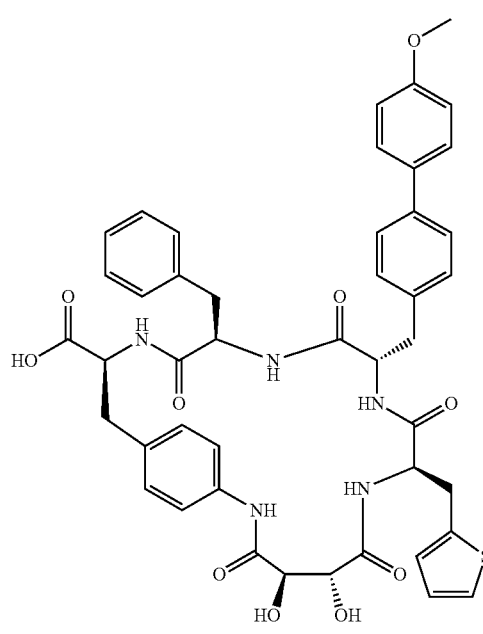 | 848.2965 | 848.2975 |

TABLE 1-continued

| Compound No. | Structure | MS Calcd | MS Observed |
|---|---|---|---|
| 334 | 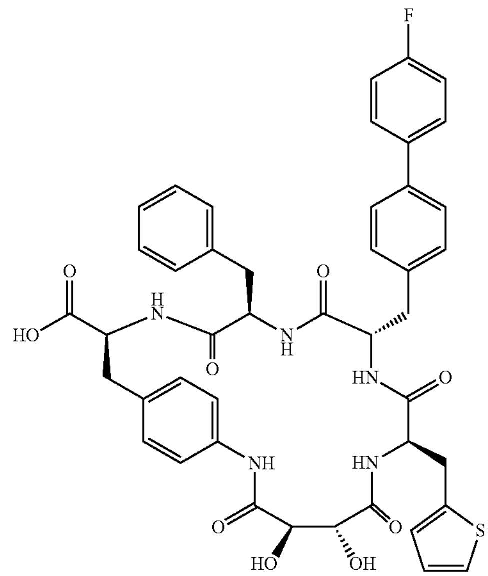 | 836.2765 | 836.2788 |
| 335 | 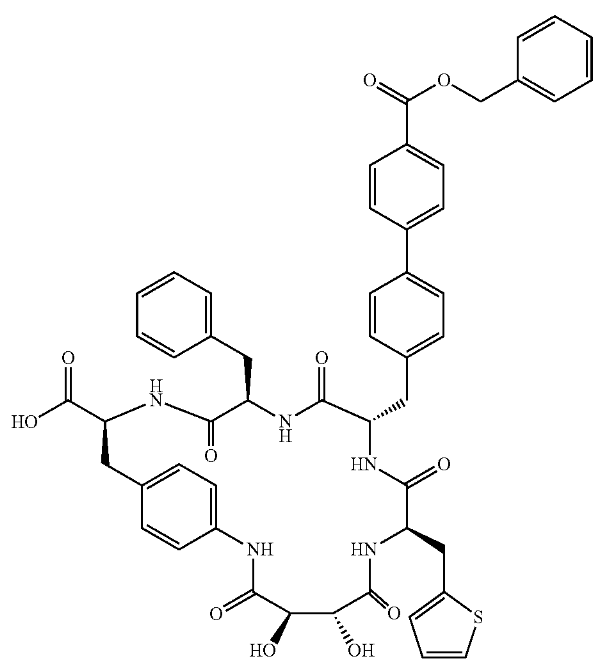 | 952.3227 | 952.3285 |

TABLE 1-continued
| Compound No. | Structure | MS Calcd | MS Observed |
|---|---|---|---|
| 336 | 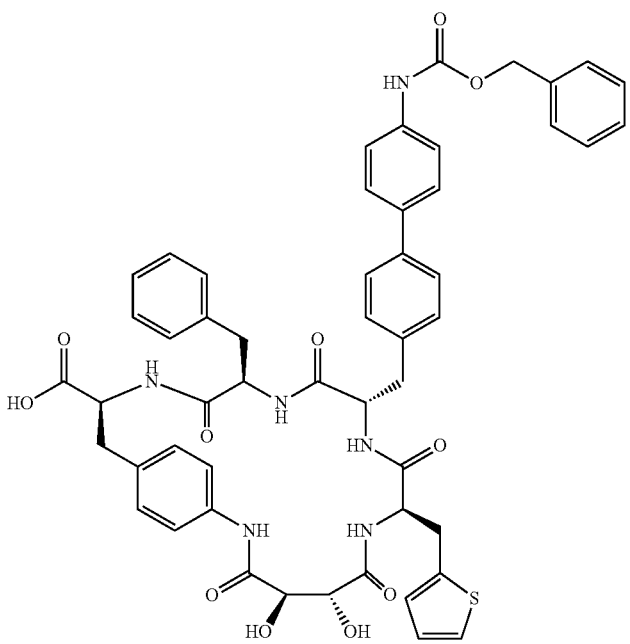 | 967.3336 | 967.3333 |
| 337 | 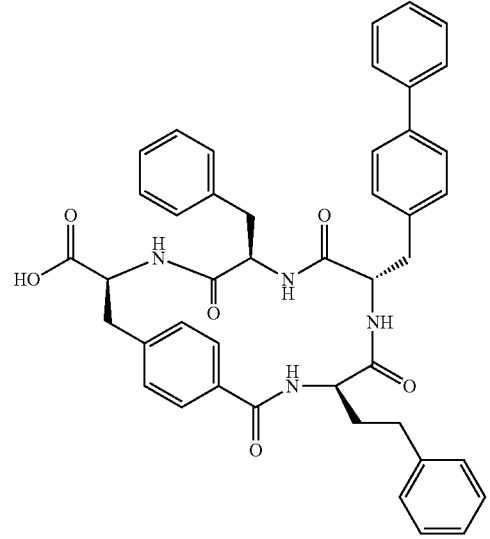 | 723.3177 | 723.3191 |

TABLE 1-continued

| Compound No. | Structure | MS Calcd | MS Observed |
|---|---|---|---|
| 338 | 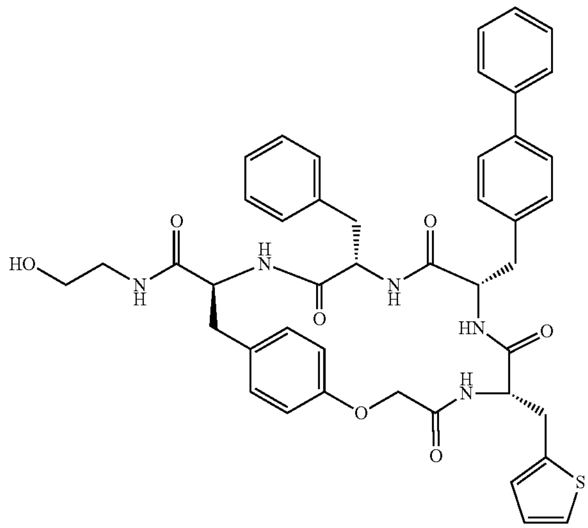 | 788.3118 | 802.2952 |
| 339 | 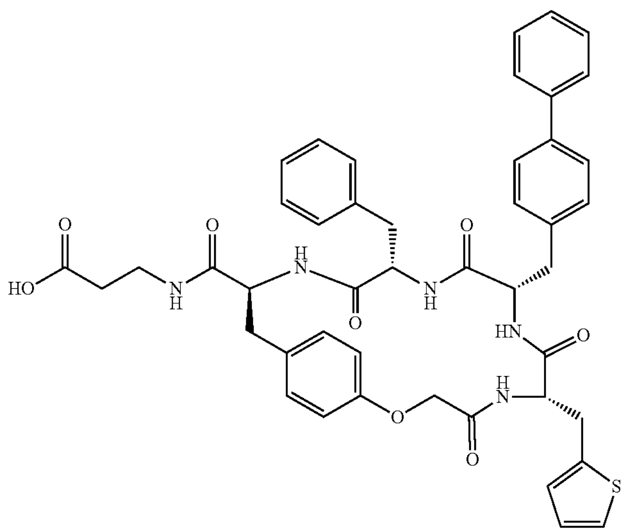 | 816.3067 | 816.3093 |
| 340 | 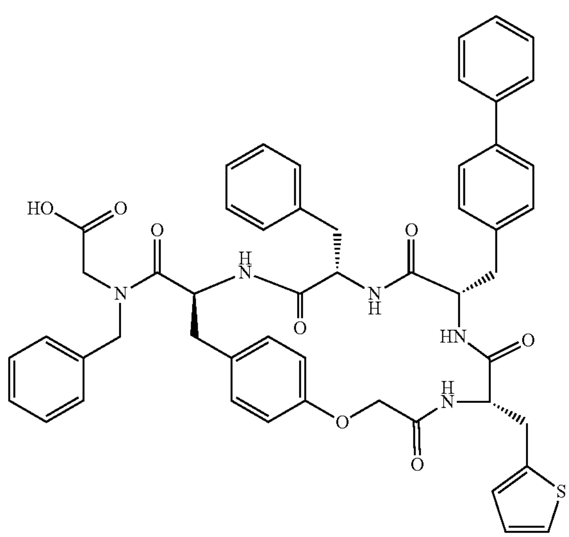 | 892.3380 | 892.3432 |

TABLE 1-continued

| Compound No. | Structure | MS Calcd | MS Observed |
|---|---|---|---|
| 341 | 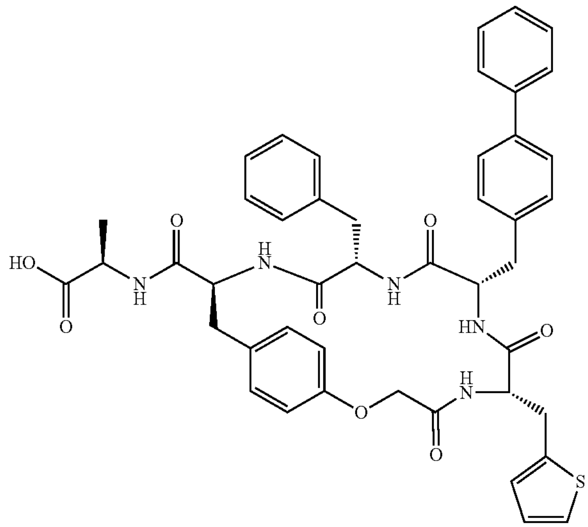 | 816.3067 | 816.3090 |
| 342 | 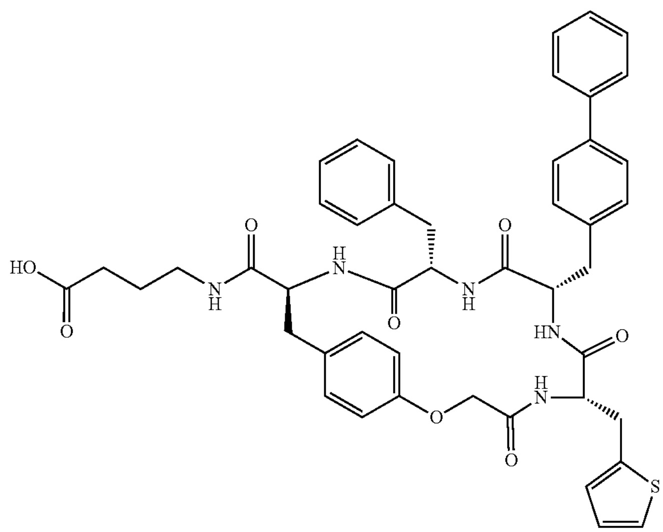 | 830.3224 | 830.3226 |
| 343 | 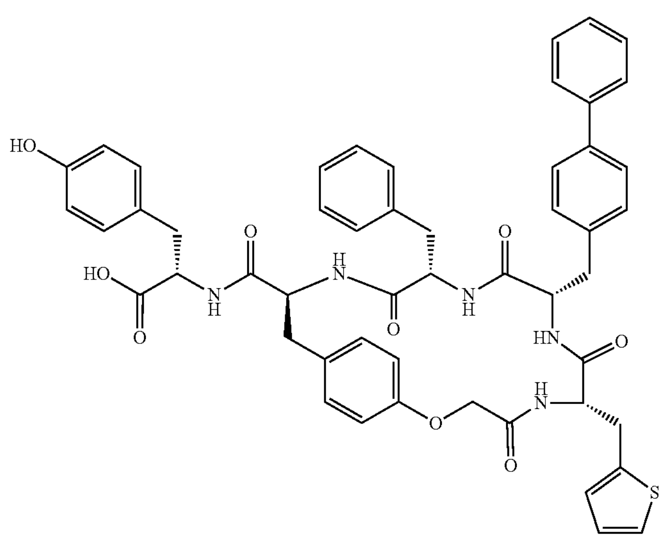 | 908.3329 | 908.3321 |

US 8,338,565 B2
TABLE 1-continued
| Compound No. | Structure | MS Calcd | MS Observed |
|---|---|---|---|
| 344 | 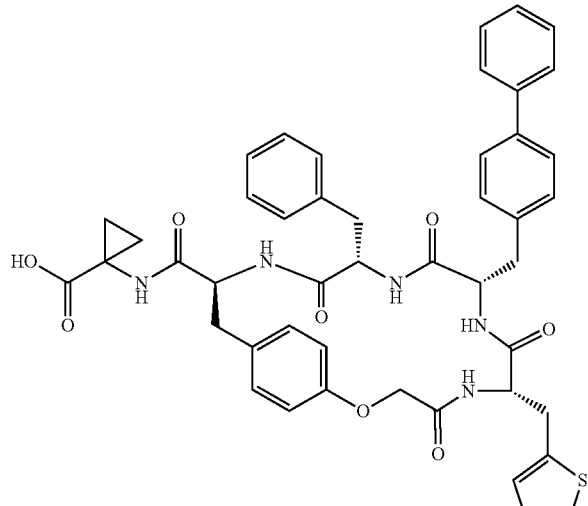 | 828.3067 | 828.3082 |
| 345 | 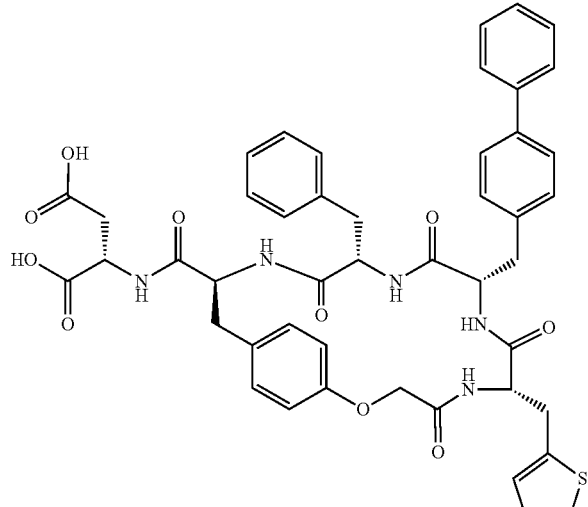 | 860.2965 | 860.2985 |
| 346 | 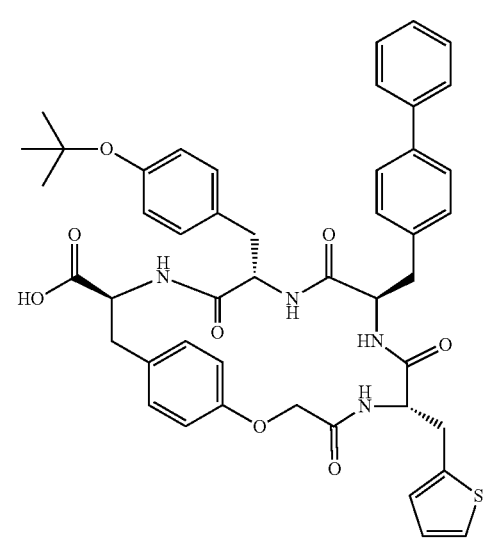 | 817.3271 | 817.3229 |

TABLE 1-continued
| Compound No. | Structure | MS Calcd | MS Observed |
|---|---|---|---|
| 347 | 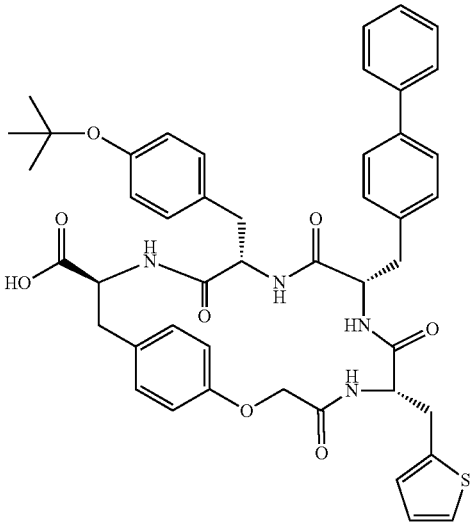 | 817.3271 | 817.3220 |
| 348 | 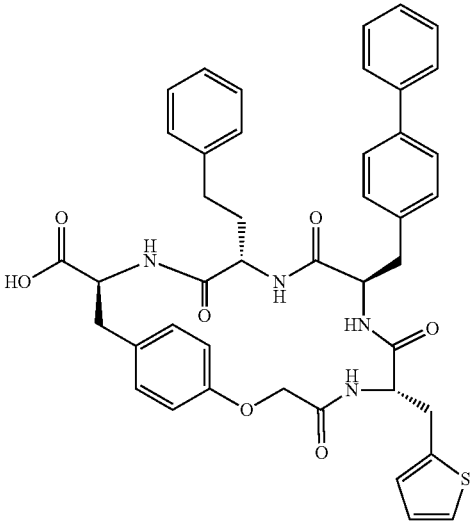 | 759.2852 | 759.2820 |
| 349 | 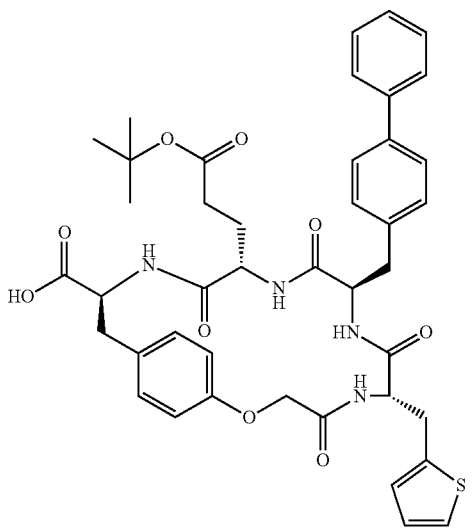 | 783.3064 | 783.3016 |

TABLE 1-continued

| Compound No. | Structure | MS Calcd | MS Observed |
|---|---|---|---|
| 350 | 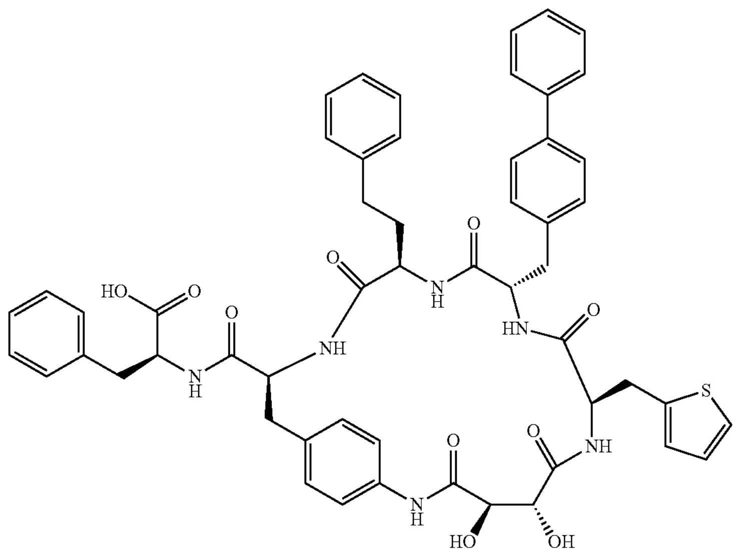 | 979.3700 | 979.3746 |
| 351 | 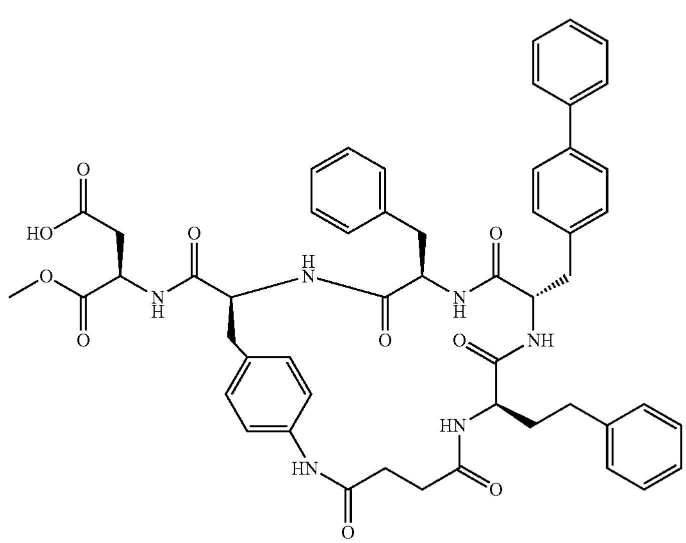 | 923.3980 | 923.4041 |

TABLE 1-continued

| Compound No. | Structure | MS Calcd | MS Observed |
|---|---|---|---|
| 352 | 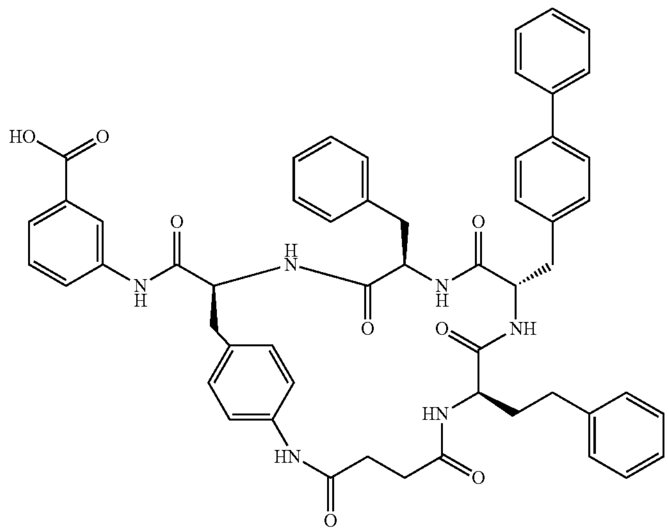 | 913.3925 | 913.3983 |
| 353 | 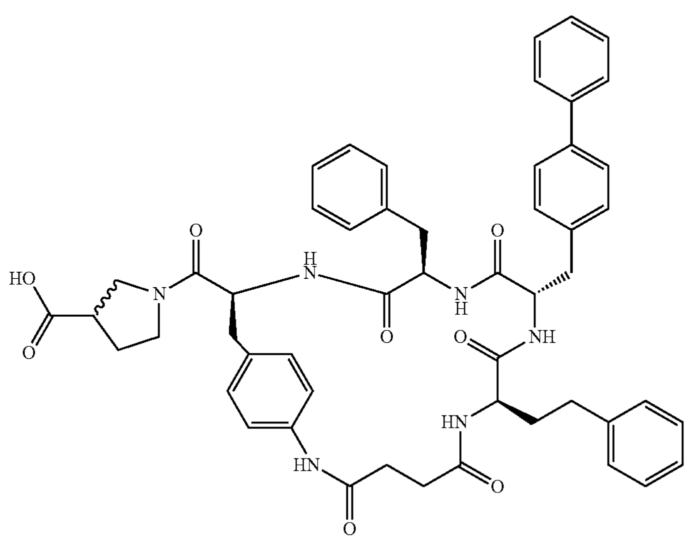 | 891.4081 | 891.4115 |

TABLE 1-continued

| Compound No. | Structure | MS Calcd | MS Observed |
|---|---|---|---|
| 354 | 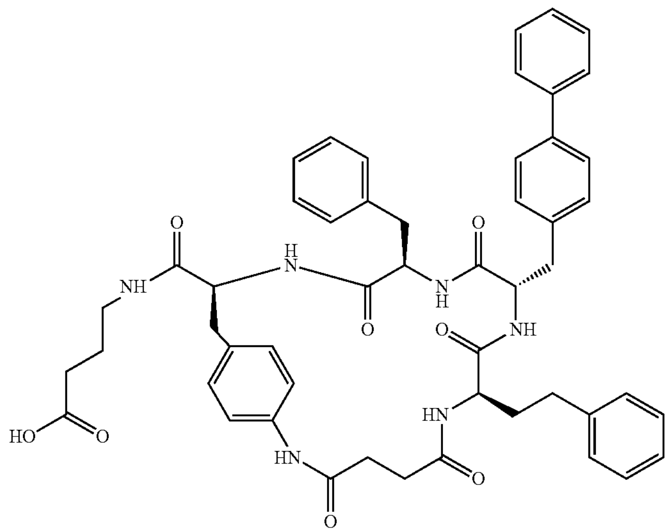 | 879.4081 | 879.4113 |
| 355 | 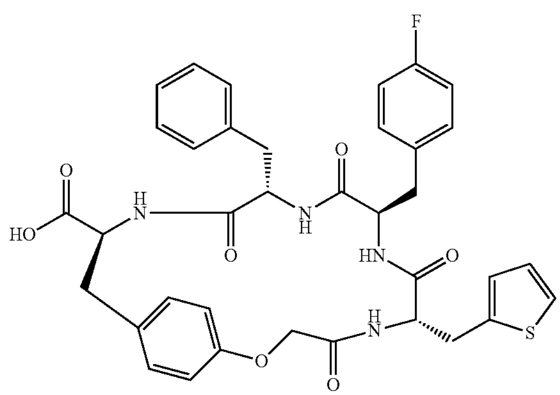 | 687.2283 | 687.2314 |
| 356 | 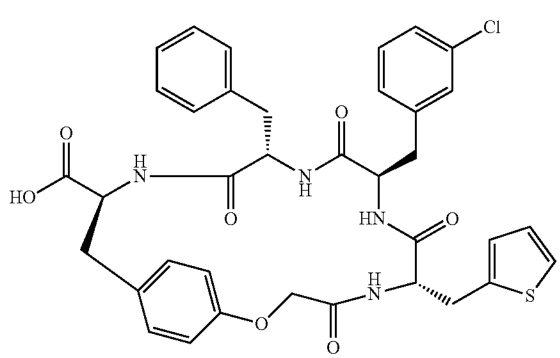 | 703.1988 | 703.1981 |

TABLE 1-continued

| Compound No. | Structure | MS Calcd | MS Observed |
|---|---|---|---|
| 357 | 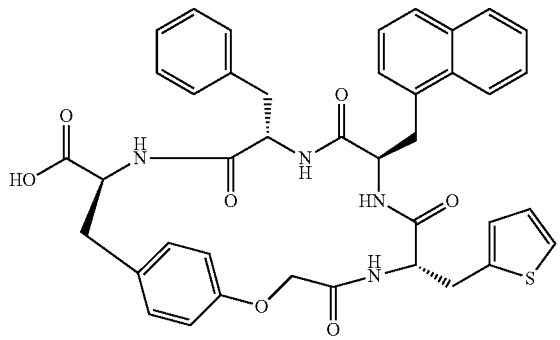 | 719.2534 | 719.2543 |
| 358 | 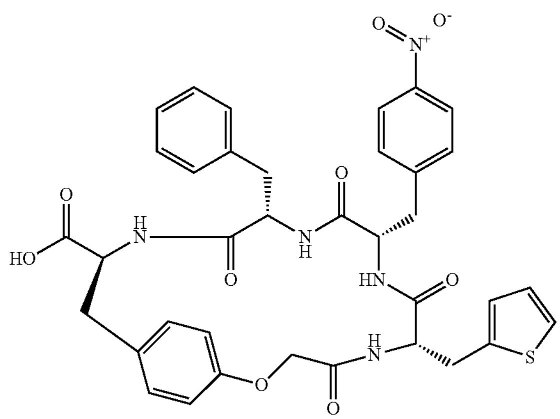 | 714.2228 | 714.2231 |
| 359 | 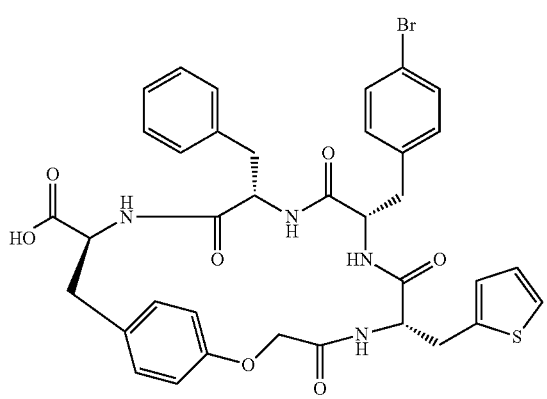 | 747.1483 | 747.1490 |

| Compound No. | Structure | MS Calcd | MS Observed |
|---|---|---|---|
| 360 | 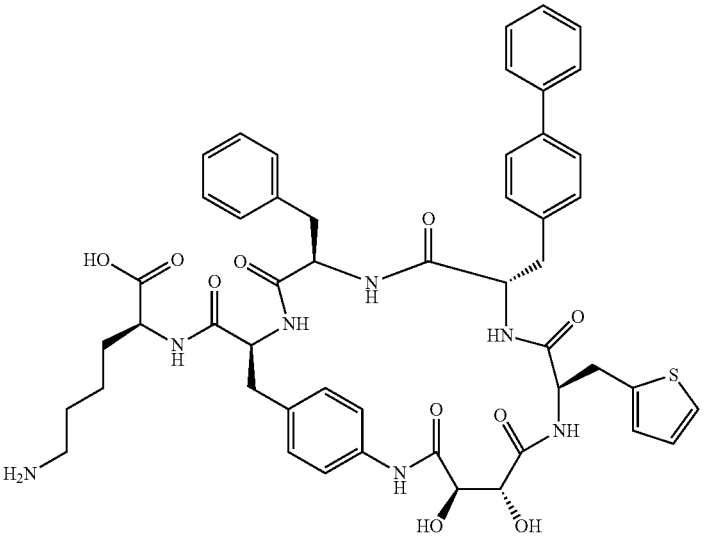 | 946.3804 | 946.3833 |
| 361 | 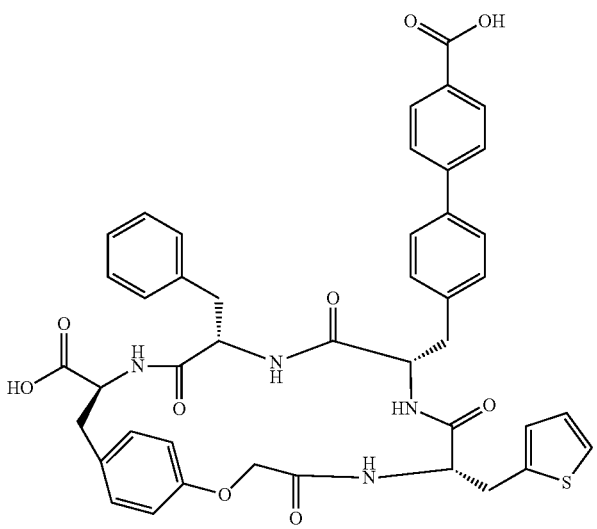 | 789.2589 | 789.2590 |

TABLE 1-continued

| Compound No. | Structure | MS Calcd | MS Observed |
|---|---|---|---|
| 362 | 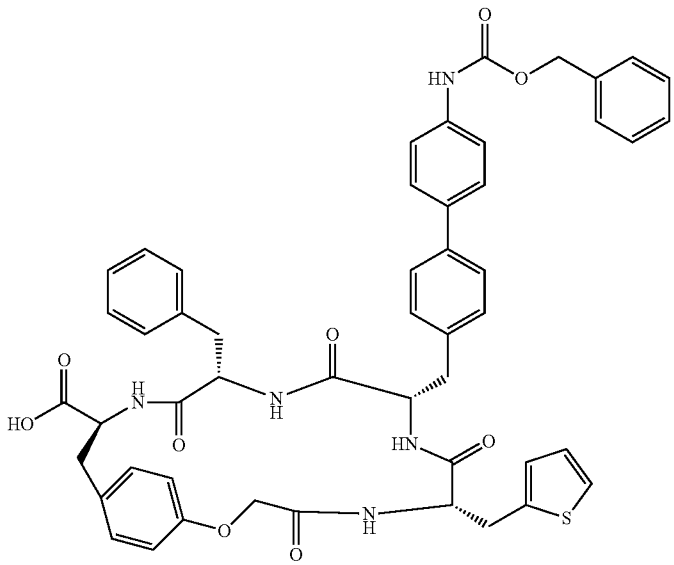 | 894.3167 | 894.3183 |
| 363 | 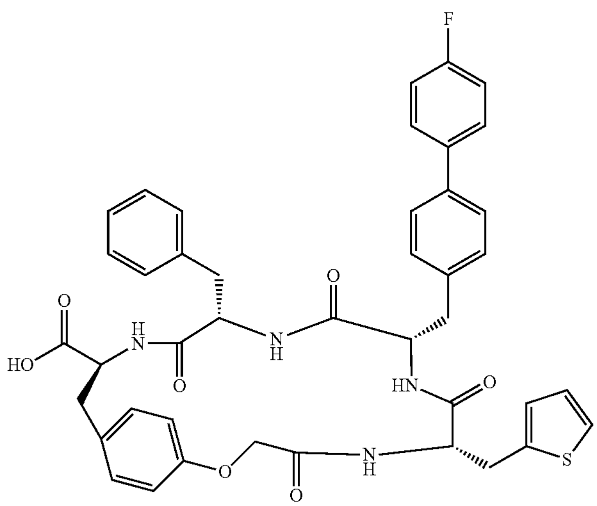 | 763.2596 | 763.2590 |
| 364 | 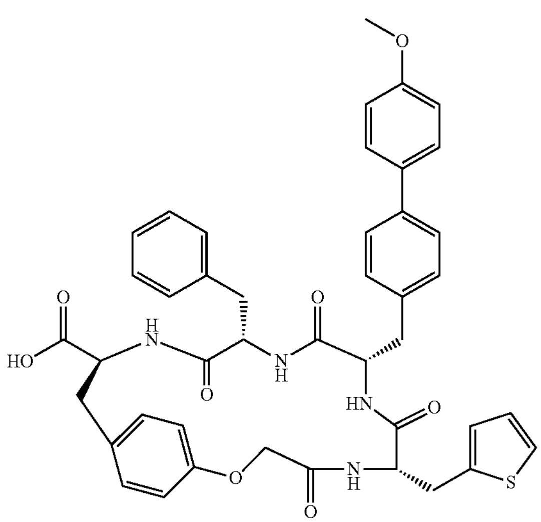 | 775.2796 | 775.2836 |

TABLE 1-continued

| Compound No. | Structure | MS Calcd | MS Observed |
| --- | --- | --- | --- |
| 365 | 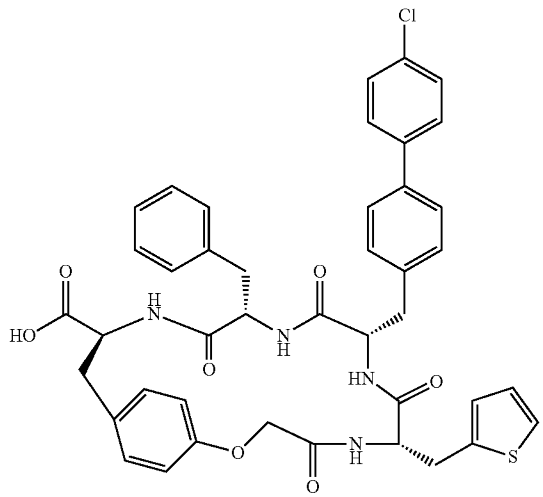 | 779.2301 | 779.2308 |
| 366 | 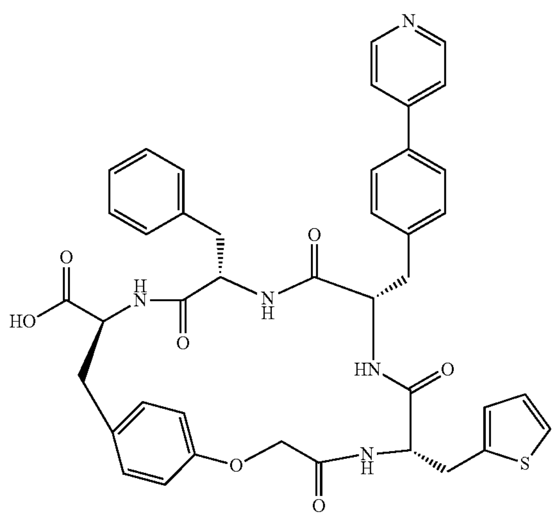 | 746.2643 | 746.413* |
| 367 | 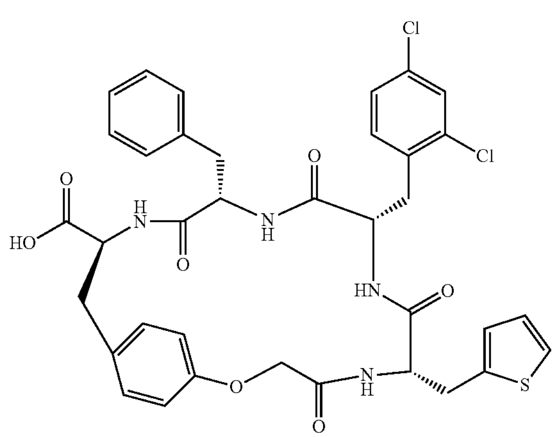 | 737.1598 | 737.191* |

TABLE 1-continued

| Compound No. | Structure | MS Calcd | MS Observed |
|---|---|---|---|
| 368 | 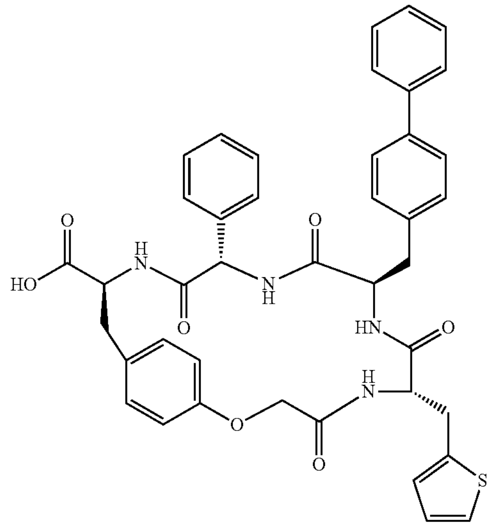 | 731.2539 | 731.2487 |
| 369 | 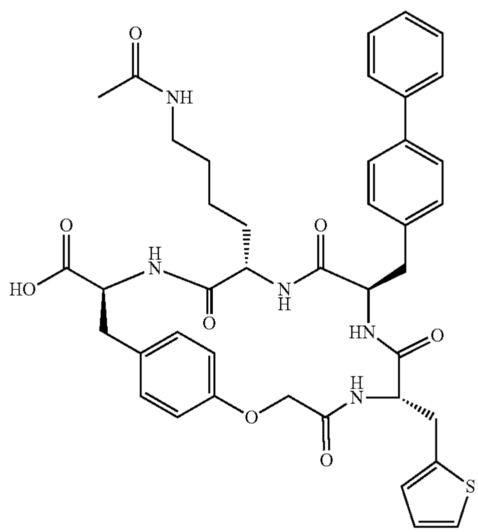 | 768.3067 | 768.3000 |
| 370 | 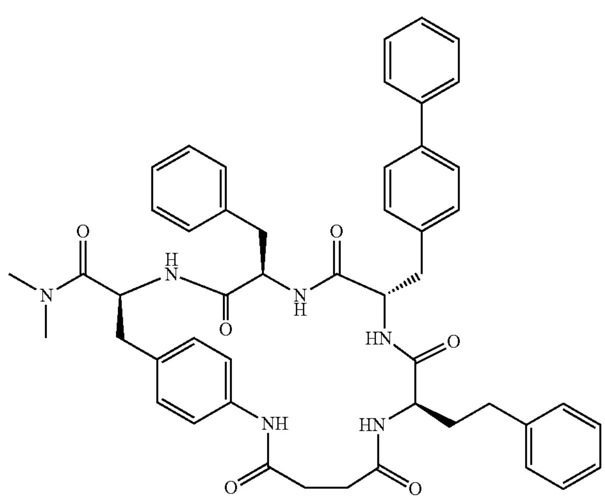 | 821.4021 | 821.4056 |

TABLE 1-continued

| Compound No. | Structure | MS Calcd | MS Observed |
|---|---|---|---|
| 371 | 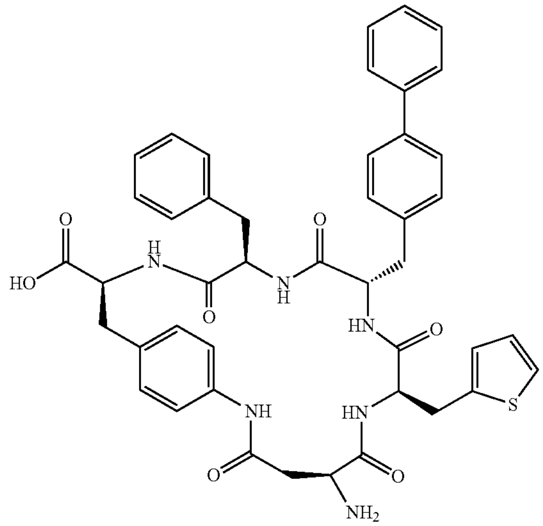 | 801.3065 | 801.3040 |
| 372 | 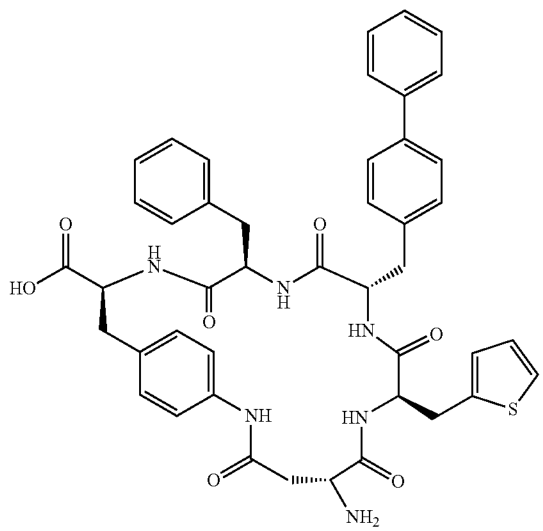 | 801.3065 | 801.3052 |
| 373 | 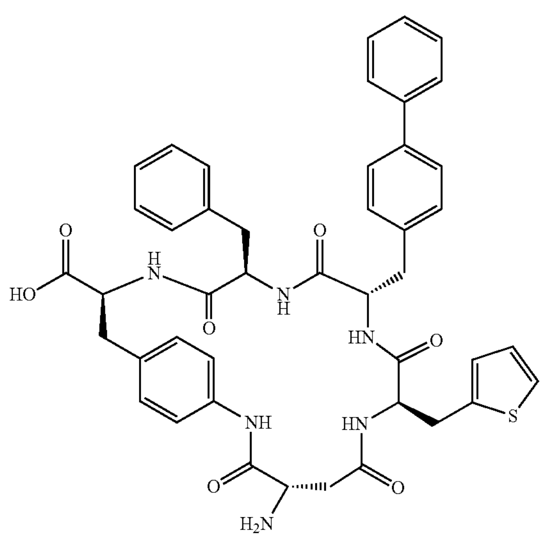 | 801.3065 | 801.3027 |

TABLE 1-continued

| Compound No. | Structure | MS Calcd | MS Observed |
|---|---|---|---|
| 374 | 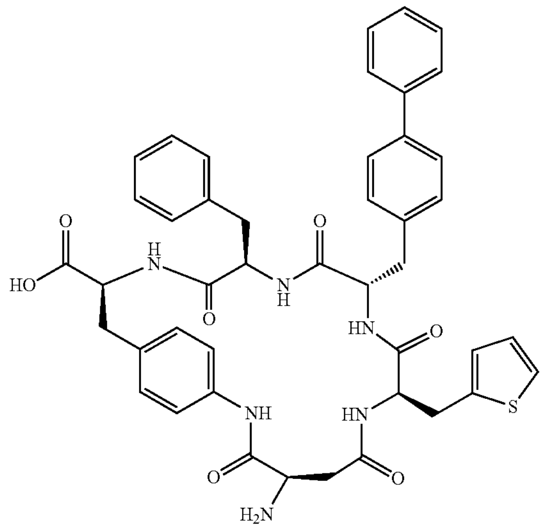 | 801.3065 | 801.3018 |
| 375 | 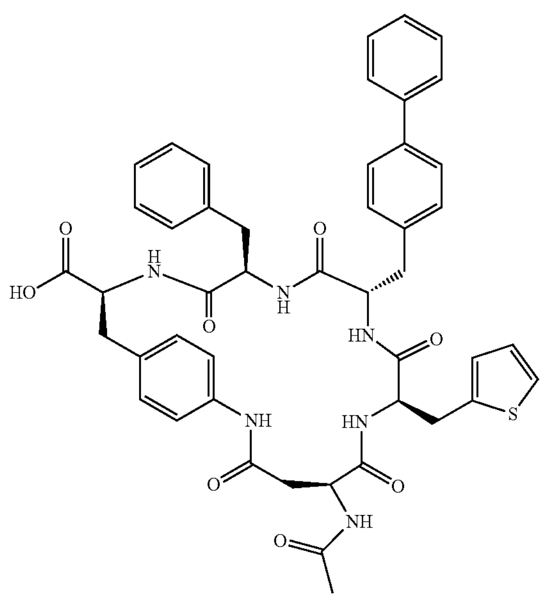 | 843.3170 | 843.3111 |

TABLE 1-continued
| Compound No. | Structure | MS Calcd | MS Observed |
|---|---|---|---|
| 376 | 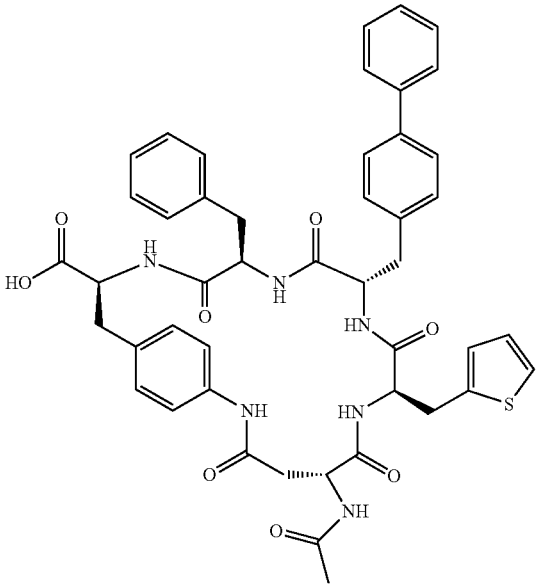 | 843.3170 | 843.3151 |
| 377 | 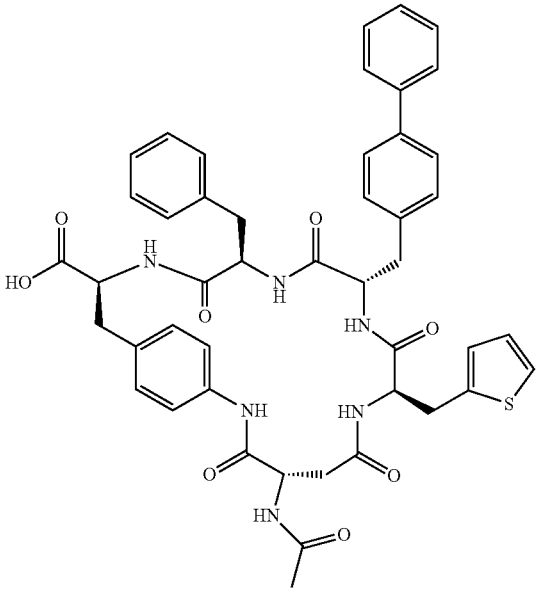 | 843.3170 | 843.3167 |

TABLE 1-continued
| Compound No. | Structure | MS Calcd | MS Observed |
|---|---|---|---|
| 378 | 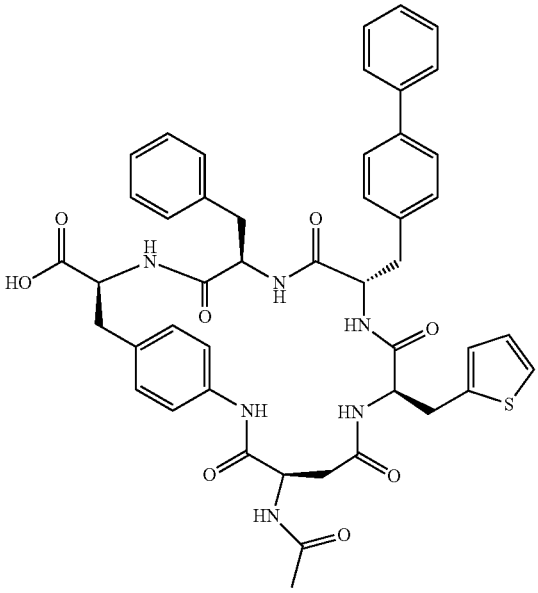 | 843.3170 | 843.3142 |
| 379 | 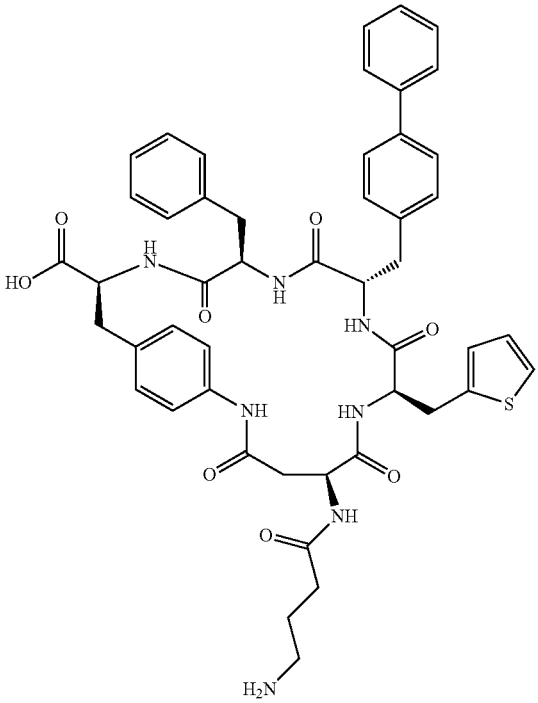 | 886.3592 | 886.3623 |

TABLE 1-continued

| Compound No. | Structure | MS Calcd | MS Observed |
|---|---|---|---|
| 380 | 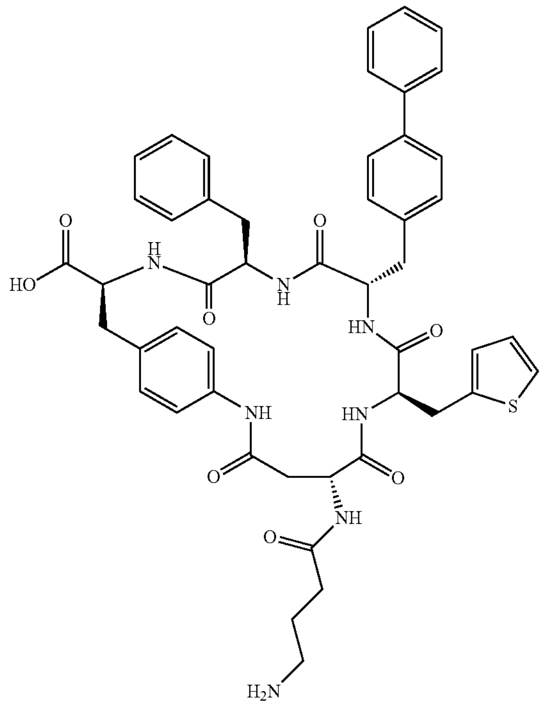 | 886.3592 | 886.3622 |
| 381 | 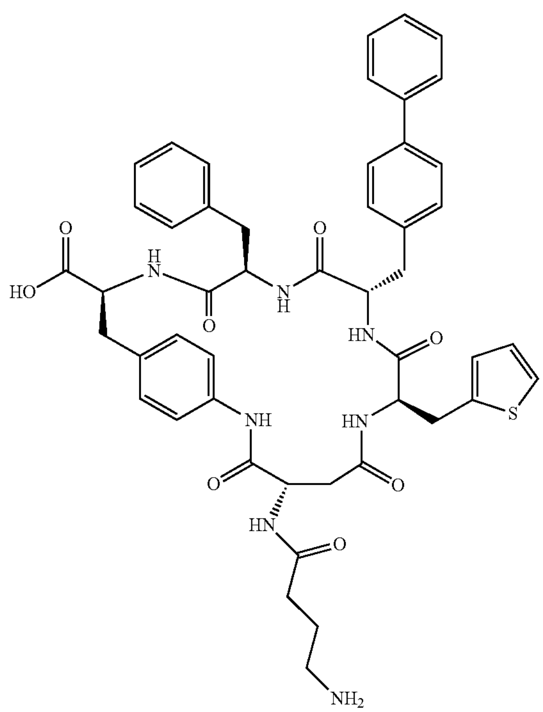 | 886.3592 | 886.3561 |

TABLE 1-continued
| Compound No. | Structure | MS Calcd | MS Observed |
|---|---|---|---|
| 382 | 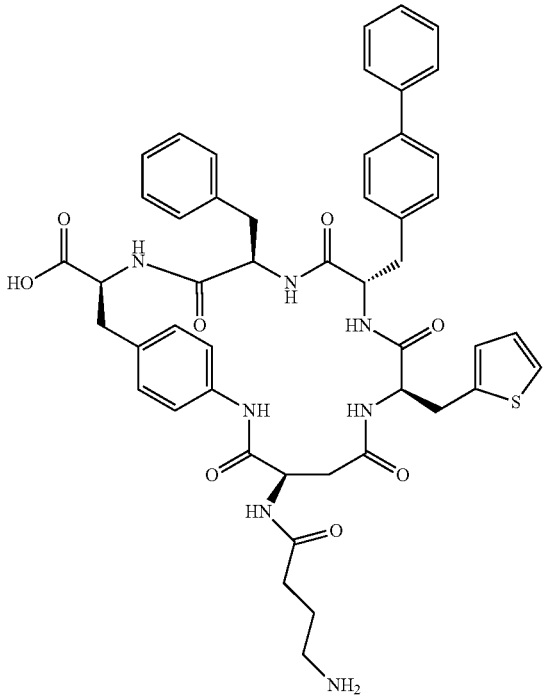 | 886.3592 | 886.3595 |
| 383 | 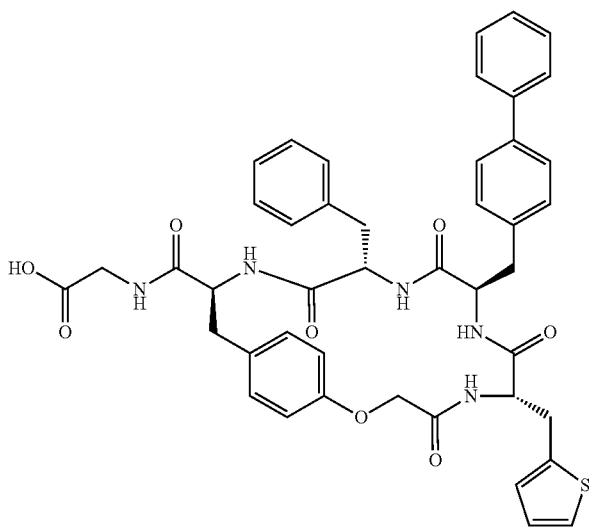 | 802.2911 | 802.2837 |

TABLE 1-continued

| Compound No. | Structure | MS Calcd | MS Observed |
|---|---|---|---|
| 384 | 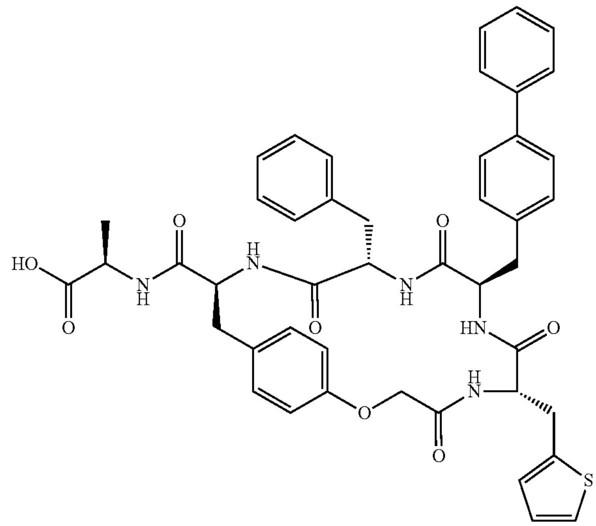 | 816.3067 | 816.2977 |
| 385 | 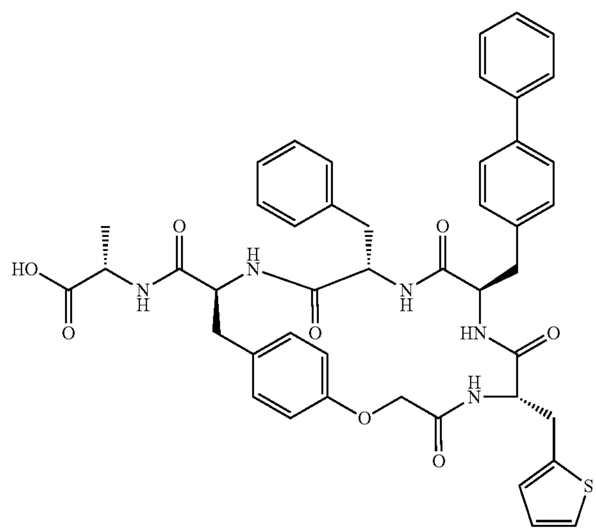 | 816.3067 | 816.3009 |
| 386 | 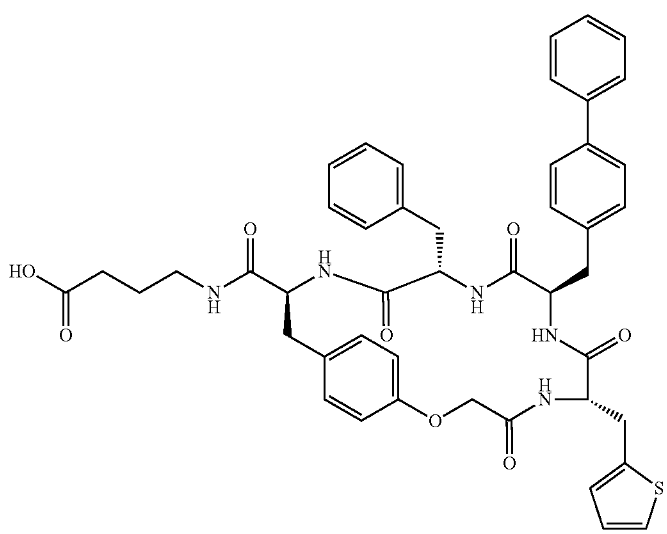 | 830.3224 | 830.3173 |

TABLE 1-continued

| Compound No. | Structure | MS Calcd | MS Observed |
|---|---|---|---|
| 387 | 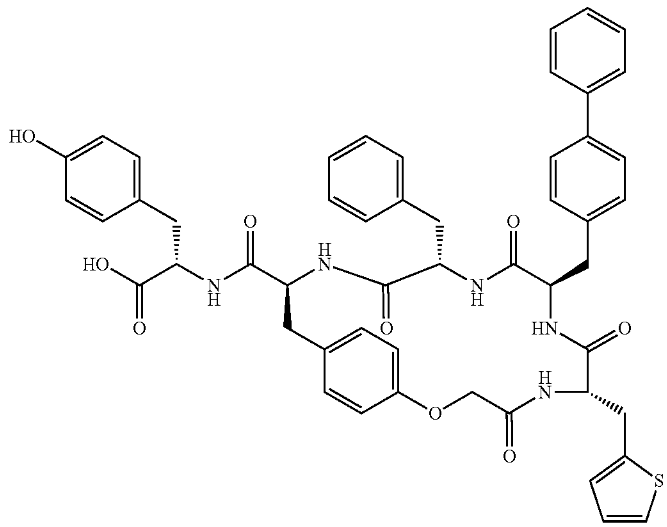 | 908.3329 | 908.3256 |
| 388 | 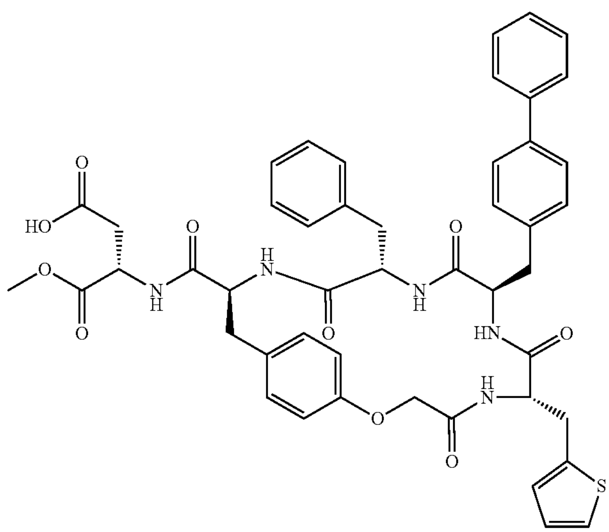 | 874.3122 | 874.3074 |
| 389 | 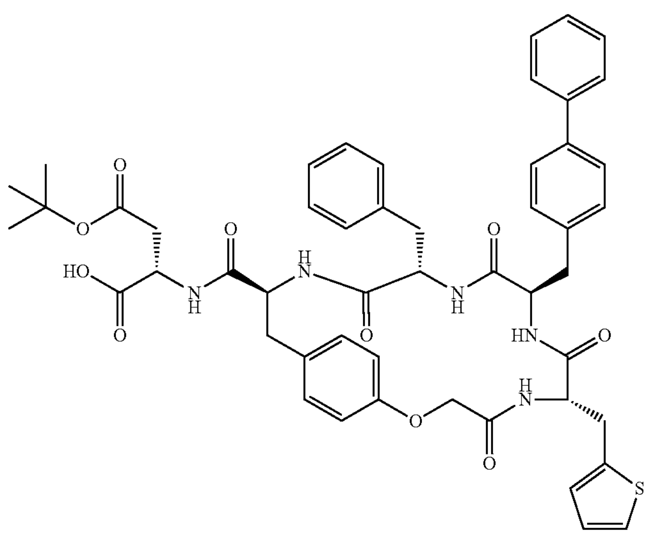 | 916.3591 | 916.3495 |

TABLE 1-continued

| Compound No. | Structure | MS Calcd | MS Observed |
|---|---|---|---|
| 390 | 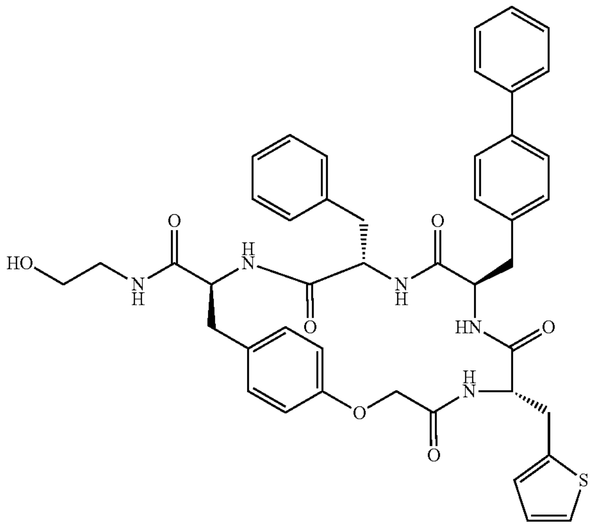 | 788.3118 | 788.3083 |
| 391 | 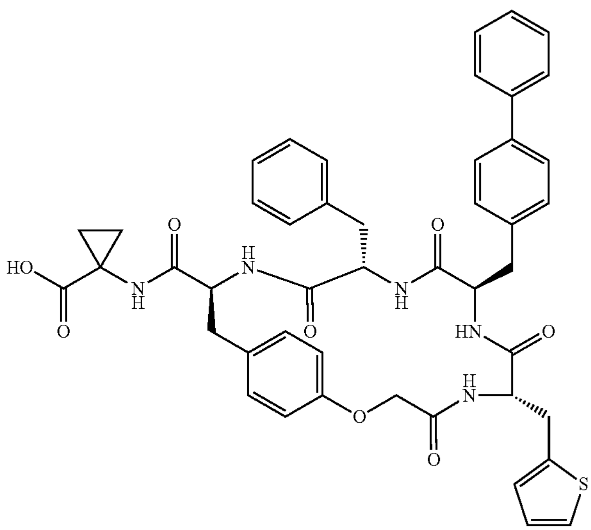 | 828.3067 | 828.3019 |
| 392 | 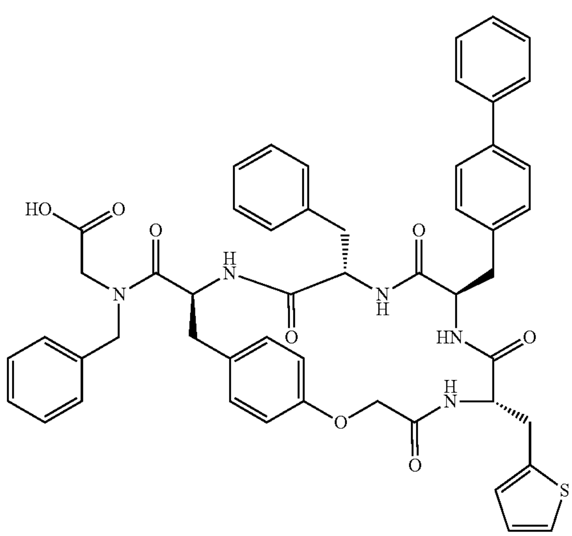 | 892.3380 | 892.3297 |

TABLE 1-continued
| Compound No. | Structure | MS Calcd | MS Observed |
|---|---|---|---|
| 393 | 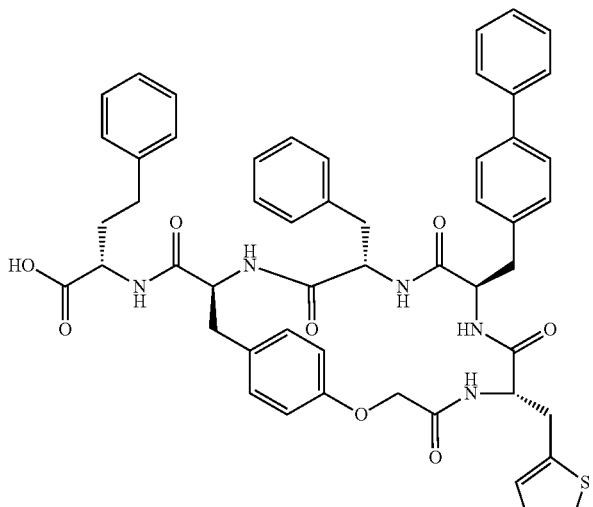 | 906.3537 | 906.3481 |
| 394 | 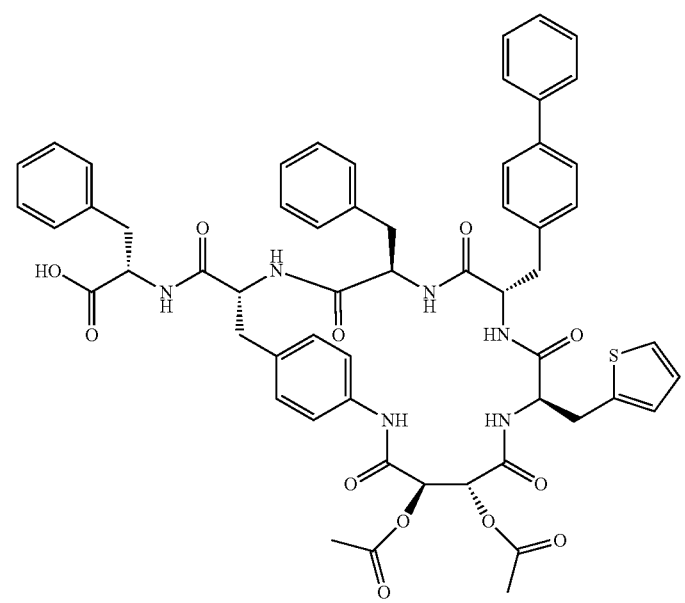 | 1049.3755 | 1049.3748 |

TABLE 1-continued
| Compound No. | Structure | MS Calcd | MS Observed |
|---|---|---|---|
| 395 | 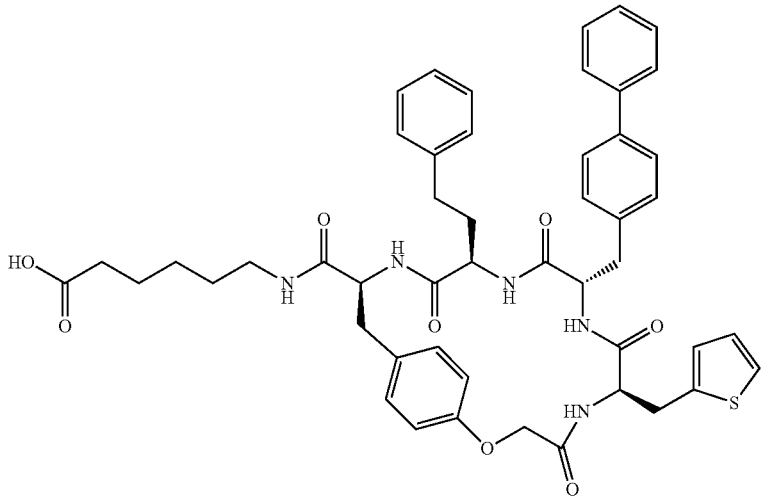 | 872.3688 | 872.3699 |
| 396 | 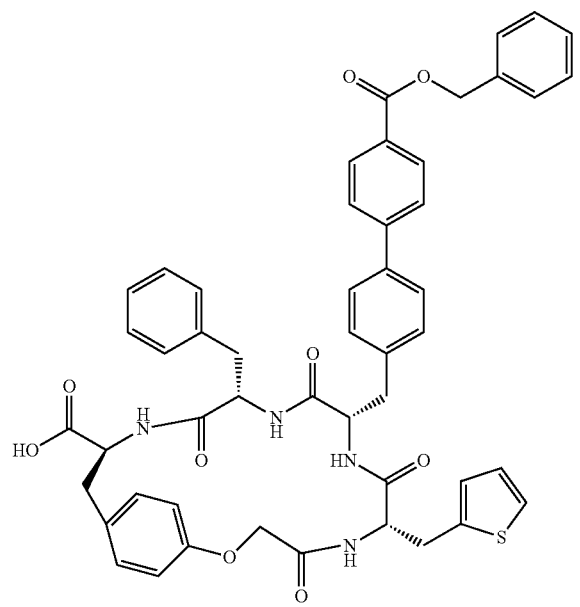 | 879.3059 | 879.3079 |
| 397 | 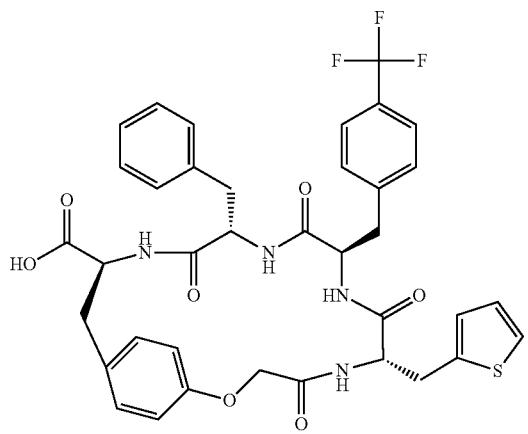 | 737.2252 | 737.191* |

TABLE 1-continued

| Compound No. | Structure | MS Calcd | MS Observed |
|---|---|---|---|
| 398 | 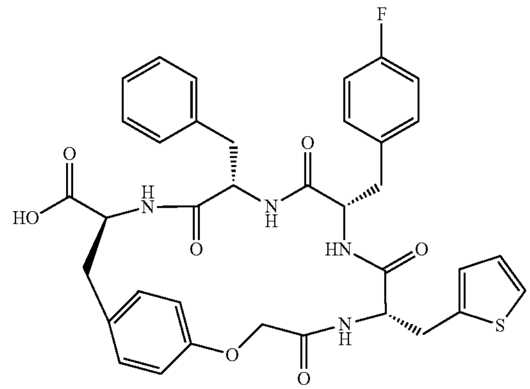 | 687.2283 | 687.307* |
| 399 | 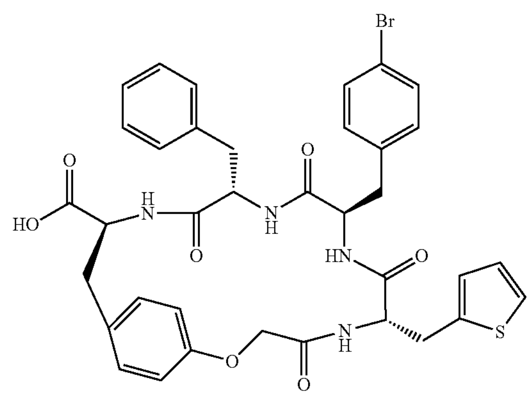 | 747.1483 | 747.1508 |
| 400 | 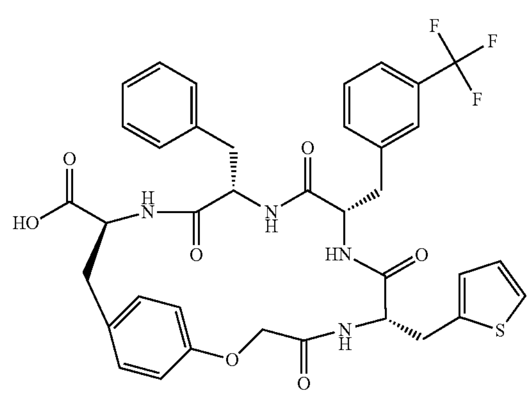 | 737.2252 | 737.463* |

TABLE 1-continued

| Compound No. | Structure | MS Calcd | MS Observed |
|---|---|---|---|
| 401 | 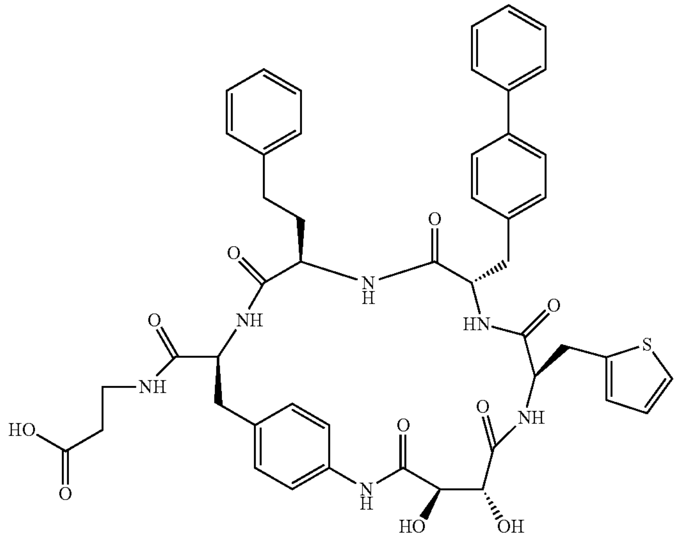 | 903.3387 | 903.3421 |
| 402 | 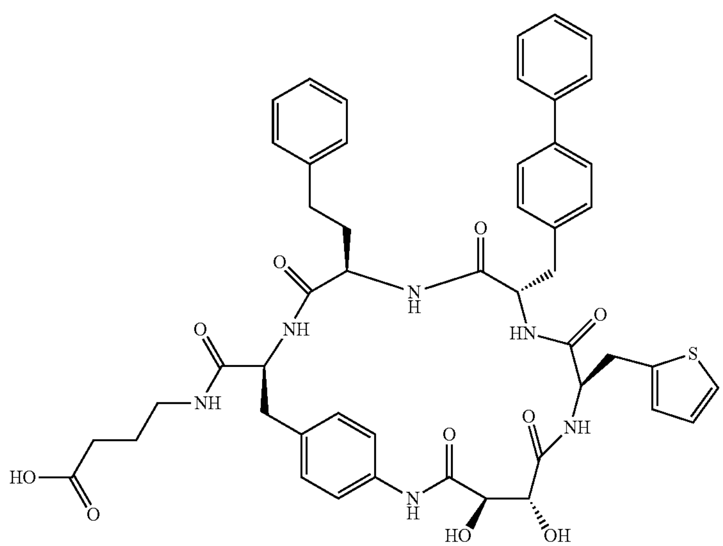 | 917.3544 | 917.3539 |

TABLE 1-continued

| Compound No. | Structure | MS Calcd | MS Observed |
|---|---|---|---|
| 403 | 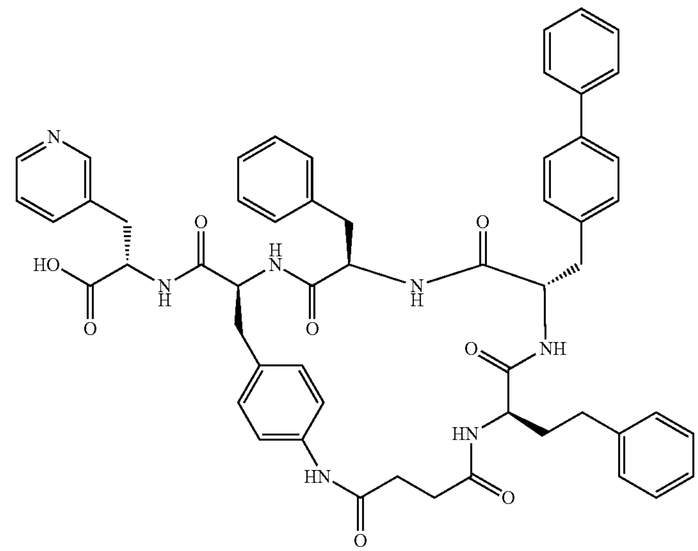 | 942.4190 | 942.4213 |
| 404 | 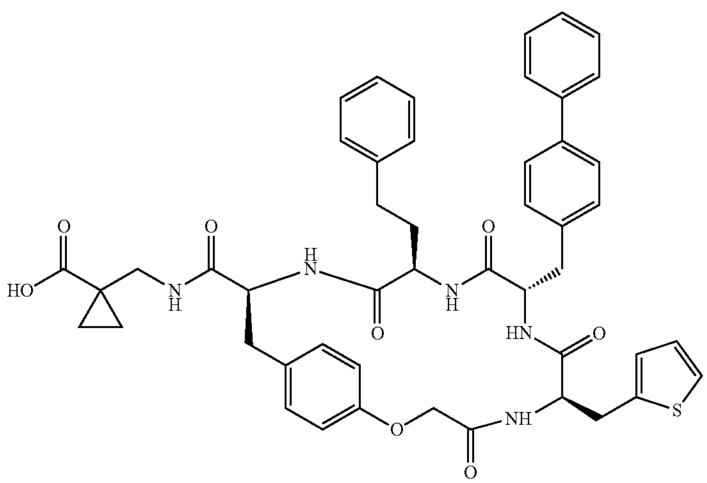 | 856.3380 | 856.3403 |
| 405 | 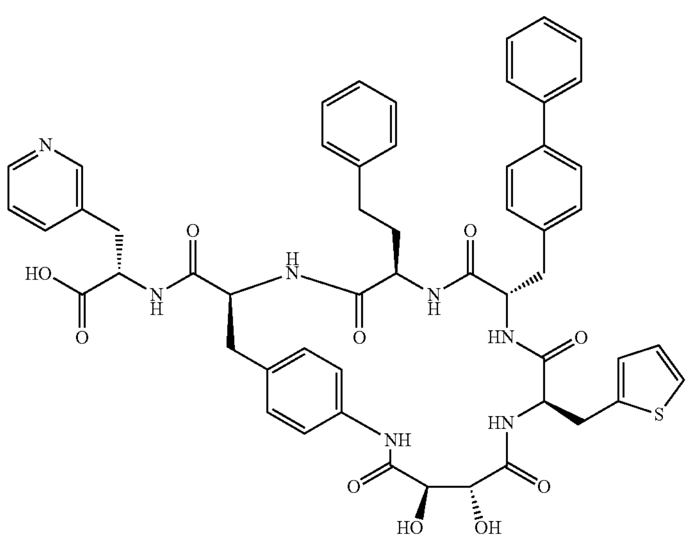 | 980.3653 | 980.3672 |

TABLE 1-continued

| Compound No. | Structure | MS Calcd | MS Observed |
|---|---|---|---|
| 406 | 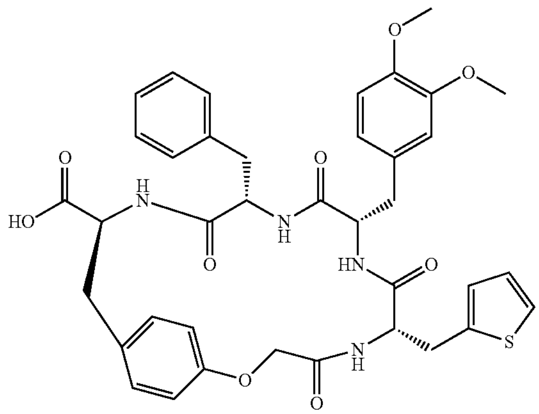 | 729.2589 | 729.2584 |
| 407 | 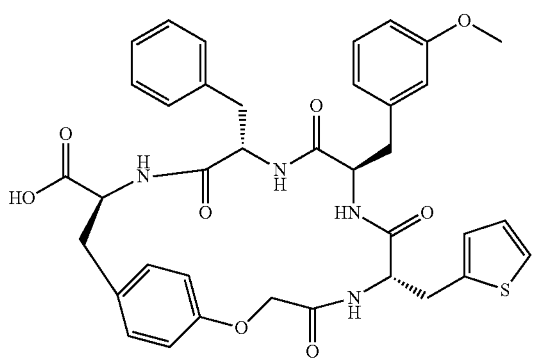 | 699.2483 | 699.2498 |
| 408 | 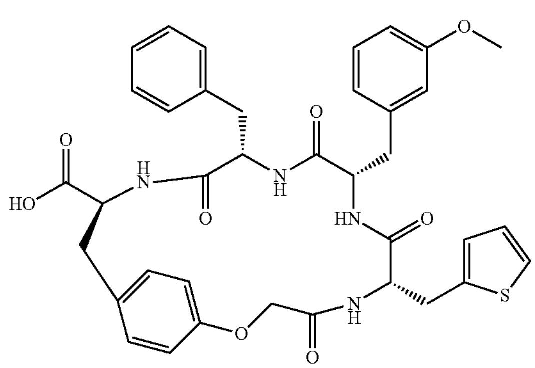 | 699.2483 | 699.404* |

TABLE 1-continued

| Compound No. | Structure | MS Calcd | MS Observed |
|---|---|---|---|
| 409 | 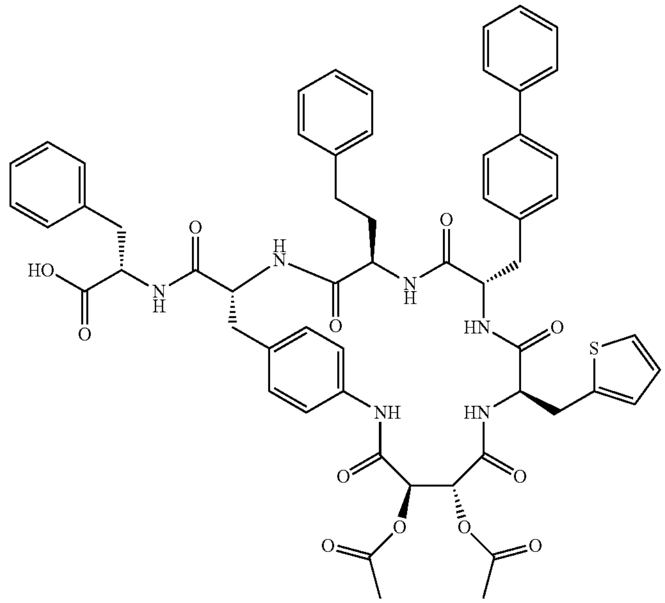 | 1063.3911 | 1063.3909 |
| 410 | 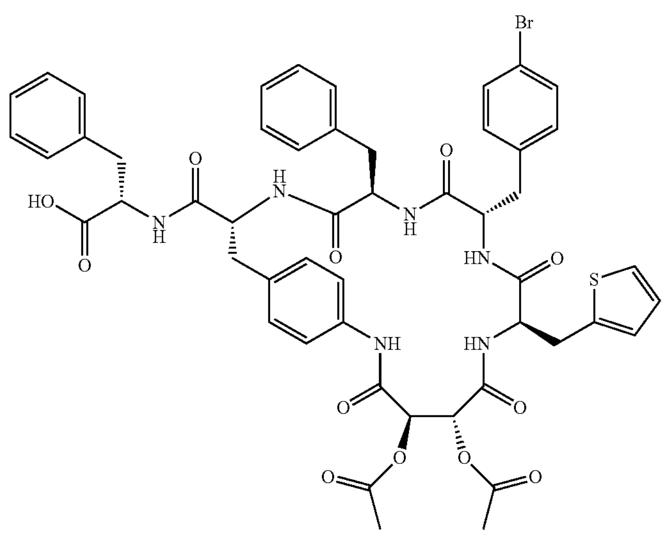 | 1051.2547 | 1051.2570 |

US 8,338,565 B2
TABLE 1-continued
| Compound No. | Structure | MS Calcd | MS Observed |
|---|---|---|---|
| 411 | 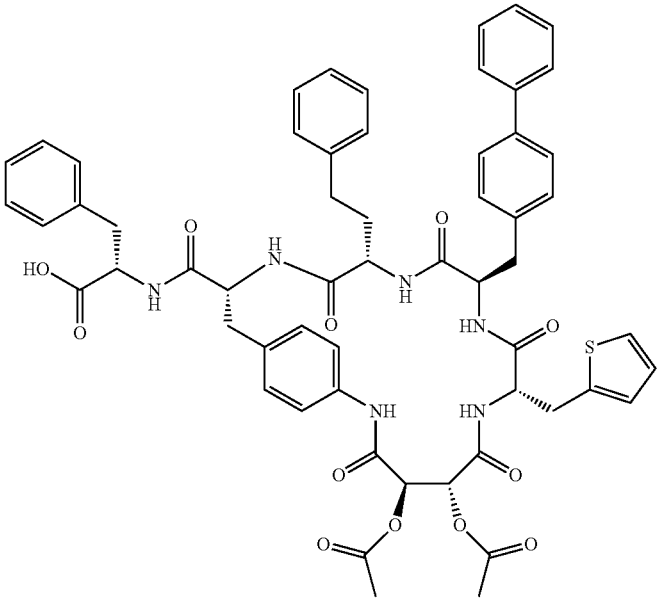 | 1063.3911 | 1063.3899 |
| 412 | 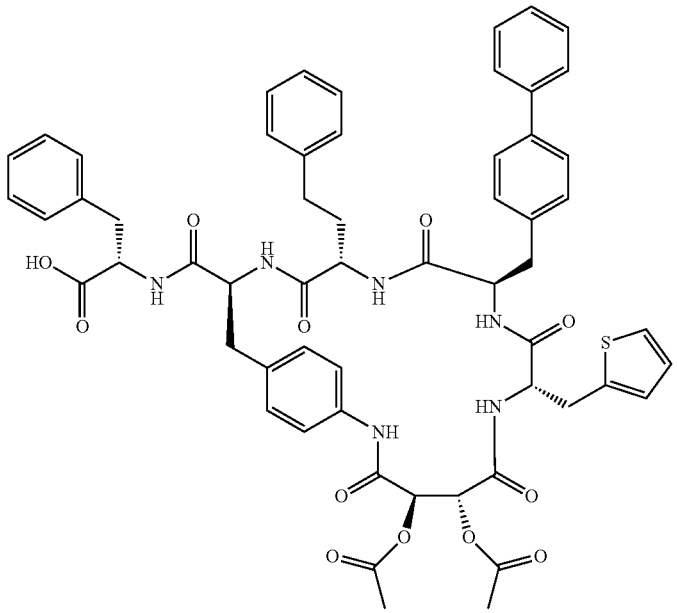 | 1063.3911 | 1063.3899 |

TABLE 1-continued

| Compound No. | Structure | MS Calcd | MS Observed |
|---|---|---|---|
| 413 | 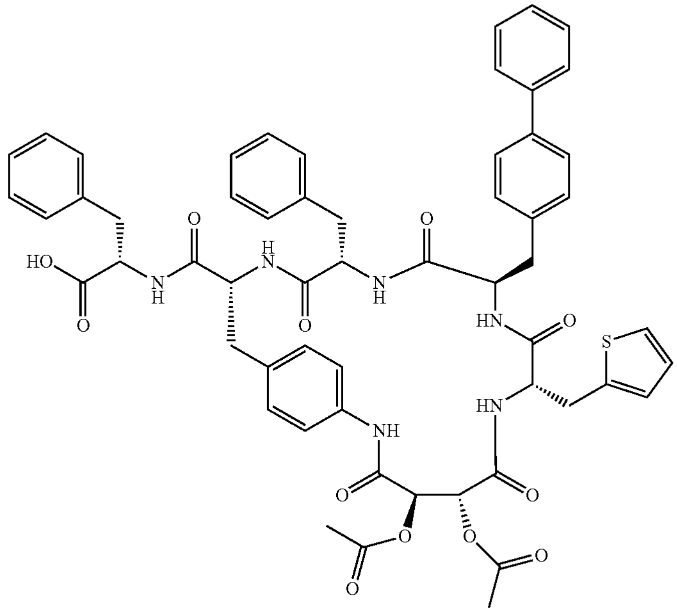 | 1049.3755 | 1049.3765 |
| 414 | 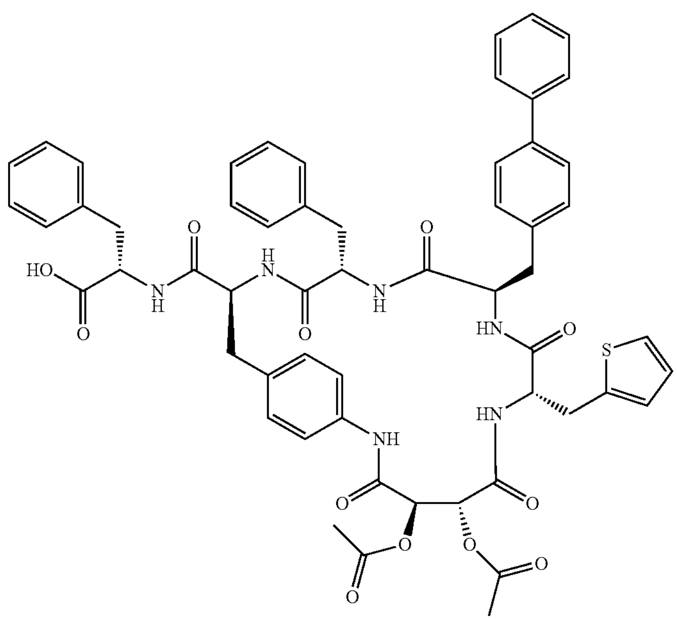 | 1049.3755 | 1049.3789 |

TABLE 1-continued
| Compound No. | Structure | MS Calcd | MS Observed |
|---|---|---|---|
| 415 | 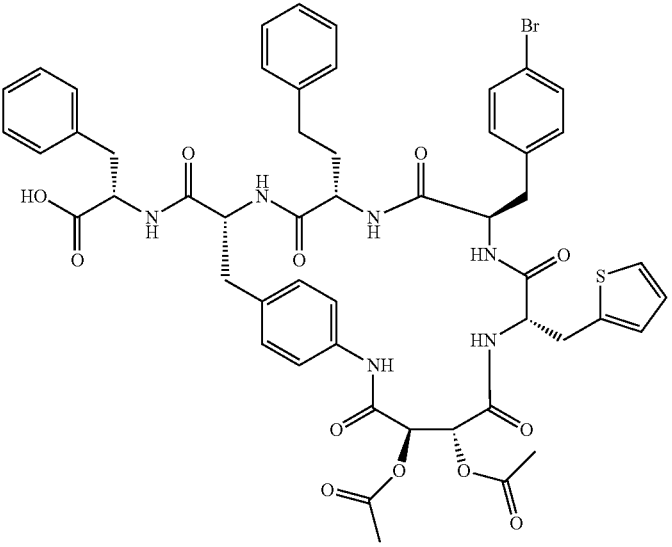 | 1065.2704 | 1065.2717 |
| 416 | 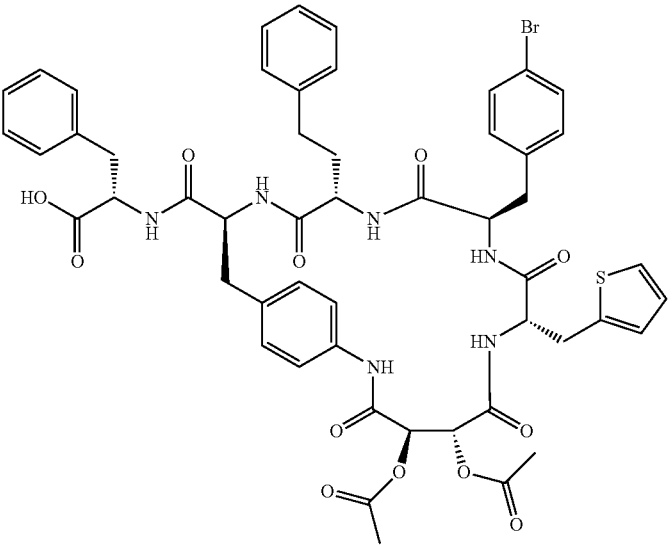 | 1065.2704 | 1065.2860 |

TABLE 1-continued
| Compound No. | Structure | MS Calcd | MS Observed |
|---|---|---|---|
| 417 | 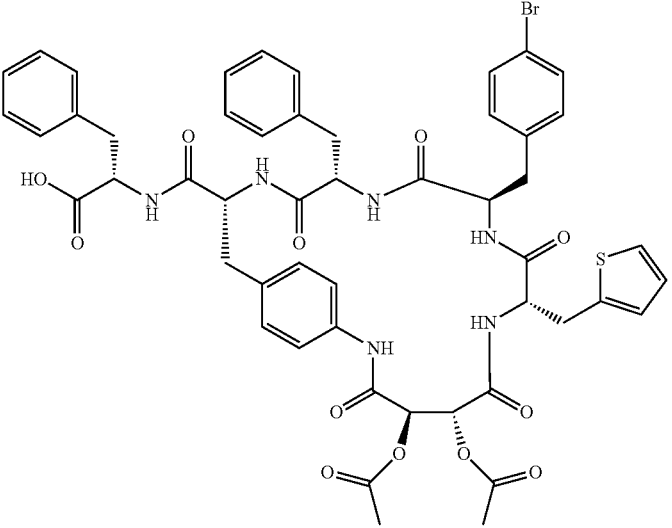 | 1051.2547 | 1051.2556 |
| 418 | 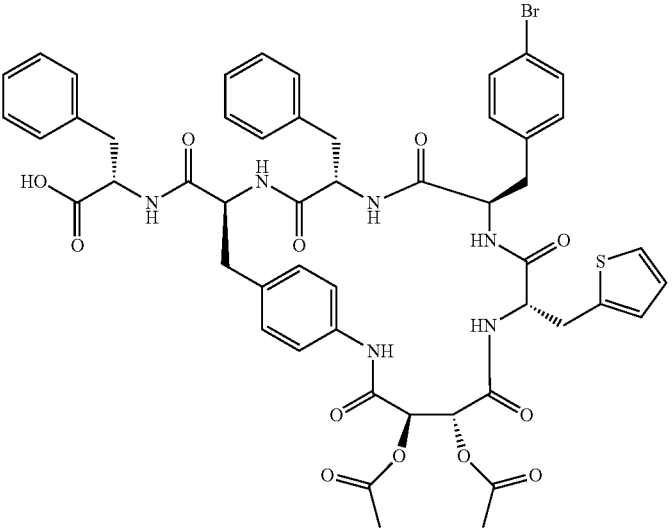 | 1051.2547 | 1051.2538 |

TABLE 1-continued

| Compound No. | Structure | MS Calcd | MS Observed |
|---|---|---|---|
| 419 | 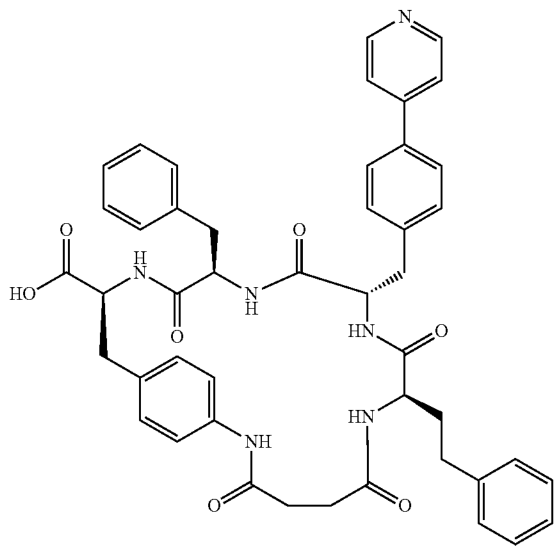 | 795.3506 | 795.3530 |
| 420 | 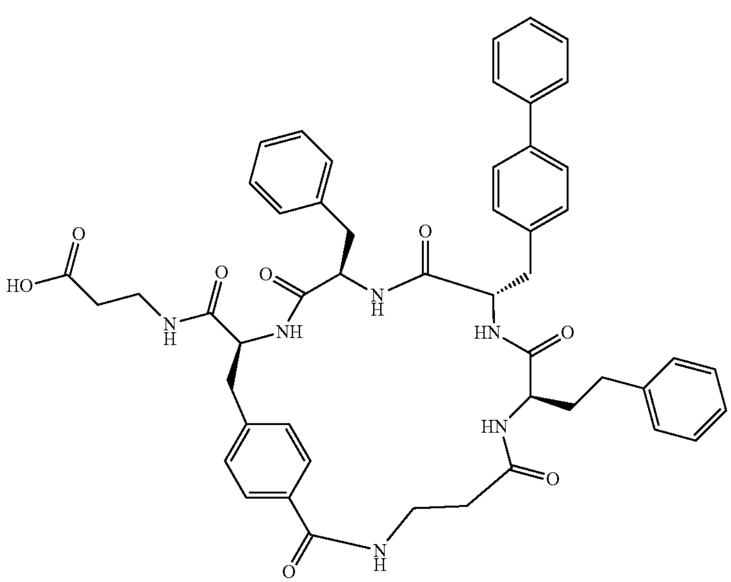 | 865.3919 | 865.3970 |

TABLE 1-continued
| Compound No. | Structure | MS Calcd | MS Observed |
|---|---|---|---|
| 421 | 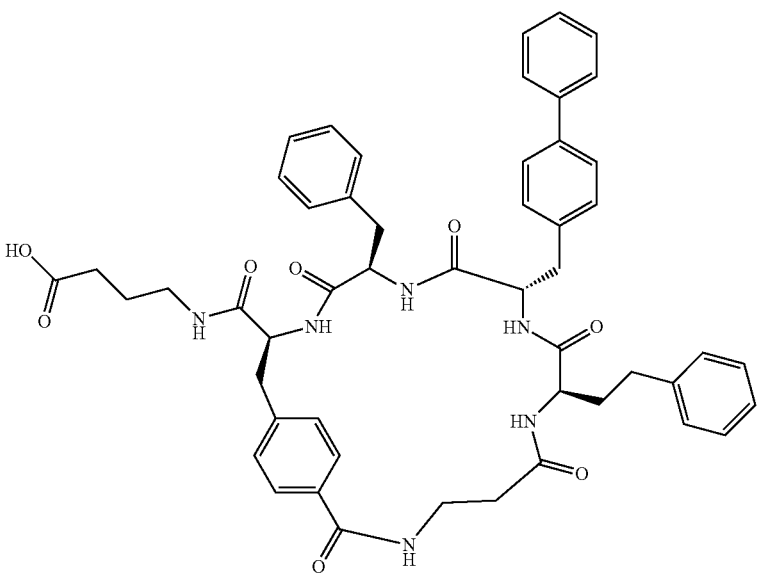 | 879.4076 | 879.4080 |
| 422 | 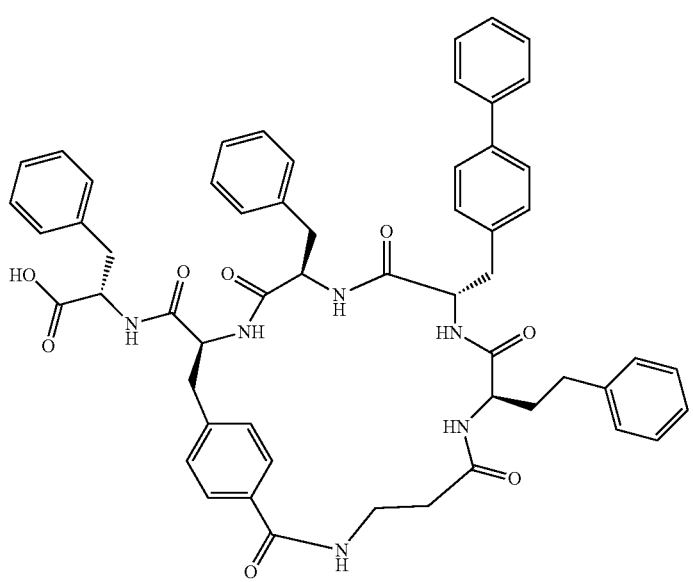 | 941.4232 | 941.4266 |

TABLE 1-continued
| Compound No. | Structure | MS Calcd | MS Observed |
|---|---|---|---|
| 423 | 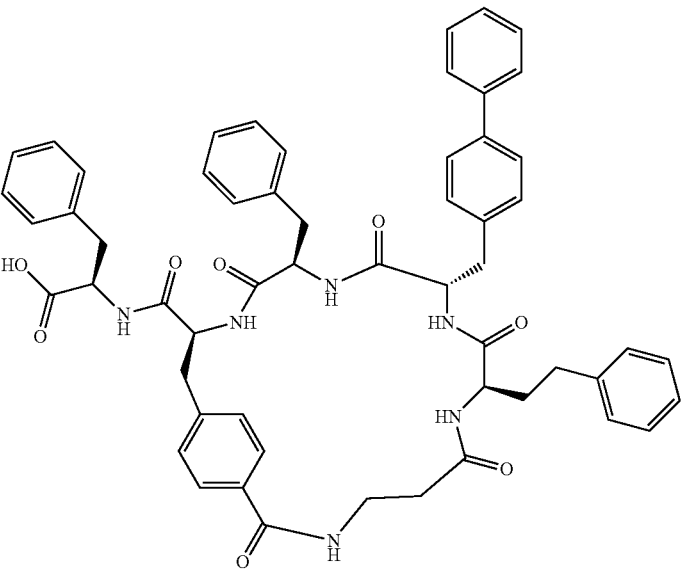 | 941.4232 | 941.4277 |
| 424 | 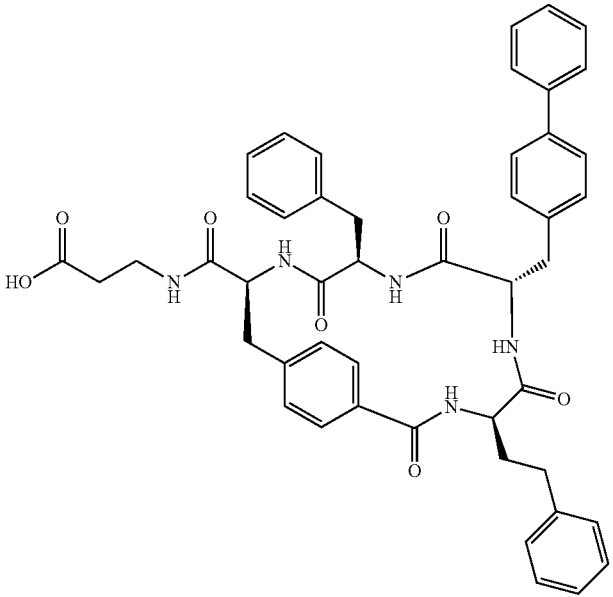 | 794.3548 | 794.3604 |

US 8,338,565 B2
333                                                                                        334
TABLE 1-continued
| Compound No. | Structure | MS Calcd | MS Observed |
|---|---|---|---|
| 425 | 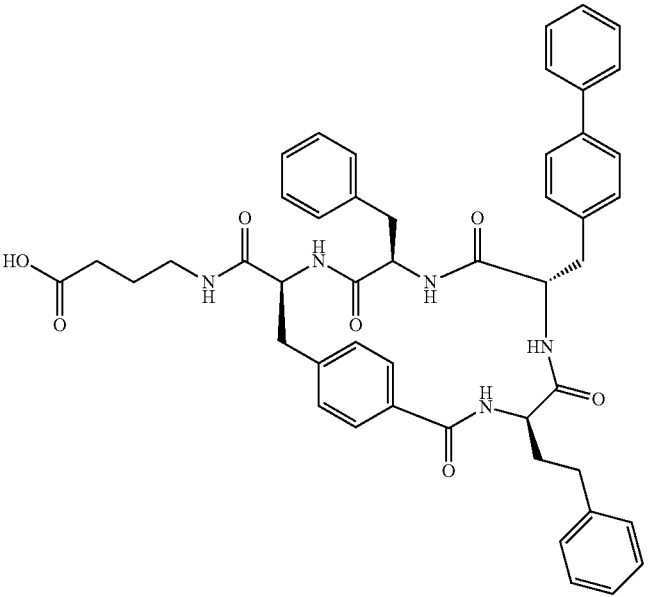 | 808.3705 | 808.3701 |
| 426 | 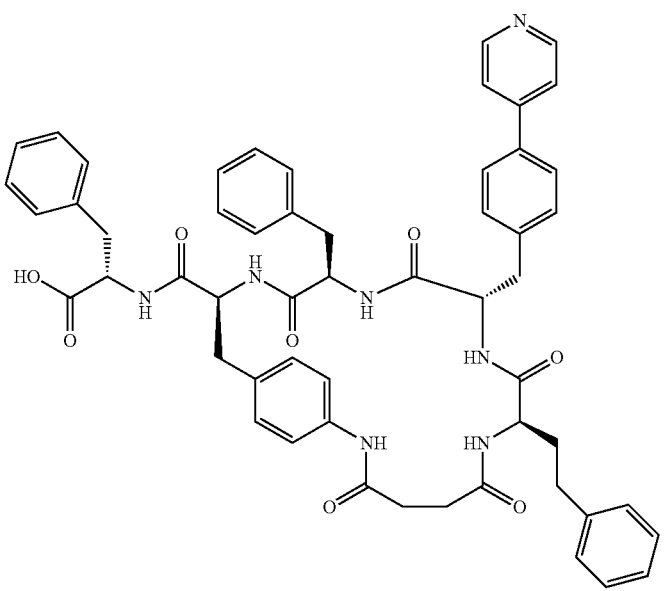 | 942.4190 | 942.4214 |

TABLE 1-continued

| Compound No. | Structure | MS Calcd | MS Observed |
| --- | --- | --- | --- |
| 427 | 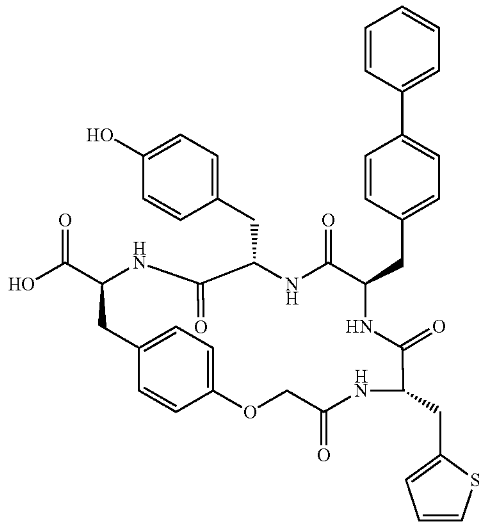 | 761.2645 | 761.2670 |
| 428 | 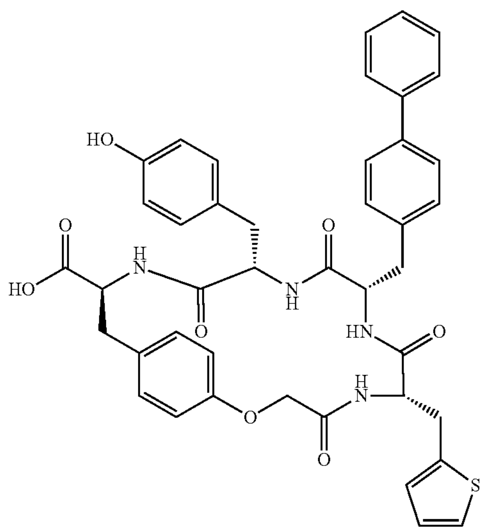 | 761.2645 | 761.2606 |
| 429 | 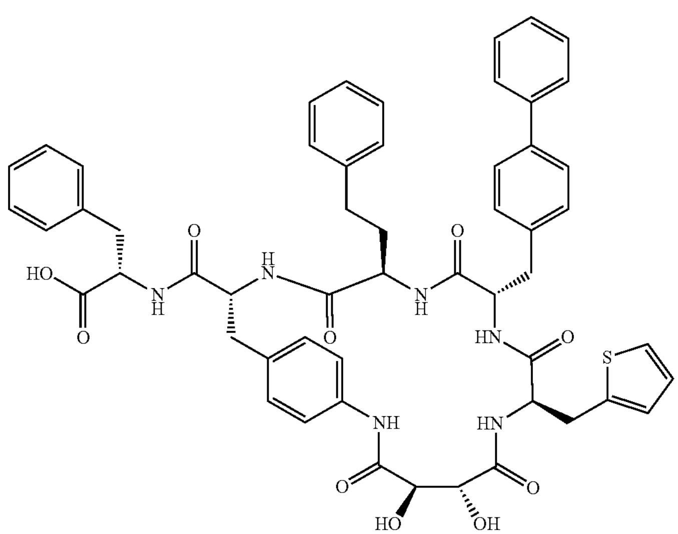 | 979.3700 | 979.3712 |

TABLE 1-continued

| Compound No. | Structure | MS Calcd | MS Observed |
|---|---|---|---|
| 430 | 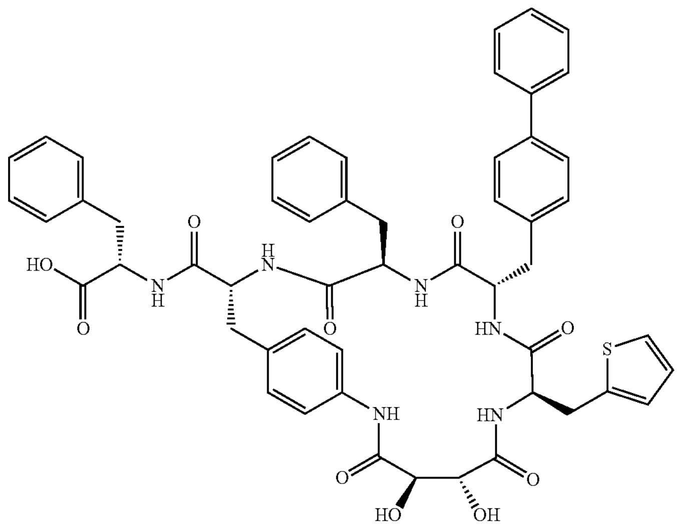 | 965.3544 | 965.3544 |
| 431 | 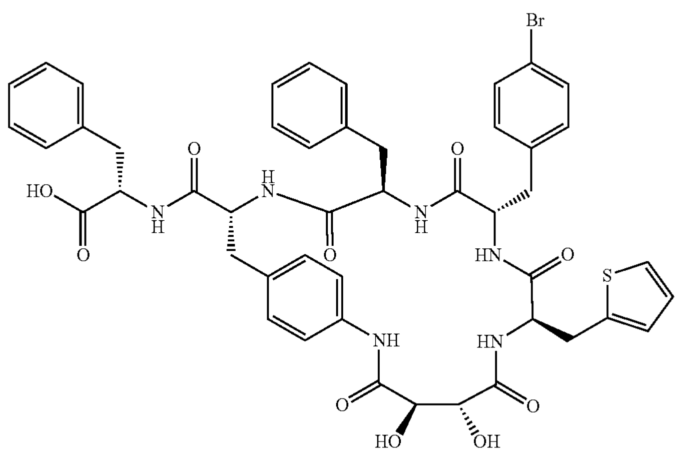 | 967.2336 | 967.2368 |
| 432 | 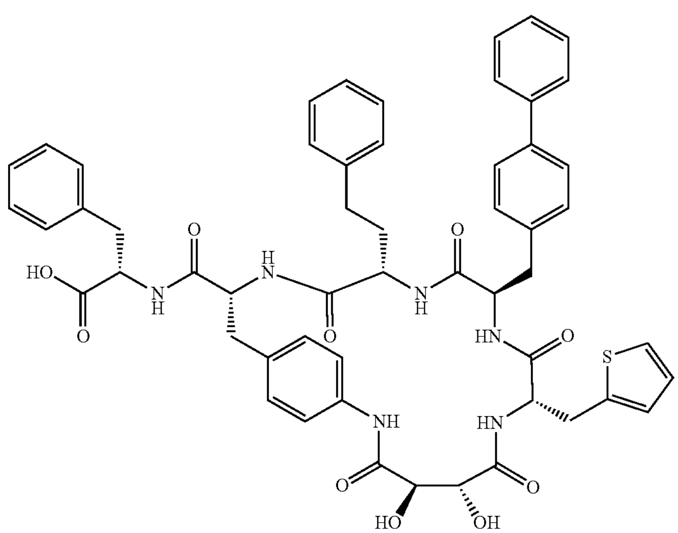 | 979.3700 | 979.3717 |

TABLE 1-continued

| Compound No. | Structure | MS Calcd | MS Observed |
|---|---|---|---|
| 433 | 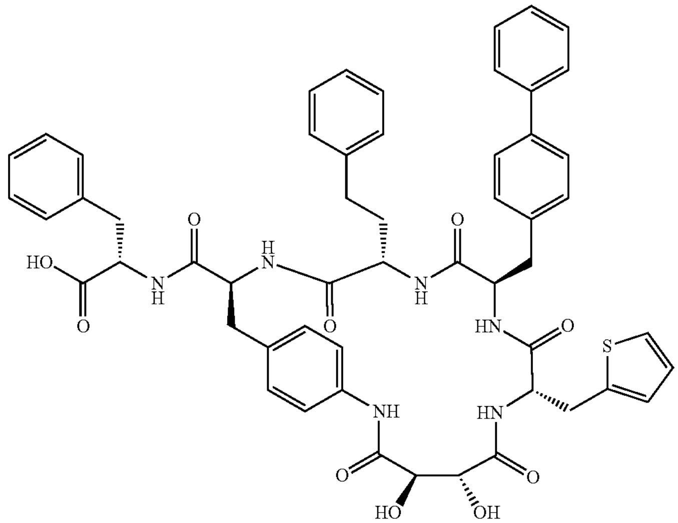 | 979.3700 | 979.3707 |
| 434 | 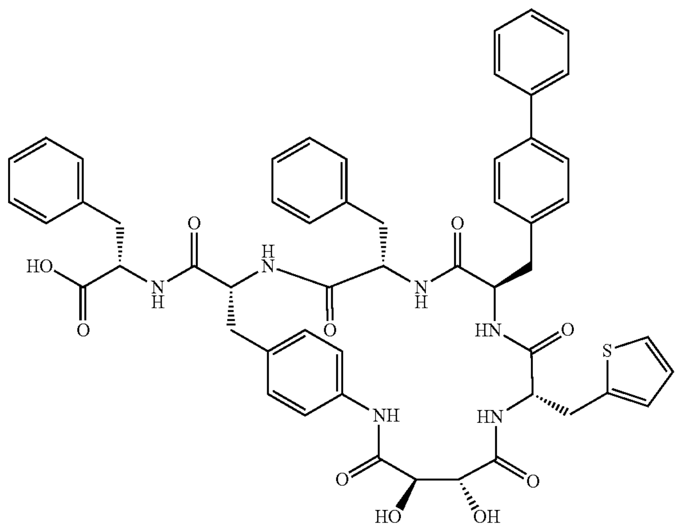 | 965.3544 | 965.3569 |
| 435 | 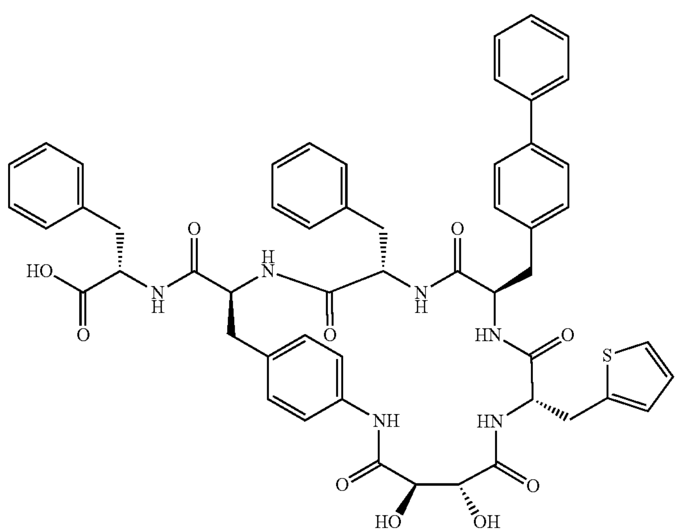 | 965.3544 | 965.3563 |

TABLE 1-continued

| Compound No. | Structure | MS Calcd | MS Observed |
|---|---|---|---|
| 436 | 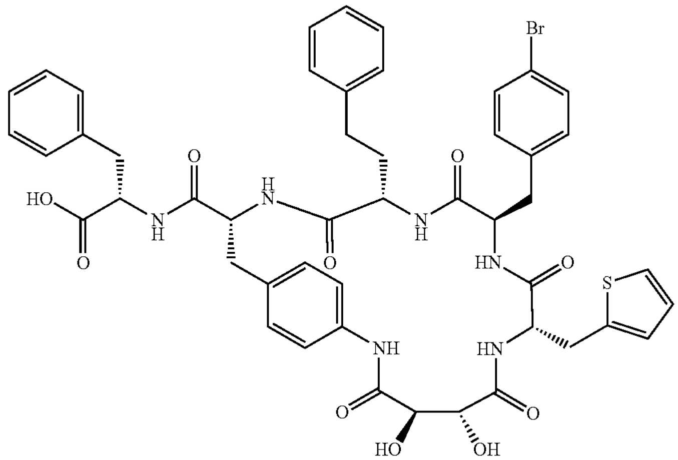 | 981.2492 | 981.2509 |
| 437 | 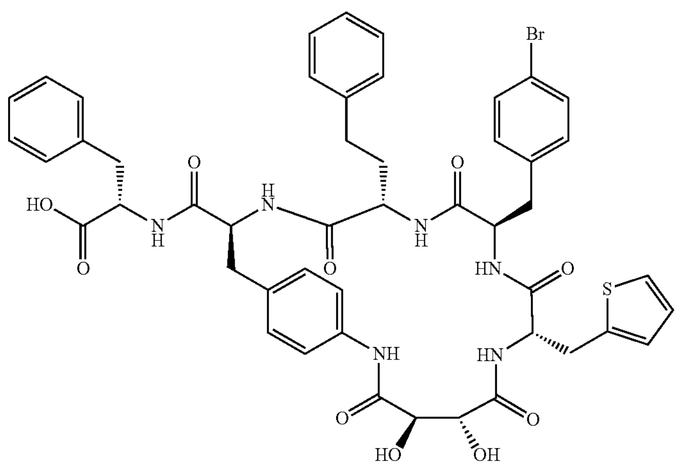 | 981.2492 | 981.2558 |
| 438 | 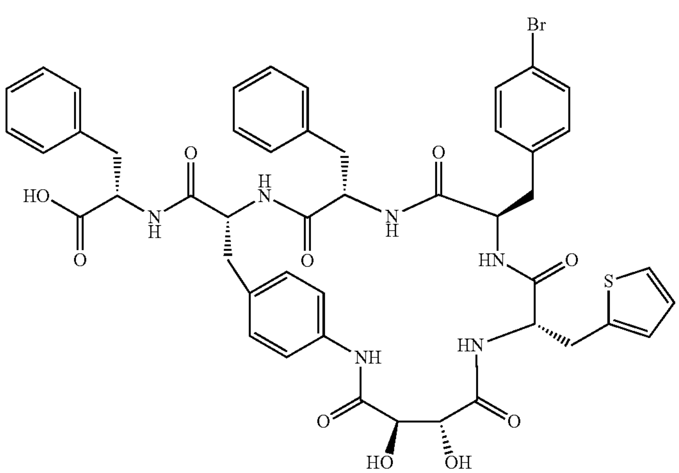 | 967.2336 | 967.2320 |

TABLE 1-continued

| Compound No. | Structure | MS Calcd | MS Observed |
|---|---|---|---|
| 439 | 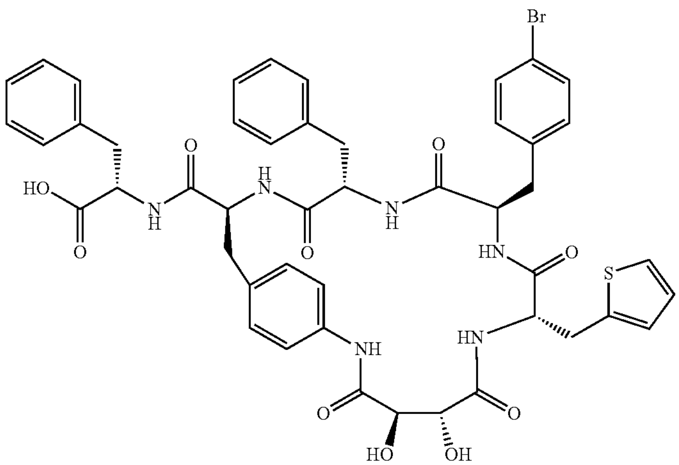 | 967.2336 | 967.2325 |
| 440 | 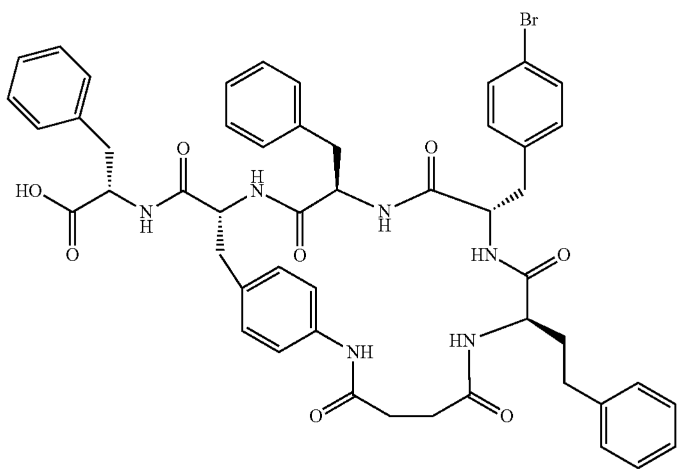 | 943.3030 | 943.3055 |
| 441 | 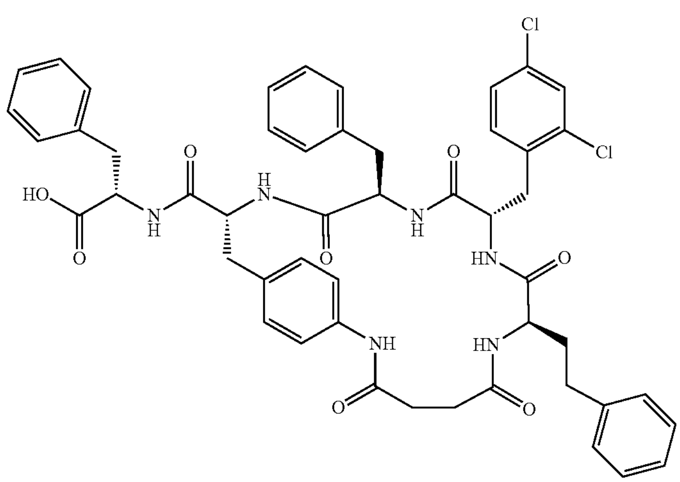 | 933.3145 | 933.3160 |

TABLE 1-continued

| Compound No. | Structure | MS Calcd | MS Observed |
|---|---|---|---|
| 442 | 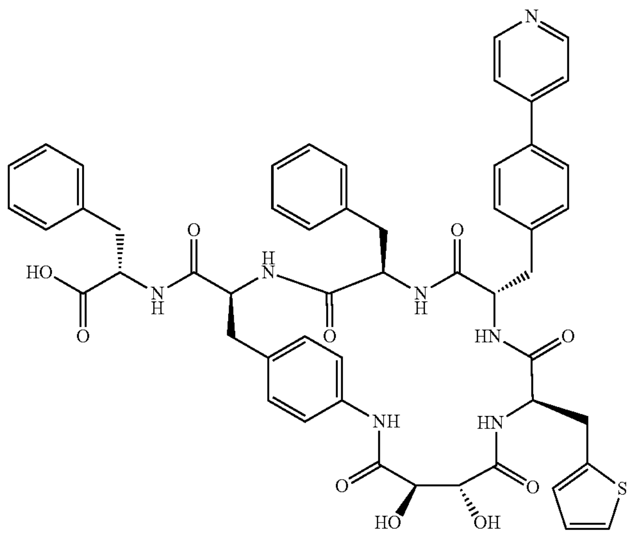 | 966.3496 | 966.3507 |
| 443 | 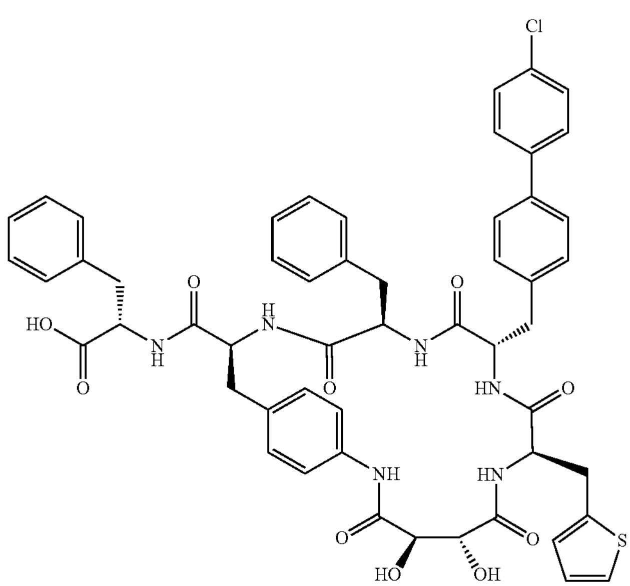 | 999.3154 | 999.3163 |

TABLE 1-continued
| Compound No. | Structure | MS Calcd | MS Observed |
|---|---|---|---|
| 444 | 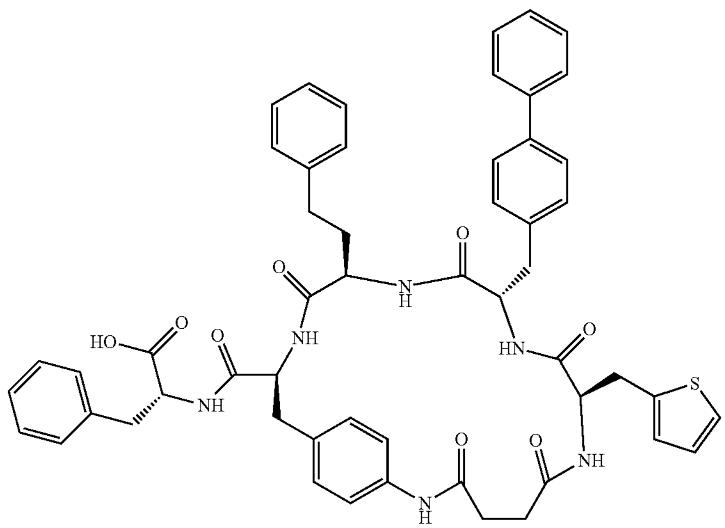 | 947.3802 | 947.3796 |
| 445 | 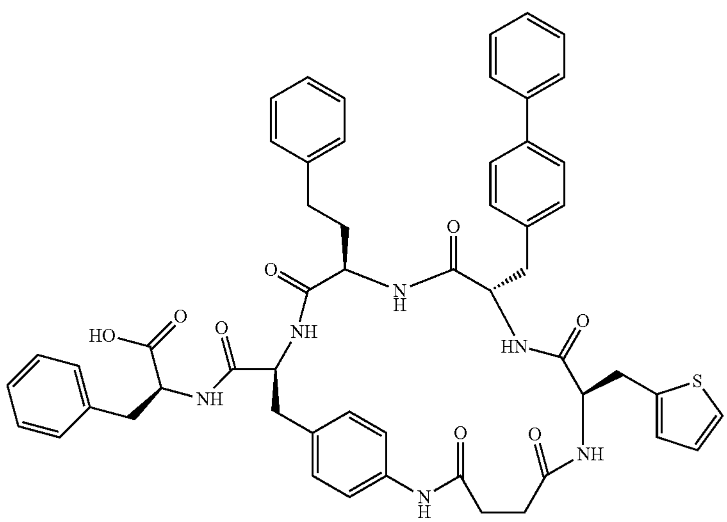 | 947.3802 | 947.3798 |
| 446 | 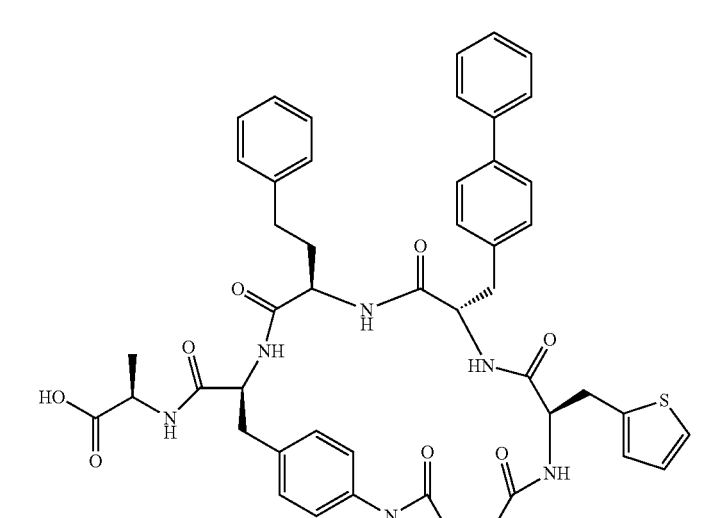 | 871.3489 | 871.3491 |

TABLE 1-continued

| Compound No. | Structure | MS Calcd | MS Observed |
|---|---|---|---|
| 447 | 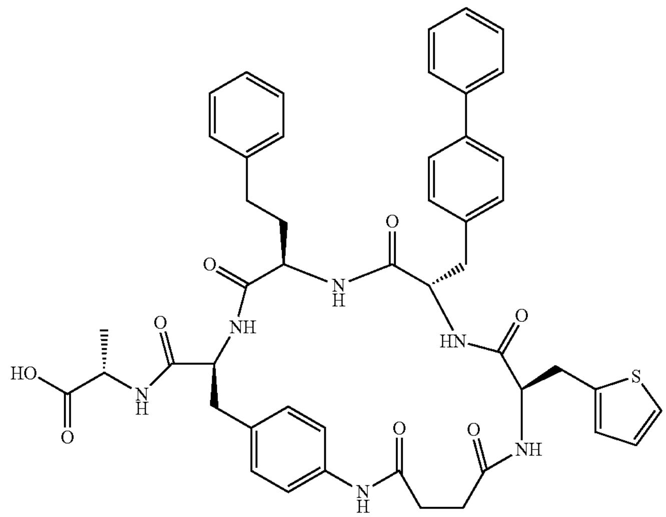 | 871.3489 | 871.3509 |
| 448 | 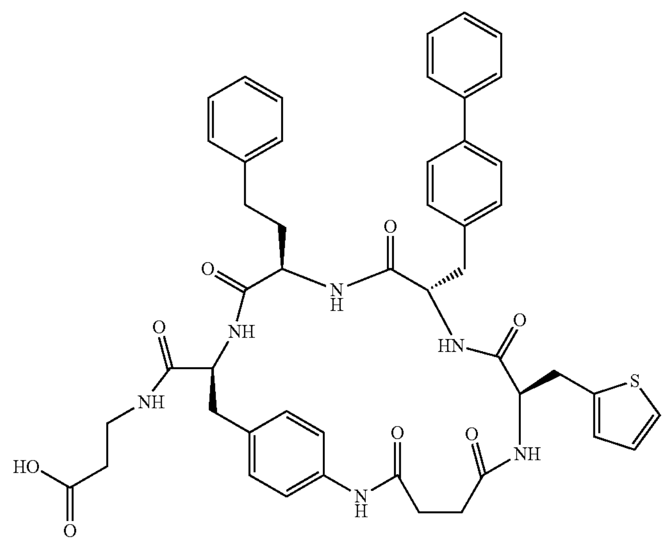 | 871.3489 | 871.3489 |
| 449 | 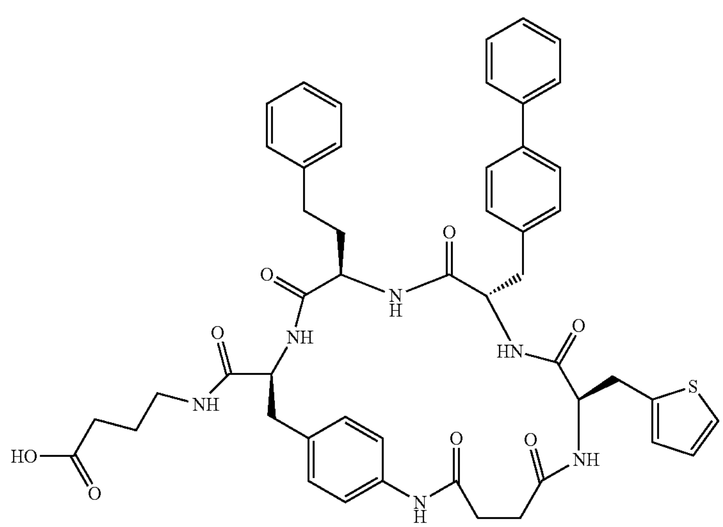 | 885.3645 | 885.374* |

TABLE 1-continued
| Compound No. | Structure | MS Calcd | MS Observed |
|---|---|---|---|
| 450 | 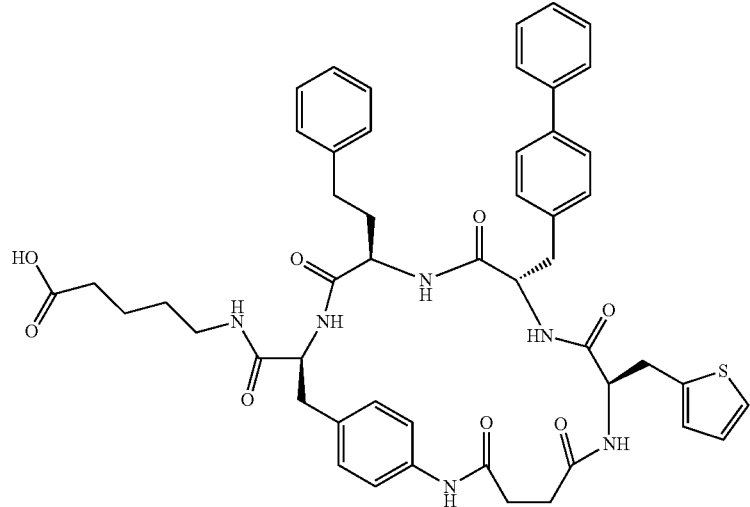 | 899.3802 | 899.3831 |
| 451 | 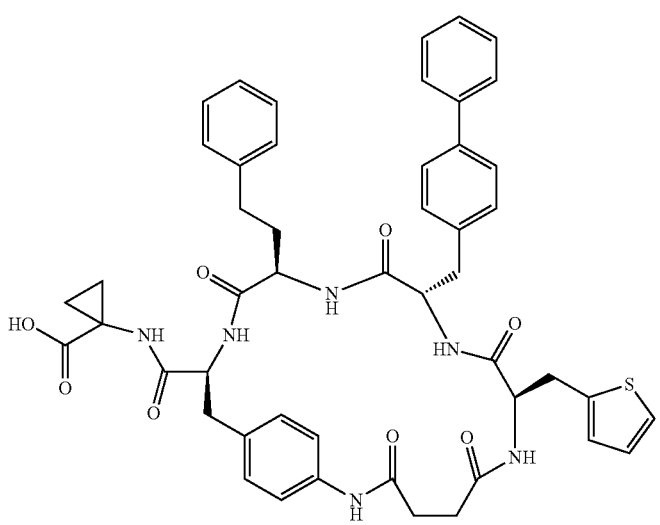 | 883.3489 | 883.3516 |
| 452 | 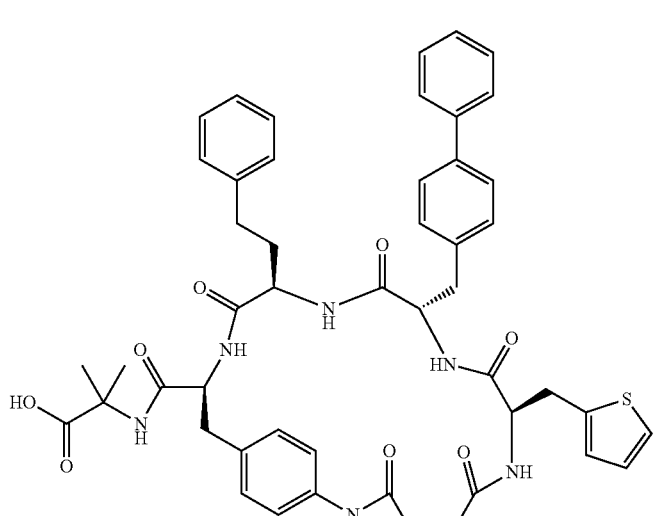 | 885.3645 | 885.3699 |

TABLE 1-continued

| Compound No. | Structure | MS Calcd | MS Observed |
|---|---|---|---|
| 453 | 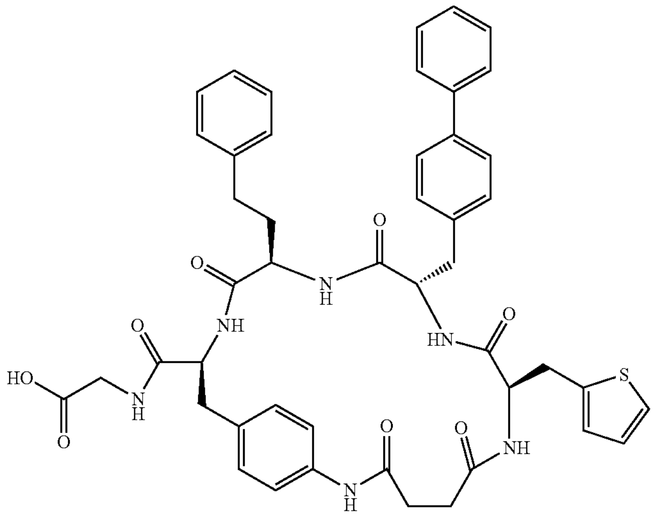 | 857.3332 | 857.3340 |
| 454 | 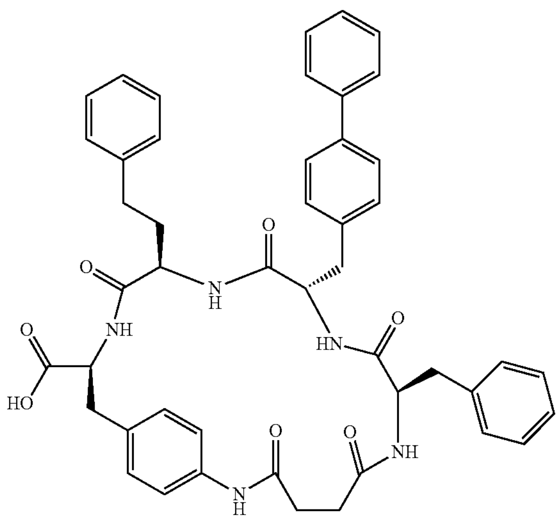 | 794.3553 | 794.415* |
| 455 | 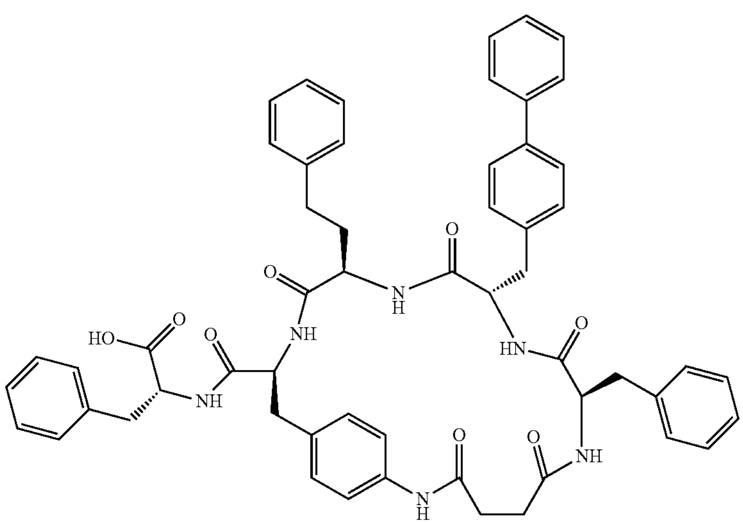 | 941.4238 | 941.4252 |

TABLE 1-continued

| Compound No. | Structure | MS Calcd | MS Observed |
|---|---|---|---|
| 456 | 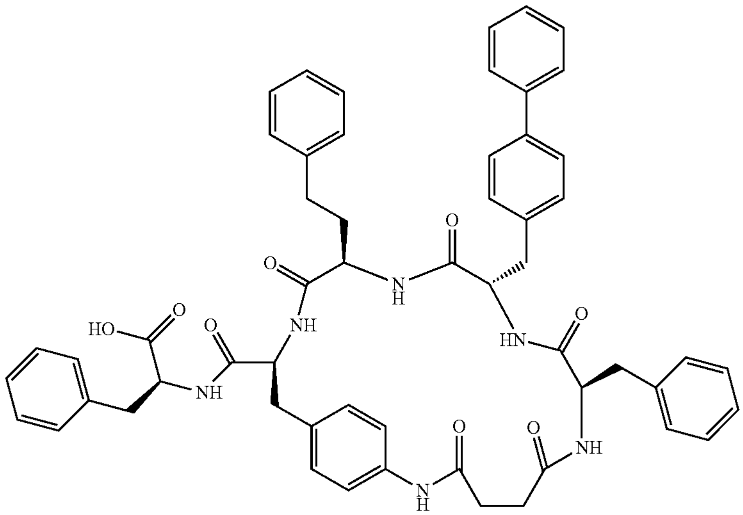 | 941.4238 | 941.4239 |
| 457 | 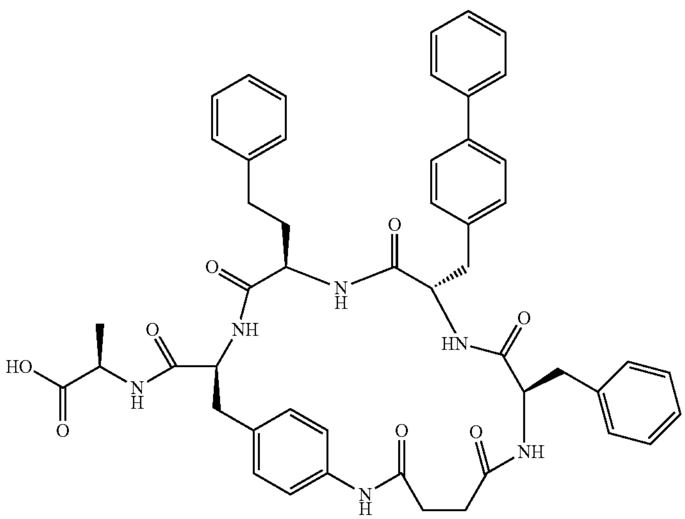 | 865.3925 | 865.3929 |
| 458 | 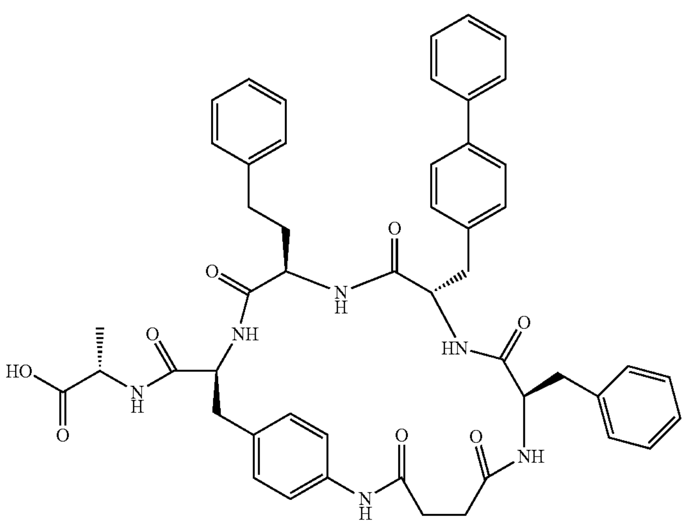 | 865.3925 | 865.3914 |

TABLE 1-continued

| Compound No. | Structure | MS Calcd | MS Observed |
|---|---|---|---|
| 459 | 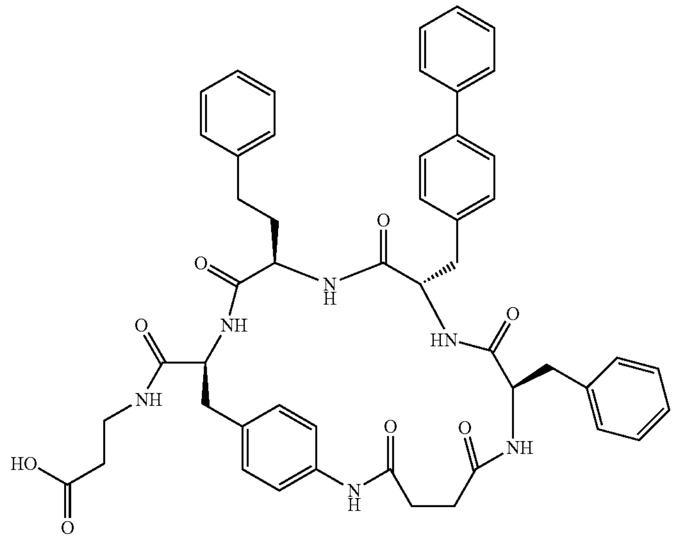 | 865.3925 | 865.3919 |
| 460 | 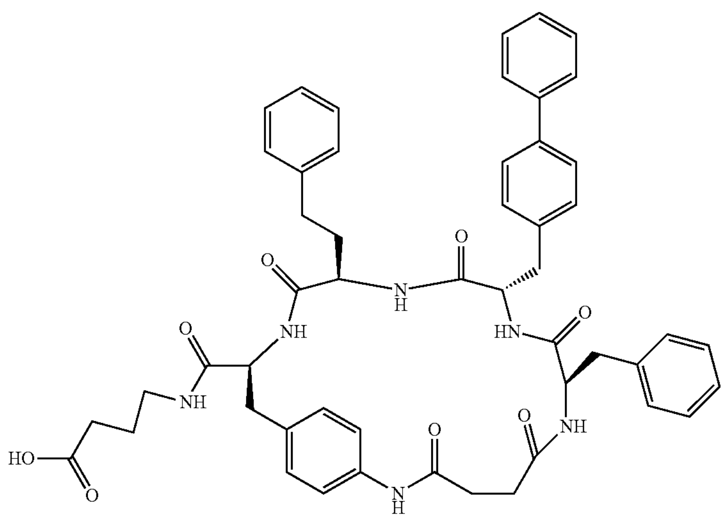 | 879.4081 | 879.4088 |
| 461 | 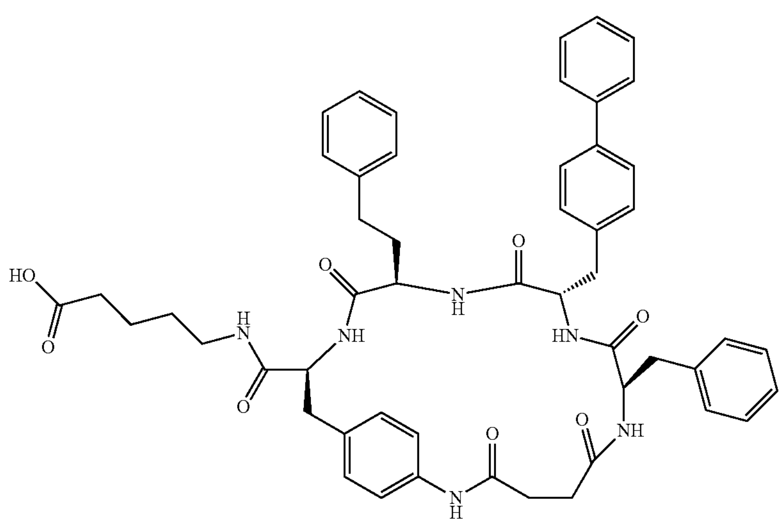 | 893.4238 | 893.4277 |

TABLE 1-continued

| Compound No. | Structure | MS Calcd | MS Observed |
|---|---|---|---|
| 462 | 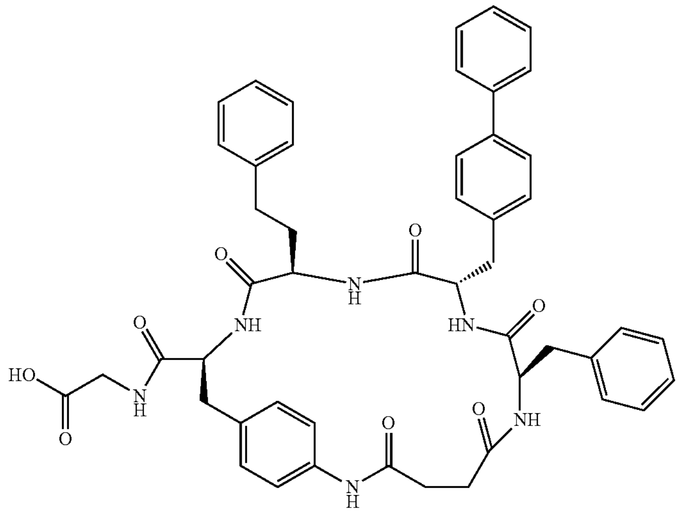 | 851.3768 | 851.3773 |
| 463 | 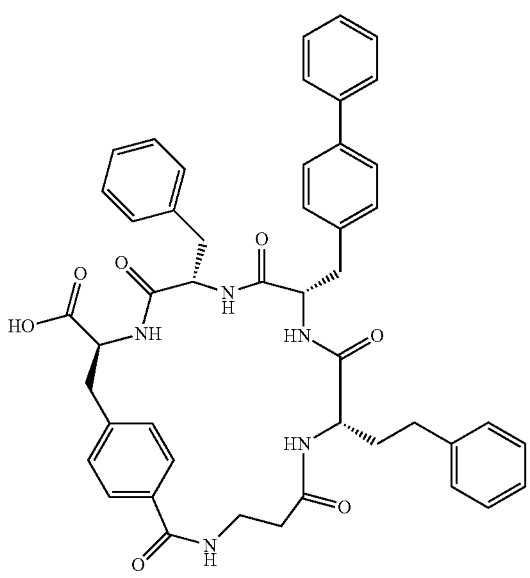 | 794.3548 | 794.3611 |

TABLE 1-continued

| Compound No. | Structure | MS Calcd | MS Observed |
|---|---|---|---|
| 464 | 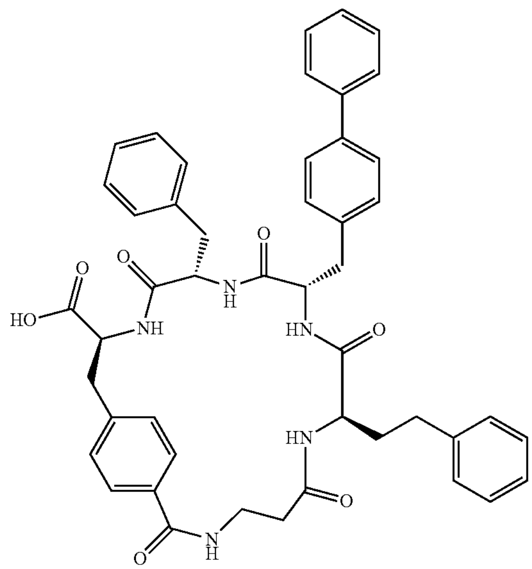 | 794.3548 | 794.3571 |
| 465 | 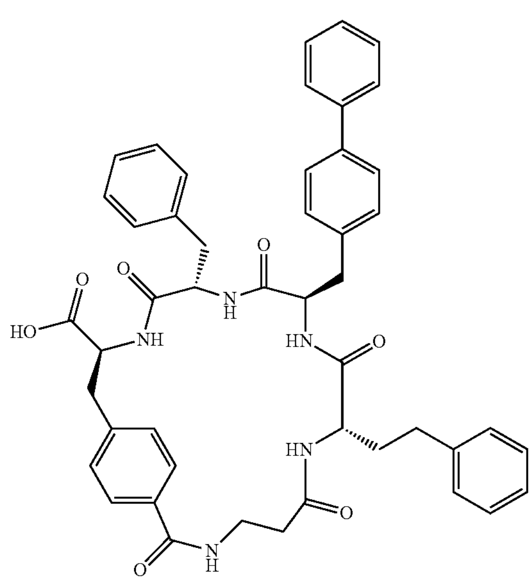 | 794.3548 | 794.3563 |

TABLE 1-continued
| Compound No. | Structure | MS Calcd | MS Observed |
|---|---|---|---|
| 466 | 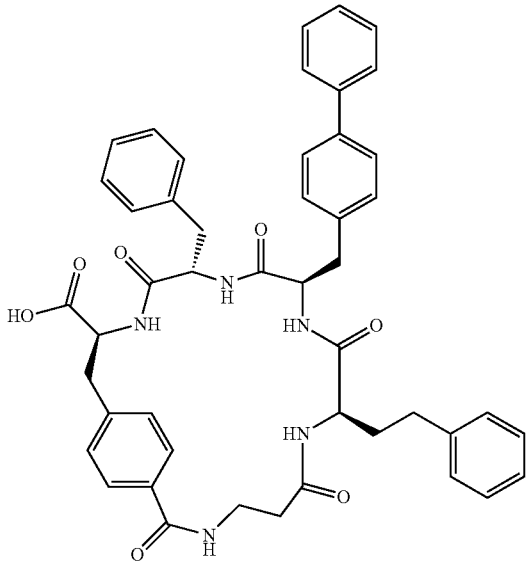 | 794.3548 | 794.3560 |
| 467 | 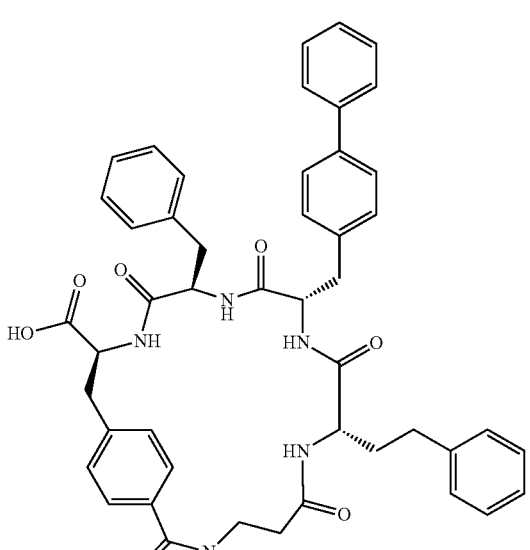 | 794.3548 | 794.3547 |

TABLE 1-continued

| Compound No. | Structure | MS Calcd | MS Observed |
|---|---|---|---|
| 468 | 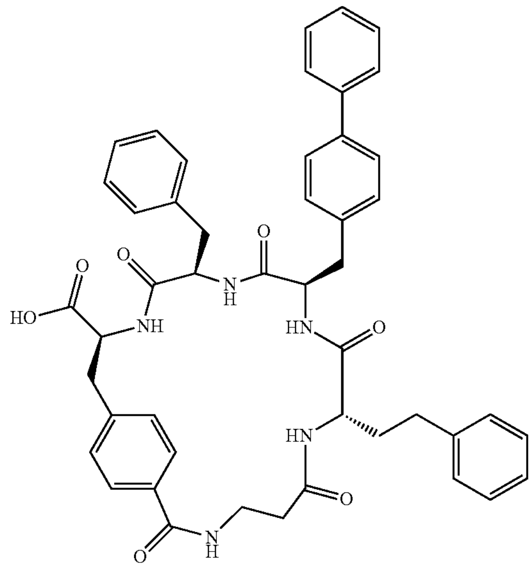 | 794.3548 | 794.3554 |
| 469 | 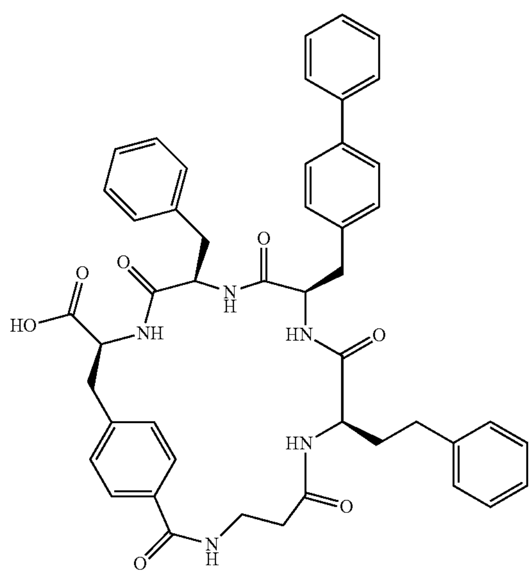 | 794.3548 | 794.3530 |

TABLE 1-continued

| Compound No. | Structure | MS Calcd | MS Observed |
|---|---|---|---|
| 470 | 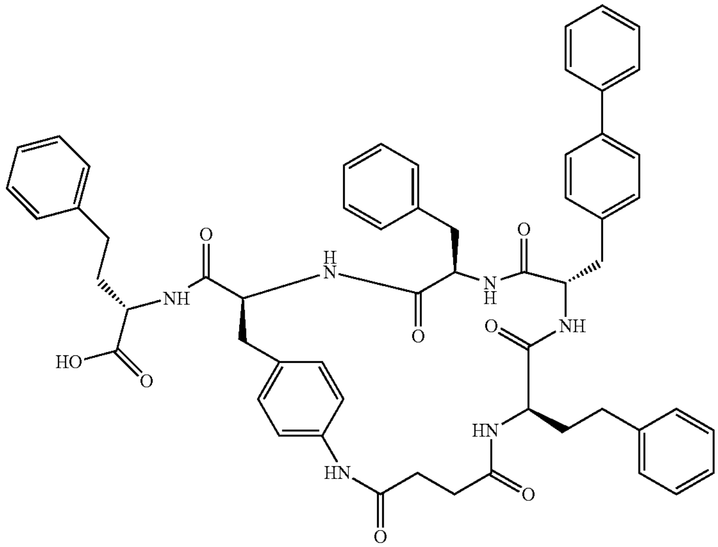 | 955.4394 | 955.4442 |
| 471 | 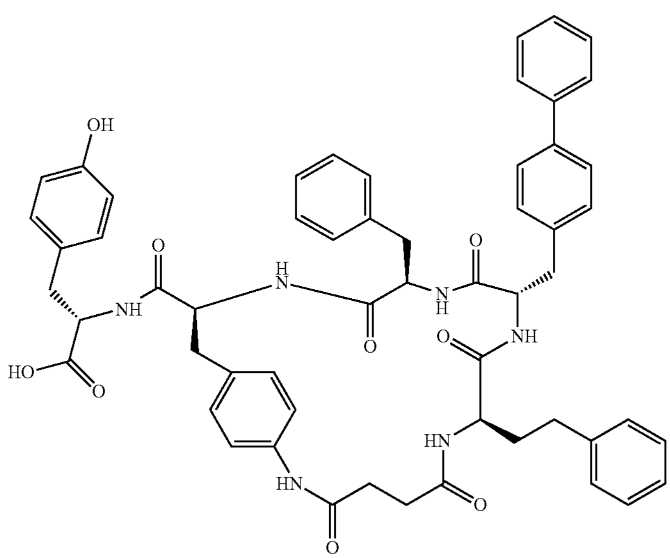 | 957.4187 | 957.4205 |

TABLE 1-continued

| Compound No. | Structure | MS Calcd | MS Observed |
|---|---|---|---|
| 472 | 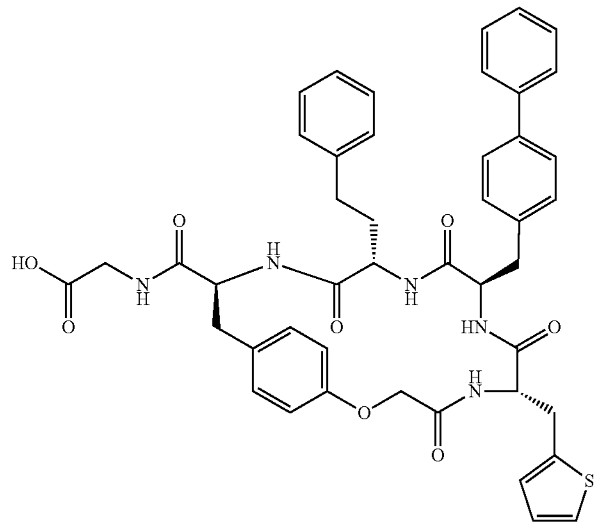 | 816.3067 | 816.3090 |
| 473 | 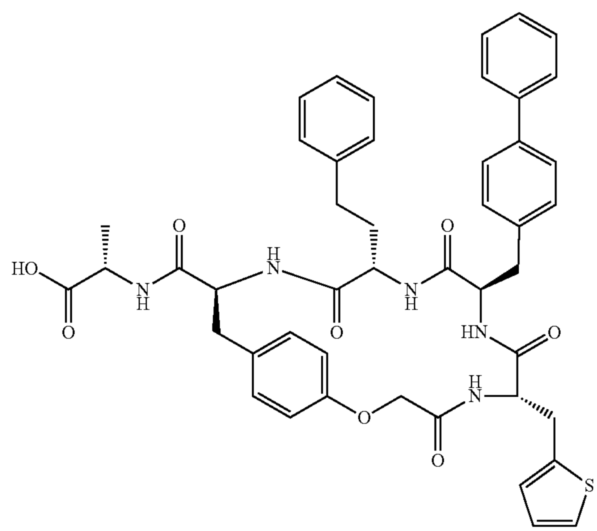 | 830.3224 | 830.3261 |
| 475 | 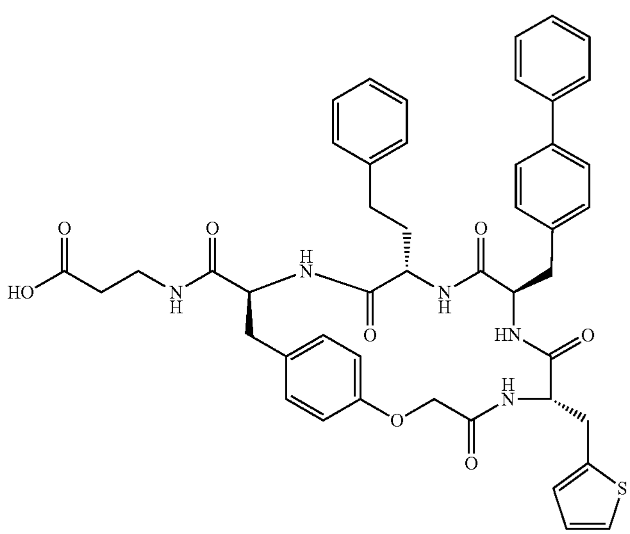 | 830.3224 | 830.3271 |

TABLE 1-continued
| Compound No. | Structure | MS Calcd | MS Observed |
|---|---|---|---|
| 477 | 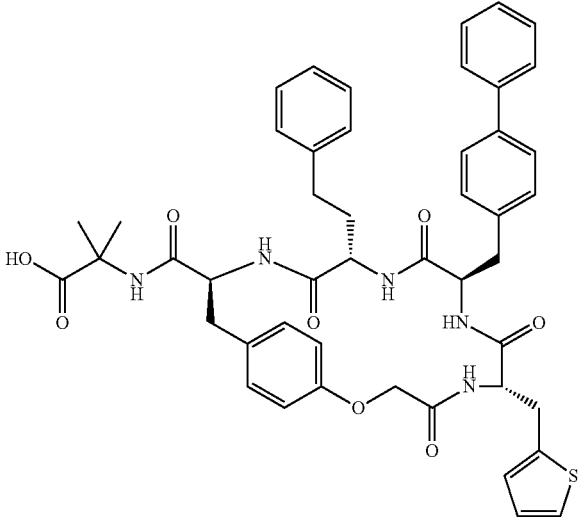 | 844.3380 | 844.3428 |
| 478 | 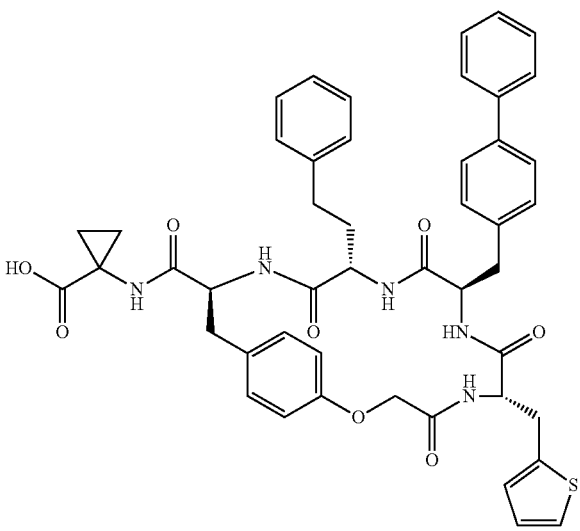 | 842.3224 | 842.3268 |
| 479 | 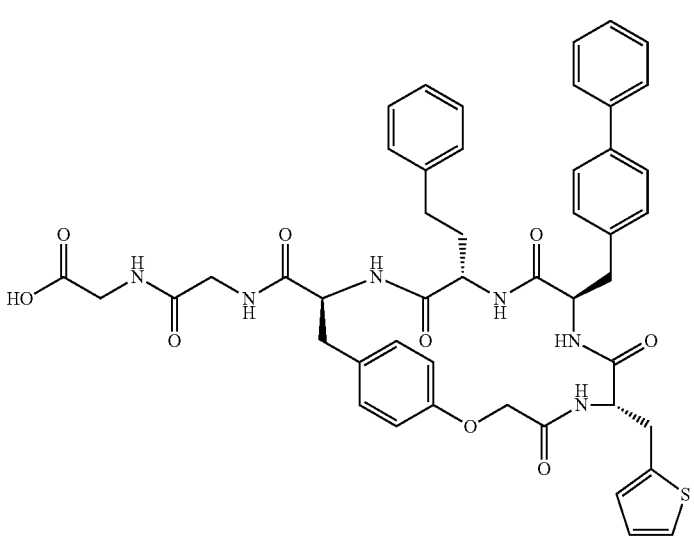 | 873.3282 | 873.3335 |

TABLE 1-continued

| Compound No. | Structure | MS Calcd | MS Observed |
|---|---|---|---|
| 480 | 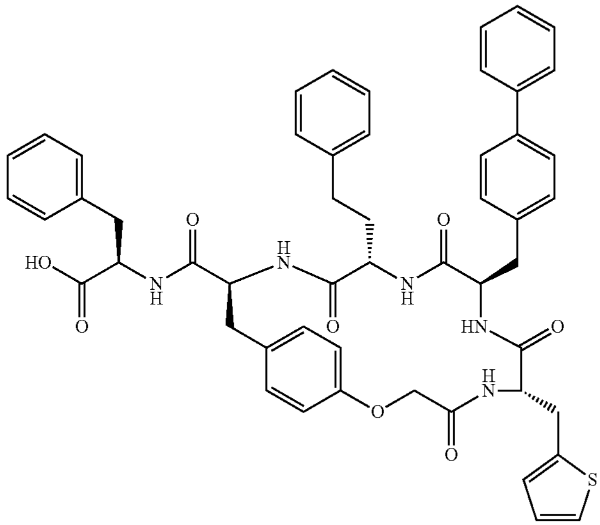 | 906.3537 | 906.3583 |
| 481 | 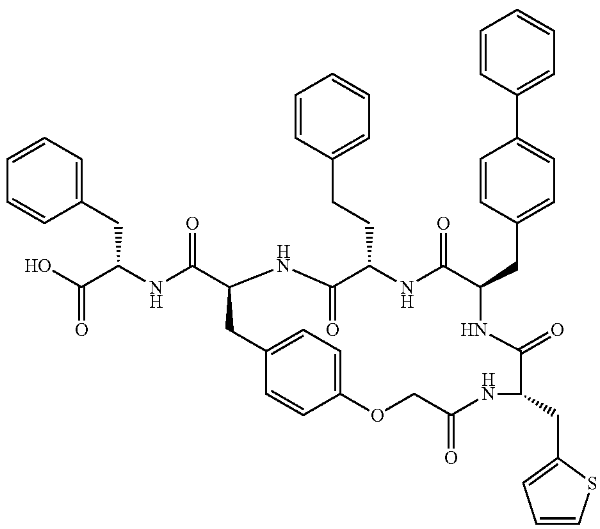 | 906.3537 | 906.3583 |
| 482 | 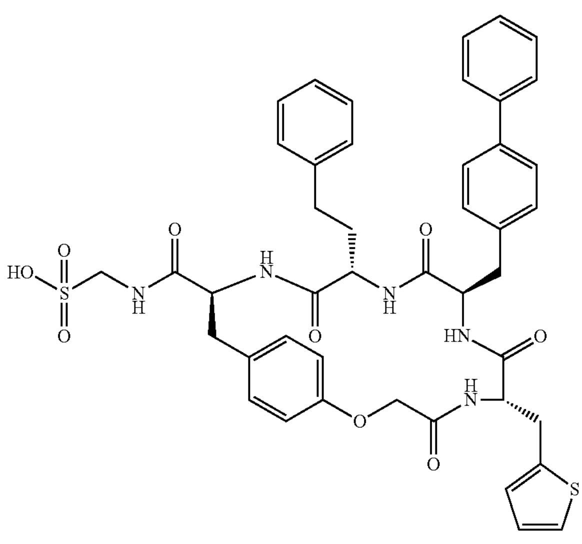 | 852.2737 | 852.2747 |

TABLE 1-continued

| Compound No. | Structure | MS Calcd | MS Observed |
|---|---|---|---|
| 483 | 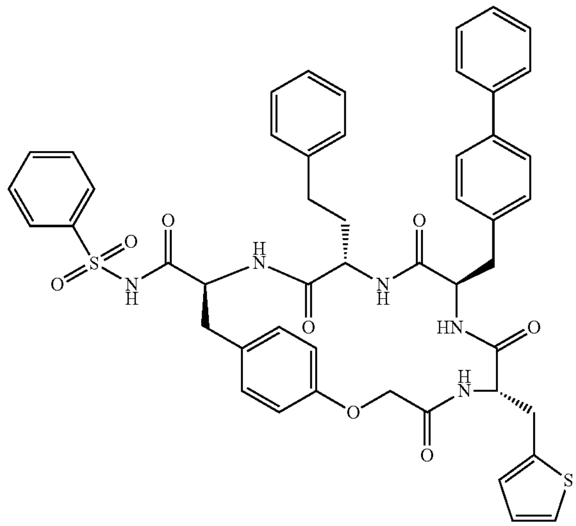 | 898.2944 | 898.2974 |
| 484 | 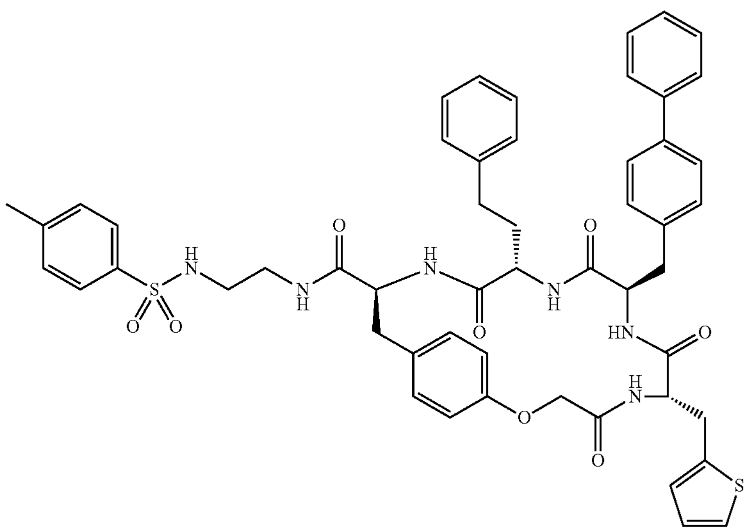 | 955.3523 | 955.3572 |
| 485 | 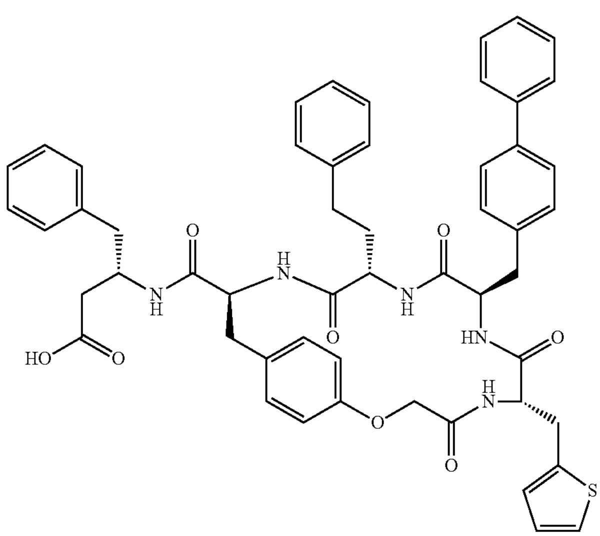 | 920.3693 | 920.3749 |

TABLE 1-continued

| Compound No. | Structure | MS Calcd | MS Observed |
|---|---|---|---|
| 486 | 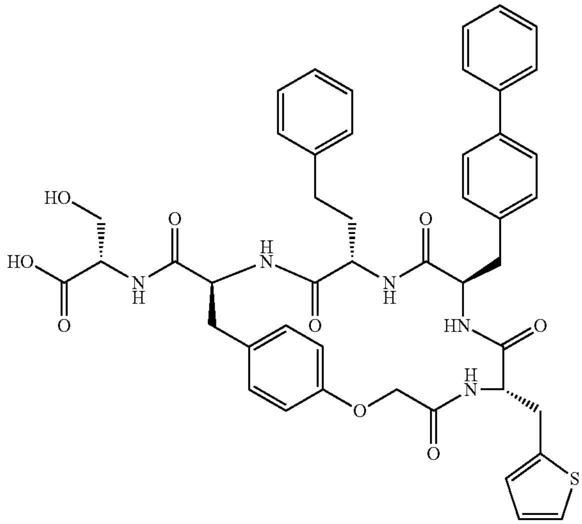 | 846.3173 | 846.3233 |
| 487 | 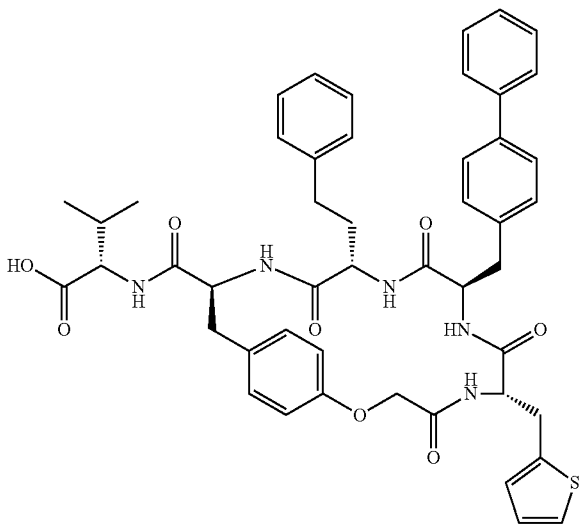 | 858.3537 | 858.3578 |
| 488 | 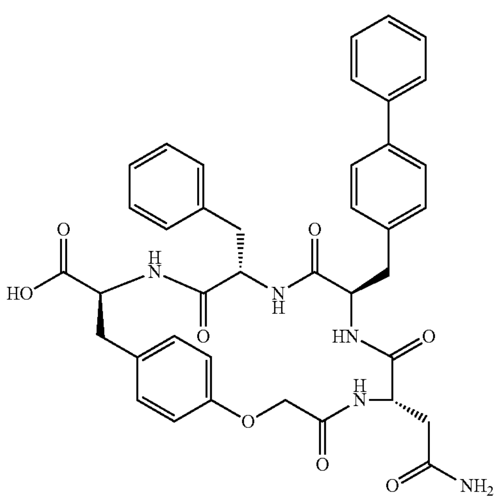 | 706.2877 | 706.2907 |

TABLE 1-continued

| Compound No. | Structure | MS Calcd | MS Observed |
|---|---|---|---|
| 489 | 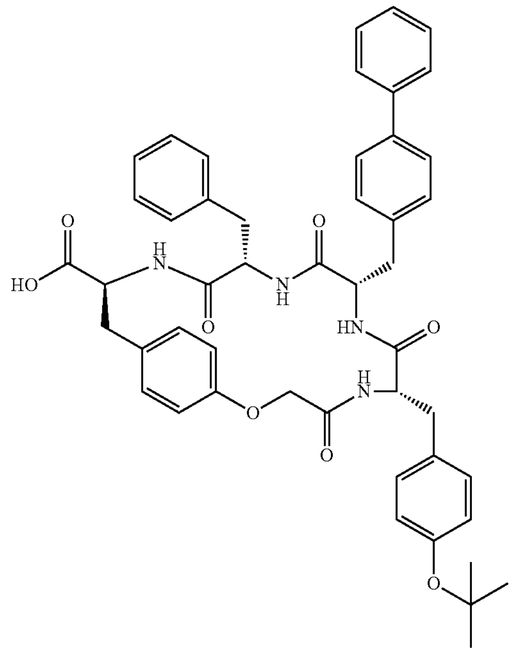 | 811.3707 | 811.3758 |
| 490 | 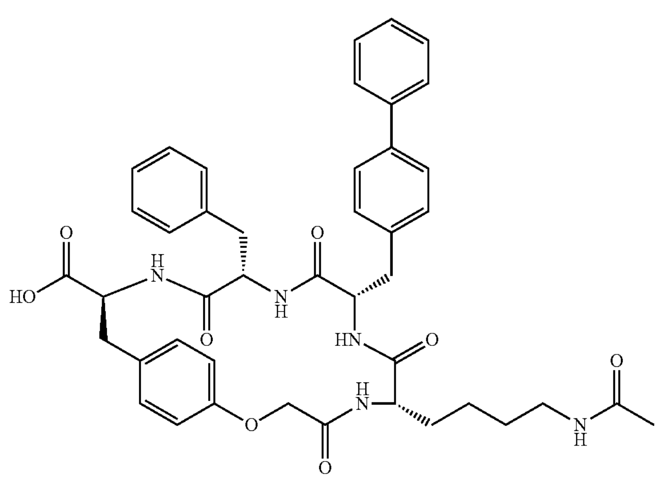 | 762.3503 | 762.3538 |

TABLE 1-continued
| Compound No. | Structure | MS Calcd | MS Observed |
|---|---|---|---|
| 491 | 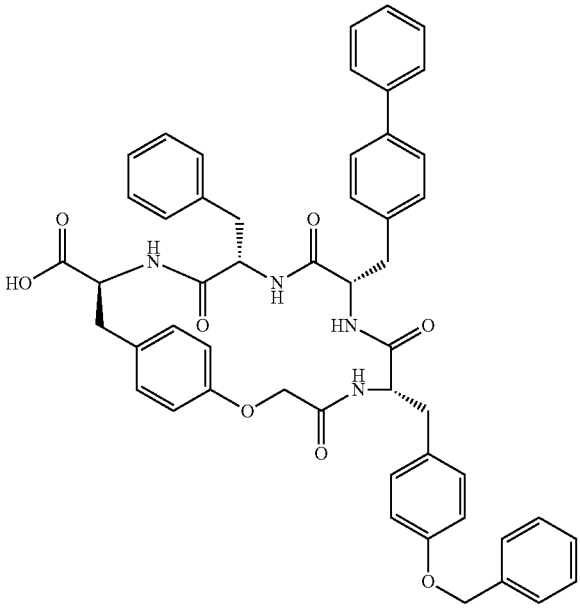 | 845.3550 | 845.3603 |
| 493 | 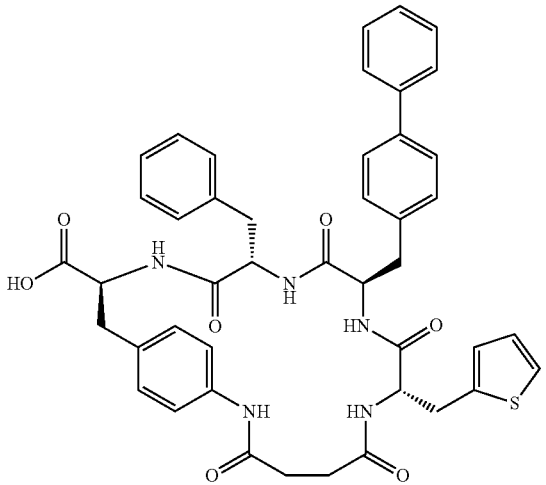 | 786.2956 | 786.2971 |
| 494 | 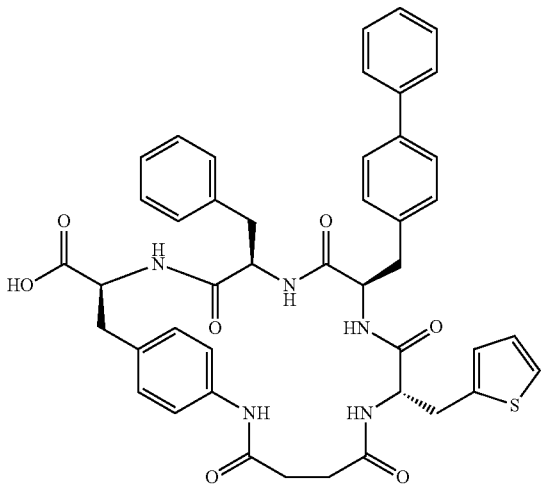 | 786.2956 | 786.2965 |

TABLE 1-continued

| Compound No. | Structure | MS Calcd | MS Observed |
|---|---|---|---|
| 495 | 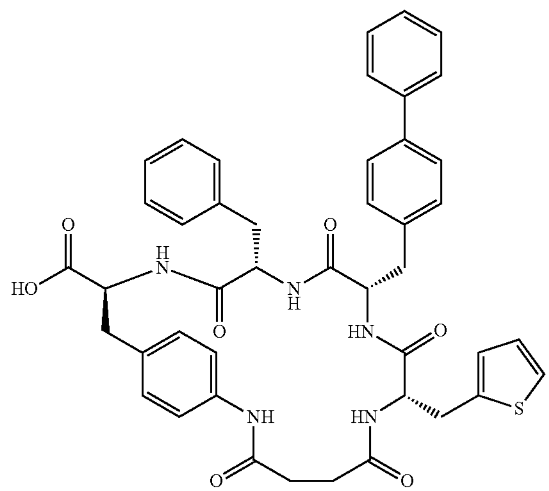 | 786.2956 | 786.2995 |
| 496 | 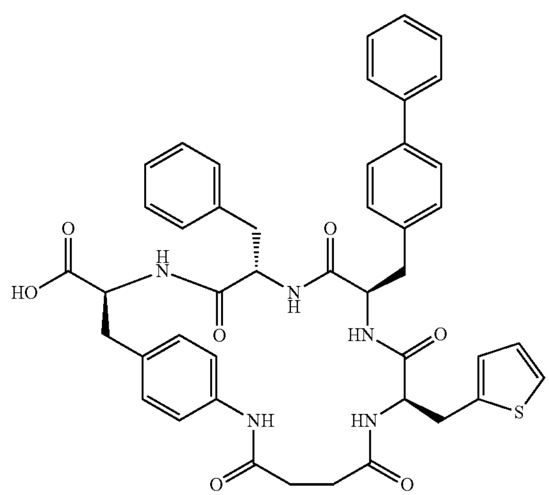 | 786.2956 | 786.2957 |
| 497 | 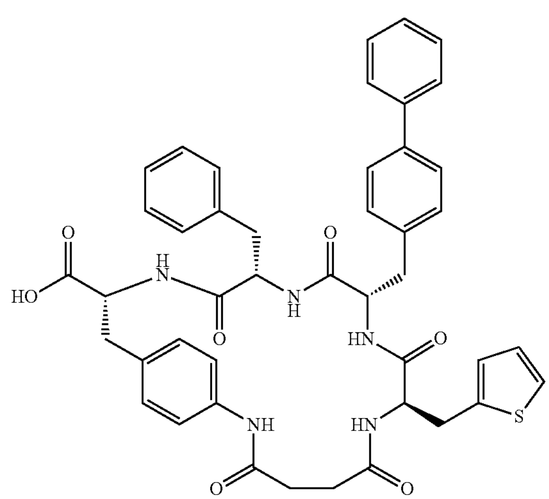 | 786.2956 | 786.2967 |

TABLE 1-continued

| Compound No. | Structure | MS Calcd | MS Observed |
|---|---|---|---|
| 498 | 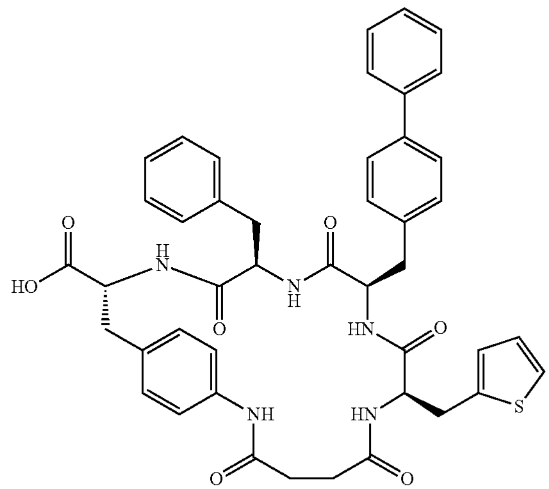 | 786.2956 | 786.2978 |
| 499 | 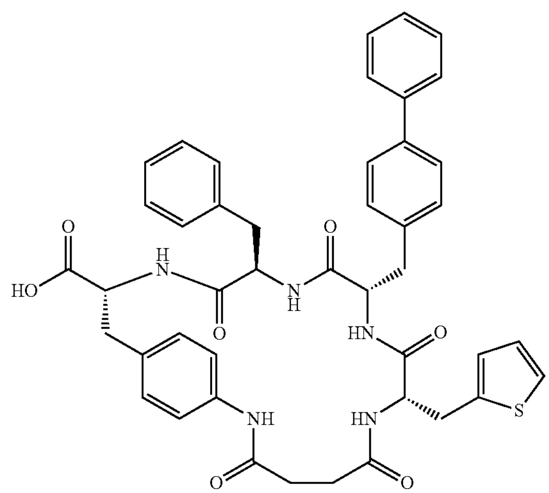 | 786.2956 | 786.2975 |
| 500 | 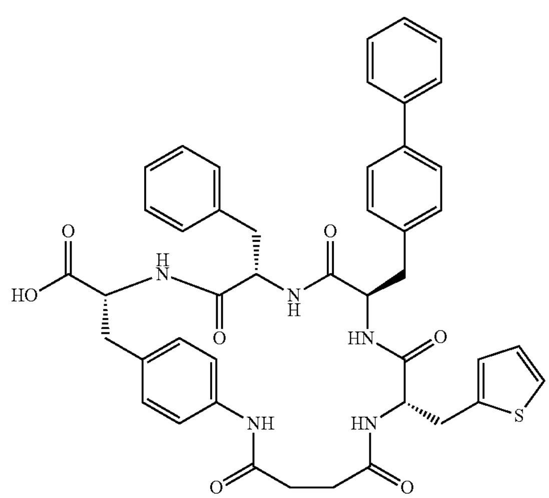 | 786.2956 | 786.2979 |

TABLE 1-continued

| Compound No. | Structure | MS Calcd | MS Observed |
|---|---|---|---|
| 501 | 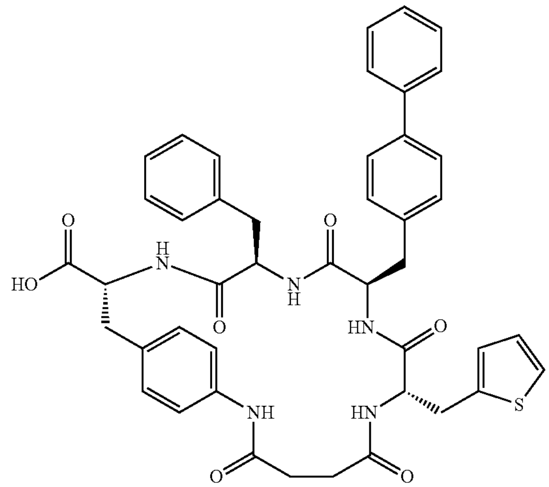 | 786.2956 | 786.2973 |
| 502 | 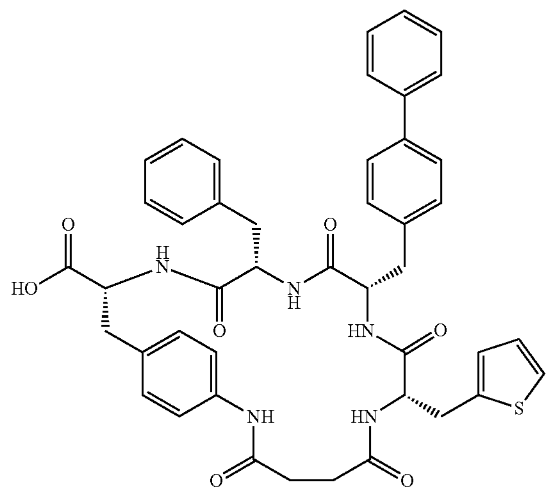 | 786.2956 | 786.2986 |
| 503 | 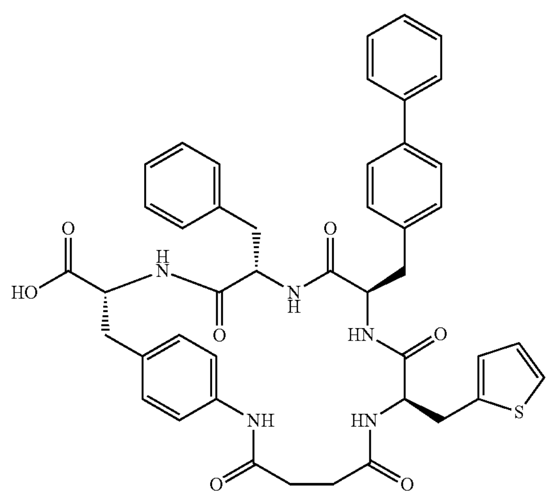 | 786.2956 | 786.2996 |

TABLE 1-continued

| Compound No. | Structure | MS Calcd | MS Observed |
|---|---|---|---|
| 504 | 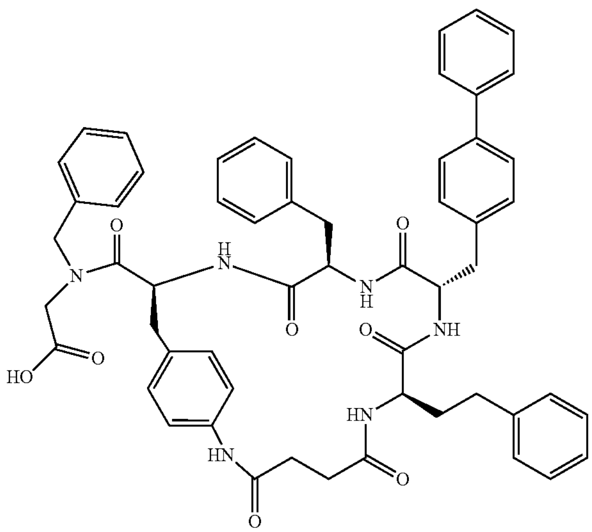 | 941.4238 | 941.4249 |
| 505 | 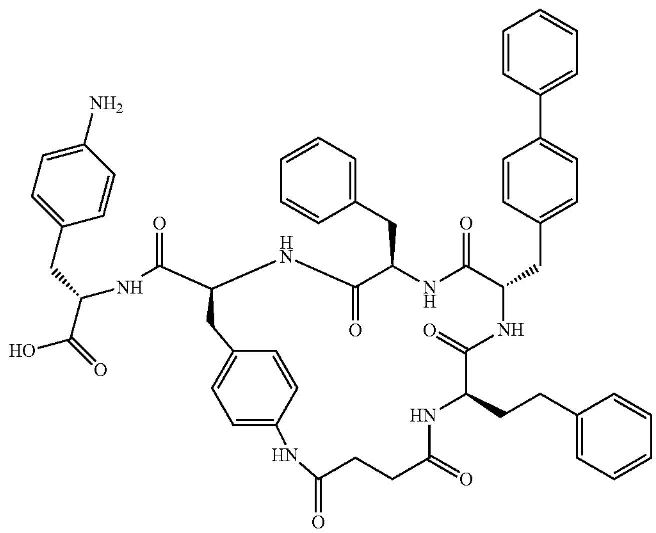 | 956.4347 | 956.4343 |
| 506 | 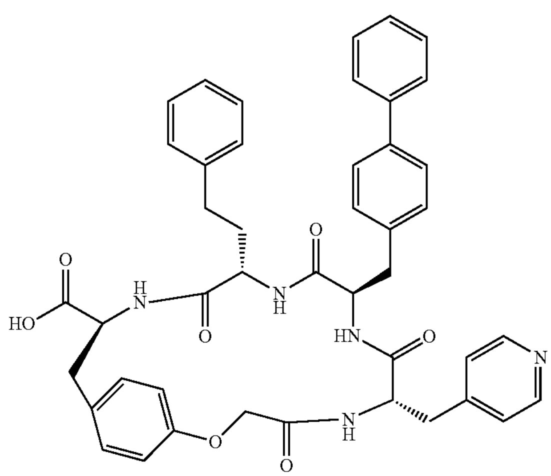 | 754.3235 | 754.3247 |

TABLE 1-continued

| Compound No. | Structure | MS Calcd | MS Observed |
|---|---|---|---|
| 507 | 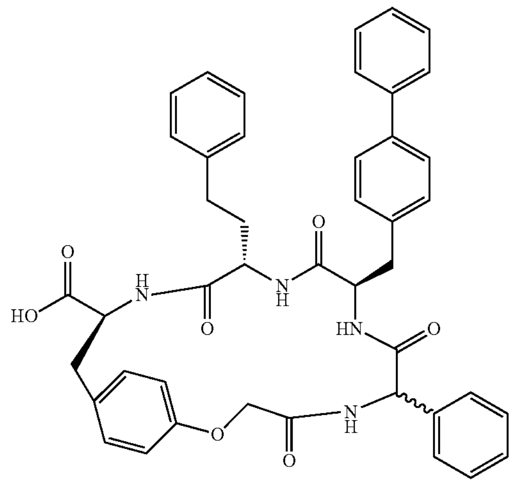 | 739.3127 | 739.3108 |
| 508 | 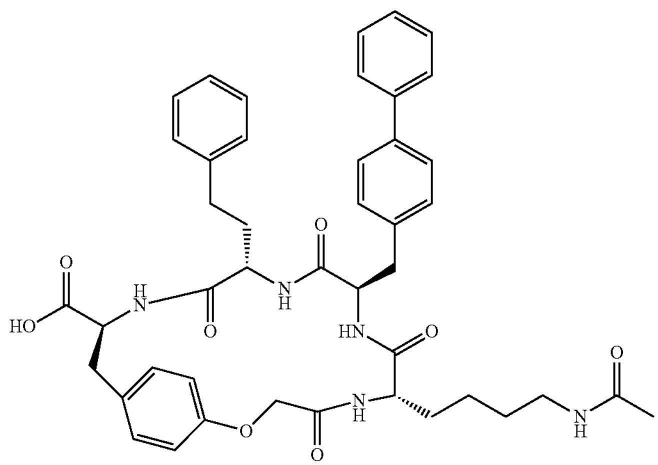 | 776.3654 | 776.3674 |
| 509 | 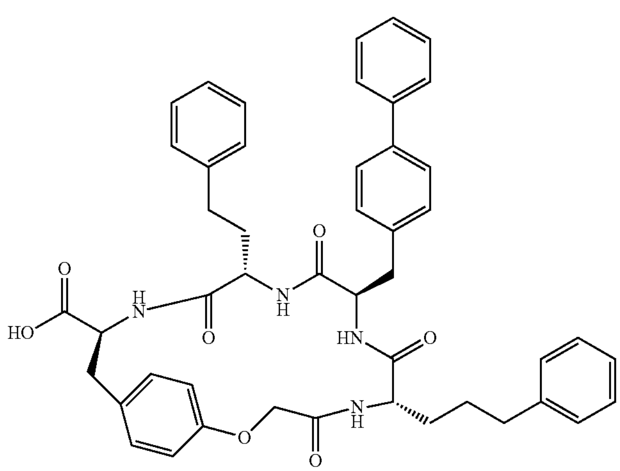 | 781.3596 | 781.3625 |

TABLE 1-continued

| Compound No. | Structure | MS Calcd | MS Observed |
|---|---|---|---|
| 510 | 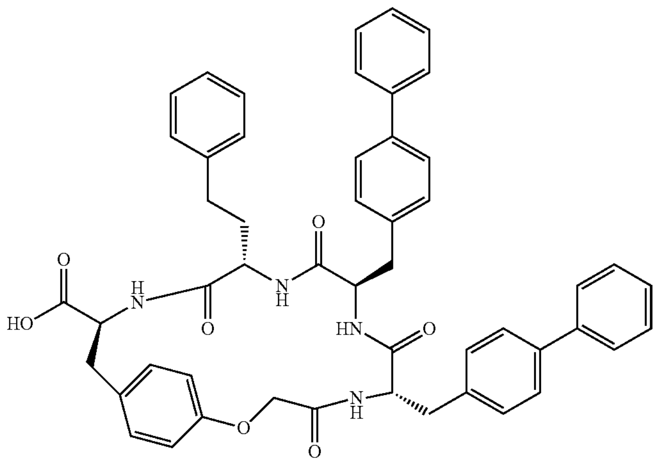 | 829.3596 | 829.3623 |
| 511 | 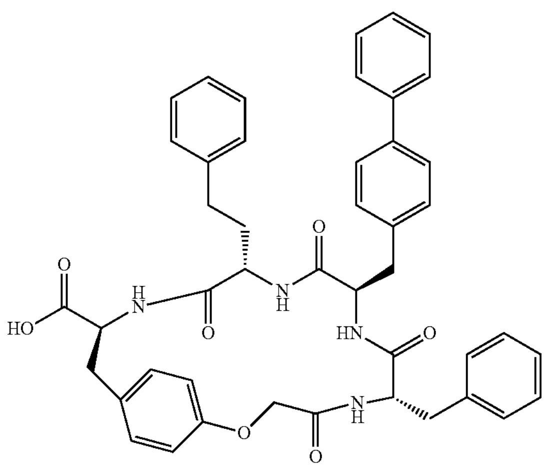 | 753.3283 | 753.3282 |
| 512 | 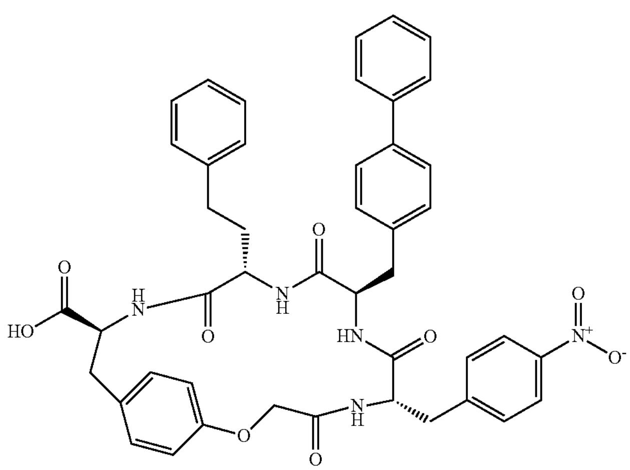 | 798.3134 | 798.3156 |

TABLE 1-continued

| Compound No. | Structure | MS Calcd | MS Observed |
|---|---|---|---|
| 513 | 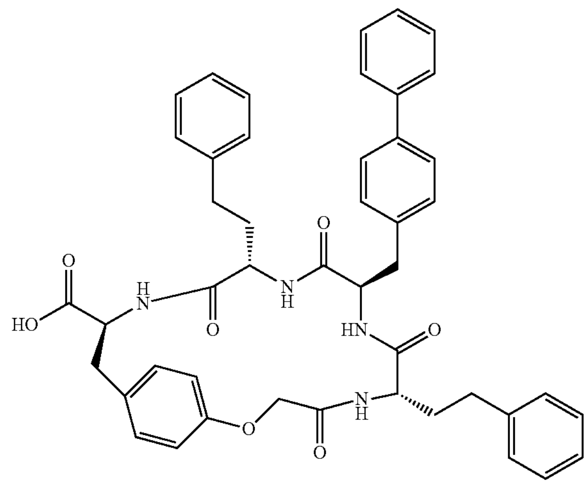 | 767.3440 | 767.3470 |
| 514 | 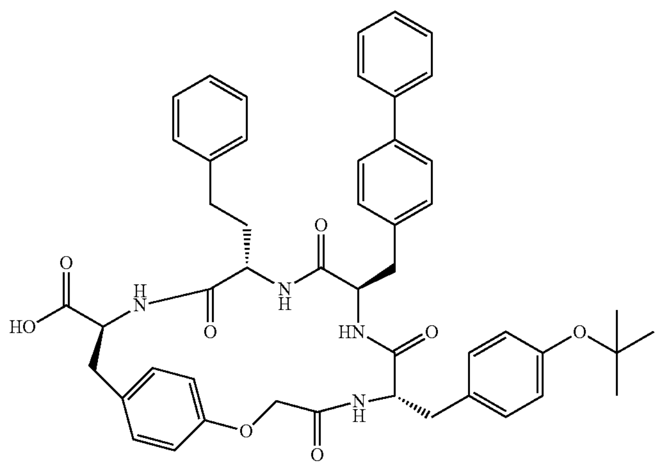 | 825.3858 | 825.3881 |
| 515 | 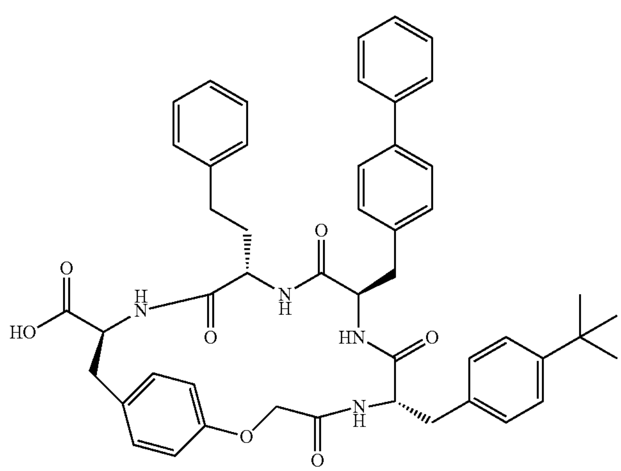 | 809.3909 | 809.3929 |

TABLE 1-continued

| Compound No. | Structure | MS Calcd | MS Observed |
|---|---|---|---|
| 516 | 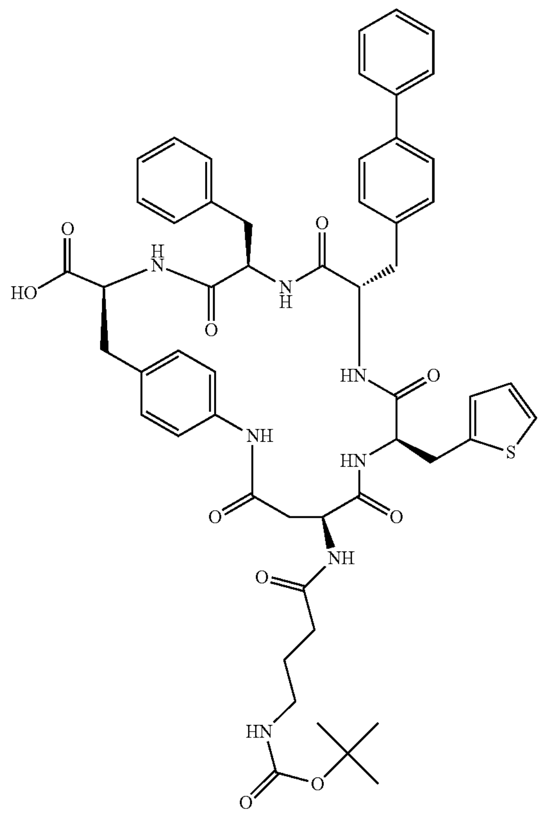 | 986.4117 | 986.4133 |
| 517 | 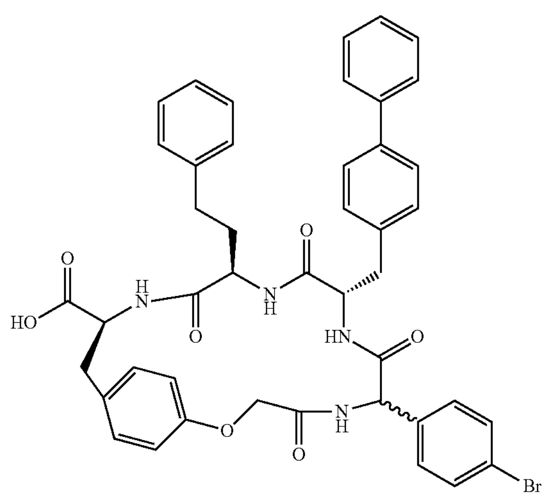 | 817.2232 | 817.2252 |

TABLE 1-continued
| Compound No. | Structure | MS Calcd | MS Observed |
|---|---|---|---|
| 518 | 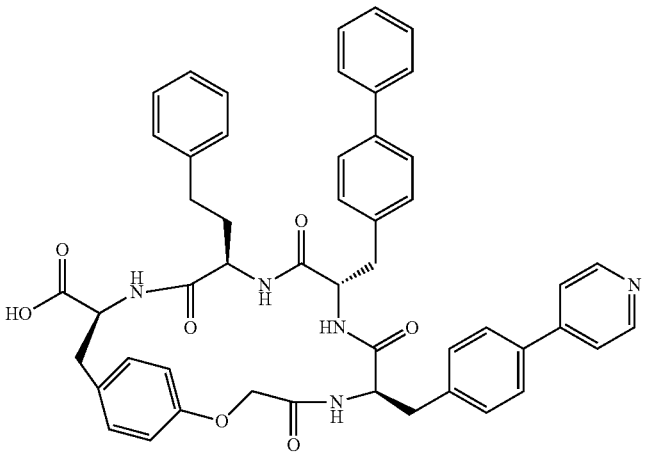 | 830.3548 | 830.3561 |
| 519 | 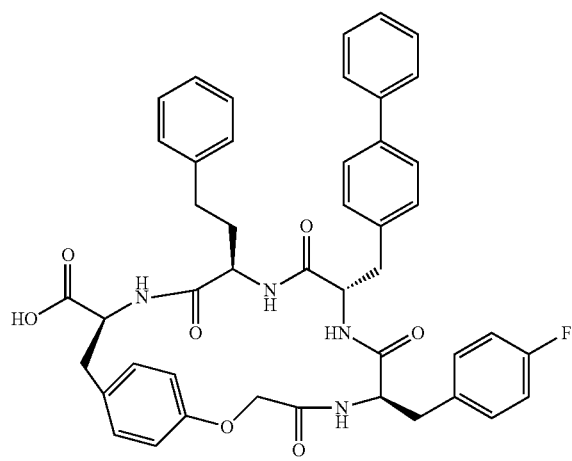 | 771.3189 | 771.3201 |
| 520 | 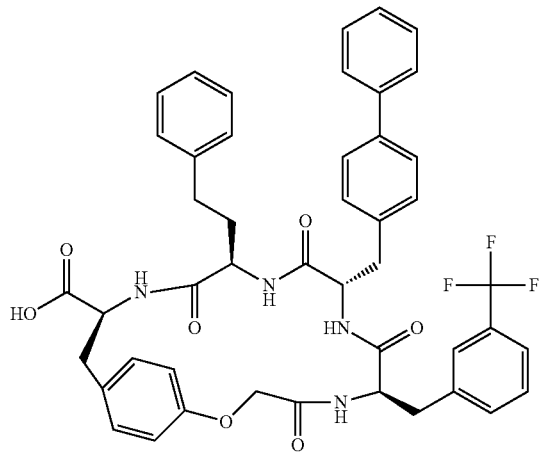 | 821.3157 | 821.3164 |

TABLE 1-continued

| Compound No. | Structure | MS Calcd | MS Observed |
|---|---|---|---|
| 521 | 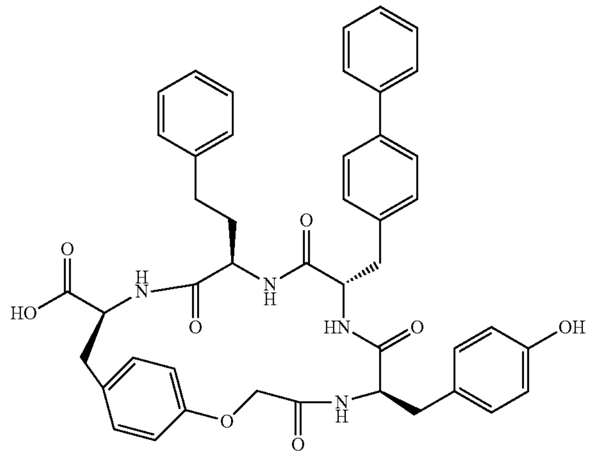 | 769.3232 | 769.3238 |
| 522 | 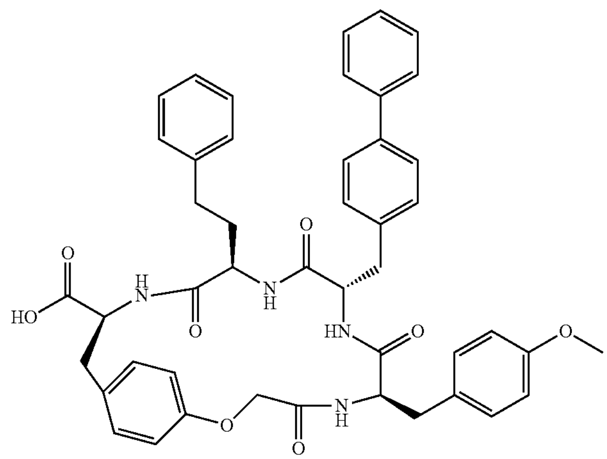 | 783.3389 | 783.3395 |
| 523 | 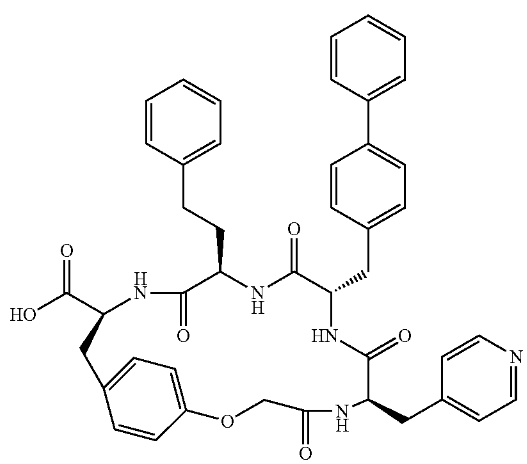 | 754.3235 | 754.3235 |

US 8,338,565 B2
403                                                                                           404
TABLE 1-continued
| Compound No. | Structure | MS Calcd | MS Observed |
|---|---|---|---|
| 524 | 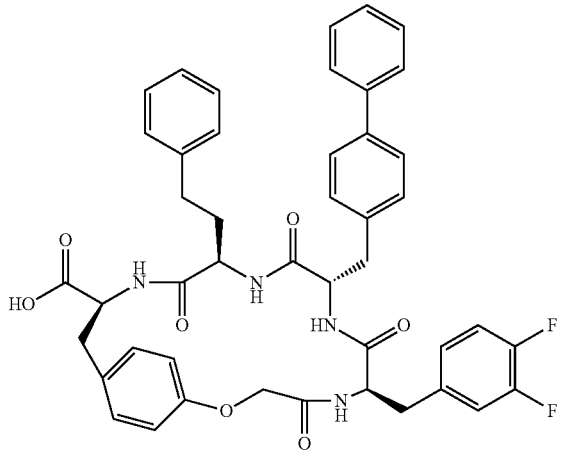 | 789.3095 | 789.3135 |
| 525 | 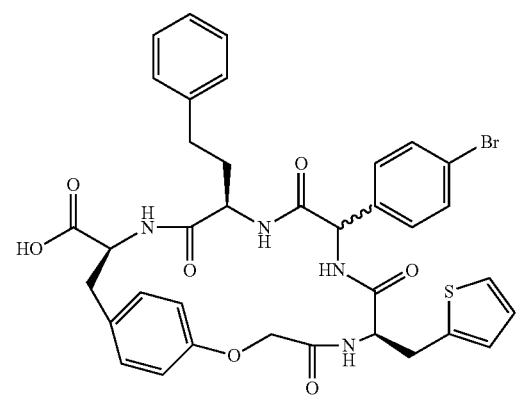 | 747.1483 | 747.1501 |
| 526 | 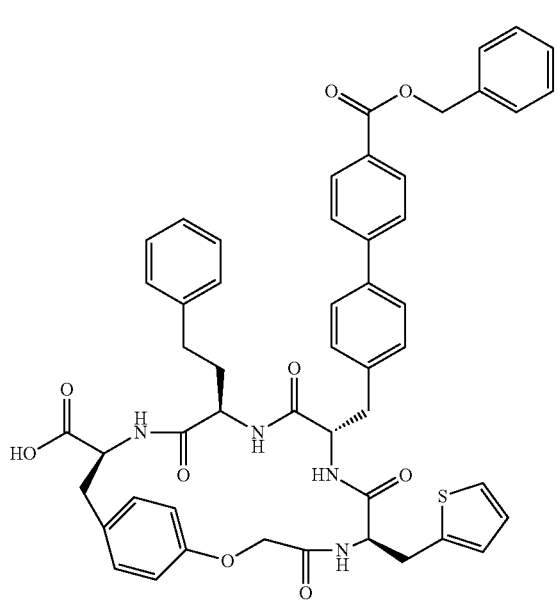 | 893.3215 | 893.3243 |

TABLE 1-continued

| Compound No. | Structure | MS Calcd | MS Observed |
|---|---|---|---|
| 527 | 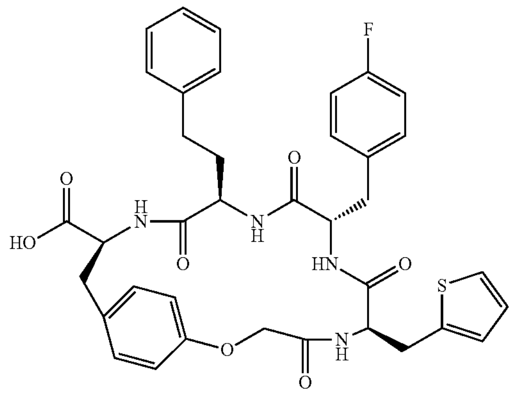 | 701.2440 | 701.2451 |
| 528 | 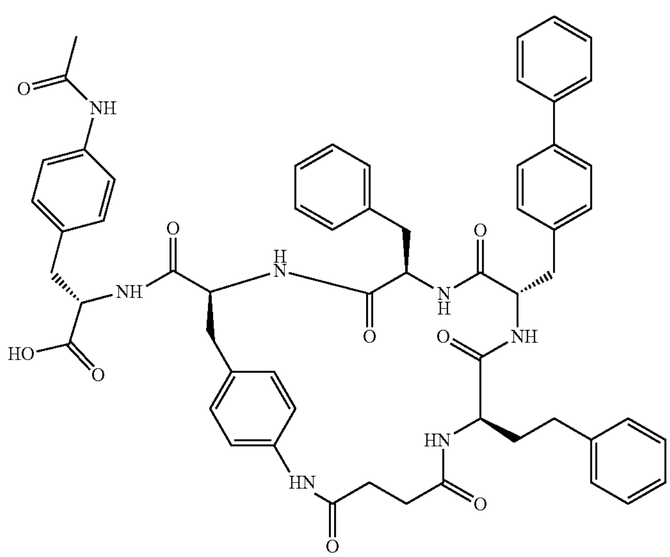 | 998.4453 | 998.4461 |

TABLE 1-continued

| Compound No. | Structure | MS Calcd | MS Observed |
|---|---|---|---|
| 529 | 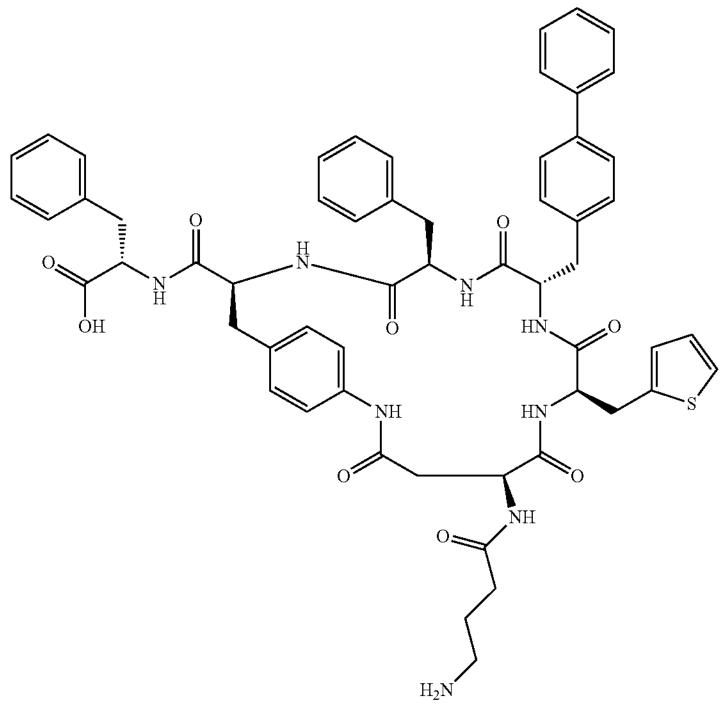 | 1033.4277 | 1033.4279 |
| 530 | 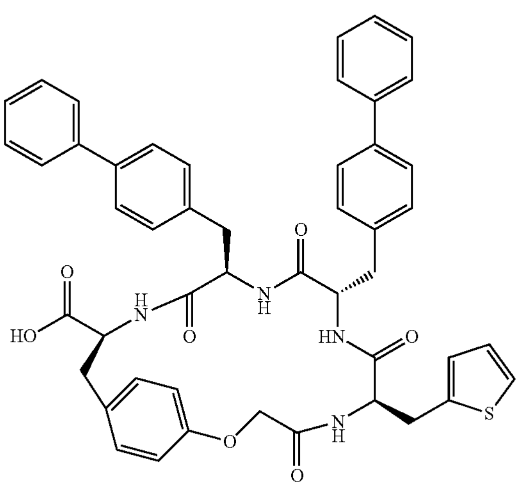 | 821.3004 | 821.3016 |

TABLE 1-continued
| Compound No. | Structure | MS Calcd | MS Observed |
|---|---|---|---|
| 531 | 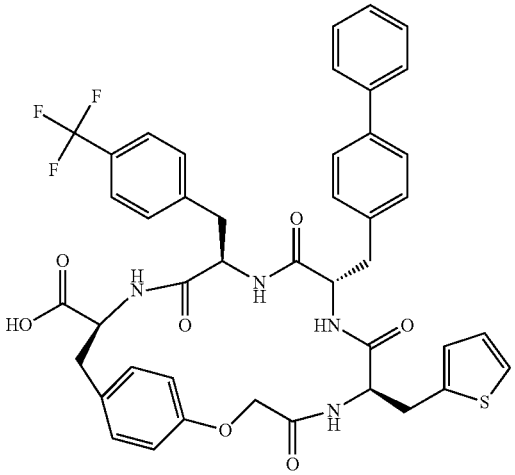 | 813.2565 | 813.2584 |
| 532 | 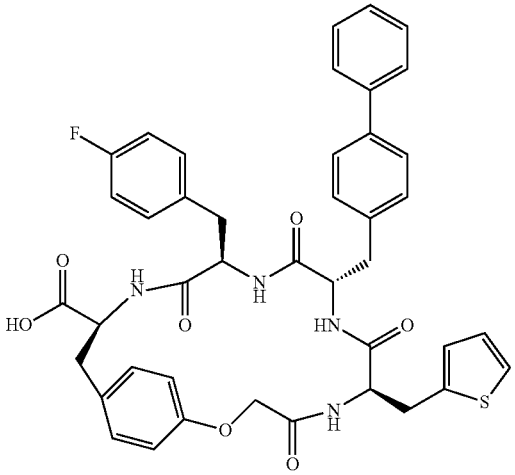 | 763.2596 | 763.2616 |
| 533 | 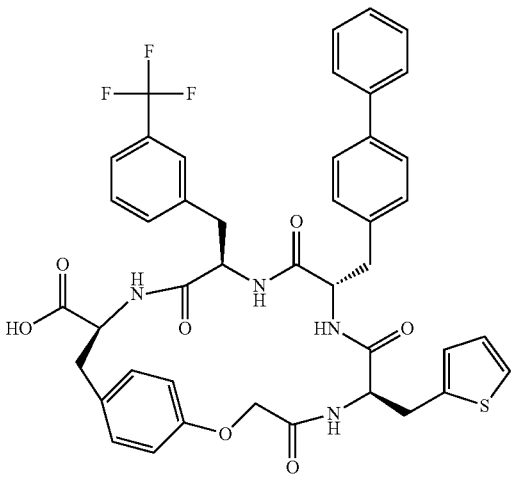 | 813.2565 | 813.2593 |

TABLE 1-continued

| Compound No. | Structure | MS Calcd | MS Observed |
|---|---|---|---|
| 534 | 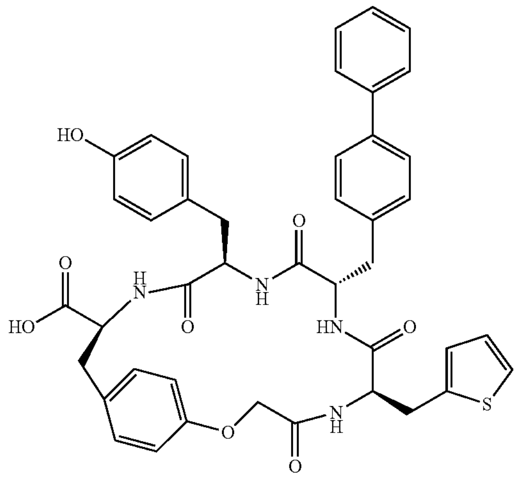 | 761.2640 | 761.2665 |
| 535 | 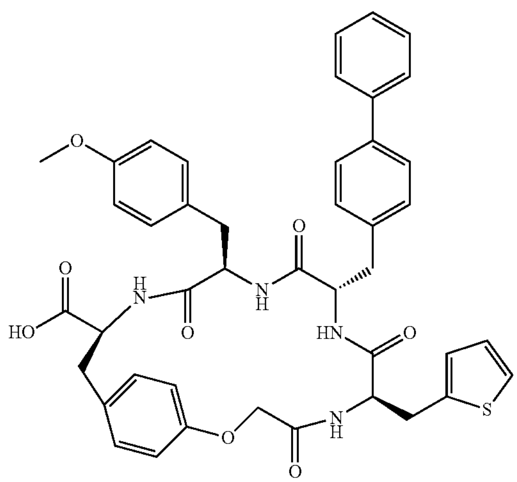 | 775.2796 | 775.2825 |
| 536 | 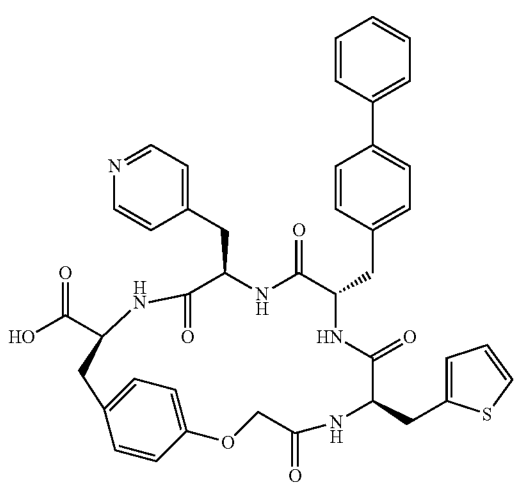 | 746.2643 | 746.2640 |

TABLE 1-continued

| Compound No. | Structure | MS Calcd | MS Observed |
|---|---|---|---|
| 537 | 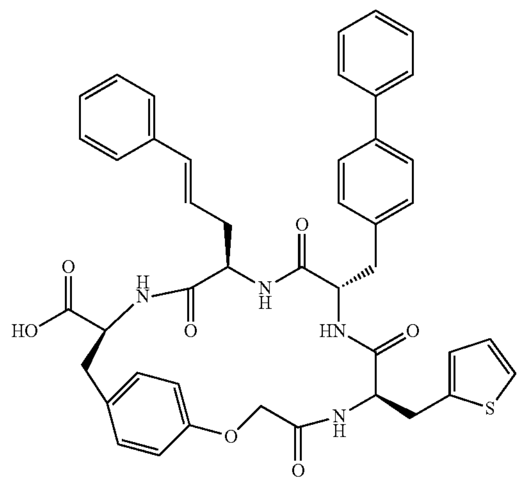 | 771.2847 | 771.2863 |
| 538 | 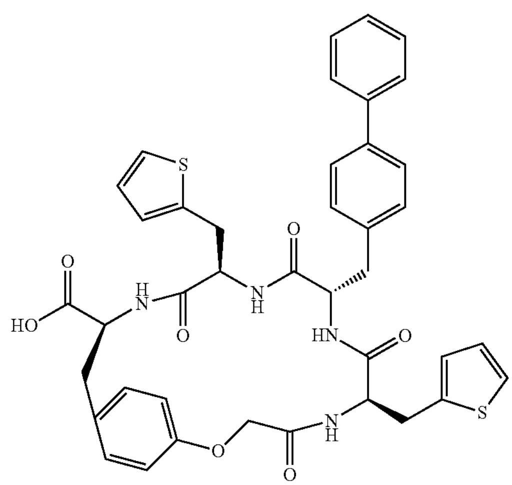 | 751.2255 | 751.2278 |
| 539 | 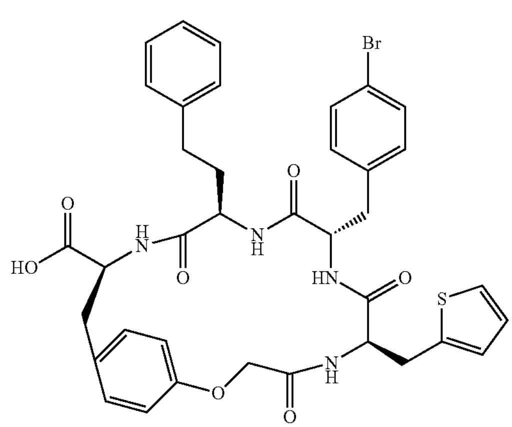 | 761.1639 | 761.1649 |

TABLE 1-continued

| Compound No. | Structure | MS Calcd | MS Observed |
|---|---|---|---|
| 540 | 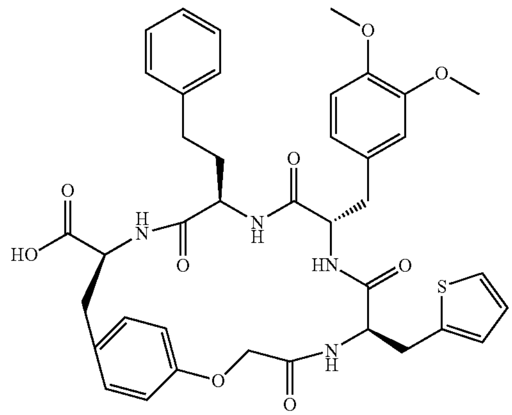 | 743.2746 | 743.2780 |
| 541 | 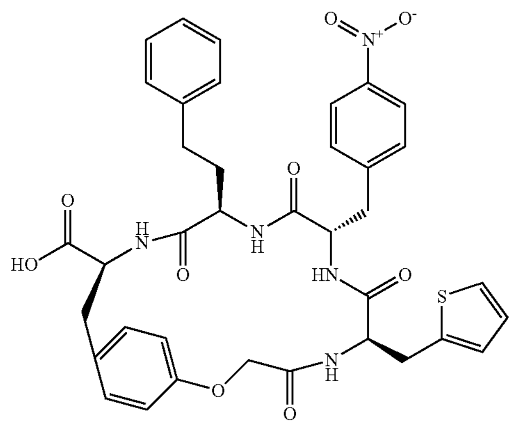 | 728.2385 | 728.2375 |
| 542 | 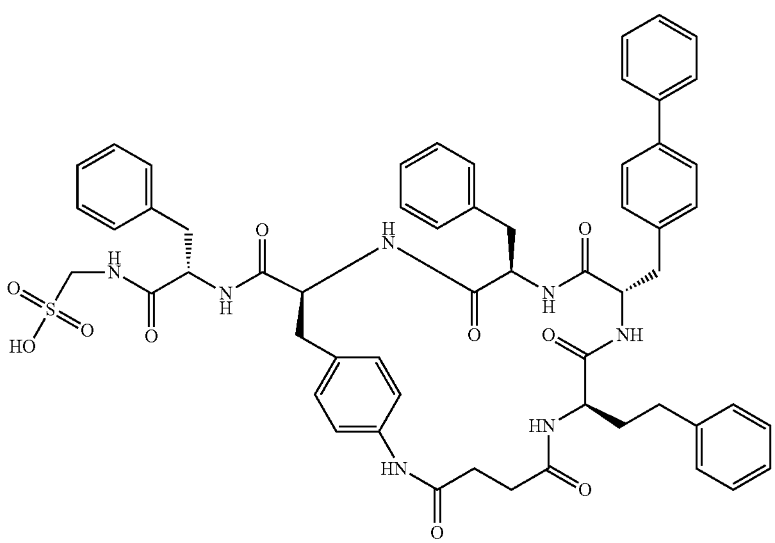 | 1034.4122 | 1034.4131 |

TABLE 1-continued

| Compound No. | Structure | MS Calcd | MS Observed |
|---|---|---|---|
| 543 | 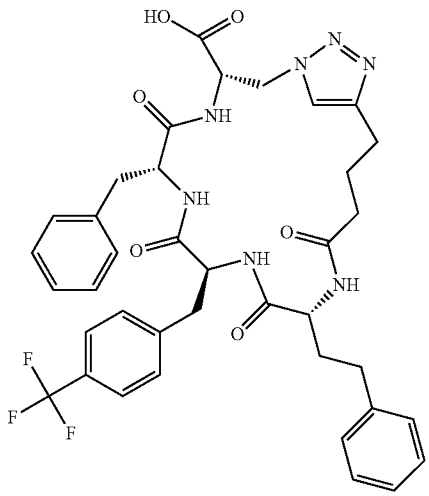 | 748.31 | 748.31 |
| 544 | 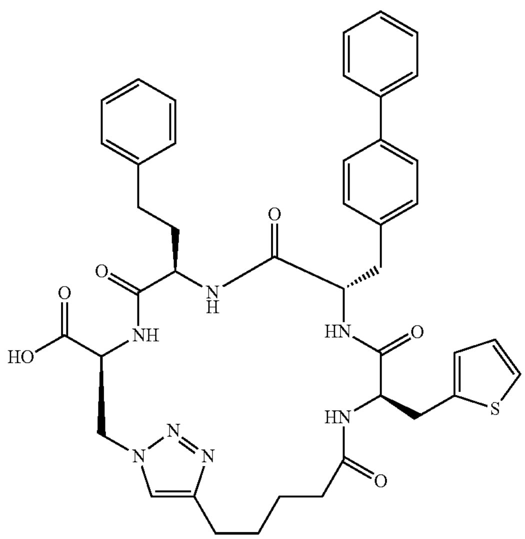 | 776.32 | 776.16 |
| 545 | 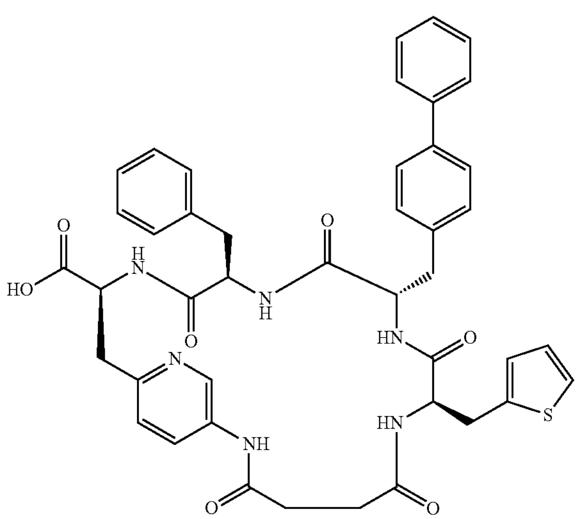 | 787.29 | 787.11 |

TABLE 1-continued

| Compound No. | Structure | MS Calcd | MS Observed |
|---|---|---|---|
| 546 | 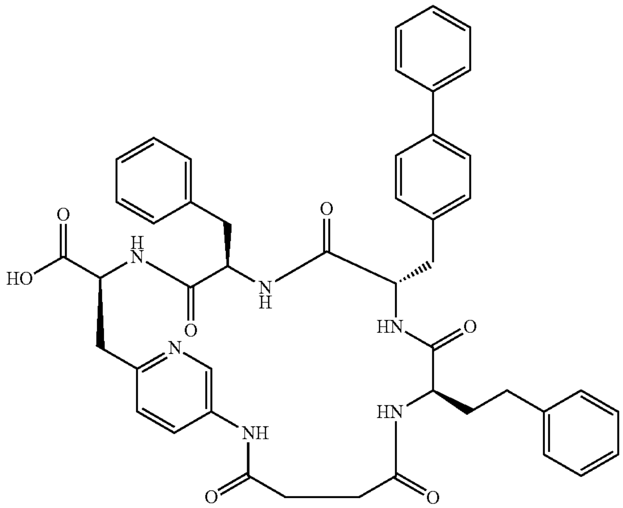 | 795.35 | 795.32 |
| 547 | 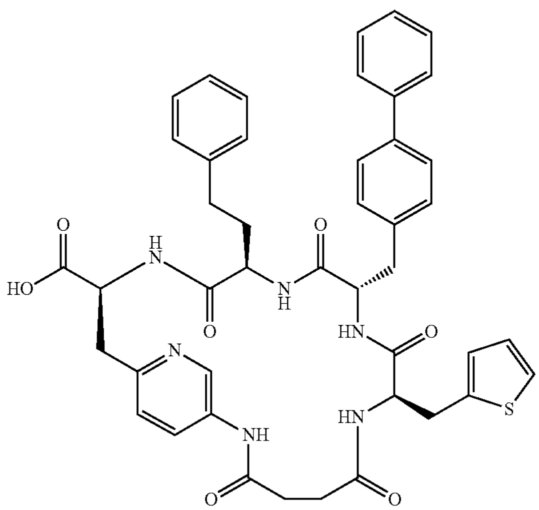 | 801.31 | 801.16 |
| 548 | 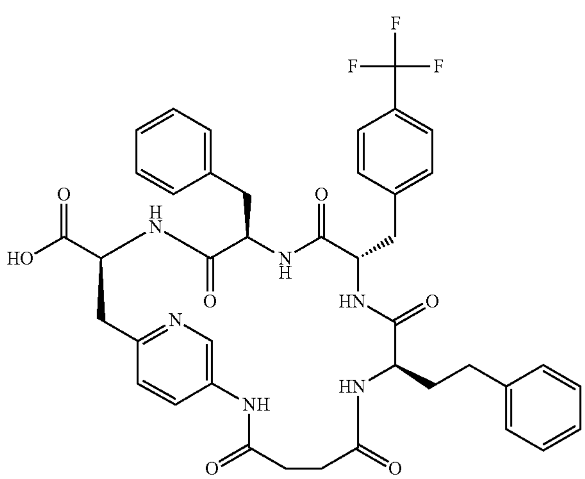 | 787.31 | 787.33 |

| Compound No. | Structure | MS Calcd | MS Observed |
|---|---|---|---|
| 549 | 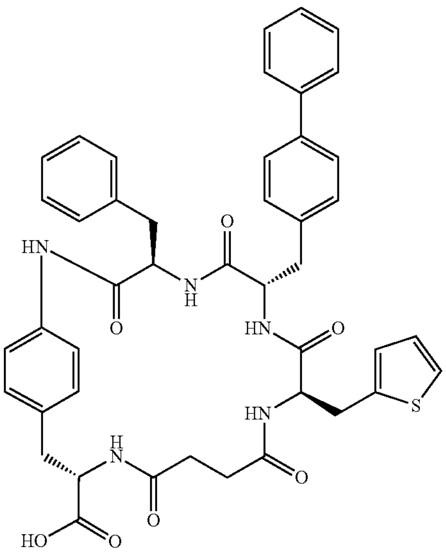 | 786.30 | 786.44 |
| 550 | 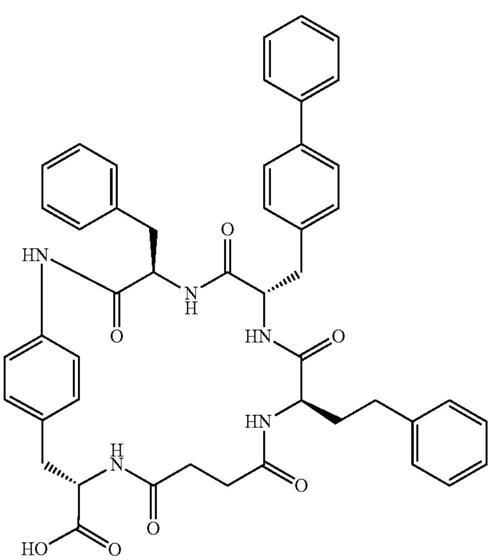 | 794.36 | 794.50 |

TABLE 1-continued
| Compound No. | Structure | MS Calcd | MS Observed |
|---|---|---|---|
| 551 | 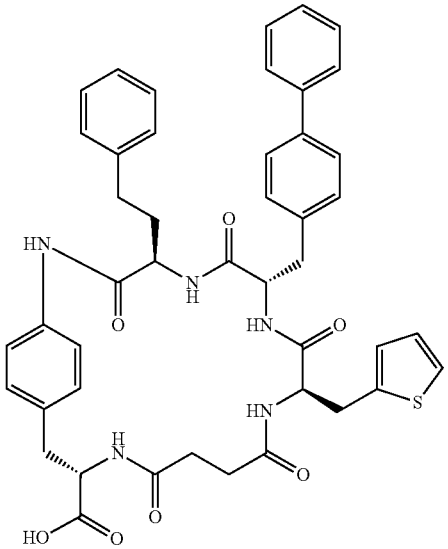 | 800.31 | 800.35 |
| 552 | 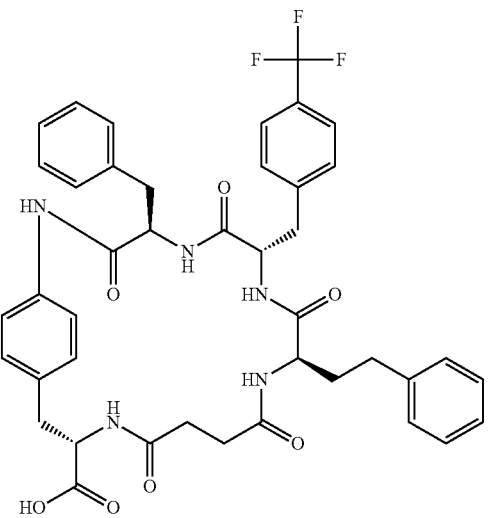 | 786.31 | 786.37 |

TABLE 1-continued
| Compound No. | Structure | MS Calcd | MS Observed |
|---|---|---|---|
| 553 | 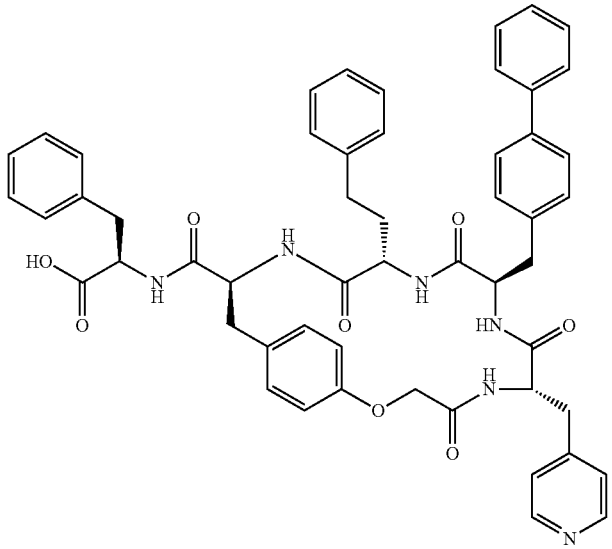 | 901.39 | 901.31 |
| 554 | 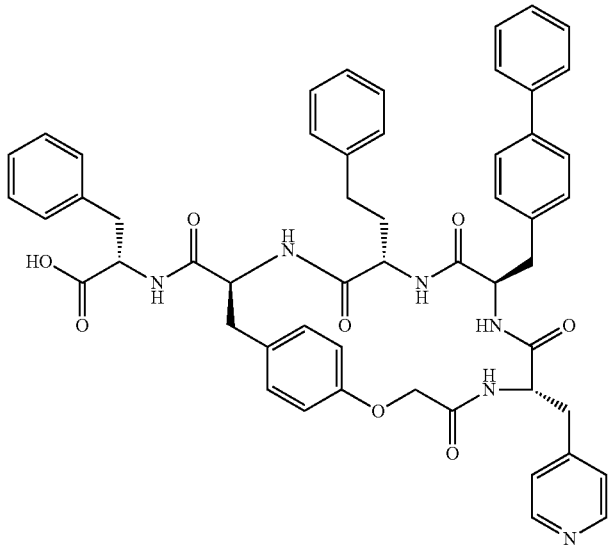 | 901.39 | 901.31 |

TABLE 1-continued

| Compound No. | Structure | MS Calcd | MS Observed |
|---|---|---|---|
| 555 | 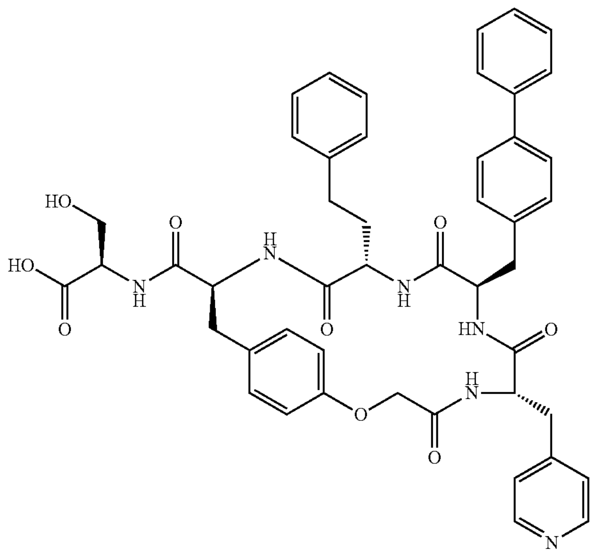 | 841.36 | 841.18 |
| 556 | 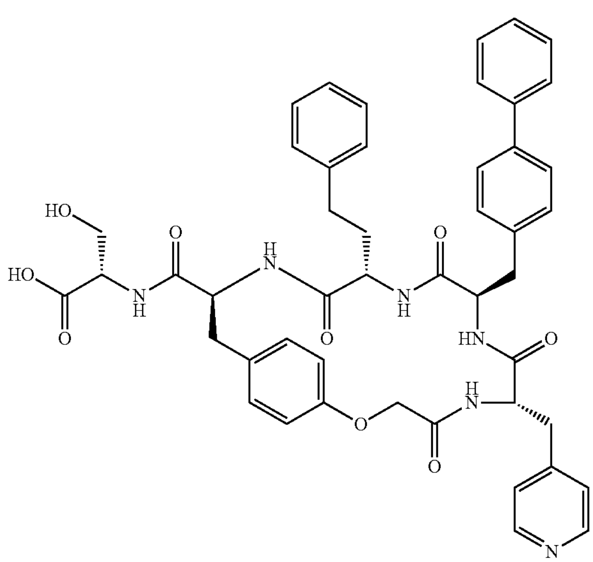 | 841.36 | 841.25 |

TABLE 1-continued

| Compound No. | Structure | MS Calcd | MS Observed |
|---|---|---|---|
| 557 | 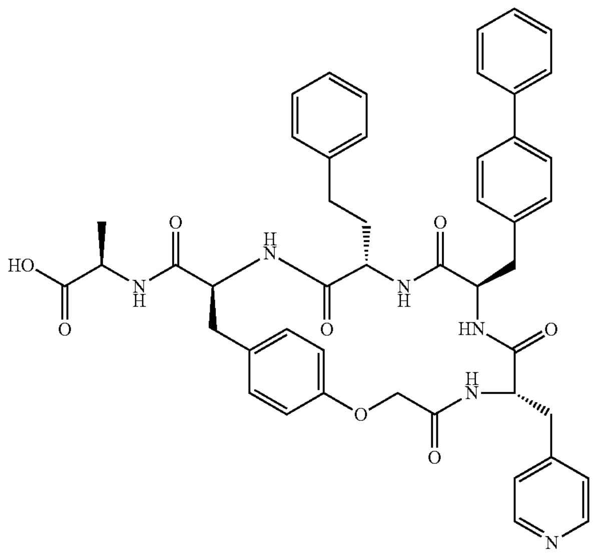 | 825.36 | 825.13 |
| 558 | 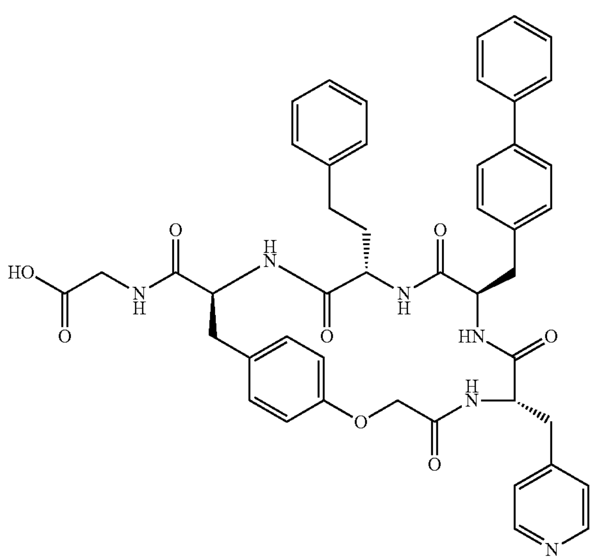 | 811.35 | 811.37 |

TABLE 1-continued

| Compound No. | Structure | MS Calcd | MS Observed |
|---|---|---|---|
| 559 | 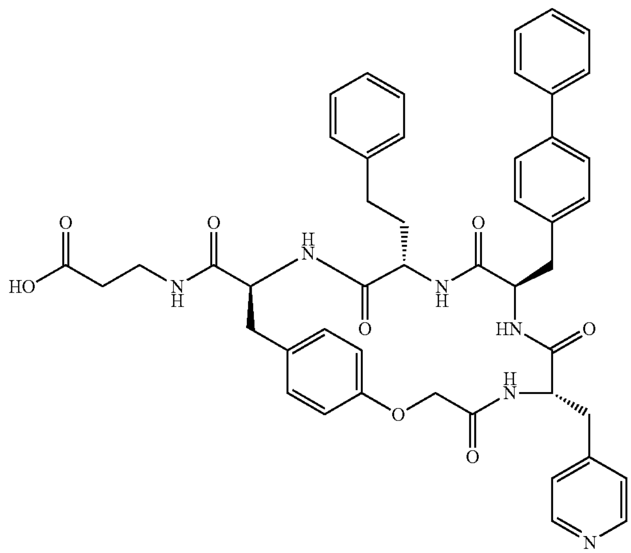 | 825.36 | 825.44 |
| 560 | 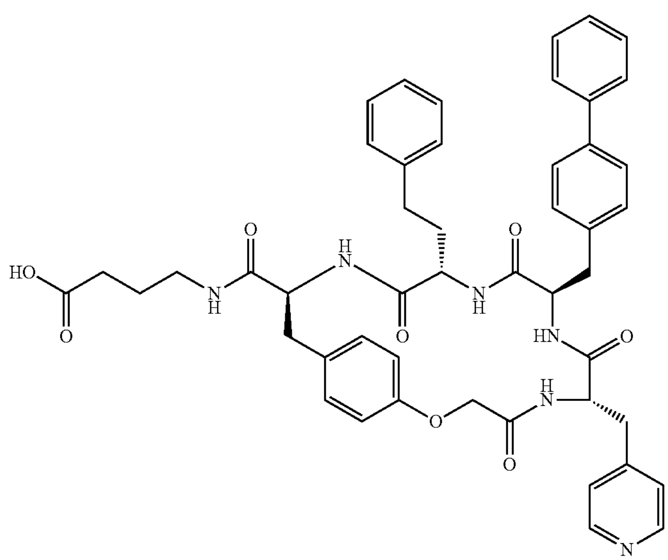 | 839.38 | 839.26 |

TABLE 1-continued

| Compound No. | Structure | MS Calcd | MS Observed |
|---|---|---|---|
| 561 | 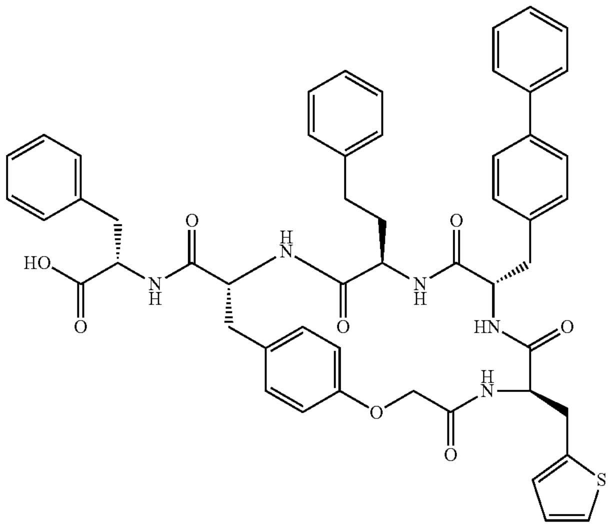 | 906.35 | 906.35 |
| 562 | 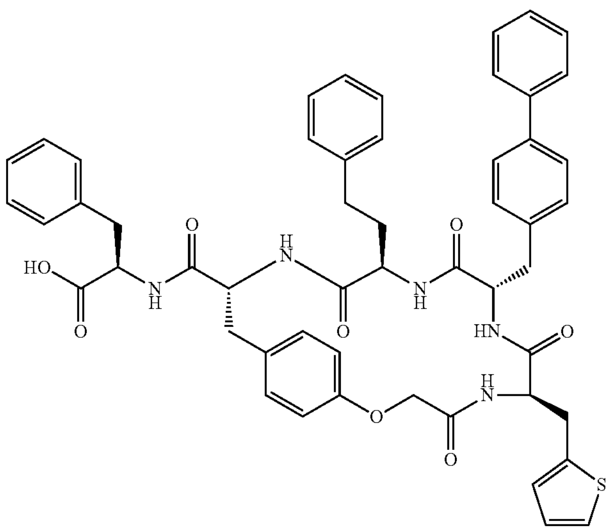 | 906.35 | 906.35 |
| 563 | 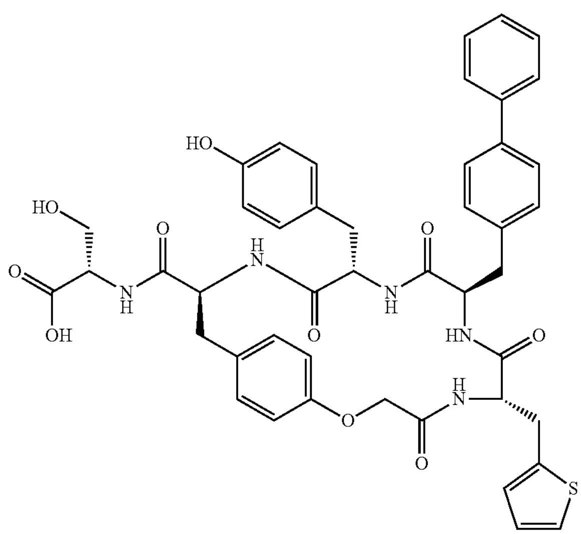 | 848.30 | 848.13 |

TABLE 1-continued

| Compound No. | Structure | MS Calcd | MS Observed |
|---|---|---|---|
| 564 | 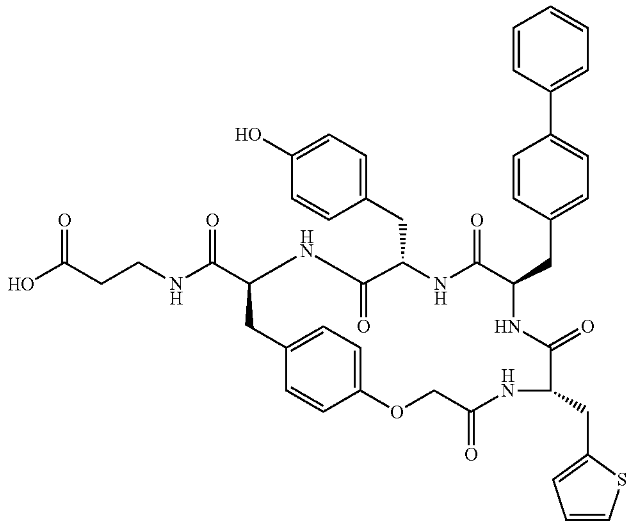 | 832.30 | 832.15 |
| 565 | 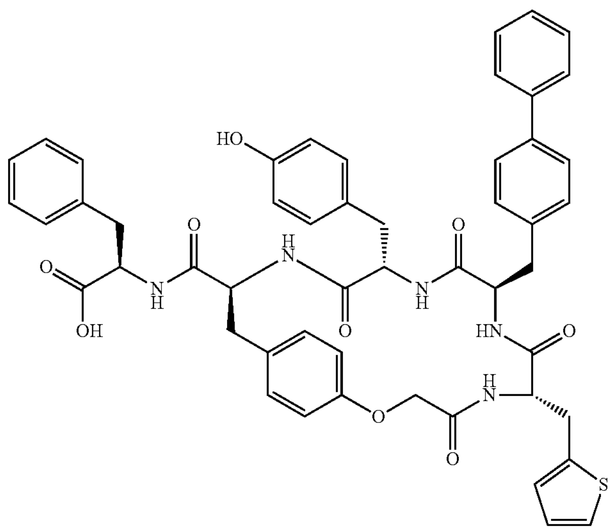 | 908.33 | 908.27 |
| 566 | 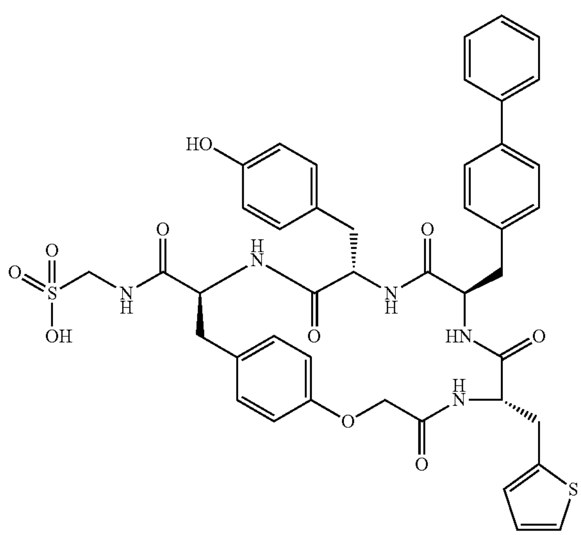 | 854.25 | 854.12 |

TABLE 1-continued

| Compound No. | Structure | MS Calcd | MS Observed |
|---|---|---|---|
| 567 | 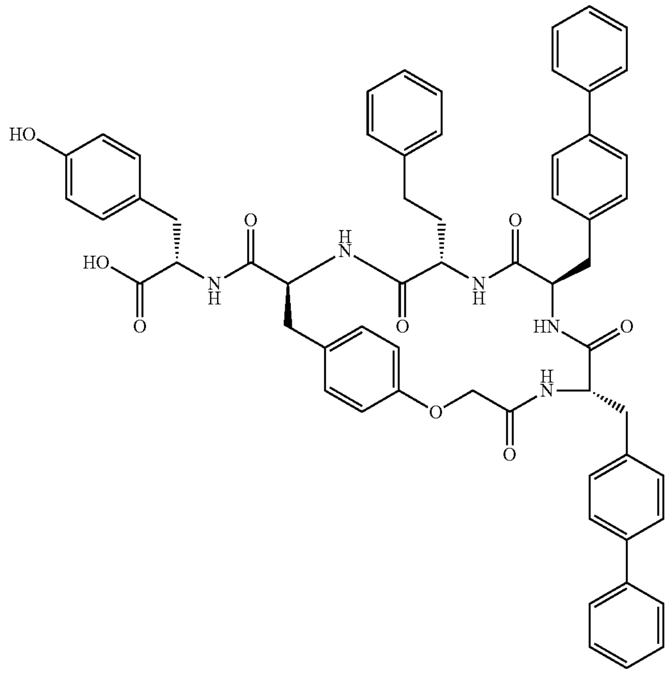 | 992.42 | 992.36 |
| 568 | 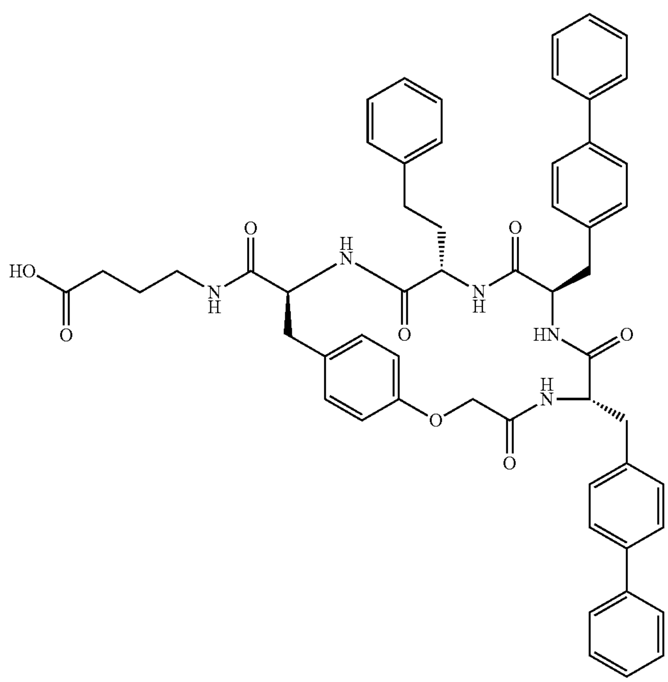 | 914.41 | 914.41 |

TABLE 1-continued

| Compound No. | Structure | MS Calcd | MS Observed |
|---|---|---|---|
| 569 | 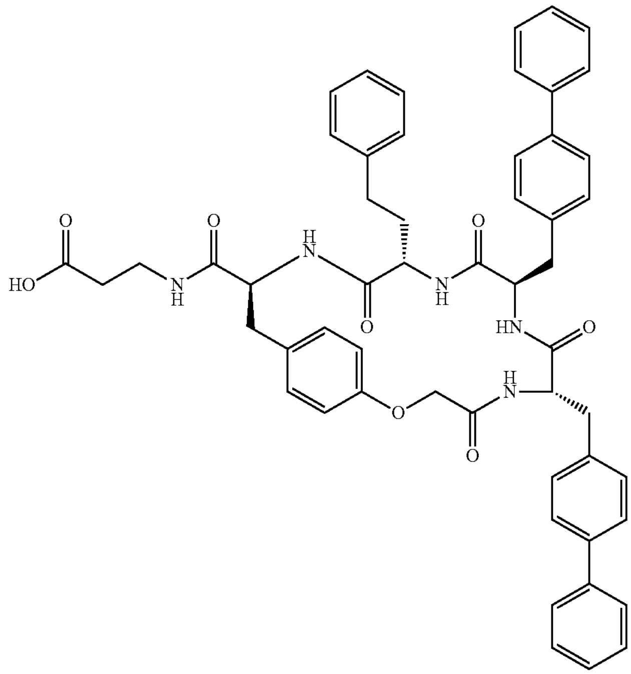 | 900.40 | |
| 570 | 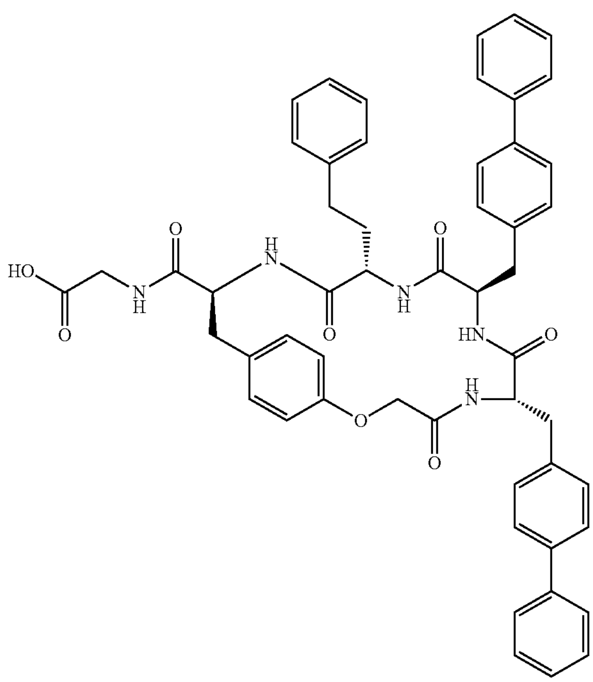 | 886.38 | 886.14 |

TABLE 1-continued

| Compound No. | Structure | MS Calcd | MS Observed |
|---|---|---|---|
| 571 | 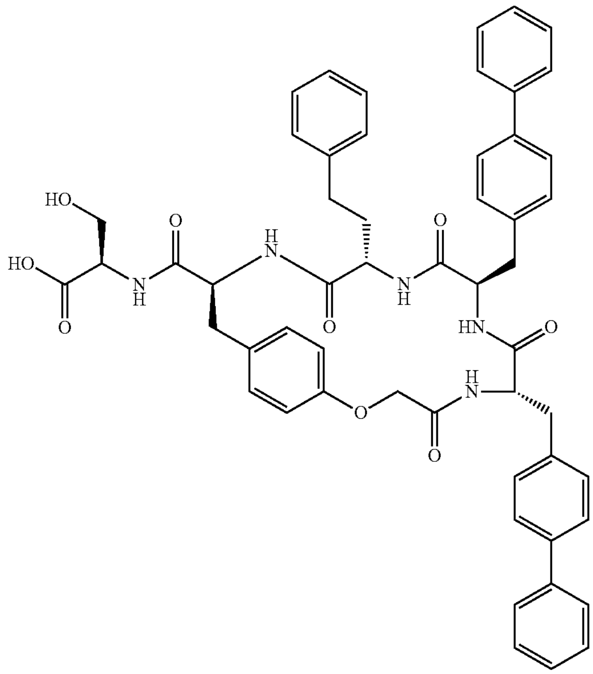 | 916.39 | 916.44 |
| 572 | 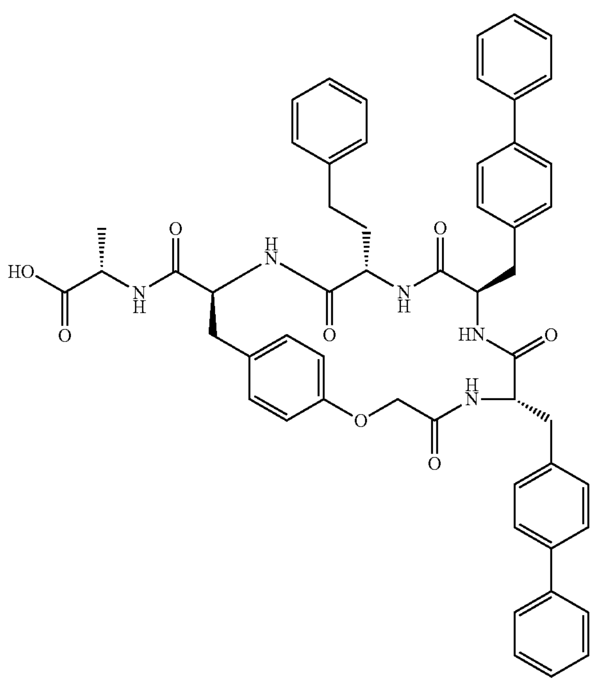 | 900.40 | 900.35 |

| Compound No. | Structure | MS Calcd | MS Observed |
|---|---|---|---|
| 573 | 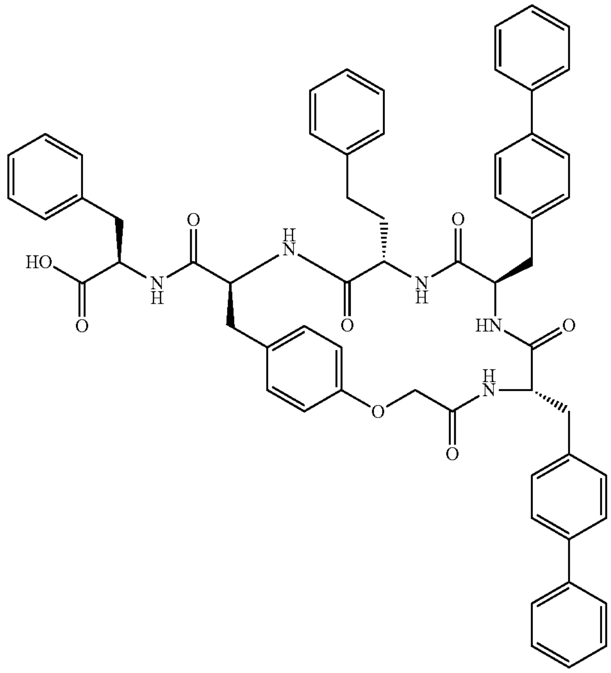 | 976.43 | 976.47 |
| 574 | 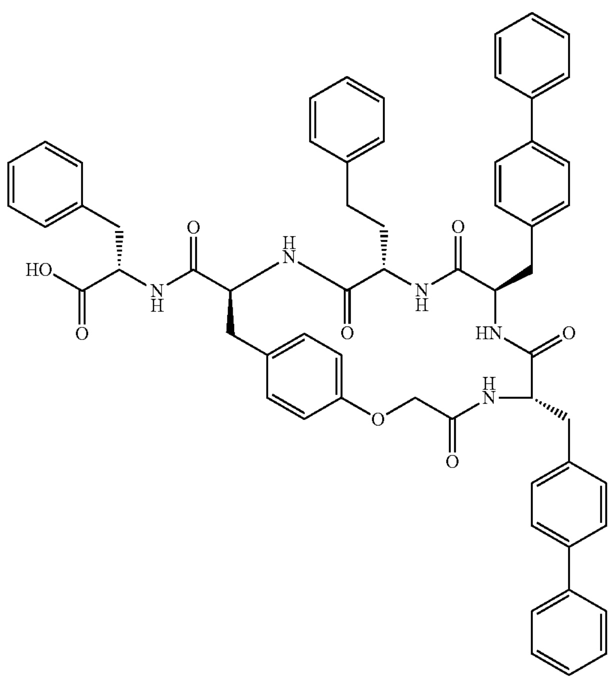 | 976.43 | 976.47 |

TABLE 1-continued

| Compound No. | Structure | MS Calcd | MS Observed |
|---|---|---|---|
| 575 | 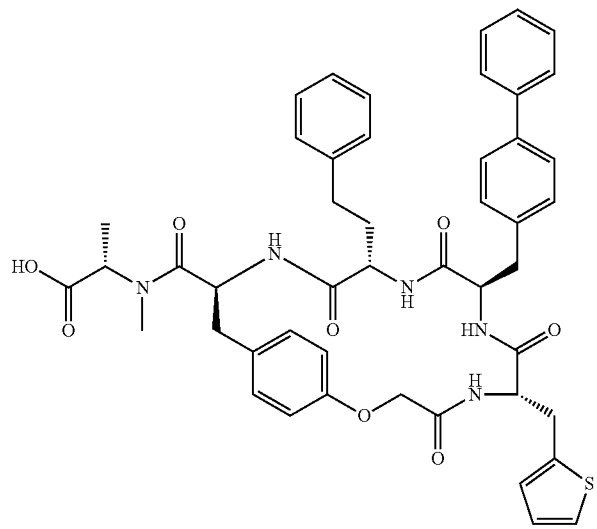 | 844.34 | 844.23 |
| 576 | 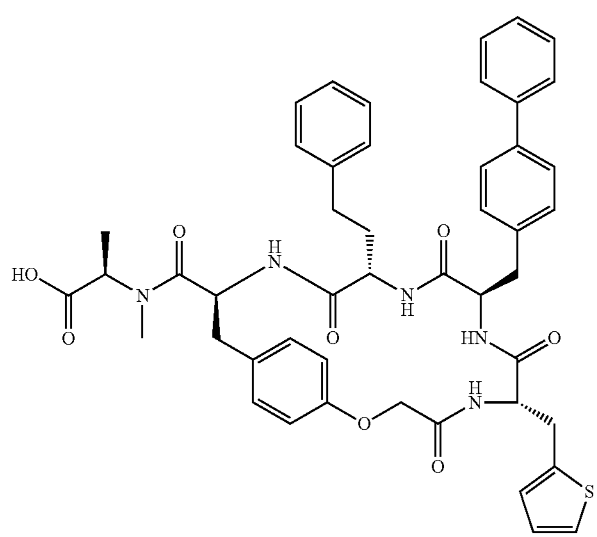 | 844.34 | 844.09 |

TABLE 1-continued

| Compound No. | Structure | MS Calcd | MS Observed |
|---|---|---|---|
| 577 | 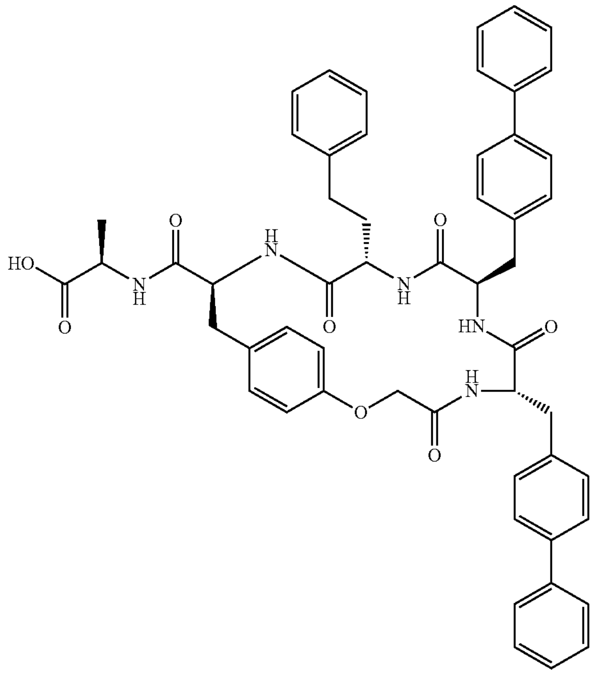 | 900.40 | 900.28 |
| 578 | 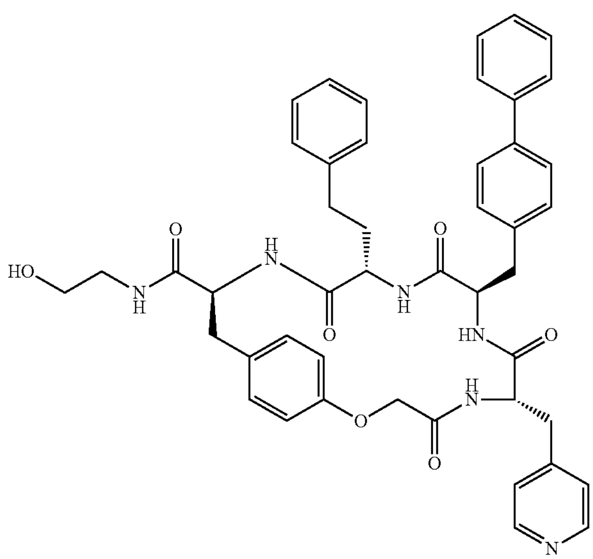 | 797.37 | 797.24 |

| Compound No. | Structure | MS Calcd | MS Observed |
|---|---|---|---|
| 579 | 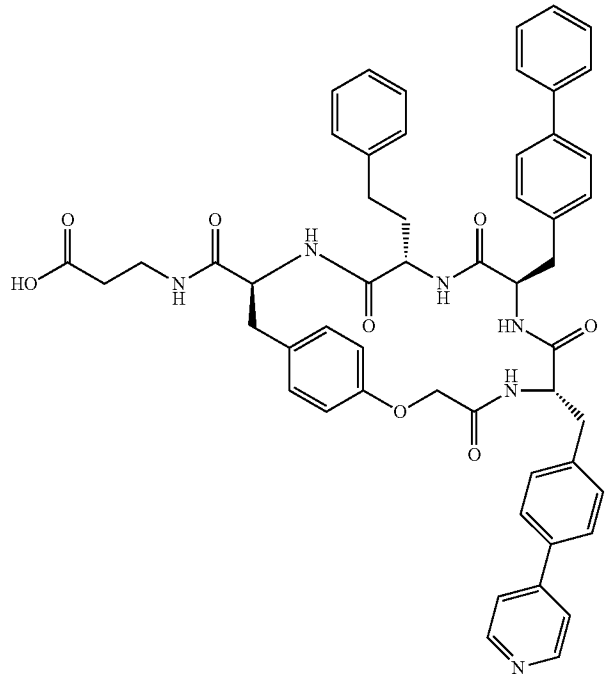 | 901.39 | 901.68 |
| 580 | 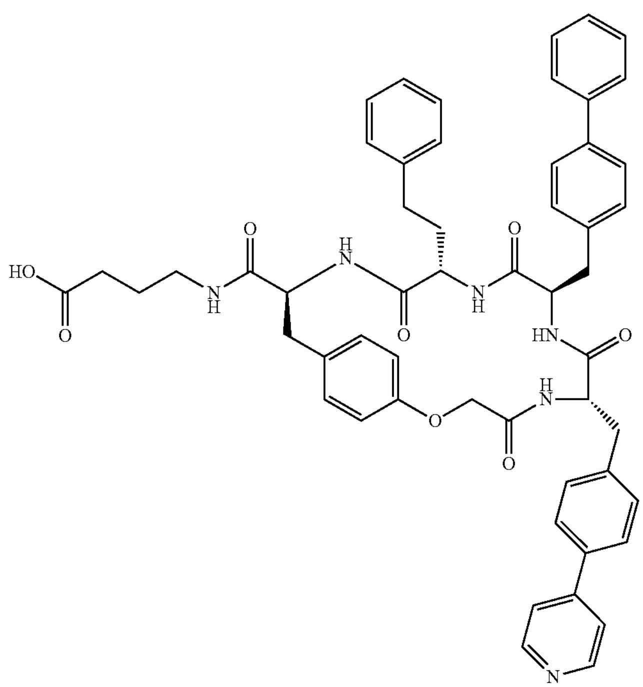 | 915.41 | 915.52 |

TABLE 1-continued

| Compound No. | Structure | MS Calcd | MS Observed |
|---|---|---|---|
| 581 | 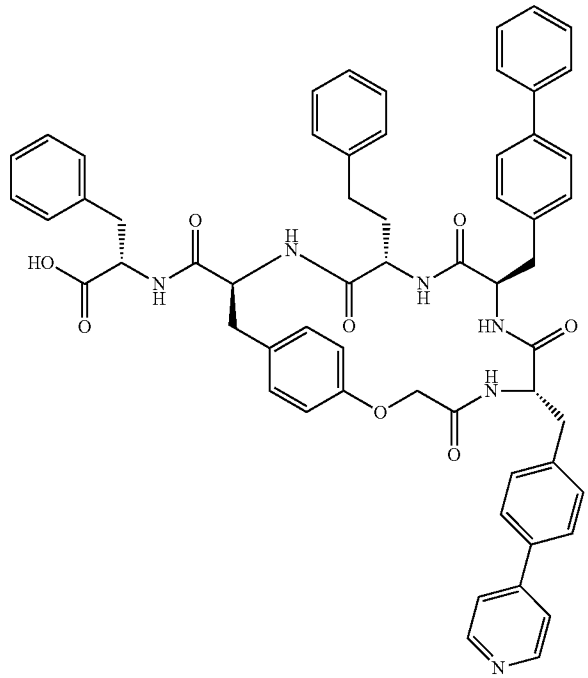 | 977.42 | 977.35 |
| 582 | 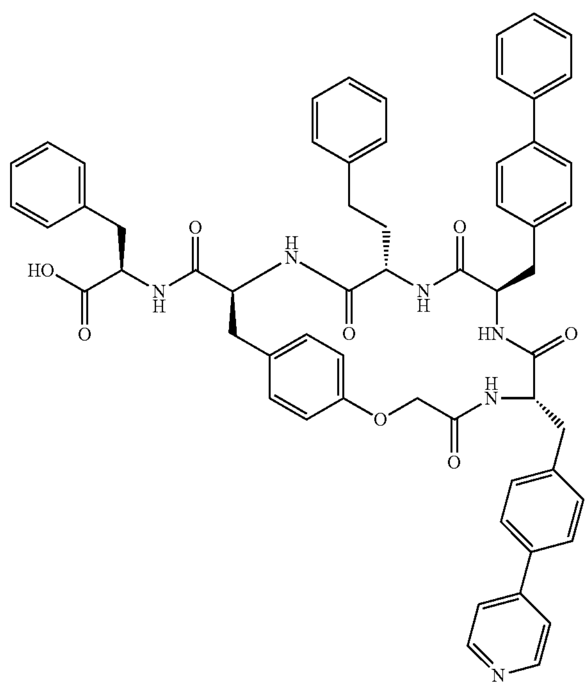 | 977.42 | 977.43 |

TABLE 1-continued

| Compound No. | Structure | MS Calcd | MS Observed |
|---|---|---|---|
| 583 | 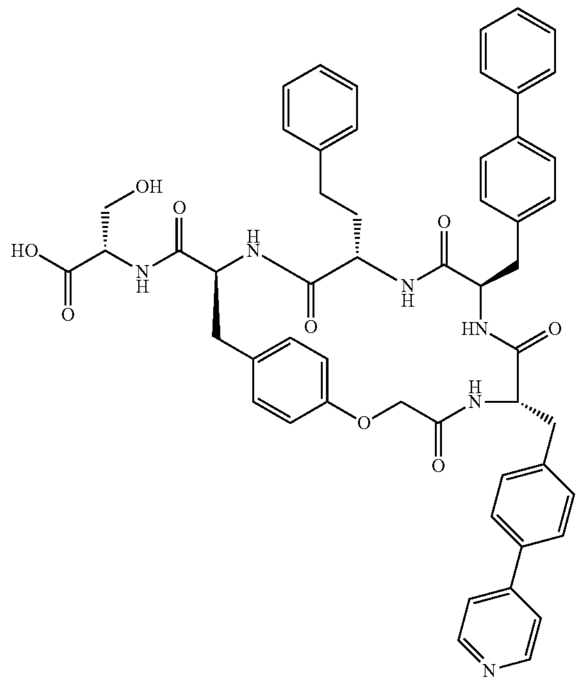 | 917.39 | 917.44 |
| 584 | 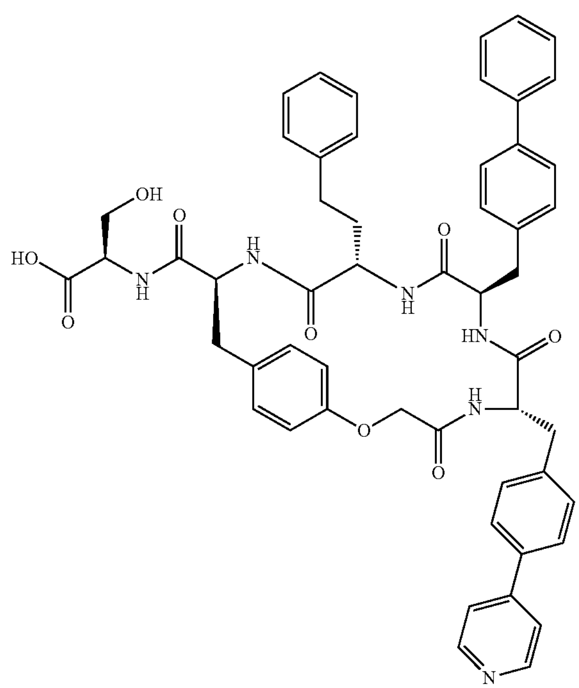 | 917.39 | 917.37 |

TABLE 1-continued

| Compound No. | Structure | MS Calcd | MS Observed |
|---|---|---|---|
| 585 | 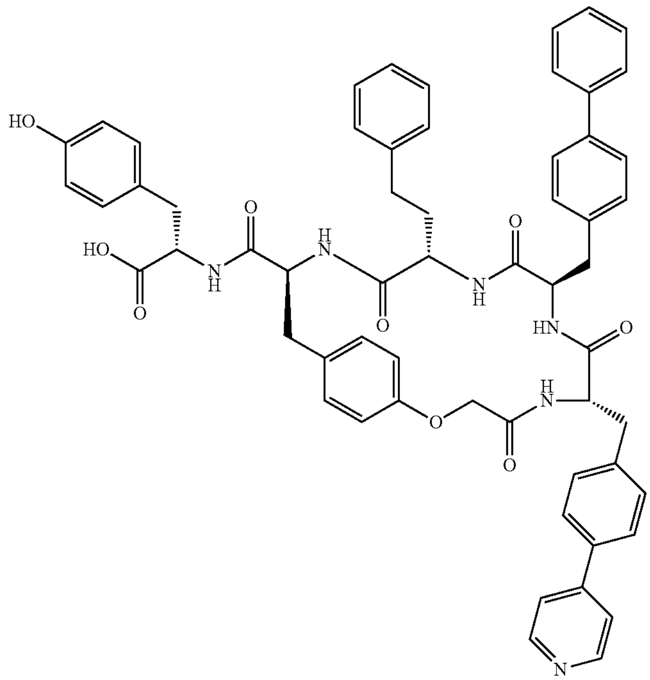 | 993.42 | 993.40 |
| 586 | 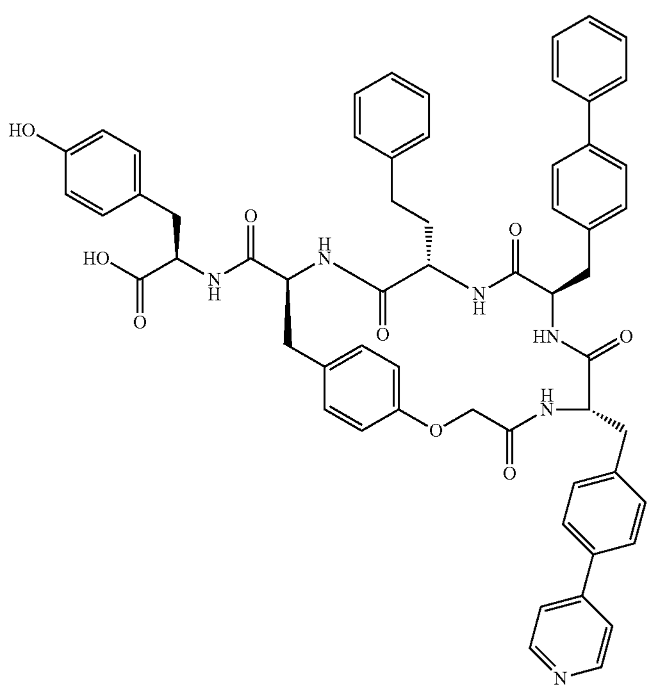 | 993.42 | 993.48 |

| Compound No. | Structure | MS Calcd | MS Observed |
|---|---|---|---|
| 587 | 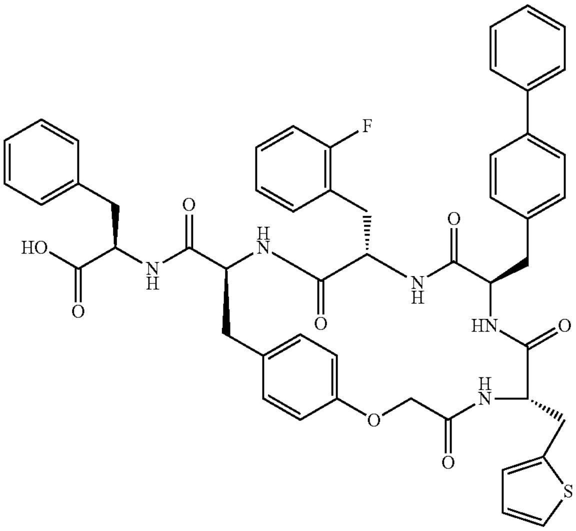 | 910.33 | 910.71 |
| 588 | 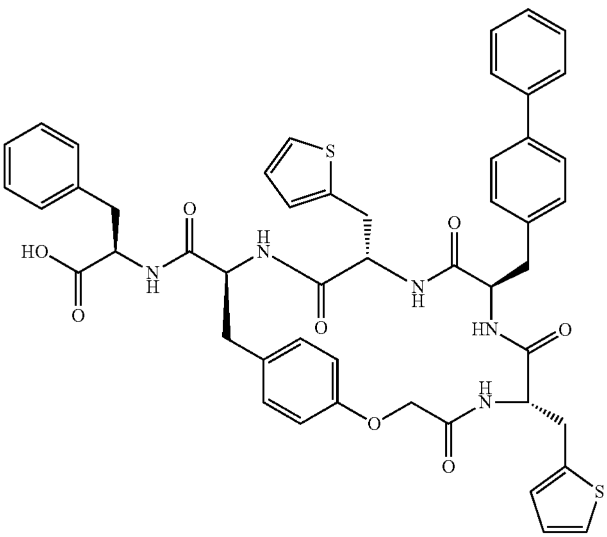 | 898.29 | 898.62 |
| 590 | 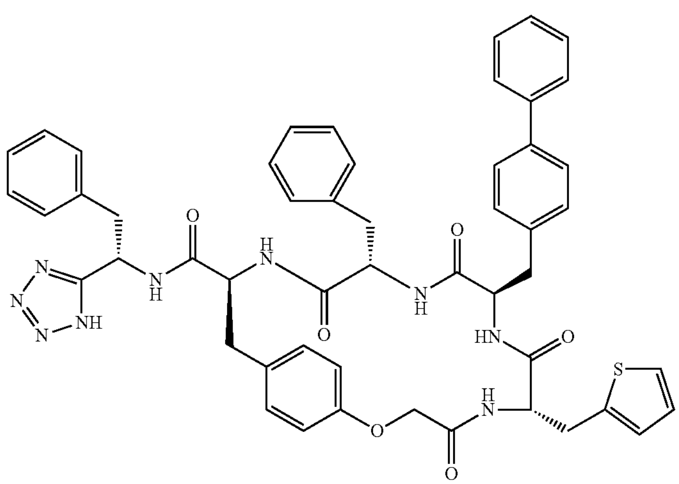 | 930.38 | 930.38 |

TABLE 1-continued

| Compound No. | Structure | MS Calcd | MS Observed |
|---|---|---|---|
| 591 | 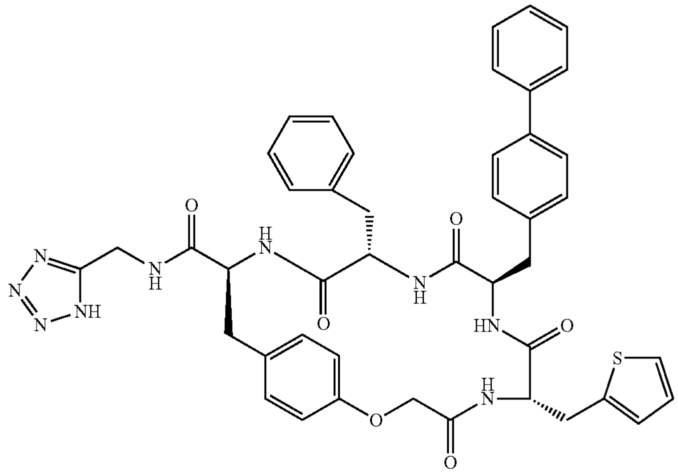 | 916.36 | 916.77 |
| 592 | 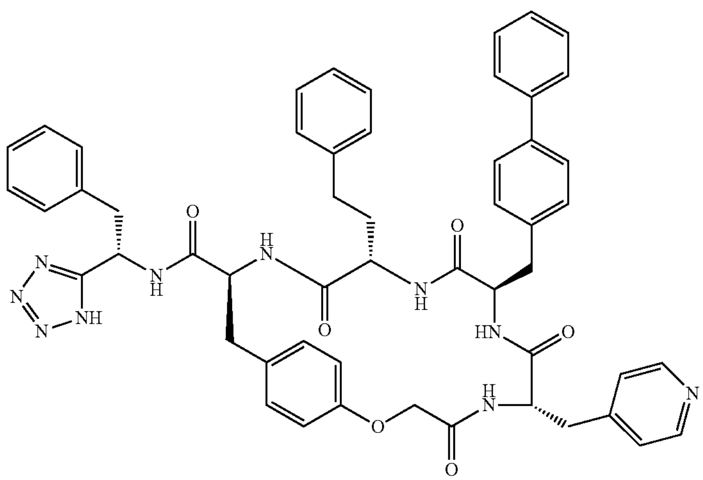 | 826.31 | 826.53 |
| 593 | 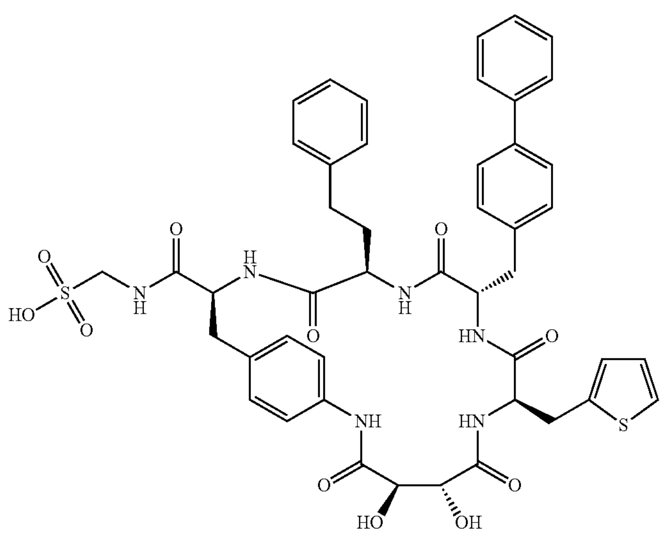 | 925.41 | 925.72 |

TABLE 1-continued

| Compound No. | Structure | MS Calcd | MS Observed |
|---|---|---|---|
| 594 | 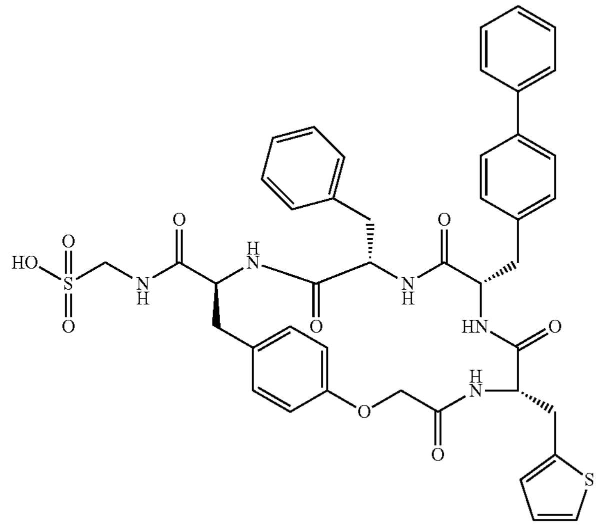 | 925.29 | 925.45 |
| 595 | 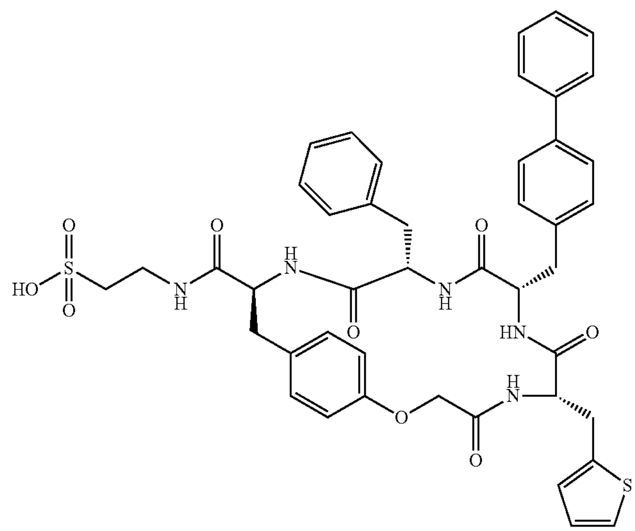 | 838.26 | 838.21 |
| 596 | 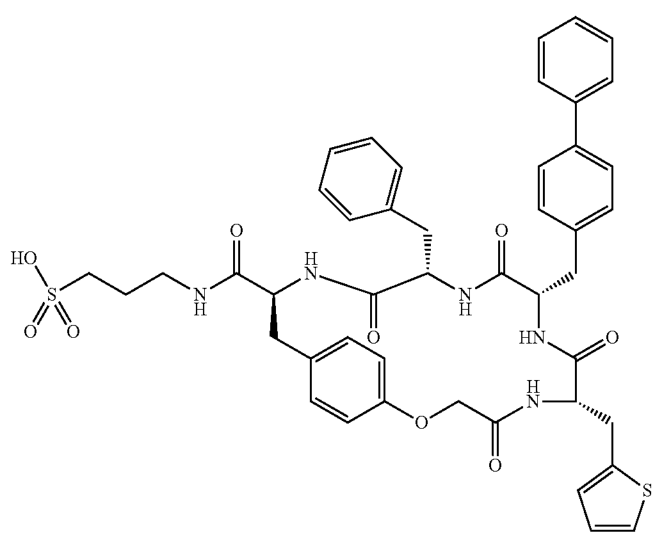 | 852.27 | 852.22 |

TABLE 1-continued

| Compound No. | Structure | MS Calcd | MS Observed |
|---|---|---|---|
| 597 | 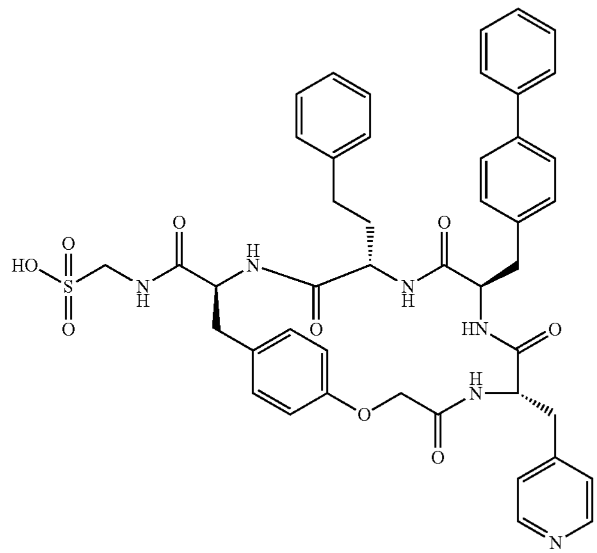 | 866.29 | 866.29 |
| 598 | 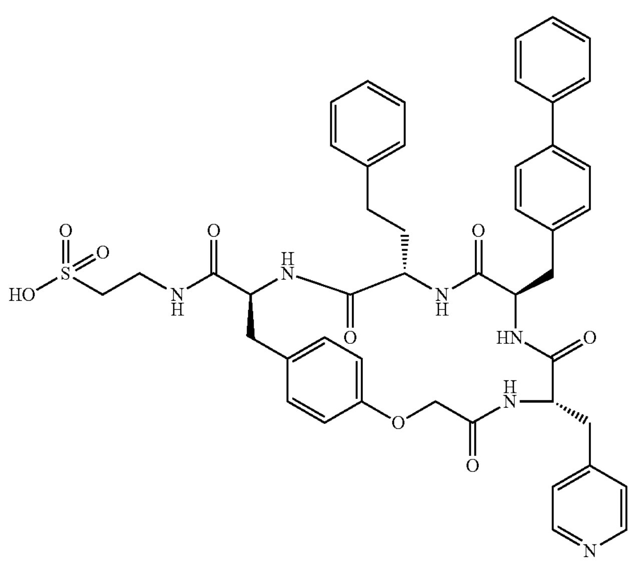 | 847.31 | 847.25 |

TABLE 1-continued

| Compound No. | Structure | MS Calcd | MS Observed |
|---|---|---|---|
| 599 | 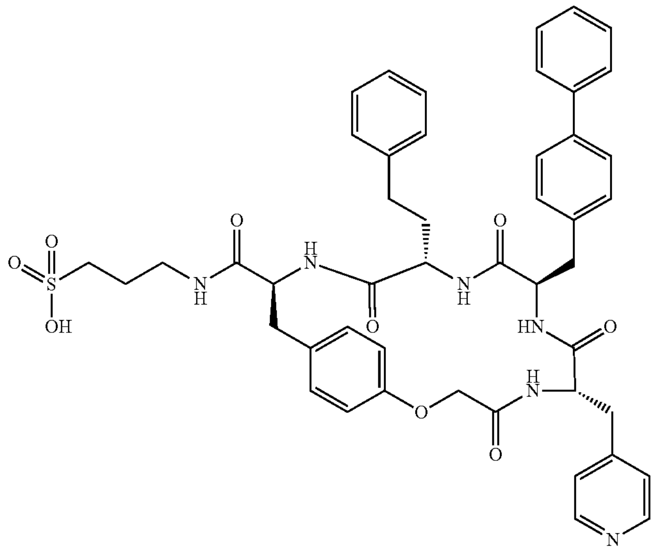 | 861.33 | 861.19 |
| 600 | 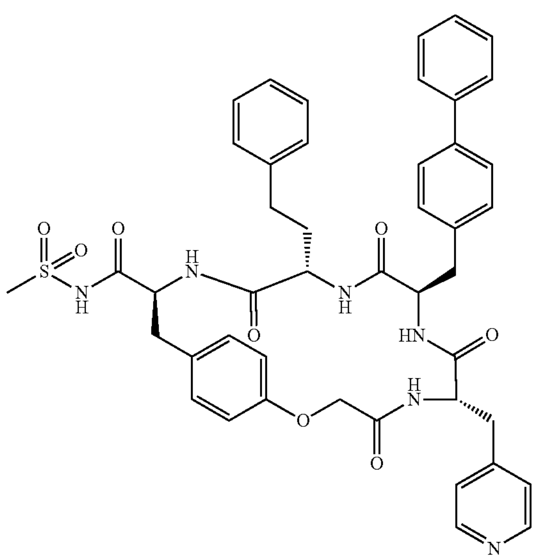 | 875.34 | 875.40 |

TABLE 1-continued

| Compound No. | Structure | MS Calcd | MS Observed |
|---|---|---|---|
| 601 | 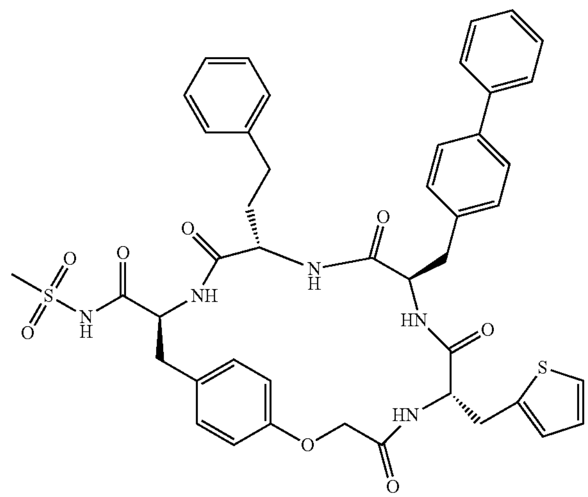 | 831.32 | 831.35 |
| 602 | 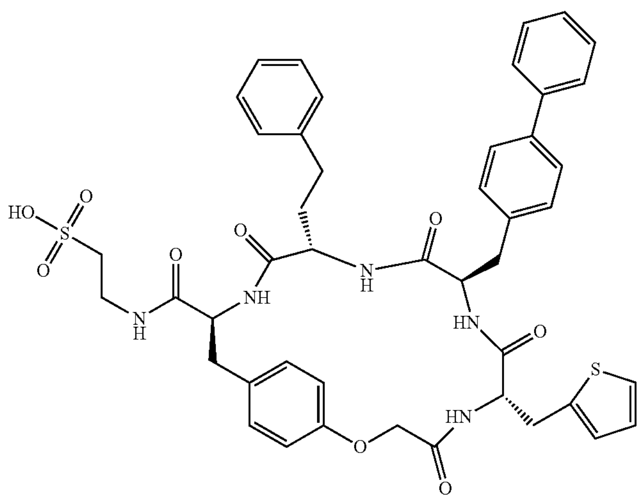 | 836.28 | 836.26 |
| 603 | 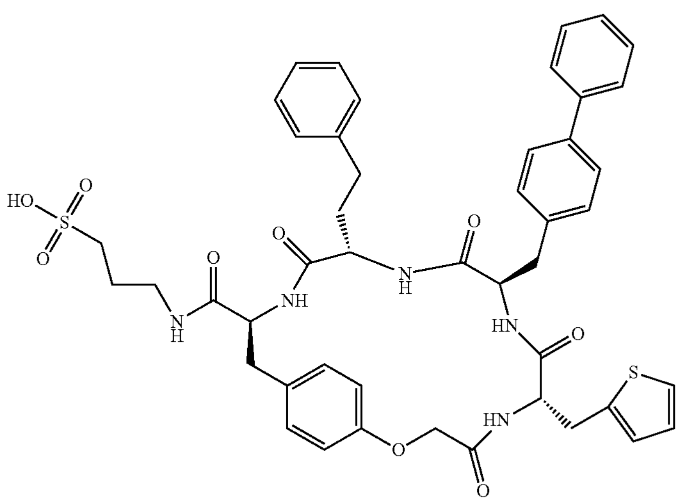 | 866.29 | 866.11 |

TABLE 1-continued

| Compound No. | Structure | MS Calcd | MS Observed |
|---|---|---|---|
| 604 | 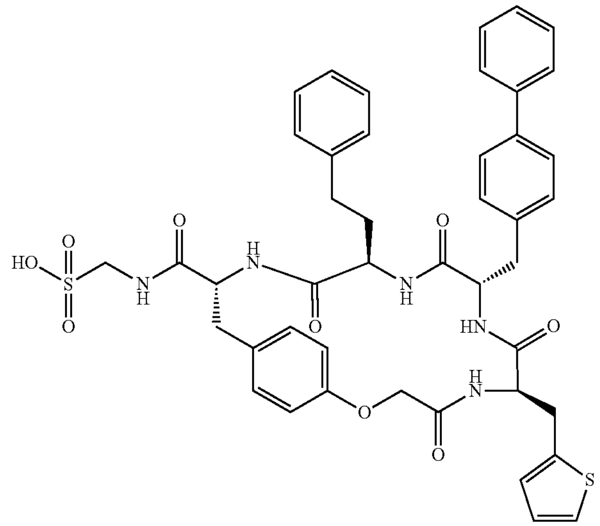 | 880.31 | 880.23 |
| 605 | 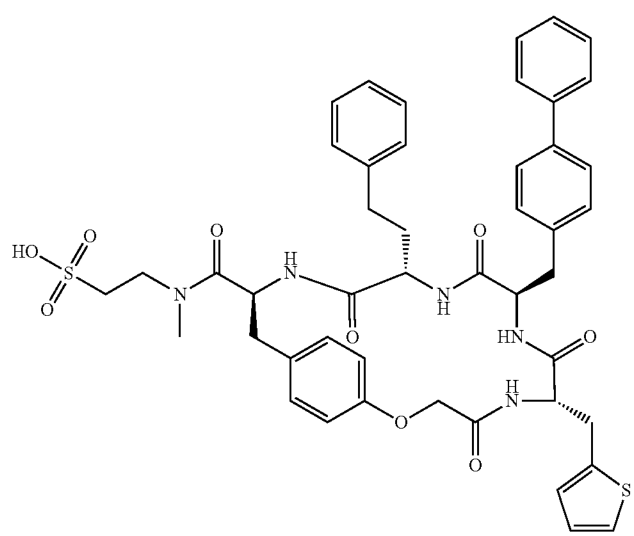 | 852.27 | 852.27 |

TABLE 1-continued

| Compound No. | Structure | MS Calcd | MS Observed |
|---|---|---|---|
| 606 | 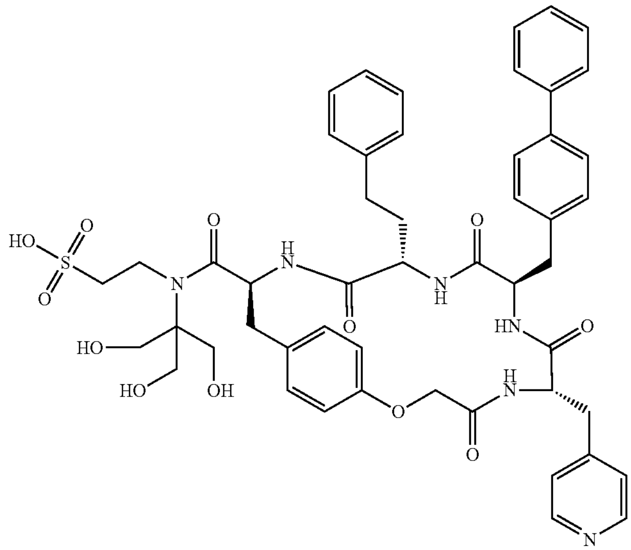 | 880.31 | 880.31 |
| 607 | 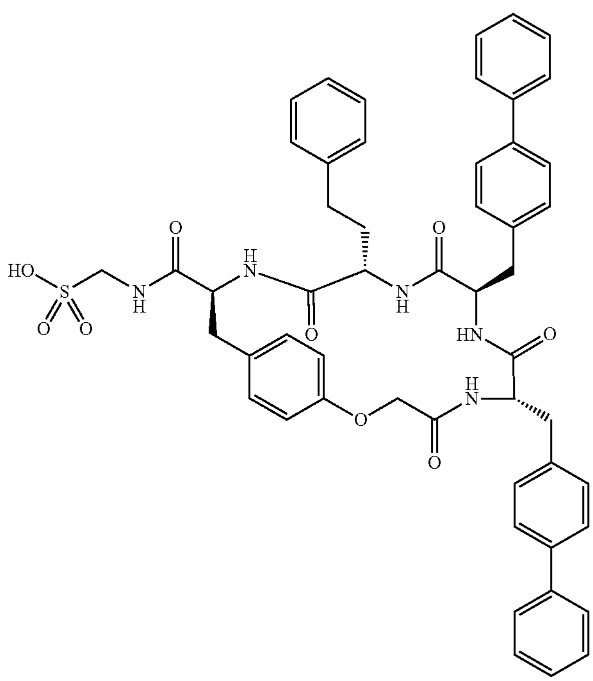 | 965.38 | 965.15 |

TABLE 1-continued

| Compound No. | Structure | MS Calcd | MS Observed |
|---|---|---|---|
| 608 | 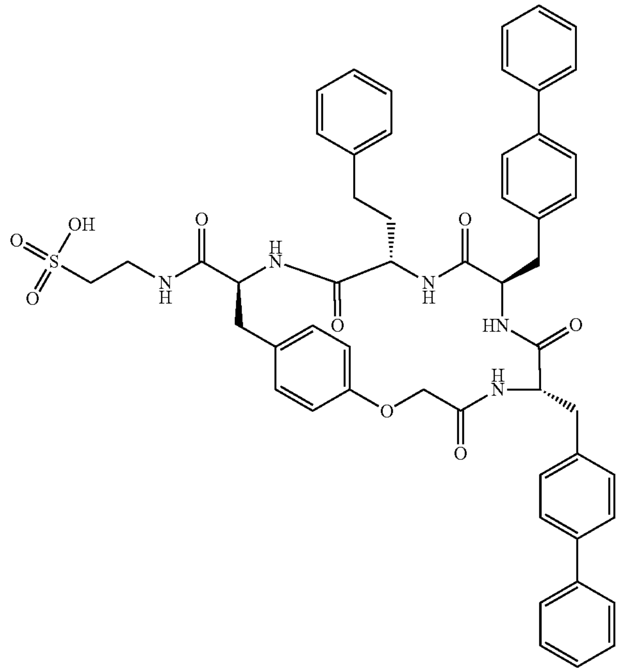 | 922.35 | 922.39 |
| 609 | 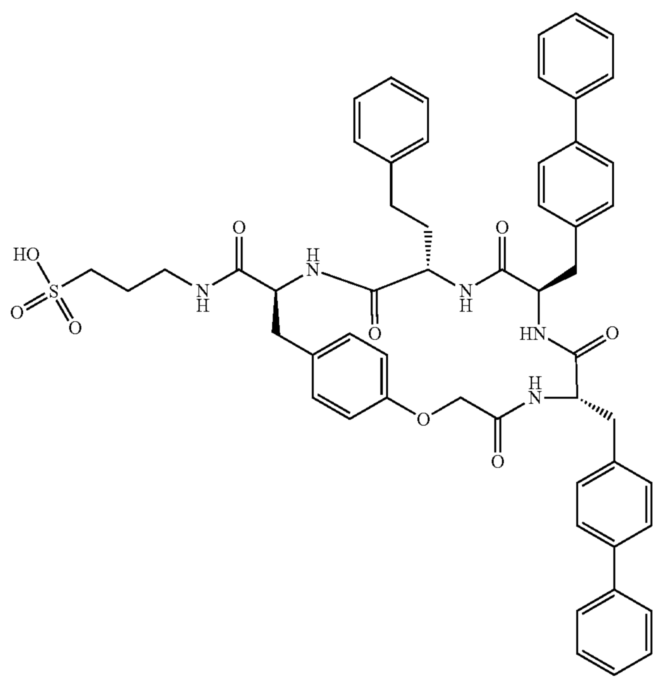 | 936.36 | 936.31 |

TABLE 1-continued

| Compound No. | Structure | MS Calcd | MS Observed |
|---|---|---|---|
| 610 | 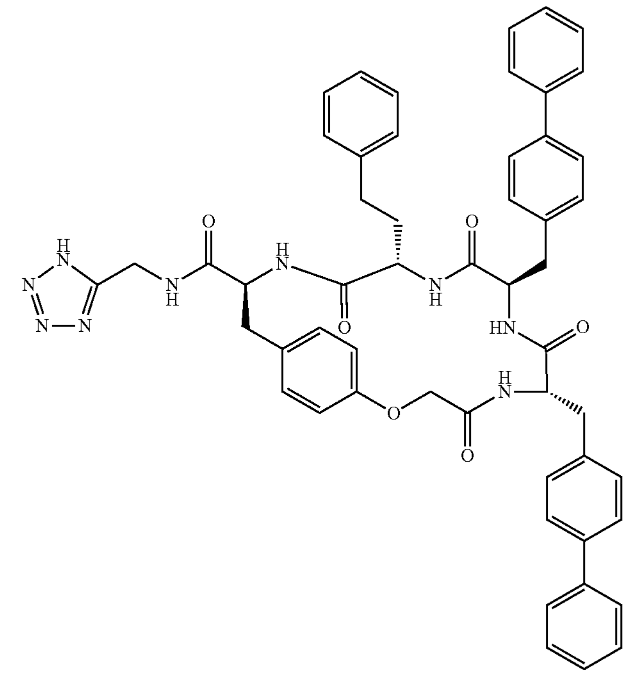 | 950.38 | 950.38 |
| 611 | 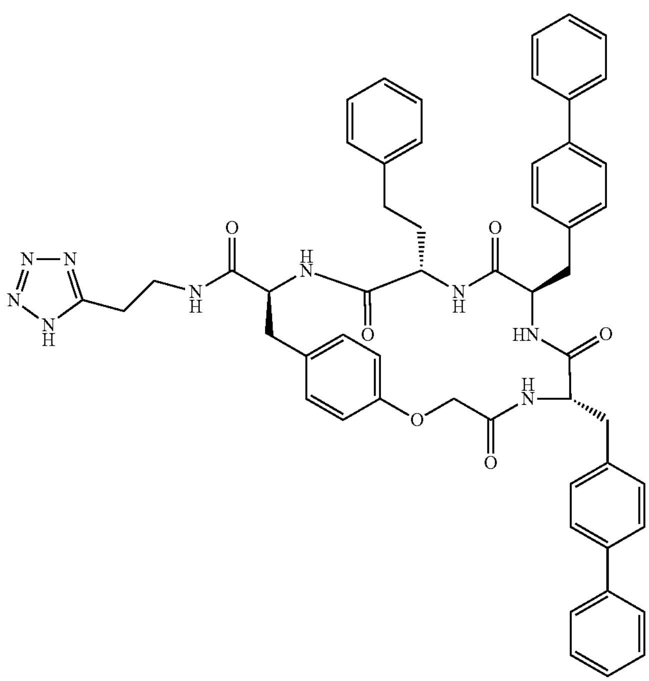 | 910.40 | 910.28 |

TABLE 1-continued

| Compound No. | Structure | MS Calcd | MS Observed |
|---|---|---|---|
| 612 | 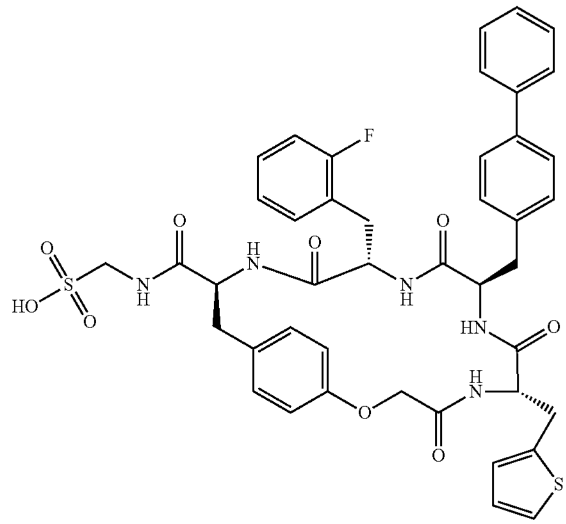 | 924.42 | 924.35 |
| 613 | 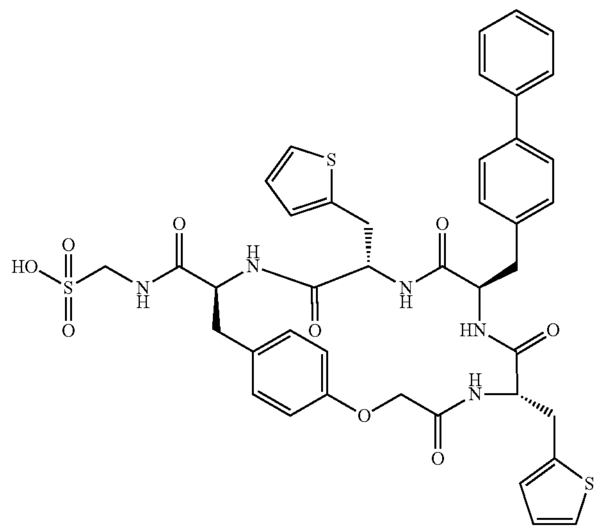 | 856.25 | 856.04 |
| 614 | 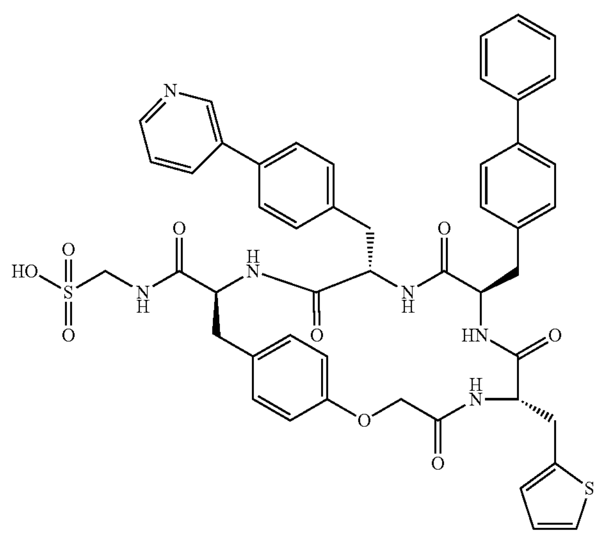 | 844.21 | 844.06 |

TABLE 1-continued

| Compound No. | Structure | MS Calcd | MS Observed |
|---|---|---|---|
| 615 | 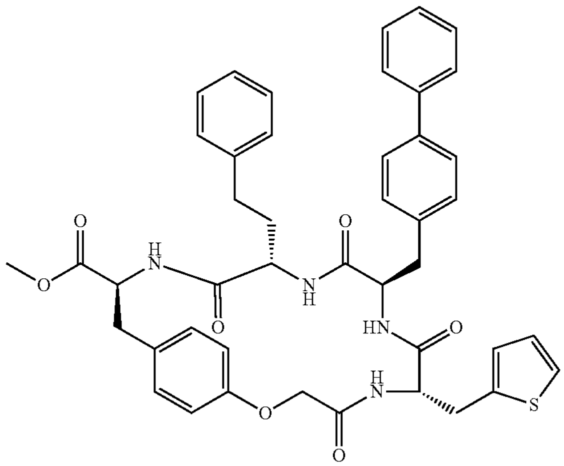 | 915.28 | 915.15 |
| 616 | 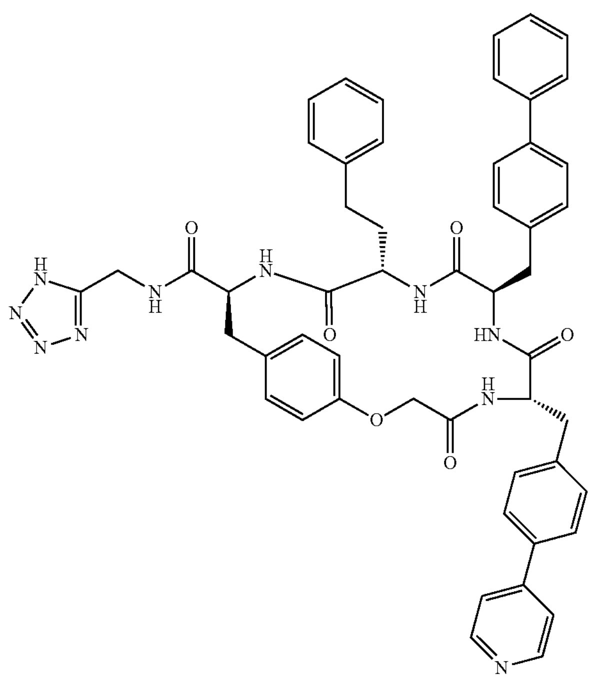 | 773.30 | 773.42 |

TABLE 1-continued

| Compound No. | Structure | MS Calcd | MS Observed |
|---|---|---|---|
| 617 | 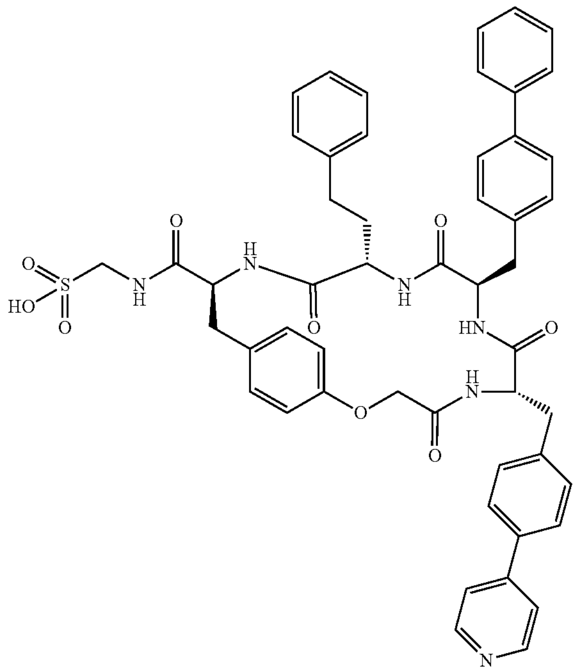 | 911.40 | 911.52 |
| 618 | 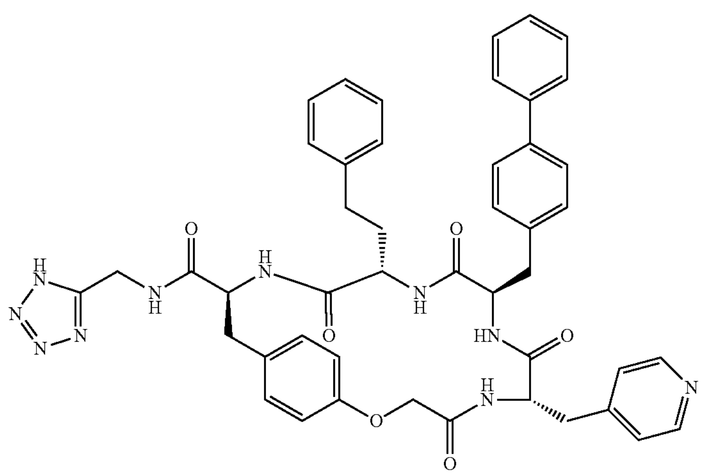 | 923.34 | 923.43 |

TABLE 1-continued

| Compound No. | Structure | MS Calcd | MS Observed |
|---|---|---|---|
| 619 | 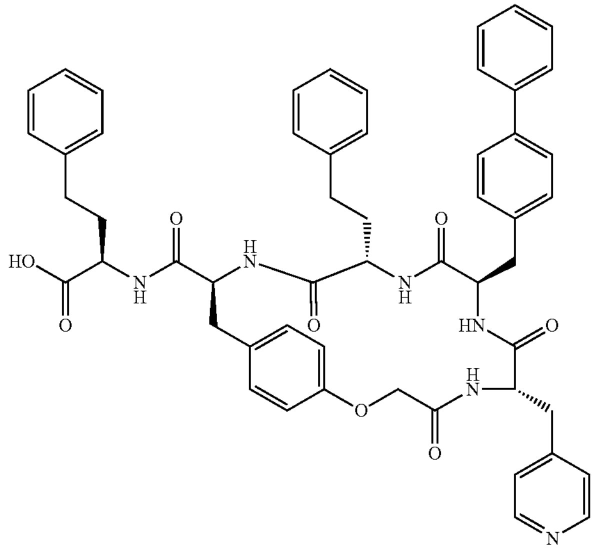 | 835.37 | 835.33 |
| 620 | 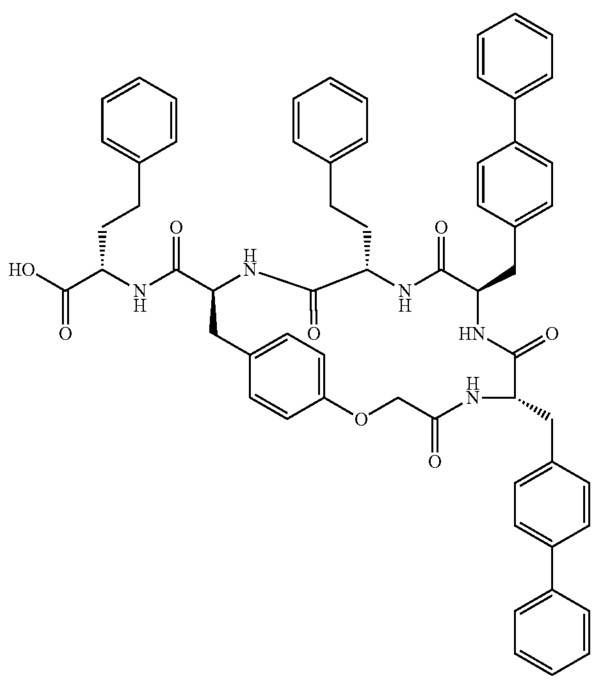 | 915.41 | 915.22 |

TABLE 1-continued

| Compound No. | Structure | MS Calcd | MS Observed |
|---|---|---|---|
| 621 | 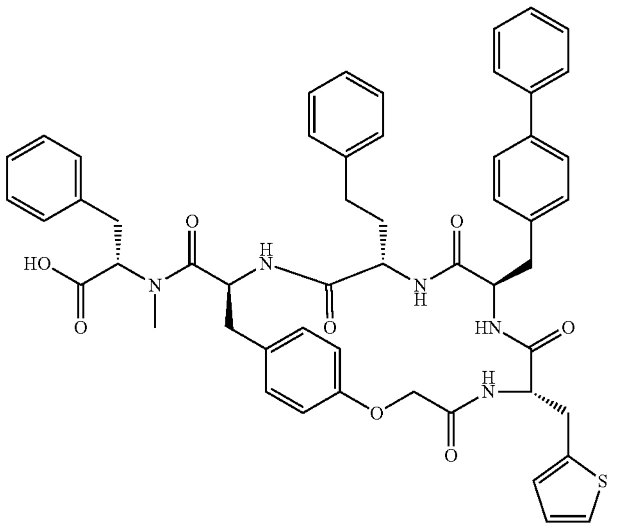 | 990.44 | 990.30 |
| 622 | 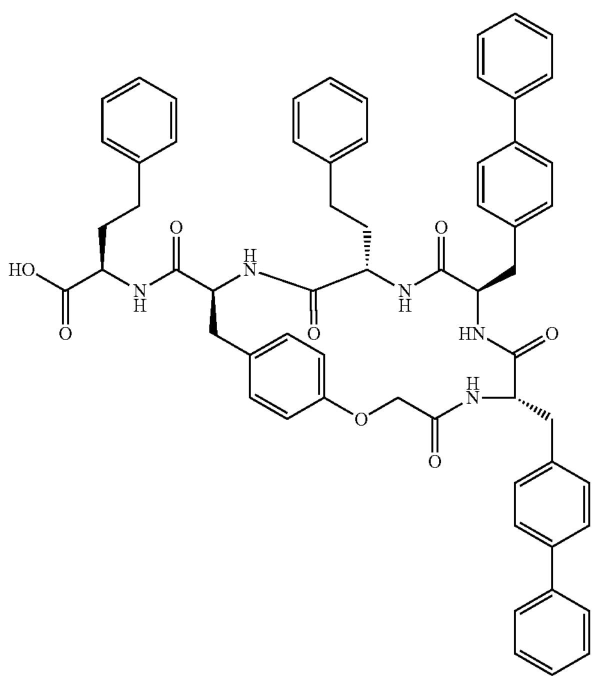 | 920.37 | 920.22 |

TABLE 1-continued

| Compound No. | Structure | MS Calcd | MS Observed |
|---|---|---|---|
| 623 | 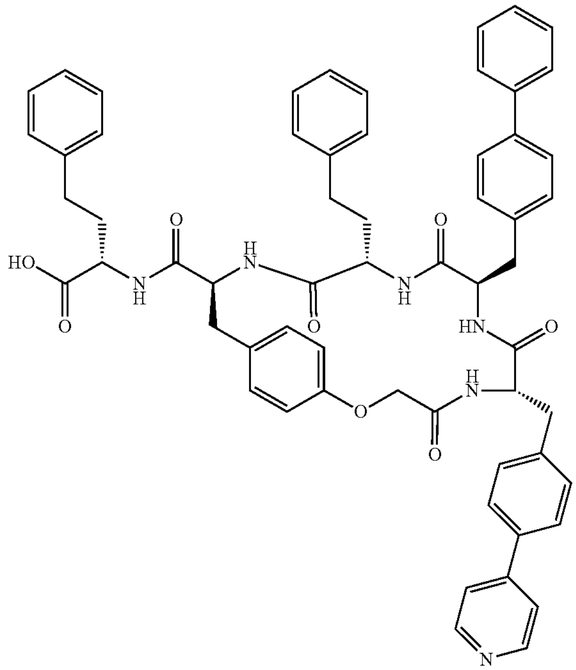 | 990.44 | 990.45 |
| 624 | 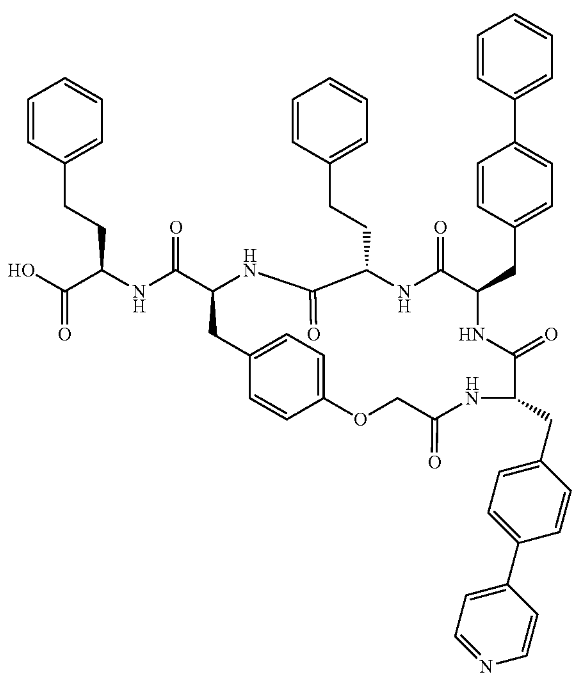 | 991.44 | 991.33 |

TABLE 1-continued

| Compound No. | Structure | MS Calcd | MS Observed |
|---|---|---|---|
| 625 | 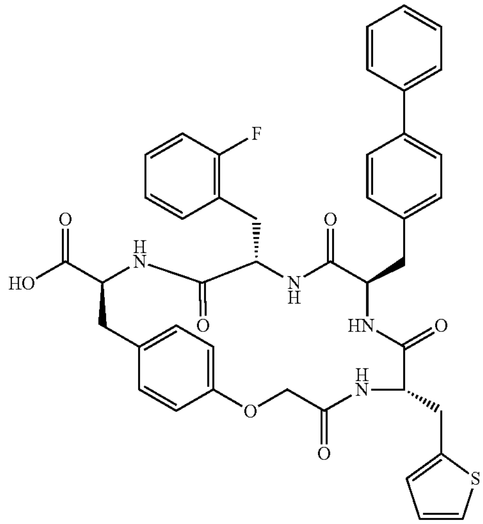 | 991.44 | 991.33 |
| 626 | 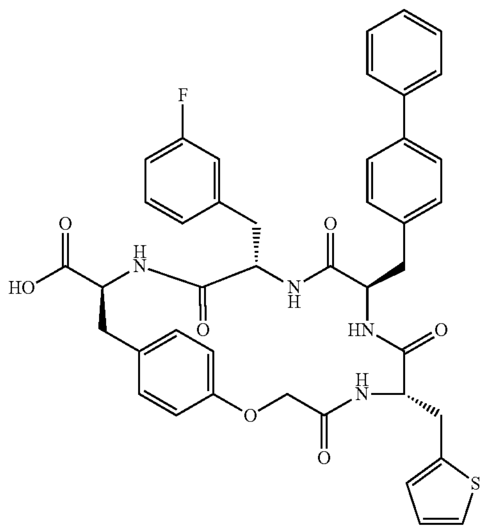 | 763.26 | 763.22 |
| 627 | 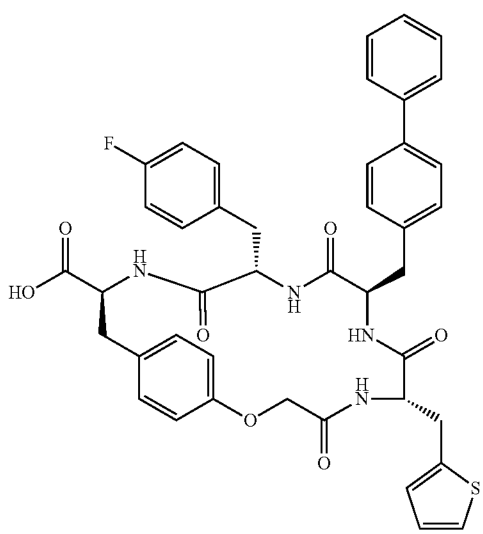 | 763.26 | 763.07 |

TABLE 1-continued

| Compound No. | Structure | MS Calcd | MS Observed |
|---|---|---|---|
| 628 | 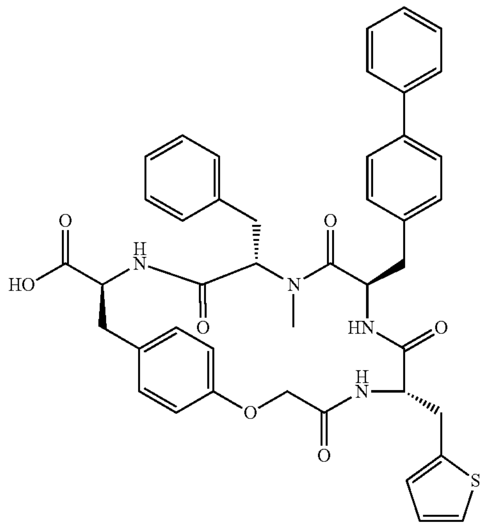 | 763.26 | 763.14 |
| 629 | 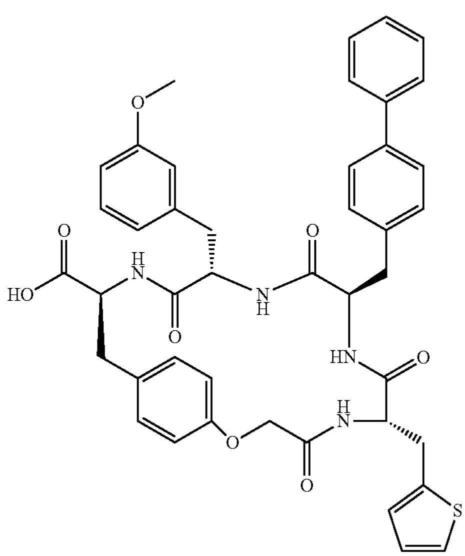 | 759.29 | 759.07 |

TABLE 1-continued
| Compound No. | Structure | MS Calcd | MS Observed |
|---|---|---|---|
| 630 | 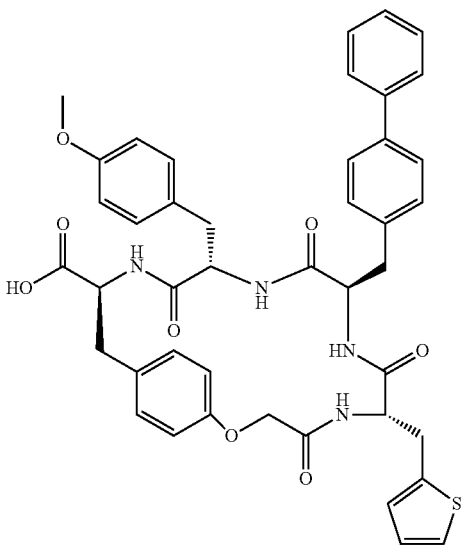 | 775.28 | 775.27 |
| 631 | 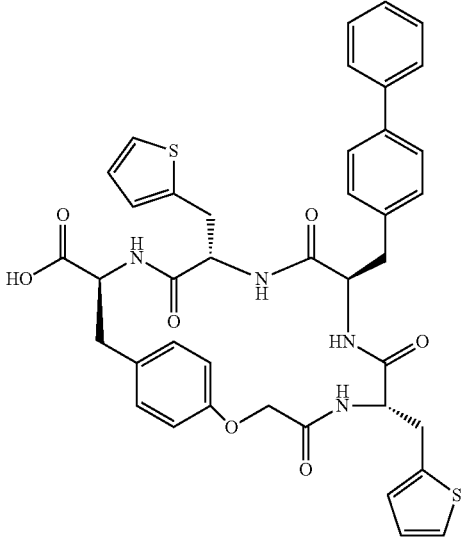 | 775.28 | 775.12 |

| Compound No. | Structure | MS Calcd | MS Observed |
|---|---|---|---|
| 632 | 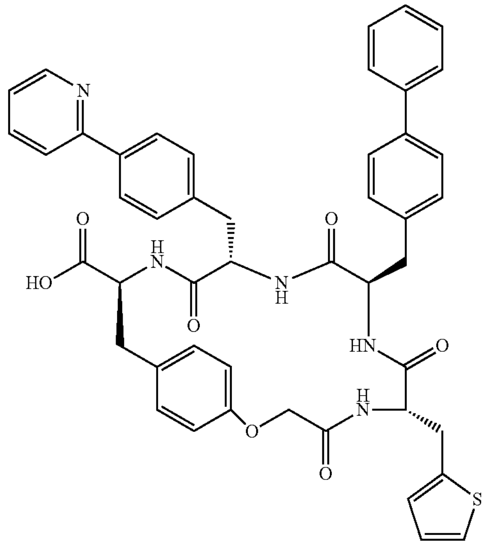 | 751.23 | 751.23 |
| 633 | 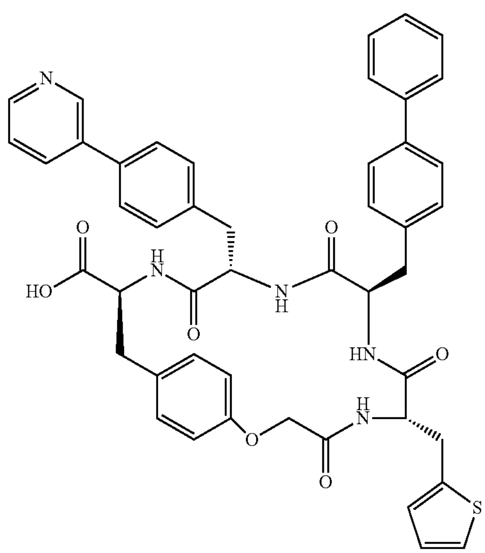 | 822.30 | 822.24 |

TABLE 1-continued
| Compound No. | Structure | MS Calcd | MS Observed |
|---|---|---|---|
| 634 | 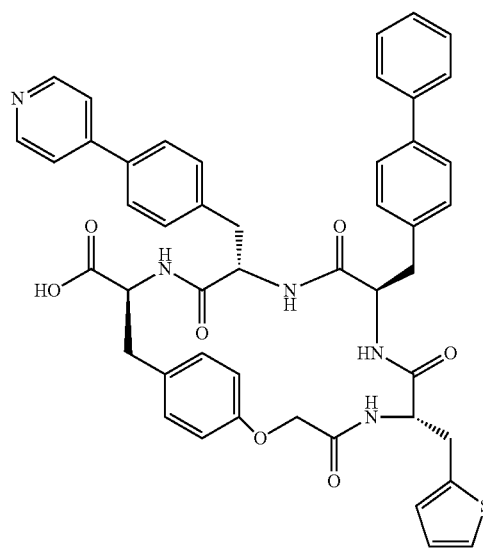 | 822.30 | 822.24 |
| 635 | 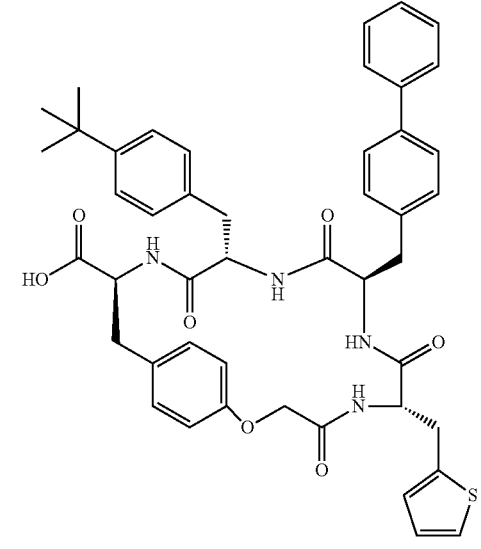 | 822.30 | 822.24 |

TABLE 1-continued

| Compound No. | Structure | MS Calcd | MS Observed |
|---|---|---|---|
| 636 | 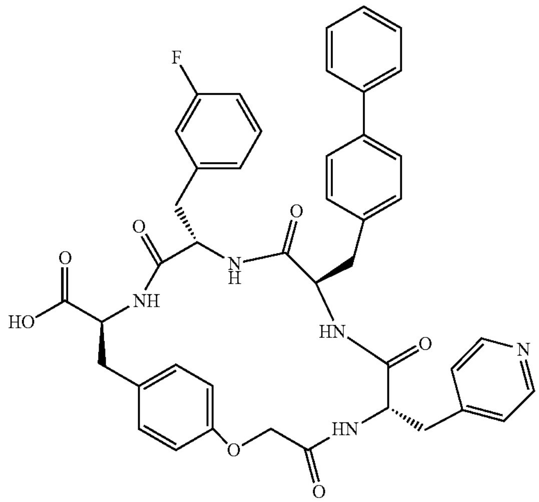 | 801.33 | 801.16 |
| 637 | 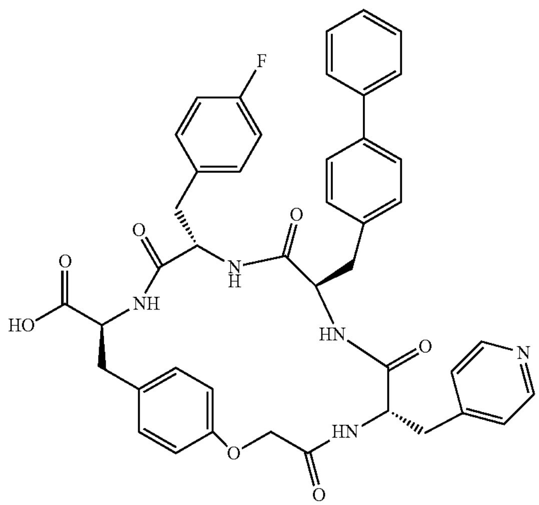 | 758.30 | 758.11 |
| 638 | 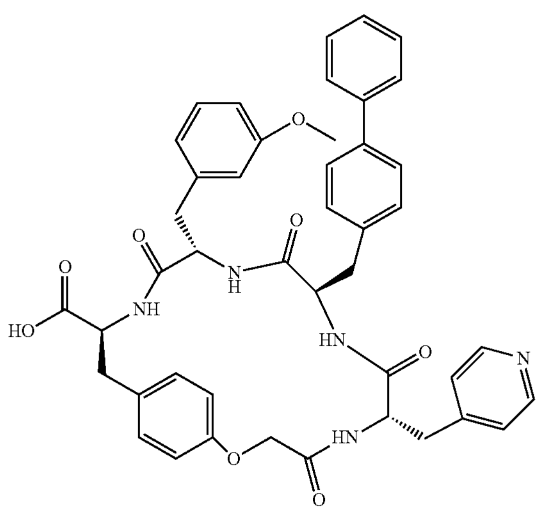 | 758.30 | 758.11 |

TABLE 1-continued

| Compound No. | Structure | MS Calcd | MS Observed |
|---|---|---|---|
| 639 | 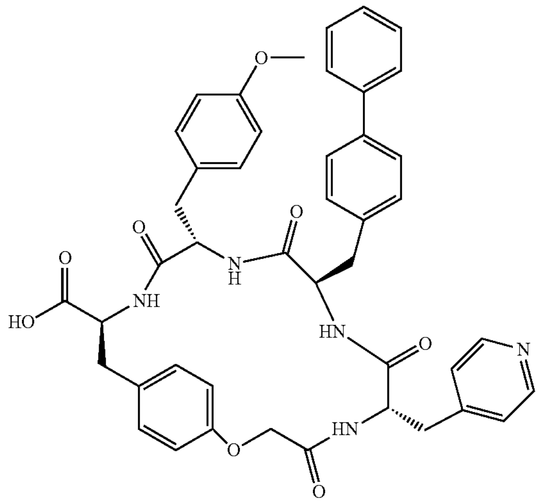 | 770.32 | 770.17 |
| 640 | 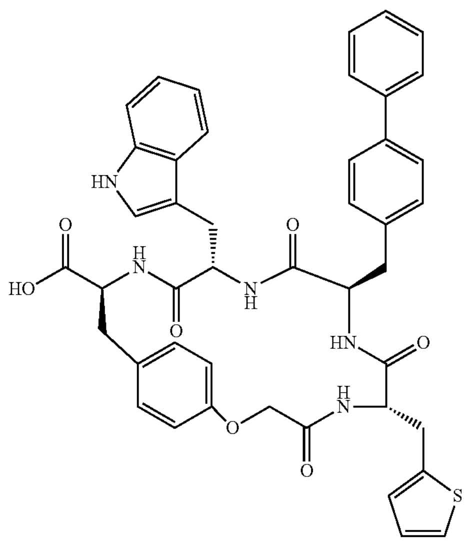 | 770.32 | 770.17 |
| 641 | 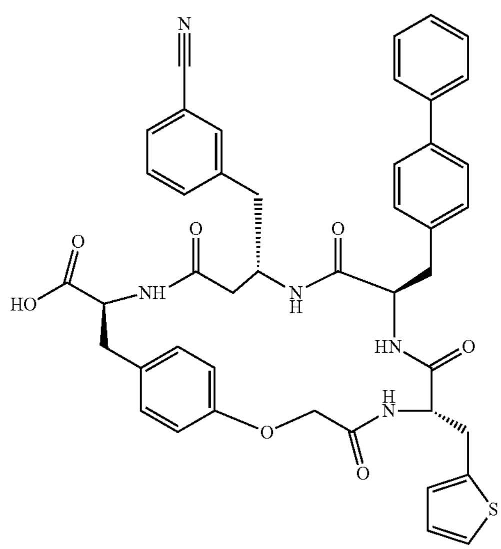 | 784.28 | 784.07 |

TABLE 1-continued

| Compound No. | Structure | MS Calcd | MS Observed |
|---|---|---|---|
| 642 | 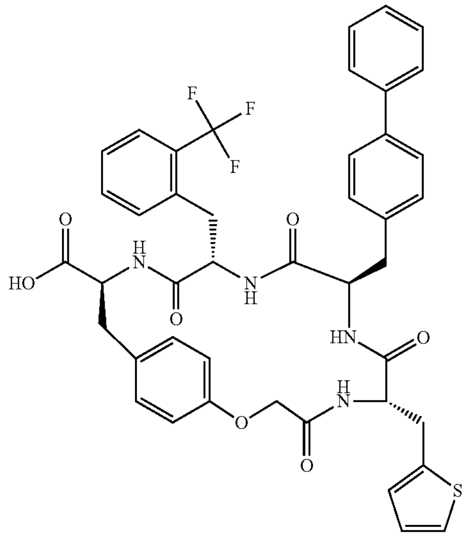 | 784.28 | 784.07 |
| 643 | 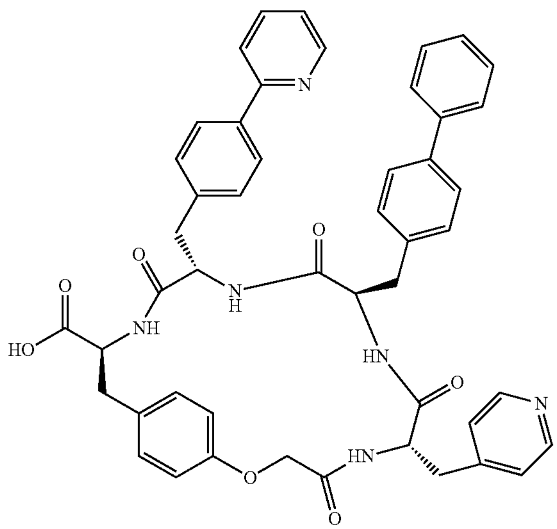 | 813.26 | 813.07 |
| 644 | 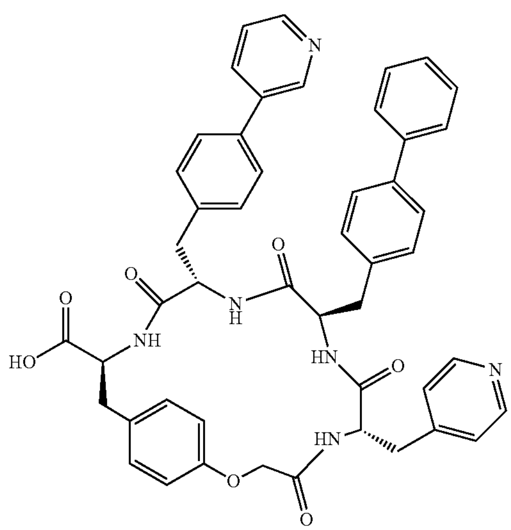 | 817.33 | 817.21 |

TABLE 1-continued

| Compound No. | Structure | MS Calcd | MS Observed |
|---|---|---|---|
| 645 | 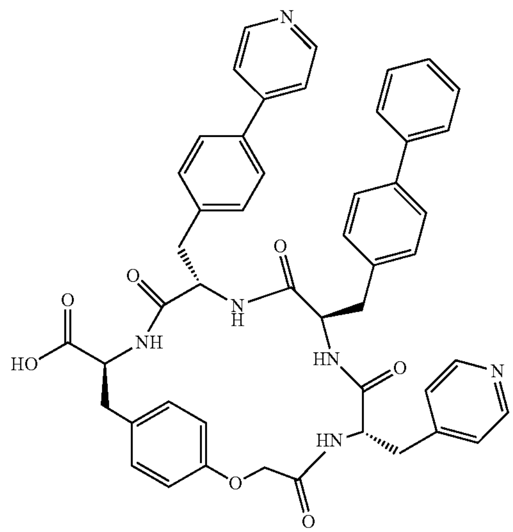 | 817.33 | 817.21 |
| 646 | 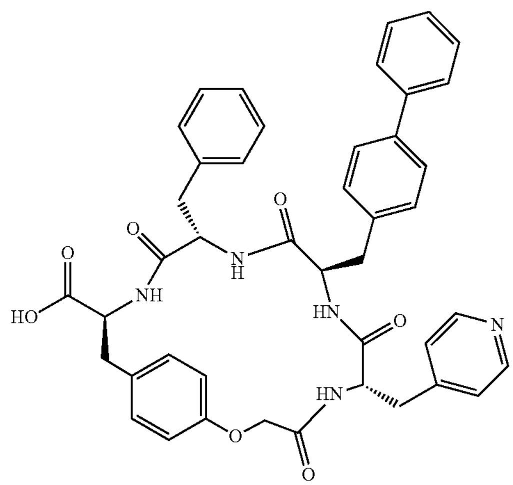 | 817.33 | 817.36 |
| 647 | 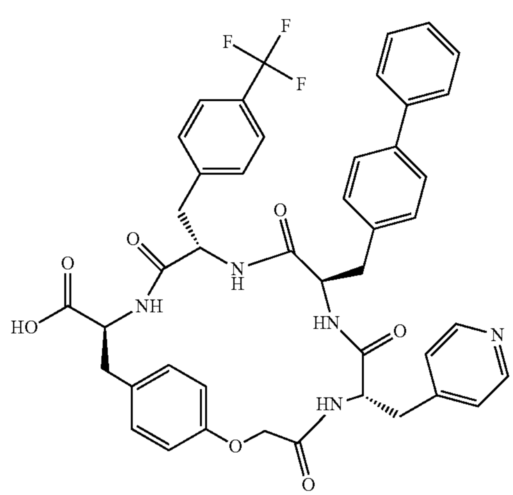 | 740.31 | 740.21 |

TABLE 1-continued

| Compound No. | Structure | MS Calcd | MS Observed |
|---|---|---|---|
| 648 | 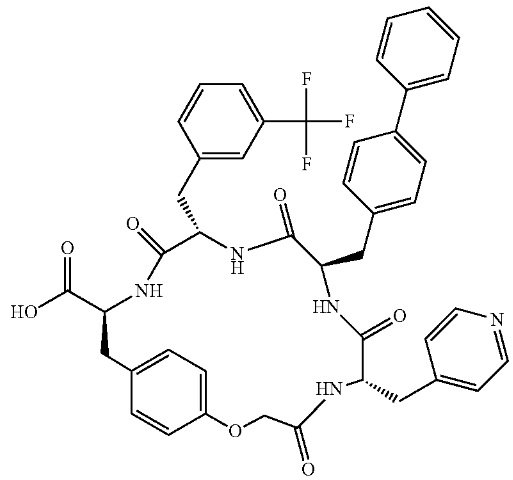 | 808.30 | 808.26 |
| 649 | 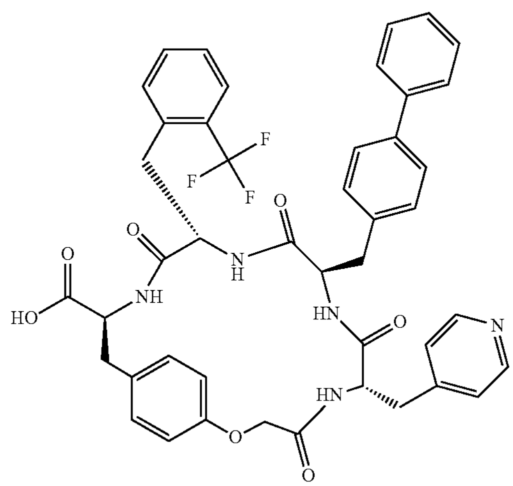 | 808.30 | 808.26 |
| 650 | 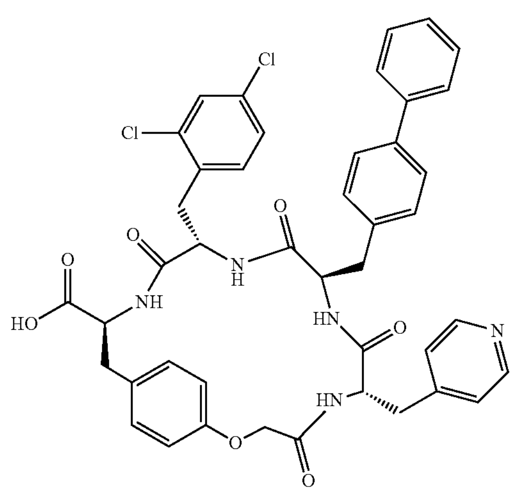 | 808.30 | 808.19 |

TABLE 1-continued

| Compound No. | Structure | MS Calcd | MS Observed |
|---|---|---|---|
| 651 | 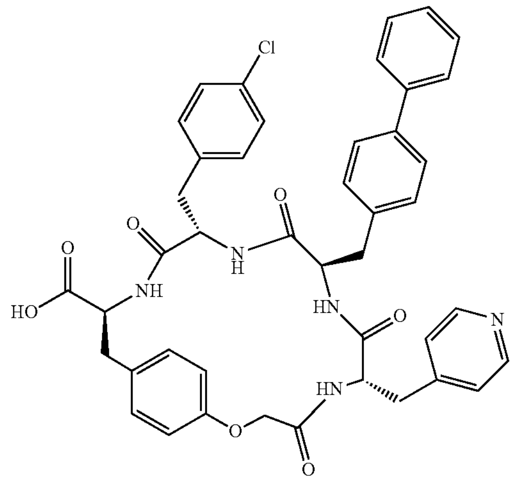 | 808.23 | 808.11 |
| 652 | 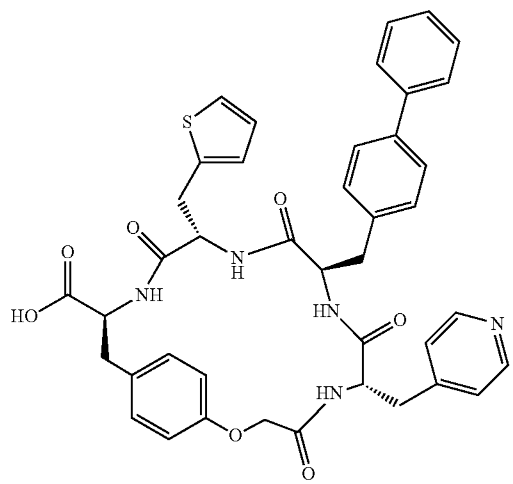 | 774.27 | 774.16 |
| 653 | 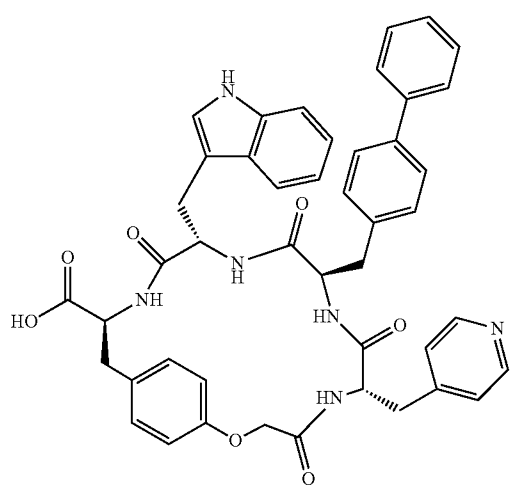 | 746.26 | 746.13 |

TABLE 1-continued
| Compound No. | Structure | MS Calcd | MS Observed |
|---|---|---|---|
| 654 | 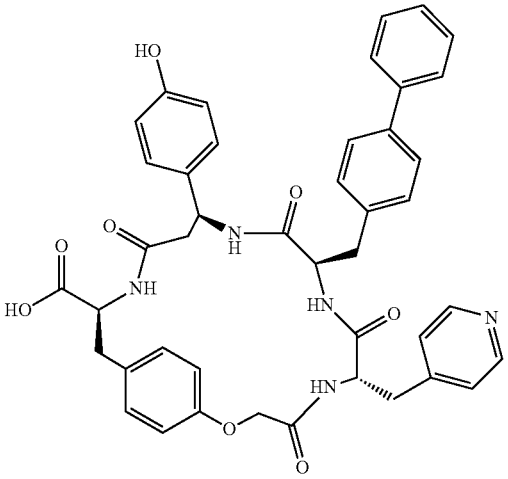 | 779.32 | 779.19 |
| 655 | 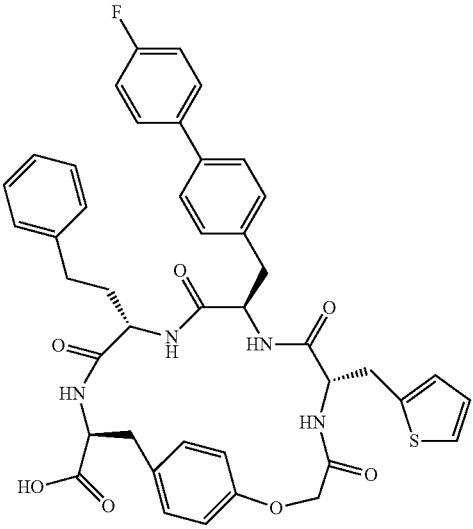 | 756.30 | 756.19 |
| 656 | 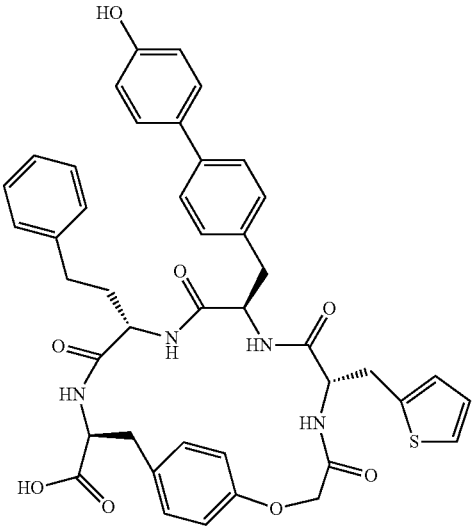 | 777.28 | 777.35 |

TABLE 1-continued

| Compound No. | Structure | MS Calcd | MS Observed |
|---|---|---|---|
| 657 | 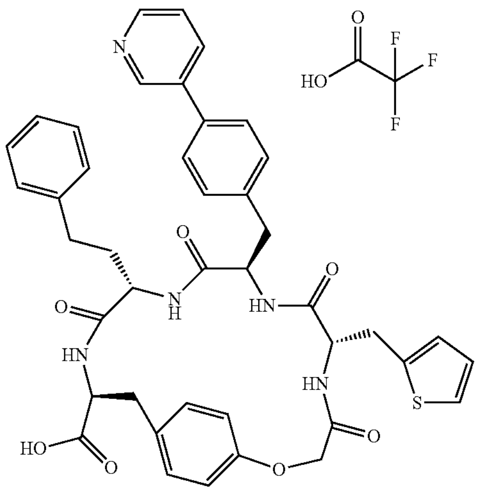 | 775.28 | 775.32 |
| 658 | 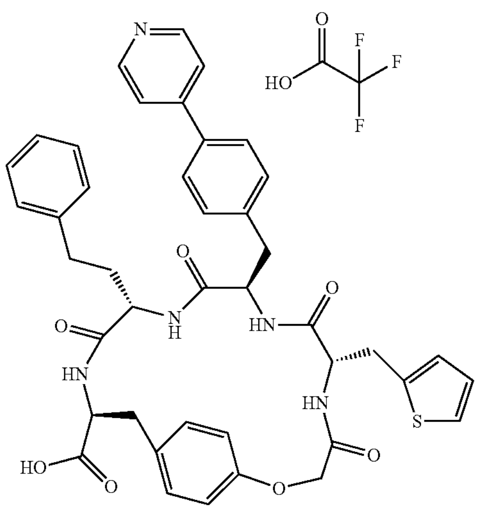 | 760.28 | 760.27 |
| 659 | 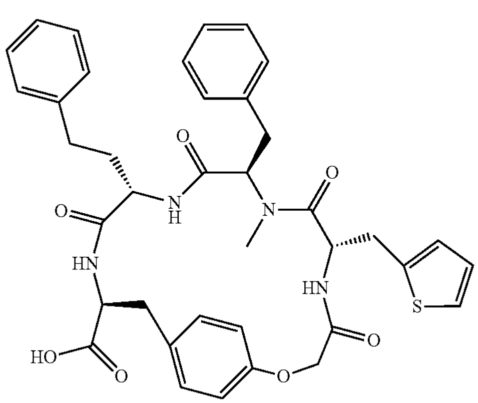 | 760.28 | 760.29 |

TABLE 1-continued

| Compound No. | Structure | MS Calcd | MS Observed |
|---|---|---|---|
| 660 | 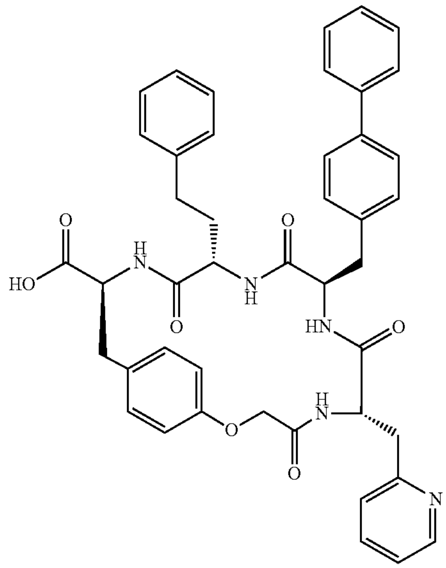 | 697.27 | 697.27 |
| 661 | 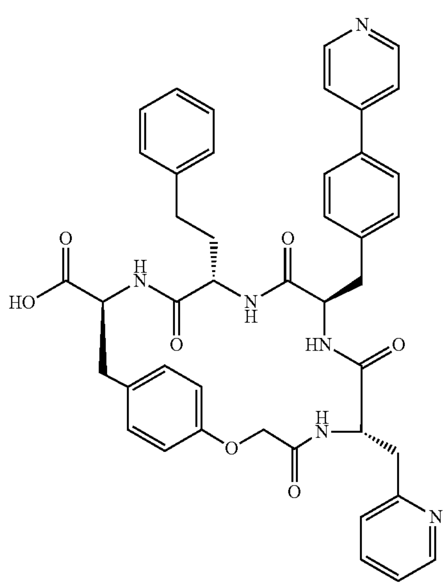 | 754.32 | 754.20 |

TABLE 1-continued

| Compound No. | Structure | MS Calcd | MS Observed |
|---|---|---|---|
| 662 | 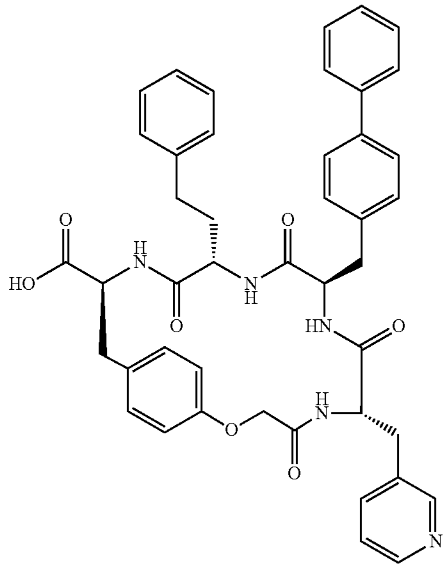 | 755.32 | 755.22 |
| 663 | 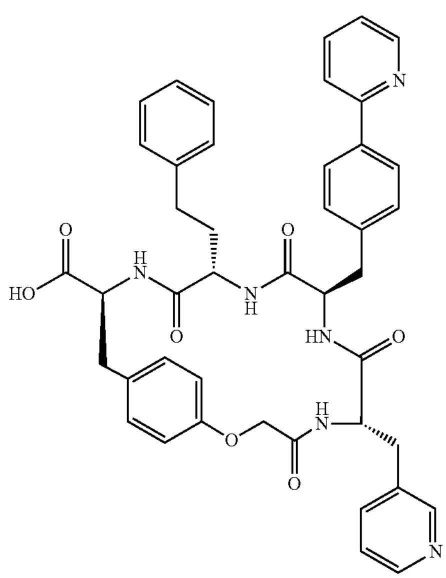 | 754.32 | 754.20 |

TABLE 1-continued

| Compound No. | Structure | MS Calcd | MS Observed |
|---|---|---|---|
| 664 | 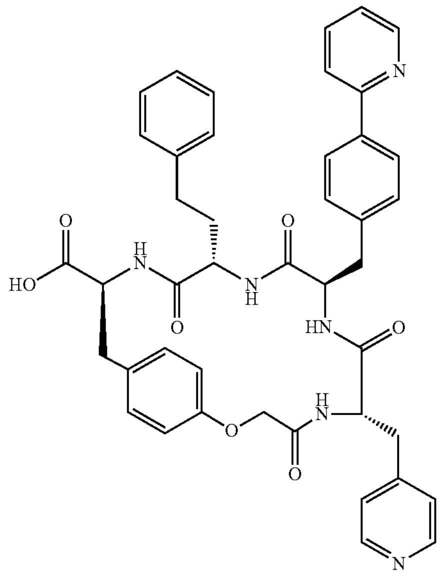 | 755.32 | 755.29 |
| 665 | 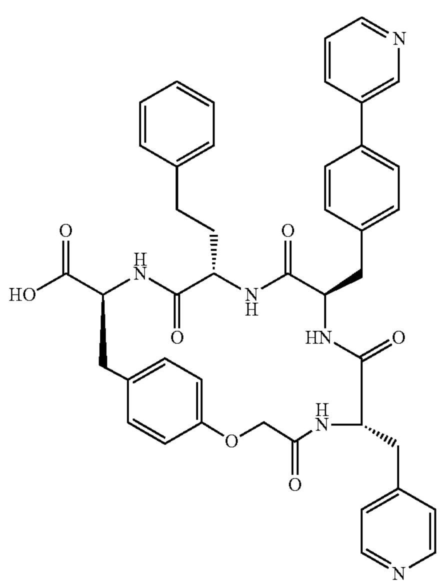 | 755.32 | 755.15 |

TABLE 1-continued

| Compound No. | Structure | MS Calcd | MS Observed |
|---|---|---|---|
| 666 | 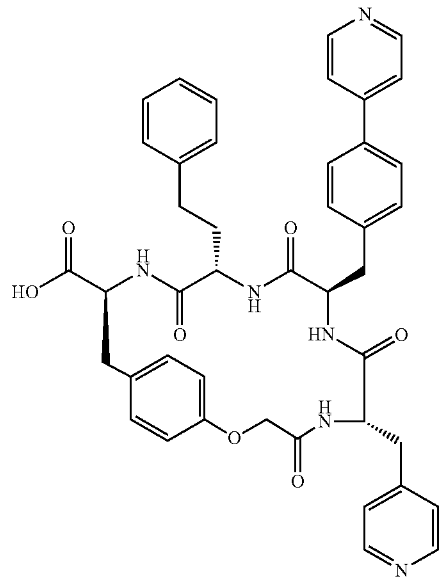 | 755.32 | 755.15 |
| 667 | 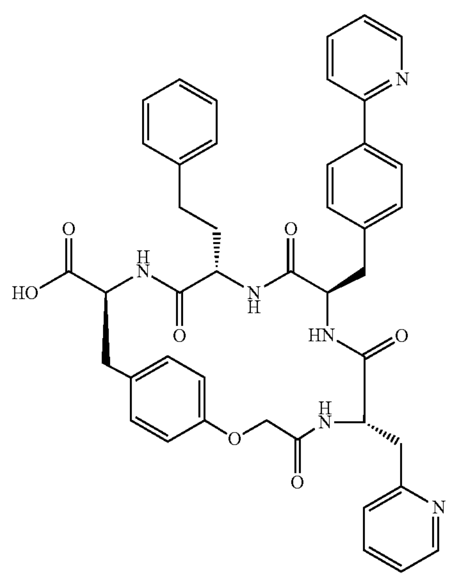 | 755.32 | 755.22 |

TABLE 1-continued

| Compound No. | Structure | MS Calcd | MS Observed |
|---|---|---|---|
| 668 | 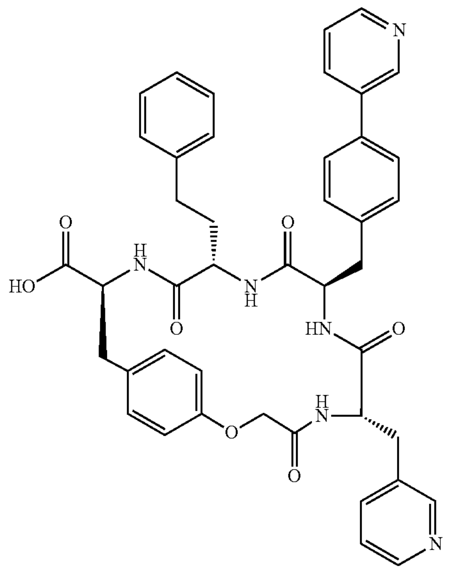 | 755.32 | 755.29 |
| 669 | 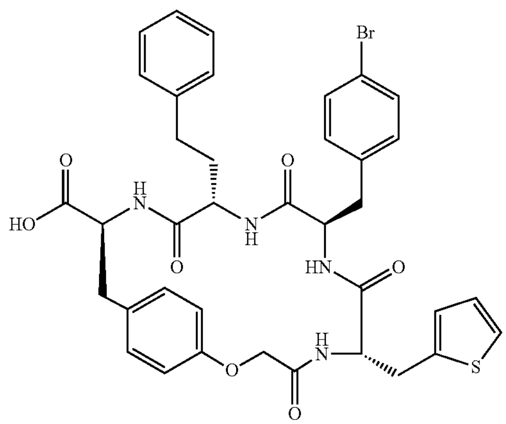 | 755.32 | 755.22 |
| 670 | 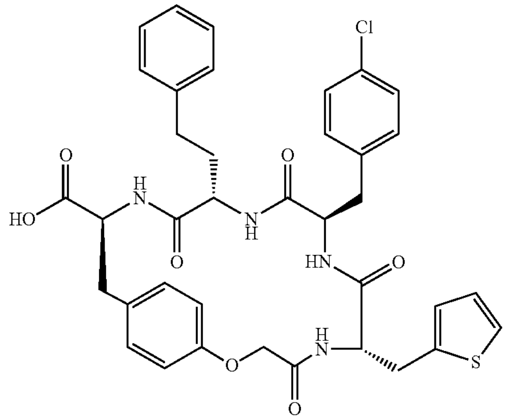 | 761.16 | 761.00 |

TABLE 1-continued

| Compound No. | Structure | MS Calcd | MS Observed |
|---|---|---|---|
| 672 | 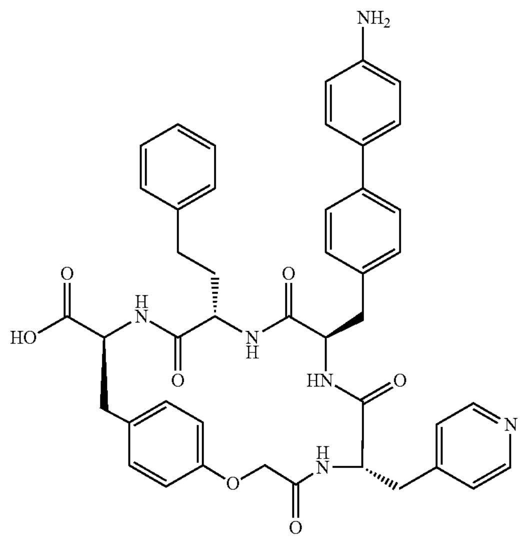 | 717.21 | 717.21 |
| 673 | 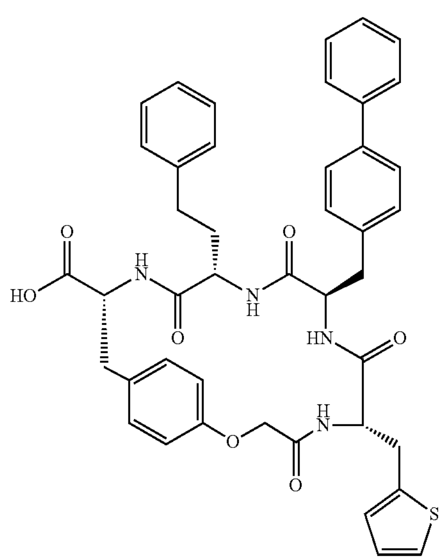 | 663.29 | 663.29 |

TABLE 1-continued

| Compound No. | Structure | MS Calcd | MS Observed |
|---|---|---|---|
| 674 | 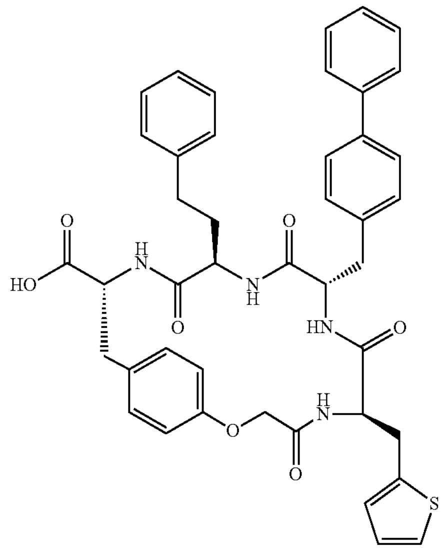 | 769.33 | 769.21 |
| 675 | 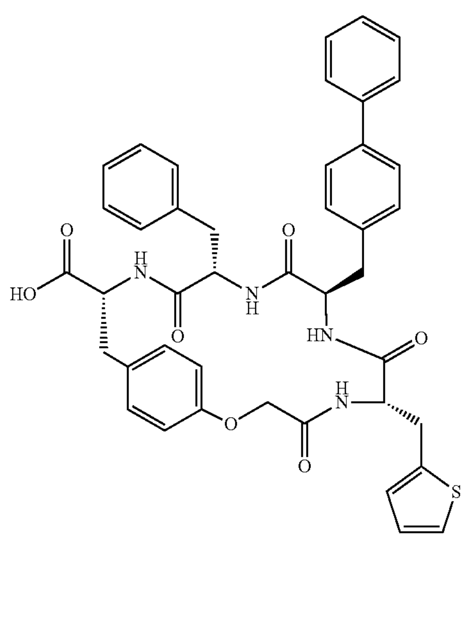 | 759.29 | 759.15 |

TABLE 1-continued

| Compound No. | Structure | MS Calcd | MS Observed |
|---|---|---|---|
| 676 | 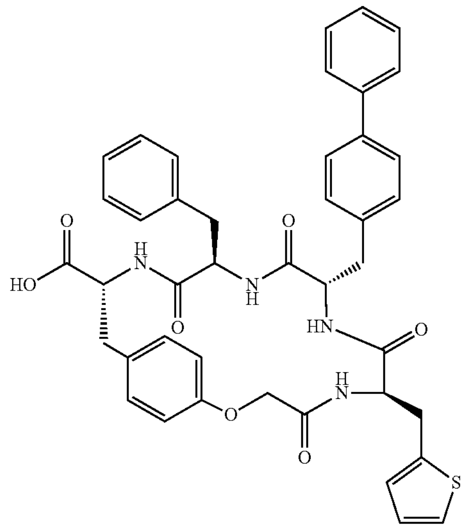 | 759.29 | 759.15 |
| 677 | 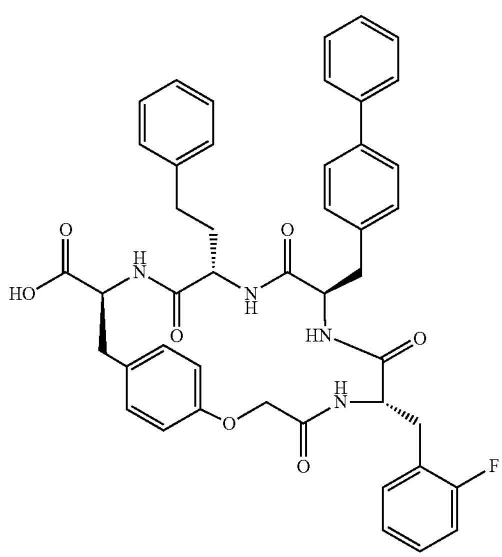 | 745.27 | 745.09 |

TABLE 1-continued

| Compound No. | Structure | MS Calcd | MS Observed |
|---|---|---|---|
| 678 | 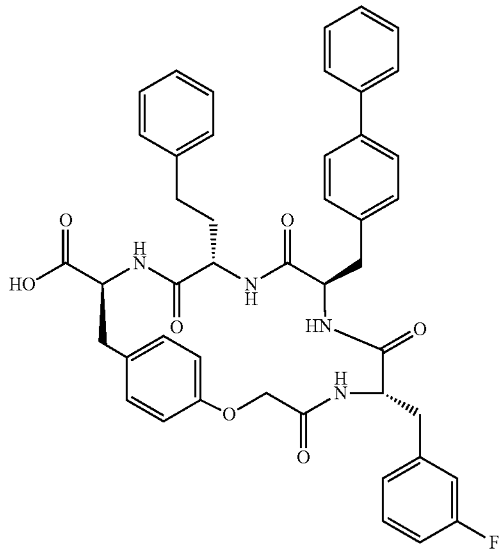 | 745.27 | 745.09 |
| 679 | 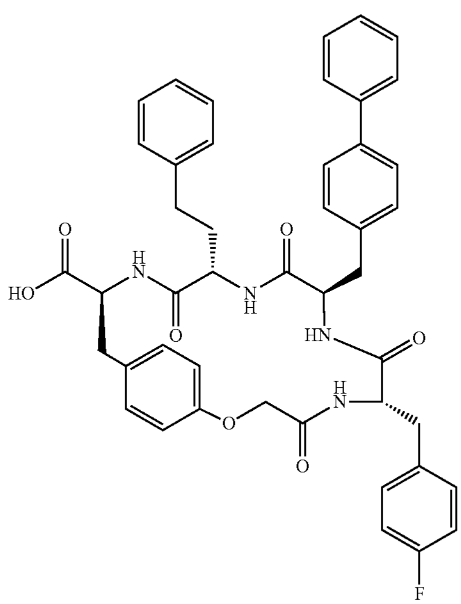 | 771.32 | 771.35 |

TABLE 1-continued

| Compound No. | Structure | MS Calcd | MS Observed |
|---|---|---|---|
| 680 | 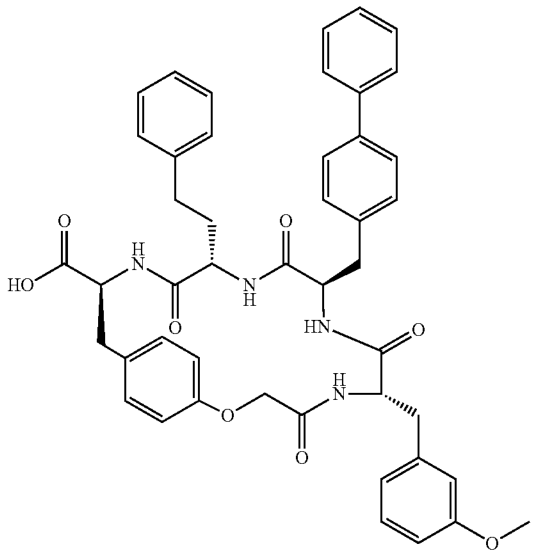 | 771.32 | 783.1866 771.1297 |
| 681 | 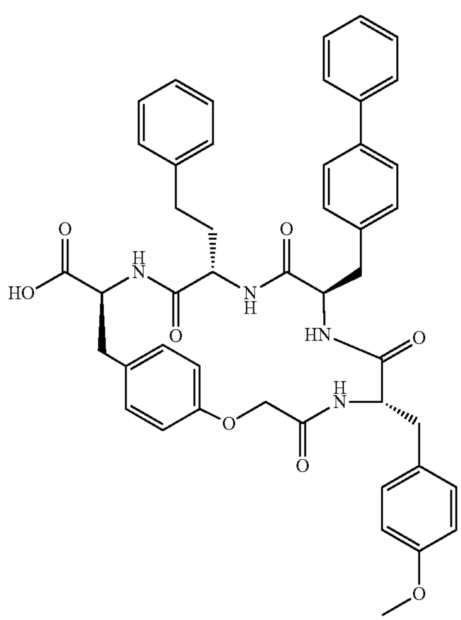 | 771.32 | 771.20 |

TABLE 1-continued

| Compound No. | Structure | MS Calcd | MS Observed |
|---|---|---|---|
| 682 | 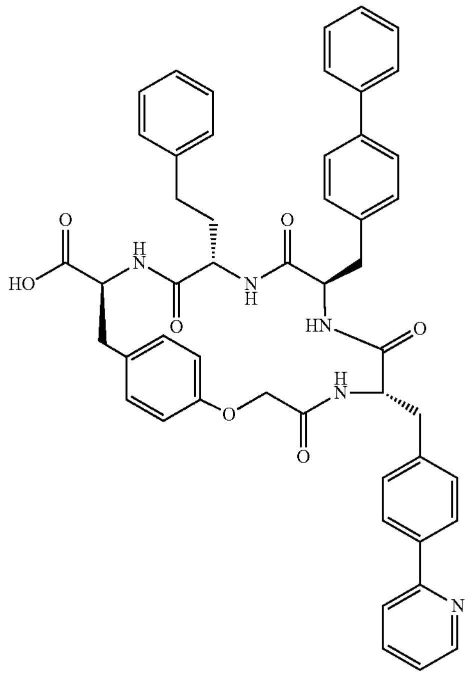 | 783.34 | 783.19 |
| 683 | 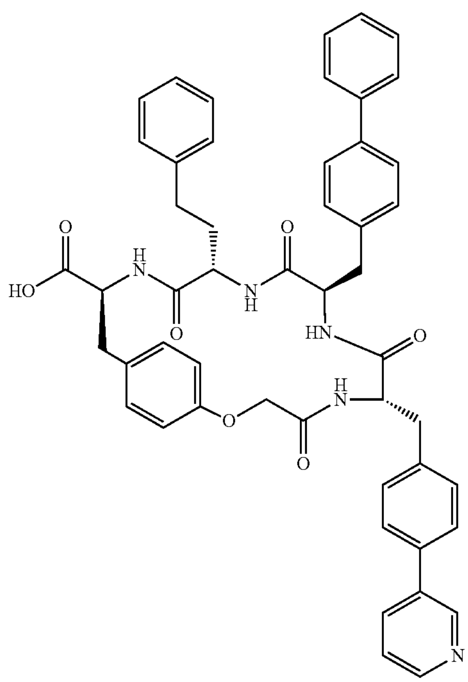 | 783.34 | 783.19 |

TABLE 1-continued

| Compound No. | Structure | MS Calcd | MS Observed |
|---|---|---|---|
| 684 | 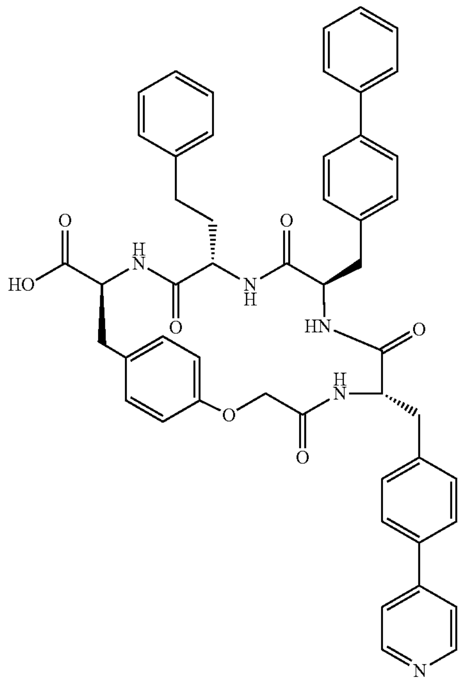 | 830.36 | 830.30 |
| 685 | 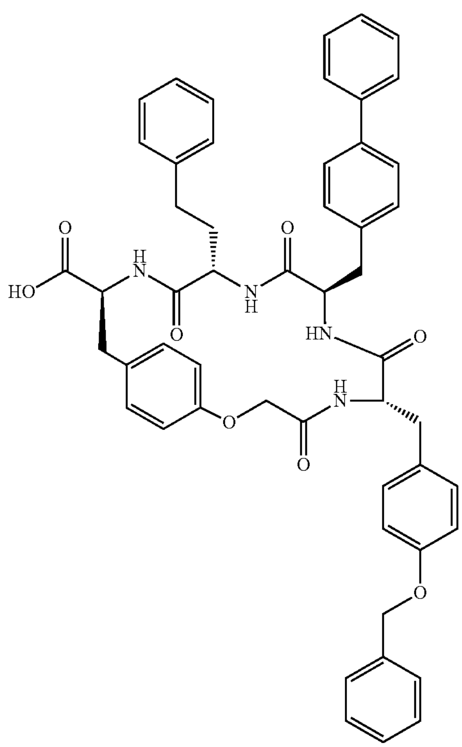 | 830.36 | 830.30 |

TABLE 1-continued

| Compound No. | Structure | MS Calcd | MS Observed |
|---|---|---|---|
| 686 | 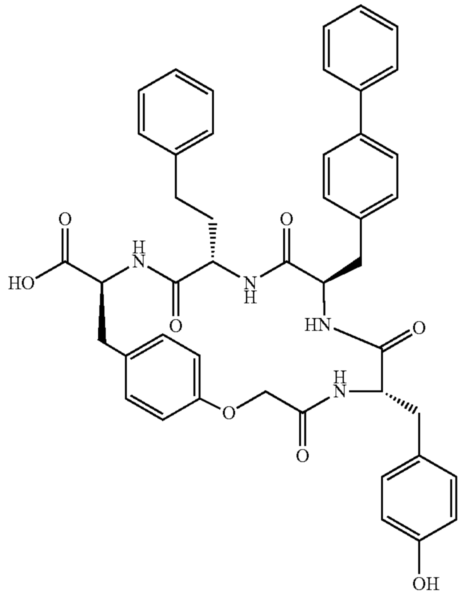 | 830.36 | 830.30 |
| 687 | 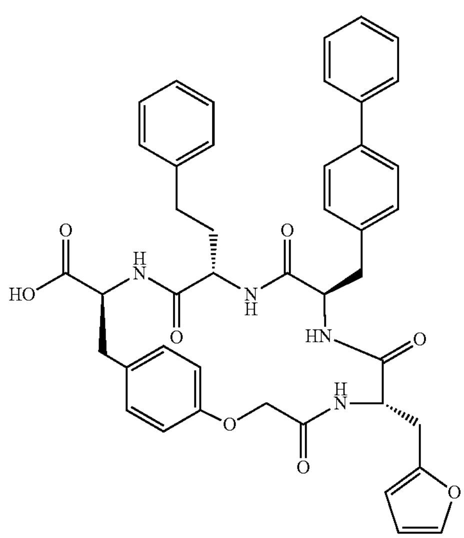 | 859.37 | 859.30 |

TABLE 1-continued

| Compound No. | Structure | MS Calcd | MS Observed |
|---|---|---|---|
| 688 | 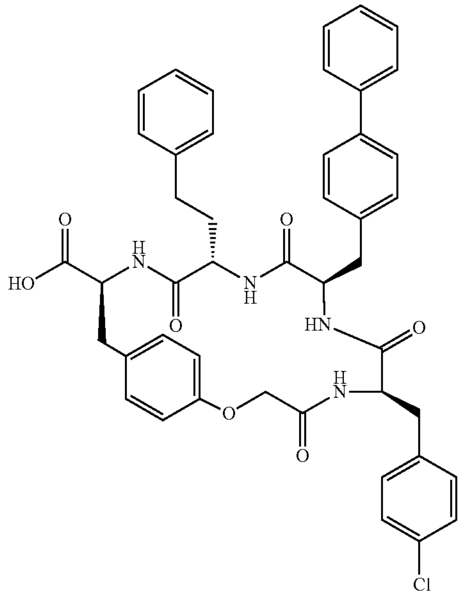 | 769.32 | 769.13 |
| 689 | 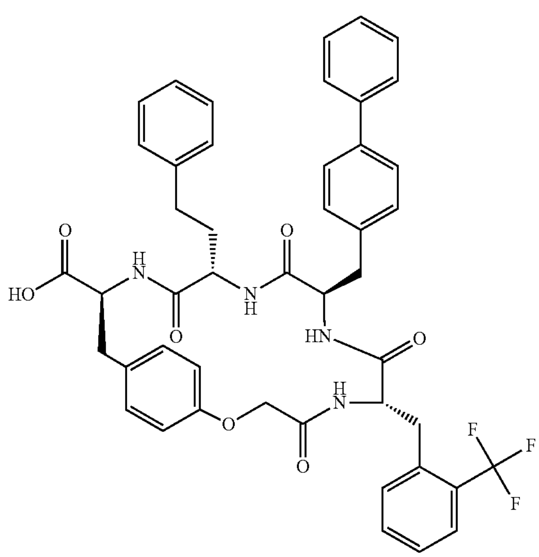 | 743.31 | 743.10 |

TABLE 1-continued

| Compound No. | Structure | MS Calcd | MS Observed |
|---|---|---|---|
| 690 | 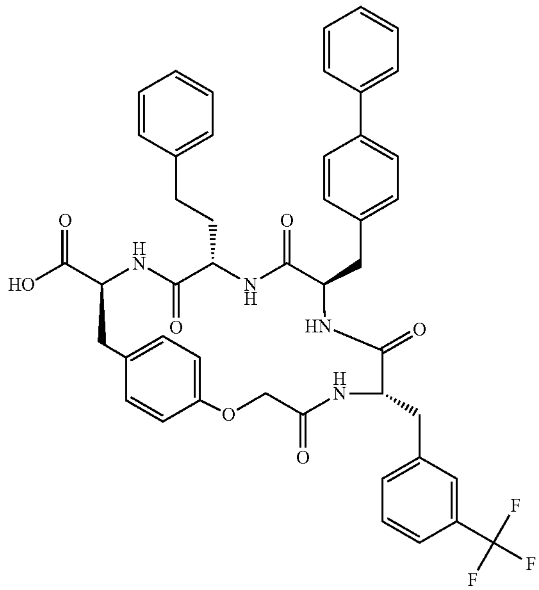 | 787.29 | 787.18 |
| 691 | 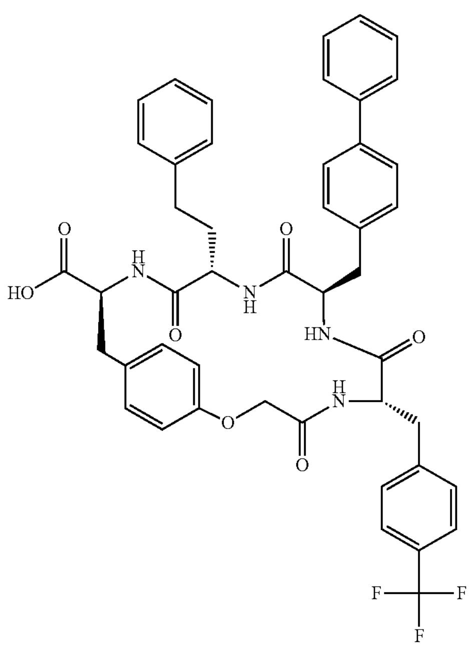 | 821.32 | 821.21 |

TABLE 1-continued

| Compound No. | Structure | MS Calcd | MS Observed |
|---|---|---|---|
| 692 | 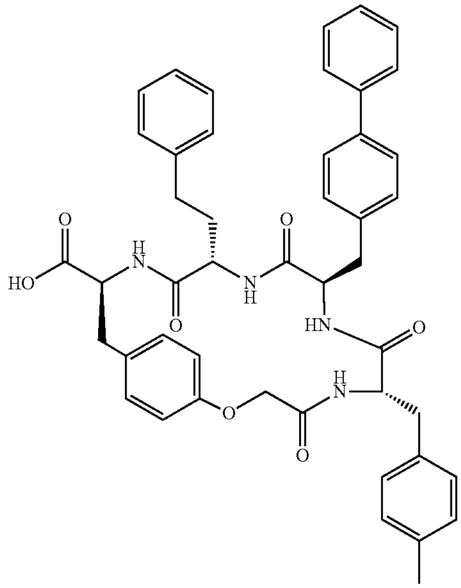 | 821.32 | 821.21 |
| 693 | 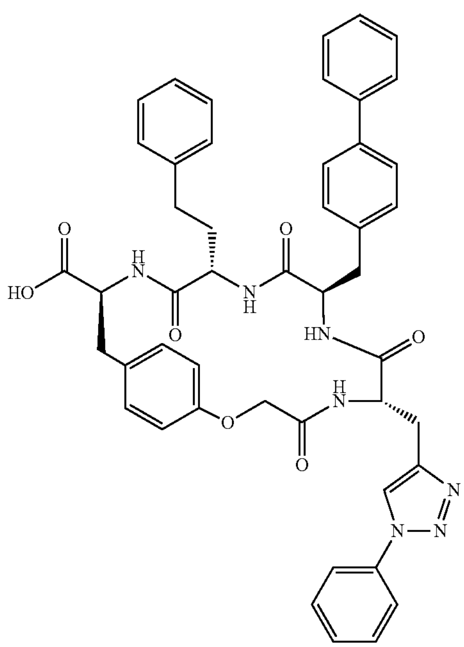 | 821.32 | 821.28 |

TABLE 1-continued
| Compound No. | Structure | MS Calcd | MS Observed |
|---|---|---|---|
| 694 | 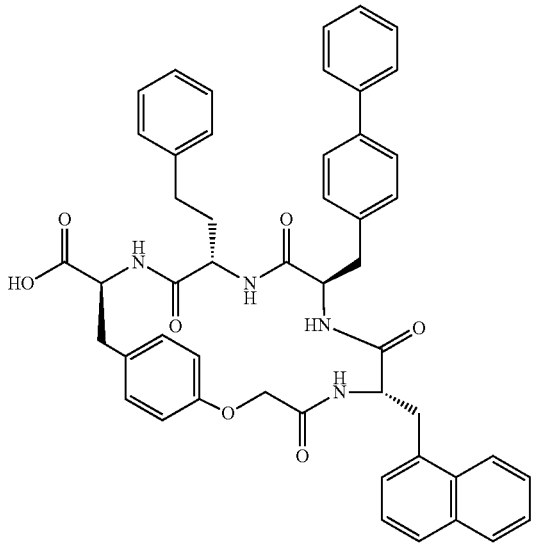 | 767.34 | 767.14 |
| 695 | 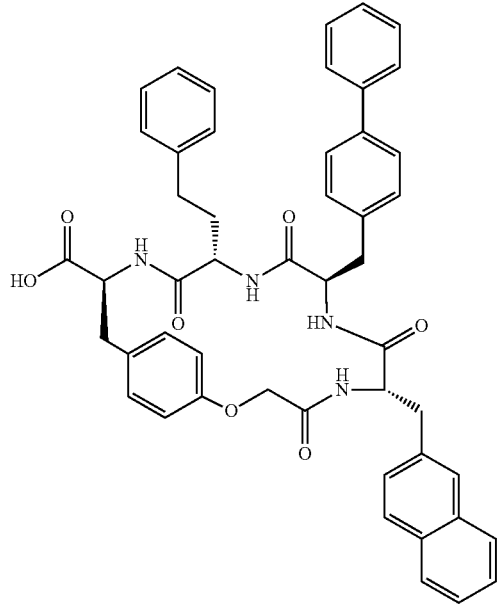 | 820.35 | 820.17 |

TABLE 1-continued

| Compound No. | Structure | MS Calcd | MS Observed |
| --- | --- | --- | --- |
| 696 | 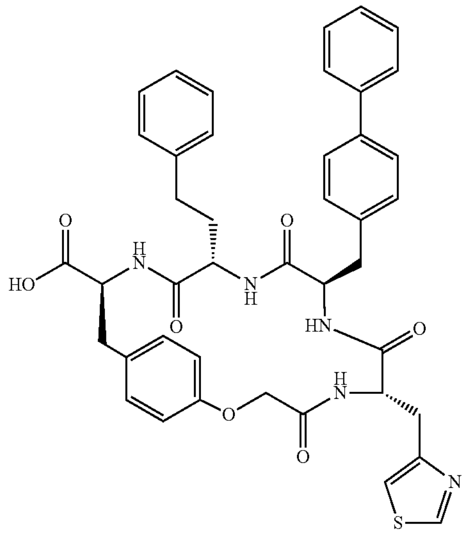 | 803.34 | 803.16 |
| 697 | 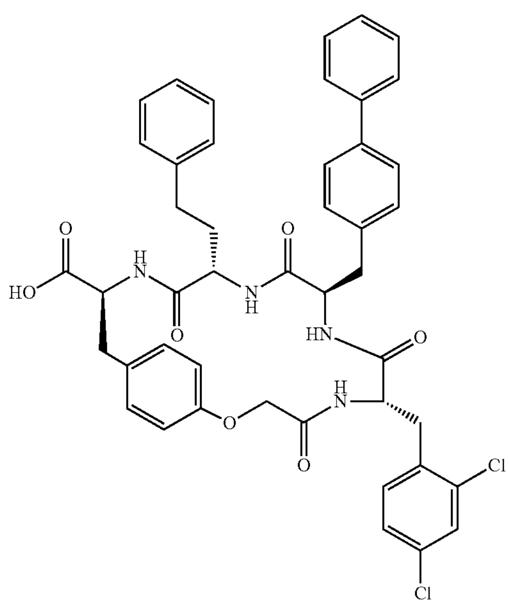 | 803.34 | 803.16 |

TABLE 1-continued

| Compound No. | Structure | MS Calcd | MS Observed |
|---|---|---|---|
| 698 | 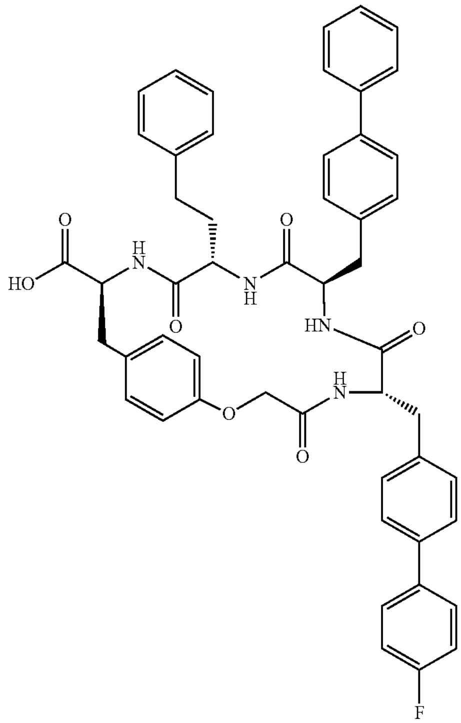 | 760.28 | 760.11 |
| 699 | 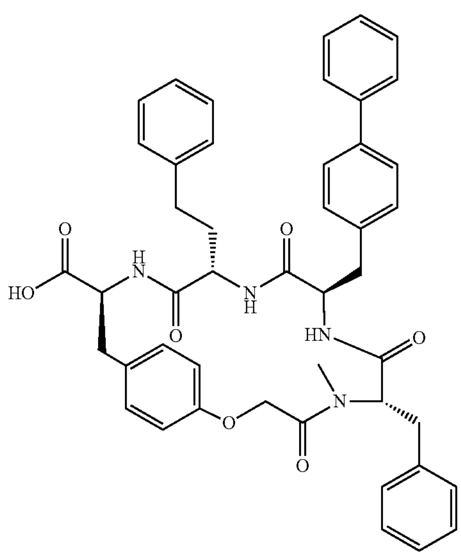 | 821.25 | 821.21 |

TABLE 1-continued
| Compound No. | Structure | MS Calcd | MS Observed |
|---|---|---|---|
| 700 | 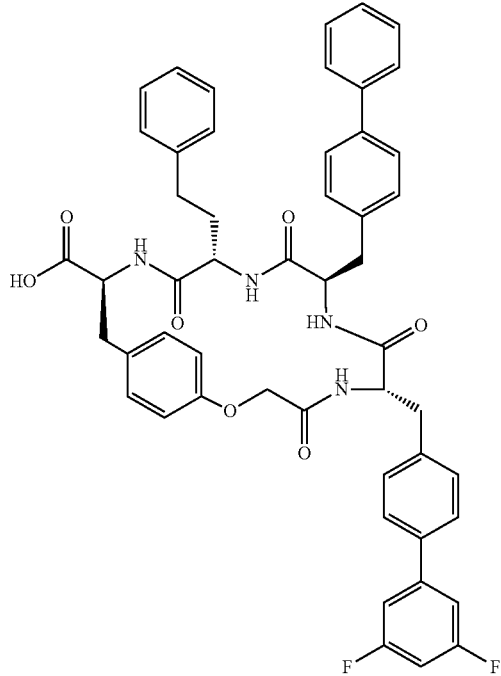 | 847.35 | 847.24 |
| 701 | 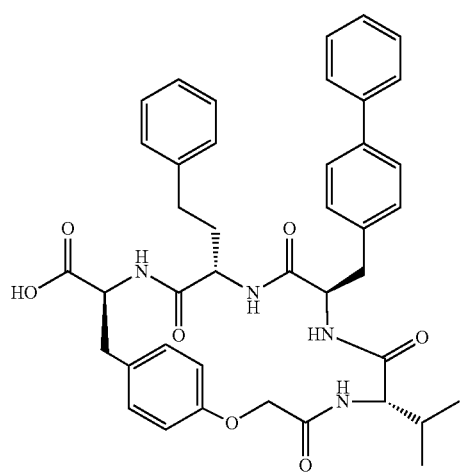 | 767.34 | 767.14 |

TABLE 1-continued
| Compound No. | Structure | MS Calcd | MS Observed |
|---|---|---|---|
| 702 | 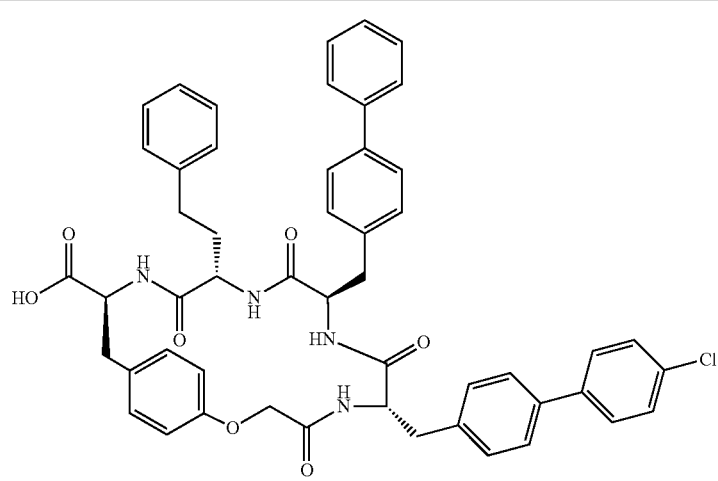 | 865.34 | 865.14 |
| 703 | 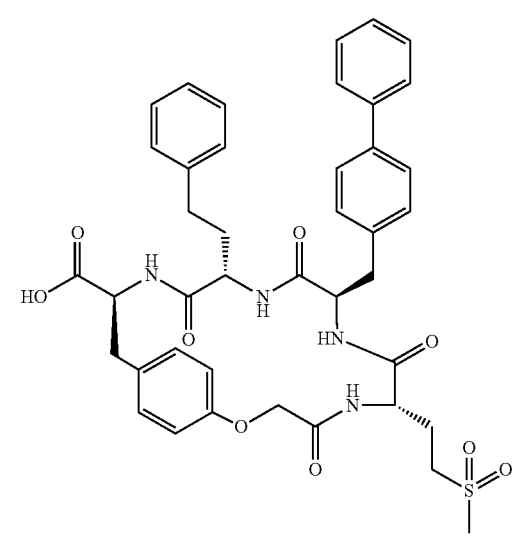 | 705.33 | 705.15 |
| 704 | 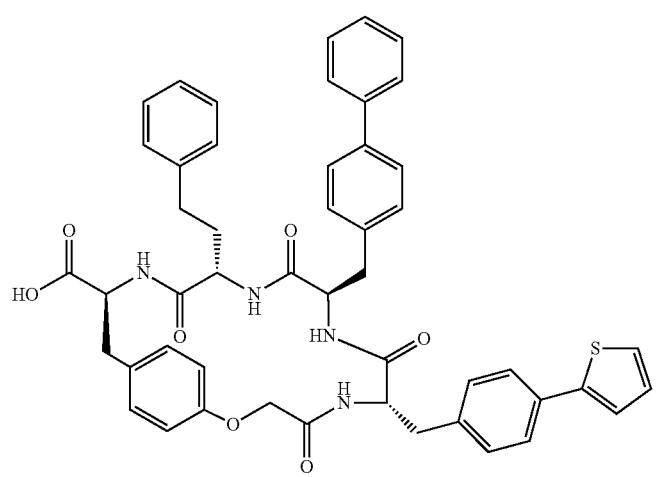 | 863.32 | 863.07 |

TABLE 1-continued
| Compound No. | Structure | MS Calcd | MS Observed |
|---|---|---|---|
| 705 | 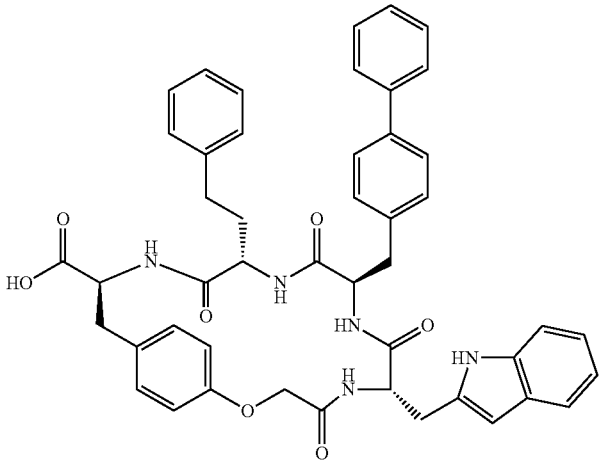 | 769.29 | 769.06 |
| 706 | 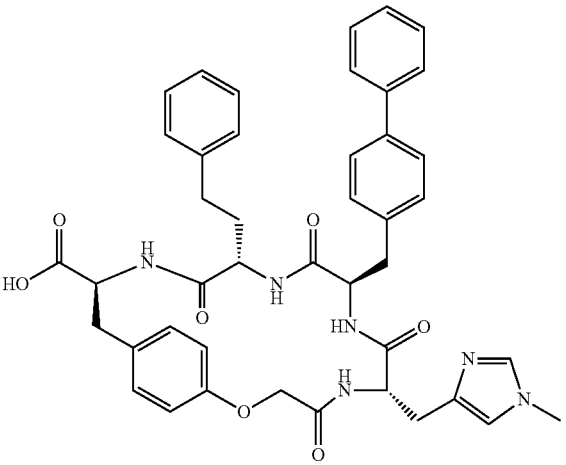 | 835.32 | 835.11 |
| 707 | 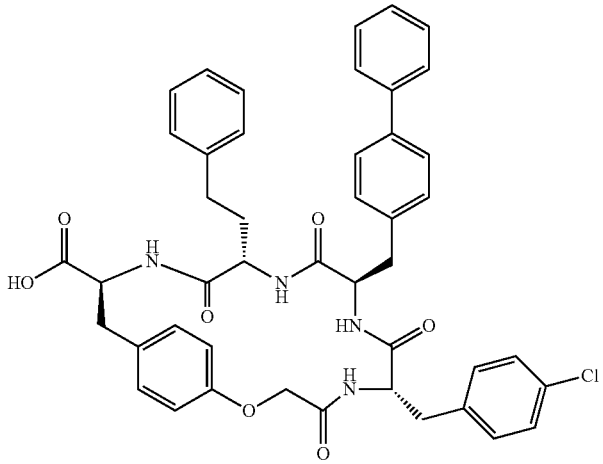 | 792.34 | 792.14 |

TABLE 1-continued
| Compound No. | Structure | MS Calcd | MS Observed |
|---|---|---|---|
| 708 | 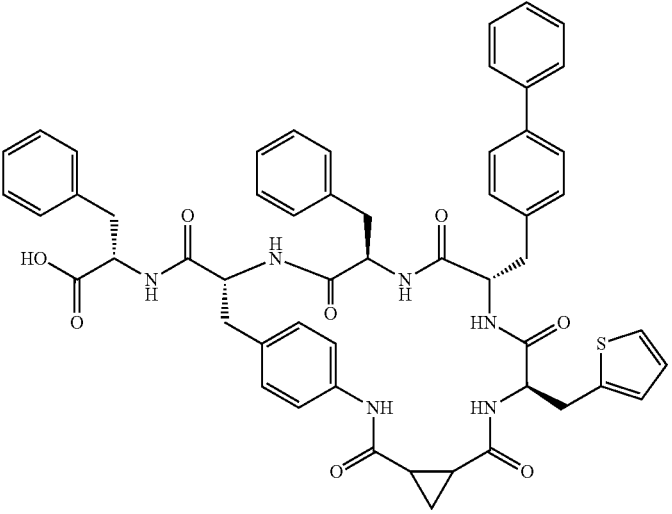 | 757.33 | 757.08 |
| 709 | 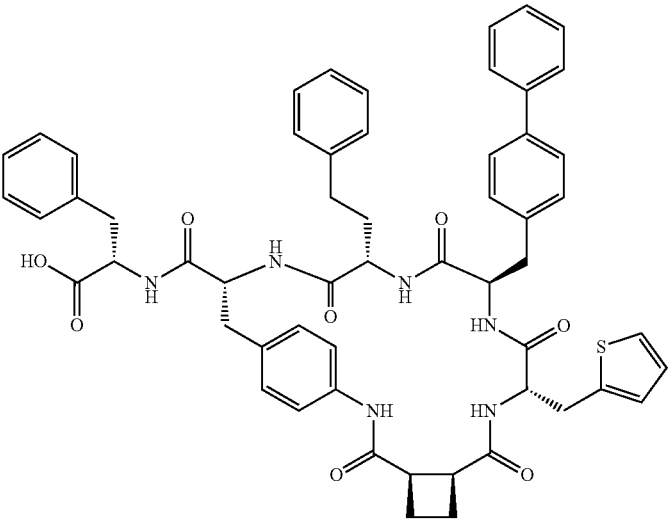 | 787.29 | 787.11 |

TABLE 1-continued
| Compound No. | Structure | MS Calcd | MS Observed |
|---|---|---|---|
| 710 | 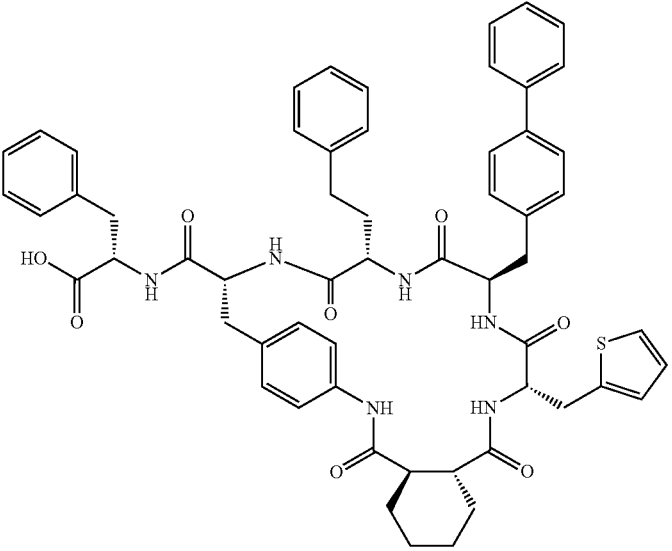 | 945.36 | 945.25 |
| 711 | 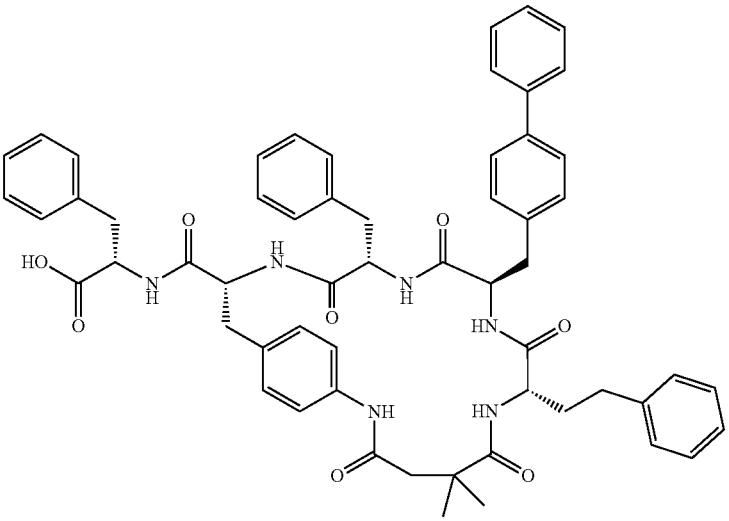 | 973.40 | 973.43 |
| 712 | 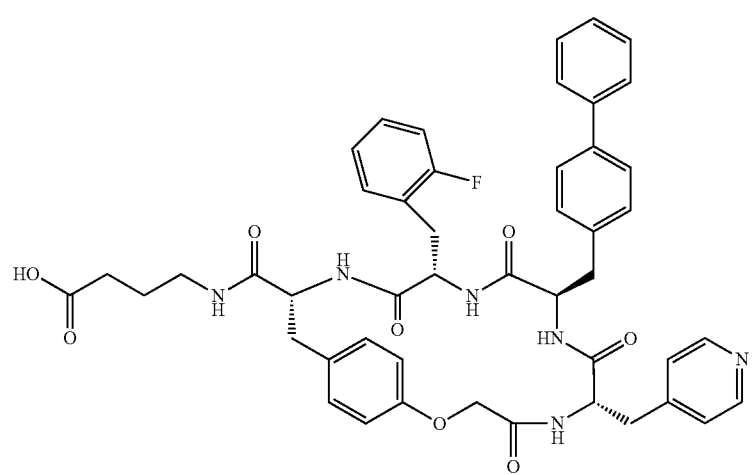 | 1001.43 | 1001.39 |

TABLE 1-continued

| Compound No. | Structure | MS Calcd | MS Observed |
|---|---|---|---|
| 713 | | 969.46 | 969.44 |
| 713 | | 843.35 | 843.37 |
| 714 | 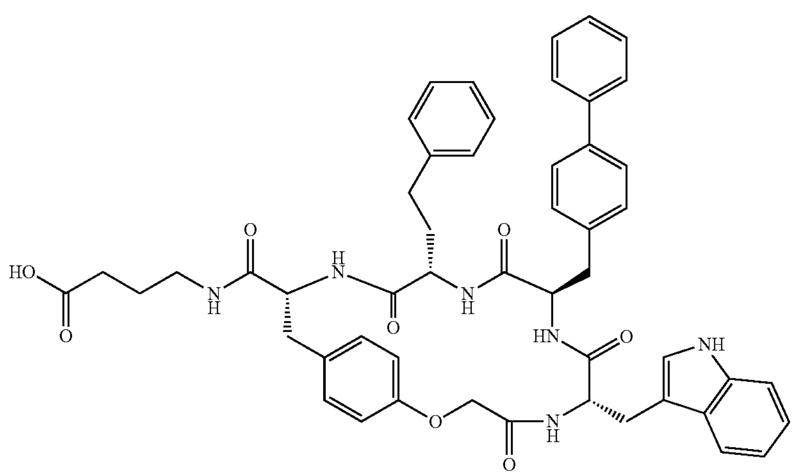 | 881.37 | 881.38 |

TABLE 1-continued

| Compound No. | Structure | MS Calcd | MS Observed |
|---|---|---|---|
| 715 | | 877.39 | 877.42 |
| 715 | | 839.38 | 839.39 |
| 716 | 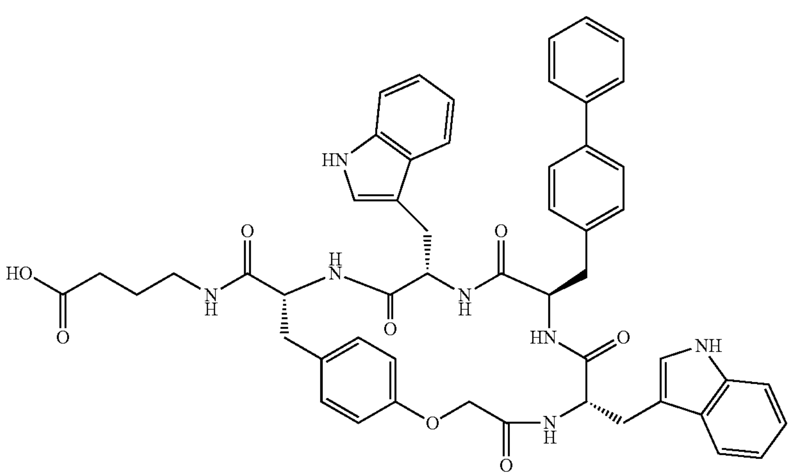 | 902.39 | 902.40 |

TABLE 1-continued

| Compound No. | Structure | MS Calcd | MS Observed |
|---|---|---|---|
| 717 | 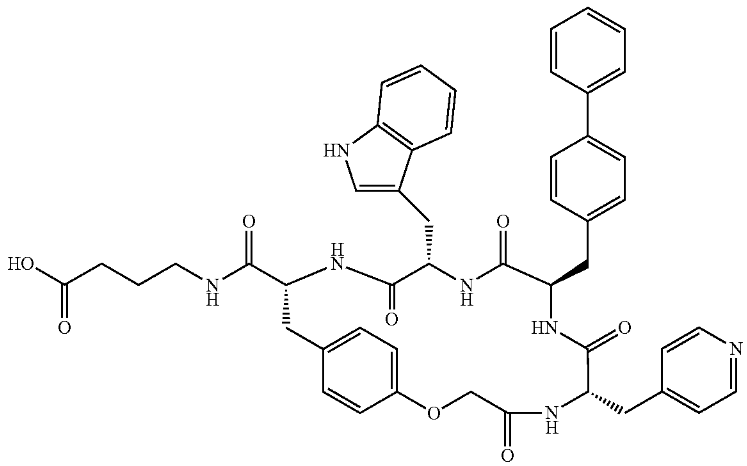 | 864.37 | 864.38 |
| 718 | 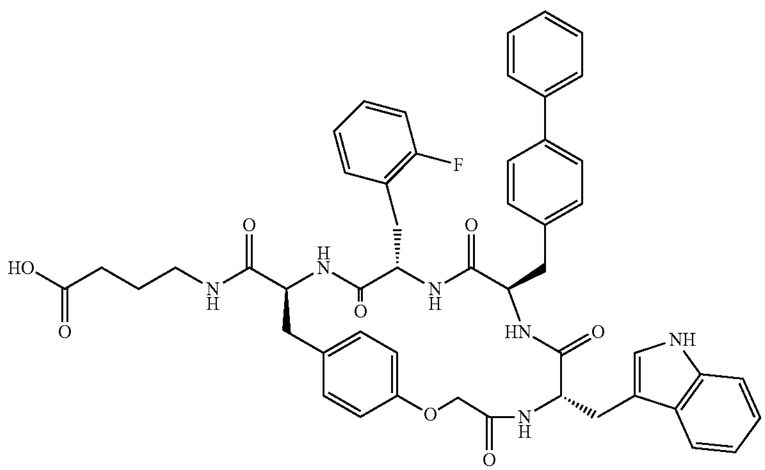 | 881.37 | 881.36 |
| 719 | 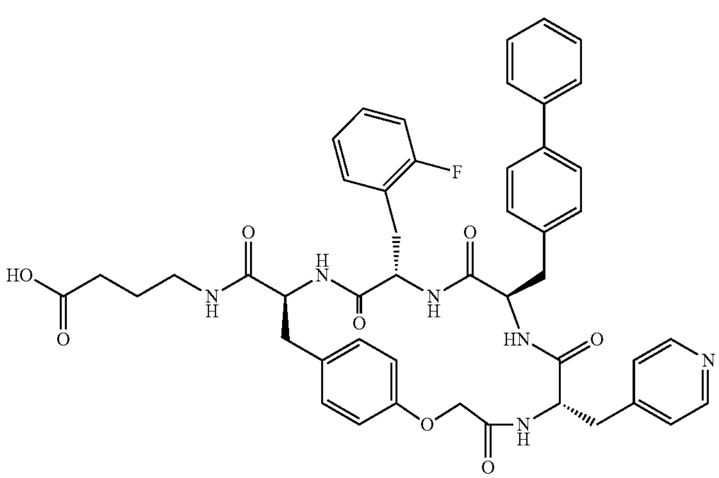 | 843.35 | 843.37 |

TABLE 1-continued

| Compound No. | Structure | MS Calcd | MS Observed |
|---|---|---|---|
| 720 | 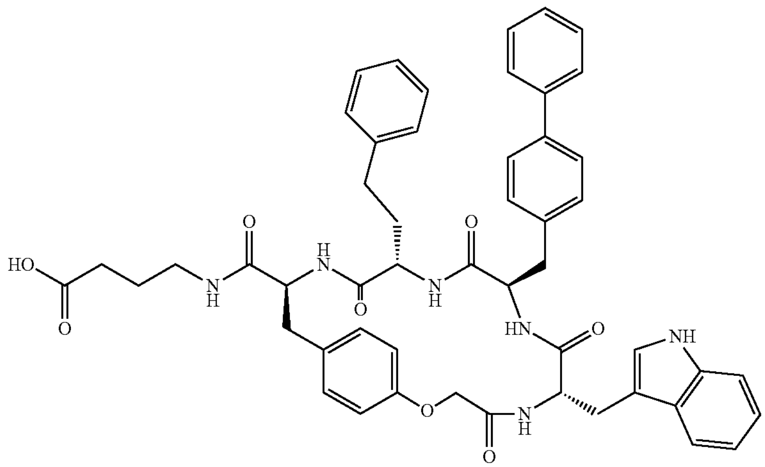 | 877.39 | 877.41 |
| 721 | 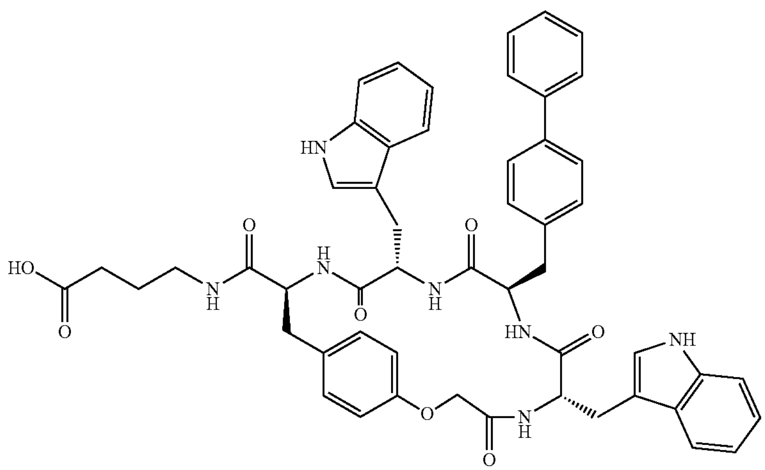 | 902.39 | 902.39 |
| 722 | 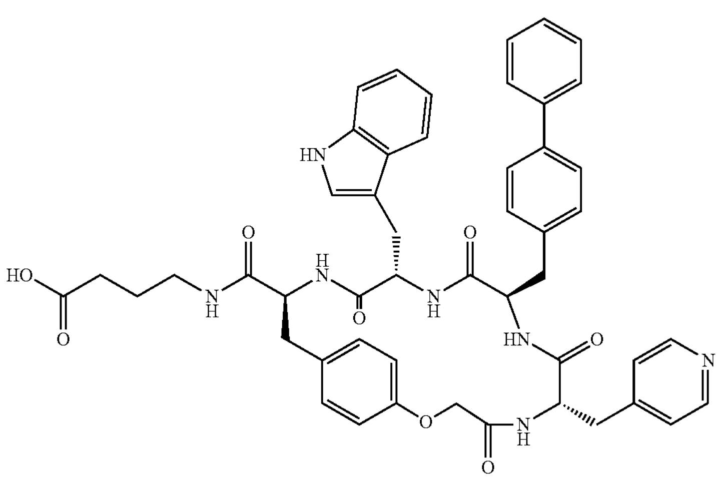 | 864.37 | 864.39 |

TABLE 1-continued

| Compound No. | Structure | MS Calcd | MS Observed |
|---|---|---|---|
| 723 | 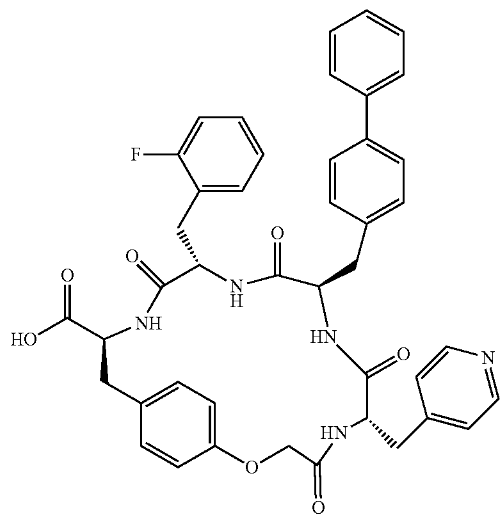 | 758.30 | 758.30 |
| 724 | 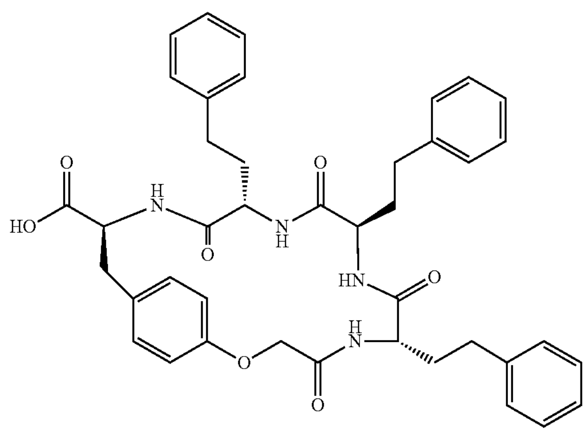 | 705.33 | 705.33 |
| 725 | 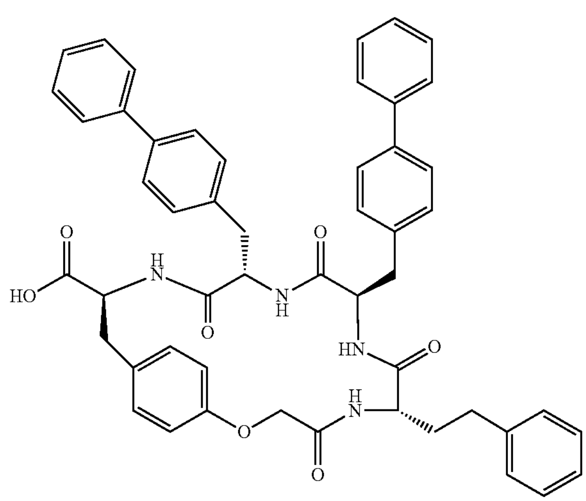 | 829.36 | 829.40 |

TABLE 1-continued
| Compound No. | Structure | MS Calcd | MS Observed |
|---|---|---|---|
| 726 | 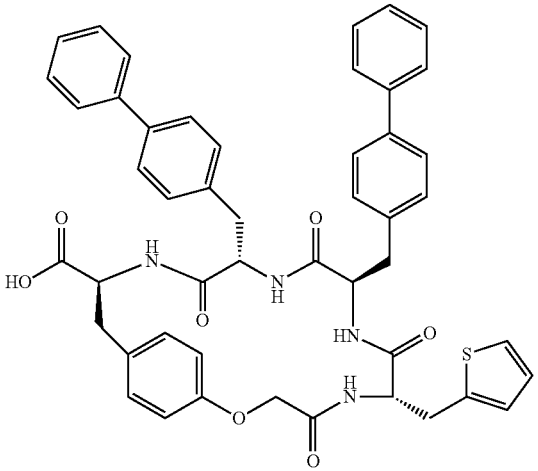 | 821.30 | 821.31 |
| 727 | 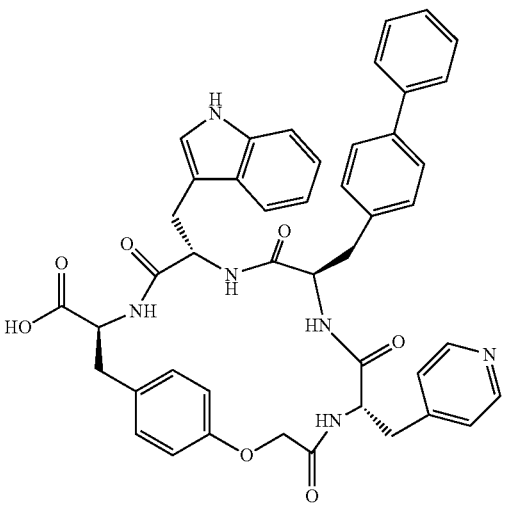 | 779.32 | 779.31 |
| 728 | 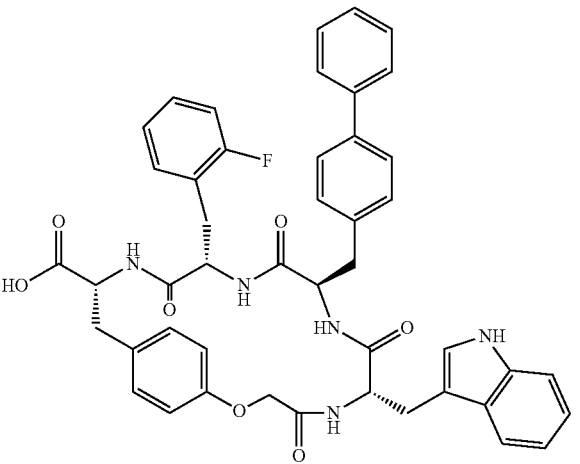 | 796.31 | 796.33 |

TABLE 1-continued

| Compound No. | Structure | MS Calcd | MS Observed |
|---|---|---|---|
| 729 | 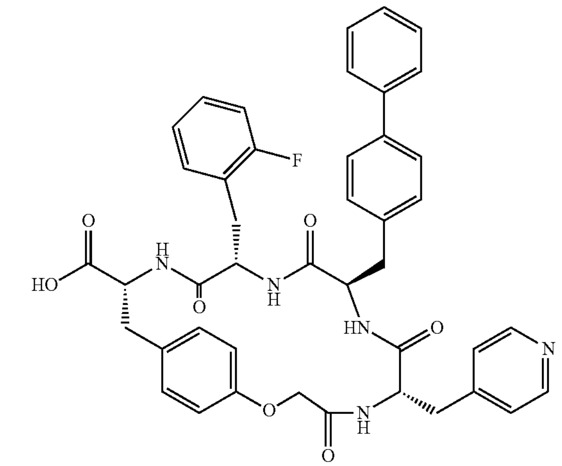 | 758.30 | 758.29 |
| 730 | 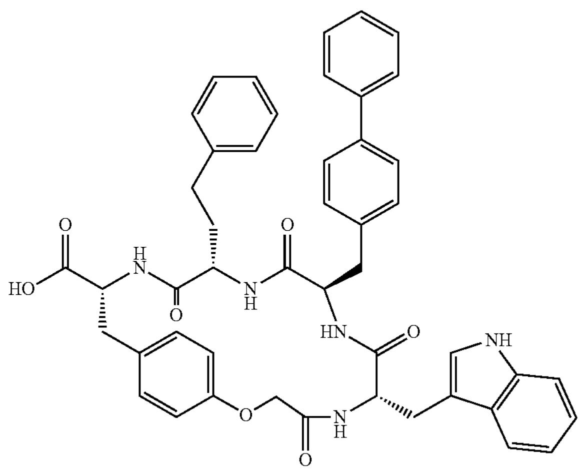 | 792.34 | 792.35 |
| 731 | 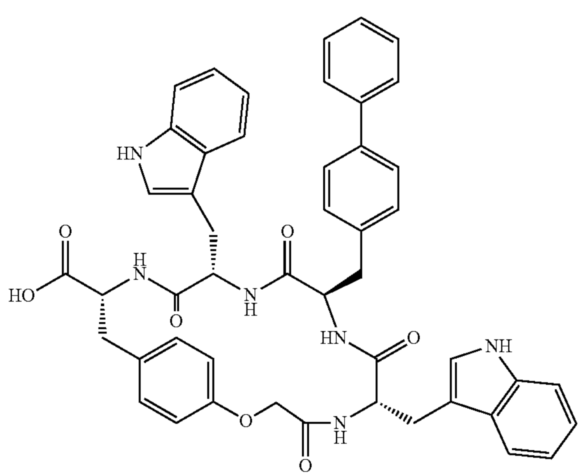 | 817.33 | 817.35 |

TABLE 1-continued

| Compound No. | Structure | MS Calcd | MS Observed |
|---|---|---|---|
| 732 | 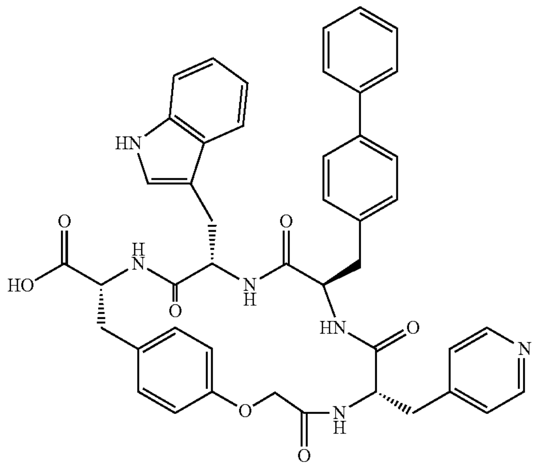 | 779.32 | 779.33 |
| 733 | 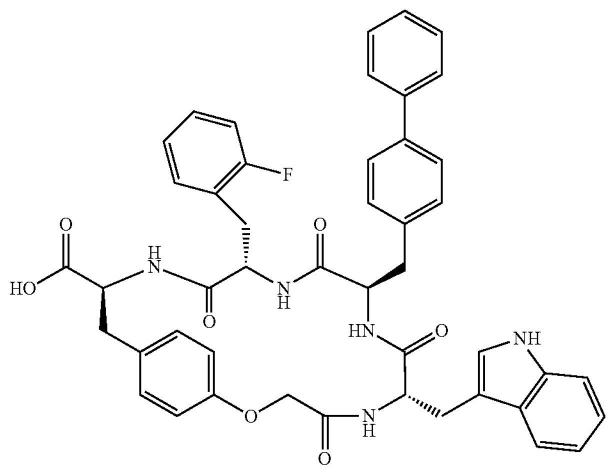 | 796.31 | 796.32 |
| 734 | 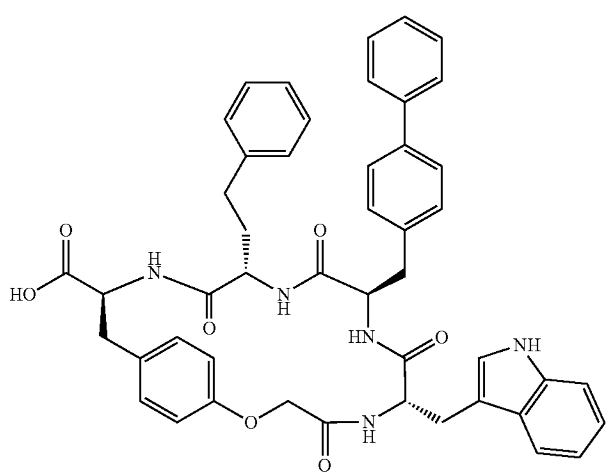 | 792.34 | 792.35 |

TABLE 1-continued

| Compound No. | Structure | MS Calcd | MS Observed |
|---|---|---|---|
| 735 | 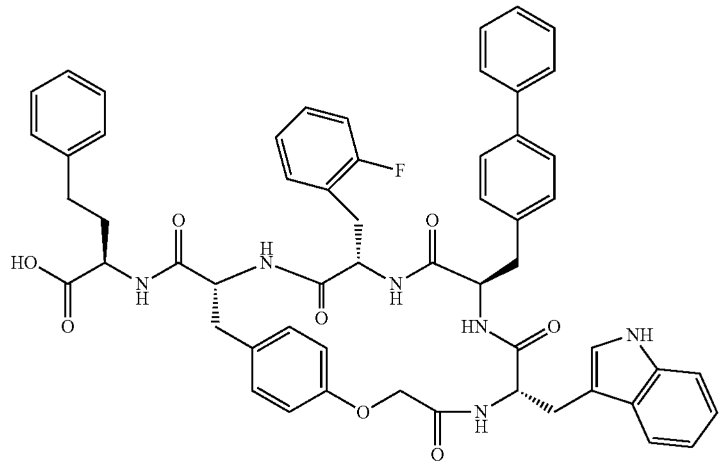 | 957.40 | 957.38 |
| 736 | 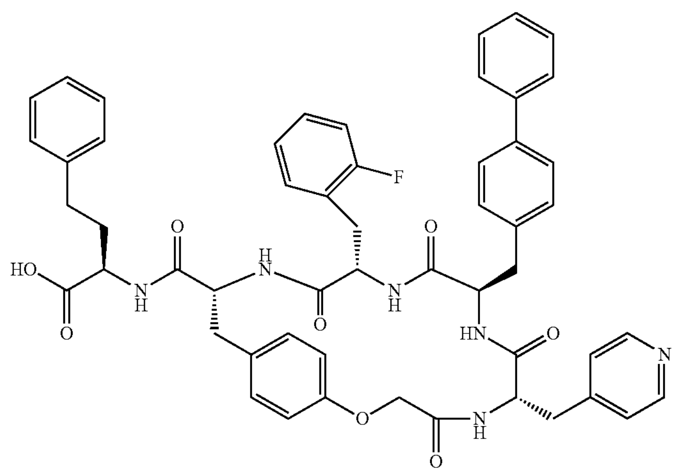 | 919.38 | 919.40 |
| 737 | 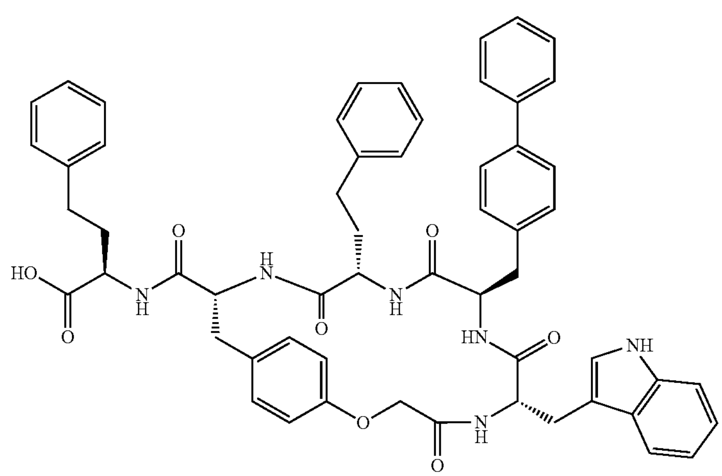 | 953.42 | 953.45 |

TABLE 1-continued

| Compound No. | Structure | MS Calcd | MS Observed |
|---|---|---|---|
| 738 | 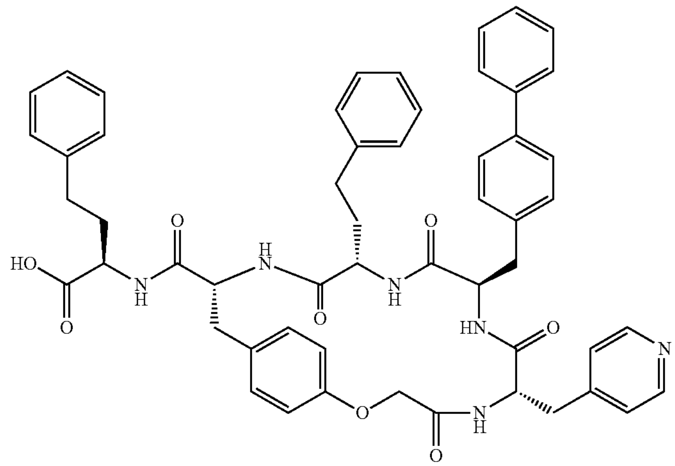 | 915.41 | 915.45 |
| 739 | 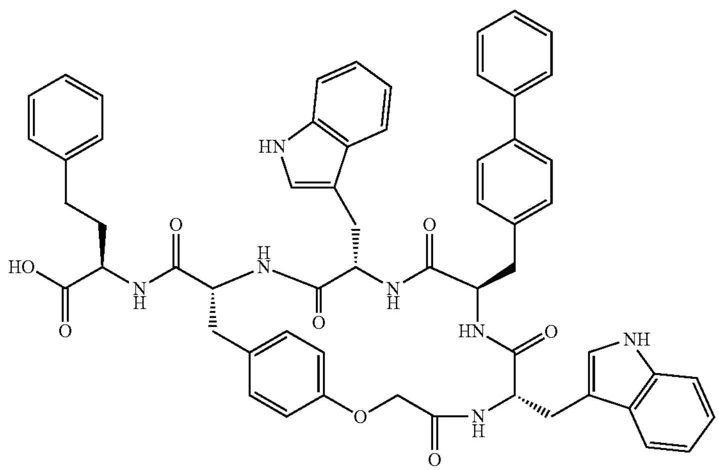 | 978.42 | 978.70 |
| 740 | 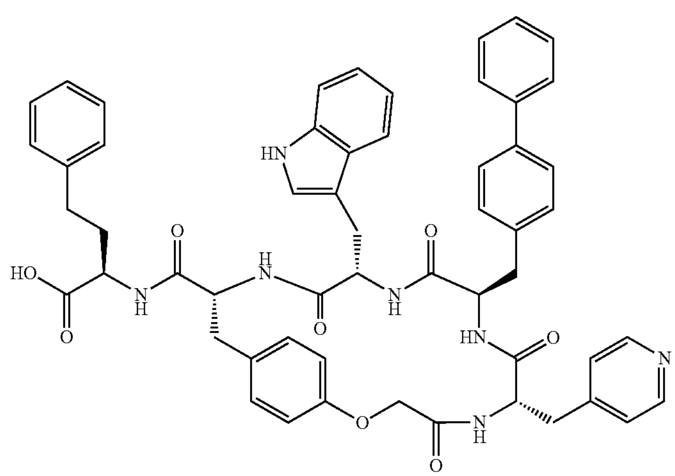 | 940.40 | 940.41 |

TABLE 1-continued

| Compound No. | Structure | MS Calcd | MS Observed |
|---|---|---|---|
| 741 | 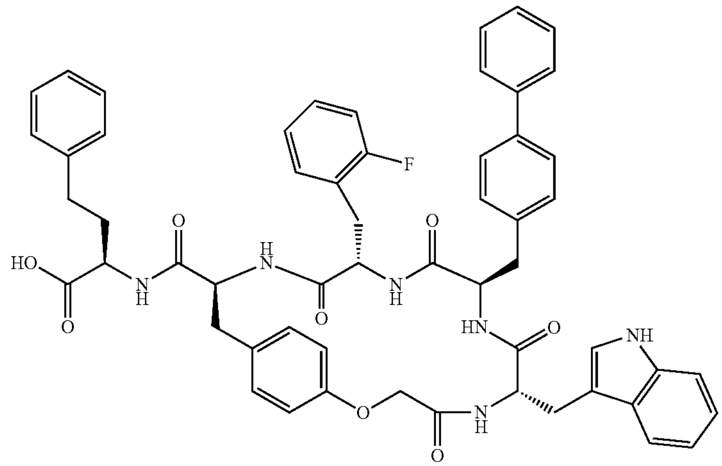 | 957.40 | 957.41 |
| 742 | 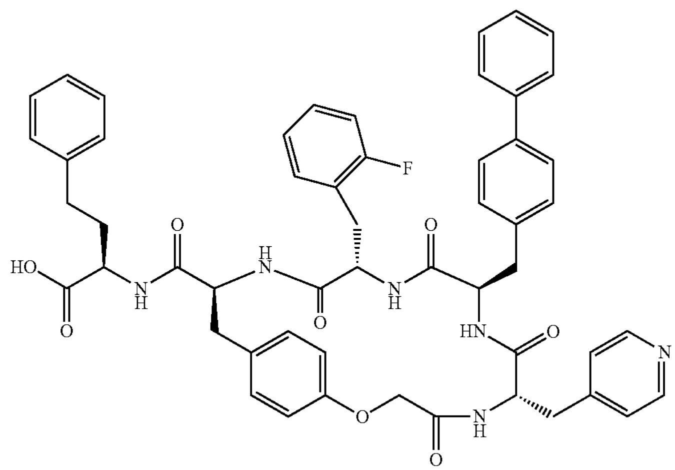 | 919.38 | 919.40 |
| 743 | 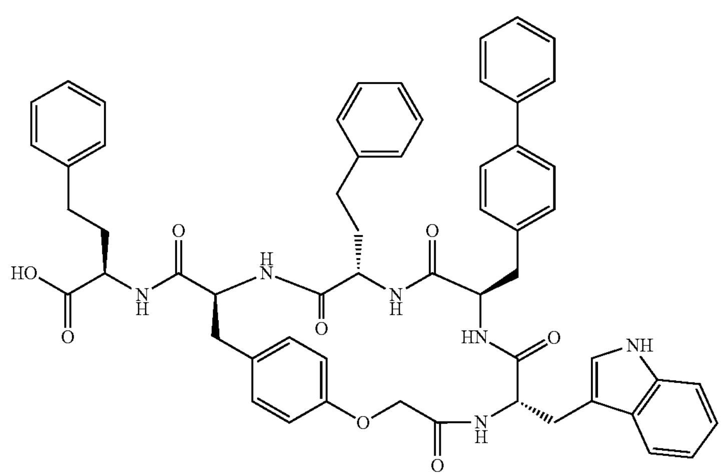 | 953.42 | 953.45 |

TABLE 1-continued

| Compound No. | Structure | MS Calcd | MS Observed |
|---|---|---|---|
| 744 | 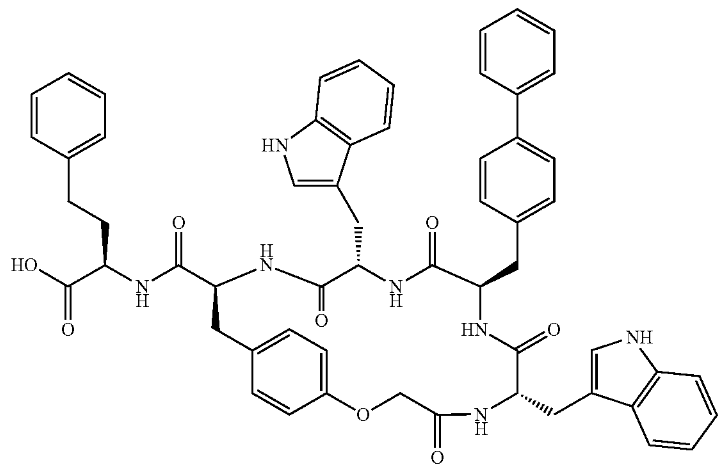 | 978.42 | 978.45 |
| 745 | 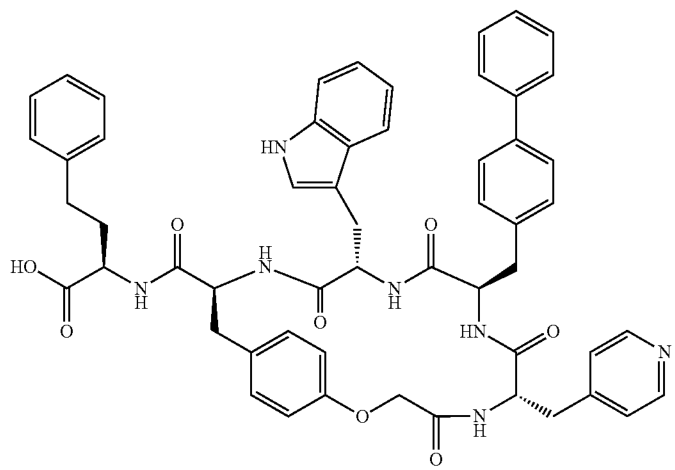 | 940.40 | 940.43 |
| 746 | 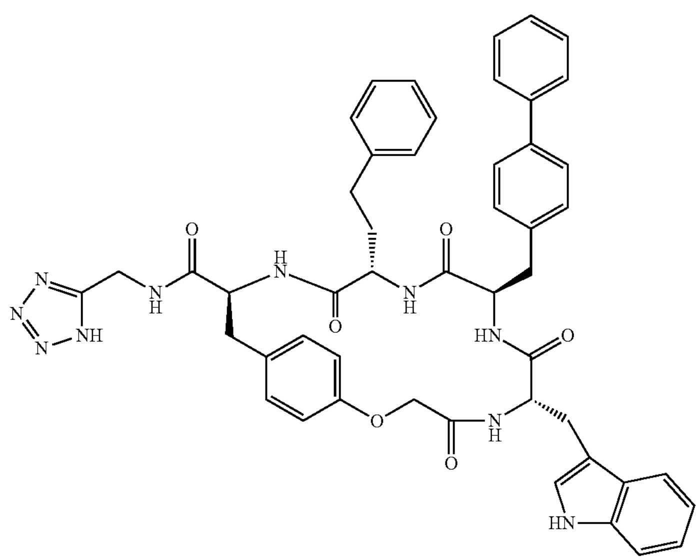 | 873.38 | 873.39 |

TABLE 1-continued

| Compound No. | Structure | MS Calcd | MS Observed |
|---|---|---|---|
| 747 | 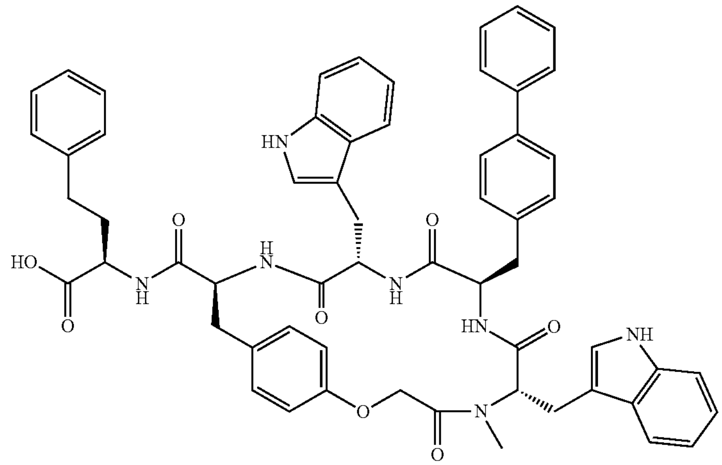 | 992.43 | 992.45 |

In the above table, calculated (MS Calcd) and observed (MS Observed) mass spectrometry values were determined for most compounds using high-resolution mass spectrometry. An "*" after the observed value indicates that the mass spectrometry value for that compound was determined using low-resolution mass spectrometry. Mass spectrometry measurements were performed using electrospray ionization (ESI).

The macrocyclic compounds described herein can be prepared using an iterative peptide coupling procedure as illustrated in following synthetic schemes. An exemplary retrosynthetic analysis is presented in Scheme 1, and exemplary general synthetic protocol is presented in Scheme 2. The schemes and accompanying description of synthetic procedures are given for the purpose of illustrating the invention, and should not be construed as limiting the scope or spirit of the invention.

Scheme 1. Exemplary Retrosynthetic Analysis

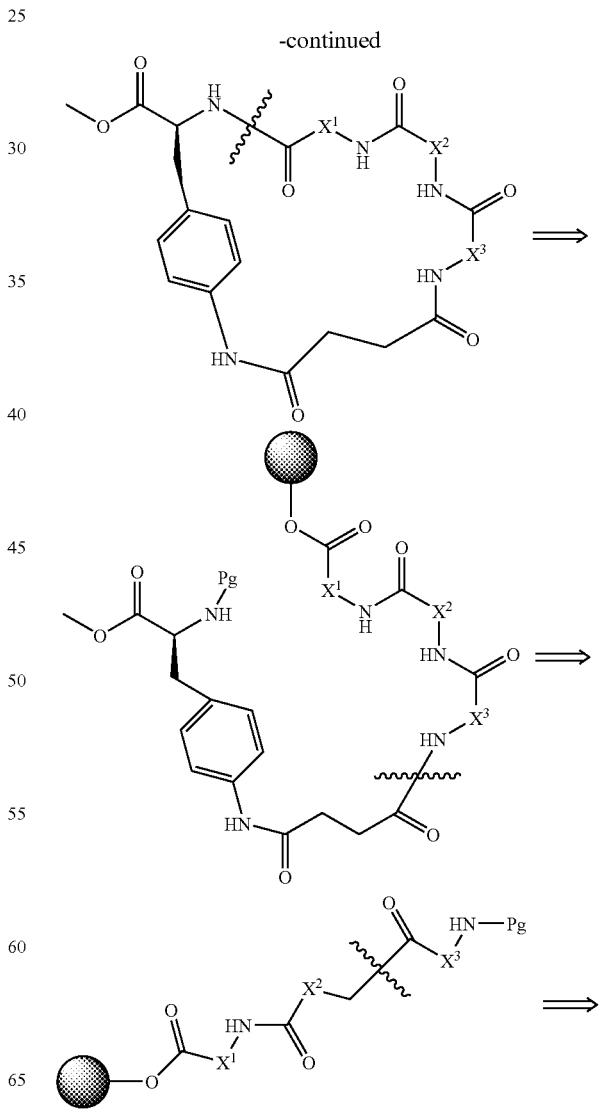

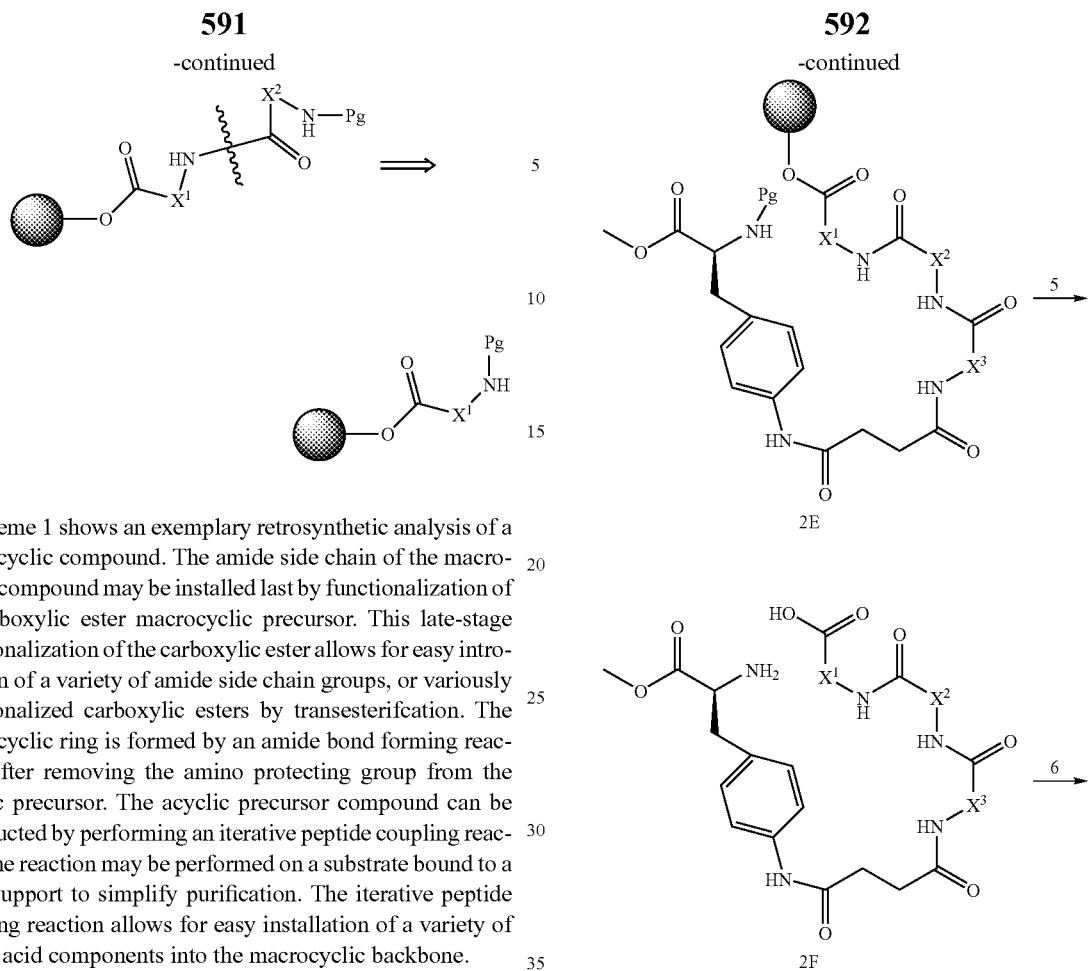

Scheme 1 shows an exemplary retrosynthetic analysis of a macrocyclic compound. The amide side chain of the macrocyclic compound may be installed last by functionalization of an carboxylic ester macrocyclic precursor. This late-stage functionalization of the carboxylic ester allows for easy introduction of a variety of amide side chain groups, or variously functionalized carboxylic esters by transesterifcation. The macrocyclic ring is formed by an amide bond forming reaction, after removing the amino protecting group from the acyclic precursor. The acyclic precursor compound can be constructed by performing an iterative peptide coupling reaction; the reaction may be performed on a substrate bound to a solid support to simplify purification. The iterative peptide coupling reaction allows for easy installation of a variety of amino acid components into the macrocyclic backbone.

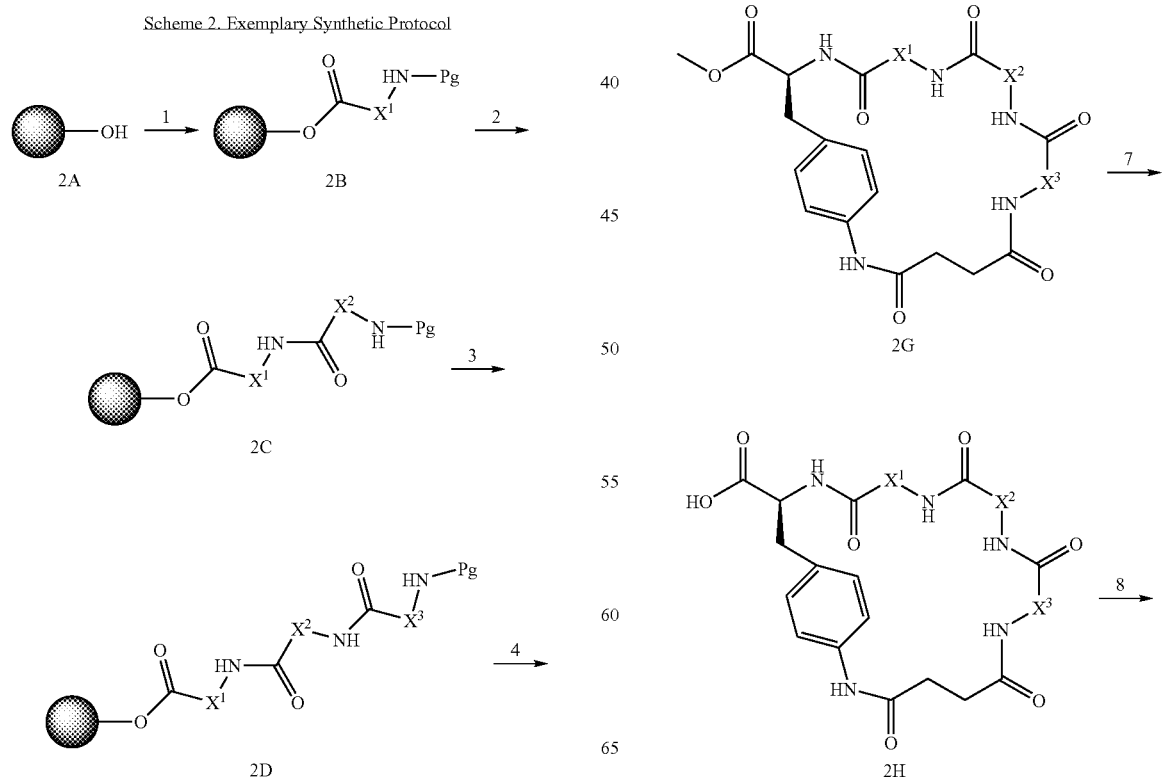

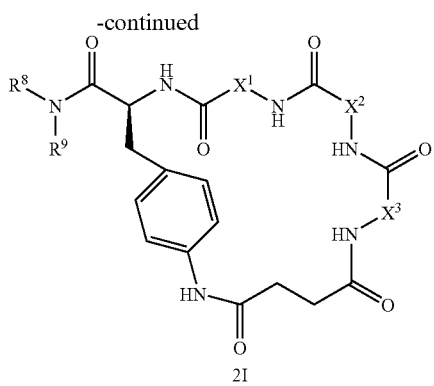

2I

Scheme 2 shows an exemplary synthetic protocol for preparing a macrocyclic compound. The synthesis may be performed on solid support in order to simplify purification of synthetic intermediates. For example, hydroxyl-bearing resin 2A can be reacted with a suitably protected amino acid. Side chain ($R^a$) of the amino acid may be varied in order to prepare macrocyclic compounds having different substituents at this position. Dipeptide 2C may be prepared by removing the protecting group (Pg) from 2B and then performing a peptide coupling reaction with amino acid $HO_2CC(H)(R_2)N(H)Pg$. The third amino acid making up the core of the macrocycle is installed by repeating the deprotection/peptide coupling process using the same or different protected amino acid to provide tripeptide 2D. The remaining portion of the macrocycle backbone is installed in step four, again using a peptide coupling reaction to splice the substituted succinic acid with the resin-bound tripeptide 2D following removal of the protecting group from tripeptide 2D. In the fifth step, the amino protecting group is removed and the substrate is cleaved from the solid support to provide acyclic intermediate 2F. The macrocyclic core is constructed by subjecting 2F to conditions suitable for amide bond formation. The carboxylic ester side chain on macrocycle 2G can be converted to various esters by transesterication, the acid by simply hydrolysis, or to various amide compounds, e.g., 2I, using standard synthetic procedures. See, for example, J. March "Advanced Organic Chemistry Reactions, Mechanisms, and Structure" $4^{th}$ Edition, John Wiley & Sons, 1992.

Additional synthetic procedures are provided in examples 1-4 below.

Combinations of substituents and variables are only those that result in the formation of compounds which possess stability sufficient to allow for their manufacture and which maintain the integrity of the compound for a sufficient period of time to be useful for the purposes detailed herein (e.g., formulation into therapeutic products, intermediates for use in production of therapeutic compounds, isolatable or storable intermediate compounds, treating a disease or condition responsive to therapeutic agents).

II. Therapeutic Applications of Macrocyclic Compounds

It is contemplated that the compounds of formula I and related macrocyclic compounds, for example, those embraced by formula II, provide therapeutic benefits to patients suffering from or susceptible to any one of rheumatoid arthritis, juvenile rheumatoid arthritis, ankylosing spondylitis, psoriatic arthritis, psoriasis, Crohn's disease, Behcet's disease, ulcerative colitis, Wegener's granulomatosis, sarcoidosis, systemic lupus erythematosus, systemic sclerosis, insulin-dependent diabetes mellitus, cancer, multiple sclerosis, septic shock syndrome, asthma, Alzheimer's disease, an inflammatory eye disease, uveitis, and inflammation.

Accordingly, one aspect of the invention provides a method of treating a patient suffering from or susceptible to a disorder selected from the group consisting of rheumatoid arthritis, juvenile rheumatoid arthritis, ankylosing spondylitis, psoriatic arthritis, psoriasis, Crohn's disease, Behcet's disease, ulcerative colitis, Wegener's granulomatosis, sarcoidosis, systemic lupus erythematosus, systemic sclerosis, insulin-dependent diabetes mellitus, cancer, multiple sclerosis, septic shock syndrome, asthma, Alzheimer's disease, an inflammatory eye disease, uveitis, and inflammation, comprising administering a therapeutically effective amount of a composition comprising a compound described herein to the patient in need thereof.

In certain instances, the disorder is rheumatoid arthritis, psoriasis, Crohn's disease, cancer, multiple sclerosis, asthma, Alzheimer's disease, or ulcerative colitis. In certain other instances, the disorder is rheumatoid arthritis, juvenile rheumatoid arthritis, ankylosing spondylitis, psoriatic arthritis, psoriasis, Crohn's disease, ulcerative colitis, Wegener's granulomatosis, or sarcoidosis. In certain other instances, the disorder is rheumatois arthritis.

In certain instances, compound is a compound of formula III, III-A, IV, V, VI, or VII.

The invention also provides for combination therapy of a macrocyclic compound described herein and a second therapeutic agent. "Combination therapy" (or "co-therapy") includes the administration of a macrocyclic compound described herein and at least a second agent as part of a specific treatment regimen intended to provide the beneficial effect from the co-action of these therapeutic agents. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days or weeks depending upon the combination selected).

Combination therapy is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single dosage form having a fixed ratio of each therapeutic agent or in multiple, single dosage forms for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. Combination therapy also can embrace the administration of the therapeutic agents as described above in further combination with other biologically active ingredients and non-drug therapies (e.g., surgery or radiation treatment.) Where the combination therapy further comprises a non-drug treatment, the non-drug treatment may be conducted at any suitable time so long as a beneficial effect from the co-action of the combination of the therapeutic agents and non-drug treatment is achieved. For example, in appropriate cases, the beneficial effect is still achieved when the non-drug treatment is temporally removed from the administration of the therapeutic agents, perhaps by days or even weeks.

Accordingly, in certain instances, the method further comprises administering a therapeutically effective amount of an anti-inflammatory agent. In certain instances, the anti-inflammatory agent is a salicylate, diclofenac, aceclofenac, acemetacin, alclofenac, bromfenac, etodolac, indometacin, nabumetone, oxametacin, proglumetacin, sulindac, tolmetin, piroxicam, droxicam, lornoxicam, meloxicam, tenoxicam, ibuprofen, alminoprofen, carprofen, dexibuprofen, dexketoprofen, fenbufen, fenoprofen, flunoxaprofen, flurbiprofen, ibuproxam, indoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, oxyphenbutazone, phenazone, phenylbutazone, sulfinpyrazone, celecoxib, etoricoxib, lumiracoxib, parecoxib, rofecoxib, valdecoxib, prednisone, methylprednisolone, hydrocortisone, or budesonide.

In certain instances, the method further comprises administering a therapeutically effective amount of an agent for treating multiple sclerosis. In certain instances, the agent for treating multiple sclerosis is interferon beta-2, interferon beta-1, glatiramer, natalizumab, or mitoxantrone.

In certain instances, the method further comprises administering infliximab, etanercept, adalimumab, or certolizumab pegol.

In certain instances, the method is designed to treat rheumatoid arthritis and further comprises the step of administering to the patient in need thereof a therapeutically effective amount of an agent selected from the group consisting of a salicylate, diclofenac, aceclofenac, acemetacin, alclofenac, bromfenac, etodolac, indometacin, nabumetone, oxametacin, proglumetacin, sulindac, tolmetin, piroxicam, droxicam, lornoxicam, meloxicam, tenoxicam, ibuprofen, alminoprofen, carprofen, dexibuprofen, dexketoprofen, fenbufen, fenoprofen, flunoxaprofen, flurbiprofen, ibuproxam, indoprofen, ketorolac, loxoprofen, naproxen, oxaprozin, pirprofen, suprofen, tiaprofenic acid, mefenamic acid, flufenamic acid, meclofenamic acid, tolfenamic acid, phenylbutazone, ampyrone, azapropazone, clofezone, kebuzone, metamizole, mofebutazone, phenazone, sulfinpyrazone, celecoxib, etoricoxib, lumiracoxib, parecoxib, prednisone, methylprednisolone, hydrocortisone, and budesonide.

Another aspect of the invention provides a method of modulating the activity of tumor necrosis factor alpha on a cell, comprising exposing a cell comprising on its surface a receptor for tumor necrosis factor alpha to a compound described herein. In certain instances, the compound reduces or inhibits the activity of tumor necrosis factor alpha on the cell.

IV. Pharmaceutical Compositions and Dosing Considerations

The invention also provides pharmaceutically acceptable compositions which comprise a therapeutically-effective amount of one or more of the compounds described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, e.g., those targeted for buccal, sublingual, and systemic absorption, boluses, powders, granules, pastes for application to the tongue; (2) parenteral administration, for example, by subcutaneous, intramuscular, intravenous or epidural injection as, for example, a sterile solution or suspension, or sustained-release formulation; (3) topical application, for example, as a cream, ointment, or a controlled-release patch or spray applied to the skin; (4) intravaginally or intrarectally, for example, as a pessary, cream or foam; (5) sublingually; (6) ocularly; (7) transdermally; or (8) nasally.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically-acceptable carrier" as used herein means a pharmaceutically-acceptable material, composition or vehicle, such as a liquid or solid filler, diluent, excipient, manufacturing aid (e.g., lubricant, talc magnesium, calcium or zinc stearate, or steric acid), or solvent encapsulating material, involved in carrying or transporting the subject compound from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

As set out above, certain embodiments of the present compounds may contain a basic functional group, such as amino or alkylamino, and are, thus, capable of forming pharmaceutically-acceptable salts with pharmaceutically-acceptable acids. The term "pharmaceutically-acceptable salts" in this respect, refers to the relatively non-toxic, inorganic and organic acid addition salts of compounds of the present invention. These salts can be prepared in situ in the administration vehicle or the dosage form manufacturing process, or by separately reacting a purified compound of the invention in its free base form with a suitable organic or inorganic acid, and isolating the salt thus formed during subsequent purification. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, napthylate, mesylate, glucoheptonate, lactobionate, and laurylsulphonate salts and the like. (See, e.g., Berge et al. (1977) "Pharmaceutical Salts", *J. Pharm. Sci.* 66:1-19)

The pharmaceutically acceptable salts of the subject compounds include the conventional nontoxic salts or quaternary ammonium salts of the compounds, e.g., from non-toxic organic or inorganic acids. For example, such conventional nontoxic salts include those derived from inorganic acids such as hydrochloride, hydrobromic, sulfuric, sulfamic, phosphoric, nitric, and the like; and the salts prepared from organic acids such as acetic, propionic, succinic, glycolic, stearic, lactic, malic, tartaric, citric, ascorbic, palmitic, maleic, hydroxymaleic, phenylacetic, glutamic, benzoic, salicyclic, sulfanilic, 2-acetoxybenzoic, fumaric, toluenesulfonic, methanesulfonic, ethane disulfonic, oxalic, isothionic, and the like.

In other cases, the compounds of the present invention may contain one or more acidic functional groups and, thus, are capable of forming pharmaceutically-acceptable salts with pharmaceutically-acceptable bases. The term "pharmaceutically-acceptable salts" in these instances refers to the relatively non-toxic, inorganic and organic base addition salts of compounds of the present invention. These salts can likewise be prepared in situ in the administration vehicle or the dosage form manufacturing process, or by separately reacting the purified compound in its free acid form with a suitable base, such as the hydroxide, carbonate or bicarbonate of a pharmaceutically-acceptable metal cation, with ammonia, or with a pharmaceutically-acceptable organic primary, secondary or tertiary amine. Representative alkali or alkaline earth salts include the lithium, sodium, potassium, calcium, magnesium, and aluminum salts and the like. Representative organic amines useful for the formation of base addition salts include ethylamine, diethylamine, ethylenediamine, ethanolamine, diethanolamine, piperazine and the like. (See, e.g., Berge et al., supra)

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically-acceptable antioxidants include: (1) water soluble antioxidants, such as ascorbic acid, cysteine hydrochloride, sodium bisulfate, sodium metabisulfite, sodium sulfite and the like; (2) oil-soluble antioxidants, such as ascorbyl palmitate, butylated hydroxyanisole (BHA), butylated hydroxytoluene (BHT), lecithin, propyl gallate, alpha-tocopherol, and the like; and (3) metal chelating agents, such as citric acid, ethylenediamine tetraacetic acid (EDTA), sorbitol, tartaric acid, phosphoric acid, and the like.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the compound which produces a therapeutic effect. Generally, out of one hundred percent, this amount will range from about 0.1 percent to about ninety-nine percent of active ingredient, preferably from about 5 percent to about 70 percent, most preferably from about 10 percent to about 30 percent.

In certain embodiments, a formulation of the present invention comprises an excipient selected from the group consisting of cyclodextrins, celluloses, liposomes, micelle forming agents, e.g., bile acids, and polymeric carriers, e.g., polyesters and polyanhydrides; and a compound of the present invention. In certain embodiments, an aforementioned formulation renders orally bioavailable a compound of the present invention.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules, trouches and the like), the active ingredient is mixed with one or more pharmaceutically-acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds and surfactants, such as poloxamer and sodium lauryl sulfate; (7) wetting agents, such as, for example, cetyl alcohol, glycerol monostearate, and non-ionic surfactants; (8) absorbents, such as kaolin and bentonite clay; (9) lubricants, such as talc, calcium stearate, magnesium stearate, solid polyethylene glycols, sodium lauryl sulfate, zinc stearate, sodium stearate, stearic acid, and mixtures thereof; (10) coloring agents; and (11) controlled release agents such as crospovidone or ethyl cellulose. In the case of capsules, tablets and pills, the pharmaceutical compositions may also comprise buffering agents. Solid compositions of a similar type may also be employed as fillers in soft and hard-shelled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be formulated for rapid release, e.g., freeze-dried. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically-acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically-acceptable sterile isotonic aqueous or nonaqueous solutions, dispersions, suspensions or emulsions, or sterile powders which may be reconstituted into sterile injectable solutions or dispersions just prior to use, which may contain sugars, alcohols, antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms upon the subject compounds may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

When the compounds of the present invention are administered as pharmaceuticals, to humans and animals, they can be given per se or as a pharmaceutical composition containing, for example, 0.1 to 99% (more preferably, 10 to 30%) of active ingredient in combination with a pharmaceutically acceptable carrier.

The preparations of the present invention may be given orally, parenterally, topically, or rectally. They are of course given in forms suitable for each administration route. For example, they are administered in tablets or capsule form, by injection or infusion, by inhalation, topically by lotion or ointment, or by suppositories. Oral administrations are preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically-acceptable dosage forms by conventional methods known to those of skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion or metabolism of the particular compound being employed, the rate and extent of absorption, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, oral, intravenous, intracerebroventricular and subcutaneous doses of the compounds of this invention for a patient will range from about 0.0001 to about 100 mg per kilogram of body weight per day.

If desired, the effective daily dose of the active compound may be administered as two, three, four, five, six or more sub-doses administered separately at appropriate intervals throughout the day, optionally, in unit dosage forms. Preferred dosing is one administration per day.

While it is possible for a compound of the present invention to be administered alone, it is preferable to administer the compound as a pharmaceutical formulation (composition).

The compounds according to the invention may be formulated for administration in any convenient way for use in human or veterinary medicine, by analogy with other pharmaceuticals.

In another aspect, the present invention provides pharmaceutically acceptable compositions which comprise a therapeutically-effective amount of one or more of the subject compounds, as described above, formulated together with one or more pharmaceutically acceptable carriers (additives) and/or diluents. As described in detail below, the pharmaceutical compositions of the present invention may be specially formulated for administration in solid or liquid form, including those adapted for the following: (1) oral administration, for example, drenches (aqueous or non-aqueous solutions or suspensions), tablets, boluses, powders, granules, pastes for application to the tongue; (2) parenteral administration, for example, by subcutaneous, intramuscular or intravenous injection as, for example, a sterile solution or suspension; (3) topical application, for example, as a cream, ointment or spray applied to the skin, lungs, or mucous membranes; or (4) intravaginally or intrarectally, for example, as a pessary, cream or foam; (5) sublingually or buccally; (6) ocularly; (7) transdermally; or (8) nasally.

In some embodiments, in vivo administration is effected in one dose, continuously or intermittently throughout the course of treatment. Methods of determining the most effective means and dosage of administration are well known to those of skill in the art and vary with the composition used for therapy, the purpose of the therapy, the target cell being treated, and the subject being treated. Single or multiple administrations are carried out with the dose level and pattern being selected by the treating physician.

Suitable dosage formulations and methods of administering the agents are readily determined by those of skill in the art. Preferably, the compounds are administered at about 0.01 mg/kg to about 200 mg/kg, more preferably at about 0.1 mg/kg to about 100 mg/kg, even more preferably at about 0.5 mg/kg to about 50 mg/kg. When the compounds described herein are co-administered with another agent (e.g., as sensitizing agents), the effective amount may be less than when the agent is used alone.

The pharmaceutical compositions can be administered orally, intranasally, parenterally or by inhalation therapy, and may take the form of tablets, lozenges, granules, capsules, pills, ampoules, suppositories or aerosol form. They may also take the form of suspensions, solutions and emulsions of the active ingredient in aqueous or non-aqueous diluents, syrups, granulates or powders. In addition to an agent of the present invention, the pharmaceutical compositions can also contain other pharmaceutically active compounds or a plurality of compounds of the invention.

In yet another embodiment, the invention provides any of the pharmaceutical compositions set forth above for use in the treatment of a disease or condition selected from rheumatoid arthritis, juvenile rheumatoid arthritis, ankylosing spondylitis, psoriatic arthritis, psoriasis, Crohn's disease, Behcet's disease, ulcerative colitis, Wegener's granulomatosis, sarcoidosis, systemic lupus erythematosus, systemic sclerosis, insulin-dependent diabetes mellitus, cancer, multiple sclerosis, septic shock syndrome, asthma, Alzheimer's disease, an inflammatory eye disease, uveitis, and inflammation. In a more specific embodiment, the invention provides a pharmaceutical composition comprising a compound of any one of Formulae I-VII, or any of Compounds 1-747 for use in the treatment of rheumatoid arthritis.

V. Pharamceutical Kits

The invention also provides kits for use to treat rheumatoid arthritis, juvenile rheumatoid arthritis, ankylosing spondylitis, psoriatic arthritis, psoriasis, Crohn's disease, Behcet's disease, ulcerative colitis, Wegener's granulomatosis, sarcoidosis, systemic lupus erythematosus, systemic sclerosis, insulin-dependent diabetes mellitus, cancer, multiple sclerosis, septic shock syndrome, asthma, Alzheimer's disease, an inflammatory eye disease, uveitis, or inflammation. The kits comprise (a) a pharmaceutical composition comprising a compound described herein or a pharmaceutically acceptable salt thereof, wherein said pharmaceutical composition is in a container; and (b) instructions describing a method of using the pharmaceutical composition to treat the specific disease.

The container may be any vessel or other sealed or sealable apparatus that can hold said pharmaceutical composition. Examples include bottles, ampules, divided or multi-chambered holders bottles, wherein each division or chamber comprises a single dose of said composition, a divided foil packet wherein each division comprises a single dose of said composition, or a dispenser that dispenses single doses of said composition. The container can be in any conventional shape or form as known in the art which is made of a pharmaceutically acceptable material, for example a paper or cardboard box, a glass or plastic bottle or jar, a re-sealable bag (for example, to hold a "refill" of tablets for placement into a different container), or a blister pack with individual doses for pressing out of the pack according to a therapeutic schedule. The container employed can depend on the exact dosage form involved, for example a conventional cardboard box would not generally be used to hold a liquid suspension. It is feasible that more than one container can be used together in a single package to market a single dosage form. For example, tablets may be contained in a bottle, which is in turn contained within a box. In one embodiment, the container is a blister pack.

The kits may also comprise a device to administer or to measure out a unit dose of the pharmaceutical composition. Such device may include an inhaler if said composition is an inhalable composition; a syringe and needle if said composition is an injectable composition; a syringe, spoon, pump, or a vessel with or without volume markings if said composition is an oral liquid composition; or any other measuring or delivery device appropriate to the dosage formulation of the composition present in the kit.

In certain instances, the kits may comprise in a separate vessel or container a pharmaceutical composition comprising a second therapeutic agent, such as one of those listed above for use for co-administration with a macrocyclic compound described herein.

VI. Definitions

To facilitate an understanding of the present invention, a number of terms and phrases are defined below.

The term "alkyl" is art-recognized, and includes saturated aliphatic groups, including straight-chain alkyl groups, branched-chain alkyl groups, cycloalkyl (alicyclic) groups, alkyl substituted cycloalkyl groups, and cycloalkyl substituted alkyl groups. In certain embodiments, a straight chain or branched chain alkyl has about 30 or fewer carbon atoms in its backbone (e.g., $C_1$-$C_{30}$ for straight chain, $C_3$-$C_{30}$ for branched chain), and alternatively, about 20 or fewer. Likewise, cycloalkyls have from about 3 to about 10 carbon atoms in their ring structure, and alternatively about 5, 6 or 7 carbons in the ring structure.

The term "substituted" refers to the replacement of a hydrogen atom in a moiety with a functional group. The term "moiety" refers to a portion of a compound of this invention comprising at least one hydrogen atom and at least one carbon atom.

The term "substituted alkyl" refers to an alkyl group that is substituted by at least one functional group. Representative functional groups include halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like. In certain instanes, the substituted alkyl group contains 1 or 2 of the foregoing substituents.

The term "alkylene" refers to the diradical of an alkyl group.

The term "haloalkyl" refers to an alkyl group that is substituted with at least one halogen. For example, —$CH_2F$, —$CHF_2$, —$CF_3$, —$CH_2CF_3$, —$CF_2CF_3$, and the like.

The term "aralkyl" refers to an alkyl group substituted with an aryl group.

The term "heteroaralkyl" refers to an alkyl group substituted with a heteroaryl group.

The terms "alkenyl" and "alkynyl" are art-recognized and refer to unsaturated aliphatic groups analogous in length and possible substitution to the alkyls described above, but that contain at least one double or triple bond, respectively.

The term "aryl" is art-recognized and refers to a carbocyclic aromatic group. Representative aryl groups include phenyl, naphthyl, anthracenyl, and the like. The term "aryl" also includes polycyclic ring systems having two or more carbocyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. If specified that the aryl group may be substituted, then the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —$CO_2$alkyl, carbonyl, carboxyl, alkylthio, sulfonyl, sulfonamido, sulfonamide, ketone, aldehyde, ester, heterocyclyl, aryl or heteroaryl moieties, —$CF_3$, —CN, or the like.

The term "arylene" refers to the diradical of an aryl group.

The "heteroaryl" is art-recognized and refers to aromatic groups that include at least one ring heteroatom. In certain instances, a heteroaryl group contains 1, 2, 3, or 4 ring heteroatoms. Representative examples of heteroaryl groups include pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. If specified that the heteroaryl group may be substituted, then the aromatic ring may be substituted at one or more ring positions with, for example, halogen, azide, alkyl, aralkyl, alkenyl, alkynyl, cycloalkyl, hydroxyl, alkoxyl, amino, nitro, sulfhydryl, imino, amido, carboxylic acid, —C(O)alkyl, —CO₂alkyl, carbonyl, carboxyl, alkylthio, sulfonyl, sulfonamido, sulfonamide, ketone, aldehyde, ester, heterocyclyl, aryl or heteroaryl moieties, —CF₃, —CN, or the like. The term "heteroaryl" also includes polycyclic ring systems having two or more rings in which two or more carbons are common to two adjoining rings (the rings are "fused rings") wherein at least one of the rings is heteroaromatic, e.g., the other cyclic rings may be cycloalkyls, cycloalkenyls, cycloalkynyls, and/or aryls.

The terms ortho, meta and para are art-recognized and refer to 1,2-, 1,3- and 1,4-disubstituted benzenes, respectively. For example, the names 1,2-dimethylbenzene and ortho-dimethylbenzene are synonymous.

The term "carbocyclyl" refers to a saturated or unsaturated carbocyclic group. Representative carbocyclyl groups include cycloalkyl groups (e.g., cyclopentyl, cyclobutyl, cyclopentyl, cyclohexyl and the like), cycloalkenyl groups (e.g., cyclopentenyl, cyclohexenyl, cyclopentadienyl, and the like), and aryl groups (e.g., phenyl, naphthyl, anthracenyl, and the like). The term "carbocyclyl" also includes polycyclic ring systems having two or more carbocyclic rings in which two or more carbons are common to two adjoining rings (the rings are "fused rings").

The term "alkyl-carbocyclyl" refers to an alkyl group that is substituted by a carbocyclyl group. For example, the term "alkyl-carbocyclyl" incompasses benzyl, —CH₂CH₂-phenyl, —CH₂CH₂-cyclopropyl, and the like.

As used herein, the terms "heterocyclic" and "heterocyclyl" are used interchangeably and represent a saturated or unsaturated cyclic group that includes at least one ring heteroatom. For example, the terms "heterocyclic" and "heterocyclyl" encompass an aromatic or nonaromatic ring containing one or more heteroatoms. The heteroatoms can be the same or different from each other. Examples of heteroatoms include, but are not limited to nitrogen, oxygen and sulfur. Aromatic and nonaromatic heterocyclic rings are well-known in the art. Some nonlimiting examples of aromatic heterocyclic rings include pyridine, pyrimidine, indole, purine, quinoline and isoquinoline. Nonlimiting examples of nonaromatic heterocyclic compounds include piperidine, piperazine, morpholine, pyrrolidine and pyrazolidine. Examples of oxygen containing heterocyclic rings include, but not limited to furan, oxirane, 2H-pyran, 4H-pyran, 2H-chromene, and benzofuran. Examples of sulfur-containing heterocyclic rings include, but are not limited to, thiophene, benzothiophene, and parathiazine. Examples of nitrogen containing rings include, but not limited to, pyrrole, pyrrolidine, pyrazole, pyrazolidine, imidazole, imidazoline, imidazolidine, pyridine, piperidine, pyrazine, piperazine, pyrimidine, indole, purine, benzimidazole, quinoline, isoquinoline, triazole, and triazine. Examples of heterocyclic rings containing two different heteroatoms include, but are not limited to, phenothiazine, morpholine, parathiazine, oxazine, oxazole, thiazine, and thiazole.

The terms "amine" and "amino" are art-recognized and refer to both unsubstituted and substituted amines, e.g., a moiety that may be represented by the general formula:

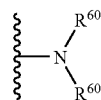

wherein each $R^{60}$ independently represent hydrogen, alkyl, alkenyl, —(CH₂)ₘ—$R^{61}$, or both $R^{60}$ taken together with the N atom to which they are attached form a heterocycle having from 4 to 8 atoms in the ring structure; $R^{61}$ represents an aryl, a cycloalkyl, a cycloalkenyl, a heterocycle or a polycycle; and m is zero or an integer in the range of 1 to 8. In certain embodiments, only one $R^{60}$ may be a carbonyl, e.g., both $R^{60}$ and the nitrogen together do not form an imide. In other embodiments, each $R^{60}$ independently represents a hydrogen, an alkyl, an alkenyl, or —(CH₂)ₘ—$R^{61}$. Thus, the term "alkylamine" includes an amine group, as defined above, having a substituted or unsubstituted alkyl attached thereto, i.e., at least one of $R^{60}$ is an alkyl group.

The terms "alkoxyl" or "alkoxy" are art-recognized and refer to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as may be represented by one of —O-alkyl, —O-alkenyl, —O-alkynyl, —O—(CH₂)ₘ—$R^{61}$, where m and $R^{61}$ are described above.

The term "heteroarylmethyl" refers to a heteroaryl moiety that is linked to the rest of the compound via a methylene (e.g.,

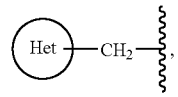

where "Het" is a heterocycle and $\xi$ represent the point of attachment to the rest of the compound. The term "4-(heteroaryl)benzyl" refers to a moiety of the structure:

Certain compounds of the present invention may exist in particular geometric or stereoisomeric forms. In addition, polymers of the present invention may also be optically active. The present invention contemplates all such compounds, including cis- and trans-isomers, R- and S-enantiomers, diastereomers, (D)-isomers, (L)-isomers, the racemic mixtures thereof, and other mixtures thereof, as falling within the scope of the invention. Additional asymmetric carbon atoms may be present in a substituent such as an alkyl group. All such isomers, as well as mixtures thereof, are intended to be included in this invention. Accordingly, a compound of the present invention may exist as either a racemic mixture or a scalemic mixture, or as individual respective stereoisomers that are substantially free from another possible stereoisomer. The term "substantially free of other stereoisomers" as used herein means less than 25% of other stereoisomers, less than 10% of other stereoisomers, less than 5% of other stereoisomers, or less than 2% of other stereoisomers.

If, for instance, a particular enantiomer of compound of the present invention is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

Unless otherwise indicated, when a disclosed compound is named or depicted by a structure without specifying the stereochemistry and has one or more chiral centers, it is understood to represent all possible stereoisomers of the compound, as well as enantiomeric mixtures thereof.

As used herein, the term "$IC_{50}$" refers to the concentration of a compound at which 50% of its maximal inhibitory effect is observed.

As used herein, the term "patient" refers to organisms to be treated by the methods of the present invention. Such organisms preferably include, but are not limited to, mammals (e.g., murines, simians, equines, bovines, porcines, canines, felines, and the like), and most preferably includes humans.

As used herein, the term "effective amount" refers to the amount of a compound (e.g., a compound of the present invention) sufficient to effect beneficial or desired results. An effective amount can be administered in one or more administrations, applications or dosages and is not intended to be limited to a particular formulation or administration route. As used herein, the term "treating" includes any effect, e.g., lessening, reducing, modulating, ameliorating or eliminating, that results in the improvement of the condition, disease, disorder, and the like, or ameliorating a symptom thereof.

As used herein, the term "pharmaceutical composition" refers to the combination of an active agent with a carrier, inert or active, making the composition especially suitable for diagnostic or therapeutic use in vivo or ex vivo.

As used herein, the term "pharmaceutically acceptable salt" refers to any pharmaceutically acceptable salt (e.g., acid or base) of a compound of the present invention which, upon administration to a subject, is capable of providing a compound of this invention or an active metabolite or residue thereof. As is known to those of skill in the art, "salts" of the compounds of the present invention may be derived from inorganic or organic acids and bases. Examples of acids include, but are not limited to, hydrochloric, hydrobromic, sulfuric, nitric, perchloric, fumaric, maleic, phosphoric, glycolic, lactic, salicylic, succinic, toluene-p-sulfonic, tartaric, acetic, citric, methanesulfonic, ethanesulfonic, formic, benzoic, malonic, naphthalene-2-sulfonic, benzenesulfonic acid, and the like. Other acids, such as oxalic, while not in themselves pharmaceutically acceptable, may be employed in the preparation of salts useful as intermediates in obtaining the compounds of the invention and their pharmaceutically acceptable acid addition salts.

Examples of bases include, but are not limited to, alkali metals (e.g., sodium) hydroxides, alkaline earth metals (e.g., magnesium), hydroxides, ammonia, and compounds of formula $NW_4^+$, wherein W is $C_{1-4}$ alkyl, and the like.

Examples of salts include, but are not limited to: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, flucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, palmoate, pectinate, persulfate, phenylpropionate, picrate, pivalate, propionate, succinate, tartrate, thiocyanate, tosylate, undecanoate, and the like. Other examples of salts include anions of the compounds of the present invention compounded with a suitable cation such as $Na^+$, $NH_4^+$, and $NW_4^+$ (wherein W is a $C_{1-4}$ alkyl group), and the like.

For therapeutic use, salts of the compounds of the present invention are contemplated as being pharmaceutically acceptable. However, salts of acids and bases that are non-pharmaceutically acceptable may also find use, for example, in the preparation or purification of a pharmaceutically acceptable compound.

EXAMPLES

The invention now being generally described, will be more readily understood by reference to the following examples, which are included merely for purposes of illustration of certain aspects and embodiments of the present invention, and are not intended to limit the invention.

Starting materials for the sythetic procedures can be obtained from commercial sources or prepared using literature procedures. Abbreviations as used herein include acetonitrile (ACN); alanine (Ala); allyloxy ($CO_2All$); α-aminoisobutyric acid (Aib); arginine (Arg); asparagine (Asp); O-(7-azabenzotriazol-1-yl)-N,N,N',N'-tetramethyluronium hexafluorophosphate (HATU); calculated (Calcd); N,N'-diisopropylcarbodiimide (DIC); diisopropylethylamine (DIPEA); dimethylaminopyridine (DMAP); dimethylformamide (DMF); 9-fluorenylmethoxycarbonyl (Fmoc); glutamine (Glu); glycine (Gly); hexafluoroisopropanol (HFIP); 1-hydroxy-7-azabenzotriazole (HOAt); acetic acid (HOAc); high resolution mass spectrometry (HRMS); high pressure liquid chromatography (HLPC); methanol (MeOH); 1-methyl-2-pyrrolidinone (NMP); methylene chloride (DCM); 2,2,4,6,7-pentamethyldihydrobenzofuran-5-sulfonyl (Pbf); phenylalanine (Phe); serine (Ser); tert-butoxycarbonyl (Boc); tert-butyl (tBu); tetrahydrofuran (THF); thienylalanine (Tha); trifluoroacetic acid (TFA); trityl (TrT); tyrosine (Tyr); O-(Benzotriazol-1-yl)-N,N,N',N'-tetramethyluronium Hexafluorophosphate (HBTU); 1-hydroxybenzotriazole (HOBt); 1,8-Diazabicyclo[5.4.0]undec-7-ene (DBU); 1-(2-Mesitylenesulfonyl)-3-nitro-1H-1,2,4-triazole (MSNT); 4-Hydroxymethylbenzoic acid PEGA resin (HMBA-PEGA); 4-methylmorpholine (NMM); Acetic Anhydride ($Ac_2O$).

In each of the synthesis schemes set forth in the example $R^a$ is —$(CH_2)_n$—$R^I$, $R^b$ is —$(CH_2)_n$—$R^{II}$, $R^c$ is —$(CH_2)_n$—$R^{III}$, and $R^d$ is —$(CR^{11}R^{12})_m$—, wherein $R^I$, $R^{II}$, $R^{III}$, x and n are defined as set forth for a compound of Formula II, and $R^{11}$, $R^{12}$, and m are defined as set forth for a compound of Formula I.

Example 1

This example describes the synthesis and characterization of macrocyclic compounds. A general synthetic sequence for preparing the macrocyclic compounds is illustrated schematically below.

Scheme 3.
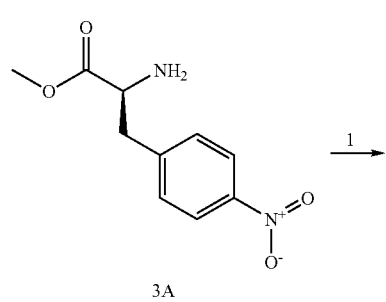
3A
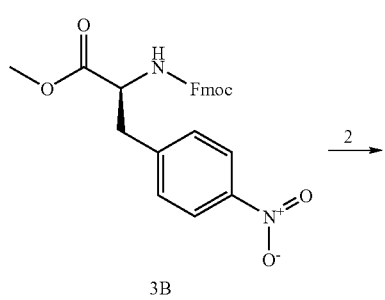
3B
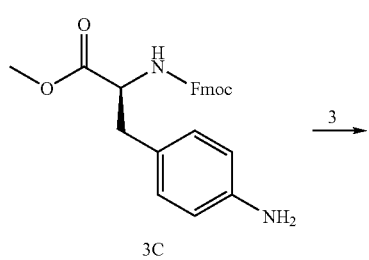
3C
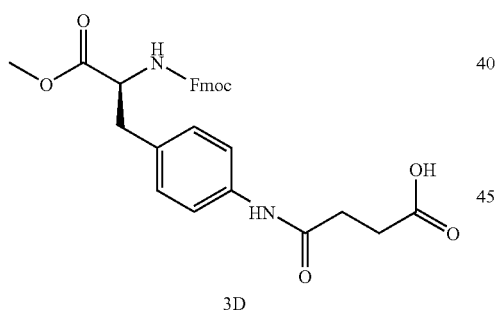
3D
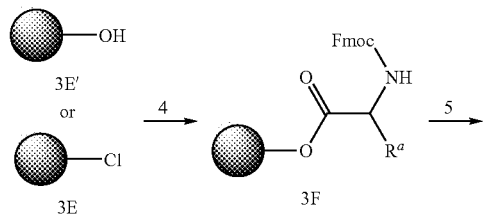
3E' or 3E → 3F → 
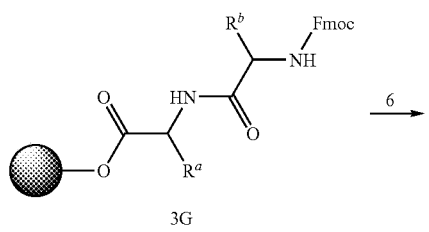
3G
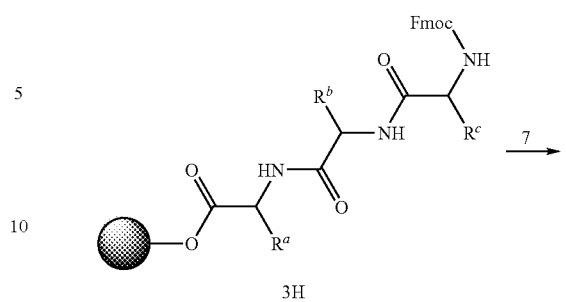
3H
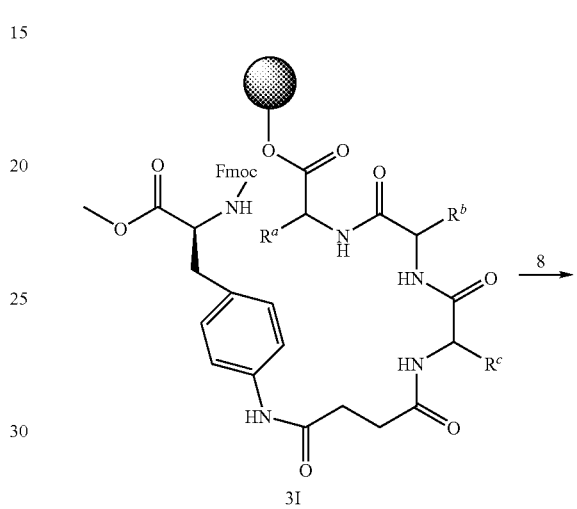
3I
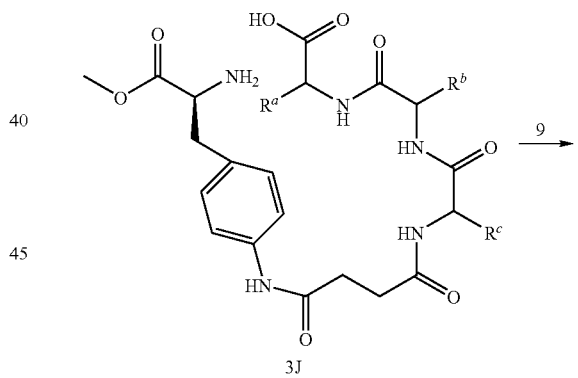
3J
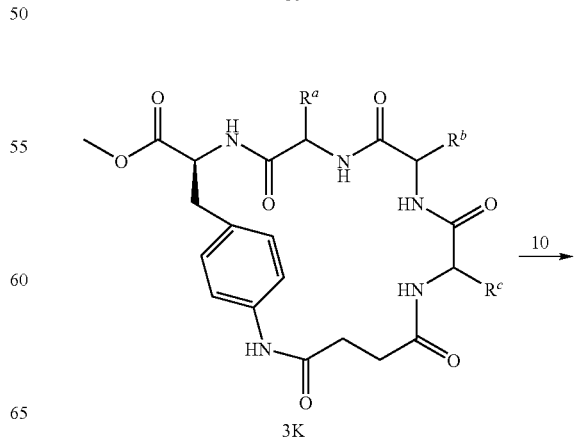
3K

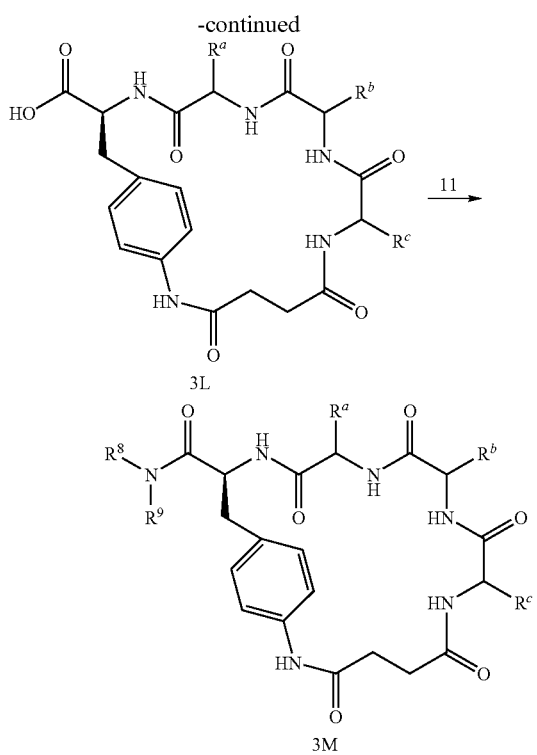

Compound 1

Step 1: Fmoc-Cl (27.6 g, 107.2 mmol) in 1,4-dioxane (950 mL) was added dropwise to a solution of (S)-methyl 2-amino-3-(4-nitrophenyl)propanoate (3A; 20 g, 89.3 mmol) and K$_2$CO$_3$ (14.8 g, 107.2 mmol) in water (80 mL) and 1,4-dioxane (150 mL) on an ice bath. After being stirred for 2 hours at room temperature, the mixture was poured into 1.2 L of water to precipitate a white solid, which was filtered and washed with cold water. The solid was dried under vacuum for 3 hours to give 40 g of (S)-methyl 2-(((9H-fluoren-9-yl)methoxy)carbonylamino)-3-(4-nitrophenyl)propanoate 3B, which was directly used in step 2.

Step 2: In a hydrogenation reactor, (S)-methyl 2-(((9H-fluoren-9-yl)methoxy)carbonylamino)-3-(4-nitrophenyl) propanoate (3B; 25 g, 56 mmol) was dissolved in THF (200 mL), and 15 mL of 4N HCl was added to the reaction mixture. Then, 10% Pd/C (2.5 g) was added to the reaction mixture. Hydrogen was introduced into the reactor until pressure reached 4 MPa. The reaction was stirred at room temperature for 1 hour. The catalyst was removed by filtration and washed with THF. The pH of the solution was adjusted to about 7 by adding saturated NaHCO$_3$ (aq) while the solution was on an ice bath. The organic layer was separated, and the aqueous layer was washed with CH$_2$Cl$_2$ (2×15 mL). The combined organic fractions were dried with anhydrous Na$_2$SO$_4$ to give a solution of (S)-methyl 2-(((9H-fluoren-9-yl)methoxy)carbonylamino)-3-(4-aminophenyl)propanoate 3C. The solution was used directly in step 3.

Step 3: Succinic anhydride (6.72 g, 67.2 mmol) was added to the solution of (S)-methyl 2-(((9H-fluoren-9-yl)methoxy)carbonylamino)-3-(4-aminophenyl)propanoate 3C from step 2. The reaction mixture was stirred at room temperature overnight. The solvent was removed, and the residual solid was washed with 30% ethyl acetate/petroleum ether (200 mL) and recrystallized in THF and 30% ethyl acetate/petroleum ether to give (S)-4-(4-(2-(((9H-fluoren-9-yl)methoxy)carbonylamino)-3-methoxy-3-oxopropyl)phenylamino)-4-oxobutanoic acid 3D as a white solid (19 g, 66% yield). $^1$HNMR (DMSO-d$_6$, 300 MHz) δ: 10-9.9 (s, 1H), 8.0-7.9 (m, 3H), 7.8-7.6 (m, 2H), 7.6-7.5(m, 2H), 7.5-7.4(m, 2H), 7.4-7.3(m, 2H), 7.3-7.1(d, 2H), 4.4-4.2 (m, 4H), 3.8-3.6 (s, 3H), 3.1-2.8 (m, 2H), 2.7-2.5 (m, 4H); ESI-MS: m/z 517.3 (M+H)$^+$.

Step 4: (R)-2-(((9H-Fluoren-9-yl)methoxy)carbonylamino)-3-phenylpropanoic acid (3D; 4.40 g, 11.37 mmol) was dissolved in DCM (35 mL) and added to 2-chloro-trityl chloride resin 3E (5.14 g, 8.12 mmol). DIPEA (7.06 mL, 40.6 mmol) was added to the resin suspension. The mixture was agitated for 1 hour under argon. The resin was then washed with 3×30 mL of 1% DIPEA in DCM. This coupling of (R)-2-(((9H-fluoren-9-yl)methoxy)carbonylamino)-3-phenylpropanoic acid was repeated once. After washing the resin with 3×30 mL of 17:2:1 DCM:MeOH:DIPEA, 3×30 mL of DMF and 3×30 mL of 1% DIPEA in DCM, resin 3F was obtained.

Step 5: Resin 3F was treated with 35 mL of 20% piperidine in DMF for 20 min, washed with 2×30 mL DMF and treated with another 35 mL of 20% piperidine in DMF. The resin was then washed with 3×30 mL of DMF and 3×30 mL of 1% DIPEA in DCM. To the resulting resin, (S)-2-(((9H-fluoren-9-yl)methoxy)carbonylamino)-3-(biphenyl-4-yl)propanoic acid (4.20 g, 9.05 mmol), HATU (3.44 g, 9.05 mmol) and DIPEA (3.15 mL, 18.10 mmol) in 35 mL of NMP was added. The mixture was agitated under argon at room temperature for 1.5 hours. The resin was filtered and washed with 2×30 mL of NMP. This coupling of (S)-2-(((9H-fluoren-9-yl)methoxy)carbonylamino)-3-(biphenyl-4-yl)propanoic acid was repeated once. After washing the resin with 2×30 mL NMP and 4×30 mL of 1% DIPEA in DCM, resin 3G was obtained.

Step 6: Resin 3G was treated with 35 mL of 20% piperidine in DMF for 20 min, washed with 2×30 mL DMF and treated with another 35 mL of 20% piperidine in DMF. The resin was then washed with 3×30 mL of DMF and 3×30 mL of 1% DIPEA in DCM. To the resulting resin, (R)-2-(((9H-fluoren-9-yl)methoxy)carbonylamino)-3-(thiophen-2-yl)propanoic acid (2.67 g, 6.79 mmol), HATU (3.44 g, 9.05 mmol) and DIPEA (3.15 mL, 18.10 mmol) in 35 mL of NMP was added. The mixture was agitated under argon at room temperature for 1.5 hours. The resin was filtered and washed with 2×30 mL of NMP. This coupling of (R)-2-(((9H-fluoren-9-yl)methoxy)carbonylamino)-3-(thiophen-2-yl)propanoic acid was repeated once. After washing the resin with 2×30mL NMP and 4×30 mL of 1% DIPEA in DCM, resin 3H was obtained.

Step 7: Resin 3H (2.569 g, 2.262 mmol) was treated with 35 mL of 20% piperidine in DMF for 20 min, washed with 2×30 mL DMF and treated with another 35 mL of 20% piperidine in DMF. The resin was then washed with 3×30 mL of DMF and 3×30 mL of 1% DIPEA in DCM. To the resulting resin, (S)-4-(4-(2-(((9H-fluoren-9-yl)methoxy)carbonylamino)-3-methoxy-3-oxopropyl)phenylamino)-4-oxobutanoic acid (1.753 g, 3.39 mmol) and HATU (1.290 g, 3.39 mmol) in 30 mL of NMP was added. DIPEA (0.591 mL, 3.39 mmol) was then added to the reaction mixture/resin suspension while agitated under argon. The mixture was agitated at room temperature for 1 hour. The resin was filtered and washed with 2×30 mL of NMP. This coupling of (S)-4-(4-(2-(((9H-fluoren-9-yl)methoxy)carbonylamino)-3-methoxy-3-oxopropyl) phenylamino)-4-oxobutanoic acid was repeated once. After washing the resin with 2×30mL NMP and 4×30 mL of 1% DIPEA in DCM, resin 3I was obtained.

Step 8: Resin 3I was treated with 35 mL of 20% piperidine in DMF for 20 min, washed with 2×30 mL DMF and treated with another 35 mL of 20% piperidine in DMF. The resin was then washed with 3×30 mL of DMF and 3×30 mL of 1%

DIPEA in DCM. The resin was then treated with 30 mL of 20% HFIP in DCM for 10 min four times. The resin was then washed with DCM (3×30mL). This cleaving solution was collected and evaporated to give 0.696 g of (R)-2-((S)-2-((R)-2-(4-(4-((S)-2-amino-3-methoxy-3-oxopropyl)phenylamino)-4-oxobutanamido)-3-(thiophen-2-yl)propanamido)-3-(biphenyl-4-yl)propanamido)-3-phenylpropanoic acid (3J). The product 3J was used without further purification in step 9.

Step 9: (R)-2-((S)-2-((R)-2-(4-(4-((S)-2-amino-3-methoxy-3-oxopropyl)phenylamino)-4-oxobutanamido)-3-(thiophen-2-yl)propanamido)-3-(biphenyl-4-yl)propanamido)-3-phenylpropanoic acid (696 mg, 0.851 mmol), HATU (647 mg, 1.702 mmol) and HOAt (232 mg, 1.702 mmol) were dissolved in anhydrous DMF (810 mL). DIPEA (0.741 mL, 4.26 mmol) was then added to the stirring solution. The mixture was stirred at room temperature for 2 hours. The solvent was then evaporated. MeOH was added to the residue and evaporated to yield a gel-like slurry, to which water was added. A solid precipitate formed and was collected by filtration. After washing the solid with water, 0.937 g of crude 3K was obtained as a white solid.

Step 10: 3K (0.937 g, crude product from step 9) was dissolved in 50 mL THF. A solution of lithium hydroxide (542 mg, 22.62 mmol) in 9 mL of $H_2O$ was then added. The reaction mixture was stirred at room temperature for 40 min, and reaction progress was monitored by LC/MS. Upon completion, the solution was neutralized with 5% HCl (3 mL). Solvents were evaporated and the crude product was purified by flash chromatography using a reverse-phase cartridge (20-65% ACN/water) to give compound 1 as an off-white solid (0.656 g, 71% yield). $^1$H-NMR (DMSO-$d_6$, 400 MHz) δ (ppm): 8.65-8.55 (d, 1H), 8.55-8.5 (d, 1H), 7.85-7.75 (m, 2H), 7.65-7.55(d, 2H), 7.55-7.5 (d, 2H), 7.45-7.35 (t, 3H), 7.4-7.3 (t, 2H), 7.3-7.1 (m, 13H), 7.05-7.0 (d, 2H), 6.8-6.75 (m, 1H), 6.45-6.4 (d, 1H), 4.75-4.6 (td, 1H), 4.6-4.5 (td, 1H), 4.55-4.45 (td, 1H), 4.1-3.95 (q, 1H), 3.15-3.0 (m, 2H), 2.9-2.8 (dd, 1H), 2.8-2.7 (m, 1H), 2.65-2.55 (m, 1H), 2.45-2.35 (m, 2H), 2.25-2.15 (t, 1H), 2.15-2.05 (dd, 1H).

Compound 2

Compound 2 was prepared according to the procedures used for the synthesis of Compound 1, except that (S)-2-(((9H-fluoren-9-yl)methoxy)carbonylamino)-3-(4-(trifluoromethyl)phenyl)propanoic acid was used as starting material at step 5 and D-homophenylalanine was used as starting material at step 6.

Compound 3

Compound 3 was prepared according to the procedures used for the synthesis of Compound 1, except that (S)-2-(((9H-fluoren-9-yl)methoxy)carbonylamino)-3-(4-(trifluoromethyl)phenyl)propanoic acid was used as starting material at step 5, (R)-2-(((9H-fluoren-9-yl)methoxy)carbonylamino)-4-phenylbutanoic acid was used as starting material at step 6, and (R)-4-(4-(2-(((9H-fluoren-9-yl)methoxy)carbonylamino)-3-methoxy-3-oxopropyl)phenylamino)-4-oxobutanoic acid was used at step 7.

Compound 4

Compound 4 was prepared according to the procedures used for the synthesis of Compound 1, except that (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7. $^1$H-NMR (400 MHz, DMSO-$d_6$, δ): 12.72 (br s, 1H), 8.94 (s, 1H), 8.71 (d, J=9.2 Hz, 1H), 8.60 (d, J=9.3 Hz, 1H), 7.81 (d, J=7.2 Hz, 1H), 7.60 (m, 2H), 7.53 (d, J=8.3 Hz, 2H), 7.45-7.15 (m, 13H), 7.06 (d, J=8.5 Hz, 2H), 6.74 (dd, J=3.4, 5.1 Hz, 1H), 6.49 (d, J=4.4 Hz, 1H), 6.44 (d, J=2.7 Hz, 1H), 4.72 (td, J=3.3, 10.0 Hz, 1H), 4.60-4.52 (m, 2H), 4.49 (d, J=6.4 Hz, 1H), 4.02-3.93 (m, 2H), 3.19-2.95 (m, 4H), 2.82-2.60 (m, 3H), 2.25, (dd, J=11.0, 13.2 Hz, 1H).

Compound 5

Compound 5 was prepared according to the procedures used for the synthesis of Compound 1, except that (S)-3-(4-(2-(((9H-fluoren-9-yl)methoxy)carbonylamino)-3-methoxy-3-oxopropyl)phenylamino)-3-oxopropanoic acid was used as starting material at step 7.

Compound 6

Compound 6 was prepared according to the procedures used for the synthesis of Compound 1, except that (S)-3-(4-(2-(((9H-fluoren-9-yl)methoxy)carbonylamino)-3-methoxy-3-oxopropyl)phenylamino)propanoic acid was used as starting material at step 7.

Compound 7

Compound 7 was prepared according to the procedures used for the synthesis of Compound 1, except that 4-(3-(((((9H-fluoren-9-yl)methoxy)carbonyl)(2-methoxy-2-oxoethyl)amino)methyl)benzylamino)-4-oxobutanoic acid was used as starting material at step 7.

Compound 8

Compound 8 was prepared according to the procedures used for the synthesis of Compound 1, except that (S)-2-(4-(2-(((9H-fluoren-9-yl)methoxy)carbonylamino)-3-methoxy-3-oxopropyl)phenoxy)acetic acid was used as starting material at step 7.

Compound 9

Compound 9 was prepared according to the procedures used for the synthesis of Compound 1, except that (1R,2R)-2-(4-((S)-2-(((9H-fluoren-9-yl)methoxy)carbonylamino)-3-methoxy-3-oxopropyl)phenylcarbamoyl)cyclohexanecarboxylic acid was used as starting material at step 7.

Compound 10

Steps 1-10 of the procedures used in the synthesis of Compound 1 were performed.

Step 11: A stock solution of HATU (19.82 mg, 0.052 mmol) and HOAt (3.55 mg, 0.026 mmol) in 0.75 mL of DMF was prepared and added to compound 1 (10.24 mg, 0.013 mmol). If necessary, the resulting mixture was sonicated to form a solution. To this solution was added a solution of (S)-tert-butyl 2-amino-3-phenylpropanoate hydrochloride (6.72 mg, 0.026 mmol) in 0.75 mL DMF, followed by DIPEA (0.023 mL, 0.130 mmol). The reaction mixture was stirred at room temperature for 1.5 hours. Solvents were evaporated, and the solid was treated with 25% TFA in DCM. Reaction progress was monitored by LC/MS, and the solvents were removed upon reaction completion. The crude product was purified by preparative HPLC to give Compound 10 as a white solid (5.5 mg, 56% yield).

Compound 11

Compound 11 was prepared according to the procedures used in the synthesis of Compound 10, except that compound 2 was used as starting material at step 11.

Compound 12

Compound 12 was prepared according to the procedures used in the synthesis of Compound 10, except that Compound 3 was used as starting material at step 11.

Compound 13

Compound 13 was prepared according to the procedures used in the synthesis of Compound 10, except that Compound 3 and (R)-tert-butyl 2-amino-3-phenylpropanoate hydrochloride were used as starting materials at step 11.

Compound 14

Compound 14 was prepared according to the procedures used in the synthesis of Compound 10, except that Compound 3 and tert-butyl 2-amino-2-methylpropanoate hydrochloride were used as starting materials at step 11.

Compound 15

Compound 15 was prepared according to the procedures used in the synthesis of Compound 10, except that Compound 3 and tert-butyl 3-aminopropanoate hydrochloride were used as starting materials at step 11.

Compound 16

Compound 16 was prepared according to the procedures used in the synthesis of Compound 10, except that Compound 4 and (R)-tert-butyl 2-amino-3-phenylpropanoate hydrochloride were used as starting materials at step 11.

Compound 17

Steps 1-10 of the procedures used in the synthesis of Compound 1 were performed.

Step 11: A stock solution of HATU (17.0 mg, 0.045 mmol) and HOAt (3.05 mg, 0.022 mmol) in 0.7 mL of DMF was prepared and added to Compound 3 (8.8 mg, 0.011 mmol). If necessary, the resulting mixture was sonicated to form a solution. To this solution was added a solution of 1-aminocyclopropane-1-carboxylic acid methyl ester hydrochloride (3.4 mg, 0.022 mmol) in 0.7 mL DMF, followed by DIPEA (0.0195 mL, 0.112 mmol). The reaction mixture was stirred at room temperature for 25 minutes, with reaction progress monitored by LC/MS. Upon completion, the solvents were evaporated, and the residue was dissolved in THF (458 µL). A solution of lithium hydroxide (2.63 mg, 0.110 mmol) in water (90 µL) was added and the reaction mixture was vortexed. A second portion of lithium hydroxide (2.63 mg, 0.110 mmol) in water (90 µL) was added after 1.5 hours, and vortexing continued for a total of 3.75 hours. Reaction progress was monitored by LC/MS and the solvents were removed upon reaction completion. The crude product was purified by preparative HPLC to give Compound 17 as a white solid (4.1 mg, 43% yield).

Compound 18

Compound 18 was prepared according to the procedures used in the synthesis of Compound 17, except that Compound 2 was used as starting material at step 11.

Compound 19

Compound 19 was prepared according to the procedures used in the synthesis of Compound 10, except that glycine tert-butyl ester was used as starting material at step 11.

Compound 20

Compound 20 was prepared according to the procedures used in the synthesis of Compound 10, except that L-alanine-t-butyl ester hydrochloride was used as starting material at step 11.

Compound 21

Compound 21 was prepared according to the procedures used in the synthesis of Compound 10, except that beta-alanine t-butyl ester hydrochloride was used as starting material at step 11.

Compound 22

Compound 22 was prepared according to the procedures used in the synthesis of Compound 10, except that H-Ser (tBu)-OtBu hydrochloride was used as starting material at step 11.

Compound 23

Compound 23 was prepared according to the procedures used in the synthesis of Compound 10, except that 4-piperidine-carboxylic acid t-butyl ester hydrochloride was used as starting material at step 11.

Compound 24

Compound 24 was prepared according to the procedures used in the synthesis of Compound 10, except that D-alanine-t-butyl ester hydrochloride was used as starting material at step 11.

Compound 25

Compound 25 was prepared according to the procedures used in the synthesis of Compound 10, except that H-Aib-OtBu hydrochloride was used as starting material at step 11.

Compound 26

Compound 26 was prepared according to the procedures used in the synthesis of Compound 10, except that L-valine t-butyl ester hydrochloride was used as starting material at step 11.

Compound 27

Compound 27 was prepared according to the procedures used in the synthesis of Compound 10, except that (S)-di-tert-butyl 2-aminosuccinate was used as starting material at step 11.

Compound 28

Compound 28 was prepared according to the procedures used in the synthesis of Compound 10, except that (S)-tert-butyl 2-amino-6-(tert-butoxycarbonylamino)hexanoate was used as starting material at step 11.

Compound 29

Compound 29 was prepared according to the procedures used in the synthesis of Compound 10, except that (S)-4-tert-butyl 1-methyl 2-aminosuccinate was used as starting material at step 11.

Compound 30

Compound 30 was prepared according to the procedures used in the synthesis of Compound 10, except that tert-butyl 2-(methylamino)acetate was used as starting material at step 11.

Compound 31

Compound 31 was prepared according to the procedures used in the synthesis of Compound 10, except that (S)-tert-butyl pyrrolidine-2-carboxylate was used as starting material at step 11.

Compound 32

Compound 32 was prepared according to the procedures used in the synthesis of Compound 10, except that (R)-tert-butyl pyrrolidine-2-carboxylate was used as starting material at step 11.

Compound 33

Compound 33 was prepared according to the procedures used in the synthesis of Compound 10, except that (R)-tert-butyl 2-amino-3-phenylpropanoate hydrochloride was used as starting material at step 11.

Compound 34

Compound 34 was prepared according to the procedures used in the synthesis of Compound 17, except that Compound 1 and 4-aminobutyrate acid ethyl ester hydrochloride were used as starting materials at step 11.

Compound 35

Compound 35 was prepared according to the procedures used in the synthesis of Compound 17, except that Compound 1 and (S)-methyl 2-amino-6-(tert-butoxycarbonylamino) hexanoate were used as starting materials at step 11.

Compound 36

Compound 36 was prepared according to the procedures used in the synthesis of Compound 17, except that Compound 1 and methyl 2-(benzylamino)acetate were used as starting materials at step 11.

Compound 37

Compound 37 was prepared according to the procedures used in the synthesis of Compound 17, except that Compound 1 and (S)-ethyl piperidine-3-carboxylate were used as starting materials at step 11.

Compound 38

Compound 38 was prepared according to the procedures used in the synthesis of Compound 17, except that Compound 1 and (R)-ethyl piperidine-3-carboxylate were used as starting materials at step 11.

Compound 39

Compound 39 was prepared according to the procedures used in the synthesis of Compound 17, except that Compound 1 and 1-aminocyclopropane-1-carboxylic acid methyl ester hydrochloride were used as starting materials at step 11.

Compound 42

Steps 1-3 of the procedures used in the synthesis of Compound 1 were performed.

Step 4: Wang resin (0.5 g, 0.325 mmol) was swelled with DMF (5.0 mL). Fmoc-(R)-phenylalanine (1.26 g, 3.25 mmol) was dissolved in DMF (10.00 mL), filtered, and DIC (0.253 mL, 1.621 mmol) was then added to the solution. The solution was stirred at room temperature for 10 minutes, then was added into resin above. DMAP (3.97 mg, 0.033 mmol) was added as a solid, and the mixture was agitated at room temperature for 1 hour. The resin was filtered, then washed with DMF (15 mL×3) and DCM (15 ml×3). This coupling of Fmoc-(R)-phenylalanine step was repeated, and resin 42-F was obtained.

Steps 5-10: Compound 42 was prepared according to the procedures used in the synthesis of Compound 1, except that (S)-4-(5-(tert-butoxycarbonylamino)-6-methoxy-6-oxohexylamino)-4-oxobutanoic acid was used as starting material in step 7.

Compound 43

Steps 1-3 of the procedures used in the synthesis of Compound 1 were performed.

Step 4: Wang resin (0.5 g, 0.325 mmol) was swelled with DMF (5.0 mL). Fmoc-(R)-phenylalanine (1.26 g, 3.25 mmol) was dissolved in DMF (10.00 mL), filtered, and DIC (0.253 mL, 1.621 mmol) was then added to the solution. The solution was stirred at room temperature for 10 minutes, then was added into resin above. DMAP (3.97 mg, 0.033 mmol) was added as a solid, and the mixture was agitated at room temperature for 1 hour. The resin was filtered, then washed with DMF (15 mL×3) and DCM (15 ml×3). This coupling of Fmoc-(R)-phenylalanine step was repeated, and resin 43-F was obtained.

Steps 5-10: Compound 43 was prepared according to the procedures used in the synthesis of Compound 1, except that Fmoc-3-L-Ala(2-thienyl)-OH was used as starting material in step 6.

Compound 44

Compound 44 was prepared according to the procedures used in the synthesis of Compound 43, except that Fmoc-(R)-alanine was used as starting material in step 4.

Compound 45

Compound 45 was prepared according to the procedures used in the synthesis of Compound 43, except that Fmoc-L-alanine was used as starting material at step 5.

Compound 46

Compound 46 was prepared according to the procedures used in the synthesis of Compound 43, except that Fmoc-D-alanine was used as starting material in step 6.

Compound 156

Compound 156 was prepared according to the procedures used for the synthesis of Compound 10, except that Compound 145 and (S)-tert-butyl 2-amino-3-phenylpropanoate hydrochloride was used as starting material.

Compound 157

Compound 157 was prepared according to the procedures used for the synthesis of Compound 10, except that Compound 146 and (S)-tert-butyl 2-amino-3-phenylpropanoate hydrochloride was used as starting material.

Compound 158

Compound 158 was prepared according to the procedures used for the synthesis of Compound 10, except that Compound 144 and (S)-tert-butyl 2-amino-3-phenylpropanoate hydrochloride was used as starting material.

Compound 162

Compound 162 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, and (R)-2-(((9H-fluoren-9-yl)methoxy)carbonylamino)-3-(4-methoxyphenyl)propanoic acid was used as starting material at step 6.

Compound 163

Compound 163 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, and (R)-2-(((9H-fluoren-9-yl)methoxy)carbonylamino)-3-(2-(trifluoromethyl)phenyl)propanoic acid was used as starting material at step 6.

Compound 164

Compound 164 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, and (R)-2-(((9H-fluoren-9-yl)methoxy)carbonylamino)-3-(benzo[b]thiophen-3-yl)propanoic acid was used as starting material at step 6.

Compound 165

Compound 165 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, and (R)-2-(((9H-fluoren-9-yl)methoxy)carbonylamino)-2-(2,3-dihydro-1H-inden-2-yl)acetic acid was used as starting material at step 6.

Compound 166

Compound 166 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, and (R)-2-(((9H-fluoren-9-yl)methoxy)carbonylamino)-3-(3-(trifluoromethyl)phenyl)propanoic acid was used as starting material at step 6.

Compound 174

Compound 174 was prepared according to the procedures used for the synthesis of Compound 10, except that Compound 4 and (S)-tert-butyl 2-amino-3-phenylpropanoate hydrochloride was used as starting material.

Compound 175

Compound 175 was prepared according to the procedures used for the synthesis of Compound 10, except that Compound 4 and tert-butyl 3-aminopropanoate hydrochloride was used as starting material.

Compound 176

Compound 176 was prepared according to the procedures used for the synthesis of Compound 10, except that Compound 4 and tert-butyl 2-amino-2-methylpropanoate hydrochloride was used as starting material.

Compound 184

Compound 184 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2S,3S)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 185

Compound 185 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((R)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 186

Compound 186 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and 4-(4-(((((9H-fluoren-9-yl)methoxy)carbonyl)(2-methoxy-2-oxoethyl)amino)methyl)benzylamino)-4-oxobutanoic acid was used as starting material at step 7.

Compound 187

Compound 187 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (1S,2R)-2-(4-((S)-2-(((9H-fluoren-9-yl)methoxy)carbonylamino)-3-methoxy-3-oxopropyl)phenylcarbamoyl)cyclohexanecarboxylic acid was used as starting material at step 7.

Compound 191

Compound 191 was prepared according to the procedures used for the synthesis of Compound 1, except that (R)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-cyclohexylpropanoic acid was used as starting material at step 6.

Compound 192

Compound 192 was prepared according to steps 1 to 9 used for the synthesis of Compound 1.

Compound 193

Compound 193 was prepared according to the procedures used for the synthesis of Compound 17, except that Compound 1 and (9H-fluoren-9-yl)methyl 2-(2-aminoethoxy)ethylcarbamate was used as starting material.

Compound 194

Compound 194 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6.

Compound 195

Compound 195 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6.

Compound 197

Compound 197 was prepared according to the procedures used for the synthesis of Compound 1, except that (R)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-cyclohexylpropanoic acid was used as starting material at step 6, and (S,Z)-4-(4-(2-(((9H-fluoren-9-yl)methoxy)carbonylamino)-3-methoxy-3-oxopropyl)phenylamino)-4-oxobut-2-enoic acid was used as starting material at step 7.

Compound 198

Compound 198 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, and (R)-2-(((9H-fluoren-9-yl)methoxy)carbonylamino)-4-tert-butoxy-4-oxobutanoic acid was used as starting material at step 6.

Compound 199

Compound 199 was prepared according to the procedures used for the synthesis of Compound 10, except that Compound 1 and (S)-tert-butyl pyrrolidine-2-carboxylate was used as starting material.

Compound 200

Compound 200 was prepared according to the procedures used for the synthesis of Compound 10, except that Compound 1 and methyl 1-aminocyclopropanecarboxylate was used as starting material.

Compound 201

Compound 201 was prepared according to the procedures used for the synthesis of Compound 10, except that Compound 85 and (S)-tert-butyl 2-amino-3-phenylpropanoate was used as starting material.

Compound 202

Compound 202 was prepared according to the procedures used for the synthesis of Compound 17, except that Compound 117 and (S)-methyl 2-amino-3-phenylpropanoate was used as starting material.

Compound 205

Compound 205 was prepared according to the procedures used for the synthesis of Compound 10, except that Compound 1 and 2-aminoethanol was used as starting material and no TFA treatment was required.

Compound 206

Compound 206 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, and (R)-2-(((9H-fluoren-9-yl)methoxy)carbonylamino)-4-tert-butoxy-4-oxobutanoic acid was used as starting material at step 6.

Compound 209

Compound 209 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6.

Compound 210

Compound 210 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6.

Compound 211

Compound 211 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6.

Compound 212

Compound 212 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6.

Compound 213

Compound 213 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6.

Compound 214

Compound 214 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6.

Compound 215

Compound 215 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6.

Compound 216

Compound 216 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, and (R)-2-(((9H-fluoren-9-yl)methoxy)carbonylamino)-4-phenylbutanoic acid was used as starting material at step 6.

Compound 227

Compound 227 was prepared according to the procedures used for the synthesis of Compound 10, except that Compound 214 and (R)-tert-butyl 2-amino-3-phenylpropanoate was used as starting material.

Compound 228

Compound 228 was prepared according to the procedures used for the synthesis of Compound 10, except that Compound 212 and (R)-tert-butyl 2-amino-3-phenylpropanoate was used as starting material.

Compound 229

Compound 229 was prepared according to the procedures used for the synthesis of Compound 10, except that Compound 212 and (S)-tert-butyl 2-amino-3-phenylpropanoate was used as starting material.

Compound 230

Compound 230 was prepared according to the procedures used for the synthesis of Compound 10, except that Compound 214 and (S)-tert-butyl 2-amino-3-phenylpropanoate was used as starting material.

Compound 246

Compound 246 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-4-phenylbutanoic acid was used as starting material at step 6.
Compound 260

Compound 260 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(4-cyanophenyl)propanoic acid was used as starting material at step 6.
Compound 261

Compound 261 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(4-fluorophenyl)propanoic acid was used as starting material at step 6.
Compound 262

Compound 262 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(3,4-difluorophenyl)propanoic acid was used as starting material at step 6.
Compound 263

Compound 263 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(4-(trifluoromethyl)phenyl)propanoic acid was used as starting material at step 6.
Compound 264

Compound 264 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-p-tolylpropanoic acid was used as starting material at step 6.
Compound 268

Compound 268 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 7.
Compound 269

Compound 269 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 7.
Compound 270

Compound 270 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 7.
Compound 271

Compound 271 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 7.
Compound 272

Compound 272 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 7.
Compound 273

Compound 273 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 7.
Compound 274

Compound 274 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-

(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 7.

Compound 275

Compound 275 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((R)-2-(((9H-fluoren-9-yl)methoxy)carbonylamino)-3-methoxy-3-oxopropyl)phenylamino)-2,3-dihydroxy-4-oxobutanoic acid was used as starting material at step 7.

Compound 276

Compound 276 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((R)-2-(((9H-fluoren-9-yl)methoxy)carbonylamino)-3-methoxy-3-oxopropyl)phenylamino)-2,3-dihydroxy-4-oxobutanoic acid was used as starting material at step 7.

Compound 277

Compound 277 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (2R,3R)-4-(4-((R)-2-(((9H-fluoren-9-yl)methoxy)carbonylamino)-3-methoxy-3-oxopropyl)phenylamino)-2,3-dihydroxy-4-oxobutanoic acid was used as starting material at step 7.

Compound 278

Compound 278 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (2R,3R)-4-(4-((R)-2-(((9H-fluoren-9-yl)methoxy)carbonylamino)-3-methoxy-3-oxopropyl)phenylamino)-2,3-dihydroxy-4-oxobutanoic acid was used as starting material at step 7.

Compound 279

Compound 279 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (2R,3R)-4-(4-((R)-2-(((9H-fluoren-9-yl)methoxy)carbonylamino)-3-methoxy-3-oxopropyl)phenylamino)-2,3-dihydroxy-4-oxobutanoic acid was used as starting material at step 7.

Compound 280

Compound 280 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (2R,3R)-4-(4-((R)-2-(((9H-fluoren-9-yl)methoxy)carbonylamino)-3-methoxy-3-oxopropyl)phenylamino)-2,3-dihydroxy-4-oxobutanoic acid was used as starting material at step 7.

Compound 281

Compound 281 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((R)-2-(((9H-fluoren-9-yl)methoxy)carbonylamino)-3-methoxy-3-oxopropyl)phenylamino)-2,3-dihydroxy-4-oxobutanoic acid was used as starting material at step 7.

Compound 282

Compound 282 was prepared according to the procedures used for the synthesis of Compound 17, except that Compound 262 and (S)-methyl 2-amino-3-phenylpropanoate was used as starting material.

Compound 295

Compound 295 was prepared according to the procedures used for the synthesis of Compound 10, except that (S)-2-(((9H-fluoren-9-yl)methoxy)carbonylamino)-4-phenylbutanoic acid was used as starting material at step 6, and that (S)-tert-butyl 2-amino-6-(tert-butoxycarbonylamino)hexanoate hydrochloride was used as starting material at step 11.

Compound 296

Compound 296 was prepared according to the procedures used for the synthesis of Compound 295, except that (2R,3R)-3-(4-((S)-2-(((9H-fluoren-9-yl)methoxy)carbonylamino)-3-methoxy-3-oxopropyl)benzamido)-2,3-diacetoxypropanoic acid was used as starting material at step 7.

Compound 297

Compound 297 was prepared according to the procedures used for the synthesis of Compound 10, except that comopund and tert-butyl 2-amino-2-methylpropanoate was used as starting material.

Compound 298

Compound 298 was prepared according to the procedures used for the synthesis of Compound 10, except that comopund and tert-butyl 4-aminobutanoate was used as starting material.

Compound 299

Compound 299 was prepared according to the procedures used for the synthesis of Compound 17, except that comopund and methyl 1-aminocyclopropanecarboxylate was used as starting material.

Compound 300

Compound 300 was prepared according to the procedures used for the synthesis of Compound 10, except that comopund and (S)-tert-butyl 2-amino-3-(4-hydroxyphenyl)propanoate was used as starting material.

Compound 301

Compound 301 was prepared according to the procedures used for the synthesis of Compound 10, except that comopund and tert-butyl 3-aminopropanoate was used as starting material.

Compound 302

Compound 302 was prepared according to the procedures used for the synthesis of Compound 10, except that comopund and (R)-tert-butyl 2-aminopropanoate was used as starting material.

Compound 303

Compound 303 was prepared according to the procedures used for the synthesis of Compound 10, except that comopund and (S)-tert-butyl pyrrolidine-2-carboxylate was used as starting material.

Compound 304

Compound 304 was prepared according to the procedures used for the synthesis of Compound 10, except that compound and (R)-tert-butyl pyrrolidine-2-carboxylate was used as starting material.

Compound 305

Compound 305 was prepared according to the procedures used for the synthesis of Compound 10, except that comopund and (S)-tert-butyl 2-aminopropanoate was used as starting material.

Compound 306

Compound 306 was prepared according to the procedures used for the synthesis of Compound 10, except that comopund and tert-butyl piperidine-4-carboxylate was used as starting material.

Compound 307

Compound 307 was prepared according to the procedures used for the synthesis of Compound 10, except that comopund and tert-butyl 2-amino-3-methylpentanoate was used as starting material.

Compound 308

Compound 308 was prepared according to the procedures used for the synthesis of Compound 10, except that comopund and di-tert-butyl 2-aminopentanedioate was used as starting material.

Compound 309

Compound 309 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-4-methoxy-4-oxobutyl)phenylamino)-2,3-diacetoxy-4-oxobutanoic acid was used as starting material at step 7.

Compound 310

Compound 310 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (S)-2-(2-(4-(2-(((9H-fluoren-9-yl)methoxy)carbonylamino)-3-methoxy-3-oxopropyl)phenylamino)-2-oxoethoxy)acetic acid was used as starting material at step 7.

Compound 311

Compound 311 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(pyridin-3-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 312

Compound 312 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-2-phenylacetic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 313

Compound 313 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-phenylpropanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 314

Compound 314 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(2-cyanophenyl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 315

Compound 315 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(2-chlorophenyl)propanoic acid was used as starting material at step 6, and (2R,3R)-4-(4-((S)-2-(((9H-fluoren-9-yl)meth- Compound 316

Compound 316 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(3-cyanophenyl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 317

Compound 317 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(3-methoxyphenyl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 318

Compound 318 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-3-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 319

Compound 319 was prepared according to the procedures used for the synthesis of Compound 10, except that Compound 214 and tert-butyl 3-aminopropanoate was used as starting material.

Compound 320

Compound 320 was prepared according to the procedures used for the synthesis of Compound 17, except that Compound 145 and HCl salt of (S)-ethyl 2-amino-4-phenylbutanoate was used as starting material.

Compound 321

Compound 321 was prepared according to the procedures used for the synthesis of Compound 10, except that Compound 145 and HCl salt of tert-butyl 2-aminoacetate was used as starting material.

Compound 322

Compound 322 was prepared according to the procedures used for the synthesis of Compound 10, except that Compound 145 and ethanolamine was used as starting material and no TFA treatment was required.

Compound 323

Compound 323 was prepared according to the procedures used for the synthesis of Compound 17, except that Compound 145 and HCl salt of ethyl 2-(benzylamino)acetate was used as starting material.

Compound 324

Compound 324 was prepared according to the procedures used for the synthesis of Compound 10, except that Compound 145 and HCl salt of (R)-tert-butyl 2-amino-3-phenylpropanoate was used as starting material.

Compound 325

Compound 325 was prepared according to the procedures used for the synthesis of Compound 10, except that Compound 145 and HCl salt of (S)-4-tert-butyl 1-methyl 2-aminosuccinate was used as starting material.

Compound 326

Compound 326 was prepared according to the procedures used for the synthesis of Compound 10, except that Compound 212 and HCl salt of (S)-tert-butyl 2-aminopropanoate was used as starting material.

Compound 327

Compound 327 was prepared according to the procedures used for the synthesis of Compound 10, except that Compound 212 and HCl salt of (S)-4-tert-butyl 1-methyl 2-aminosuccinate was used as starting material.

Compound 328

Compound 328 was prepared according to the procedures used for the synthesis of Compound 10, except that Compound 212 and HCl salt of (S)-tert-butyl 2-amino-4-phenylbutanoate was used as starting material.

Compound 329

Compound 329 was prepared according to the procedures used for the synthesis of Compound 10, except that Compound 212 and HCl salt of tert-butyl 2-aminoacetate was used as starting material.

Compound 338

Compound 338 was prepared according to the procedures used for the synthesis of Compound 10, except that Compound 212 and HCl salt of tert-butyl 2-aminoacetate was used as starting material.

Compound 339

Compound 339 was prepared according to the procedures used for the synthesis of Compound 10, except that Compound 212 and HCl salt of tert-butyl 3-aminopropanoate was used as starting material.

Compound 340

Compound 340 was prepared according to the procedures used for the synthesis of Compound 17, except that Compound 212 and ethyl 2-(benzylamino)acetate was used as starting material.

Compound 341

Compound 341 was prepared according to the procedures used for the synthesis of Compound 17, except that Compound 212 and HCl salt of (R)-tert-butyl 2-aminopropanoate was used as starting material.

Compound 342

Compound 342 was prepared according to the procedures used for the synthesis of Compound 17, except that Compound 212 and HCl salt of methyl 4-aminobutanoate was used as starting material.

Compound 343

Compound 343 was prepared according to the procedures used for the synthesis of Compound 17, except that Compound 212 and HCl salt of methyl 4-aminobutanoate was used as starting material.

Compound 344

Compound 344 was prepared according to the procedures used for the synthesis of Compound 17, except that Compound 212 and HCl salt of methyl 4-aminobutanoate was used as starting material.

Compound 345

Compound 345 was prepared according to the procedures used for the synthesis of Compound 10, except that Compound 212 and HCl salt of (S)-4-tert-butyl 1-methyl 2-aminosuccinate was used as starting material.

Compound 350

Compound 350 was prepared according to the procedures used for the synthesis of Compound 17, except that Compound 289 and (S)-methyl 2-amino-3-phenylpropanoate was used as starting material.

Compound 351

Compound 351 was prepared according to the procedures used for the synthesis of Compound 10, except that Compound 117 and (R)-4-tert-butyl 1-methyl 2-aminosuccinate was used as starting material.

Compound 352

Compound 352 was prepared according to the procedures used for the synthesis of Compound 17, except that Compound 117 and methyl 3-aminobenzoate was used as starting material.

Compound 353

Compound 353 was prepared according to the procedures used for the synthesis of Compound 17, except that Compound 117 and methyl pyrrolidine-3-carboxylate was used as starting material.

Compound 354

Compound 354 was prepared according to the procedures used for the synthesis of Compound 10, except that Compound 117 and 4-tert-butoxybutanoic acid was used as starting material.

Compound 370

Compound 370 was prepared according to the procedures used for the synthesis of Compound 10, except that Compound 117 and dimethylamine hydrochloride was used as starting material and no TFA treatment was required.

Compound 383

Compound 383 was prepared according to the procedures used for the synthesis of Compound 10, except that Compound 214 and HCl salt of tert-butyl 2-aminoacetate was used as starting material.

Compound 384

Compound 384 was prepared according to the procedures used for the synthesis of Compound 10, except that Compound 214 and HCl salt of (R)-tert-butyl 2-aminopropanoate was used as starting material.

Compound 385

Compound 385 was prepared according to the procedures used for the synthesis of Compound 10, except that Compound 214 and HCl salt of (S)-tert-butyl 2-aminopropanoate was used as starting material.

Compound 386

Compound 386 was prepared according to the procedures used for the synthesis of Compound 10, except that Compound 214 and HCl salt of tert-butyl 4-aminobutanoate was used as starting material.

Compound 387

Compound 387 was prepared according to the procedures used for the synthesis of Compound 10, except that Compound 214 and HCl salt of (S)-tert-butyl 2-amino-3-(4-tert-butoxyphenyl)propanoate was used as starting material.

Compound 388

Compound 388 was prepared according to the procedures used for the synthesis of Compound 10, except that Compound 214 and HCl salt of (S)-5-tert-butyl 1-methyl 2-aminopentanedioate was used as starting material.

Compound 389

Compound 389 was prepared according to the procedures used for the synthesis of Compound 10, except that Compound 214 and HCl salt of (S)-5-tert-butyl 1-methyl 2-aminopentanedioate was used as starting material.

Compound 390

Compound 390 was prepared according to the procedures used for the synthesis of Compound 10, except that Compound 214 and ethanolamine was used as starting material and no TFA treatment was required.

Compound 391

Compound 391 was prepared according to the procedures used for the synthesis of Compound 17, except that Compound 214 and methyl 1-aminocyclopropanecarboxylate was used as starting material.

Compound 392

Compound 392 was prepared according to the procedures used for the synthesis of Compound 17, except that Compound 214 and ethyl 2-(benzylamino)acetate was used as starting material.

Compound 393

Compound 393 was prepared according to the procedures used for the synthesis of Compound 17, except that Compound 214 and (S)-ethyl 2-amino-4-phenylbutanoate was used as starting material.

Compound 395

Compound 395 was prepared according to the procedures used for the synthesis of Compound 17, except that comopund and methyl 6-aminohexanoate was used as starting material.

Compound 401

Compound 401 was prepared according to the procedures used for the synthesis of Compound 17, except that Compound 289 and methyl 3-aminopropanoate was used as starting material.

Compound 402

Compound 402 was prepared according to the procedures used for the synthesis of Compound 17, except that Compound 289 and methyl 4-aminobutanoate was used as starting material.

Compound 403

Compound 403 was prepared according to the procedures used for the synthesis of Compound 17, except that Compound 117 and (S)-methyl 2-amino-3-(pyridin-3-yl)propanoate was used as starting material.

Compound 404

Compound 404 was prepared according to the procedures used for the synthesis of Compound 10, except that Compound 145 and ethyl 1-(aminomethyl)cyclopropanecarboxylate was used as starting material.

Compound 405

Compound 405 was prepared according to the procedures used for the synthesis of Compound 17, except that Compound 289 and (S)-methyl 2-amino-3-(pyridin-3-yl)propanoate was used as starting material.

Compound 426

Compound 426 was prepared according to the procedures used for the synthesis of Compound 17, except that Compound 419 and (S)-methyl 2-amino-3-phenylpropanoate hydrochloride was used as starting material.

Compound 440

Compound 440 was prepared according to the procedures used for the synthesis of Compound 17, except that Compound 111 and (S)-methyl 2-amino-3-phenylpropanoate hydrochloride was used as starting material.

Compound 441

Compound 441 was prepared according to the procedures used for the synthesis of Compound 17, except that Compound 112 and (S)-methyl 2-amino-3-phenylpropanoate hydrochloride was used as starting material.

Compound 442

Compound 442 was prepared according to the procedures used for the synthesis of Compound 17, except that Compound 330 and (S)-methyl 2-amino-3-phenylpropanoate hydrochloride was used as starting material.

Compound 443

Compound 443 was prepared according to the procedures used for the synthesis of Compound 17, except that Compound 180 and (S)-methyl 2-amino-3-phenylpropanoate hydrochloride was used as starting material.

Compound 444

Compound 444 was prepared according to the procedures used for the synthesis of Compound 17, except that Compound 289 and (R)-methyl 2-amino-3-phenylpropanoate was used as starting material.

Compound 445

Compound 445 was prepared according to the procedures used for the synthesis of Compound 17, except that Compound 289 and (S)-methyl 2-amino-3-phenylpropanoate was used as starting material.

Compound 446

Compound 446 was prepared according to the procedures used for the synthesis of Compound 17, except that Compound 289 and (R)-methyl 2-aminopropanoate was used as starting material.

Compound 447

Compound 447 was prepared according to the procedures used for the synthesis of Compound 17, except that Compound 289 and (S)-methyl 2-aminopropanoate was used as starting material.

Compound 448

Compound 448 was prepared according to the procedures used for the synthesis of Compound 17, except that Compound 289 and methyl 3-aminopropanoate was used as starting material.

Compound 449

Compound 449 was prepared according to the procedures used for the synthesis of Compound 17, except that Compound 289 and methyl 4-aminobutanoate was used as starting material.

Compound 450

Compound 450 was prepared according to the procedures used for the synthesis of Compound 10, except that Compound 289 and tert-butyl 5-aminopentanoate was used as starting material.

Compound 451

Compound 451 was prepared according to the procedures used for the synthesis of Compound 10, except that Compound 289 and tert-butyl 1-aminocyclopropanecarboxylate was used as starting material.

Compound 452

Compound 452 was prepared according to the procedures used for the synthesis of Compound 17, except that Compound 289 and methyl 2-amino-2-methylpropanoate was used as starting material.

Compound 453

Compound 453 was prepared according to the procedures used for the synthesis of Compound 17, except that Compound 289 and methyl 2-aminoacetate was used as starting material.

Compound 454

Compound 454 was prepared according to the procedures used for the synthesis of Compound 1, except that (R)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-phenylpropanoic acid was used as starting material at step 6, and L-AP succinate was used as starting material at step 7.

Compound 455

Compound 455 was prepared according to the procedures used for the synthesis of Compound 17, except that Compound 454 and (R)-methyl 2-amino-3-phenylpropanoate was used as starting material.

Compound 456

Compound 456 was prepared according to the procedures used for the synthesis of Compound 17, except that Compound 454 and (S)-methyl 2-amino-3-phenylpropanoate was used as starting material.

Compound 457

Compound 457 was prepared according to the procedures used for the synthesis of Compound 17, except that Compound 454 and (R)-methyl 2-aminopropanoate was used as starting material.

Compound 458

Compound 458 was prepared according to the procedures used for the synthesis of Compound 17, except that Compound 454 and (S)-methyl 2-aminopropanoate was used as starting material.

Compound 459

Compound 459 was prepared according to the procedures used for the synthesis of Compound 17, except that Compound 454 and methyl 3-aminopropanoate was used as starting material.

Compound 460

Compound 460 was prepared according to the procedures used for the synthesis of Compound 17, except that Compound 454 and methyl 4-aminobutanoate was used as starting material.

Compound 461

Compound 461 was prepared according to the procedures used for the synthesis of Compound 10, except that Compound 454 and tert-butyl 5-aminopentanoate was used as starting material.

Compound 462

Compound 462 was prepared according to the procedures used for the synthesis of Compound 17, except that Compound 454 and methyl 2-aminoacetate was used as starting material.

Compound 470

Compound 470 was prepared according to the procedures used for the synthesis of Compound 17, except that Compound 117 and (S)-ethyl 2-amino-4-phenylbutanoate hydrochloride was used as starting material.

Compound 471

Compound 471 was prepared according to the procedures used for the synthesis of Compound 10, except that Compound 117 and (S)-neopentyl 2-amino-3-(4-tert-butoxyphenyl)propanoate hydrochloride was used as starting material.

Compound 472

Compound 472 was prepared according to the procedures used for the synthesis of Compound 10, except that Compound 348 and HCl salt of tert-butyl 2-aminoacetate was used as starting material.

Compound 473

Compound 473 was prepared according to the procedures used for the synthesis of Compound 10, except that Compound 348 and HCl salt of (S)-tert-butyl 2-aminopropanoate was used as starting material.

Compound 475

Compound 475 was prepared according to the procedures used for the synthesis of Compound 10, except that Compound 348 and HCl salt of tert-butyl 4-aminobutanoate was used as starting material.

Compound 477

Compound 477 was prepared according to the procedures used for the synthesis of Compound 10, except that Compound 348 and HCl salt of tert-butyl 2-amino-2-methylpropanoate was used as starting material.

Compound 478

Compound 478 was prepared according to the procedures used for the synthesis of Compound 10, except that Compound 348 and HCl salt of tert-butyl 1-aminocyclopropanecarboxylate was used as starting material.

Compound 479

Compound 479 was prepared according to the procedures used for the synthesis of Compound 17, except that Compound 348 and HCl salt of methyl 2-(2-aminoacetamido)acetate was used as starting material.

Compound 480

Compound 480 was prepared according to the procedures used for the synthesis of Compound 10, except that Compound 348 and HCl salt of (R)-tert-butyl 2-amino-3-phenylpropanoate was used as starting material.

Compound 481

Compound 481 was prepared according to the procedures used for the synthesis of Compound 10, except that Compound 348 and HCl salt of (S)-tert-butyl 2-amino-3-phenylpropanoate was used as starting material.

Compound 482

Compound 482 was prepared according to the procedures used for the synthesis of Compound 10, except that Compound 348 and aminomethanesulfonic acid was used as starting material and no TFA treatment was required.

Compound 483

Compound 483 was prepared according to the procedures used for the synthesis of Compound 10, except that Compound 348 and benzenesulfonamide and N,N-dimethylpyridin-4-amine was used as starting material and no TFA treatment was required.

Compound 484

Compound 484 was prepared according to the procedures used for the synthesis of Compound 10, except that Compound 348 and N-(2-aminoethyl)-4-methylbenzenesulfonamide was used as starting material and no TFA treatment was required.

Compound 485

Compound 485 was prepared according to the procedures used for the synthesis of Compound 10, except that Compound 348 and (S)-tert-butyl 3-amino-4-phenylbutanoate was used as starting material.

Compound 486

Compound 486 was prepared according to the procedures used for the synthesis of Compound 10, except that Compound 348 and (S)-tert-butyl 2-amino-3-(trityloxy)propanoate was used as starting material.

Compound 487

Compound 487 was prepared according to the procedures used for the synthesis of Compound 17, except that Compound 348 and HCl salt of methyl 2-(2-aminoacetamido)acetate was used as starting material.

Compound 488

Compound 488 was prepared according to the procedures used for the synthesis of Compound 1, except that (S)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-4-amino-4-oxobutanoic acid was used as starting material at step 6.

Compound 489

Compound 489 was prepared according to the procedures used for the synthesis of Compound 1, except that (S)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(4-tert-butoxyphenyl)propanoic acid was used as starting material at step 6.

Compound 490

Compound 490 was prepared according to the procedures used for the synthesis of Compound 1, except that (S)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(4-tert-butoxyphenyl)propanoic acid was used as starting material at step 6.

Compound 491

Compound 491 was prepared according to the procedures used for the synthesis of Compound 1, except that (S)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(4-(benzyloxy)phenyl)propanoic acid was used as starting material at step 6.

Compound 493

Compound 493 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6.

Compound 494

Compound 494 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6.

Compound 495

Compound 495 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6.

Compound 496

Compound 496 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6.

Compound 497

Compound 497 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (R)-4-(4-(2-(((9H-fluoren-9-yl)methoxy)carbonylamino)-3-methoxy-3-oxopropyl)phenylamino)-4-oxobutanoic acid was used as starting material at step 7.

Compound 498

Compound 498 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (R)-4-(4-(2-(((9H-fluoren-9-yl)methoxy)carbonylamino)-3-methoxy-3-oxopropyl)phenylamino)-4-oxobutanoic acid was used as starting material at step 7.

Compound 499

Compound 499 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (R)-4-(4-(2-(((9H-fluoren-9-yl)methoxy)carbonylamino)-3-methoxy-3-oxopropyl)phenylamino)-4-oxobutanoic acid was used as starting material at step 7.

Compound 500

Compound 500 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (R)-4-(4-(2-(((9H-fluoren-9-yl)methoxy)carbonylamino)-3-methoxy-3-oxopropyl)phenylamino)-4-oxobutanoic acid was used as starting material at step 7.

Compound 501

Compound 501 was prepared according to the procedures used for the synthesis of Compound 1, except that (R)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (R)-4-(4-(2-(((9H-fluoren-9-yl)methoxy)carbonylamino)-3-methoxy-3-oxopropyl)phenylamino)-4-oxobutanoic acid was used as starting material at step 7.

Compound 502

Compound 502 was prepared according to the procedures used for the synthesis of Compound 1, except that (S)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, and (S)-2-(((9H-fluoren-9-yl)methoxy)carbonylamino)-3-(thiophen-2-yl)propanoic acid was used as starting material at step 6, and (R)-4-(4-(2-(((9H-fluoren-9-yl)methoxy)carbonylamino)-3-methoxy-3-oxopropyl)phenylamino)-4-oxobutanoic acid was used as starting material at step 7.

Compound 503

Compound 503 was prepared according to the procedures used for the synthesis of Compound 1, except that (S)-2-(((9H-fluoren-9-yl)methoxy)carbonylamino)-3-phenylpropanoic acid was used as starting material at step 4, (R)-2-(((9H-fluoren-9-yl)methoxy)carbonylamino)-3-(biphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (R)-4-(4-(2-(((9H-fluoren-9-yl)methoxy)carbonylamino)-3-methoxy-3-oxopropyl)phenylamino)-4-oxobutanoic acid was used as starting material at step 7.

Compound 504

Compound 504 was prepared according to the procedures used for the synthesis of Compound 17, except that Compound 117 and ethyl 2-(benzylamino)acetate was used as starting material.

Compound 505

Compound 505 was prepared according to the procedures used for the synthesis of Compound 17, except that Compound 117 and (S)-methyl 2-amino-3-(4-(tert-butoxycarbonylamino)phenyl)propanoate was used as starting material and treatment with 25% TFA was required after treatment with lithium hydroxide in step 11.

Compound 528

Compound 505 (2.7 mg, 2.82 µmol) was dissolved in DCM (1 mL). Acetic Anhydride (20 uL, 212 µmol) and DIPEA (20 uL, 113 µmol) was added to the stirring mixture. The reaction was monitored by LC/MS and after 1 hour was complete. The reaction mixture was concentrated and the desired material was precipitated with 1.5 mL of water. The solids were pelleted and the water removed. The solids were washed with water (1 mL) and dried. The crude solid was purified by preparative HPLC to give Compound 528 as a white solid (0.5 mg, 0.45 umol, 90% yield).

Compound 542

Compound 542 was prepared according to the procedures used for the synthesis of Compound 17, except that Compound 117 and (S)-2-(((9H-fluoren-9-yl)methoxy)carbonylamino)-3-phenylpropanoic acid was used as starting material.

Compound 543

Compound 543 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, (R)-2-(((9H-fluoren-9-yl)methoxy)carbonylamino)-4-phenylbutanoic acid was used as starting material at step 6, and (S)-4-(1-(2-(((9H-fluoren-9-yl)methoxy)carbonylamino)-3-methoxy-3-oxopropyl)-1H-1,2,3-triazol-4-yl)butanoic acid was used as starting material at step 7.

Compound 544

Compound 544 was prepared according to the procedures used for the synthesis of Compound 1, except that (R)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, (R)-2-(((9H-fluoren-9-yl)methoxy)carbonylamino)-3-(thiophen-2-yl)propanoic acid was used as starting material at step 6, and (S)-5-(1-(2-(((9H-fluoren-9-yl)methoxy)carbonylamino)-3-methoxy-3-oxopropyl)-1H-1,2,3-triazol-4-yl)pentanoic acid was used as starting material at step 7.

Compound 545

Compound 545 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, (R)-2-(((9H-fluoren-9-yl)methoxy)carbonylamino)-3-(thiophen-2-yl)propanoic acid was used as starting material at step 6, and (S)-4-(6-(2-(tert-butoxycarbonylamino)-3-ethoxy-3-oxopropyl)pyridin-3-ylamino)-4-oxobutanoic acid was used as starting material at step 7.

Compound 546

Compound 546 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, (R)-2-(((9H-fluoren-9-yl)methoxy)carbonylamino)-4-phenylbutanoic acid was used as starting material at step 6, and (S)-4-(6-(2-(tert-butoxycarbonylamino)-3-ethoxy-3-oxopropyl)pyridin-3-ylamino)-4-oxobutanoic acid was used as starting material at step 7.

Compound 547

Compound 547 was prepared according to the procedures used for the synthesis of Compound 1, except that (R)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, (R)-2-(((9H-fluoren-9-yl)methoxy)carbonylamino)-3-(thiophen-2-yl)propanoic acid was used as starting material at step 6, and (S)-4-(6-(2-(tert-butoxycarbonylamino)-3-ethoxy-3-oxopropyl)pyridin-3-ylamino)-4-oxobutanoic acid was used as starting material at step 7.

Compound 548

Compound 548 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, (R)-2-(((9H-fluoren-9-yl)methoxy)carbonylamino)-4-phenylbutanoic acid was used as starting material at step 6, and (S)-4-(6-(2-(tert-butoxycarbonylamino)-3-ethoxy-3-oxopropyl)pyridin-3-ylamino)-4-oxobutanoic acid was used as starting material at step 7.

Compound 549

Compound 549 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(biphenyl-4-yl)propanoic acid was used as starting material at step 5, (R)-2-(((9H-fluoren-9-yl)methoxy)carbonylamino)-3-(thiophen-2-yl)propanoic acid was used as starting material at step 6, and (S)-4-(3-(4-(((9H-fluoren-9-yl)methoxy)carbonylamino)phenyl)-1-methoxy-1-oxopropan-2-ylamino)-4-oxobutanoic acid was used as starting material at step 7.

Compound 550

Compound 550 was prepared according to the procedures used for the synthesis of Compound 1, except that (R)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, (R)-2-(((9H-fluoren-9-yl)methoxy)carbonylamino)-4-phenylbutanoic acid was used as starting material at step 6, and (S)-4-(3-(4-(((9H-fluoren-9-yl)methoxy)carbonylamino)phenyl)-1-methoxy-1-oxopropan-2-ylamino)-4-oxobutanoic acid was used as starting material at step 7.

Compound 551

Compound 551 was prepared according to the procedures used for the synthesis of Compound 1, except that (R)-2-(((9H-fluoren-9-yl)methoxy)carbonylamino)-4-phenylbutanoic acid was used as starting material at step 4, (S)-2-(((9H-fluoren-9-yl)methoxy)carbonylamino)-3-(biphenyl-4-yl)propanoic acid was used as starting material at step 5, (R)-2-(((9H-fluoren-9-yl)methoxy)carbonylamino)-3-(thiophen-2-yl)propanoic acid was used as starting material at step 6, and (S)-4-(3-(4-(((9H-fluoren-9-yl)methoxy)carbonylamino)phenyl)-1-methoxy-1-oxopropan-2-ylamino)-4-oxobutanoic acid was used as starting material at step 7.

Compound 552

Compound 552 was prepared according to the procedures used for the synthesis of Compound 1, except that (R)-2-(((9H-fluoren-9-yl)methoxy)carbonylamino)-3-phenylpropanoic acid was used as starting material at step 4, (S)-2-(((9H-fluoren-9-yl)methoxy)carbonylamino)-3-(4-(trifluoromethyl)phenyl)propanoic acid was used as starting material at step 5, (R)-2-(((9H-fluoren-9-yl)methoxy)carbonylamino)-4-phenylbutanoic acid was used as starting material at step 6, and (S)-4-(3-(4-(((9H-fluoren-9-yl)methoxy)carbonylamino)phenyl)-1-methoxy-1-oxopropan-2-ylamino)-4-oxobutanoic acid was used as starting material at step 7.

Compound 553

Compound 553 was prepared according to the procedures used for the synthesis of Compound 10, except that Compound 506 and (R)-tent-butyl 2-amino-3-phenylpropanoate hydrochloride were used as starting materials.

Compound 554

Compound 554 was prepared according to the procedures used for the synthesis of Compound 10, except that Compound 506 and (S)-tert-butyl 2-amino-3-phenylpropanoate hydrochloride were used as starting materials.

Compound 555

Compound 555 was prepared according to the procedures used for the synthesis of Compound 10, except that Compound 506 and (R)-tert-butyl 2-amino-3-tert-butoxypropanoate hydrochloride were used as starting materials.

Compound 556

Compound 556 was prepared according to the procedures used for the synthesis of Compound 10, except that Compound 506 and (S)-tert-butyl 2-amino-3-tert-butoxypropanoate hydrochloride were used as starting materials.

Compound 557

Compound 557 was prepared according to the procedures used for the synthesis of Compound 10, except that Compound 506 and (R)-tert-butyl 2-aminopropanoate hydrochloride were used as starting materials.

Compound 558

Compound 558 was prepared according to the procedures used for the synthesis of Compound 10, except that Compound 506 and tert-butyl 2-aminoacetate hydrochloride were used as starting materials.

Compound 559

Compound 559 was prepared according to the procedures used for the synthesis of Compound 10, except that Compound 506 and tert-butyl 3-aminopropanoate hydrochloride were used as starting materials.

Compound 560

Compound 560 was prepared according to the procedures used for the synthesis of Compound 10, except that Compound 506 and tert-butyl 4-aminobutanoate hydrochloride were used as starting materials.

Compound 561

Compound 561 was prepared according to the procedures used for the synthesis of Compound 10, except that Compound 674 and (S)-tert-butyl 2-amino-3-phenylpropanoate were used as starting materials.

Compound 562

Compound 562 was prepared according to the procedures used for the synthesis of Compound 10, except that Compound 674 and (R)-tert-butyl 2-amino-3-phenylpropanoate were used as starting materials.

Compound 563

Compound 563 was prepared according to the procedures used for the synthesis of Compound 10, except that Compound 346 and (S)-tert-butyl 2-amino-3-tert-butoxypropanoate were used as starting materials.

Compound 564

Compound 564 was prepared according to the procedures used for the synthesis of Compound 10, except that Compound 346 and tent-butyl 3-aminopropanoate were used as starting materials.

Compound 565

Compound 565 was prepared according to the procedures used for the synthesis of Compound 10, except that Compound 346 and (R)-tent-butyl 2-amino-3-phenylpropanoate were used as starting materials.

Compound 566

Compound 566 was prepared according to the procedures used for the synthesis of Compound 10, except that Compound 346 and aminomethanesulfonic acid were used as starting materials.

Compound 567

Compound 567 was prepared according to the procedures used for the synthesis of Compound 10, except that Compound 510 and (S)-tert-butyl 2-amino-3-(4-tert-butoxyphenyl)propanoate were used as starting materials.

Compound 568

Compound 568 was prepared according to the procedures used for the synthesis of Compound 10, except that Compound 510 and tert-butyl 4-aminobutanoate hydrochloride were used as starting materials.

Compound 569

Compound 569 was prepared according to the procedures used for the synthesis of Compound 10, except that Compound 510 and tert-butyl 3-aminopropanoate hydrochloride were used as starting materials.

Compound 570

Compound 570 was prepared according to the procedures used for the synthesis of Compound 10, except that Compound 510 and tert-butyl 2-aminoacetate hydrochloride were used as starting materials.

Compound 571

Compound 571 was prepared according to the procedures used for the synthesis of Compound 10, except that Compound 510 and (R)-tent-butyl 2-amino-3-tert-butoxypropanoate hydrochloride were used as starting materials.

Compound 572

Compound 572 was prepared according to the procedures used for the synthesis of Compound 10, except that Compound 510 and (S)-tert-butyl 2-aminopropanoate were used as starting materials.

Compound 573

Compound 573 was prepared according to the procedures used for the synthesis of Compound 10, except that Compound 510 and (R)-tert-butyl 2-amino-3-phenylpropanoate were used as starting materials.

Compound 574

Compound 574 was prepared according to the procedures used for the synthesis of Compound 10, except that Compound 510 and (S)-tert-butyl 2-amino-3-phenylpropanoate were used as starting materials.

Compound 575

Compound 575 was prepared according to the procedures used for the synthesis of Compound 10, except that Compound 348 and (S)-tert-butyl 2-(methylamino)propanoate were used as starting materials.

Compound 576

Compound 576 was prepared according to the procedures used for the synthesis of Compound 10, except that Compound 348 and (R)-tert-butyl 2-(methylamino)propanoate were used as starting materials.

Compound 577

Compound 577 was prepared according to the procedures used for the synthesis of Compound 10, except that Compound 510 and (S)-tert-butyl 2-aminopropanoate were used as starting materials.

Compound 578

Compound 578 was prepared according to the procedures used for the synthesis of Compound 10, except that Compound 506 and 2-aminoethanol were used as starting materials.

Compound 579

Compound 579 was prepared according to the procedures used for the synthesis of Compound 10, except that Compound 684 and tert-butyl 3-aminopropanoate hydrochloride were used as starting materials.

Compound 580

Compound 580 was prepared according to the procedures used for the synthesis of Compound 10, except that Compound 684 and tert-butyl 4-aminobutanoate hydrochloride were used as starting materials.

Compound 581

Compound 581 was prepared according to the procedures used for the synthesis of Compound 10, except that Compound 684 and (S)-tert-butyl 2-amino-3-phenylpropanoate were used as starting materials.

Compound 582

Compound 582 was prepared according to the procedures used for the synthesis of Compound 10, except that Compound 684 and (R)-tert-butyl 2-amino-3-phenylpropanoate were used as starting materials.

Compound 583
Compound 583 was prepared according to the procedures used for the synthesis of Compound 10, except that Compound 684 and (S)-tert-butyl 2-amino-3-tert-butoxypropanoate were used as starting materials.
Compound 584
Compound 584 was prepared according to the procedures used for the synthesis of Compound 10, except that Compound 684 and (R)-tert-butyl 2-amino-3-tert-butoxypropanoate were used as starting materials.
Compound 585
Compound 585 was prepared according to the procedures used for the synthesis of Compound 10, except that Compound 684 and (S)-tert-butyl 2-amino-3-(4-tert-butoxyphenyl)propanoate were used as starting materials.
Compound 586
Compound 586 was prepared according to the procedures used for the synthesis of Compound 10, except that Compound 684 and (R)-tert-butyl 2-amino-3-(4-tert-butoxyphenyl)propanoate were used as starting materials.
Compound 587
Compound 587 was prepared according to the procedures used for the synthesis of Compound 10, except that Compound 625 and (R)-tert-butyl 2-amino-3-phenylpropanoate were used as starting materials.
Compound 588
Compound 588 was prepared according to the procedures used for the synthesis of Compound 10, except that Compound 631 and (R)-tert-butyl 2-amino-3-phenylpropanoate were used as starting materials.
Compound 589
Compound 589 was prepared according to the procedures used for the synthesis of Compound 10, except that Compound 348 and (S)-2-phenyl-1-(1-trityl-1H-tetrazol-5-yl)ethanamine were used as starting materials.
Compound 590
Compound 590 was prepared according to the procedures used for the synthesis of Compound 10, except that Compound 214 and (S)-2-phenyl-1-(1-trityl-1H-tetrazol-5-yl)ethanamine were used as starting materials.
Compound 591
Compound 591 was prepared according to the procedures used for the synthesis of Compound 10, except that Compound 214 and (1-trityl-1H-tetrazol-5-yl)methanamine were used as starting materials.
Compound 592
Compound 592 was prepared according to the procedures used for the synthesis of Compound 10, except that Compound 506 and (S)-2-phenyl-1-(1-trityl-1H-tetrazol-5-yl)ethanamine were used as starting materials.
Compound 593
Compound 593 was prepared according to the procedures used for the synthesis of Compound 10, except that Compound 289 and aminomethanesulfonic acid were used as starting materials and no TFA treatment was required.
Compound 594
Compound 594 was prepared according to the procedures used for the synthesis of Compound 10, except that Compound 212 and aminomethanesulfonic acid were used as starting materials and no TFA treatment was required.
Compound 595
Compound 595 was prepared according to the procedures used for the synthesis of Compound 10, except that Compound 213 and aminoethanesulfonic acid were used as starting materials and no TFA treatment was required.
Compound 596
Compound 596 was prepared according to the procedures used for the synthesis of Compound 10, except that Compound 214 and aminopropanesulfonic acid were used as starting materials and no TFA treatment was required.
Compound 597
Compound 597 was prepared according to the procedures used for the synthesis of Compound 10, except that Compound 506 and aminomethanesulfonic acid were used as starting materials and no TFA treatment was required.
Compound 598
Compound 598 was prepared according to the procedures used for the synthesis of Compound 10, except that Compound 506 and aminoethanesulfonic acid were used as starting materials and no TFA treatment was required.
Compound 599
Compound 599 was prepared according to the procedures used for the synthesis of Compound 10, except that Compound 506 and aminopropanesulfonic acid were used as starting materials and no TFA treatment was required.
Compound 600
Compound 600 was prepared according to the procedures used for the synthesis of Compound 10, except that Compound 506 and methanesulfonamide and DMAP were used as starting materials and no TFA treatment was required.
Compound 601
Compound 601 was prepared according to the procedures used for the synthesis of Compound 10, except that Compound 348 and methanesulfonamide and DMAP were used as starting materials and no TFA treatment was required.
Compound 602
Compound 602 was prepared according to the procedures used for the synthesis of Compound 10, except that Compound 348 and 2-aminoethanesulfonic acid were used as starting materials and no TFA treatment was required.
Compound 603
Compound 603 was prepared according to the procedures used for the synthesis of Compound 10, except that Compound 348 and aminopropanesulfonic acid were used as starting materials and no TFA treatment was required.
Compound 604
Compound 604 was prepared according to the procedures used for the synthesis of Compound 10, except that Compound 674 and aminomethanesulfonic acid were used as starting materials and no TFA treatment was required.
Compound 605
Compound 605 was prepared according to the procedures used for the synthesis of Compound 10, except that Compound 348 and 2-(methylamino)ethanesulfonic acid were used as starting materials and no TFA treatment was required.
Compound 606
Compound 606 was prepared according to the procedures used for the synthesis of Compound 10, except that Compound 506 and 2-(1,3-dihydroxy-2-(hydroxymethyl)propan-2-ylamino)ethanesulfonic acid were used as starting materials and no TFA treatment was required.
Compound 607
Compound 607 was prepared according to the procedures used for the synthesis of Compound 10, except that Compound 510 and aminomethanesulfonic acid were used as starting materials and no TFA treatment was required.
Compound 608
Compound 608 was prepared according to the procedures used for the synthesis of Compound 10, except that Compound 510 and aminoethanesulfonic acid were used as starting materials and no TFA treatment was required.

Compound 609

Compound 609 was prepared according to the procedures used for the synthesis of Compound 10, except that Compound 510 and aminopropanesulfonic acid were used as starting materials and no TFA treatment was required.

Compound 610

Compound 610 was prepared according to the procedures used for the synthesis of Compound 10, except that Compound 510 and (1H-tetrazol-5-yl)methanamine hydrobromide were used as starting materials and no TFA treatment was required.

Compound 611

Compound 611 was prepared according to the procedures used for the synthesis of Compound 10, except that Compound 510 and 2-(1H-tetrazol-5-yl)ethanamine were used as starting materials and no TFA treatment was required.

Compound 612

Compound 612 was prepared according to the procedures used for the synthesis of Compound 10, except that Compound 625 and aminomethanesulfonic acid were used as starting materials and no TFA treatment was required.

Compound 613

Compound 613 was prepared according to the procedures used for the synthesis of Compound 10, except that Compound 631 and aminomethanesulfonic acid were used as starting materials and no TFA treatment was required.

Compound 614

Compound 614 was prepared according to the procedures used for the synthesis of Compound 10, except that Compound 633 and aminomethanesulfonic acid were used as starting materials and no TFA treatment was required.

Compound 615

Compound 615 was prepared according to the procedures used for the synthesis of Compound 10, except that Compound 348 and MeOH, DCC and DMAP were used as starting materials and no TFA treatment was required.

Compound 616

Compound 616 was prepared according to the procedures used for the synthesis of Compound 10, except that Compound 684 and (1H-tetrazol-5-yl)methanamine hydrobromide were used as starting materials and no TFA treatment was required.

Compound 617

Compound 617 was prepared according to the procedures used for the synthesis of Compound 10, except that Compound 684 and aminomethanesulfonic acid were used as starting materials and no TFA treatment was required.

Compound 618

Compound 618 was prepared according to the procedures used for the synthesis of Compound 10, except that Compound 506 and (1H-tetrazol-5-yl)methanamine hydrobromide were used as starting materials and no TFA treatment was required.

Compound 619

Compound 619 was prepared according to the procedures used for the synthesis of Compound 17, except that Compound 506 and (R)-ethyl 2-amino-4-phenylbutanoate hydrochloride were used as starting materials.

Compound 620

Compound 620 was prepared according to the procedures used for the synthesis of Compound 17, except that Compound 510 and (S)-ethyl 2-amino-4-phenylbutanoate hydrochloride were used as starting materials.

Compound 621

Compound 621 was prepared according to the procedures used for the synthesis of Compound 17, except that Compound 348 and (S)-methyl 2-(methylamino)-3-phenylpropanoate were used as starting materials.

Compound 622

Compound 622 was prepared according to the procedures used for the synthesis of Compound 17, except that Compound 510 and (R)-ethyl 2-amino-4-phenylbutanoate hydrochloride were used as starting materials.

Compound 623

Compound 623 was prepared according to the procedures used for the synthesis of Compound 17, except that Compound 684 and (S)-ethyl 2-amino-4-phenylbutanoate were used as starting materials.

Compound 624

Compound 624 was prepared according to the procedures used for the synthesis of Compound 17, except that Compound 684 and (R)-ethyl 2-amino-4-phenylbutanoate were used as starting materials.

Example 2

This example describes the synthesis and characterization of additional macrocyclic compounds. A general synthetic sequence for preparing the macrocyclic compounds is illustrated schematically below.

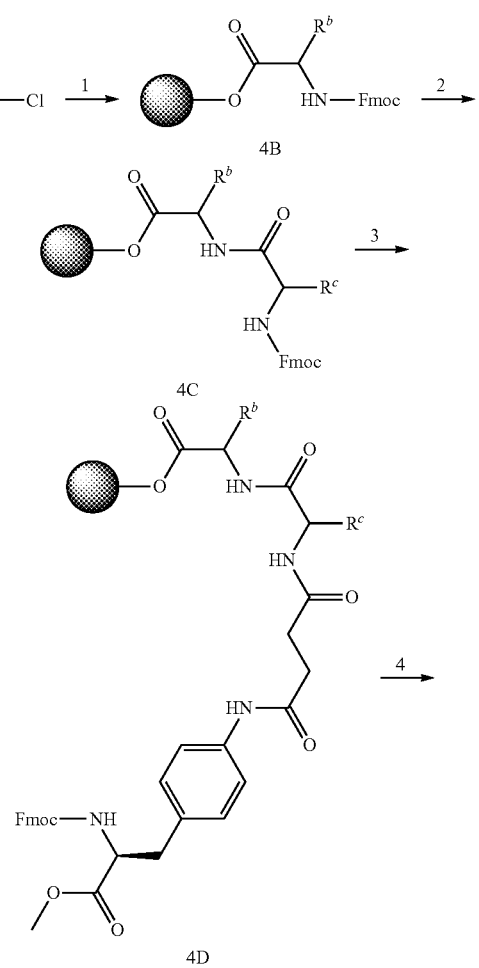

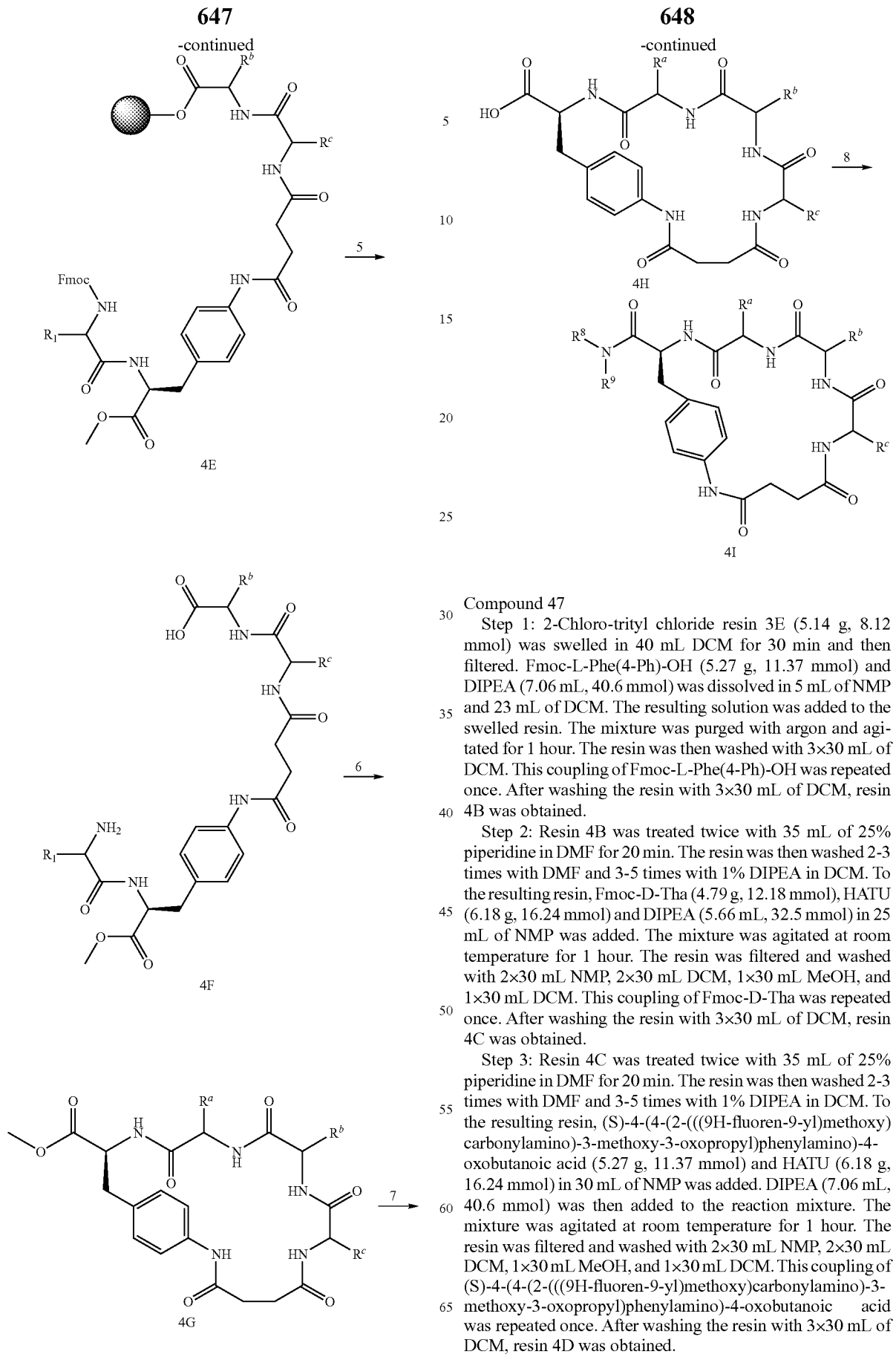

Compound 47

Step 1: 2-Chloro-trityl chloride resin 3E (5.14 g, 8.12 mmol) was swelled in 40 mL DCM for 30 min and then filtered. Fmoc-L-Phe(4-Ph)-OH (5.27 g, 11.37 mmol) and DIPEA (7.06 mL, 40.6 mmol) was dissolved in 5 mL of NMP and 23 mL of DCM. The resulting solution was added to the swelled resin. The mixture was purged with argon and agitated for 1 hour. The resin was then washed with 3×30 mL of DCM. This coupling of Fmoc-L-Phe(4-Ph)-OH was repeated once. After washing the resin with 3×30 mL of DCM, resin 4B was obtained.

Step 2: Resin 4B was treated twice with 35 mL of 25% piperidine in DMF for 20 min. The resin was then washed 2-3 times with DMF and 3-5 times with 1% DIPEA in DCM. To the resulting resin, Fmoc-D-Tha (4.79 g, 12.18 mmol), HATU (6.18 g, 16.24 mmol) and DIPEA (5.66 mL, 32.5 mmol) in 25 mL of NMP was added. The mixture was agitated at room temperature for 1 hour. The resin was filtered and washed with 2×30 mL NMP, 2×30 mL DCM, 1×30 mL MeOH, and 1×30 mL DCM. This coupling of Fmoc-D-Tha was repeated once. After washing the resin with 3×30 mL of DCM, resin 4C was obtained.

Step 3: Resin 4C was treated twice with 35 mL of 25% piperidine in DMF for 20 min. The resin was then washed 2-3 times with DMF and 3-5 times with 1% DIPEA in DCM. To the resulting resin, (S)-4-(4-(2-(((9H-fluoren-9-yl)methoxy)carbonylamino)-3-methoxy-3-oxopropyl)phenylamino)-4-oxobutanoic acid (5.27 g, 11.37 mmol) and HATU (6.18 g, 16.24 mmol) in 30 mL of NMP was added. DIPEA (7.06 mL, 40.6 mmol) was then added to the reaction mixture. The mixture was agitated at room temperature for 1 hour. The resin was filtered and washed with 2×30 mL NMP, 2×30 mL DCM, 1×30 mL MeOH, and 1×30 mL DCM. This coupling of (S)-4-(4-(2-(((9H-fluoren-9-yl)methoxy)carbonylamino)-3-methoxy-3-oxopropyl)phenylamino)-4-oxobutanoic acid was repeated once. After washing the resin with 3×30 mL of DCM, resin 4D was obtained.

Step 4: Resin 4D (100 mg) was treated twice with 2 mL of 25% piperidine in DMF for 20 min. The resin was then washed 2-3 times with DMF and 3-5 times with 1% DIPEA in DCM. To the resulting resin, Fmoc-D-HOPhe (0.175 g, 0.45 mmol), HATU (0.228 g, 0.60 mmol) and DIPEA (0.207, 1.2 mmol) in 2 mL of NMP was added. The mixture was agitated at room temperature overnight. The resin was filtered and washed with 2×5 mL NMP, 2×5 mL DCM, 1×5 mL MeOH, and 1×5 mL DCM. After washing the resin with 3×5 mL of DCM, resin 4E was obtained.

Step 5: Resin 4E was treated twice with 2 mL of 25% piperidine in DMF for 20 min. The resin was then washed 2-3 times with DMF and 3-5 times with 1% DIPEA in DCM. The resin was then treated with 2 mL of 25% TFA in DCM for 30 min. This cleaving solution was then collected by filtration and evaporated to give 75 mg of (S)-2-((R)-2-(4-(4-((S)-2-((R)-2-amino-4-phenylbutanamido)-3-methoxy-3-oxopropyl)phenylamino)-4-oxobutanamido)-3-(thiophen-2-yl)propanamido)-3-(biphenyl-4-yl)propanoic acid (4F). The crude product 4F was used directly in step 6.

Step 6: (S)-2-((R)-2-(4-(4-((S)-2-((R)-2-amino-4-phenylbutanamido)-3-methoxy-3-oxopropyl)phenylamino)-4-oxobutanamido)-3-(thiophen-2-yl)propanamido)-3-(biphenyl-4-yl)propanoic acid (75 mg, 0.092 mmol), HATU (25.1 mg, 0.184 mmol) and HOAt (25.1 mg, 0.184 mmol) were dissolved in anhydrous DMF (74 mL) and DCM (18 mL). DIPEA (0.080 mL, 0.461 mmol) was then added to the stirring solution. The mixture was stirred at room temperature for 2 hours. The solvents were evaporated. MeOH was added and evaporated to yield a gel-like slurry, to which water was added. A solid precipitate formed and was collected by filtration. After washing the solid with water, 0.1 g of crude 4G was obtained as a white solid.

Step 7: 4G (0.1 g, crude product from step 6) was dissolved in 4 mL of THF. Lithium hydroxide (29.4 mg, 1.229 mmol) in 0.87 mL of $H_2O$ was then added. The reaction mixture was stirred at room temperature for 40 min. The solution was then neutralized with 38% HCl (0.097 mL). The solvents were evaporated, and the crude product was purified by preparative HPLC to give Compound 47 as a white solid.

Compound 48

Compound 48 was prepared according to the procedures used in the synthesis of Compound 47, except that (S)-2-(((9H-fluoren-9-yl)methoxy)carbonylamino)-3-(furan-2-yl)propanoic acid was used as starting material at step 4.

Compound 49

Compound 49 was prepared according to the procedures used in the synthesis of Compound 47, except that Fmoc-L-4-pyridyl-Ala was used as starting material at step 4.

Compound 50

Compound 50 was prepared according to the procedures used in the synthesis of Compound 47, except that Fmoc-D-4-pyridyl-Ala was used as starting material at step 4.

Compound 51

Compound 51 was prepared according to the procedures used in the synthesis of Compound 47, except that Fmoc-L-3-pyridyl-Ala was used as starting material at step 4.

Compound 52

Compound 52 was prepared according to the procedures used in the synthesis of Compound 47, except that Fmoc-D-3-pyridyl-Ala was used as starting material at step 4.

Compound 53

Compound 53 was prepared according to the procedures used in the synthesis of Compound 47, except that Fmoc-L-2-pyridyl-Ala was used as starting material at step 4.

Compound 54

Compound 54 was prepared according to the procedures used in the synthesis of Compound 47, except that Fmoc-Leucine-OH was used as starting material at step 4.

Compound 55

Compound 55 was prepared according to the procedures used in the synthesis of Compound 47, except that Fmoc-N-benzylglycine was used as starting material at step 4.

Compound 56

Compound 56 was prepared according to the procedures used in the synthesis of Compound 47a, except that (s)-3-(Fmoc-amino-)-4-phenylbutyric acid was used as starting material at step 4.

Compound 57

Compound 57 was prepared according to the procedures used in the synthesis of Compound 47, except that Fmoc-N-Me-Phe-OH was used as starting material at step 4.

Compound 58

Compound 58 was prepared according to the procedures used in the synthesis of Compound 47, except that Fmoc-L-Tyr-OH was used as starting material at step 4.

Compound 59

Compound 59 was prepared according to the procedures used in the synthesis of Compound 47, except that Fmoc-D-Tyr-OH was used as starting material at step 4.

Compound 60

Compound 60 was prepared according to the procedures used in the synthesis of Compound 47, except that Fmoc-L-Ser(TrT)-OH was used as starting material at step 4.

Compound 61

Compound 61 was prepared according to the procedures used in the synthesis of Compound 47, except that Fmoc-L-Ser(TrT)-OH was used as starting material at step 4.

Compound 62

Compound 62 was prepared according to the procedures used in the synthesis of Compound 47, except that Fmoc-L-Asp-OtBu was used as starting material at step 4.

Compound 63

Compound 63 was prepared according to the procedures used in the synthesis of Compound 47, except that Fmoc-D-Asp-OtBu was used as starting material at step 4.

Compound 64

Compound 64 was prepared according to the procedures used in the synthesis of Compound 47, except that Fmoc-L-Asp-OtBu was used as starting material at step 4.

Compound 65

Compound 65 was prepared according to the procedures used in the synthesis of Compound 47, except that Fmoc-D-Asp-OtBu was used as starting material at step 4.

Compound 66

Compound 66 was prepared according to the procedures used in the synthesis of Compound 47, except that Fmoc-L-Glu-OtBu was used as starting material at step 4.

Compound 67

Compound 67 was prepared according to the procedures used in the synthesis of Compound 47, except that Fmoc-D-Glu-OtBu was used as starting material at step 4.

Compound 68

Compound 68 was prepared according to the procedures used in the synthesis of Compound 47, except that Fmoc-L-Glu-OtBu was used as starting material at step 4.

Compound 69

Compound 69 was prepared according to the procedures used in the synthesis of Compound 47, except that Fmoc-D-Glu-OtBu was used as starting material at step 4.

Compound 72

Compound 72 was prepared according to the procedures used in the synthesis of Compound 47, except that Fmoc-L-Arg(Pbf)-OH was used as starting material at step 4.

Compound 73

Compound 73 was prepared according to the procedures used in the synthesis of Compound 47, except that Fmoc-D-Arg(Pbf)-OH was used as starting material at step 4.

Compound 74

Compound 74 was prepared according to the procedures used in the synthesis of Compound 47, except that Fmoc-L-2-Furyl-Ala was used as starting material at step 4.

Compound 75

Compound 75 was prepared according to the procedures used in the synthesis of Compound 47, except that Fmoc-D-2-Furyl-Ala was used as starting material at step 4.

Compound 76

Compound 76 was prepared according to the procedures used in the synthesis of Compound 47, except that Fmoc-D-Phe-Gly was used as starting material at step 4.

Compound 77

Compound 77 was prepared according to the procedures used in the synthesis of Compound 47, except that Fmoc-D-2-CF3-Phe was used as starting material at step 4.

Compound 78

Compound 78 was prepared according to the procedures used in the synthesis of Compound 47, except that Fmoc-D-3-CF3-Phe was used as starting material at step 4.

Compound 79

Compound 79 was prepared according to the procedures used in the synthesis of Compound 47, except that Fmoc-D-4-CF3-Phe was used as starting material at step 4.

Compound 80

Compound 80 was prepared according to the procedures used in the synthesis of Compound 47, except that Fmoc-D-2-CH3-Phe was used as starting material at step 4.

Compound 81

Compound 81 was prepared according to the procedures used in the synthesis of Compound 47, except that Fmoc-D-4-Cl-Phe was used as starting material at step 4.

Compound 224

Compound 224 was prepared according to the procedures used for the synthesis of Compound 47, except that (S)-2-(((9H-fluoren-9-yl)methoxy)carbonylamino)-3-(furan-2-yl)propanoic acid was used as starting material at step 2, (S)-2-(((9H-fluoren-9-yl)methoxy)carbonylamino)-3-(4-(trifluoromethyl)phenyl)propanoic acid was used as starting material at step 3, and (R)-2-(((9H-fluoren-9-yl)methoxy)carbonylamino)-4-phenylbutanoic acid was used as starting material at step 4.

Compound 225

Compound 225 was prepared according to the procedures used for the synthesis of Compound 47, except that (R)-2-(((9H-fluoren-9-yl)methoxy)carbonylamino)-3-(2-cyanophenyl)propanoic acid was used as starting material at step 2, (S)-2-(((9H-fluoren-9-yl)methoxy)carbonylamino)-3-(4-(trifluoromethyl)phenyl)propanoic acid was used as starting material at step 3, and (R)-2-(((9H-fluoren-9-yl)methoxy)carbonylamino)-4-phenylbutanoic acid was used as starting material at step 4.

Compound 226

Compound 226 was prepared according to the procedures used for the synthesis of Compound 47, except that (R)-2-(((9H-fluoren-9-yl)methoxy)carbonylamino)-3-(2-chlorophenyl)propanoic acid was used as starting material at step 2, (S)-2-(((9H-fluoren-9-yl)methoxy)carbonylamino)-3-(4-(trifluoromethyl)phenyl)propanoic acid was used as starting material at step 3, and (R)-2-(((9H-fluoren-9-yl)methoxy)carbonylamino)-4-phenylbutanoic acid was used as starting material at step 4.

Compound 250

Compound 250 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and S-Fmoc-Proline-OH was used as starting material at step 4.

Compound 251

Compound 251 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and S-Fmoc-Proline-OH was used as starting material at step 4.

Compound 252

Compound 252 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and S-Fmoc-Proline-OH was used as starting material at step 4.

Compound 253

Compound 253 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and 2-((((9H-fluoren-9-yl)methoxy)carbonyl)(benzyl)amino)acetic acid was used as starting material at step 4.

Compound 254

Compound 254 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-4-phenylbutanoic acid was used as starting material at step 4.

Compound 255

Compound 255 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and S-Fmoc-Proline-OH was used as starting material at step 4.

Compound 256

Compound 256 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-6-acetamidohexanoic acid was used as starting material at step 4.

Compound 257

Compound 257 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and 2-((((9H-fluoren-9-yl)methoxy)carbonyl)(benzyl)amino)acetic acid was used as starting material at step 4.

Compound 258

Compound 258 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-5-tert-butoxy-5-oxopentanoic acid was used as starting material at step 4.

Compound 259

Compound 259 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-5-tert-butoxy-5-oxopentanoic acid was used as starting material at step 4.

Compound 283

Compound 283 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 3, and (R)-2-(((9H-fluoren-9-yl)methoxy)carbonylamino)-3-(thiophen-2-yl)propanoic acid was used as starting material at step 4.

Compound 284

Compound 284 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 3, and (R)-2-(((9H-fluoren-9-yl)methoxy)carbonylamino)-3-(furan-2-yl)propanoic acid was used as starting material at step 4.

Compound 285

Compound 285 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 3, and (R)-2-(((9H-fluoren-9-yl)methoxy)carbonylamino)-3-(2-cyanophenyl)propanoic acid was used as starting material at step 4.

Compound 286

Compound 286 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 3, and (R)-2-(((9H-fluoren-9-yl)methoxy)carbonylamino)-3-(2-chlorophenyl)propanoic acid was used as starting material at step 4.

Compound 287

Compound 287 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 3, and (R)-2-(((9H-fluoren-9-yl)methoxy)carbonylamino)-3-(2,4-dichlorophenyl)propanoic acid was used as starting material at step 4.

Compound 288

Compound 288 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 3, and (R)-2-(((9H-fluoren-9-yl)methoxy)carbonylamino)-3-(4-fluorophenyl)propanoic acid was used as starting material at step 4.

Compound 289

Compound 289 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 3, and (R)-2-(((9H-fluoren-9-yl)methoxy)carbonylamino)-4-phenylbutanoic acid was used as starting material at step 4.

Compound 290

Compound 290 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (2R,3R)-4-(4-((S)-2-(((9H-fluoren-9-yl)methoxy)carbonylamino)-3-methoxy-3-oxopropyl)phenylamino)-2,3-dihydroxy-4-oxobutanoic acid was used as starting material at step 3, and (S)-2-(((9H-fluoren-9-yl)methoxy)carbonylamino)-4-phenylbutanoic acid was used as starting material at step 4.

Compound 291

Compound 291 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-2-phenylacetic acid was used as starting material at step 4.

Compound 346

Compound 346 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-tert-butoxyphenyl)propanoic acid was used as starting material at step 4.

Compound 347

Compound 347 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-tert-butoxyphenyl)propanoic acid was used as starting material at step 4.

Compound 348

Compound 348 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-4-phenylbutanoic acid was used as starting material at step 4.

Compound 349

Compound 349 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-5-tert-butoxy-5-oxopentanoic acid was used as starting material at step 4.

Compound 368

Compound 368 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-2-phenylacetic acid was used as starting material at step 4.

Compound 369

Compound 369 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-6-acetamidohexanoic acid was used as starting material at step 4.

Compound 427

Compound 427 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-tert-butoxyphenyl)propanoic acid was used as starting material at step 4.

Compound 428

Compound 428 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-tert-butoxyphenyl)propanoic acid was used as starting material at step 4.

Compound 530

Compound 530 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(biphenyl-4-yl)propanoic acid was used as starting material at step 4.

Compound 531

Compound 531 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(4-(trifluoromethyl)phenyl)propanoic acid was used as starting material at step 4.

Compound 532

Compound 532 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(4-fluorophenyl)propanoic acid was used as starting material at step 4.

Compound 533

Compound 533 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(3-(trifluoromethyl)phenyl)propanoic acid was used as starting material at step 4.

Compound 534

Compound 534 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(4-hydroxyphenyl)propanoic acid was used as starting material at step 4.

Compound 535

Compound 535 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(4-methoxyphenyl)propanoic acid was used as starting material at step 4.

Compound 536

Compound 536 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(pyridin-4-yl)propanoic acid was used as starting material at step 4.

Compound 537

Compound 537 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R,E)-2-(((9H-fluoren-9-yl)methoxy)carbonylamino)-5-phenylpent-4-enoic acid was used as starting material at step 4.

Compound 538

Compound 538 was prepared according to the procedures used for the synthesis of Compound 47, except that (S)-2-(((9H-fluoren-9-yl)methoxy)carbonylamino)-3-(biphenyl-4-yl)propanoic acid was used as starting material at step 1, (R)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(thiophen-2-yl)propanoic acid was used as starting material at step 4.

Compound 625

Compound 625 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(2-fluorophenyl)propanoic acid was used as starting material at step 4.

Compound 626

Compound 626 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(3-fluorophenyl)propanoic acid was used as starting material at step 4.

Compound 627

Compound 627 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-fluorophenyl)propanoic acid was used as starting material at step 4.

Compound 628

Compound 628 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-((((9H-fluoren-9-yl)methoxy)carbonyl)(methyl)amino)-3-phenylpropanoic acid was used as starting material at step 4.

Compound 629

Compound 629 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(3-methoxyphenyl)propanoic acid was used as starting material at step 4.

Compound 630

Compound 630 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-methoxyphenyl)propanoic acid was used as starting material at step 4.

Compound 631

Compound 631 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(thiophen-2-yl)propanoic acid was used as starting material at step 4.

Compound 632

Compound 632 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(tert-butoxycarbonylamino)-3-(4-(pyridin-2-yl)phenyl)propanoic acid was used as starting material at step 4.

Compound 633

Compound 633 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(tert-butoxycarbonylamino)-3-(4-(pyridin-3-yl)phenyl)propanoic acid was used as starting material at step 4.

Compound 634

Compound 634 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(tert-butoxycarbonylamino)-3-(4-(pyridin-4-yl)phenyl)propanoic acid was used as starting material at step 4.

Compound 635

Compound 635 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-tert-butylphenyl)propanoic acid was used as starting material at step 4.

Compound 636

Compound 636 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(3-fluorophenyl)propanoic acid was used as starting material at step 4.

Compound 637

Compound 637 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-fluorophenyl)propanoic acid was used as starting material at step 4.

Compound 638

Compound 638 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(3-methoxyphenyl)propanoic acid was used as starting material at step 4.

Compound 639

Compound 639 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(4-methoxyphenyl)propanoic acid was used as starting material at step 4.

Compound 640

Compound 640 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(1H-indol-3-yl)propanoic acid was used as starting material at step 4.

Compound 641

Compound 641 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(3-cyanophenyl)propanoic acid was used as starting material at step 4.

Compound 642

Compound 642 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(thiophen-2-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(2-(trifluoromethyl)phenyl)propanoic acid was used as starting material at step 4.

Compound 643

Compound 643 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(tert-butoxycarbonylamino)-3-(4-(pyridin-2-yl)phenyl)propanoic acid was used as starting material at step 4.

Compound 644

Compound 644 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(tert-butoxycarbonylamino)-3-(4-(pyridin-3-yl)phenyl)propanoic acid was used as starting material at step 4.

Compound 645

Compound 645 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(tert-butoxycarbonylamino)-3-(4-(pyridin-4-yl)phenyl)propanoic acid was used as starting material at step 4.

Compound 646

Compound 646 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-phenylpropanoic acid was used as starting material at step 4.

Compound 647

Compound 647 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(4-(trifluoromethyl)phenyl)propanoic acid was used as starting material at step 4.

Compound 648

Compound 648 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(3-(trifluoromethyl)phenyl)propanoic acid was used as starting material at step 4.

Compound 649

Compound 649 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(2-(trifluoromethyl)phenyl)propanoic acid was used as starting material at step 4.

Compound 650

Compound 650 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(2,4-dichloro-phenyl)propanoic acid was used as starting material at step 4.

Compound 651

Compound 651 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (R)-2-(((9H-fluoren-9-yl)methoxy)carbonylamino)-3-(4-chloro-phenyl)propanoic acid was used as starting material at step 4.

Compound 652

Compound 652 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(thiophen-2-yl)propanoic acid was used as starting material at step 4.

Compound 653

Compound 653 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-2-(((9H-fluoren-9-yl)methoxy)carbonylamino)-3-(1H-indol-3-yl)propanoic acid was used as starting material at step 4.

Compound 654

Compound 654 was prepared according to the procedures used for the synthesis of Compound 47, except that (R)-2-(((9H-fluoren-9-yl)methoxy)carbonylamino)-3-(biphenyl-4-yl)propanoic acid was used as starting material at step 1, (S)-2-(((9H-fluoren-9-yl)methoxy)carbonylamino)-3-(pyridin-4-yl)propanoic acid was used as starting material at step 2, (S)-2-(4-(2-(((9H-fluoren-9-yl)methoxy)carbonylamino)-3-methoxy-3-oxopropyl)phenoxy)acetic acid was used as starting material at step 3, and (S)-3-(((9H-fluoren-9-yl)methoxy)carbonylamino)-4-phenylbutanoic acid was used as starting material at step 4.

Example 3

This example describes the synthesis and characterization of additional macrocyclic compounds. A general synthetic sequence for preparing the macrocyclic compounds is illustrated schematically below.

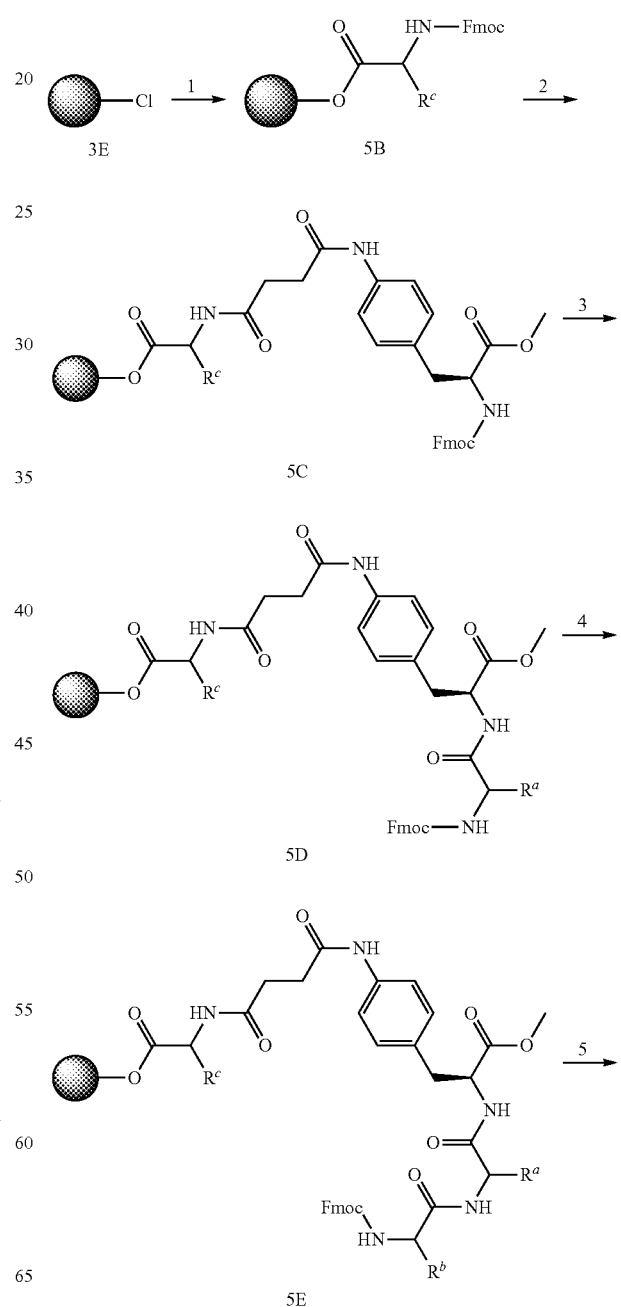

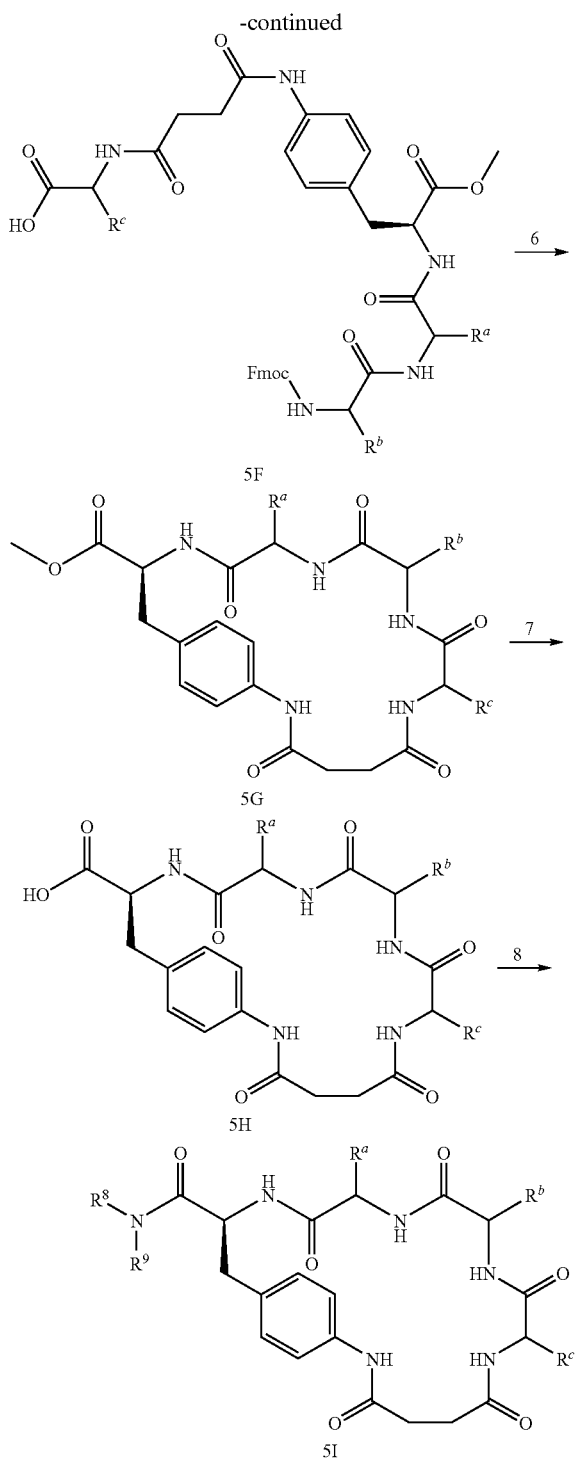

5F

5G

5H

5I

Compound 82

Step 1: 2-Chloro-trityl chloride resin 3E (4.00 g, 6.32 mmol) was swelled in 20 mL DCM for 30 min and then filtered. (R)-2-(((9H-fluoren-9-yl)methoxy)carbonylamino)-3-(thiophen-2-yl)propanoic acid (2.98 g, 7.58 mmol) and DIPEA (5.50 mL, 31.6 mmol) were dissolved in 40 mL of DCM. The resulting solution was added to the swelled resin. The mixture was purged with argon and agitated for 2 hours. The resin was then washed with (34 mL DCM, 4 mL MeOH, 2 mL DIPEA)×3; DCM (40 mL×3), DMF (40 mL×2), DCM (40 mL×2). After flushing with argon and drying under vacuum, resin 5B was obtained.

Step 2: Resin 5B was treated with 35 mL of 20% piperidine in DMF for 20 min, washed with 2×30 mL DMF, and treated with another 35 mL of 20% piperidine in DMF. The resin was then washed with 3×30 mL of DMF and 3×30 mL of 1% DIPEA in DCM. To the resulting resin, (S)-4-(4-(2-(((9H-fluoren-9-yl)methoxy)carbonylamino)-3-methoxy-3-oxo-propyl)phenylamino)-4-oxobutanoic acid (3.27 g, 6.33 mmol) and HATU (3.21 g, 8.44 mmol) in 30 mL of NMP were added. DIPEA (2.94 mL, 16.87 mmol) was then added to the reaction mixture. The mixture was agitated at room temperature for 1 hour. The resin was filtered and after washing with 2×30mL NMP and 4×30 mL of 1% DIPEA in DCM, resin 5C was obtained.

Step 3: Resin 5C was treated with 35 mL of 20% piperidine in DMF for 20 min, washed with 2×30 mL DMF, and treated with another 35 mL of 20% piperidine in DMF. The resin was then washed with 3×30 mL of DMF and 3×30 mL of 1% DIPEA in DCM. To the resulting resin, (R)-2-(((9H-fluoren-9-yl)methoxy)carbonylamino)-3-phenylpropanoic acid (4.9 g, 12.66 mmol), HATU (8.02 g, 21.1 mmol) and DIPEA (7.35, 42.2 mmol) in 30 mL of NMP were added. The mixture was agitated at room temperature overnight. The resin was filtered and after washing with 2×30mL NMP and 4×30 mL of 1% DIPEA in DCM, resin 5D was obtained.

Step 4: Resin 5D (150 mg) was treated with 2 mL of 20% piperidine in DMF for 20 min, washed with 2×4 mL DMF and treated with another 2 mL of 20% piperidine in DMF. The resin was then washed with 3×4 mL of DMF and 3×4 mL of 1% DIPEA in DCM. To the resulting resin, (S)-2-(((9H-fluoren-9-yl)methoxy)carbonylamino)-3-(3,4-dichlorophenyl)propanoic acid (0.115 g, 0.252 mmol) and HATU (0.16 g, 0.42 mmol) in 1.5 mL of NMP were added. DIPEA (0.147 mL, 0.84 mmol) was then added to the reaction mixture. The mixture was agitated at room temperature for 1 hour. After washing the resin with 2×5mL NMP and 4×5 mL of 1% DIPEA in DCM, resin 5E was obtained.

Step 5: Resin 5E was treated with 2 mL of 20% piperidine in DMF for 20 min, washed with 2×4 mL DMF and treated with another 2 mL of 20% piperidine in DMF. The resin was then washed with 3×4 mL of DMF and 3×4 mL of 1% DIPEA in DCM. The resin was treated with 3 mL of 20% HFIP in DCM for 10 min four times. The resin was then washed with DCM (3×3 mL). This cleaving solution was then collected by filtration. The solution was combined and evaporated to give 116 mg of (R)-2-(4-(4-(((S)-2-((R)-2-((S)-2-amino-3-(2,4-dichlorophenyl)propanamido)-3-phenylpropanamido)-3-methoxy-3-oxopropyl)phenylamino)-4-oxobutanamido)-3-(thiophen-2-yl)propanoic acid (5F). The crude product 5F was used directly in step 6.

Step 6: (R)-2-(4-(4-(((S)-2-((R)-2-((S)-2-amino-3-(2,4-dichlorophenyl)propanamido)-3-phenylpropanamido)-3-methoxy-3-oxopropyl)phenylamino)-4-oxobutanamido)-3-(thiophen-2-yl)propanoic acid (99 mg, 0.122 mmol), HATU (93 mg, 0.244 mmol) and HOAt (33 mg, 0.224 mmol) were dissolved in anhydrous DMF (80 mL). DIPEA (0.4 mL, 2.29 mmol) was then added to the stirring solution. The mixture was stirred at room temperature for 2 hours. The solvents were evaporated to give 80 mg of crude 5G as an orange solid.

Step 7: 5G (80 mg, 0.101 mmol) was dissolved in 4 mL of THF. A solution of lithium hydroxide (145 mg, 6.06 mmol) in 0.5 mL of $H_2O$ was then added. The reaction mixture was stirred at room temperature for 40 min. The solution was then neutralized with aqueous HCl. The solvents were evaporated, and the crude product was purified by preparative HPLC to give Compound 82 as a white solid.

Compound 83

Compound 83 was prepared according to the procedures used in the synthesis of Compound 82, except that (S)-2-(((9H-fluoren-9-yl)methoxy)carbonylamino)-3-phenylpropanoic acid was used as starting material at step 4.

Compound 84

Compound 84 was prepared according to the procedures used in the synthesis of Compound 82, except that (S)-2-(((9H-fluoren-9-yl)methoxy)carbonylamino)-3-cyclohexylpropanoic acid was used as starting material at step 4.

Compound 85

Compound 85 was prepared according to the procedures used in the synthesis of Compound 82, except that (S)-2-(((9H-fluoren-9-yl)methoxy)carbonylamino)-3-(4-bromophenyl)propanoic acid was used as starting material at step 4.

Compound 86

Compound 86 was prepared according to the procedures used in the synthesis of Compound 82, except that (S)-2-(((9H-fluoren-9-yl)methoxy)carbonylamino)-3-(4-tert-butoxyphenyl)propanoic acid was used as starting material at step 4.

Compound 87

Compound 87 was prepared according to the procedures used in the synthesis of Compound 82, except that (S)-2-(((9H-fluoren-9-yl)methoxy)carbonylamino)-3-(4-hydroxyphenyl)propanoic acid was used as starting material at step 4.

Compound 88

Compound 88 was prepared according to the procedures used in the synthesis of Compound 82, except that (S)-2-(((9H-fluoren-9-yl)methoxy)carbonylamino)-3-(4-methoxyphenyl)propanoic acid was used as starting material at step 4.

Compound 89

Compound 89 was prepared according to the procedures used in the synthesis of Compound 82, except that (S)-2-(((9H-fluoren-9-yl)methoxy)carbonylamino)-3-(4-(trifluoromethyl)phenyl)propanoic acid was used as starting material at step 4.

Compound 90

Compound 90 was prepared according to the procedures used in the synthesis of Compound 82, except that (S)-2-(((9H-fluoren-9-yl)methoxy)carbonylamino)-3-(4-tert-butylphenyl)propanoic acid was used as starting material at step 4.

Compound 91

Compound 91 was prepared according to the procedures used in the synthesis of Compound 82, except that (S)-2-(((9H-fluoren-9-yl)methoxy)carbonylamino)-4-phenylbutanoic acid was used as starting material at step 4.

Compound 92

Compound 92 was prepared according to the procedures used in the synthesis of Compound 82, except that (S)-2-(((9H-fluoren-9-yl)methoxy)carbonylamino)-3-(4-(benzyloxy)phenyl)propanoic acid was used as starting material at step 4.

Compound 93

Compound 93 was prepared according to the procedures used in the synthesis of Compound 82, except that (S)-2-(((9H-fluoren-9-yl)methoxy)carbonylamino)-3-(3,4-dimethoxyphenyl)propanoic acid was used as starting material at step 4.

Compound 94

Compound 94 was prepared according to the procedures used in the synthesis of Compound 82, except that (S)-2-(((9H-fluoren-9-yl)methoxy)carbonylamino)-3-(4-cyanophenyl)propanoic acid was used as starting material at step 4.

Compound 95

Compound 95 was prepared according to the procedures used in the synthesis of Compound 82, except that (S)-2-(((9H-fluoren-9-yl)methoxy)carbonylamino)-3-(2'-methylbiphenyl-4-yl)propanoic acid was used as starting material at step 4.

Compound 96

Compound 96 was prepared according to the procedures used in the synthesis of Compound 82, except that (S)-2-(((9H-fluoren-9-yl)methoxy)carbonylamino)-6-(nicotinamido)hexanoic acid was used as starting material at step 4.

Compound 97

Compound 97 was prepared according to the procedures used in the synthesis of Compound 82, except that (S)-2-(((9H-fluoren-9-yl)methoxy)carbonylamino)-3-(thiophen-2-yl)propanoic acid was used as starting material at step 4.

Compound 98

Compound 98 was prepared according to the procedures used in the synthesis of Compound 82, except that (S)-2-(((9H-fluoren-9-yl)methoxy)carbonylamino)-4-(methylsulfonyl)butanoic acid was used as starting material at step 4.

Compound 99

Compound 99 was prepared according to the procedures used in the synthesis of Compound 82, except that (S)-2-(((9H-fluoren-9-yl)methoxy)carbonylamino)-2-(2,3-dihydro-1H-inden-2-yl)acetic acid was used as starting material at step 4.

Compound 100

Compound 100 was prepared according to the procedures used in the synthesis of Compound 82, except that (S)-2-(((9H-fluoren-9-yl)methoxy)carbonylamino)-3-(1-methyl-1H-imidazol-4-yl)propanoic acid was used as starting material at step 4.

Compound 101

Compound 101 was prepared according to the procedures used in the synthesis of Compound 82, except that 2-((((9H-fluoren-9-yl)methoxy)carbonyl)(benzyl)amino)acetic acid was used as starting material at step 4.

Compound 102

Compound 102 was prepared according to the procedures used in the synthesis of Compound 82, except that (S)-2-(((9H-fluoren-9-yl)methoxy)carbonylamino)-3-(3-hydroxyphenyl)propanoic acid was used as starting material at step 4.

Compound 103

Compound 103 was prepared according to the procedures used in the synthesis of Compound 82, except that (S)-2-(((9H-fluoren-9-yl)methoxy)carbonylamino)-3-(4-methylphenyl)propanoic acid was used as starting material at step 4.

Compound 104

Compound 104 was prepared according to the procedures used in the synthesis of Compound 82, except that (S)-2-(((9H-fluoren-9-yl)methoxy)carbonylamino)-3-(4-methoxyphenyl)propanoic acid was used as starting material at step 4.

Compound 105

Compound 105 was prepared according to the procedures used in the synthesis of Compound 82, except that (S)-2-(((9H-fluoren-9-yl)methoxy)carbonylamino)-3-(4-chlorophenyl)propanoic acid was used as starting material at step 4.

Compound 106

Compound 106 was prepared according to the procedures used in the synthesis of Compound 82, except that (S)-2-(((9H-fluoren-9-yl)methoxy)carbonylamino)-3-(4-nitrophenyl)propanoic acid was used as starting material at step 4.

Compound 107

Compound 107 was prepared according to the procedures used in the synthesis of Compound 82, except that (S)-3-(((9H-fluoren-9-yl)methoxy)carbonylamino)-3-(4-bromophenyl)propanoic acid was used as starting material at step 4.

Compound 108

Compound 108 was prepared according to the procedures used in the synthesis of Compound 82, except that (R)-2-(((9H-fluoren-9-yl)methoxy)carbonylamino)-4-phenylbutanoic acid was used as starting material in step 1; and (S)-2-(((9H-fluoren-9-yl)methoxy)carbonylamino)-3-(naphthalen-1-yl)propanoic acid was used as starting material at step 4.

Compound 109

Compound 109 was prepared according to the procedures used in the synthesis of Compound 82, except that (R)-2-(((9H-fluoren-9-yl)methoxy)carbonylamino)-4-phenylbutanoic acid was used as starting material in step 1; and (S)-2-(((9H-fluoren-9-yl)methoxy)carbonylamino)-3-(naphthalen-2-yl)propanoic acid was used as starting material at step 4.

Compound 110

Compound 110 was prepared according to the procedures used in the synthesis of Compound 82, except that (R)-2-(((9H-fluoren-9-yl)methoxy)carbonylamino)-4-phenylbutanoic acid was used as starting material in step 1; and (S)-2-(tert-butoxycarbonylamino)-3-(3'-methoxybiphenyl-4-yl)propanoic acid was used as starting material at step 4. In step 5, the Fmoc group was not removed. In addition, trifluoroacetic acid (⅓ volume of solution) was added to facilitate removal of the Boc group.

Compound 111

Compound 111 was prepared according to the procedures used in the synthesis of Compound 82, except that (R)-2-(((9H-fluoren-9-yl)methoxy)carbonylamino)-4-phenylbutanoic acid was used as starting material in step 1; (R)-4-(4-(2-(((9H-fluoren-9-yl)methoxy)carbonylamino)-3-methoxy-3-oxopropyl)phenylamino)-4-oxobutanoic acid was used as starting material in step 2; and (S)-3-(((9H-fluoren-9-yl)methoxy)carbonylamino)-3-(4-bromophenyl)propanoic acid was used as starting material at step 4.

Compound 112

Compound 112 was prepared according to the procedures used in the synthesis of Compound 82, except that (R)-2-(((9H-fluoren-9-yl)methoxy)carbonylamino)-4-phenylbutanoic acid was used as starting material in step 1; (R)-4-(4-(2-(((9H-fluoren-9-yl)methoxy)carbonylamino)-3-methoxy-3-oxopropyl)phenylamino)-4-oxobutanoic acid was used as starting material in step 2; and (S)-3-(((9H-fluoren-9-yl)methoxy)carbonylamino)-3-(2,4-dichlorophenyl)propanoic acid was used as starting material at step 4.

Compound 113

Compound 113 was prepared according to the procedures used in the synthesis of Compound 82, except that (R)-2-(((9H-fluoren-9-yl)methoxy)carbonylamino)-4-phenylbutanoic acid was used as starting material in step 1; and (S)-2-(tert-butoxycarbonylamino)-3-(biphenyl-3-yl)propanoic acid was used as starting material at step 4. In step 5, the Fmoc group was not removed. In addition, trifluoroacetic acid (⅓ volume of solution) was added to facilitate removal of the Boc group.

Compound 114

Compound 114 was prepared according to the procedures used in the synthesis of Compound 82, except that (R)-2-(((9H-fluoren-9-yl)methoxy)carbonylamino)-4-phenylbutanoic acid was used as starting material in step 1; and (S)-2-(tert-butoxycarbonylamino)-3-(4-(pyrimidin-2-yl)phenyl)propanoic acid was used as starting material at step 4. In step 5, the Fmoc group was not removed. In addition, trifluoroacetic acid (⅓ volume of solution) was added to facilitate removal of the Boc group.

Compound 115

Compound 115 was prepared according to the procedures used in the synthesis of Compound 82, except that (R)-2-(((9H-fluoren-9-yl)methoxy)carbonylamino)-4-phenylbutanoic acid was used as starting material in step 1; and (S)-3-(4-(1H-pyrazol-1-yl)phenyl)-2-(tert-butoxycarbonylamino)propanoic acid was used as starting material at step 4. In step 5, the Fmoc group was not removed. In addition, trifluoroacetic acid (⅓ volume of solution) was added to facilitate removal of the Boc group.

Compound 116

Compound 116 was prepared according to the procedures used in the synthesis of Compound 82, except that (R)-2-(((9H-fluoren-9-yl)methoxy)carbonylamino)-4-phenylbutanoic acid was used as starting material in step 1; and (S)-2-(tert-butoxycarbonylamino)-3-(4'-chlorobiphenyl-4-yl)propanoic acid was used as starting material at step 4. In step 5, the Fmoc group was not removed. In addition, trifluoroacetic acid (⅓ volume of solution) was added to facilitate removal of the Boc group.

Compound 167

Compound 167 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-3-(2'-methoxybiphenyl-4-yl)propanoic acid was used as starting material at step 4.

Compound 168

Compound 168 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-3-(4'-methoxybiphenyl-4-yl)propanoic acid was used as starting material at step 4.

Compound 169

Compound 169 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-3-(3'-hydroxybiphenyl-4-yl)propanoic acid was used as starting material at step 4.

Compound 170

Compound 170 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-3-(2'-chlorobiphenyl-4-yl)propanoic acid was used as starting material at step 4.
Compound 171

Compound 171 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-3-(3'-chlorobiphenyl-4-yl)propanoic acid was used as starting material at step 4.
Compound 172

Compound 172 was prepared according to the procedures used for the synthesis of Compound 82, except that (R)-2-(((9H-fluoren-9-yl)methoxy)carbonylamino)-4-phenylbutanoic acid was used as starting material at step 1, (R)-4-(4-(2-(((9H-fluoren-9-yl)methoxy)carbonylamino)-3-methoxy-3-oxopropyl)phenylamino)-4-oxobutanoic acid was used as starting material at step 2, (R)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(biphenyl-4-yl)propanoic acid was used as starting material at step 4.
Compound 173

Compound 173 was prepared according to the procedures used for the synthesis of Compound 82, except that (R)-2-(((9H-fluoren-9-yl)methoxy)carbonylamino)-4-phenylbutanoic acid was used as starting material at step 1, (R)-4-(4-(2-(((9H-fluoren-9-yl)methoxy)carbonylamino)-3-methoxy-3-oxopropyl)phenylamino)-4-oxobutanoic acid was used as starting material at step 2, (R)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4-(benzyloxy)phenyl)propanoic acid was used as starting material at step 4.
Compound 177

Compound 177 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-(4-(trifluoromethyl)phenyl)propanoic acid was used as starting material at step 3, and (S)-2-(((9H-fluoren-9-yl)methoxy)carbonylamino)-3-(4-(benzyloxy)phenyl)propanoic acid was used as starting material at step 4.
Compound 178

Compound 178 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-(4-(trifluoromethyl)phenyl)propanoic acid was used as starting material at step 3, and (S)-2-(((9H-fluoren-9-yl)methoxy)carbonylamino)-3-(4-(trifluoromethyl)phenyl)propanoic acid was used as starting material at step 4.
Compound 180

Compound 180 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-(4-(trifluoromethyl)phenyl)propanoic acid was used as starting material at step 3, and (S)-2-(((9H-fluoren-9-yl)methoxy)carbonylamino)-3-(4'-chlorobiphenyl-4-yl)propanoic acid was used as starting material at step 4.
Compound 181

Compound 181 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-3-(3'-fluorobiphenyl-4-yl)propanoic acid was used as starting material at step 4.
Compound 182

Compound 182 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-3-(3',5'-difluorobiphenyl-4-yl)propanoic acid was used as starting material at step 4.
Compound 183

Compound 183 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and 2-(4-bromophenyl)-2-(tert-butoxycarbonylamino)acetic acid was used as starting material at step 4.
Compound 188

Compound 188 was prepared according to the procedures used for the synthesis of Compound 82, except that (R)-2-(((9H-fluoren-9-yl)methoxy)carbonylamino)-3-(4-(trifluoromethyl)phenyl)propanoic acid was used as starting material at step 4, (S)-2-(((9H-fluoren-9-yl)methoxy)carbonylamino)-3-(3'-hydroxybiphenyl-4-yl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.
Compound 189

Compound 189 was prepared according to the procedures used for the synthesis of Compound 82, except that (R)-2-(((9H-fluoren-9-yl)methoxy)carbonylamino)-3-(4-(trifluoromethyl)phenyl)propanoic acid was used as starting material at step 4, (S)-2-(((9H-fluoren-9-yl)methoxy)carbonylamino)-3-(2,4-dichlorophenyl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.
Compound 190

Compound 190 was prepared according to the procedures used for the synthesis of Compound 82, except that (R)-2-(((9H-fluoren-9-yl)methoxy)carbonylamino)-3-(4-(trifluoromethyl)phenyl)propanoic acid was used as starting material at step 4, (S)-2-(((9H-fluoren-9-yl)methoxy)carbonylamino)-3-(2,4-dichlorophenyl)propanoic acid was used as starting material at step 5, and (R)-2-(((9H-fluoren-9-yl)methoxy)carbonylamino)-3-(thiophen-2-yl)propanoic acid was used as starting material at step 6, and (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 7.

Compound 203

Compound 203 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-6-(dimethylamino)hexanoic acid was used as starting material at step 4.

Compound 208

Compound 208 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (R)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(3-(trifluoromethyl)phenyl)propanoic acid was used as starting material at step 4.

Compound 292

Compound 292 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(2,4-dichlorophenyl)propanoic acid was used as starting material at step 4.

Compound 293

Compound 293 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4-bromophenyl)propanoic acid was used as starting material at step 4.

Compound 294

Compound 294 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and 2-(4-bromophenyl)-2-(tert-butoxycarbonylamino)acetic acid was used as starting material at step 4.

Compound 330

Compound 330 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and (S)-2-(tert-butoxycarbonylamino)-3-(4-(pyridin-4-yl)phenyl)propanoic acid was used as starting material at step 4.

Compound 332

Compound 332 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and (S)-2-(tert-butoxycarbonylamino)-3-(4'-(methoxycarbonyl)biphenyl-4-yl)propanoic acid was used as starting material at step 4.

Compound 333

Compound 333 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and (S)-2-(tert-butoxycarbonylamino)-3-(4'-methoxybiphenyl-4-yl)propanoic acid was used as starting material at step 4.

Compound 334

Compound 334 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and (S)-2-(tert-butoxycarbonylamino)-3-(4'-fluorobiphenyl-4-yl)propanoic acid was used as starting material at step 4.

Compound 335

Compound 335 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and (S)-3-(4'-(benzyloxycarbonyl)biphenyl-4-yl)-2-(tert-butoxycarbonylamino)propanoic acid was used as starting material at step 4.

Compound 336

Compound 336 was prepared according to the procedures used for the synthesis of Compound 82, except that (R)-2-(((9H-fluoren-9-yl)methoxy)carbonylamino)-3-(thiophen- 2-yl)propanoic acid was used as starting material at step 1, (2R,3R)-4-(4-((S)-2-(((9H-fluoren-9-yl)methoxy)carbonylamino)-3-methoxy-3-oxopropyl)phenylamino)-2,3-diacetoxy-4-oxobutanoic acid was used as starting material at step 2, (R)-2-(((9H-fluoren-9-yl)methoxy)carbonylamino)-3-phenylpropanoic acid was used as starting material at step 3, and (S)-3-(4'-(benzyloxycarbonylamino)biphenyl-4-yl)-2-(tert-butoxycarbonylamino)propanoic acid was used as starting material at step 4.

Compound 355

Compound 355 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (R)-2-(((9H-fluoren-9-yl)methoxy)carbonylamino)-3-(4-fluorophenyl)propanoic acid was used as starting material at step 4.

Compound 356

Compound 356 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (R)-2-(((9H-fluoren-9-yl)methoxy)carbonylamino)-3-(3-chlorophenyl)propanoic acid was used as starting material at step 4.

Compound 357

Compound 357 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (R)-2-(((9H-fluoren-9-yl)methoxy)carbonylamino)-3-(naphthalen-1-yl)propanoic acid was used as starting material at step 4.

Compound 358

Compound 358 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (R)-2-(((9H-fluoren-9-yl)methoxy)carbonylamino)-3-(4-nitrophenyl)propanoic acid was used as starting material at step 4.

Compound 359

Compound 359 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4-bromophenyl)propanoic acid was used as starting material at step 4.

Compound 361

Compound 361 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-4'-(2-(((9H-fluoren-9-yl)methoxy)carbonylamino)-2-carboxyethyl)biphenyl-4-carboxylic acid was used as starting material at step 4.

Compound 362

Compound 362 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4'-(benzyloxycarbonylamino)biphenyl-4-yl)propanoic acid was used as starting material at step 4.

Compound 363

Compound 363 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4'-fluorobiphenyl-4-yl)propanoic acid was used as starting material at step 4.

Compound 364

Compound 364 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4'-methoxybiphenyl-4-yl)propanoic acid was used as starting material at step 4.

Compound 365

Compound 365 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4'-chlorobiphenyl-4-yl)propanoic acid was used as starting material at step 4.

Compound 366

Compound 366 was prepared according to the procedures used for the synthesis of Compound 82, except that (S)-2-(((9H-fluoren-9-yl)methoxy)carbonylamino)-3-(thiophen- 2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4-(pyridin-4-yl)phenyl)propanoic acid was used as starting material at step 4.

Compound 367

Compound 367 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(2,4-dichlorophenyl)propanoic acid was used as starting material at step 4.

Compound 396

Compound 396 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4'-(benzyloxycarbonyl)biphenyl-4-yl)propanoic acid was used as starting material at step 4.

Compound 397

Compound 397 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (R)-2-(((9H-fluoren-9-yl)methoxy)carbonylamino)-3-(4-(trifluoromethyl)phenyl)propanoic acid was used as starting material at step 4.

Compound 398

Compound 398 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(4-fluorophenyl)propanoic acid was used as starting material at step 4.

Compound 399

Compound 399 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (R)-2-(((9H-fluoren-9-yl)methoxy)carbonylamino)-3-(4-bromophenyl)propanoic acid was used as starting material at step 4.

Compound 400

Compound 400 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(3-(trifluoromethyl)phenyl)propanoic acid was used as starting material at step 4.

Compound 406

Compound 406 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(3,4-dimethoxyphenyl)propanoic acid was used as starting material at step 4.

Compound 407

Compound 407 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (R)-2-(((9H-fluoren-9-yl)methoxy)carbonylamino)-3-(3-methoxyphenyl)propanoic acid was used as starting material at step 4.

Compound 408

Compound 408 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-phenylpropanoic acid was used as starting material at step 3, and (S)-2-(((9H-fluoren-9-yl)methoxy)carbonylamino)-3-(3-methoxyphenyl)propanoic acid was used as starting material at step 4.

Compound 419

Compound 419 was prepared according to the procedures used for the synthesis of Compound 82, except that (R)-2-(((9H-fluoren-9-yl)methoxy)carbonylamino)-4-phenylbutanoic acid was used as starting material at step 1, (R)-2-(((9H-fluoren-9-yl)methoxy)carbonylamino)-3-phenylpropanoic acid was used as starting material at step 3, and (S)-2-(tert-butoxycarbonylamino)-3-(4-(pyridin-4-yl)phenyl)propanoic acid was used as starting material at step 4.

Compound 525

Compound 525 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (R)-2-(((9H-fluoren-9-yl)methoxy)carbonylamino)-4-phenylbutanoic acid was used as starting material at step 3, and 2-(((9H-fluoren-9-yl)methoxy)carbonylamino)-2-(4-bromophenyl)acetic acid was used as starting material at step 4.

Compound 526

Compound 526 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (R)-2-(((9H-fluoren-9-yl)methoxy)carbonylamino)-4-phenylbutanoic acid was used as starting material at step 3, and (S)-2-(((9H-fluoren-9-yl)methoxy)carbonylamino)-3-(4'-(benzyloxycarbonyl)biphenyl-4-yl)propanoic acid was used as starting material at step 4.

Compound 527

Compound 527 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (R)-2-(((9H-fluoren-9-yl)methoxy)carbonylamino)-4-phenylbutanoic acid was used as starting material at step 3, and (S)-2-(((9H-fluoren-9-yl)methoxy)carbonylamino)-3-(4-fluorophenyl)propanoic acid was used as starting material at step 4.

Compound 539

Compound 539 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (R)-2-(((9H-fluoren-9-yl)methoxy)carbonylamino)-4-phenylbutanoic acid was used as starting material at step 3, and (S)-2-(((9H-fluoren-9-yl)methoxy)carbonylamino)-3-(4-bromophenyl)propanoic acid was used as starting material at step 4.

Compound 540

Compound 540 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (R)-2-(((9H-fluoren-9-yl)methoxy)carbonylamino)-4-phenylbutanoic acid was used as starting material at step 3, and (S)-2-(((9H-fluoren-9-yl)methoxy)carbonylamino)-3-(3,4-dimethoxyphenyl)propanoic acid was used as starting material at step 4.

Compound 541

Compound 541 was prepared according to the procedures used for the synthesis of Compound 82, except that (R)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (R)-2-(((9H-fluoren-9-yl)methoxy)carbonylamino)-4-phenylbutanoic acid was used as starting material at step 3, and (S)-2-(((9H-fluoren-9-yl)methoxy)carbonylamino)-3-(4-nitrophenyl)propanoic acid was used as starting material at step 4.

Compound 655

Compound 655 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-(4'-fluorobiphenyl-4-yl)propanoic acid was used as starting material at step 4.

Compound 656

Compound 656 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-(4'-hydroxybiphenyl-4-yl)propanoic acid was used as starting material at step 4.

Compound 657

Compound 657 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-(4-(pyridin-3-yl)phenyl)propanoic acid was used as starting material at step 4.

Compound 658

Compound 658 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-(4-(pyridin-4-yl)phenyl)propanoic acid was used as starting material at step 4.

Compound 659

Compound 659 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-phenylpropanoic acid was used as starting material at step 4.

Compound 660

Compound 660 was prepared according to the procedures used for the synthesis of Compound 82, except that (S)-2-(((9H-fluoren-9-yl)methoxy)carbonylamino)-3-(pyridin-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-(biphenyl-4-yl)propanoic acid was used as starting material at step 4.

Compound 661

Compound 661 was prepared according to the procedures used for the synthesis of Compound 82, except that (S)-2-(((9H-fluoren-9-yl)methoxy)carbonylamino)-3-(pyridin-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(tert-butoxycarbonylamino)-3-(4-(pyridin-4-yl)phenyl)propanoic acid was used as starting material at step 4.

Compound 662

Compound 662 was prepared according to the procedures used for the synthesis of Compound 82, except that (S)-2-(((9H-fluoren-9-yl)methoxy)carbonylamino)-3-(pyridin-3-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-(biphenyl-4-yl)propanoic acid was used as starting material at step 4.

Compound 663

Compound 663 was prepared according to the procedures used for the synthesis of Compound 82, except that (S)-2-(((9H-fluoren-9-yl)methoxy)carbonylamino)-3-(pyridin-3-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(tert-butoxycarbonylamino)-3-(4-(pyridin-2-yl)phenyl)propanoic acid was used as starting material at step 4.

Compound 664

Compound 664 was prepared according to the procedures used for the synthesis of Compound 82, except that (S)-2-(((9H-fluoren-9-yl)methoxy)carbonylamino)-3-(pyridin-3-yl)propanoic acid was used as starting material at step 1, (S)-2-(((9H-fluoren-9-yl)methoxy)carbonylamino)-3-(pyridin-2-yl)propanoic acid was used as starting material at step 2, (S)-2-(((9H-fluoren-9-yl)methoxy)carbonylamino)-4-phenylbutanoic acid was used as starting material at step 3, and (R)-2-(tert-butoxycarbonylamino)-3-(4-(pyridin-2-yl)phenyl)propanoic acid was used as starting material at step 4.

Compound 665

Compound 665 was prepared according to the procedures used for the synthesis of Compound 82, except that (S)-2-(((9H-fluoren-9-yl)methoxy)carbonylamino)-3-(pyridin-3-yl)propanoic acid was used as starting material at step 1, (S)-2-(((9H-fluoren-9-yl)methoxy)carbonylamino)-3-(pyridin-2-yl)propanoic acid was used as starting material at step 2, (S)-2-(((9H-fluoren-9-yl)methoxy)carbonylamino)-4-phenylbutanoic acid was used as starting material at step 3, and (R)-2-(tert-butoxycarbonylamino)-3-(4-(pyridin-3-yl)phenyl)propanoic acid was used as starting material at step 4.

Compound 666

Compound 666 was prepared according to the procedures used for the synthesis of Compound 82, except that (S)-2-(((9H-fluoren-9-yl)methoxy)carbonylamino)-3-(pyridin-3-yl)propanoic acid was used as starting material at step 1, (S)-2-(((9H-fluoren-9-yl)methoxy)carbonylamino)-3-(pyridin-2-yl)propanoic acid was used as starting material at step 2, (S)-2-(((9H-fluoren-9-yl)methoxy)carbonylamino)-4-phenylbutanoic acid was used as starting material at step 3, and (R)-2-(tert-butoxycarbonylamino)-3-(4-(pyridin-4-yl)phenyl)propanoic acid was used as starting material at step 4.

Compound 667

Compound 667 was prepared according to the procedures used for the synthesis of Compound 82, except that (S)-2-(((9H-fluoren-9-yl)methoxy)carbonylamino)-3-(pyridin-2-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(tert-butoxycarbonylamino)-3-(4-(pyridin-2-yl)phenyl)propanoic acid was used as starting material at step 4.

Compound 668

Compound 668 was prepared according to the procedures used for the synthesis of Compound 82, except that (S)-2-(((9H-fluoren-9-yl)methoxy)carbonylamino)-3-(pyridin-3-yl)propanoic acid was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, and (R)-2-(tert-butoxycarbonylamino)-3-(4-(pyridin-3-yl)phenyl)propanoic acid was used as starting material at step 4.

Compound 669

Compound 669 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-4-(4-(2-(((9H-fluoren-9-yl)methoxy)carbonylamino)-3-methoxy-3-oxopropyl)phenylamino)-4-oxobutanoic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-(4-bromophenyl)propanoic acid was used as starting material at step 4.

Compound 670

Compound 670 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-4-(4-(2-(((9H-fluoren-9-yl)methoxy)carbonylamino)-3-methoxy-3-oxopropyl)phenylamino)-4-oxobutanoic acid was used as starting material at step 2, (S)-2-(((9H-fluoren-9-yl)methoxy)carbonylamino)-4-phenylbutanoic acid was used as starting material at step 3, and (R)-2-(((9H-fluoren-9-yl)methoxy)carbonylamino)-3-(4-chlorophenyl)propanoic acid was used as starting material at step 4.

Compound 671

Compound 671 was prepared according to the procedures used for the synthesis of Compound 82, except that (S)-2-(((9H-fluoren-9-yl)methoxy)carbonylamino)-3-(thiophen-2-yl)propanoic acid was used as starting material at step 1, (S)-4-(4-(2-(((9H-fluoren-9-yl)methoxy)carbonylamino)-3-methoxy-3-oxopropyl)phenylamino)-4-oxobutanoic acid was used as starting material at step 2, (S)-2-(((9H-fluoren-9-yl)methoxy)carbonylamino)-4-phenylbutanoic acid was used as starting material at step 3, and (R)-2-((((9H-fluoren-9-yl)methoxy)carbonyl)(methyl)amino)-4-methylpentanoic acid was used as starting material at step 4.

Compound 672

Compound 672 was prepared according to the procedures used for the synthesis of Compound 82, except that (S)-2-(((9H-fluoren-9-yl)methoxy)carbonylamino)-3-(pyridin-4-yl)propanoic acid was used as starting material at step 1, (S)-4-(4-(2-(((9H-fluoren-9-yl)methoxy)carbonylamino)-3-methoxy-3-oxopropyl)phenylamino)-4-oxobutanoic acid was used as starting material at step 2, (S)-2-(((9H-fluoren-9-yl)methoxy)carbonylamino)-4-phenylbutanoic acid was used as starting material at step 3, and (R)-3-(4'-(benzyloxycarbonylamino)biphenyl-4-yl)-2-(tert-butoxycarbonylamino)propanoic acid was used as starting material at step 4.

Example 4

This example describes the synthesis and characterization of additional macrocyclic compounds. A general synthetic sequence for preparing the macrocyclic compounds is illustrated schematically below. The synthetic sequence involves attaching a substituted succinate to a solid support.

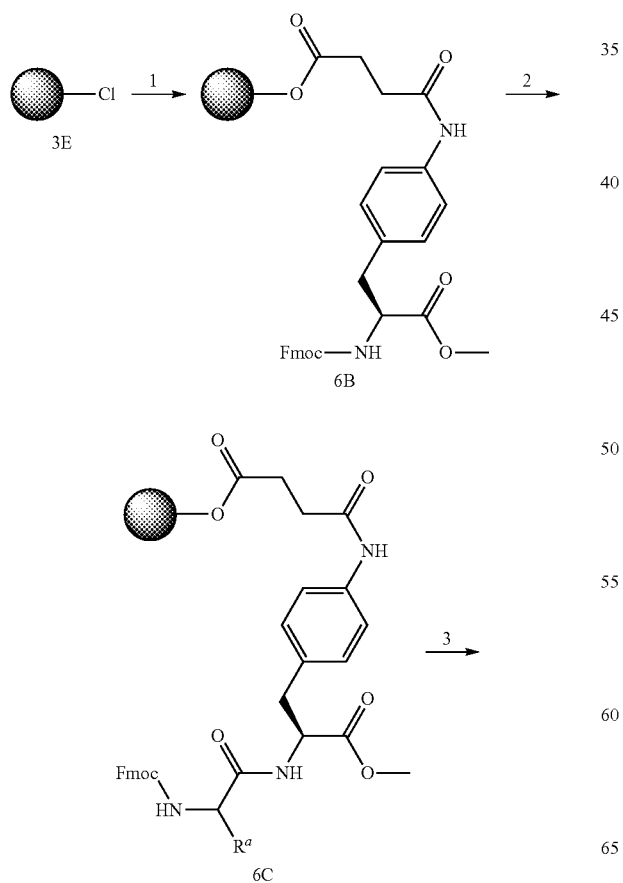

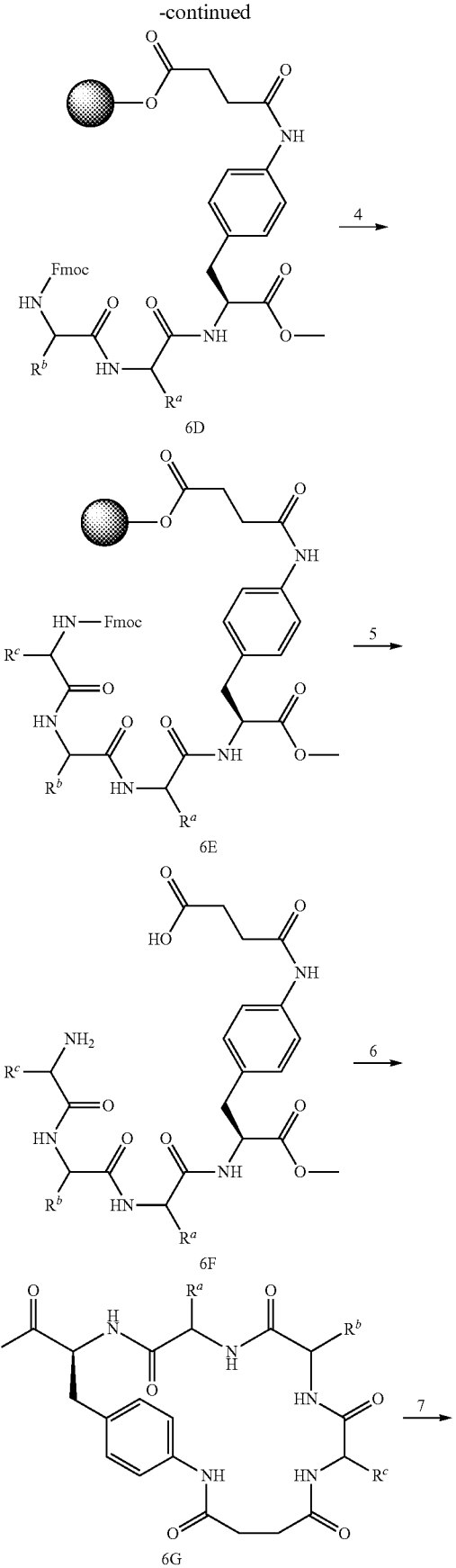

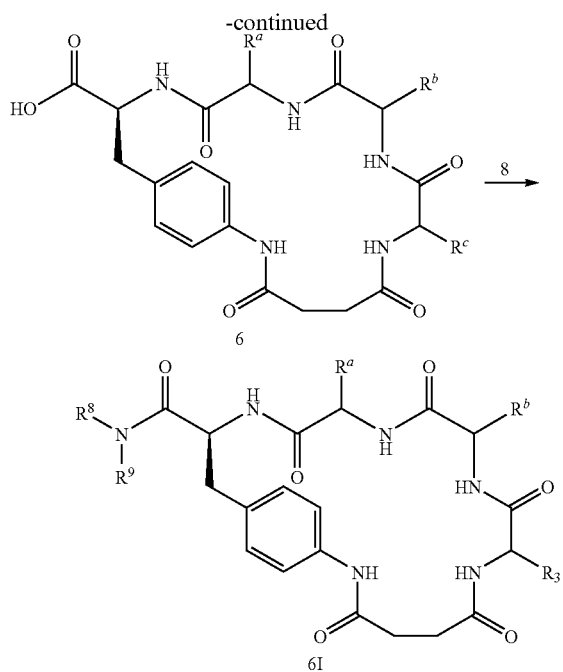

Compound 117

Step 1: 2-Chloro-trityl chloride resin (3E; 1.5 g, 2.37 mmol) was swelled in 20 mL DCM for 30 min and then filtered. (S)-4-(4-(2-(((9H-fluoren-9-yl)methoxy)carbonylamino)-3-methoxy-3-oxopropyl)phenylamino)-4-oxobutanoic acid (1.224 g, 2.37 mmol) and DIPEA (0.824 mL, 4.74 mmol) was dissolved in 12 mL of DCM. The resulting solution was added to the swelled resin. The mixture was purged with argon and agitated for 4 hours. The resin was then washed with 3×5 mL (17:2:1 DCM:MeOH:DIPEA), 3×5 mL 1% DIPEA in DCM, 2×5 mL DMF and 2×5 mL 1% DIPEA in DCM. After the resin was flushed with argon and dried under vacuum, resin 6B was obtained.

Step 2: Resin 6B (4×375 mg batches) Each batch was treated with 7 mL of 20% piperidine in DMF for 20 min, washed with 2×5 mL DMF and treated with another 7 mL of 20% piperidine in DMF. The resin was then washed with 3×5 mL DMF, 3×5 mL DCM and 2×5 mL NMP. To the resulting resin, (R)-2-(((9H-fluoren-9-yl)methoxy)carbonylamino)-3-phenylpropanoic acid (1.01 g, 2.61 mmol) and HATU (0.992 g, 2.61 mmol) in 12 mL of NMP were added evenly across the four batches of resin. DIPEA (0.908 mL, 5.22 mmol) was then added evenly across each batch. The four reaction mixtures were agitated at room temperature for 40 min. The combined resin was filtered and washed with 4×5 mL DMF and 4×5mL 1% DIPEA in DCM to give resin 6C.

Step 3: Resin 6C (4×375 mg batches) Each batch was treated with 4 mL of 20% piperidine in DMF for 20 min, washed with 2×5 mL DMF and treated with another 4 mL of 20% piperidine in DMF. The resin was then washed with 3×5 mL DMF, 3×5 mL DCM and 2×5 mL NMP. To the resulting resin, (S)-2-(((9H-fluoren-9-yl)methoxy)carbonylamino)-3-(biphenyl-4-yl)propanoic acid (1.210 g, 2.61 mmol), HATU (0.992 g, 2.61 mmol) and DIPEA (0.908 mL, 5.22 mmol) in 8 mL of NMP were added evenly across the four batches of resin. The four reaction mixtures were agitated at room temperature for one hour. The combined resin was filtered and washed with 3×5 mL DMF and 3×5 mL 1% DIPEA in DCM to give resin 6D.

Step 4: Resin 6D (200 mg) was treated with 4 mL of 20% piperidine in DMF for 20 min, washed with 2×5 mL DMF and treated with another 4 mL of 20% piperidine in DMF. The resin was then washed with 3×5 mL DMF, 3×5 mL 1% DIPEA in DCM and 2×5 mL NMP. To the resulting resin, (R)-2-(((9H-fluoren-9-yl)methoxy)carbonylamino)-4-phenylbutanoic acid (140 mg, 0.348 mmol), HATU (132 mg, 0.348 mmol) and DIPEA (0.121 mL, 0.696 mmol) in 1 mL of NMP were added. The mixture was agitated at room temperature for 1 hour. The resin was filtered and washed with 3×5 mL DMF and 3×5 mL 1% DIPEA in DCM to yield resin 6E.

Step 5: Resin 6E was treated with 4 mL of 20% piperidine in DMF for 20 min, washed with 2×5 mL DMF and treated with another 4 mL of 20% piperidine in DMF. The resin was then washed with 3×5 mL DMF, and 3×5 mL 1% DIPEA in DCM. The resin was treated with 5 mL of 2% TFA in DCM for 15 min and then collected by filtration. The cleaving reaction was repeated once. The filtrates were combined and evaporated to give 96 mg of 4-(4-((S)-2-((R)-2-((S)-2-((R)-2-amino-4-phenylbutanamido)-3-(biphenyl-4-yl)propanamido)-3-phenylpropanamido)-3-methoxy-3-oxopropyl)phenylamino)-4-oxobutanoic acid (6F). The crude product 6F was used directly in step 6.

Step 6: 4-(4-((S)-2-((R)-2-((S)-2-((R)-2-amino-4-phenylbutanamido)-3-(biphenyl-4-yl)propanamido)-3-phenylpropanamido)-3-methoxy-3-oxopropyl)phenylamino)-4-oxobutanoic acid (96 mg, 0.116 mmol), HATU (88 mg, 0.232 mmol) and HOAt (31.6 mg, 0.232 mmol) were dissolved in anhydrous DMF (38.7 mL). DIPEA (0.101 mL, 0.581 mmol) was then added to the stirring solution. The mixture was stirred at room temperature for 20 min and progress was monitored by LC/MS. The solvents were evaporated to give 94 mg of crude 6G as a brown solid.

Step 7: 6G (94 mg, 0.116 mmol) was dissolved in 1.6 mL of THF. Lithium hydroxide (27.9 mg, 1.163 mmol) in 0.4 mL of H$_2$O was then added. The reaction mixture was stirred at room temperature for 2 hours. The solution was then neutralized with aqueous HCl. The solvents were evaporated, and the crude product was purified by preparative HPLC to give Compound 117 as a white solid (14 mg, 15% yield).

Compound 118

Compound 118 was prepared according to the procedures used in the synthesis of Compound 117, except that (R)-2-(((9H-fluoren-9-yl)methoxy)carbonylamino)-3-(4-(trifluoromethyl)phenyl)propanoic acid was used as starting material at step 4.

Compound 119

Compound 119 was prepared according to the procedures used in the synthesis of Compound 117, except that 2-((((9H-fluoren-9-yl)methoxy)carbonyl)(benzyl)amino)acetic acid was used as starting material at step 4.

Compound 120

Compound 120 was prepared according to the procedures used in the synthesis of Compound 117, except that (R)-2-(((9H-fluoren-9-yl)methoxy)carbonylamino)-2-phenylacetic acid was used as starting material at step 4.

Compound 121

Compound 121 was prepared according to the procedures used in the synthesis of Compound 117, except that (R)-2-(((9H-fluoren-9-yl)methoxy)carbonylamino)-3-(4-hydroxyphenyl)propanoic acid was used as starting material at step 4.

Compound 122

Compound 122 was prepared according to the procedures used in the synthesis of Compound 117, except that (R)-2-(((9H-fluoren-9-yl)methoxy)carbonylamino)-3-(thiophen-3-yl)propanoic acid was used as starting material at step 4.

Compound 123

Compound 123 was prepared according to the procedures used in the synthesis of Compound 117, except that (R)-2-(((9H-fluoren-9-yl)methoxy)carbonylamino)-3-(furan-2-yl)propanoic acid was used as starting material at step 4.

Compound 124

Compound 124 was prepared according to the procedures used in the synthesis of Compound 117, except that (R)-2-(((9H-fluoren-9-yl)methoxy)carbonylamino)-3-cyclohexyl-propanoic acid was used as starting material at step 4.

Compound 125

Compound 125 was prepared according to the procedures used in the synthesis of Compound 117, except that (R)-2-(((9H-fluoren-9-yl)methoxy)carbonylamino)-3-(1H-indol-3-yl)propanoic acid was used as starting material at step 4.

Compound 126

Compound 126 was prepared according to the procedures used in the synthesis of Compound 117, except that (R)-2-(((9H-fluoren-9-yl)methoxy)carbonylamino)-3-(pyridin-3-yl)propanoic acid was used as starting material at step 4.

Compound 127

Compound 127 was prepared according to the procedures used in the synthesis of Compound 117, except that (R)-2-(((9H-fluoren-9-yl)methoxy)carbonylamino)-3-(pyridin-4-yl)propanoic acid was used as starting material at step 4.

Compound 128

Compound 128 was prepared according to the procedures used in the synthesis of Compound 117, except that (R)-2-(((9H-fluoren-9-yl)methoxy)carbonylamino)-3-phenylpropanoic acid was used as starting material at step 4.

Compound 129

Compound 129 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(2-cyanophenyl)propanoic acid was used as starting material at step 4.

Compound 130

Compound 130 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(3-cyanophenyl)propanoic acid was used as starting material at step 4.

Compound 131

Compound 131 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(4-cyanophenyl)propanoic acid was used as starting material at step 4.

Compound 132

Compound 132 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(2-chlorophenyl)propanoic acid was used as starting material at step 4.

Compound 133

Compound 133 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(3-chlorophenyl)propanoic acid was used as starting material at step 4.

Compound 134

Compound 134 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(4-fluorophenyl)propanoic acid was used as starting material at step 4.

Compound 135

Compound 135 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(3,4-difluorophenyl)propanoic acid was used as starting material at step 4.

Compound 136

Compound 136 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-5-phenylpentanoic acid was used as starting material at step 4.

Compound 137

Compound 137 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(benzyloxy)propanoic acid was used as starting material at step 4.

Compound 138

Compound 138 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(3-methoxyphenyl)propanoic acid was used as starting material at step 4.

Compound 139

Compound 139 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-o-tolylpropanoic acid was used as starting material at step 4.

Compound 140

Compound 140 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3,3-diphenylpropanoic acid was used as starting material at step 4.

Compound 141

Compound 141 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-5-(3-(2,2,4,6,7-pentamethyl-2,3- dihydrobenzofuran-5-ylsulfonyl)guanidino)pentanoic acid was used as starting material at step 4.

Compound 142

Compound 142 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(naphthalen-1-yl)propanoic acid was used as starting material at step 4.

Compound 143

Compound 143 was prepared according to the procedures used in the synthesis of Compound 117, except that (S)-2-(((9H-fluoren-9-yl)methoxy)carbonylamino)-3-(4-(trifluoromethyl)phenyl)propanoic acid was used as starting material at step 3 and (R)-2-(((9H-fluoren-9-yl)methoxy)carbonylamino)-3-(naphthalen-2-yl)propanoic acid was used as starting material at step 4.

Compound 144

Compound 144 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-4-phenylbutanoic acid was used as starting material at step 4.

Compound 145

Compound 145 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(thiophen-2-yl)propanoic acid was used as starting material at step 4.

Compound 146

Compound 146 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(4-(trifluoromethyl)phenyl)propanoic acid was used as starting material at step 3, and (R)-2-(((9H-fluoren-9-yl)methoxy)carbonylamino)-3-(4-(trifluoromethyl)phenyl)propanoic acid was used as starting material at step 4.

Compound 147

Compound 147 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(2,4-dichlorophenyl)propanoic acid was used as starting material at step 3, and (R)-2-(((9H-fluoren-9-yl)methoxy)carbonylamino)-3-(thiophen-2-yl)propanoic acid was used as starting material at step 4.

Compound 148

Compound 148 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(2,4-dichlorophenyl)propanoic acid was used as starting material at step 3, and (R)-2-(((9H-fluoren-9-yl)methoxy)carbonylamino)-3-(4-(trifluoromethyl)phenyl)propanoic acid was used as starting material at step 4.

Compound 149

Compound 149 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(2,4-dichlorophenyl)propanoic acid was used as starting material at step 3, and (R)-2-(((9H-fluoren-9-yl)methoxy)carbonylamino)-4-phenylbutanoic acid was used as starting material at step 4.

Compound 150

Compound 150 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(4-(trifluoromethyl)phenyl)propanoic acid was used as starting material at step 4.

Compound 151

Compound 151 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(4-(trifluoromethyl)phenyl)propanoic acid was used as starting material at step 3, and (R)-2-(((9H-fluoren-9-yl)methoxy)carbonylamino)-4-phenylbutanoic acid was used as starting material at step 4.

Compound 152

Compound 152 was prepared according to the procedures used in the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(4-(trifluoromethyl)phenyl)propanoic acid was used as starting material at step 3, and (R)-2-(((9H-fluoren-9-yl)methoxy)carbonylamino)-3-(thiophen-2-yl)propanoic acid was used as starting material at step 4.

Compound 506

Compound 506 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(pyridin-4-yl)propanoic acid was used as starting material at step 4.

Compound 507

Compound 507 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and 2-(((9H-fluoren-9-yl)methoxy)carbonylamino)-2-phenylacetic acid was used as starting material at step 4.

Compound 508

Compound 508 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-6-acetamidohexanoic acid was used as starting material at step 4.

Compound 509

Compound 509 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-5-phenylpentanoic acid was used as starting material at step 4.

Compound 510

Compound 510 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(biphenyl-4-yl)propanoic acid was used as starting material at step 4.

Compound 511

Compound 511 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-phenylpropanoic acid was used as starting material at step 4.

Compound 512

Compound 512 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-nitrophenyl)propanoic acid was used as starting material at step 4.

Compound 513

Compound 513 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-4-phenylbutanoic acid was used as starting material at step 4.

Compound 514

Compound 514 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-tert-butoxyphenyl)propanoic acid was used as starting material at step 4.

Compound 515

Compound 515 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, and (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-tert-butylphenyl)propanoic acid was used as starting material at step 4.

Compound 517

Compound 517 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, and (S)-2-(((9H-fluoren-9-yl)methoxy)carbonylamino)-3-(biphenyl-4-yl)propanoic acid was used as starting material at step 3, and 2-(((9H-fluoren-9-yl)methoxy)carbonylamino)-2-(4-bromophenyl)acetic acid was used as starting material at step 4.

Compound 518

Compound 518 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, and (S)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-(pyridin-4-yl)phenyl)propanoic acid was used as starting material at step 4.

Compound 519

Compound 519 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, and (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(4-fluorophenyl)propanoic acid was used as starting material at step 4.

Compound 520

Compound 520 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, and (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(3-(trifluoromethyl)phenyl)propanoic acid was used as starting material at step 4.

Compound 521

Compound 521 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, and (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(4-hydroxyphenyl)propanoic acid was used as starting material at step 4.

Compound 522

Compound 522 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, and (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(4-methoxyphenyl)propanoic acid was used as starting material at step 4.

Compound 523

Compound 523 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, and (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(pyridin-4-yl)propanoic acid was used as starting material at step 4.

Compound 524

Compound 524 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, and (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(3,4-difluorophenyl)propanoic acid was used as starting material at step 4.

Compound 673

Compound 673 was prepared according to the procedures used for the synthesis of Compound 117, except that (R)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(thiophen-2-yl)propanoic acid was used as starting material at step 4.

Compound 674

Compound 674 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(thiophen-2-yl)propanoic acid was used as starting material at step 4.

Compound 675

Compound 675 was prepared according to the procedures used for the synthesis of Compound 117, except that (R)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-3-phenylpropanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(thiophen-2-yl)propanoic acid was used as starting material at step 4.

Compound 676

Compound 676 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(thiophen-2-yl)propanoic acid was used as starting material at step 4.

Compound 677

Compound 677 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(2-fluorophenyl)propanoic acid was used as starting material at step 4.

Compound 678

Compound 678 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(3-fluorophenyl)propanoic acid was used as starting material at step 4.

Compound 679

Compound 679 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-fluorophenyl)propanoic acid was used as starting material at step 4.

Compound 680

Compound 680 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(3-methoxyphenyl)propanoic acid was used as starting material at step 4.

Compound 681

Compound 681 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-methoxyphenyl)propanoic acid was used as starting material at step 4.

Compound 682

Compound 682 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (R)-2-(tert-butoxycarbonylamino)-3-(4-(pyridin-2-yl)phenyl)propanoic acid was used as starting material at step 4.

Compound 683

Compound 683 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (R)-2-(tert-butoxycarbonylamino)-3-(4-(pyridin-3-yl)phenyl)propanoic acid was used as starting material at step 4.

Compound 684

Compound 684 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (R)-2-(tert-butoxycarbonylamino)-3-(4-(pyridin-4-yl)phenyl)propanoic acid was used as starting material at step 4.

Compound 685

Compound 685 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-(benzyloxy)phenyl)propanoic acid was used as starting material at step 4.

Compound 686

Compound 686 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-tert-butoxyphenyl)propanoic acid was used as starting material at step 4.

Compound 687

Compound 687 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(furan-2-yl)propanoic acid was used as starting material at step 4.

Compound 688

Compound 688 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting mate- Compound 689

Compound 689 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(2-(trifluoromethyl)phenyl)propanoic acid was used as starting material at step 4.

Compound 690

Compound 690 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(3-(trifluoromethyl)phenyl)propanoic acid was used as starting material at step 4.

Compound 691

Compound 691 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-(trifluoromethyl)phenyl)propanoic acid was used as starting material at step 4.

Compound 692

Compound 692 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-p-tolylpropanoic acid was used as starting material at step 4.

Compound 693

Compound 693 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(1-phenyl-1H-1,2,3-triazol-4-yl)propanoic acid was used as starting material at step 4.

Compound 694

Compound 694 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(naphthalen-1-yl)propanoic acid was used as starting material at step 4.

Compound 695

Compound 695 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(naphthalen-2-yl)propanoic acid was used as starting material at step 4.

Compound 696

Compound 696 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(thiazol-4-yl)propanoic acid was used as starting material at step 4.

Compound 697

Compound 697 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(2,4-dichlorophenyl)propanoic acid was used as starting material at step 4.

Compound 698

Compound 698 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(tert-butoxycarbonylamino)-3-(4'-fluorobiphenyl-4-yl)propanoic acid was used as starting material at step 4.

Compound 699

Compound 699 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-((((9H-fluoren-9-yl)methoxy)carbonyl)(methyl)amino)-3-phenylpropanoic acid was used as starting material at step 4.

Compound 700

Compound 700 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(tert-butoxycarbonylamino)-3-(3',5'-difluorobiphenyl-4-yl)propanoic acid was used as starting material at step 4.

Compound 701

Compound 701 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-methylbutanoic acid was used as starting material at step 4.

Compound 702

Compound 702 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(tert-butoxycarbonylamino)-3-(4'-chlorobiphenyl-4-yl)propanoic acid was used as starting material at step 4.

Compound 703

Compound 703 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-4-(methylsulfonyl)butanoic acid was used as starting material at step 4.

Compound 704

Compound 704 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-(thiophen-2-yl)phenyl)propanoic acid was used as starting material at step 4.

Compound 705

Compound 705 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(1H-indol-3-yl)propanoic acid was used as starting material at step 4.

Compound 706

Compound 706 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(1-methyl-1H-imidazol-4-yl)propanoic acid was used as starting material at step 4.

Compound 707

Compound 707 was prepared according to the procedures used for the synthesis of Compound 117, except that (S)-2-(4-(2-(((9H-fluoren-9-yl)methoxy)carbonylamino)-3-methoxy-3-oxopropyl)phenoxy)acetic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(4-chlorophenyl)propanoic acid was used as starting material at step 4.

Example 5

This example describes the synthesis and characterization of additional macrocyclic compounds. A general synthetic sequence for preparing the macrocyclic compounds is illustrated schematically below. The synthetic sequence involves attaching a substituted succinate to a solid support.

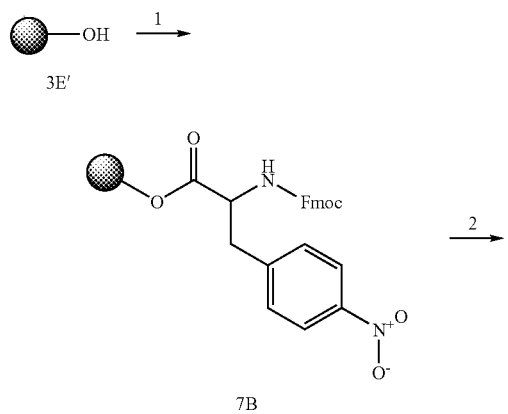

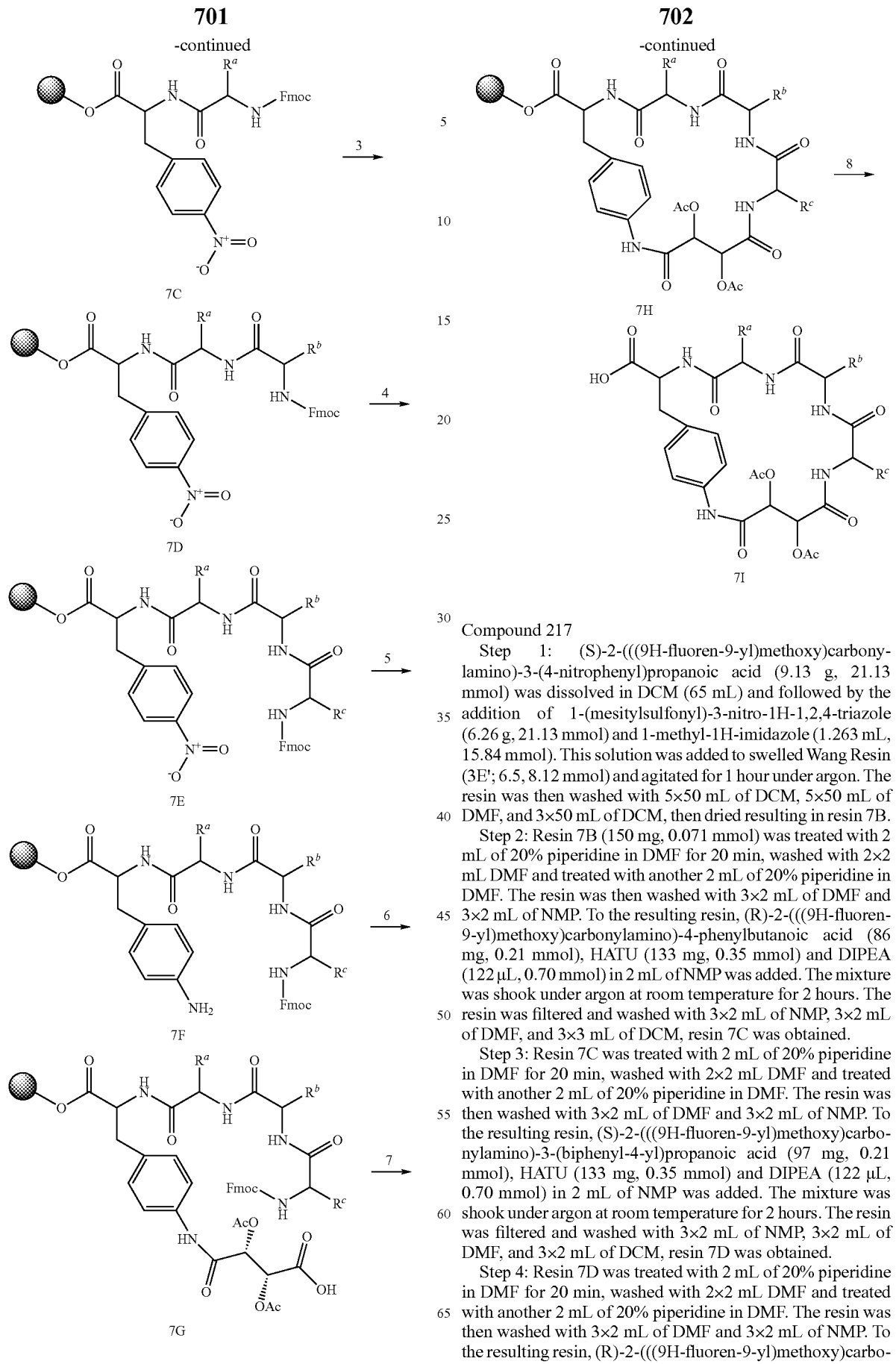

Compound 217

Step 1: (S)-2-(((9H-fluoren-9-yl)methoxy)carbonylamino)-3-(4-nitrophenyl)propanoic acid (9.13 g, 21.13 mmol) was dissolved in DCM (65 mL) and followed by the addition of 1-(mesitylsulfonyl)-3-nitro-1H-1,2,4-triazole (6.26 g, 21.13 mmol) and 1-methyl-1H-imidazole (1.263 mL, 15.84 mmol). This solution was added to swelled Wang Resin (3E'; 6.5, 8.12 mmol) and agitated for 1 hour under argon. The resin was then washed with 5×50 mL of DCM, 5×50 mL of DMF, and 3×50 mL of DCM, then dried resulting in resin 7B.

Step 2: Resin 7B (150 mg, 0.071 mmol) was treated with 2 mL of 20% piperidine in DMF for 20 min, washed with 2×2 mL DMF and treated with another 2 mL of 20% piperidine in DMF. The resin was then washed with 3×2 mL of DMF and 3×2 mL of NMP. To the resulting resin, (R)-2-(((9H-fluoren-9-yl)methoxy)carbonylamino)-4-phenylbutanoic acid (86 mg, 0.21 mmol), HATU (133 mg, 0.35 mmol) and DIPEA (122 µL, 0.70 mmol) in 2 mL of NMP was added. The mixture was shook under argon at room temperature for 2 hours. The resin was filtered and washed with 3×2 mL of NMP, 3×2 mL of DMF, and 3×3 mL of DCM, resin 7C was obtained.

Step 3: Resin 7C was treated with 2 mL of 20% piperidine in DMF for 20 min, washed with 2×2 mL DMF and treated with another 2 mL of 20% piperidine in DMF. The resin was then washed with 3×2 mL of DMF and 3×2 mL of NMP. To the resulting resin, (S)-2-(((9H-fluoren-9-yl)methoxy)carbonylamino)-3-(biphenyl-4-yl)propanoic acid (97 mg, 0.21 mmol), HATU (133 mg, 0.35 mmol) and DIPEA (122 µL, 0.70 mmol) in 2 mL of NMP was added. The mixture was shook under argon at room temperature for 2 hours. The resin was filtered and washed with 3×2 mL of NMP, 3×2 mL of DMF, and 3×2 mL of DCM, resin 7D was obtained.

Step 4: Resin 7D was treated with 2 mL of 20% piperidine in DMF for 20 min, washed with 2×2 mL DMF and treated with another 2 mL of 20% piperidine in DMF. The resin was then washed with 3×2 mL of DMF and 3×2 mL of NMP. To the resulting resin, (R)-2-(((9H-fluoren-9-yl)methoxy)carbonylamino)-3-(thiophen-2-yl)propanoic acid (83 mg, 0.21 mmol), HATU (133 mg, 0.35 mmol) and DIPEA (122 µL, 0.70 mmol) in 2 mL of NMP was added. The mixture was shook under argon at room temperature for 2 hours. The resin was filtered and washed with 3×2 mL of NMP, 3×2 mL of DMF, and 3×2 mL of DCM, resin 7E was obtained.

Step 5: Resin 7E was treated with a 0.7M Tin Chloride solution in DMF (2 mL, 1.4 mmol) and the mixture was shook under argon at room temperature for 16 hours. The resin was filtered and washed with 3×2 mL of DMF, and 3×2 mL of DCM, resin 7F was obtained.

Step 6: Resin 7F was treated with a 0.5M (3R,4R)-2,5-dioxotetrahydrofuran-3,4-diyl diacetate (3 mL, 1.5 mmol) and the mixture was shook under argon at room temperature for 4 hours. The resin was filtered and washed with 3×2 mL DCM, 3×2 mL of DMF, and 3×2 mL of DCM, resin 7G was obtained.

Resin 7G was treated with 2 mL of 2% piperidine, 2% DBU in DMF for 20 min, washed with 2×2 mL DMF and treated with another 2 mL of 2% piperidine, 2% DBU in DMF for 20 min. The resin was then washed with 5×2 mL of DMF and 5×2 mL of DCM and dried thoroughly. Perfluorophenyl diphenylphosphinate (81 mg, 0.21 mmol) and DIPEA (73 µL, 0.42 mmol) was dissolved in DMF (20 mL) and this was added to the resin and shook under argon at room temperature for 16 hours. The resin was filtered and washed with 3×2 mL of DMF, and 3×2 mL of DCM, resin 7H was obtained.

Resin 7H was swelled in DCM (1.8 mL) followed by the addition of triisopropyl silane (0.2 mL), and this mixture was rocked for 10 minutes. TFA (2 mL) was added and the solution was rocked for 2 hrs. The resin was filtered collecting the solution. The resin was then washed with a 50% TFA in DCM solution (4 mL×3), combining washes. Evaporation of volatiles left a crude oil which was purified by was purified by preparative HPLC to give Compound 217 (7I) as a white solid (4.5 mg, 7% overall).

Compound 153

Compound 153 was prepared according to the procedures used for the synthesis of Compound 217, except that (R)-2-(((9H-fluoren-9-yl)methoxy)carbonylamino)-3-(furan-2-yl)propanoic acid was used as starting material at step 2, (S)-2-(((9H-fluoren-9-yl)methoxy)carbonylamino)-3-(4-bromophenyl)propanoic acid was used as starting material at step 3, (R)-2-(((9H-fluoren-9-yl)methoxy)carbonylamino)-3-phenylpropanoic acid was used as starting material at step 4, and maleic anhydride was used as starting material at step 6.

Compound 154

Compound 154 was prepared according to the procedures used for the synthesis of Compound 217, except that (R)-2-(((9H-fluoren-9-yl)methoxy)carbonylamino)-3-(furan-2-yl)propanoic acid was used as starting material at step 2, (S)-2-(((9H-fluoren-9-yl)methoxy)carbonylamino)-3-(4-bromophenyl)propanoic acid was used as starting material at step 3, and (R)-2-(((9H-fluoren-9-yl)methoxy)carbonylamino)-3-(thiophen-2-yl)propanoic acid was used as starting material at step 4.

Compound 159

Compound 159 was prepared according to the procedures used for the synthesis of Compound 217, except that (R)-2-(((9H-fluoren-9-yl)methoxy)carbonylamino)-3-(furan-2-yl)propanoic acid was used as starting material at step 2, (S)-2-(((9H-fluoren-9-yl)methoxy)carbonylamino)-3-(4-bromophenyl)propanoic acid was used as starting material at step 3, (R)-2-(((9H-fluoren-9-yl)methoxy)carbonylamino)-3-(thiophen-2-yl)propanoic acid was used as starting material at step 4, and maleic anhydride was used as starting material at step 6.

Compound 160

Compound 160 was prepared according to the procedures used for the synthesis of Compound 217, except that (R)-2-(((9H-fluoren-9-yl)methoxy)carbonylamino)-3-(furan-2-yl)propanoic acid was used as starting material at step 2, (S)-2-(((9H-fluoren-9-yl)methoxy)carbonylamino)-3-(4-bromophenyl)propanoic acid was used as starting material at step 3, and (R)-2-(((9H-fluoren-9-yl)methoxy)carbonylamino)-3-phenylpropanoic acid was used as starting material at step 4.

Compound 196

Compound 196 was prepared according to the procedures used for the synthesis of Compound 217, except that (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(biphenyl-4-yl)propanoic acid was used as starting material at step 3, (R)-2-(((9H-fluoren-9-yl)methoxy)carbonylamino)-3-(thiophen-2-yl)propanoic acid was used as starting material at step 4, and maleic anhydride was used as starting material at step 6.

Compound 218

Compound 218 was prepared according to the procedures used for the synthesis of Compound 217, except that (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(4-bromophenyl)propanoic acid was used as starting material at step 3, and (R)-2-(((9H-fluoren-9-yl)methoxy)carbonylamino)-3-phenylpropanoic acid was used as starting material at step 4.

Compound 219

Compound 219 was prepared according to the procedures used for the synthesis of Compound 217, except that (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(4-bromophenyl)propanoic acid was used as starting material at step 3, and (R)-2-(((9H-fluoren-9-yl)methoxy)carbonylamino)-3-(thiophen-2-yl)propanoic acid was used as starting material at step 4.

Compound 220

Compound 220 was prepared according to the procedures used for the synthesis of Compound 217, except that (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(2,4-dichlorophenyl)propanoic acid was used as starting material at step 3, and (R)-2-(((9H-fluoren-9-yl)methoxy)carbonylamino)-3-phenylpropanoic acid was used as starting material at step 4.

Compound 221

Compound 221 was prepared according to the procedures used for the synthesis of Compound 217, except that (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(2,4-dichlorophenyl)propanoic acid was used as starting material at step 3, and (R)-2-(((9H-fluoren-9-yl)methoxy)carbonylamino)-3-(thiophen-2-yl)propanoic acid was used as starting material at step 4.

Compound 222

Compound 222 was prepared according to the procedures used for the synthesis of Compound 217, except that (R)-2-

(((9H-fluoren-9-yl)methoxy)carbonylamino)-3-phenylpropanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-phenylpropanoic acid was used as starting material at step 4.

Compound 223

Compound 223 was prepared according to the procedures used for the synthesis of Compound 217, except that (S)-2-(((9H-fluoren-9-yl)methoxy)carbonylamino)-3-(4-nitrophenyl)propanoic acid was used as starting material at step 1, (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(thiophen-2-yl)propanoic acid was used as starting material at step 4.

Compound 231

Compound 231 was prepared according to the procedures used for the synthesis of Compound 217, except that (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(4-bromophenyl)propanoic acid was used as starting material at step 3, and (R)-2-(((9H-fluoren-9-yl)methoxy)carbonylamino)-3-phenylpropanoic acid was used as starting material at step 4.

Compound 232

Compound 232 was prepared according to the procedures used for the synthesis of Compound 217, except that (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(4-bromophenyl)propanoic acid was used as starting material at step 3, and (R)-2-(((9H-fluoren-9-yl)methoxy)carbonylamino)-3-(thiophen-2-yl)propanoic acid was used as starting material at step 4.

Compound 233

Compound 233 was prepared according to the procedures used for the synthesis of Compound 217, except that (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(2,4-dichlorophenyl)propanoic acid was used as starting material at step 3, and (R)-2-(((9H-fluoren-9-yl)methoxy)carbonylamino)-3-phenylpropanoic acid was used as starting material at step 4.

Compound 234

Compound 234 was prepared according to the procedures used for the synthesis of Compound 217, except that (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(2,4-dichlorophenyl)propanoic acid was used as starting material at step 3, and (R)-2-(((9H-fluoren-9-yl)methoxy)carbonylamino)-3-(thiophen-2-yl)propanoic acid was used as starting material at step 4.

Compound 235

Compound 235 was prepared according to the procedures used for the synthesis of Compound 217, except that (S)-2-(((9H-fluoren-9-yl)methoxy)carbonylamino)-3-(4-nitrophenyl)propanoic acid was used as starting material at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-phenylpropanoic acid was used as starting material at step 4.

Compound 394

Compound 394 was prepared according to the procedures used for the synthesis of Compound 217, except that Fmoc PheWang Resin (Polymer Laboratories, a division of Varian, Inc., Palo Alto, Calif.; Cat #PL3463-47995) was used as starting resin at step 1, (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(thiophen-2-yl)propanoic acid was used as starting material at step 4.

Compound 409

Compound 409 was prepared according to the procedures used for the synthesis of Compound 217, except that Wang resin preloaded with L-phenylalanine was used as starting resin at step 1, (R)-2-(((9H-fluoren-9-yl)methoxy)carbonylamino)-4-phenylbutanoic acid was used as starting material at step 2, (S)-2-(((9H-fluoren-9-yl)methoxy)carbonylamino)-3-(biphenyl-4-yl)propanoic acid was used as starting material at step 3, and (R)-2-(((9H-fluoren-9-yl)methoxy)carbonylamino)-3-(thiophen-2-yl)propanoic acid was used as starting material at step 4.

Compound 410

Compound 410 was prepared according to the procedures used for the synthesis of Compound 217, except that Wang resin preloaded with L-phenylalanine was used as starting resin at step 1, (R)-2-(((9H-fluoren-9-yl)methoxy)carbonylamino)-3-phenylpropanoic acid was used as starting material at step 2, (S)-2-(((9H-fluoren-9-yl)methoxy)carbonylamino)-3-(4-bromophenyl)propanoic acid was used as starting material at step 3, and (R)-2-(((9H-fluoren-9-yl)methoxy)carbonylamino)-3-(thiophen-2-yl)propanoic acid was used as starting material at step 4.

Compound 411

Compound 411 was prepared according to the procedures used for the synthesis of Compound 217, except that Wang resin preloaded with L-phenylalanine was used as starting resin at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(thiophen-2-yl)propanoic acid was used as starting material at step 4.

Compound 412

Compound 412 was prepared according to the procedures used for the synthesis of Compound 217, except that Wang resin preloaded with L-phenylalanine was used as starting resin and (S)-2-(((9H-fluoren-9-yl)methoxy)carbonylamino)-3-(4-nitrophenyl)propanoic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(thiophen-2-yl)propanoic acid was used as starting material at step 4.

Compound 413

Compound 413 was prepared according to the procedures used for the synthesis of Compound 217, except that Wang resin preloaded with L-phenylalanine was used as starting resin at step 1, (S)-2-(((9H-fluoren-9-yl)methoxy)carbonylamino)-3-phenylpropanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(thiophen-2-yl)propanoic acid was used as starting material at step 4.

Compound 414

Compound 414 was prepared according to the procedures used for the synthesis of Compound 217, except that Wang resin preloaded with L-phenylalanine was used as starting resin and (S)-2-(((9H-fluoren-9-yl)methoxy)carbonylamino)-3-(4-nitrophenyl)propanoic acid was used as starting material at step 1, (S)-2-(((9H-fluoren-9-yl)methoxy)carbonylamino)-3-phenylpropanoic acid was used as starting material at step 2, (R)-2-(((9H-fluoren-9-yl)methoxy)carbonylamino)-3-(biphenyl-4-yl)propanoic acid was used as starting material at step 3, and (S)-2-(((9H-fluoren-9-yl)methoxy)carbonylamino)-3-(thiophen-2-yl)propanoic acid was used as starting material at step 4.

Compound 415

Compound 415 was prepared according to the procedures used for the synthesis of Compound 217, except that Wang resin preloaded with L-phenylalanine was used as starting resin at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(4-bromophenyl)propanoic acid was used as starting material at step 3, and (S)-2-(((9H-fluoren-9-yl)methoxy)carbonylamino)-3-(thiophen-2-yl)propanoic acid was used as starting material at step 4.

Compound 416

Compound 416 was prepared according to the procedures used for the synthesis of Compound 217, except that Wang resin preloaded with L-phenylalanine was used as starting resin and (S)-2-(((9H-fluoren-9-yl)methoxy)carbonylamino)-3-(4-nitrophenyl)propanoic acid was used as starting material at step 1, (S)-2-(((9H-fluoren-9-yl)methoxy)carbonylamino)-4-phenylbutanoic acid was used as starting material at step 2, (R)-2-(((9H-fluoren-9-yl)methoxy)carbonylamino)-3-(4-bromophenyl)propanoic acid was used as starting material at step 3, and (S)-2-(((9H-fluoren-9-yl)methoxy)carbonylamino)-3-(thiophen-2-yl)propanoic acid was used as starting material at step 4.

Compound 417

Compound 417 was prepared according to the procedures used for the synthesis of Compound 217, except that Wang resin preloaded with L-phenylalanine was used as starting resin at step 1, (S)-2-(((9H-fluoren-9-yl)methoxy)carbonylamino)-3-phenylpropanoic acid was used as starting material at step 2, (R)-2-(((9H-fluoren-9-yl)methoxy)carbonylamino)-3-(4-bromophenyl)propanoic acid was used as starting material at step 3, and (S)-2-(((9H-fluoren-9-yl)methoxy)carbonylamino)-3-(thiophen-2-yl)propanoic acid was used as starting material at step 4.

Compound 418

Compound 418 was prepared according to the procedures used for the synthesis of Compound 217, except that Wang resin preloaded with L-phenylalanine was used as starting resin and (S)-2-(((9H-fluoren-9-yl)methoxy)carbonylamino)-3-(4-nitrophenyl)propanoic acid was used as starting material at step 1, (S)-2-(((9H-fluoren-9-yl)methoxy)carbonylamino)-3-phenylpropanoic acid was used as starting material at step 2, (R)-2-(((9H-fluoren-9-yl)methoxy)carbonylamino)-3-(4-bromophenyl)propanoic acid was used as starting material at step 3, and (S)-2-(((9H-fluoren-9-yl)methoxy)carbonylamino)-3-(thiophen-2-yl)propanoic acid was used as starting material at step 4.

Compound 708

Compound 708 was prepared according to the procedures used for the synthesis of Compound 217, except that 3-oxabicyclo[3.1.0]hexane-2,4-dione was used as starting material at step 6.

Compound 709

Compound 709 was prepared according to the procedures used for the synthesis of Compound 217, except that 3-oxabicyclo[3.2.0]heptane-2,4-dione was used as starting material at step 6.

Compound 710

Compound 710 was prepared according to the procedures used for the synthesis of Compound 217, except that (3aS,7aS)-hexahydroisobenzofuran-1,3-dione was used as starting material at step 6.

Compound 711

Compound 711 was prepared according to the procedures used for the synthesis of Compound 217, except that (S)-2-(((9H-fluoren-9-yl)methoxy)carbonylamino)-4-phenylbutanoic acid was used as starting material at step 5 and 3,3-dimethyldihydrofuran-2,5-dione was used as starting material at step 6.

Example 6

Compounds of formula 711 were coverted into the corresponding diols by dissolving in THF (0.5 mL) followed by the addition of 40% methylamine/water (10 uL, 0.16 mmol). After vortexing for 30 minutes, volatiles were evaporated, and the resulting solid was washed with water (0.2 mL×2), put up in acetonitrile/water and lyophilized.

Compound 236

Compound 217 (1.5 mg, 1.6 µmol) (7I) was dissolved in THF (0.5 mL) followed by the addition of 40% methylamine/water (10 uL, 0.16 mmol). After vortexing for 30 minutes, volatiles were evaporated, and resulting solid was washed with water (0.2 mL×2), put up in acetonitrile/water and lyophilized, leaving Compound 236 as a white powder (0.72 mg, 0.87 µmol, 53%).

Compound 155

Compound 155 was prepared according to the procedures used for the synthesis of Compound 236 except that Compound 154 was used as starting material.

Compound 161

Compound 161 was prepared according to the procedures used for the synthesis of Compound 236 except that Compound 160 was used as starting material.

Compound 237

Compound 237 was prepared according to the procedures used for the synthesis of Compound 236 except that Compound 218 was used as starting material.

Compound 238

Compound 238 was prepared according to the procedures used for the synthesis of Compound 236 except that Compound 219 was used as starting material.

Compound 239

Compound 239 was prepared according to the procedures used for the synthesis of Compound 236 except that Compound 220 was used as starting material.

Compound 240

Compound 240 was prepared according to the procedures used for the synthesis of Compound 236 except that Compound 221 was used as starting material.

Compound 241

Compound 241 was prepared according to the procedures used for the synthesis of Compound 236 except that Compound 222 was used as starting material.

Compound 242
Compound 242 was prepared according to the procedures used for the synthesis of Compound 236 except that Compound 232 was used as starting material.
Compound 243
Compound 243 was prepared according to the procedures used for the synthesis of Compound 236 except that Compound 233 was used as starting material.
Compound 244
Compound 244 was prepared according to the procedures used for the synthesis of Compound 236 except that Compound 234 was used as starting material.
Compound 245
Compound 245 was prepared according to the procedures used for the synthesis of Compound 236 except that Compound 235 was used as starting material.
Compound 429
Compound 429 was prepared according to the procedures used for the synthesis of Compound 236 except that Compound 409 was used as starting material.
Compound 430
Compound 430 was prepared according to the procedures used for the synthesis of Compound 236 except that Compound 394 was used as starting material.
Compound 431
Compound 431 was prepared according to the procedures used for the synthesis of Compound 236 except that Compound 410 was used as starting material.
Compound 432
Compound 432 was prepared according to the procedures used for the synthesis of Compound 236 except that Compound 411 was used as starting material.
Compound 433
Compound 433 was prepared according to the procedures used for the synthesis of Compound 236 except that Compound 412 was used as starting material.
Compound 434
Compound 434 was prepared according to the procedures used for the synthesis of Compound 236 except that Compound 413 was used as starting material.
Compound 435
Compound 435 was prepared according to the procedures used for the synthesis of Compound 236 except that Compound 414 was used as starting material.
Compound 436
Compound 436 was prepared according to the procedures used for the synthesis of Compound 236 except that Compound 415 was used as starting material.
Compound 437
Compound 437 was prepared according to the procedures used for the synthesis of Compound 236 except that Compound 416 was used as starting material.
Compound 438
Compound 438 was prepared according to the procedures used for the synthesis of Compound 236 except that Compound 417 was used as starting material.
Compound 439
Compound 439 was prepared according to the procedures used for the synthesis of Compound 236 except that Compound 418 was used as starting material.

Example 7

This example describes the synthesis and characterization of additional macrocyclic compounds. A general synthetic sequence for preparing the macrocyclic compounds is illustrated schematically below.

Scheme 8.

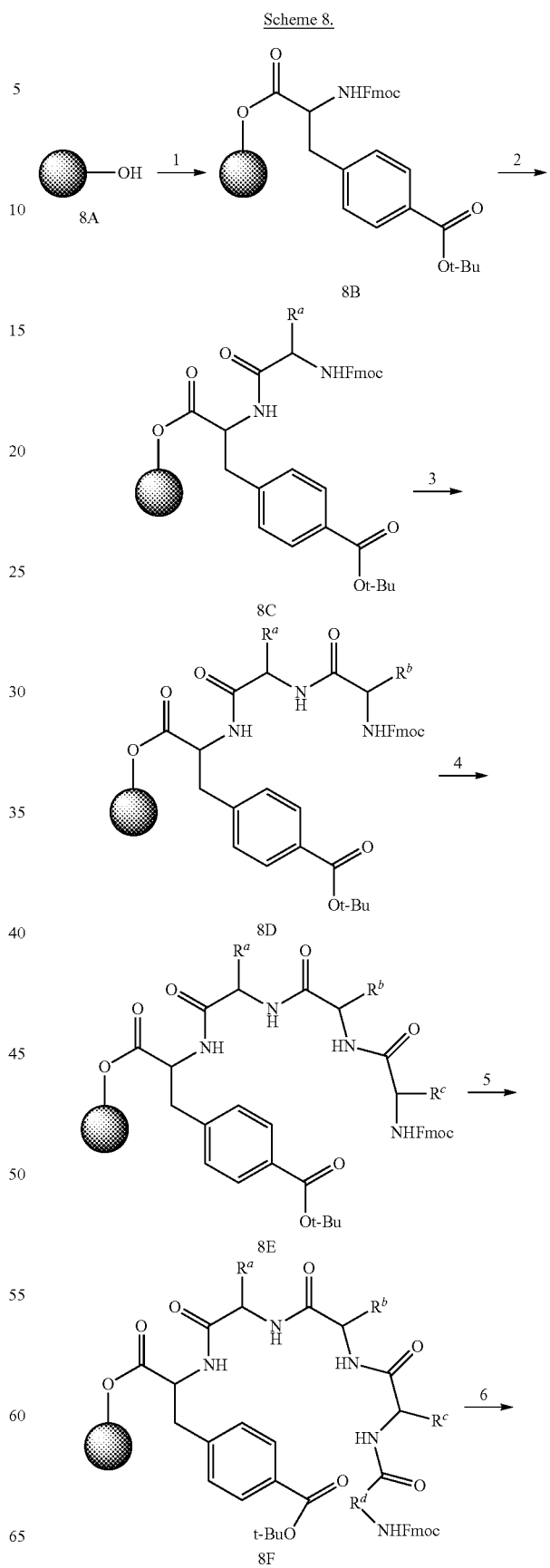

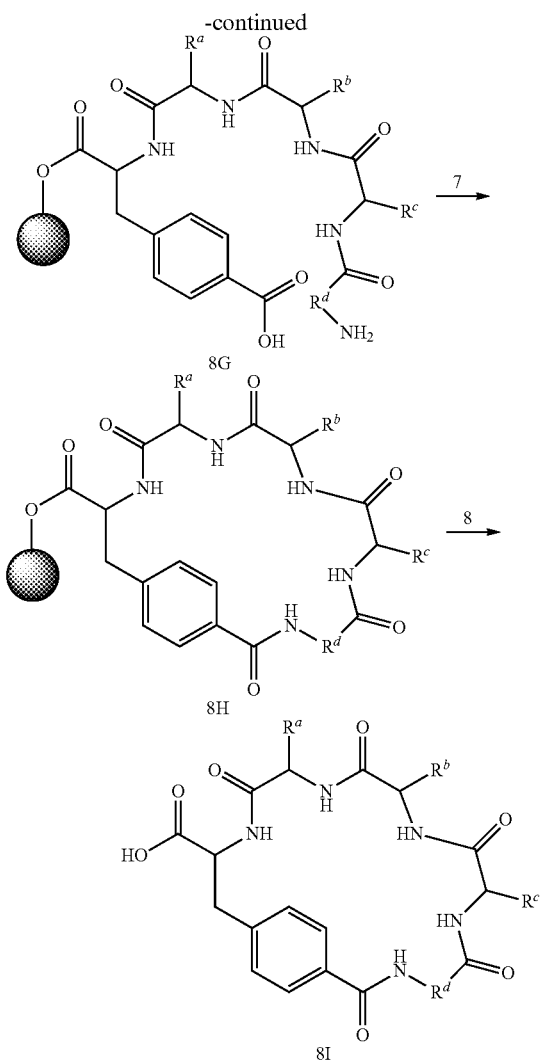

Compound 247

Step 1: HMBA-PEGA Resin, 8A (0.74 mmol, 0.37 mmol/g) was swelled in 20 mL NMP for 30 min, washed with 2×20 mL DMF and 3×20 mL of DCM. A solution of (S)-2-(((9H-fluoren-9-yl)methoxy)carbonylamino)-3-(4-(tert-butoxycarbonylamino)phenyl)propanoic acid (1.08 g, 2.22 mmol),
Compound 713

Compound 713 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 714

Compound 714 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 715

Compound 715 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 716

Compound 716 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 717

Compound 717 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 718

Compound 718 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 719

Compound 719 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 720

Compound 720 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 721

Compound 721 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 722

Compound 722 was prepared according to the procedures used for the synthesis of Compound 712, except that (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 723

Compound 723 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 724

Compound 724 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-4-phenylbutanoic acid was used as starting material at step 4 and (S)-2-(((9H-fluoren-9-yl)methoxy)carbonylamino)-4-phenylbutanoic acid was used as starting material at step 5.

Compound 725

Compound 725 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(biphenyl-4-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-4-phenylbutanoic acid was used as starting material at step 5.

Compound 726

Compound 726 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(biphenyl-4-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(thiophen-2-yl)propanoic acid was used as starting material at step 5.

Compound 727

Compound 727 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 728

Compound 728 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 729

Compound 729 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 730

Compound 730 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 731

Compound 731 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 732

Compound 732 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 733

Compound 733 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 734

Compound 734 was prepared according to the procedures used for the synthesis of Compound 712, except that step 1 was omitted, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 735

Compound 735 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 736

Compound 736 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 737

Compound 737 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 738

Compound 738 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 739

Compound 739 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 740

Compound 740 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 741

Compound 741 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 742

Compound 742 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(2-fluorophenyl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 743

Compound 743 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 744

Compound 744 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 745

Compound 745 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(pyridin-4-yl)propanoic acid was used as starting material at step 5.

Compound 746

Compound 746 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-4-phenylbutanoic acid was used as starting material at step 3, (R)-2-(((9H-fluoren-9-yl)methoxy)carbonylamino)-3-(biphenyl-4-yl)propanoic acid was used as starting material at step 4 and (S)-2-(((9H-fluoren-9-yl)methoxy)carbonylamino)-3-(1H-indol-3-yl)propanoic acid was used as starting material at step 5.

Compound 747

Compound 747 was prepared according to the procedures used for the synthesis of Compound 712, except that was used as starting material at step 1, (S)-2-(4-(2-(((9H-fluoren-9-yl)methoxy)carbonylamino)-3-methoxy-3-oxopropyl)phenoxy)acetic acid was used as starting material at step 2, (S)-2-(((9H-fluoren-9-yl)methoxy)carbonylamino)-3-(1H-indol-3-yl)propanoic acid was used as starting material at step 3, (R)-2-(((9H-fluoren-9-yl)methoxy)carbonylamino)-3-(biphenyl-4-yl)propanoic acid was used as starting material at step 4 and (S)-2-((((9H-fluoren-9-yl)methoxy)carbonyl)(methyl)amino)-3-(1H-indol-3-yl)propanoic acid was used as starting material at step 5.

Example 10

The compounds listed in Table 2 below were assayed for ability to inhibit binding of TNFα to the TNFα receptor (TNFα R1/Fc). The assays were performed as described in the following procedure: TNFα (R&D Systems) was coated on high binding plate wells (Corning 96-well) at a single uniform concentration of 15 nM, 100 µL/well in PBS. The coating proceeded for 30 minutes at 37° C. then 10 minutes at 4° C. The coated plate was washed with PBST, then 250 µL/well of blocking solution (PBST 0.1% BSA, bovine serum albumin) was added and incubation proceeded for 30-45 minutes at room temperature with agitation. The solution phase competition proceeded separately with the dilutions of test compound in PBST (phosphate buffered saline with Tween 20), 2% DMSO in a polypropylene plate (Corning 96-well storage plate) with a single concentration, 8.33 nM of the high affinity receptor for TNFα (R&D Systems). This solution phase incubation proceeded for 30 minutes at room temperature with agitation and was then added to the washed TNFα coated assay plate, 100 µL/well, and was incubated for a further 30 minutes at room temperature with agitation. The assay plate was washed and 100 µL goat anti-human IgG (Fc) HRP labeled antibody in PBST, 13 pM, (KPL Cat#04-10-2) was added to each well. This incubation proceeded for 25-30 minutes at room temperature with agitation. Following this incubation step, the plate was washed and a 100 µL TMB solution (SUREBLUE™ TMB Peroxidase substrate, KPL) was added per well and allowed to stand approximately 3-5 minutes for development. The TMB reaction was stopped with the addition of 0.5N HCl and then the plate was read for absorbance at 450 nm. $IC_{50}$ values are reported as follows: + indicates an $IC_{50}$ value greater than 100 µM or that the compound had no activity at the concentration tested, ++ indicates an $IC_{50}$ value of 30 µM to 100 µM, +++ indicates an $IC_{50}$ value of greater than 10 µM and less than 30 µM, ++++ indicates an $IC_{50}$ value of 10 µM or less.

TABLE 2

| Compound No. | Activity |
| --- | --- |
| 1 | +++ |
| 2 | + |
| 3 | +++ |
| 4 | +++ |
| 5 | ++ |
| 6 | + |
| 7 | + |
| 8 | ++ |
| 9 | +++ |

TABLE 2-continued

| Compound No. | Activity |
|---|---|
| 10 | +++ |
| 11 | ++++ |
| 12 | ++++ |
| 13 | + |
| 14 | ++ |
| 15 | +++ |
| 16 | ++++ |
| 17 | +++ |
| 18 | +++ |
| 19 | +++ |
| 20 | ++++ |
| 21 | ++++ |
| 22 | ++ |
| 23 | + |
| 24 | ++ |
| 25 | ++++ |
| 26 | +++ |
| 27 | + |
| 28 | ++++ |
| 29 | ++++ |
| 30 | +++ |
| 31 | + |
| 32 | + |
| 33 | ++++ |
| 34 | ++++ |
| 35 | +++ |
| 36 | ++++ |
| 37 | + |
| 38 | ++ |
| 39 | ++++ |
| 42 | + |
| 43 | + |
| 44 | + |
| 45 | + |
| 46 | + |
| 47 | ++++ |
| 48 | +++ |
| 49 | + |
| 50 | + |
| 51 | + |
| 52 | + |
| 53 | + |
| 54 | + |
| 55 | + |
| 56 | + |
| 57 | + |
| 58 | + |
| 59 | + |
| 60 | + |
| 61 | + |
| 62 | + |
| 63 | + |
| 64 | + |
| 65 | + |
| 66 | + |
| 67 | ++ |
| 68 | + |
| 69 | + |
| 72 | + |
| 73 | + |
| 74 | ++ |
| 75 | ++ |
| 76 | +++ |
| 77 | ++ |
| 78 | + |
| 79 | + |
| 80 | + |
| 81 | + |
| 82 | +++ |
| 83 | + |
| 84 | + |
| 85 | +++ |
| 86 | + |
| 87 | + |
| 88 | + |
| 89 | +++ |
| 90 | + |
| 91 | + |

TABLE 2-continued

| Compound No. | Activity |
|---|---|
| 92 | ++ |
| 93 | + |
| 94 | + |
| 95 | ++ |
| 96 | + |
| 97 | + |
| 98 | + |
| 99 | + |
| 100 | + |
| 101 | + |
| 102 | + |
| 103 | + |
| 104 | + |
| 105 | ++ |
| 106 | + |
| 107 | + |
| 108 | +++ |
| 109 | +++ |
| 110 | +++ |
| 111 | +++ |
| 112 | ++++ |
| 113 | +++ |
| 114 | + |
| 115 | + |
| 116 | ++++ |
| 117 | ++++ |
| 118 | +++ |
| 119 | ++ |
| 120 | + |
| 121 | + |
| 122 | ++ |
| 123 | ++ |
| 124 | + |
| 125 | + |
| 126 | + |
| 127 | + |
| 128 | ++ |
| 129 | ++ |
| 130 | +++ |
| 131 | ++ |
| 132 | ++ |
| 133 | ++ |
| 134 | + |
| 135 | ++ |
| 136 | ++ |
| 137 | ++ |
| 138 | + |
| 139 | + |
| 140 | + |
| 141 | + |
| 142 | ++ |
| 143 | + |
| 144 | +++ |
| 145 | +++ |
| 146 | +++ |
| 147 | ++ |
| 148 | ++ |
| 149 | +++ |
| 150 | ++ |
| 151 | ++ |
| 152 | + |
| 153 | + |
| 154 | + |
| 155 | + |
| 156 | ++++ |
| 157 | ++++ |
| 158 | ++++ |
| 159 | +++ |
| 160 | ++ |
| 161 | + |
| 162 | + |
| 163 | ++ |
| 164 | ++ |
| 165 | + |
| 166 | ++ |
| 167 | + |
| 168 | ++ |
| 169 | + |

TABLE 2-continued

| Compound No. | Activity |
| --- | --- |
| 170 | ++ |
| 171 | + |
| 172 | ++++ |
| 173 | +++ |
| 174 | ++++ |
| 175 | ++++ |
| 176 | + |
| 177 | ++ |
| 178 | + |
| 179 | ++++ |
| 180 | ++++ |
| 181 | +++ |
| 182 | ++ |
| 183 | +++ |
| 184 | + |
| 185 | + |
| 186 | ++ |
| 187 | + |
| 188 | + |
| 189 | + |
| 190 | +++ |
| 191 | ++++ |
| 192 | ++++ |
| 193 | ++++ |
| 194 | + |
| 195 | + |
| 196 | ++++ |
| 197 | ++++ |
| 198 | ++++ |
| 199 | + |
| 200 | ++ |
| 201 | ++++ |
| 202 | ++++ |
| 203 | + |
| 205 | + |
| 206 | + |
| 208 | + |
| 209 | + |
| 210 | + |
| 211 | ++ |
| 212 | ++++ |
| 213 | + |
| 214 | ++++ |
| 215 | ++ |
| 216 | + |
| 217 | ++++ |
| 218 | +++ |
| 219 | ++++ |
| 220 | +++ |
| 221 | ++ |
| 222 | + |
| 223 | ++ |
| 224 | + |
| 225 | + |
| 226 | +++ |
| 227 | ++++ |
| 228 | ++++ |
| 229 | ++++ |
| 230 | +++ |
| 231 | + |
| 232 | + |
| 233 | ++ |
| 234 | + |
| 235 | +++ |
| 236 | ++++ |
| 237 | ++++ |
| 238 | ++++ |
| 239 | ++++ |
| 240 | +++ |
| 241 | ++ |
| 242 | ++ |
| 243 | ++ |
| 244 | ++ |
| 245 | +++ |
| 246 | ++ |
| 247 | + |
| 248 | ++++ |
| 249 | + |
| 250 | + |
| 251 | + |
| 252 | + |
| 253 | + |
| 254 | +++ |
| 255 | + |
| 256 | + |
| 257 | + |
| 258 | + |
| 259 | ++ |
| 260 | ++ |
| 261 | ++ |
| 262 | +++ |
| 263 | + |
| 264 | + |
| 265 | + |
| 266 | + |
| 267 | + |
| 268 | + |
| 269 | + |
| 270 | + |
| 271 | + |
| 272 | + |
| 273 | + |
| 274 | + |
| 275 | + |
| 276 | + |
| 277 | + |
| 278 | + |
| 279 | + |
| 280 | + |
| 281 | + |
| 282 | ++++ |
| 283 | ++++ |
| 284 | +++ |
| 285 | ++ |
| 286 | +++ |
| 287 | +++ |
| 288 | + |
| 289 | ++++ |
| 290 | ++++ |
| 291 | + |
| 292 | + |
| 293 | + |
| 294 | ++ |
| 295 | +++ |
| 296 | ++ |
| 297 | ++++ |
| 298 | ++++ |
| 299 | ++++ |
| 300 | ++++ |
| 301 | ++++ |
| 302 | ++++ |
| 303 | +++ |
| 304 | +++ |
| 305 | ++++ |
| 306 | ++++ |
| 307 | ++++ |
| 308 | + |
| 309 | +++ |
| 310 | + |
| 311 | ++ |
| 312 | + |
| 313 | ++++ |
| 314 | +++ |
| 315 | +++ |
| 316 | +++ |
| 317 | +++ |
| 318 | ++++ |
| 319 | ++++ |
| 320 | ++++ |
| 321 | ++++ |
| 322 | +++ |
| 323 | ++++ |
| 324 | ++++ |
| 325 | ++++ |
| 326 | ++++ |
| 327 | ++++ |

TABLE 2-continued

| Compound No. | Activity |
|---|---|
| 328 | ++++ |
| 329 | ++++ |
| 330 | ++++ |
| 332 | ++++ |
| 333 | ++ |
| 334 | ++ |
| 335 | +++ |
| 336 | +++ |
| 337 | + |
| 338 | +++ |
| 339 | ++++ |
| 340 | ++++ |
| 341 | ++++ |
| 342 | ++++ |
| 343 | ++++ |
| 344 | ++++ |
| 345 | ++ |
| 346 | ++++ |
| 347 | ++ |
| 348 | ++++ |
| 349 | +++ |
| 350 | ++++ |
| 351 | +++ |
| 352 | + |
| 353 | + |
| 354 | + |
| 355 | + |
| 356 | + |
| 357 | + |
| 358 | + |
| 359 | + |
| 360 | + |
| 361 | + |
| 362 | ++++ |
| 363 | ++++ |
| 364 | ++++ |
| 365 | ++ |
| 366 | ++++ |
| 367 | + |
| 368 | + |
| 369 | +++ |
| 370 | + |
| 371 | + |
| 372 | + |
| 373 | + |
| 374 | + |
| 375 | + |
| 376 | +++ |
| 377 | + |
| 378 | +++ |
| 379 | ++++ |
| 380 | ++++ |
| 381 | ++++ |
| 382 | ++++ |
| 383 | ++++ |
| 384 | ++++ |
| 385 | ++++ |
| 386 | ++++ |
| 387 | + |
| 388 | ++++ |
| 389 | + |
| 390 | ++++ |
| 391 | ++++ |
| 392 | +++ |
| 393 | ++++ |
| 394 | ++++ |
| 395 | ++++ |
| 396 | ++++ |
| 397 | + |
| 398 | ++++ |
| 399 | + |
| 400 | ++++ |
| 401 | ++++ |
| 402 | +++ |
| 403 | + |
| 404 | ++++ |
| 405 | + |
| 406 | + |
| 407 | + |
| 408 | + |
| 409 | ++++ |
| 410 | ++++ |
| 411 | + |
| 412 | ++++ |
| 413 | + |
| 414 | + |
| 415 | + |
| 416 | + |
| 417 | + |
| 418 | + |
| 419 | +++ |
| 420 | + |
| 421 | ++++ |
| 422 | ++++ |
| 423 | ++++ |
| 424 | ++++ |
| 425 | ++ |
| 426 | ++++ |
| 427 | + |
| 428 | ++++ |
| 429 | ++++ |
| 430 | +++ |
| 431 | + |
| 432 | ++++ |
| 433 | + |
| 434 | ++++ |
| 435 | ++++ |
| 436 | ++++ |
| 437 | +++ |
| 438 | ++++ |
| 439 | ++ |
| 440 | +++ |
| 441 | +++ |
| 442 | ++++ |
| 443 | +++ |
| 444 | ++ |
| 445 | +++ |
| 446 | + |
| 447 | + |
| 448 | +++ |
| 449 | + |
| 450 | ++ |
| 451 | ++ |
| 452 | + |
| 453 | + |
| 454 | +++ |
| 455 | + |
| 456 | + |
| 457 | + |
| 458 | + |
| 459 | + |
| 460 | + |
| 461 | + |
| 462 | + |
| 463 | + |
| 464 | ++++ |
| 465 | ++++ |
| 466 | + |
| 467 | + |
| 468 | + |
| 469 | + |
| 470 | ++++ |
| 471 | ++++ |
| 472 | ++++ |
| 473 | ++++ |
| 475 | ++++ |
| 477 | ++++ |
| 478 | ++++ |
| 479 | ++++ |
| 480 | +++ |
| 481 | ++++ |
| 482 | ++++ |
| 483 | + |
| 484 | + |
| 485 | +++ |
| 486 | ++++ |

TABLE 2-continued

| Compound No. | Activity |
|---|---|
| 487 | +++ |
| 488 | + |
| 489 | + |
| 490 | + |
| 491 | + |
| 493 | ++++ |
| 494 | + |
| 495 | + |
| 496 | + |
| 497 | + |
| 498 | + |
| 499 | + |
| 500 | +++ |
| 501 | + |
| 502 | + |
| 503 | + |
| 504 | ++++ |
| 505 | +++ |
| 506 | ++++ |
| 507 | +++ |
| 508 | ++++ |
| 509 | ++++ |
| 510 | ++++ |
| 511 | ++++ |
| 512 | ++++ |
| 513 | ++++ |
| 514 | ++++ |
| 515 | +++ |
| 516 | ++ |
| 517 | +++ |
| 518 | ++++ |
| 519 | +++ |
| 520 | ++++ |
| 521 | + |
| 522 | + |
| 523 | + |
| 524 | +++ |
| 525 | ++++ |
| 526 | + |
| 527 | + |
| 528 | ++++ |
| 529 | + |
| 530 | + |
| 531 | + |
| 532 | + |
| 533 | + |
| 534 | + |
| 535 | + |
| 536 | ++++ |
| 537 | + |
| 538 | + |
| 539 | + |
| 540 | + |
| 541 | + |
| 542 | ++++ |
| 543 | + |
| 544 | ++++ |
| 545 | +++ |
| 546 | ++++ |
| 547 | ++++ |
| 548 | ++ |
| 549 | + |
| 550 | ++ |
| 551 | ++ |
| 552 | +++ |
| 553 | ++++ |
| 554 | ++++ |
| 555 | ++++ |
| 556 | ++++ |
| 557 | ++++ |
| 558 | ++++ |
| 559 | ++++ |
| 560 | ++++ |
| 561 | ++++ |
| 562 | ++++ |
| 563 | ++ |
| 564 | ++++ |
| 565 | ++++ |
| 566 | +++ |
| 567 | ++++ |
| 568 | ++ |
| 569 | ++++ |
| 570 | +++ |
| 571 | ++++ |
| 572 | ++++ |
| 573 | ++++ |
| 574 | + |
| 575 | ++++ |
| 576 | ++++ |
| 577 | ++++ |
| 578 | + |
| 579 | ++++ |
| 580 | ++++ |
| 581 | ++++ |
| 582 | ++++ |
| 583 | ++++ |
| 584 | ++++ |
| 585 | ++++ |
| 586 | ++++ |
| 448 | +++ |
| 449 | + |
| 450 | ++ |
| 451 | ++ |
| 452 | + |
| 453 | + |
| 454 | +++ |
| 455 | + |
| 456 | + |
| 457 | + |
| 458 | + |
| 459 | + |
| 460 | + |
| 461 | + |
| 462 | + |
| 463 | + |
| 464 | ++++ |
| 465 | ++++ |
| 466 | + |
| 467 | + |
| 468 | + |
| 469 | + |
| 470 | ++++ |
| 471 | ++++ |
| 472 | ++++ |
| 473 | ++++ |
| 475 | ++++ |
| 477 | ++++ |
| 478 | ++++ |
| 479 | ++++ |
| 480 | +++ |
| 481 | ++++ |
| 482 | ++++ |
| 483 | + |
| 484 | + |
| 485 | +++ |
| 486 | ++++ |
| 487 | +++ |
| 488 | + |
| 489 | + |
| 490 | + |
| 491 | + |
| 493 | ++++ |
| 494 | + |
| 495 | + |
| 496 | + |
| 497 | + |
| 498 | + |
| 499 | + |
| 500 | +++ |
| 501 | + |
| 502 | + |
| 503 | + |
| 504 | ++++ |
| 505 | +++ |
| 506 | ++++ |
| 507 | +++ |

TABLE 2-continued

| Compound No. | Activity |
|---|---|
| 508 | ++++ |
| 509 | ++++ |
| 510 | ++++ |
| 511 | ++++ |
| 512 | ++++ |
| 513 | ++++ |
| 514 | ++++ |
| 515 | +++ |
| 516 | ++ |
| 517 | +++ |
| 518 | ++++ |
| 519 | +++ |
| 520 | ++++ |
| 521 | + |
| 522 | + |
| 523 | + |
| 524 | +++ |
| 525 | ++++ |
| 526 | + |
| 527 | + |
| 528 | ++++ |
| 529 | + |
| 530 | + |
| 531 | + |
| 532 | + |
| 533 | + |
| 534 | + |
| 535 | + |
| 536 | ++++ |
| 537 | + |
| 538 | + |
| 539 | + |
| 540 | + |
| 541 | + |
| 542 | ++++ |
| 543 | + |
| 544 | ++++ |
| 545 | +++ |
| 546 | ++++ |
| 547 | ++++ |
| 548 | ++ |
| 549 | + |
| 550 | ++ |
| 551 | ++ |
| 552 | +++ |
| 553 | ++++ |
| 554 | ++++ |
| 555 | ++++ |
| 556 | ++++ |
| 557 | ++++ |
| 558 | ++++ |
| 559 | ++++ |
| 560 | ++++ |
| 561 | ++++ |
| 562 | ++++ |
| 563 | ++ |
| 564 | ++++ |
| 565 | ++++ |
| 566 | +++ |
| 567 | ++++ |
| 568 | ++ |
| 569 | ++++ |
| 570 | +++ |
| 571 | ++++ |
| 572 | ++++ |
| 573 | ++++ |
| 574 | + |
| 575 | ++++ |
| 576 | ++++ |
| 577 | ++++ |
| 578 | + |
| 579 | ++++ |
| 580 | ++++ |
| 581 | ++++ |
| 582 | ++++ |
| 583 | ++++ |
| 584 | ++++ |
| 585 | ++++ |

TABLE 2-continued

| Compound No. | Activity |
|---|---|
| 586 | ++++ |
| 587 | ++++ |
| 588 | ++++ |
| 590 | ++++ |
| 591 | ++++ |
| 592 | ++++ |
| 593 | ++++ |
| 594 | + |
| 595 | + |
| 596 | + |
| 597 | +++ |
| 598 | ++++ |
| 599 | ++++ |
| 600 | +++ |
| 601 | ++++ |
| 602 | ++++ |
| 603 | + |
| 604 | ++++ |
| 605 | ++++ |
| 606 | ++++ |
| 607 | + |
| 608 | +++ |
| 609 | +++ |
| 610 | ++++ |
| 611 | ++++ |
| 612 | +++ |
| 613 | + |
| 614 | ++++ |
| 615 | + |
| 616 | ++++ |
| 617 | ++++ |
| 618 | ++++ |
| 619 | ++++ |
| 620 | + |
| 621 | ++++ |
| 622 | ++++ |
| 623 | ++++ |
| 624 | ++++ |
| 625 | ++++ |
| 626 | + |
| 627 | + |
| 628 | + |
| 629 | +++ |
| 630 | +++ |
| 631 | ++++ |
| 632 | ++++ |
| 633 | ++++ |
| 634 | ++++ |
| 635 | ++++ |
| 636 | ++++ |
| 637 | ++++ |
| 638 | ++++ |
| 639 | ++++ |
| 640 | ++++ |
| 641 | ++++ |
| 642 | + |
| 643 | ++++ |
| 644 | ++++ |
| 645 | ++++ |
| 646 | ++++ |
| 647 | ++++ |
| 648 | ++++ |
| 649 | ++++ |
| 650 | ++++ |
| 651 | + |
| 652 | ++++ |
| 653 | ++++ |
| 654 | + |
| 655 | ++++ |
| 656 | ++++ |
| 657 | ++++ |
| 658 | ++++ |
| 659 | ++++ |
| 660 | ++++ |
| 661 | ++ |
| 662 | ++++ |
| 663 | + |
| 664 | ++ |

TABLE 2-continued

| Compound No. | Activity |
|---|---|
| 665 | +++ |
| 666 | +++ |
| 667 | + |
| 668 | + |
| 669 | ++++ |
| 670 | +++ |
| 672 | ++++ |
| 673 | ++++ |
| 674 | ++++ |
| 675 | + |
| 676 | ++++ |
| 677 | ++++ |
| 678 | ++++ |
| 679 | ++++ |
| 680 | ++++ |
| 681 | ++++ |
| 682 | ++++ |
| 683 | ++++ |
| 684 | ++++ |
| 685 | ++++ |
| 686 | ++++ |
| 687 | ++++ |
| 688 | ++++ |
| 689 | ++++ |
| 690 | +++ |
| 691 | ++++ |
| 692 | ++++ |
| 693 | ++++ |
| 694 | ++++ |
| 695 | ++++ |
| 696 | ++++ |
| 697 | ++++ |
| 698 | ++++ |
| 699 | + |
| 700 | ++++ |
| 701 | ++++ |
| 702 | ++++ |
| 703 | ++++ |
| 704 | ++++ |
| 705 | ++++ |
| 706 | +++ |
| 707 | ++++ |
| 708 | ++++ |
| 709 | ++++ |
| 710 | ++++ |
| 711 | ++++ |
| 712 | ++++ |
| 713 | ++++ |
| 713 | ++++ |
| 714 | ++++ |
| 715 | +++ |
| 715 | + |
| 716 | ++++ |
| 717 | +++ |
| 718 | ++++ |
| 719 | ++++ |
| 720 | ++++ |
| 721 | ++++ |
| 722 | ++++ |
| 723 | ++++ |
| 724 | ++++ |
| 725 | ++++ |
| 726 | ++ |
| 727 | ++++ |
| 728 | +++ |
| 729 | + |
| 730 | ++++ |
| 731 | +++ |
| 732 | + |
| 733 | ++++ |
| 734 | ++++ |
| 735 | +++ |
| 736 | ++++ |
| 737 | ++++ |
| 738 | ++++ |
| 739 | ++++ |
| 740 | +++ |
| 741 | ++++ |
| 742 | ++++ |
| 743 | ++++ |
| 744 | ++++ |
| 745 | +++ |
| 746 | ++++ |
| 747 | ++++ |

Example 10

Compounds 3, 4, 10 and 202 were tested in a rat paw edema model to determine anti-inflammatory activity. Seven groups (one for Vehicle A [15 mL PEG400, 3 mL Graves Grain alcohol (190 proof), 1.8 mL dimethylacetamide and 10.2 mL deionized water] alone as a negative control, one for Vehicle B [0.1M $NaHCO_3$] alone as a negative control, one for each of the four test compounds dissolved in Vehicle A, and one for indomethacin dissolved in Vehicle B as a positive control), each group containing six Sprague-Dawley (SD) rats (180-200 g) randomized by weight. Initial paw volumes were measured by placing the right hind limb of the rat up to the top of the hock in a beaker of water sitting on a scale that had been tared to zero and recording the readout.

Rats were pre-treated with either i) one of the test compounds, or ii) a positive or negative control. Vehicle A alone and test compound dissolved in Vehicle A (Compound 3-1.0 mg/kg; Compound 4-0.4 mg/kg; Compound 10-0.5 mg/kg; Compound 202-0.3 mg/kg) were administered by intravenous injection. Vehicle B alone and indomethacin (5 mg/kg in 0.1M $NaHCO_3$) was administered by intraperitoneal injection. Thirty minutes after this pretreatment, rats were anesthetized and injected with 0.1 mL of carrageenan (10 mg/mL in water) in the subplantar region of the right hind foot using a ½ inch 26 gauge needle attached to a 1 cc syringe.

At 2, 4 and 6 hours post-carrageenan injection, the right hind foot of each rat was measured for paw volume as described above. The results of this experiment are shown in Table 3, below.

TABLE 3

| | Change in Paw Volume (mL) | | | |
|---|---|---|---|---|
| Treatment (n = 6) | 0 h | 2 h | 4 h | 6 h |
| Vehicle A alone (IV) | 0 | 1.11 ± 0.23 | 1.55 ± 0.18 | 1.50 ± 0.12 |
| Compound 3 (IV) | 0 | 0.69 ± 0.14 | 1.16 ± 0.32 | 1.22 ± 0.31 |
| Compound 4 (IV) | 0 | 0.72 ± 0.13 | 1.16 ± 0.16 | 1.16 ± 0.25 |
| Compound 10 (IV) | 0 | 0.54 ± 0.23 | 1.11 ± 0.31 | 1.23 ± 0.28 |
| Compound 202 (IV) | 0 | 0.42 ± 0.20 | 1.01 ± 0.31 | 1.16 ± 0.20 |
| Vehicle B alone (IP) | 0 | 1.15 ± 0.16 | 1.76 ± 0.17 | 1.80 ± 0.15 |
| Indomethacin (IP) | 0 | 0.61 ± 0.10 | 0.92 ± 0.12 | 0.99 ± 0.10 |

The above experiment was repeated with Compounds 11, 33, 342 and 393 (each at 1 mg/kg intravenous doses. The results are set forth below in Table 4, below.

TABLE 4

| | Change in Paw Volume (mL) | | | |
|---|---|---|---|---|
| Treatment (n = 6) | 0 h | 2 h | 4 h | 6 h |
| Vehicle A alone (IV) | 0 | 1.26 ± 0.17 | 1.61 ± 0.18 | 1.66 ± 0.10 |
| Compound 11 (IV) | 0 | 1.37 ± 0.16 | 1.43 ± 0.13 | 1.45 ± 0.08 |

TABLE 4-continued

| Treatment (n = 6) | Change in Paw Volume (mL) | | | |
| --- | --- | --- | --- | --- |
| | 0 h | 2 h | 4 h | 6 h |
| Compound 33 (IV) | 0 | 1.10 ± 0.22 | 1.49 ± 0.11 | 1.46 ± 0.07 |
| Compound 342 (IV) | 0 | 1.36 ± 0.10 | 1.49 ± 0.20 | 1.51 ± 0.15 |
| Compound 393 (IV) | 0 | 1.24 ± 0.18 | 1.54 ± 0.25 | 1.56 ± 0.17 |
| Indomethacin (IP) | 0 | 0.61 ± 0.08 | 0.82 ± 0.05 | 0.90 ± 0.11 |

The experiment was again repeated with Compounds 362, 426, 442, 482 and 506 (each at 1 mg/kg intravenous doses). The results are set forth below in Table 5, below.

TABLE 5

| Treatment (n = 6) | Change in Paw Volume (mL) | | | |
| --- | --- | --- | --- | --- |
| | 0 h | 2 h | 4 h | 6 h |
| Vehicle A alone (IV) | 0 | 1.56 ± 0.21 | 1.64 ± 0.19 | 1.54 ± 0.12 |
| Compound 362 (IV) | 0 | 1.17 ± 0.07 | 1.22 ± 0.21 | 1.15 ± 0.19 |
| Compound 426 (IV) | 0 | 0.90 ± 0.15 | 1.11 ± 0.18 | 1.11 ± 0.23 |
| Compound 442 (IV) | 0 | 0.86 ± 0.15 | 1.08 ± 0.16 | 1.01 ± 0.14 |
| Compound 482 (IV) | 0 | 0.73 ± 0.19 | 0.99 ± 0.34 | 0.86 ± 0.27 |
| Compound 506 (IV) | 0 | 0.74 ± 0.18 | 1.05 ± 0.17 | 0.86 ± 0.15 |
| Indomethacin (IP) | 0 | 0.82 ± 0.08 | 0.94 ± 0.10 | 0.87 ± 0.11 |

The experiment was again repeated with Compounds 330, 346, 348, and a re-test of 393 (each at 1 mg/kg intravenous doses). The results are set forth below in Table 6, below.

TABLE 6

| Treatment (n = 6) | Change in Paw Volume (mL) | | | |
| --- | --- | --- | --- | --- |
| | 0 h | 2 h | 4 h | 6 h |
| Vehicle A alone (IV) | 0 | 1.46 ± 0.12 | 1.70 ± 0.26 | 1.57 ± 0.24 |
| Compound 330 (IV) | 0 | 1.20 ± 0.20 | 1.32 ± 0.17 | 1.33 ± 0.22 |
| Compound 346 (IV) | 0 | 1.17 ± 0.06 | 1.20 ± 0.09 | 1.34 ± 0.09 |
| Compound 348 (IV) | 0 | 1.13 ± 0.10 | 1.30 ± 0.20 | 1.32 ± 0.11 |
| Compound 393 (IV) | 0 | 1.27 ± 0.07 | 1.28 ± 0.08 | 1.42 ± 0.12 |
| Indomethacin (IP) | 0 | 0.63 ± 0.08 | 0.79 ± 0.17 | 0.82 ± 0.21 |

The experiment was again repeated with Compounds 156, 174, and 273 (each at 1 mg/kg intravenous doses). The results are set forth below in Table 7, below.

TABLE 7

| Treatment (n = 6) | Change in Paw Volume (mL) | | | |
| --- | --- | --- | --- | --- |
| | 0 h | 2 h | 4 h | 6 h |
| Vehicle A alone (IV) | 0 | 1.52 ± 0.11 | 1.83 ± 0.21 | 1.84 ± 0.17 |
| Compound 156 (IV) | 0 | 1.49 ± 0.24 | 1.51 ± 0.12 | 1.81 ± 0.16 |
| Compound 174 (IV) | 0 | 1.22 ± 0.08 | 1.53 ± 0.13 | 1.70 ± 0.22 |
| Compound 273 (IV) | 0 | 1.13 ± 0.09 | 1.52 ± 0.12 | 1.59 ± 0.16 |
| Indomethacin (IP) | 0 | 0.75 ± 0.14 | 1.02 ± 0.09 | 1.07 ± 0.08 |

The experiment was again repeated with Compounds 419, 428, 493, and 500 (each at 1 mg/kg intravenous doses), as well as with an oral dose (3 mg/kg) of Compound 482. ENBREL® (etanercept) (30 mg/kg subcutaneous) was also used as another positive control. The results are set forth below in Table 8, below.

TABLE 8

| Treatment (n = 6) | Change in Paw Volume (mL) | | | |
| --- | --- | --- | --- | --- |
| | 0 h | 2 h | 4 h | 6 h |
| Vehicle A alone (IV) | 0 | 1.35 ± 0.16 | 1.52 ± 0.13 | 1.32 ± 0.15 |
| Compound 419 (IV) | 0 | 1.22 ± 0.21 | 1.32 ± 0.18 | 1.16 ± 0.16 |
| Compound 428 (IV) | 0 | 1.27 ± 0.15 | 1.43 ± 0.22 | 1.39 ± 0.22 |
| Compound 493 (IV) | 0 | 1.04 ± 0.15 | 1.12 ± 0.10 | 1.03 ± 0.15 |
| Compound 500 (IV) | 0 | 0.98 ± 0.24 | 1.07 ± 0.21 | 0.98 ± 0.14 |
| Compound 482 (3 mg/kg PO) | 0 | 1.13 ± 0.15 | 1.18 ± 0.10 | 1.14 ± 0.10 |
| Indomethacin (IP) | 0 | 0.76 ± 0.13 | 0.92 ± 0.09 | 0.74 ± 0.08 |
| ENBREL ® (etanercept) (30 mg/kg SC) | 0 | 0.74 ± 0.18 | 1.07 ± 0.14 | 0.96 ± 0.12 |

We next investigated the effect of varying intravenous doses of Compound 202 (0.05, 0.10, 0.30, and 1.00 mg/kg) in the same model using the same protocol (6 rats per group). These results are shown in FIG. 1 and in Table 9, below. We also investigated the affect of oral dosing (10 mg/kg) of Compound 202 in the same model. For oral dosing, a 2.5 mg/mL suspension of Compound 202 was prepared in Vehicle A. Rats were orally administered 4 mL/kg of that suspension. These results are also show in Table 9.

TABLE 9

| Treatment (n = 6) | Change in Paw Volume (mL) | | | |
| --- | --- | --- | --- | --- |
| | 0 h | 2 h | 4 h | 6 h |
| Vehicle B (IP) | 0 | 1.52 ± 0.11 | 1.83 ± 0.21 | 1.84 ± 0.17 |
| Indomethacin (IP) | 0 | 0.75 ± 0.14 | 1.02 ± 0.09 | 1.07 ± 0.08 |
| 0.05 mg/kg Compound 202 (IV) | 0 | 1.20 ± 0.09 | 1.56 ± 0.22 | 1.67 ± 0.18 |
| 0.1 mg/kg Compound 202 (IV) | 0 | 0.99 ± 0.15 | 1.41 ± 0.26 | 1.62 ± 0.19 |
| 0.3 mg/kg Compound 202 (IV) | 0 | 0.70 ± 0.13 | 1.09 ± 0.06 | 1.15 ± 0.12 |
| 1.0 mg/kg Compound 202 (IV) | 0 | 0.60 ± 0.04 | 0.98 ± 0.08 | 1.14 ± 0.05 |
| 10 mg/kg Compound 202 (PO) | 0 | 1.12 ± 0.15 | 1.35 ± 0.27 | 1.42 ± 0.22 |

Oral dosing of Compound 202 at 0.3, 1, 3 and 10 mg/kg was further explored in a subsequent experiment in the same model using the same protocol (6 rats per group). The results are shown in Table 10, below.

TABLE 10

| Treatment (n = 6) | Change in Paw Volume (mL) | | | |
| --- | --- | --- | --- | --- |
| | 0 h | 2 h | 4 h | 6 h |
| Vehicle A alone (IV) | 0 | 1.46 ± 0.12 | 1.70 ± 0.26 | 1.57 ± 0.24 |
| Indomethacin (IP) | 0 | 0.63 ± 0.08 | 0.79 ± 0.17 | 0.82 ± 0.21 |
| 0.3 mg/kg Compound 202 (PO) | 0 | 1.49 ± 0.14 | 1.59 ± 0013 | 1.65 ± 0.10 |
| 1.0 mg/kg Compound 202 (PO) | 0 | 1.43 ± 0.18 | 1.45 ± 0.16 | 1.62 ± 0.14 |
| 3.0 mg/kg Compound 202 (PO) | 0 | 1.25 ± 0.08 | 1.42 ± 0.09 | 1.50 ± 0.09 |
| 10 mg/kg Compound 202 (PO) | 0 | 1.17 ± 0.17 | 1.29 ± 0.06 | 1.51 ± 0.06 |

Example 11

We used a human cell-based assay to determine the TNF-α antagonistic activity of the compounds of this invention based upon the ability of the compounds to inhibit the degradation of IkB in those cells. The assay was performed on either HeLa cells or A431 cells.

On Day 1, wells of a 24-well tissue culture plate were seeded with cells that had been harvested from cultures in T-75 flasks by standard trypsin/EDTA treatment. The harvested cells were suspended in EMEM/10% FBS/P/S (100,000 HeLa cells/mL or 200,000 A431 cells/mL) and 1 mL aliquots were placed into each well. The cells were incubated overnight at 37° C. in a humidified $CO_2$ incubator. On day 2, the cells were approximately 95% confluent.

Test and control compounds were diluted to a 1 mM solution by dilution in DMSO. The assay was run in Costar tubes. Into each tube was placed 2.5 or 5.0 μL of test compound (for testing 5 μM and 10 μM concentrations, respectively), 2.5 μL of 100× TNF-α solution (200 ng/mL TNF-α in EMEM containing 1μg/mL cycloheximide) and, for those tubes containing 2.5 μL of compound, an additional 2.5 μL of DMSO. To each tube was then added 0.5 mL of EMEM containing 1μg/mL cycloheximide. Negative control tubes contained either a) no compound, or b) no TNF-α. Tubes were then incubated for 30 minutes at room temperature.

Once incubation had begun, the media was aspirated from the cells in the 24-well plates. Sufficient EMEM/10% FBS/P/S containing 1 ug/mL cycloheximide was then added to cover the cells (approximately 3 mL) and the cells were retuned to the 37° C. humidified $CO_2$ incubator until compound incubation was completed. The media was then aspirated from the cells, 0.2 mL of the compound solution was added and the cells re-incubated at 37° C. for 30 minutes. The plates were then placed on ice, the compound solution was aspirated from each well, and the cells washed once with 1 mL of cold PBS. Cells were then fixed with 500 μL of 3.7% formaldehyde in PBS ("fix solution") for 20 minutes at room temperature. The fix solution was decanted and the cells permeabilized by 4× washing with 500 uL PBS/0.1% Triton X-100. After the final permeabilization wash, the cells were treated with 500 uL of Odyssey blocking buffer (OBB) and incubated at room temperature with shaking for 90 minutes.

The OBB was decanted and then to each well was then added 125 μL each of mouse anti-IkB CST#4814 (diluted 1:200 in OBB) and rabbit anti-beta-tubulin CST#2146 (diluted 1:200 in OBB). Plates were sealed with parafin and incubated overnight at room temperature with shaking.

On day 3, the antibody solution was removed from the cells and the cells were washed 5× with 0.5 mL PBST for five minutes each on a shaker. To each well was then aded 125 μL of a secondary antibody solution containing goat anti-mouse IgG-IRDye 800 and goat anti-rabbit IgG-IRDye (each diluted 1:500 in OBB+0.2% Tween 20). The plates were covered with aluminum foil and incubated for 1 hour at room temperature with shaking. The secondary antibody solution was removed and the cells washed 3× with 0.5 mL PBST for five minutes each on a shaker. Cells were then scanned by LICOR with the following settings: 700 intensity=6.0, 800 intensity=6.5; microplate2 settings with 3.0 mm offset; 169 resolution. LICOR values were fitted to an equation for a sigmoidal curve and $IC_{50}$ values calculated from the fitted parameters. These results are also show in Table 11, where + indicates less than 10% inhibition, ++ indicates 10% to less than 50% inhibition, +++ indicates 50% to 80% inhibition, and ++++ indicates greater than 80% inhibition. Blank cells indicate that the compound was not tested at that concentration. Certain compounds that were tested more than once and the values reflect the average of the multiple tests.

TABLE 11

| Compound No. | Inhibition at Various Compound Concentrations | | |
| --- | --- | --- | --- |
| | 25 μM | 10 μM | 5 μM |
| 1 | ++ | | |
| 3 | | + | + |
| 4 | | + | |
| 10 | ++++ | | |
| 11 | | +++ | ++ |
| 12 | | ++ | ++ |
| 15 | | + | |
| 16 | | + | |
| 18 | | ++ | +++ |
| 19 | + | | |
| 20 | + | | |
| 21 | + | | |
| 24 | + | | |
| 26 | ++ | | |
| 29 | + | | |
| 33 | | +++ | ++ |
| 34 | + | | |
| 35 | +++ | | |
| 36 | + | +++ | ++ |
| 39 | | ++ | |
| 43 | + | | |
| 47 | | + | |
| 82 | | + | + |
| 85 | + | | |
| 89 | + | | |
| 111 | | + | |
| 112 | | + | |
| 116 | | + | ++ |
| 117 | | +++ | + |
| 118 | | ++ | |
| 156 | | ++++ | +++ |
| 157 | | +++ | ++ |
| 158 | | +++ | +++ |
| 174 | | ++ | + |
| 180 | | + | + |
| 194 | + | | |
| 196 | + | | |
| 198 | +++ | | |
| 201 | | ++ | |
| 202 | | +++ | ++ |
| 212 | | + | + |
| 217 | | + | + |
| 236 | | ++ | ++ |
| 237 | | + | + |
| 239 | | + | + |
| 248 | | ++ | + |
| 273 | | + | ++ |
| 282 | | ++ | +++ |
| 289 | | + | + |
| 290 | | + | + |
| 297 | | + | + |
| 298 | | + | + |
| 299 | | + | + |
| 300 | | ++ | |
| 301 | | + | + |
| 302 | | ++ | ++ |
| 305 | | + | |
| 307 | | + | |
| 313 | | ++ | + |
| 318 | | ++ | + |
| 319 | | + | + |
| 320 | | ++++ | ++ |
| 321 | | ++ | + |
| 323 | | ++ | ++ |
| 324 | | ++ | ++ |
| 325 | | + | |
| 326 | | ++ | ++ |
| 327 | | + | ++ |
| 328 | | ++ | |
| 330 | | ++ | ++++ |
| 332 | | | + |
| 339 | | ++ | + |
| 341 | | + | |
| 342 | | ++ | + |
| 343 | | ++ | + |

TABLE 11-continued

| Compound No. | Inhibition at Various Compound Concentrations | | |
|---|---|---|---|
| | 25 μM | 10 μM | 5 μM |
| 344 | | +++ | ++ |
| 346 | | +++ | ++++ |
| 348 | | +++ | ++ |
| 350 | | ++ | ++ |
| 362 | | ++ | + |
| 363 | | ++ | +++ |
| 364 | | ++ | +++ |
| 366 | | + | + |
| 369 | | + | + |
| 379 | | ++ | +++ |
| 380 | | + | + |
| 381 | | + | + |
| 382 | | + | ++ |
| 384 | | + | + |
| 385 | | ++++ | +++ |
| 386 | | + | + |
| 388 | | ++ | + |
| 390 | | +++ | + |
| 391 | | ++ | ++ |
| 393 | | ++++ | ++ |
| 395 | | + | + |
| 396 | | +++ | ++ |
| 410 | | ++ | + |
| 419 | | + | + |
| 426 | | ++ | ++ |
| 428 | | + | + |
| 442 | | ++ | ++ |
| 482 | | ++ | ++ |

Incorporation by Reference

The entire disclosure of each of the patent documents and scientific articles referred to herein is incorporated by reference for all purposes.

Equivalents

The invention may be embodied in other specific forms without departing from the spirit or essential characteristics thereof. The foregoing embodiments are therefore to be considered in all respects illustrative rather than limiting the invention described herein. Scope of the invention is thus indicated by the appended claims rather than by the foregoing description, and all changes that come within the meaning and range of equivalency of the claims are intended to be embraced therein.

We claim:

1. A compound represented by formula VII:

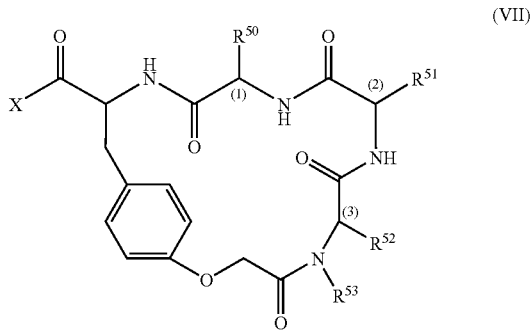

(VII)

including pharmaceutically acceptable salts thereof, wherein:
$R^{50}$ is benzyl, phenylethyl, indol-3-ylmethyl, thien-2-ylmethyl, biphenyl-4-ylmethyl, 4-(pyridin-4-yl)benzyl, 4-(pyridin-3-yl)benzyl, or 4-(pyridin-2-yl)benzyl, wherein the benzyl, biphenyl-4-yl or phenylethyl group in $R^{50}$ is optionally substituted on a terminal phenyl ring with a single substituent selected from the group consisting of halo, methoxy, $CF_3$, hydroxy, cyano, and $C_1$-$C_4$ alkyl; or is optionally substituted with chloro at each of the 2 and 4 positions of the terminal phenyl ring;

$R^{51}$ is biphenyl-4-ylmethyl, 4-(pyridin-4-yl)benzyl, or 4-(pyridin-3-yl)benzyl, wherein the biphenyl group in $R^{51}$ is optionally monosubstituted at the 4-position of the terminal phenyl ring with amino, halo or hydroxy;

$R^{52}$ is phenyl, naphthyl, benzyl, naphthylmethyl, phenylethyl, heteroarylmethyl, 4-(heteroaryl)benzyl, or biphenyl-4-ylmethyl, wherein the phenyl, naphthyl, benzyl, naphthylmethyl, phenylethyl or biphenyl-4-ylmethyl group in $R^{52}$ is optionally on a terminal phenyl ring with 1 to 2 substituents independently selected from the group consisting of halo, methoxy, hydroxy, $C_1$-$C_4$ alkyl, and $C_1$-$C_4$ haloalkyl;

$R^{53}$ is hydrogen or methyl;

X is —OH, —N($R^W$)—[C($R^V$)$_2$]$_{1-4}$—COOH, —N($R^W$)—[C($R^V$)$_2$]$_{1-3}$—SO$_3$H, —N($R^W$)—[C($R^V$)$_2$]$_{0-4}$—S(O)$_2$CH$_3$, or —N($R^W$)—[C($R^V$)$_2$]$_{1-3}$-1H-tetrazol-5-yl, wherein:

$R^W$ represents hydrogen, methyl or benzyl; and each $R^V$ independently represents hydrogen, —($C_1$-$C_6$)-alkyl, —($C_1$-$C_6$)-alkyl-heterocyclyl, —($C_1$-$C_6$)-alkyl-carbocyclyl, or —CO$_2$-alkyl, wherein each $R^V$ is optionally substituted with a substituent selected independently from the group consisting of —NH$_2$, —NH—C(O)—($C_1$-$C_4$)-alkyl and —OH; or two $R^V$ are taken together with the carbon atom to which they are bound to form a 3-7 membered cycloalkane ring, the stereochemistry at (1) is the same as the stereochemistry at (3); and the stereochemistry at (1) is opposite the stereochemistry at (2).

2. The compound of claim 1, wherein:
$R^{50}$ is benzyl, 2-fluorobenzyl, 4-fluorobenzyl, 2-trifluoromethylbenzyl, 4-trifluoromethylbenzyl, 2,4-dichlorobenzyl, 3-methoxybenzyl, 4-hydroxybenzyl, 4-cyanobenzyl, 4-methoxybenzyl, 4-t-butylbenzyl, phenylethyl, 2-fluorophenylethyl, indol-3-ylmethyl, thien-2-ylmethyl, biphenyl-4-ylmethyl, 4-(pyridin-4-yl)benzyl, 4-(pyridin-3-yl)benzyl, or 4-(pyridin-2-yl)benzyl;

$R^{51}$ is biphenyl-4-ylmethyl, 4-(pyridin-4-yl)benzyl, 4-(pyridin-3-yl)benzyl, 4-(4-aminophenyl)benzyl, 4-(4-bromophenyl)benzyl, 4-(4-fluorophenyl)benzyl, or 4-(4-hydroxyphenyl)benzyl;

$R^{52}$ is 2,4-dichlorobenzyl, 2-fluorobenzyl, 3-fluorobenzyl, 3-methoxybenzyl, 3-trifluoromethylbenzyl, 4-trifluoromethylbenzyl, 4-hydroxybenzyl, 4-chlorobenzyl, 4-fluorobenzyl, 4-methylbenzyl, biphenyl-4-ylmethyl, indol-3-ylmethyl, thien-2-ylmethyl, 4-(pyridin-4-yl)benzyl, 4-(pyridin-3-yl)benzyl, 4-(pyridin-2-yl)benzyl, pyridin-2-ylmethyl, pyridin-3-ylmethyl, pyridin-4-ylmethyl, naphthyl, naphthylmethyl, phenylethyl, thiazol-3ylmethyl, 4-(thien-2-yl)benzyl, furan-2ylmethyl, N-phenyl-1H-triazol-4ylmethyl, 4-(4-fluorophenyl)benzyl, or 4-(4-chlorophenyl)benzyl; and X is —N(CH$_3$)CH$_2$SO$_3$H, —N(CH$_3$)CH(benzyl)COOH, —N(CH$_3$)CH(CH$_3$)COOH, —NHCH$_2$COOH, —NHCH$_2$SO$_3$H, —NHCH$_2$-1H-tetrazol-5-yl, —NH(CH$_2$)$_2$COOH, —NH(CH$_2$)$_2$SO$_3$H, —NH(CH$_2$)$_3$COOH, —NH(CH$_2$)$_3$SO$_3$H, —NH(CH$_2$)$_2$-1H-tetrazol-5-yl, —NHCH(4-hydroxybenzyl)COOH, —NHCH(benzyl)COOH, —NHCH(benzyl)-1H-tetrazol-5-yl, —NHCH(CH$_2$OH)COOH, —NHCH(phenylethyl)COOH, or —NHS(O)$_2$CH$_3$.

3. The compound of claim 1, wherein the compound is Compound 482:
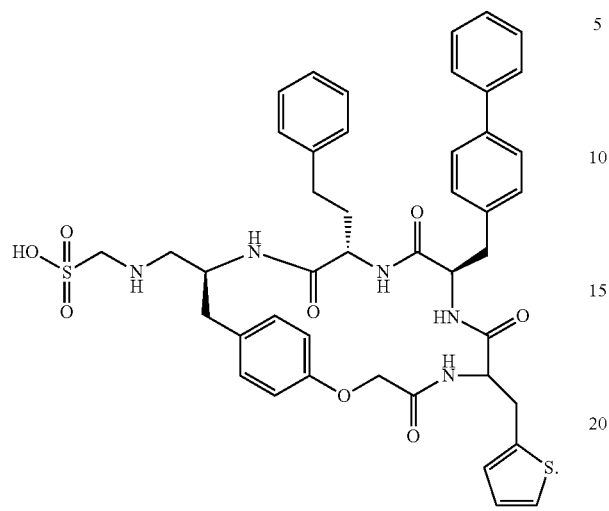
4. A pharmaceutical composition comprising a compound of claim 1 and a pharmaceutically acceptable carrier.
* * * * *

UNITED STATES PATENT AND TRADEMARK OFFICE
CERTIFICATE OF CORRECTION

PATENT NO. : 8,338,565 B2　　　　　　　　　　　　　　　　　　　　　　　Page 1 of 1
APPLICATION NO. : 12/544604
DATED : December 25, 2012
INVENTOR(S) : Jinbo Lee et al.

It is certified that error appears in the above-identified patent and that said Letters Patent is hereby corrected as shown below:

Claim number 3, column 737, lines 5-23, replace

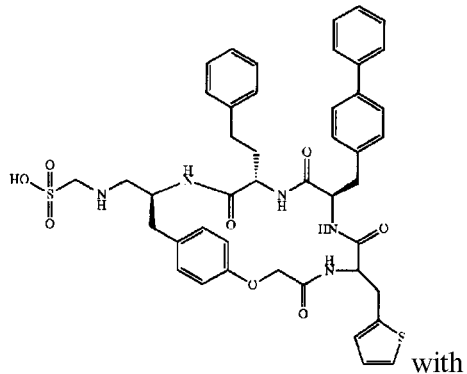 with

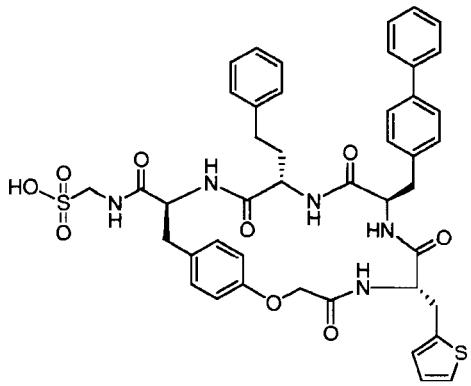

Signed and Sealed this
Second Day of April, 2013

Teresa Stanek Rea
*Acting Director of the United States Patent and Trademark Office*